United States Patent
Galan et al.

(10) Patent No.: US 8,088,767 B2
(45) Date of Patent: Jan. 3, 2012

(54) JAK-2 MODULATORS AND METHODS OF USE

(75) Inventors: Adam Antoni Galan, Alameda, CA (US); Jeff Chen, San Francisco, CA (US); Hongwang Du, Millbrae, CA (US); Timothy Forsyth, Hayward, CA (US); Tai Phat Huynh, Oakland, CA (US); Henry William Beecroft Johnson, San Bruno, CA (US); Patrick Kearney, San Francisco, CA (US); James W. Leahy, San Leandro, CA (US); Matthew Sangyup Lee, San Francisco, CA (US); Grace Mann, San Mateo, CA (US); Brian Hugh Ridgway, Belmont, CA (US); Craig Stacy Takeuchi, Burlingame, CA (US); Peiwen Zhou, Palo Alto, CA (US)

(73) Assignee: Exelixis, Inc., South San Francisco, CA (US)

( * ) Notice: Subject to any disclaimer, the term of this patent is extended or adjusted under 35 U.S.C. 154(b) by 0 days.

(21) Appl. No.: 12/443,103

(22) PCT Filed: Sep. 28, 2007

(86) PCT No.: PCT/US2007/020982
§ 371 (c)(1),
(2), (4) Date: Jan. 27, 2010

(87) PCT Pub. No.: WO2008/042282
PCT Pub. Date: Apr. 10, 2008

(65) Prior Publication Data
US 2010/0136136 A1 Jun. 3, 2010

Related U.S. Application Data

(60) Provisional application No. 60/847,762, filed on Sep. 28, 2006.

(51) Int. Cl.
*A61K 31/5377* (2006.01)
*A61K 31/4439* (2006.01)
*A61K 31/4184* (2006.01)
*C07D 413/14* (2006.01)
*C07D 401/14* (2006.01)
*C07D 403/12* (2006.01)

(52) U.S. Cl. ............. 514/234.5; 514/338; 514/395; 544/139; 546/273.4; 548/306.1

(58) Field of Classification Search ............ 548/313.7, 548/306.1; 546/273.4, 199; 544/370, 139; 514/397, 210.21, 394, 338, 322, 254.06, 514/233.8, 283
See application file for complete search history.

(56) References Cited

FOREIGN PATENT DOCUMENTS

| WO | 00/55128 A | 9/2000 |
|---|---|---|
| WO | 2005/013982 A | 2/2005 |

OTHER PUBLICATIONS

Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Vippagunta et al., Crystalline solids, 2001, Advanced Drug Delivery Reviews, 48, pp. 3 and 18.*
Perchellet, E. M. et al., "Imidazole-4,5-dicarboxamde Derivatives with Antiproliferative Activity against HL-60 Cells", Journal of Medicinal Chemistry, 2005, 48(19), 5955-5965.
Baures, P. W. et al., "The Influence by Substituents on the Intermolecular Hydrogen-Bonding Interactions in Imidazole-4,5-dicarboxylic Acid Derivatives", Crystal Growth & Design, 2006, 6(9), 2047-2052.
Nonoyama, K. et al., "Copper(II) and nickel(II) complexes of binucleating N,N'-disubstituted imidazole-4,5-dicarboxamides", Polyhedron, 1994, 13(6-7), 891-7.
Ivanov, Y. E. et al., "Transformation of 5-(azidocarbonyl)-4-[(phenylamino)carbonyl]imidazole in the Curtius reaction", Database CA Chemical Abstracts Service, Accession No. 2004:662614, 2004.
Database Chemcats Chemical Abstracts Service, XP002470720, Feb. 7, 2006.

* cited by examiner

*Primary Examiner* — Kamal Saeed
*Assistant Examiner* — Kristin Bianchi
(74) *Attorney, Agent, or Firm* — McDonnell Boehnen Hulbert & Berghoff LLP

(57) ABSTRACT

This invention relates to the field of protein tyrosine kinases and inhibitors thereof. In particular, the invention relates to inhibitors of JAK-2, pharmaceutical compositions of the compounds for inhibiting JAK-2, methods of inhibiting JAK-2 in a cell, comprising contacting a cell in which inhibition of JAK-2 is desired with a compound or pharmaceutical composition comprising a compound according to the invention. The also comprises methods of treating a disease or condition that involves JAK-2 comprising administering to a patient a pharmaceutical composition comprising a compound according to the invention.

12 Claims, No Drawings

JAK-2 MODULATORS AND METHODS OF USE

This application is a US national phase of International Application No. PCT/US2007/020982, filed on Sep. 28, 2007, which claims the benefit of U.S. Application No. 60/847,762, filed on Sep. 28, 2006, which is herein incorporated by reference in its entirety.

FIELD OF THE INVENTION

This invention relates to the field of protein tyrosine kinases and inhibitors thereof. In particular, the invention relates to inhibitors of JAK-2 that involve the cytokine receptor signaling pathways.

BACKGROUND OF THE INVENTION

Janus kinases (JAKs) are protein tyrosine kinases ubiquitously expressed in cells. JAKs are involved in membrane signalling events which are triggered by a variety of extracellular factors that interact with cell surface receptors. JAKs initiate the cytoplasmic signal transduction cascades of cytokine receptors that lack a protein tyrosine kinase domain. The signal transduction cascades are initiated after oligomerisation of surface receptors due to ligand binding. Cytoplasmic receptor-associated JAKs are then activated which subsequently phosphorylate tyrosine residues along the receptor chains. These phosphotyrosine residues are targets for a variety of SH2 domain-containing transducer proteins, such as the signal transducers and activators of transcription (STAT) proteins. After STAT binds to receptor chains, they are phosphorylated by the JAK proteins, dimerise and translocate into the nucleus. In the nucleus, STAT alter the expression of cytokine-regulated genes.

Mammalian JAK-2 belongs to a kinase family that include JAK-1, JAK-3 and TYK-2. JAK-1, JAK-2, and TYK-2 are ubiquitously expressed, while JAK-3 is predominantly expressed in hematopoietic cells. These kinases consist of approximately 1150 amino acids, with molecular weights of about 120 kDa to 130 kDa. The amino acid sequences of the JAK kinase family are characterised by the presence of highly conserved domains. These domains include the JAK homology (JH) domains, C-terminal domain (JH1) responsible for the tyrosine kinase function, the tyrosine kinase-like domain (JH2) that shows high similarity to functional kinases but does not possess any catalytic activity, and the N-terminal domain that spans JH7 to JH3) that is important for receptor association and non-catalytic activity. Although the function of the N-terminal domain is not well established, there is some evidence for a regulatory role on the JH1 domain, thus modulating catalytic activity.

The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas.

Signal transducer and activator of transcription (STAT) proteins are activated by JAK family kinases. Recent studies suggested the possibility of modulating the JAK/STAT signaling pathway by targeting JAK family kinases with specific inhibitors for the treatment of leukemia (see Sudbeck, et al, Clin. Cancer Res. 5: 1569-1582 (1999)). In animal models, TEL/JAK-2 fusion proteins induced myeloproliferative disorders. In hematopoietic cell lines, introduction of TEL/JAK2 resulted in activation of STAT1, STAT3, STAT5, and cytokine-independent growth.

The JAK/STAT pathway is involved in abnormal cell growth. STAT3, STAT5, JAK1 and JAK2 are constitutively activated in mouse T cell lymphoma characterized initially by LCK over-expression. In addition, IL-6-mediated STAT3 activation was blocked by inhibition of JAK, leading to sensitization of myeloma cells to apoptosis.

One particularly attractive target for small-molecule modulation, with respect to antiproliferative and antiangiogenic activity, is JAK-2. Accumulating evidence shows that constitutive activation of JAK/STAT pathway promotes cell growth, survival, differentiation, neoplastic transformation, and angiogenesis in response to growth factors, cytokines, and hormones. JAK-2 is also activated in a wide variety of human cancers such as prostrate, colon, ovarian, breast cancers, melanoma, leukemia and other haematopoietic malignancies. In addition, somatic point mutation of the JAK-2 gene has been identified to be highly associated with classic myeloproliferative disorders (MPD) and infrequently in other myeloid disorders. Constitutive activation of JAK-2 activity is also caused by chromosomal translocation in hematopoeitic malignancies, such as in TEL-JAK-2 which is primarily associated with T-ALL, and in PCM1-JAK-2 which is associated with B-ALL and CML. It has been shown that inhibition of the JAK/STAT pathway, and in particular inhibition of JAK-2 activity, results in anti-proliferative and pro-apoptotic effects largely due to inhibition of phosphorylation of STAT. Furthermore, inhibition of JAK-2 activity by pharmacological agents or by expression of dominant negative JAK-2 effectively block tumor growth and induce apoptosis by reducing the STAT phosphorylation in cell culture and human tumor xenografts in vivo. Therefore, the JAK/STAT signal transduction pathway is a well-validated target pathway for therapeutic intervention.

Accordingly, the identification of small-molecule compounds that specifically inhibit, regulate and/or modulate the signal transduction of kinases, particularly JAK-2, is desirable as a means to treat or prevent diseases and conditions associated with cancers. Thus, an object of this invention is the identification of JAK-2 inhibitors as new therapeutic agents to treat human diseases.

SUMMARY OF THE INVENTION

The invention comprises compounds and pharmaceutical compositions of the compounds for inhibiting JAK-2.

One aspect of the invention relates to compounds that inhibit JAK-2 function. The compounds are exemplified by Formula I as described herein.

Another aspect the invention relates to a pharmaceutical composition comprising an inhibitor of JAK-2 of Formula I and a pharmaceutically acceptable carrier, excipient, or diluent.

Another aspect of the invention relates to a method of inhibiting JAK-2 in a cell, comprising contacting a cell, in which inhibition of JAK-2 is desired, with a compound of Formula I, or a pharmaceutical composition comprising a compound according to Formula I.

Another aspect of the invention relates to a method of treating a disease or condition that involves JAK-2 comprising administering to a patient, in need of the treatment, a compound of Formula I, or a pharmaceutical composition comprising a compound of Formula I.

There are many different aspects of the invention as described hereinbelow, and each aspect is non-limiting in regard to the scope of the invention. The term "invention" is meant to be non-limiting such that "invention" refers to an "aspect" or a "non-limiting embodiment" regardless of whether the terms "aspect" or "embodiment" appear in conjunction with the term "invention." The transitional term "comprising" as used herein, which is synonymous with "including," "containing," or "characterized by," is inclusive or open-ended and does not exclude additional, unrecited elements or method steps.

The foregoing only summarizes certain aspects of the invention and is not intended to be limiting in nature. These aspects and other aspects and embodiments are described more fully below. All references any sort referred to in this specification are hereby incorporated by reference in their entirety. In the event of a discrepancy between the express disclosure of this specification and the references incorporated by reference, the express disclosure of this specification shall control.

DETAILED DESCRIPTION OF THE INVENTION

One aspect of the invention provides compounds of the Formula I

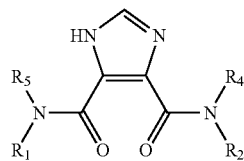

I or a pharmaceutically acceptable salt or solvate thereof, wherein $R_1$ is selected from -(5-10 membered)heteroaryl, —($C_1$-$C_6$)alkyl(5-10 membered)heteroaryl, —($C_6$-$C_{10}$)aryl and -(4-10 membered)heterocycloalkyl, wherein each -(5-10 membered)heteroaryl, —($C_1$-$C_6$)alkyl(5-10 membered) heteroaryl, —($C_6$-$C_{10}$)aryl and -(4-10 membered) heterocycloalkyl is optionally substituted with 1 or 2 substituents selected from halo, —($C_3$-$C_{10}$)cycloalkyl, —($C_1$-$C_6$)alkyl, —($C_1$-$C_6$)alkoxy, -(4-10 membered)heterocycloalkyl, -(4-10 membered)heterocycloalkyl, —O-(4-10 membered)heterocycloalkyl-$R_{10}$, —C(O)O($C_1$-$C_6$)alkyl, —O—($C_1$-$C_6$)alkyl-C(O)N$R_8R_{11}$, —O—($C_1$-$C_6$)alkyl-C(O)O$R_8$, —O—($C_1$-$C_6$)alkyl(5-10 membered)heteroaryl, —O—($C_1$-$C_6$)alkyl(4-10 membered)heterocycloalkyl-C(O)O—($C_1$-$C_6$)alkyl, -(4-10 membered) heterocycloalkyl($C_1$-$C_6$)alkyl, -(4-10 membered)heterocycloalkyl($C_1$-$C_6$)alkyl ($C_6$-$C_{10}$)aryl, -(4-10 membered)heterocycloalkyl($C_1$-$C_6$)alkyl(4-10 membered)heterocycloalkyl, -(4-10 membered) heterocycloalkyl($C_1$-$C_6$)alkyl(5-10 membered)heteroaryl, —O—($C_1$-$C_6$)alkyl-(4-10 membered)heterocycloalkyl, —O—($C_1$-$C_6$)alkyl-(4-10 membered)heterocycloalkyl-$R_{10}$, —O($C_1$-$C_6$)alkyl-C(O)NH($C_5$-$C_{10}$)cycloalkyl, -(4-10 membered)heterocycloalkyl($C_6$-$C_{10}$)aryl, —($C_1$-$C_6$)alkyl-N[($C_1$-$C_6$)alkyl]$_2$, —O—($C_1$-$C_6$)alkylN[($C_1$-$C_6$)alkyl]$_2$, -(4-10 membered)heterocycloalkyl($C_1$-$C_6$)alkyl, —($C_1$-$C_6$)alkoxy-di[($C_1$-$C_6$)alkyl]amino, —($C_6$-$C_{10}$)aryl, —($C_1$-$C_6$)alkoxy ($C_1$-$C_6$)alkoxy, -(4-10 membered)heterocycloalkyl-C(O)O—($C_1$-$C_6$)alkyl, —ON(H)C(O)NH($C_1$-$C_6$)alkyl($C_6$-$C_{10}$)aryl, -(4-10 membered)heterocycloalkyl($C_1$-$C_6$)alkyl-O—($C_1$-$C_6$)alkyl-($C_6$-$C_{10}$)aryl, and —($C_1$-$C_6$)alkoxy(4-10 membered)heterocycloalkyl, wherein the aryl, heteroaryl, cycloalkyl or heterocycloalkyl portion of any of the above optional substituents for $R_1$ can be further substituted by —($C_1$-$C_6$)alkyl;

$R_2$ is selected from —($C_6$-$C_{10}$)aryl, —($C_1$-$C_6$)alkyl($C_6$-$C_{10}$)aryl, —NHC(O)($C_4$-$C_{10}$)heterocycloalkyl($C_1$-$C_6$) alkyl, -(5-10 membered)heteroaryl, -(5-10 membered)heteroaryl($C_1$-$C_6$)alkyl, -(4-6 membered)heterocycloalkyl, —O—($C_1$-$C_6$)alkyl(4-10 membered)heterocycloalkyl-C(O) O—($C_1$-$C_6$)alkyl, —O—($C_1$-$C_6$)alkyl-(4-10 membered)heterocycloalkyl, —($C_1$-$C_6$)alkyl-($C_3$-$C_{10}$)cycloalkyl, and —($C_1$-$C_6$)alkyl-(5-10 membered)heteroaryl, wherein each —($C_6$-$C_{10}$)aryl, —NHC(O)($C_4$-$C_{10}$)heterocycloalkyl($C_1$-$C_6$)alkyl, —($C_1$-$C_6$)alkyl($C_6$-$C_{10}$)aryl, -(5-10 membered) heteroaryl, -(5-10 membered)heteroaryl($C_1$-$C_6$)alkyl, -(4-10 membered)heterocycloalkyl, —O—($C_1$-$C_6$)alkyl(4-10 membered)heterocycloalkyl-C(O)O—($C_1$-$C_6$)alkyl, —O—($C_1$-$C_6$)alkyl-(4-10 membered)heterocycloalkyl, —($C_1$-$C_6$) alkyl-($C_3$-$C_{10}$)cycloalkyl, and —($C_1$-$C_6$)alkyl-(5-10 membered)heteroaryl is optionally substituted with 1, 2, 3, 4 or 5 substituents selected from —($C_1$-$C_6$)alkyl, —($C_1$-$C_6$)alkyl-$R_{12}$, —($C_1$-$C_6$)alkyl)NHC(O)O($C_1$-$C_6$)alkyl, —($C_1$-$C_6$) alkylhydroxy, —($C_1$-$C_6$)alkoxy($C_1$-$C_6$)alkoxy($C_6$-$C_{10}$)aryl, —($C_5$-$C_{10}$)heteroaryl, -(4-10 membered)heterocycloalkyl-S (O)$_2$—($C_6$-$C_{10}$)aryl, -(4-10 membered)heterocycloalkyl, -(4-10 membered)heterocycloalkyl($C_6$-$C_{10}$)aryl, -(4-10 membered)heterocycloalkyl($C_6$-$C_{10}$)aryl-$R_{12}$, —NHC(O)($C_4$-$C_{10}$)heterocycloalkyl($C_t$—$C_6$)alkyl, -(4-10 membered heterocycloalkyl)C(O)NH($C_6$-$C_{10}$)aryl, -(4-10 membered) heterocycloalkylC(O)NH($C_1$-$C_6$)alkyl, —O—($C_1$-$C_6$)alkyl (4-10 membered)heterocycloalkyl, —O—($C_1$-$C_6$)alkyl(4-10 membered)heterocycloalkyl-S(O)$_2$—($C_6$-$C_{10}$)aryl, —S—($C_1$-$C_6$)alkyl, halo, —($C_1$-$C_6$)alkoxy, cyano, -(4-10 membered)heterocycloalkyl, —NH$_2$, —CF$_3$, —NHC(O)O($C_1$-$C_6$)alkyl, —C(O)CH$_3$, —C(O)O$R_{10}$, -(4-10 membered) heterocycloalkyl-C(O)O($C_1$-$C_6$)alkyl, -(4-10 membered) heterocycloalkyl-C(O)O($C_1$-$C_6$)alkyl, —S(O)O($C_1$-$C_6$) alkyl, —($C_5$-$C_6$)cycloalkly($C_1$-$C_3$)alkyl, —($C_5$-$C_{10}$) cycloalkly($C_1$-$C_6$)alkyl-amino($C_1$-$C_6$)alkyl, —NHC(O)-(4-10 membered)heterocycloalkyl, —($C_1$-$C_6$)alkyl-N$R_{10}$ ($C_1$-$C_6$)alkyl($C_5$-$C_6$)cycloalkly, -(4-10 membered) heterocycloalkyl)C(O)N$R_7R_8$, —($C_6$-$C_{10}$)aryl, —NH($C_6$-$C_{10}$)aryl, -(4-10 membered)heterocycloalkyl($C_1$-$C_6$)alkyl, - (4-10 membered)heterocycloalkyl($C_6$-$C_{10}$)aryl, —O-(4-10 membered)heterocycloalkyl($C_1$-$C_6$)alkyl-($C_6$-$C_{10}$)aryl, —O-(4-10 membered)heterocycloalkyl-C(O)CN, —NH($C_1$-$C_6$) alkyl, —OCF$_3$, —NHC(O)(4-10 membered) heterocycloalkyl($C_1$-$C_6$)alkyl, dimethylaminoalkyl, —N[($C_1$-$C_6$)alkyl]$_2$, —NH($C_1$-$C_6$)alkyl), —($C_1$-$C_6$)alkyl)N [$C_1$-$C_6$)alkyl]$_2$, —O-heterocycloalkyl, —O-(4-10 membered)heterocycloalkyl($C_6$-$C_{10}$)aryl, and —($C_1$-$C_6$)alkoxyhydroxy;

$R_4$ and $R_5$ are each independently H or ($C_1$-$C_6$)alkyl; or $R_1$ and $R_5$, together with the nitrogen atom to which they are attached, form a (5-10 membered)heteroaryl or (5-10 membered)heterocycloalkyl, wherein each of the -(5-10 membered)heteroaryl and
-(5-10 membered)heterocycloalkyl groups is optionally substituted with one or more groups independently selected from —($C_1$-$C_6$)alkyl, —($C_1$-$C_6$)alkyl($C_6$-$C_{10}$)aryl, and -(5-10 membered)heteroaryl;

or $R_2$ and $R_4$ together with the nitrogen atom to which they are attached form a -(5-10 membered)heteroaryl or -(5-10 membered)heterocycloalkyl, wherein each of the -(5-10 membered)heteroaryl or -(5-10 membered)heterocycloalkyl groups is optionally substituted with one or more groups independently selected from —($C_1$-$C_6$)alkyl, —($C_1$-$C_6$)alkyl ($C_6$-$C_{10}$)aryl, and -(5-10 membered)heteroaryl;

R$_6$ and R$_7$ are each independently selected from hydrogen, hydroxy, (5-10 membered)heteroaryl, (4-10 membered)heterocycloalkyl, and (C$_6$-C$_{10}$)aryl, and each R$_6$ and R$_7$ are independently selected when more than one R$_6$ or R$_7$ occurs;

R$_8$, R$_9$ and R$_{10}$ are each independently selected from H and (C$_1$-C$_6$)alkyl, and R$_8$, R$_9$ and R$_{10}$ are each independently selected when more than one R$_8$, R$_9$ or R$_{10}$ occurs;

R$_{11}$ is selected from hydrogen, (C$_1$-C$_6$)alkyl, —(C$_1$-C$_6$)alkyl(R$_6$)R$_7$, and —(C$_1$-C$_6$)alkyl(R$_8$)R$_9$, (C$_5$-C$_{10}$)cycloalkyl; and R$_{12}$ is halo, —OH or —NH$_2$;

with the proviso that when R$_1$ is

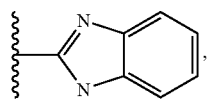

and R$_4$, and R$_5$ are each H, then R$_2$ is not

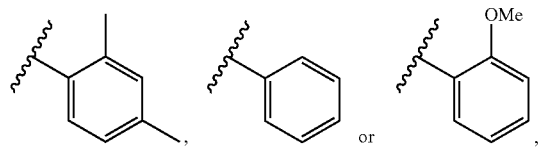

and R$_1$ and R$_2$ cannot both be

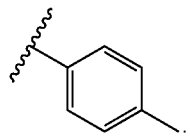

In another embodiment of Formula I, R$_1$ is selected from benzimidazole, indole, quinoline, dihydroquinoline, imidazole, piperazine, benzimidazole, pyridine, —CH$_2$-pyridine, and —CH$_2$-benzimidazole, wherein each benzimidazole, indole, quinoline, dihydroquinoline, imidazole, piperazine, benzothiazole, pyridine, —CH$_2$-pyridine, and —CH$_2$— benzimidazole is optionally substituted with 1, 2, or 3 substituents selected from halo, —(C$_3$-C$_{10}$)cycloalkyl, —(C$_1$-C$_6$)alkyl, —(C$_1$-C$_6$)alkoxy, -(4-10 membered)heterocycloalkyl, —O-(4-10 membered)heterocycloalkyl, —C(O)O(C$_1$-C$_6$)alkyl, —O—(C$_1$-C$_6$)alkyl-C(O)NR$_8$R$_9$, —O—(C$_1$-C$_6$)alkyl-C(O)O(C$_1$-C$_6$)alkyl, —O—(C$_1$-C$_6$)alkyl(4-10 membered)heterocycloalkyl-C(O)O—(C$_1$-C$_6$)alkyl, -(4-10 membered)heterocycloalkyl(C$_1$-C$_6$)alkyl, -(4-10 membered)heterocycloalkyl(C$_1$-C$_6$)alkyl(C$_6$-C$_{10}$)aryl, -(4-10 membered)heterocycloalkyl(C$_1$-C$_6$)alkyl(4-10 membered)heterocycloalkyl, -(4-10 membered)heterocycloalkyl(C$_1$-C$_6$)alkyl(5-10 membered)heteroaryl, —O—(C$_1$-C$_6$)alkyl-(4-10 membered)heterocycloalkyl, —O(C$_1$-C$_6$)alkyl-C(O)NH(C$_5$-C$_{10}$)cycloalkyl, —O(C$_1$-C$_6$)alkyl-C(O)NH(C$_1$-C$_6$)alkyl(R$_6$)(R$_7$), -(4-10 membered)heterocycloalkyl(C$_6$-C$_{10}$)aryl, —(C$_1$-C$_6$)alkyl-NH[(C$_1$-C$_6$)alkyl]$_2$, —O—(C$_1$-C$_6$)alkyl-NH[(C$_1$-C$_6$)alkyl]$_2$, -(4-10 membered)heterocycloalkyl(C$_1$-C$_6$)alkyl, —(C$_1$-C$_6$)alkoxy-NH[(C$_1$-C$_6$)alkyl]$_2$, —(C$_6$-C$_{10}$)aryl, —(C$_1$-C$_6$)alkoxy(C$_1$-C$_6$)alkoxy, -(4-10 membered)heterocycloalkyl-C(O)O—(C$_1$-C$_6$)alkyl, —(C$_1$-C$_6$)alkoxy (4-10 membered)heterocycloalkyl and —O—(C$_1$-C$_6$)alkyl-C(O)OH.

In another embodiment of Formula I, R$_2$ is selected from phenyl, —CH$_2$-phenyl, pyrazole, imidazole, naphthalene, piperidine, piperazine, —CH$_2$-cyclohexane, dihydroindole, and dihydroisoquinoline, wherein each phenyl, —CH$_2$-phenyl, pyrazole, imidazole, naphthalene, piperidine, piperazine, —CH$_2$-cyclohexane, dihydroindole, or dihydroisoquinoline is optionally substituted with 1, 2 or 3 substituents selected from —(C$_1$-C$_6$)alkyl, —(C$_1$-C$_6$)alkylhydroxy, -(4-10 membered)heterocycloalkyl(C$_6$-C$_{10}$)aryl, —(C$_1$-C$_6$)alkylthio, halo, —(C$_1$-C$_6$)alkoxy, cyano, membered)heterocycloalkyl, amino, —CF$_3$, —NHC(O)OC(CH$_3$)$_3$, —C(O)CH$_3$, —C(O)OCH$_3$, —O-(4-10 membered)heterocycloalkyl-C(O)OC(C$_1$-C$_6$)alkyl, -(4-10 membered)heterocycloalkyl-C(O)OC(C$_1$-C$_6$)alkyl, methylsulfonyl, —(C$_5$-C$_6$)cycloalkly(C$_1$-C$_3$)alkyl, —(C$_5$-C$_6$)cycloalkly(C$_1$-C$_3$)alkyl-amino(C$_1$-C$_3$)alkyl, —O—(C$_1$-C$_6$)alkyl, —NHC(O)-(4-10 membered)heterocycloalkyl, —(C$_1$-C$_6$)alkylamino(C$_1$-C$_6$)alkyl(C$_5$-C$_6$)cycloalkly, -(4-10 membered) heterocycloalkyl)C(O)NR$_7$R$_8$, —NH(C$_6$-C$_{10}$)aryl, —O-(4-10 membered)heterocycloalkyl (C$_1$-C$_6$)alkyl, —O-(4-10 membered)heterocycloalkylaryl, amino(C$_1$-C$_6$)alkyl, —OCF$_3$, —NHC(O)(4-10 membered) heterocycloalkylalkyl, dimethylaminoalkyl, —NH(C$_1$-C$_6$)alkyl), —O-heterocycloalkyl, —O-(4-10 membered)heterocycloalkyl(C$_6$-C$_{10}$)aryl, and —(C$_1$-C$_6$)alkoxyhydroxy.

In another embodiment of Formula I, R$_4$ and R$_5$ are each hydrogen.

In another embodiment of Formula I, R$_1$ is selected from benzimidazole, indole, quinoline, dihydroquinoline, imidazole, piperazine, benzimidazole, pyridine, —CH$_2$-pyridine, and —CH$_2$— benzimidazole, wherein each benzimidazole, indole, quinoline, dihydroquinoline, imidazole, piperazine, benzothiazole, pyridine, —CH$_2$-pyridine, and —CH$_2$— benzimidazole is optionally substituted with 1 or 2 substituents selected from halo, —(C$_3$-C$_{10}$)cycloalkyl, —(C$_1$-C$_6$)alkyl, —(C$_1$-C$_6$)alkoxy, -(4-10 membered)heterocycloalkyl, —O-(4-10 membered)heterocycloalkyl, —C(O)O(C$_1$-C$_6$)alkyl, —O—(C$_1$-C$_6$)alkyl-C(O)NR$_8$R$_9$, —O—(C$_1$-C$_6$)alkyl-C(O)O(C$_1$-C$_6$)alkyl, —O—(C$_1$-C$_6$)alkyl(4-10 membered) heterocycloalkyl-C(O)O—(C$_1$-C$_6$)alkyl, -(4-10 membered) heterocycloalkyl(C$_1$-C$_6$)alkyl, -(4-10 membered)heterocycloalkyl (C$_1$-C$_6$)alkyl(C$_6$-C$_{10}$)aryl, -(4-10 membered) heterocycloalkyl(C$_1$-C$_6$)alkyl(4-10 membered) heterocycloalkyl, -(4-10 membered)heterocycloalkyl(C$_1$-C$_6$) alkyl(5-10 membered)heteroaryl, —O—(C$_1$-C$_6$)alkyl-(4-10 membered)heterocycloalkyl, —O(C$_1$-C$_6$)alkyl-C(O)NH(C$_5$-C$_{10}$)cycloalkyl, —O(C$_1$-C$_6$)alkyl-C(O)NH(C$_1$-C$_6$)alkyl(R$_6$)(R$_7$), -(4-10 membered)heterocycloalkyl(C$_6$-C$_{10}$)aryl, —(C$_1$-C$_6$)alkyl-N[(C$_1$-C$_6$)alkyl]$_2$, —O—(C$_1$-C$_6$)alkyl N[(C$_1$-C$_6$)alkyl]$_2$, -(4-10 membered)heterocycloalkyl(C$_1$-C$_6$)alkyl, —(C$_1$-C$_6$)alkoxy-di[(C$_1$-C$_6$)alkyl]amino, —(C$_6$-C$_{10}$)aryl, —(C$_1$-C$_6$)alkoxy(C$_1$-C$_6$)alkoxy, -(4-10 membered) heterocycloalkyl-C(O)O—(C$_1$-C$_6$)alkyl, —(C$_1$-C$_6$)alkoxy (4-10 membered)heterocycloalkyl and —O—(C$_1$-C$_6$)alkyl-C(O)OH; and R$_2$ is selected from phenyl, —CH$_2$-phenyl, pyrazole, imidazole, naphthalene, piperidine, piperazine, —CH$_2$-cyclohexane, dihydroindole, and dihydroisoquinoline, wherein each phenyl, —CH$_2$-phenyl, pyrazole, imidazole, naphthalene, piperidine, piperazine, —CH$_2$-cyclohexane, dihydroindole, and dihydroisoquinoline is optionally substituted with 1, 2, 3, 4 or 5 substituents selected from —(C$_1$-C$_6$)alkyl, —(C$_1$-C$_6$)alkylhydroxy, -(4-10 membered)heterocycloalkyl (C$_6$-C$_{10}$)aryl, —(C$_1$-C$_6$)alkylthio, halo, —(C$_1$-C$_6$)alkoxy, cyano, membered)heterocycloalkyl, amino, —CF$_3$, —NHC(O)OC(CH$_3$)$_3$, —C(O)CH$_3$, —C(O)OCH$_3$, —O-(4-10 membered)heterocycloalkyl-C(O)O(C$_1$-C$_6$)alkyl, -(4-10 membered)heterocycloalkyl-C(O)O(C$_1$-C$_6$)alkyl, methylsulfonyl, —($C_5$-$C_6$)cycloalkly($C_1$-$C_3$)alkyl, —($C_5$-$C_6$)cycloalkly($C_1$-$C_3$)alkyl-NH($C_1$-$C_3$)alkyl, —O—($C_1$-$C_6$)alkyl, —NHC(O)-(4-10 membered)heterocycloalkyl, —($C_1$-$C_6$)alkyl-NH($C_1$-$C_6$)alkyl($C_5$-$C_6$)cycloalkly, -(4-10 membered)heterocycloalkylC(O)N$R_7R_8$, ($C_6$-$C_{10}$)aryl, —NH—($C_6$-$C_{10}$)aryl, —O-(4-10 membered)heterocycloalkyl($C_1$-$C_6$)alkyl, —O-(4-10 membered)heterocycloalkyl($C_5$-$C_6$)aryl, —NH($C_1$-$C_6$)alkyl, —OCF$_3$, —NHC(O)(4-10 membered)heterocycloalkylalkyl, —($C_1$-$C_6$)alkyl-N(CH$_3$)$_2$, —N[($C_1$-$C_6$)alkyl]$_2$, —NH($C_1$-$C_6$)alkyl), —O-(4-10 membered)heterocycloalkyl, —O-(4-10 membered)heterocycloalkyl($C_6$-$C_{10}$)aryl, and —($C_1$-$C_6$)alkoxyhydroxy.

In another embodiment of Formula I, $R_1$ is benzimidazole optionally substituted with 1 or 2 substituents selected from —($C_1$-$C_6$)alkoxy($C_1$-$C_6$)alkoxy, —O—($C_1$-$C_6$)alkyl(5-6 membered)heterocycloalkyl, —O—($C_1$-$C_6$)alkyl-C(O)NH($C_1$-$C_6$)alkyl-(five to six membered)heteroaryl, —O—($C_1$-$C_6$)alkyl-N[($C_1$-$C_6$)alkyl]$_2$, and piperazine optionally substituted with 1 or 2 groups selected from —($C_1$-$C_6$)alkyl, —C(O)O($C_1$-$C_6$)alkyl, —($C_1$-$C_6$)alkyl($C_5$-$C_6$)aryl, and ($C_1$-$C_6$)alkyl(5-6 membered)heterocycloalkyl.

In another embodiment of Formula I, $R_2$ is phenyl substituted with 1, 2 or 3 substituents selected from halo, methyl, methoxy, —O-piperidine, —O-piperazine, —O—($C_1$-$C_6$)alkyl-piperazine, and —O—($C_1$-$C_6$)alkylpiperidine.

In another embodiment of Formula I, $R_1$ is benzimidazole optionally substituted with 1 or 2 substituents selected from —($C_1$-$C_6$)alkoxy($C_1$-$C_6$)alkoxy, —O—($C_1$-$C_6$)alkyl(5-6 membered)heterocycloalkyl, —O—($C_1$-$C_6$)alkyl-C(O)NH($C_1$-$C_6$)alkyl-(5-6 membered)heteroaryl, —O—($C_1$-$C_6$)alkyl-N[($C_1$-$C_6$)alkyl]$_2$, and piperazine optionally substituted with 1 or 2 groups selected from —($C_1$-$C_6$)alkyl, —C(O)O($C_1$-$C_6$)alkyl, —($C_1$-$C_6$)alkyl($C_5$-$C_6$)aryl, and ($C_1$-$C_6$)alkyl(5-6 membered)heterocycloalkyl; and $R_2$ is phenyl substituted with 1, 2 or 3 substituents selected from halo, methyl, methoxy, —O-piperidine, —O-piperazine, —O—($C_1$-$C_6$)alkyl-piperazine, and —O—($C_1$-$C_6$)alkylpiperidine.

In another embodiment of Formula I, $R_2$ is a substituent selected from

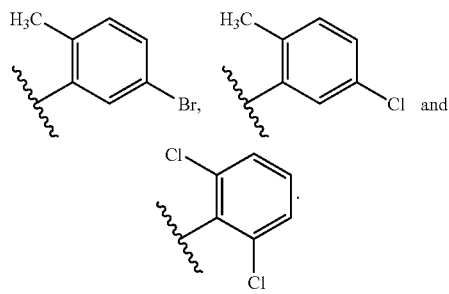

In another embodiment of Formula I, $R_2$ is

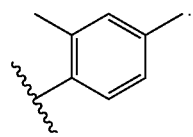

In another embodiment of Formula I, $R_2$ is

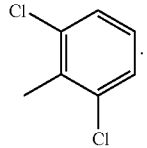

In another embodiment of Formula I, $R_2$ is phenyl substituted with 1, 2 or 3 substituents selected from halo, —($C_1$-$C_3$)alkyl, methoxy, —O-piperidine, —O-piperazine, —O—($C_1$-$C_6$)alkyl-piperazine, and —O—($C_1$-$C_6$)alkylpiperidine.

In another embodiment of Formula I, $R_2$ is phenyl substituted with 1, 2 or 3 substituents selected from halo, —($C_1$-$C_3$)alkyl.

In another embodiment of Formula I, $R_1$ is benzimidazole optionally substituted with 1 or 2 substituents selected from —($C_1$-$C_6$)alkoxy($C_1$-$C_6$)alkoxy, —O—($C_1$-$C_6$)alkyl(5-6 membered)heterocycloalkyl, —O—($C_1$-$C_6$)alkyl-C(O)NH($C_1$-$C_6$)alkyl-(5-6 membered)heteroaryl, —O—($C_1$-$C_6$)alkyl-N[($C_1$-$C_6$)alkyl]$_2$, and piperazine optionally substituted with 1 or 2 groups selected from —($C_1$-$C_6$)alkyl, —C(O)O($C_1$-$C_6$)alkyl, —($C_1$-$C_6$)alkyl($C_5$-$C_6$)aryl, or ($C_1$-$C_6$)alkyl(5-6 membered)heterocycloalkyl; $R_2$ is phenyl substituted with 1, 2 or 3 substituents selected from halo, —($C_1$-$C_3$)alkyl, methoxy, —O-piperidine, —O-piperizine, —O—($C_1$-$C_6$)alkyl-piperazine, and —O—($C_1$-$C_6$)alkylpiperidine;
$R_4$ is H; and
$R_5$ is H.

In another embodiment of Formula I, $R_1$ is benzimidazole optionally substituted with 1 or 2 substituents selected from —($C_1$-$C_6$)alkoxy($C_1$-$C_6$)alkoxy, —O—($C_1$-$C_6$)alkyl(5-6 membered)heterocycloalkyl, —O—($C_1$-$C_6$)alkyl-C(O)NH($C_1$-$C_6$)alkyl-(5-6 membered)heteroaryl, —O—($C_1$-$C_6$)alkyl-N[($C_1$-$C_6$)alkyl]$_2$, and piperazine optionally substituted with 1 or 2 groups selected from —($C_1$-$C_6$)alkyl, —C(O)O($C_1$-$C_6$)alkyl, —($C_1$-$C_6$)alkyl($C_5$-$C_6$)aryl, or ($C_1$-$C_6$)alkyl(5-6 membered)heterocycloalkyl; $R_2$ is phenyl substituted with 1, 2 or 3 substituents selected from halo, —($C_1$-$C_3$)alkyl and methoxy;
$R_4$ is H; and
$R_5$ is H.

In another embodiment of Formula I, $R_1$ is benzimidazole, optionally substituted with 1 or 2 substituents selected from —($C_1$-$C_6$)alkoxy($C_1$-$C_6$)alkoxy, —O—($C_1$-$C_6$)alkyl(5-6 membered)heterocycloalkyl, —O—($C_1$-$C_6$)alkyl-C(O)NH($C_1$-$C_6$)alkyl-(5-6 membered)heteroaryl, —O—($C_1$-$C_6$)alkyl-N[($C_1$-$C_6$)alkyl]$_2$, and piperazine optionally substituted with 1 or 2 groups selected from —($C_1$-$C_6$)alkyl, —C(O)O($C_1$-$C_6$)alkyl, —($C_1$-$C_6$)alkyl($C_5$-$C_6$)aryl, or ($C_1$-$C_6$)alkyl(5-6 membered)heterocycloalkyl; $R_2$ is phenyl substituted with 1, 2 or 3 substituents selected from halo, —($C_1$-$C_3$)alkyl, methoxy, —O-piperidine, —O-piperazine, —O—($C_1$-$C_6$)alkyl-piperazine, and —O—($C_1$-$C_6$)alkylpiperidine;
$R_4$ is H; and
$R_5$ is H.

In another embodiment of Formula I, $R_1$ is benzimidazole, optionally substituted with 1 or 2 substituents selected from —($C_1$-$C_6$)alkoxy($C_1$-$C_6$)alkoxy, —O—($C_1$-$C_6$)alkyl(5-6 membered)heterocycloalkyl, —O—($C_1$-$C_6$)alkyl-C(O)NH($C_1$-$C_6$)alkyl-(5-6 membered)heteroaryl, —O—($C_1$-$C_6$)alkyl-N[($C_1$-$C_6$)alkyl]$_2$, and piperazine optionally substituted with 1 or 2 groups selected from —($C_1$-$C_6$)alkyl, —C(O)O($C_1$-$C_6$)alkyl, —($C_1$-$C_6$)alkyl($C_5$-$C_6$)aryl, or ($C_1$-

$C_6$)alkyl(5-6 membered)heterocycloalkyl; $R_2$ is phenyl substituted with 1, 2 or 3 substituents selected from halo, —($C_1$-$C_3$)alkyl and methoxy;

$R_4$ is H; and
$R_5$ is H.

In another embodiment of Formula I, $R_1$ is benzimidazole, optionally substituted with 1 or 2 substituents selected from —($C_1$-$C_6$)alkoxy($C_1$-$C_6$)alkoxy, —O—($C_1$-$C_6$)alkyl(5-6 membered)heterocycloalkyl, —O—($C_1$-$C_6$)alkyl-C(O)NH($C_1$-$C_6$)alkyl-(5-6 membered)heteroaryl, —O—($C_1$-$C_6$)alkyl-N[($C_1$-$C_6$)alkyl]$_2$, and piperazine optionally substituted with 1 or 2 groups selected from —($C_1$-$C_6$)alkyl, —C(O)O($C_1$-$C_6$)alkyl, —($C_1$-$C_6$)alkyl($C_5$-$C_6$)aryl, or ($C_1$-$C_6$)alkyl(5-6 membered)heterocycloalkyl; $R_2$ is phenyl substituted with 1, 2 or 3 substituents selected from —O-piperidine, —O-piperazine, —O—($C_1$-$C_6$)alkyl-piperazine, and —O—($C_1$-$C_6$)alkylpiperidine;

$R_4$ is H; and
$R_5$ is H.

In another embodiment of Formula I, $R_2$ is phenyl substituted with 1, 2 or 3 substituents selected from halo, —($C_1$-$C_3$)alkyl and methoxy, —O-piperidine, —O— piperazine, —O—($C_1$-$C_6$)alkyl-piperazine, and —O—($C_1$-$C_6$)alkylpiperidine;

$R_4$ is H; and
$R_5$ is H.

In another embodiment of Formula I, $R_1$ is benzimidazole, indole, quinoline, dihydroquinoline, imidazole, piperazine, benzothiazole, pyridine, —$CH_2$-pyridine, —$CH_2$-benzimidazole, wherein each benzimidazole, indole, quinoline, dihydroquinoline, imidazole, piperazine, benzothiazole, pyridine, —$CH_2$-pyridine, or —$CH_2$— benzimidazole is substituted with 1 or 2 substituents selected from -(5-10 membered) heteroaryl, —($C_1$-$C_6$)alkyl(5-10 membered)heteroaryl, —($C_6$-$C_{10}$)aryl and -(4-10 membered)heterocycloalkyl is optionally substituted with 1, 2, 3, 4, or 5 substituents selected from halo, —($C_3$-$C_{10}$)cycloalkyl, —($C_1$-$C_6$)alkyl, —($C_1$-$C_6$)alkoxy, -(4-10 membered)heterocycloalkyl, —O-(4-10 membered)heterocycloalkyl, —O-(4-10 membered)heterocycloalkyl-$R_{10}$, —C(O)O($C_1$-$C_6$)alkyl, —O—($C_1$-$C_6$)alkyl-C(O)$NR_8R_{11}$, —O—($C_1$-$C_6$)alkyl-C(O)$OR_8$, —O—($C_1$-$C_6$)alkyl(5-10 membered)heteroaryl, —O—($C_1$-$C_6$)alkyl(4-10 membered)heterocycloalkyl-C(O)O—($C_1$-$C_6$)alkyl, -(4-10 membered) heterocycloalkyl($C_1$-$C_6$)alkyl, -(4-10 membered)heterocycloalkyl($C_1$-$C_6$)alkyl($C_6$-$C_{10}$)aryl, -(4-10 membered)heterocycloalkyl($C_1$-$C_6$)alkyl(4-10 membered)heterocycloalkyl, -(4-10 membered)heterocycloalkyl($C_1$-$C_6$)alkyl(5-10 membered)heteroaryl, —O—($C_1$-$C_6$)alkyl-(4-10 membered)heterocycloalkyl, —O—($C_1$-$C_6$)alkyl-(4-10 membered)heterocycloalkyl-$R_{10}$, —O($C_1$-$C_6$)alkyl-C(O)NH($C_5$-$C_{10}$)cycloalkyl, -(4-10 membered)heterocycloalkyl($C_6$-$C_{10}$)aryl, —($C_1$-$C_6$)alkyl-N[($C_1$-$C_6$)alkyl]$_2$, —O—($C_1$-$C_6$)alkylN[($C_1$-$C_6$)alkyl]$_2$, -(4-10 membered)heterocycloalkyl($C_1$-$C_6$)alkyl, ($C_1$-$C_6$)alkoxy-di[($C_1$-$C_6$)alkyl]amino, —($C_6$-$C_{10}$)aryl, —($C_1$-$C_6$)alkoxy($C_1$-$C_6$)alkoxy, -(4-10 membered)heterocycloalkyl-C(O)O—($C_1$-$C_6$)alkyl, —ON(H)C(O)NH($C_1$-$C_6$)alkyl($C_6$-$C_{10}$)aryl, -(4-10 membered)heterocycloalkyl($C_1$-$C_6$)alkyl-O—($C_1$-$C_6$)alkyl-($C_6$-$C_{10}$)aryl, and —($C_1$-$C_6$)alkoxy(4-10 membered)heterocycloalkyl, wherein the aryl, heteroaryl, cycloalkyl or heterocycloalkyl portion of any of the above optional substituents can be further substituted by —($C_1$-$C_6$) alkyl;

$R_2$ is phenyl substituted with 1, 2 or 3 substituents selected from halo, —($C_1$-$C_3$)alkyl and methoxy, —O-piperidine, —O-piperazine, —O—($C_1$-$C_6$)alkyl-piperazine, and —O—($C_1$-$C_6$)alkylpiperidine;

$R_4$ is H; and
$R_5$ is H.

In another embodiment of Formula I, $R_1$ is benzimidazole, wherein benzimidazole is substituted by 1 or 2 of any of the substituents for benzimidazole described above.

In another embodiment of Formula I, $R_1$ is a substituted benzimidazole, indole, quinoline, dihydroquinoline, imidazole, piperazine, benzothiazole, pyridine, —$CH_2$-pyridine, —$CH_2$— benzimidazole, wherein each benzimidazole, indole, quinoline, dihydroquinoline, imidazole, piperazine, benzothiazole, pyridine, —$CH_2$-pyridine, or —$CH_2$-benzimidazole is substituted with 1 or 2 substituents selected from -(5-10 membered)heteroaryl, —($C_1$-$C_6$)alkyl(5-10 membered)heteroaryl, —($C_6$-$C_{10}$)aryl and -(4-10 membered)heterocycloalkyl is optionally substituted with 1, 2, 3, 4, or 5 substituents selected from halo, —($C_3$-$C_{10}$)cycloalkyl, —($C_1$-$C_6$)alkoxy, -(4-10 membered)heterocycloalkyl, —O-(4-10 membered)heterocycloalkyl, —O-(4-10 membered)heterocycloalkyl-$R_{10}$, —C(O)O($C_1$-$C_6$)alkyl, —O—($C_1$-$C_6$)alkyl-C(O)$NR_8R_{11}$, —O—($C_1$-$C_6$)alkyl-C(O)$OR_8$, —O—($C_1$-$C_6$)alkyl(5-10 membered)heteroaryl, —O—($C_1$-$C_6$)alkyl(4-membered)heterocycloalkyl-C(O)O—($C_1$-$C_6$)alkyl, -(4-10 membered) heterocycloalkyl($C_1$-$C_6$)alkyl, -(4-10 membered)heterocycloalkyl($C_1$-$C_6$)alkyl($C_6$-$C_{10}$)aryl, -(4-10 membered)heterocycloalkyl($C_1$-$C_6$)alkyl (4-10 membered)heterocycloalkyl, -(4-10 membered)heterocycloalkyl ($C_1$-$C_6$)alkyl(5-10 membered)heteroaryl, —O—($C_1$-$C_6$)alkyl-(4-10 membered)heterocycloalkyl, —O—($C_1$-$C_6$)alkyl-(4-10 membered)heterocycloalkyl-$R_{10}$, —O($C_1$-$C_6$)alkyl-C(O)NH($C_5$-$C_{10}$)cycloalkyl, -(4-10 membered) heterocycloalkyl($C_6$-$C_{10}$)aryl, —($C_1$-$C_6$)alkyl-N[($C_1$-$C_6$)alkyl]$_2$, —O—($C_1$-$C_6$)alkylN[($C_1$-$C_6$)alkyl]$_2$, -(4-10 membered)heterocycloalkyl($C_1$-$C_6$)alkyl, ($C_1$-$C_6$)alkoxy-di[($C_1$-$C_6$)alkyl]amino, —($C_6$-$C_{10}$)aryl, —($C_1$-$C_6$)alkoxy($C_1$-$C_6$)alkoxy, -(4-10 membered)heterocycloalkyl-C(O)O—($C_1$-$C_6$)alkyl, —ON(H)C(O)NH($C_1$-$C_6$)alkyl($C_6$-$C_{10}$)aryl, -(4-10 membered)heterocycloalkyl($C_1$-$C_6$)alkyl-O—($C_1$-$C_6$)alkyl-($C_6$-$C_{10}$)aryl, and —($C_1$-$C_6$)alkoxy(4-10 membered)heterocycloalkyl, wherein the aryl, heteroaryl, cycloalkyl or heterocycloalkyl portion of any of the above substituents can be further substituted by —($C_1$-$C_6$) alkyl.

In another embodiment of Formula I, $R_2$ is a substituted or unsubstituted phenyl, pyrazole, imidazole, naphthalene, piperidine, piperazine, —$CH_2$-cyclohexane, dihydroindole, or dihydroisoquinoline, wherein each phenyl, pyrazole, imidazole, naphthalene, piperidine, piperazine, —$CH_2$-cyclohexane, dihydroindole, or dihydroisoquinoline, wherein the substituents can be any one of the substituents described herein for $R_1$.

In another embodiment of Formula I, $R_1$ is benzimidazole, pyrazole or imidazole optionally substituted with 1 or 2 substituents selected from —($C_1$-$C_6$)alkoxy($C_1$-$C_6$)alkoxy, —O—($C_1$-$C_6$)alkyl(5-6 membered)heterocycloalkyl, —O—($C_1$-$C_6$)alkyl-C(O)NH($C_1$-$C_6$)alkyl-(5-6 membered)heteroaryl, —O—($C_1$-$C_6$)alkyl-N[($C_1$-$C_6$)alkyl]$_2$, and piperazine optionally substituted with 1 or 2 groups selected from —($C_1$-$C_6$)alkyl, —C(O)O($C_1$-$C_6$)alkyl, —($C_1$-$C_6$)alkyl($C_5$-$C_6$)aryl, or ($C_1$-$C_6$)alkyl(5-6 membered)heterocycloalkyl; and $R_2$ is a substituent selected from

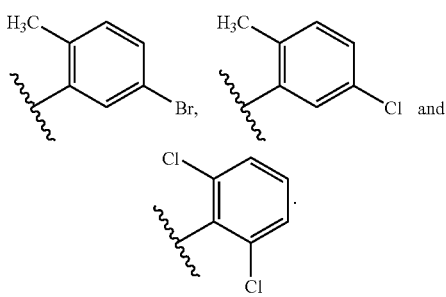

In another embodiment of Formula I, $R_1$ is

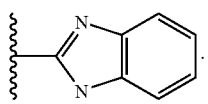

In another embodiment of Formula I, $R_1$ is

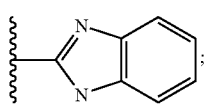

$R_2$ is phenyl substituted with 1, 2 or 3 substituents selected from halo, —$(C_1$-$C_3)$alkyl and methoxy, —O-piperidine, —O-piperazine, —O—$(C_1$-$C_6)$alkyl-piperazine, and —O—$(C_1$-$C_6)$alkylpiperidine;

$R_4$ is H; and $R_5$ is H.

Another aspect of the invention relates to pharmaceutical compositions comprising a compound of Formula I and a pharmaceutically acceptable carrier, excipient, or diluent.

Another aspect of the invention relates to a method for treating a disease, disorder, or syndrome mediated, at least in part, by inhibiting JAK-2, which method comprises administering to a patient in need of said treatment a therapeutically effective amount of a compound of Formula I, or a pharmaceutically acceptable salt or solvate thereof.

Another aspect of the invention relates to a method for treating a disease, disorder, or syndrome mediated, at least in part, by inhibiting JAK-2, which method comprises administering to an patient in need of said treatment a pharmaceutical composition comprising a therapeutically effective amount of a compound of Formula I, or a pharmaceutically acceptable salt or solvate thereof.

The disease being treated in these aspects of the invention can be a myeloproliferative disorder, cancer, cardiovascular disease, and/or hematopoietic abnormality where hyperactivation of JAK-STAT signaling is present. Nonlimiting examples of myeloproliferative disorders that are contemplated as being treatable by the compounds of the invention include myelofibrosis, thrombocythemia, polycythemia vera (PV), essential thrombocythemia (ET), agnogenic myeloid metaplasia (AMM), also referred to as idiopathic myelofibrosis (IMF), and chronic myelogenous leukemia (CML). Nonlimiting examples of cancers that are contemplated as being treatable by the compounds of the invention include leukemias, lymphomas, multiple myeoloma, prostate cancers, lung cancers, breast cancers, and ovarian cancers. Nonlimiting examples of cardiovascular diseases that are contemplated as being treatable by the compounds of the invention include congestive heart failure and hypertension. Nonlimiting examples of hematopoitic abnormalities that are contemplated as being treatable by the compounds of the invention include thrombocytosis.

In another embodiment, the disease or condition being treated by the compound of Formula I is cancer or a myeloproliferative disorder.

In another embodiment, the disease or condition being treated by the compound of Formula I is cancer such as ovarian cancer, cervical cancer, breast cancer, colorectal cancer, glioblastoma, prostrate cancer, colon cancer, melanoma, leukemia or haematopoietic malignancies.

In another embodiment, the disease or condition being treated by the pharmaceutical composition of Formula I is cancer or a myeloproliferative disorder.

In another embodiment, the disease or condition being treated by the pharmaceutical composition of Formula I cancer, such as ovarian cancer, cervical cancer, breast cancer, colorectal cancer, glioblastoma, prostrate cancer, colon cancer, melanoma, leukemia or haematopoietic malignancies.

Another aspect of the invention relates to a method of treating a disease, disorder, or syndrome mediated, at least in part, by inhibiting JAK-2, which method comprises administering to an patient a compound of Formula I, or a pharmaceutically acceptable salt thereof, in combination with one or more treatment(s) selected from surgery, one or more therapeutic agent(s), plateletpheresis, and radiation.

Another aspect of the invention relates to a method of treating a disease, disorder, or syndrome mediated, at least in part, by inhibiting JAK-2, which method comprises administering to an patient a pharmaceutical composition comprising a therapeutically effective amount of a compound of Formula I or a pharmaceutically acceptable salt thereof, in combination with one or more treatment(s) selected from surgery, one or more therapeutic agent(s), plateletpheresis, and radiation.

Another aspect of the invention relates to a method of inhibiting JAK-2 in a cell, comprising contacting a cell in which inhibition of JAK-2 is desired with a compound according to Formula I.

Another aspect of the invention relates to a method comprising contacting a cell in which inhibition of JAK-2 is desired with a pharmaceutical composition comprising a compound according to Formula I and a pharmaceutically acceptable carrier, excipient, or diluent.

When treating myeloproliferative disorders, the compound of Formula I can also be administered with one or more additional treatment(s) selected from plateletpheresis and one or more therapeutic agent(s) selected from interferon-α; aspirin; a platelet-decreasing drug, such as anagrelide; and a myelsuppressive agent (such as a radiophosphorus and alkylating agents). Non-limiting examples of the myelsuppressive agent include hydroxyurea, melphalan, and busulfan.

When treating cancer, the compound of Formula I can be administered in combination with one or more chemotherapeutic agent(s) selected from fludaribine, vinblastine, adriamycin and cisplatin.

Table 1 illustrates some examples of the compounds of the invention. The examples in Table 1 merely illustrate some embodiments of the invention, and do not limit the scope of the invention in any way.

TABLE 1

| Cpd No. | Structure | Name |
|---|---|---|
| 1 | 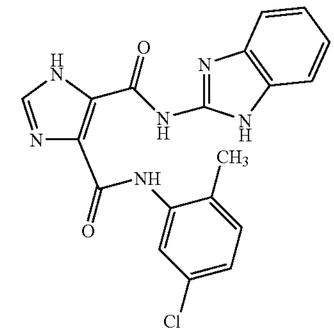 | N⁵-1H-benzimidazol-2-yl-N⁴-(5-chloro-2-methylphenyl)-1H-imidazole-4,5-dicarboxamide |
| 2 | 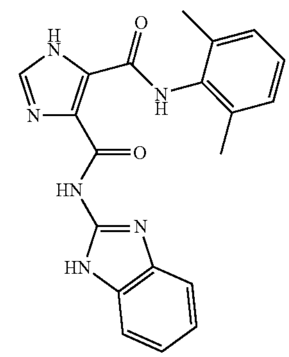 | N⁴-1H-benzimidazol-2-yl-N⁵-(2,6-dimethylphenyl)-1H-imidazole-4,5-dicarboxamide |
| 3 | 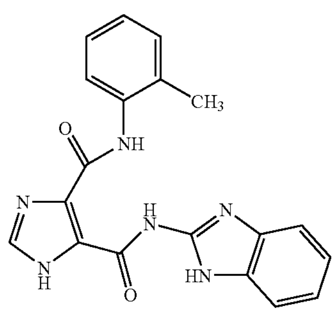 | N⁵-1H-benzimidazol-2-yl-N⁴-(2-methylphenyl)-1H-imidazol-4,5-dicarboxamide |
| 4 | 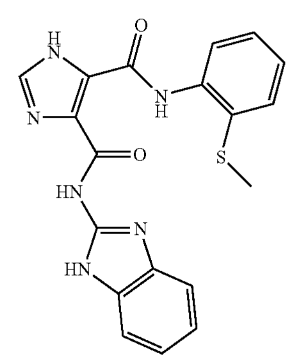 | N⁴-1H-benzimidazol-2-yl-N⁵-[2-(methylthio)phenyl]-1H-imidazole-4,5-dicarboxamide |

TABLE 1-continued

| Cpd No. | Structure | Name |
|---|---|---|
| 5 | 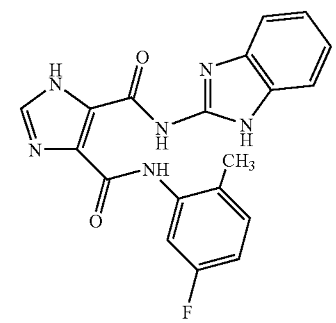 | $N^5$-1H-benzimidazol-2-yl-$N^4$-(5-fluoro-2-methylphenyl)-1H-imidazole-4,5-dicarboxamide |
| 6 | 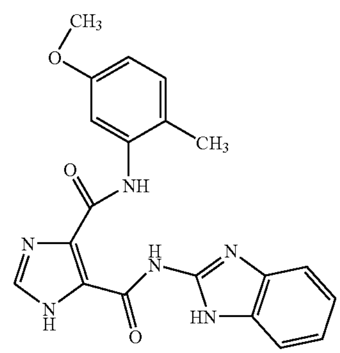 | $N^5$-1H-benzimidazol-2-yl-$N^4$-[2-methyl-5-(methyloxy)phenyl]-1H-imidazole-4,5-dicarboxamide |
| 7 | 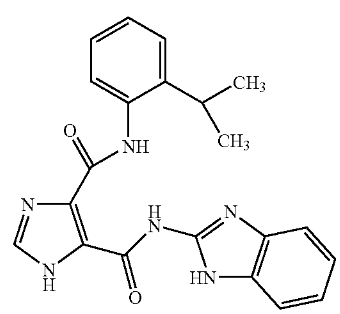 | $N^5$-1H-benzimidazol-2-yl-$N^4$-[2-(1-methylethyl)phenyl]-1H-imidazole-4,5-dicarboxamide |
| 8 | 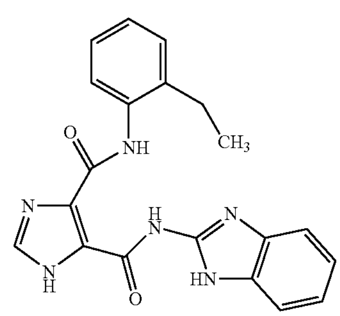 | $N^5$-1H-benzimidazol-2-yl-$N^4$-(2-ethylphenyl)-1H-imidazole-4,5-dicarboxamide |

TABLE 1-continued

| Cpd No. | Structure | Name |
| --- | --- | --- |
| 9 | 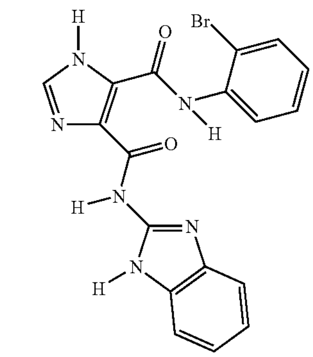 | $N^4$-1H-benzimidazol-2-yl-$N^5$-(2-bromophenyl)-1H-imidazole-4,5-dicarboxamide |
| 10 | 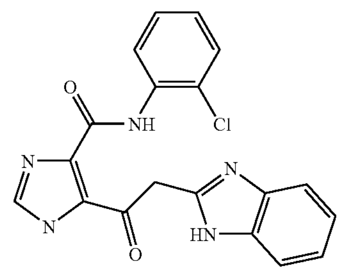 | $N^5$-1H-benzimidazol-2-yl-$N^4$-(2-chlorophenyl)-1H-imidazole-4,5-dicarboxamide |
| 11 | 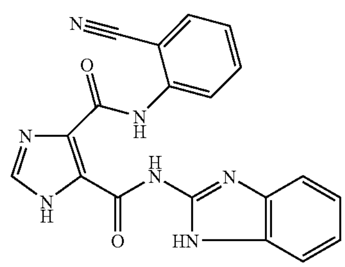 | $N^5$-1H-benzimidazol-2-yl-$N^4$-(2-cyanophenyl)-1H-imidazole-4,5-dicarboxamide |
| 12 | 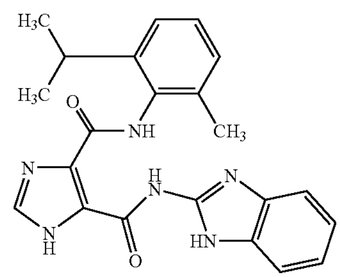 | $N^5$-1H-benzimidazol-2-yl-$N^4$-[2-methyl-6-(1-methylethyl)phenyl]-1H-imidazole-4,5-dicarboxamide |
| 13 | 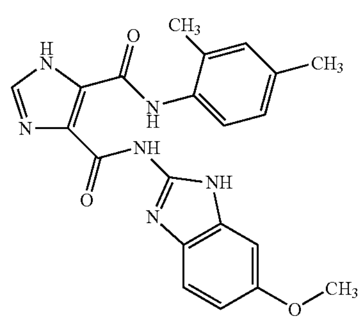 | $N^5$-(2,4-dimethylphenyl)-$N^4$-[6-(methyloxy)-1H-benzimidazol-2-yl]-1H-imidazole-4,5-dicarboxamide |

TABLE 1-continued

| Cpd No. | Structure | Name |
|---|---|---|
| 14 | 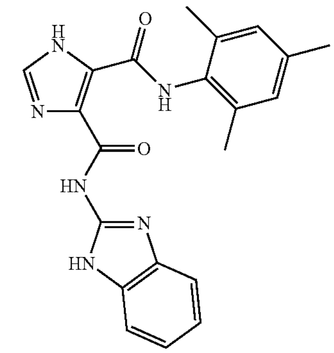 | $N^4$-1H-benzimidazol-2-yl-$N^5$-(2,4,6-trimethylphenyl)-1H-imidazole-4,5-dicarboxamide |
| 15 | 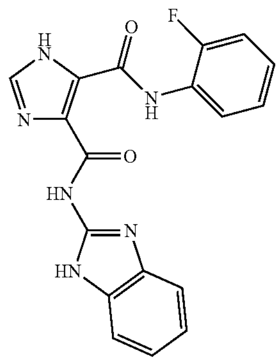 | $N^4$-1H-benzimidazol-2-yl-$N^5$-(2-fluorophenyl)-1H-imidazole-4,5-dicarboxamide |
| 16 | 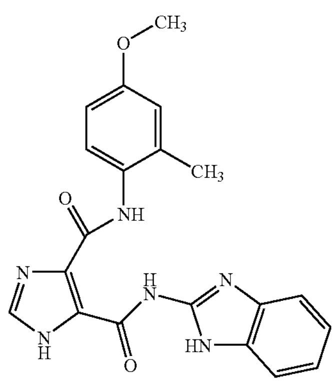 | $N^5$-1H-benzimidazol-2-yl-$N^4$-[2-methyl-4-(methyloxy)phenyl]-1H-imidazole-4,5-dicarboxamide |
| 17 | 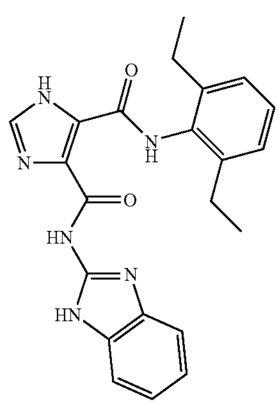 | $N^4$-1H-benzimidazol-2-yl-$N^5$-(2,6-diethylphenyl)-1H-imidazole-4,5-dicarboxamide |

TABLE 1-continued

| Cpd No. | Structure | Name |
|---|---|---|
| 18 | 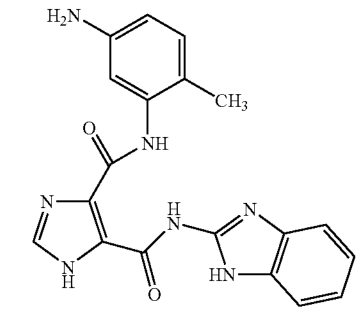 | $N^4$-(5-amino-2-methylphenyl)-$N^5$-1H-benzimidazol-2-yl-1H-imidazole-4,5-dicarboxamide |
| 19 | 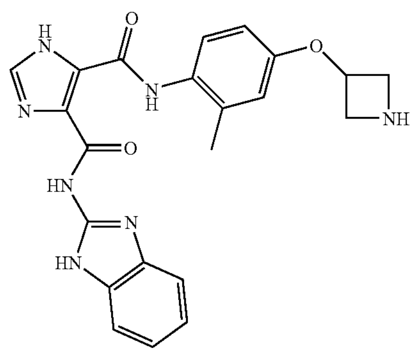 | $N^5$-[4-(azetidin-3-yloxy)-2-methylphenyl]-$N^4$-1H-benzimidazol-2-yl-1H-imidazole-4,5-dicarboxamide |
| 20 | 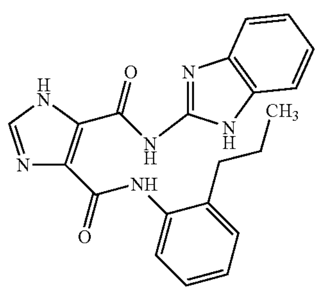 | $N^5$-1H-benzimidazol-2-yl-$N^4$-(2-propylphenyl)-1H-imidazole-4,5-dicarboxamide |
| 21 | 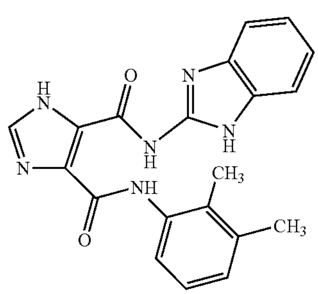 | $N^5$-1H-benzimidazol-2-yl-$N^4$-(2,3-dimethylphenyl)-1H-imidazole-4,5-dicarboxamide |
| 22 | 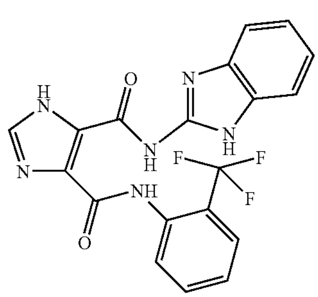 | $N^5$-1H-benzimidazol-2-yl-$N^4$-[2-(trifluoromethyl)phenyl]-1H-imidazole-4,5-dicarboxamide |

TABLE 1-continued

| Cpd No. | Structure | Name |
|---|---|---|
| 23 | 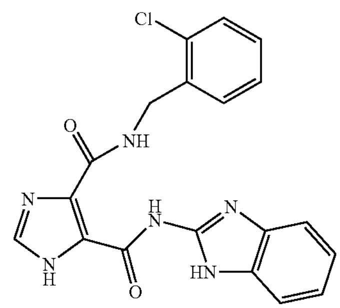 | $N^5$-1H-benzimidazol-2-yl-$N^4$-[(2-chlorophenyl)methyl]-1H-imidazole-4,5-dicarboxamide |
| 24 | 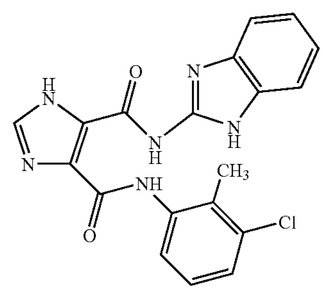 | $N^5$-1H-benzimidazol-2-yl-$N^4$-(3-chloro-2-methylphenyl)-1H-imidazole-4,5-dicarboxamide |
| 25 | 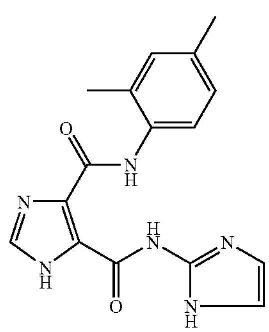 | $N^4$-(2,4-dimethylphenyl)-$N^5$-1H-imidazol-2-yl-1H-imidazole-4,5-dicarboxamide |
| 26 | 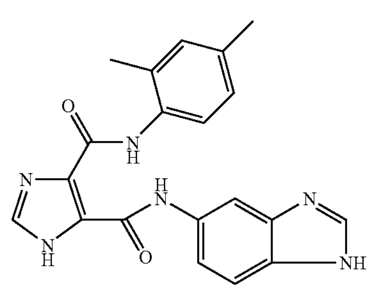 | $N^5$-1H-benzimidazol-5-yl-$N^4$-(2,4-dimethylphenyl)-1H-imidazole-4,5-dicarboxamide |
| 27 | 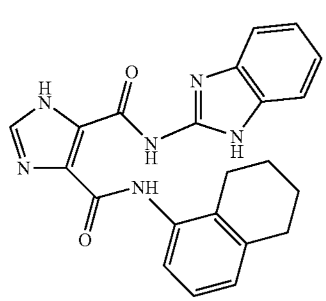 | $N^5$-1H-benzimidazol-2-yl-$N^4$-(5,6,7,8-tetrahydronaphthalen-1-yl)-1H-imidazole-4,5-dicarboxamide |

TABLE 1-continued

| Cpd No. | Structure | Name |
|---|---|---|
| 28 | 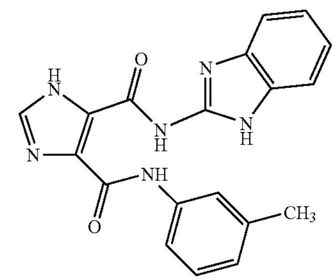 | $N^5$-1H-benzimidazol-2-yl-$N^4$-(3-methylphenyl)-1H-imidazole-4,5-dicarboxamide |
| 29 | 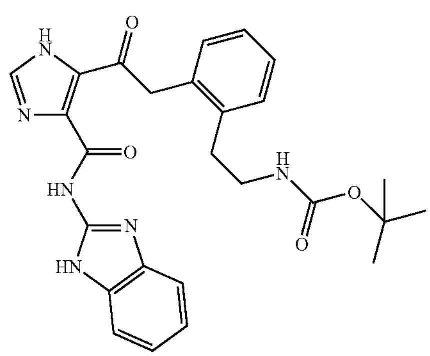 | 1,1-dimethylethyl(2-{2-[({4-[(1H-benzimidazol-2-ylamino)carbonyl]-1H-imidazol-5-yl}carbonyl)amino]phenyl}ethyl)carbamate |
| 30 | 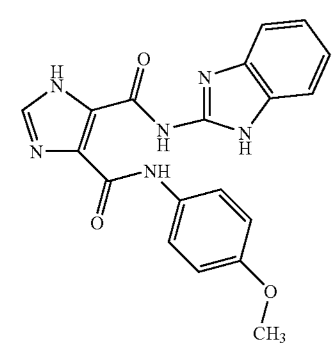 | $N^5$-1H-benzimidazol-2-yl-$N^4$-[4-(methyloxy)phenyl]-1H-imidazole-4,5-dicarboxamide |
| 31 | 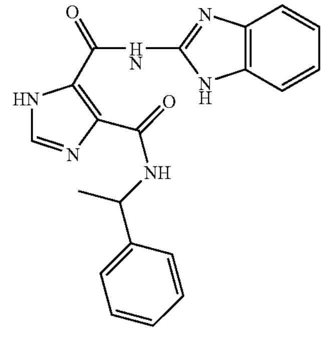 | $N^5$-1H-benzimidazol-2-yl-$N^4$-(1-phenylethyl)-1H-imidazole-4,5-dicarboxamide |

TABLE 1-continued

| Cpd No. | Structure | Name |
|---|---|---|
| 32 | 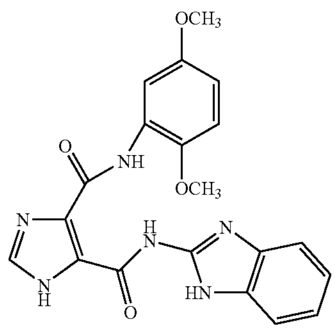 | $N^5$-1H-benzimidazol-2-yl-$N^4$-[2,5-bis(methyloxy)phenyl]-1H-imidazole-4,5-dicarboxamide |
| 33 | 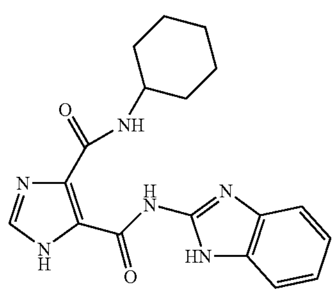 | $N^5$-1H-benzimidazol-2-yl-$N^4$-cyclohexyl-1H-imidazole-4,5-dicarboxamide |
| 34 | 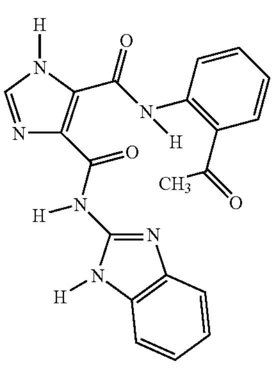 | $N^5$-(2-acetylphenyl)-$N^4$-1H-benzimidazol-2-yl-1H-imidazole-4,5-dicarboxamide |
| 35 | 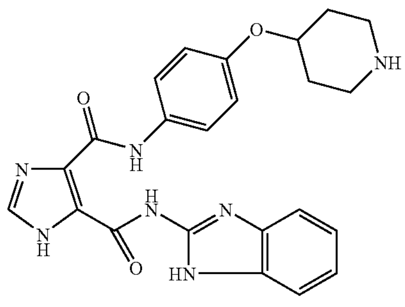 | $N^5$-1H-benzimidazol-2-yl-$N^4$-[4-(piperidin-4-yloxy)phenyl]-1H-imidazole-4,5-dicarboxamide |

TABLE 1-continued

| Cpd No. | Structure | Name |
|---|---|---|
| 36 | 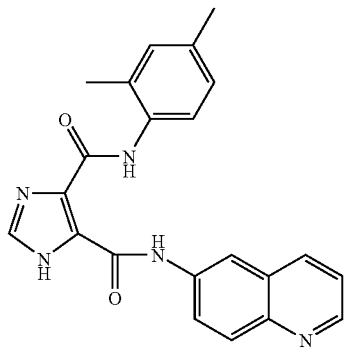 | $N^4$-(2,4-dimethylphenyl)-$N^5$-quinolin-6-yl-1H-imidazole-4,5-dicarboxamide |
| 37 | 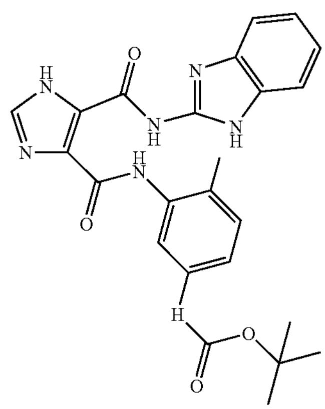 | 1,1-dimethylethyl{3-[({5-[({1H-benzimidazol-2-ylamino)carbonyl]-1H-imidazol-4-yl}carbonyl)amino]-4-methylphenyl}carbamate |
| 38 | 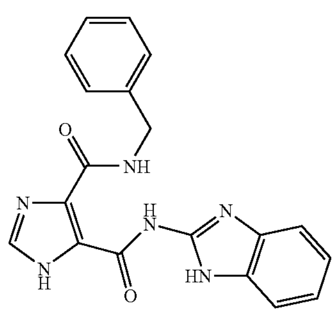 | $N^5$-1H-benzimidazol-2-yl-$N^4$-(phenylmethyl)-1H-imidazole-4,5-dicarboxamide |
| 39 | 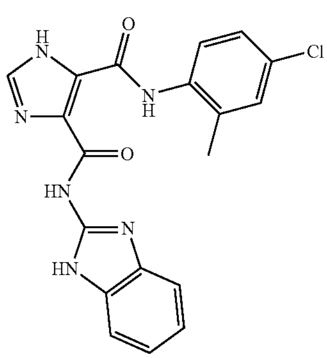 | $N^4$-1H-benzimidazol-2-yl-$N^5$-(4-chloro-2-methylphenyl)-1H-imidazole-4,5-dicarboxamide |

TABLE 1-continued

| Cpd No. | Structure | Name |
| --- | --- | --- |
| 40 | 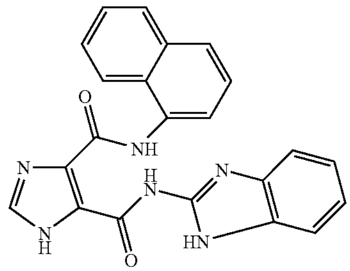 | $N^5$-1H-benzimidazol-2-yl-$N^4$-naphthalen-1-yl-1H-imidazole-4,5-dicarboxamide |
| 41 | 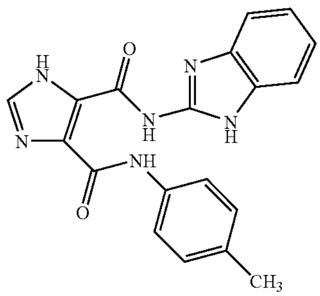 | $N^5$-1H-benzimidazol-2-yl-$N^4$-(4-methylphenyl)-1H-imidazole-4,5-dicarboxamide |
| 42 | 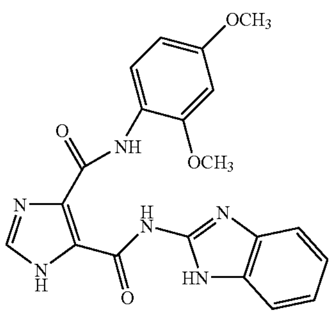 | $N^5$-1H-benzimidazol-2-yl-$N^4$-[2,4-bis(methyloxy)phenyl]-1H-imidazole-4,5-dicarboxamide |
| 43 | 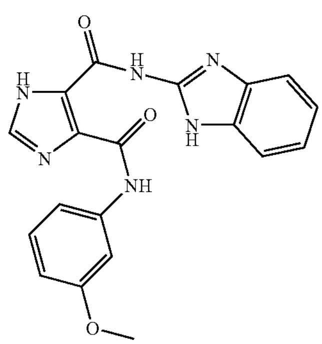 | $N^5$-1H-benzimidazol-2-yl-$N^4$-[3-(methyloxy)phenyl]-1H-imidazole-4,5-dicarboxamide |
| 44 | 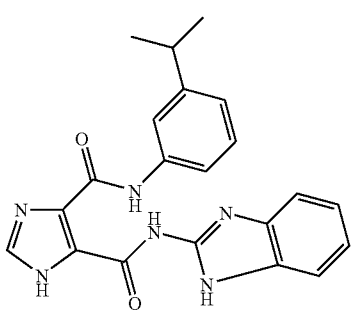 | $N^5$-1H-benzimidazol-2-yl-$N^4$-[3-(1-methylethyl)phenyl]-1H-imidazole-4,5-dicarboxamide |

TABLE 1-continued

| Cpd No. | Structure | Name |
|---|---|---|
| 45 | 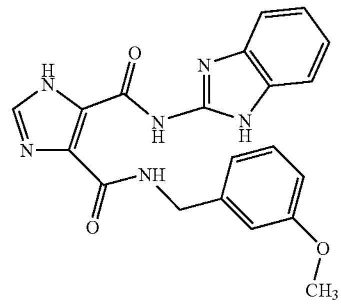 | $N^5$-1H-benzimidazol-2-yl-$N^4$-{[3-(methyloxy)phenyl]methyl}-1H-imidazole-4,5-dicarboxamide |
| 46 | 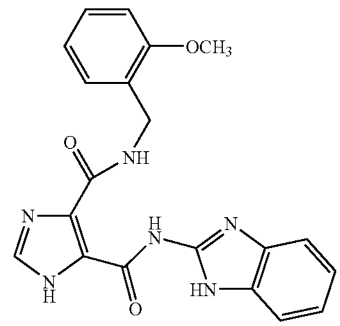 | $N^5$-1H-benzimidazol-2-yl-$N^4$-{[2-(methyloxy)phenyl]methyl}-1H-imidazole-4,5-dicarboxamide |
| 47 | 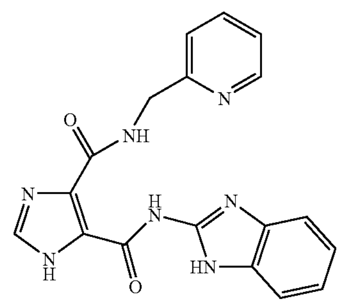 | $N^5$-1H-benzimidazol-2-yl-$N^4$-(pyridin-2-ylmethyl)-1H-imidazole-4,5-dicarboxamide |
| 48 | 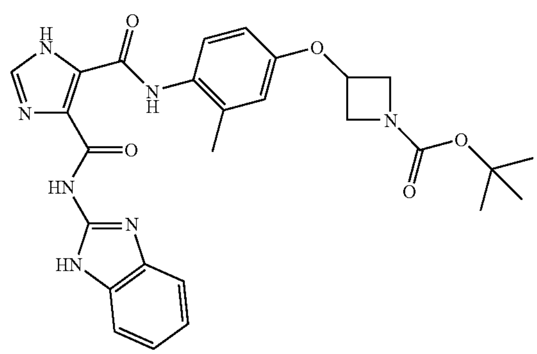 | 1,1-dimethylethyl 3-({4-[({4-[(1H-benzimidazol-2-ylamino)carbonyl]-1H-imidazol-5-yl}carbonyl)amino]-3-methylphenyl}oxy)azetidine-1-carboxylate |
| 49 | 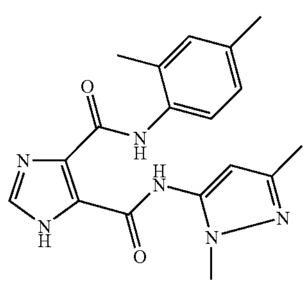 | $N^4$-(2,4-dimethylphenyl)-$N^5$-(1,3-dimethyl-1H-pyrazol-5-yl)-1H-imidazole-4,5-dicarboxamide |

TABLE 1-continued

| Cpd No. | Structure | Name |
|---|---|---|
| 50 | 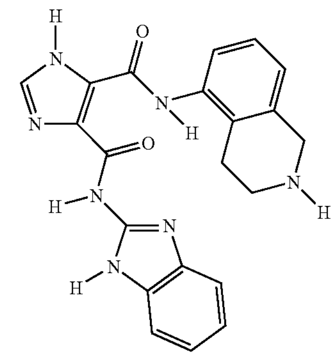 | $N^4$-1H-benzimidazol-2-yl-$N^5$-(1,2,3,4-tetrahydroisoquinolin-5-yl)-1H-imidazole-4,5-dicarboxamide |
| 51 | 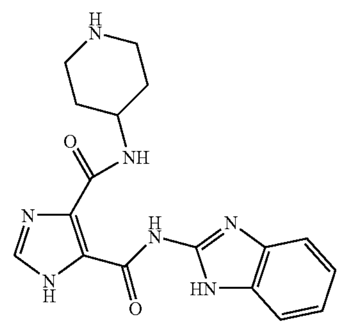 | $N^5$-1H-benzimidazol-2-yl-$N^4$-piperidin-4-yl-1H-imidazole-4,5-dicarboxamide |
| 52 | 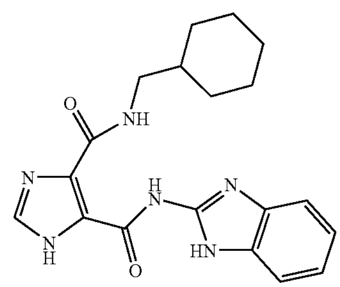 | $N^5$-1H-benzimidazol-2-yl-$N^4$-(cyclohexylmethyl)-1H-imidazole-4,5-dicarboxamide |
| 53 | 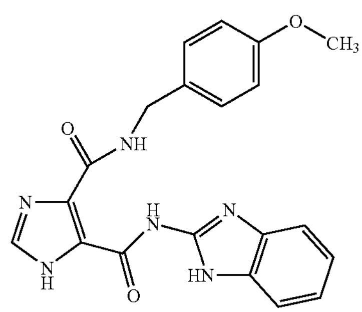 | $N^5$-1H-benzimidazol-2-yl-$N^4$-{[4-(methyloxy)phenyl]methyl}-1H-imidazole-4,5-dicarboxamide |
| 54 | 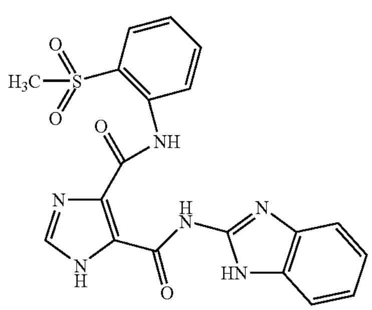 | $N^5$-1H-benzimidazol-2-yl-$N^4$-[2-(methylsulfonyl)phenyl]-1H-imidazol-4,5-dicarboxamide |

TABLE 1-continued

| Cpd No. | Structure | Name |
|---|---|---|
| 55 | 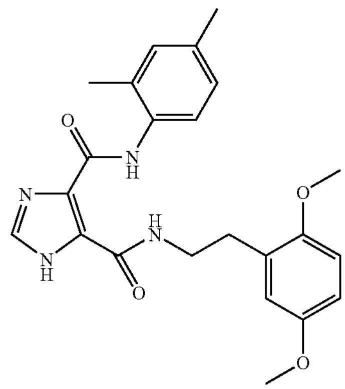 | $N^5$-{2-[2,5-bis(methyloxy)phenyl]ethyl}-$N^4$-(2,4-dimethylphenyl)-1H-imidazole-4,5-dicarboxamide |
| 56 | 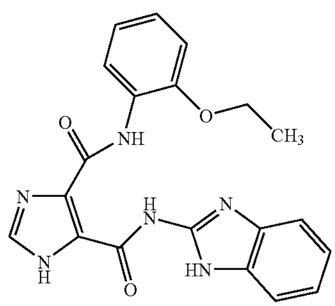 | $N^5$-1H-benzimidazol-2-yl-$N^4$-[2-(ethyloxy)phenyl]-1H-imidazole-4,5-dicarboxamide |
| 57 | 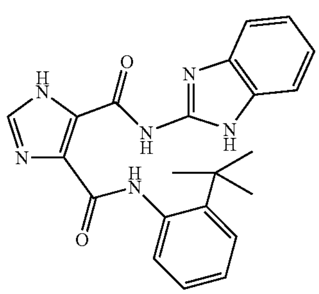 | $N^4$-(2,4-dimethylphenyl)-$N^5$-methyl-$N^5$-(2-pyridin-2-ylethyl)-1H-imidazole-4,5-dicarboxamide |
| 58 | 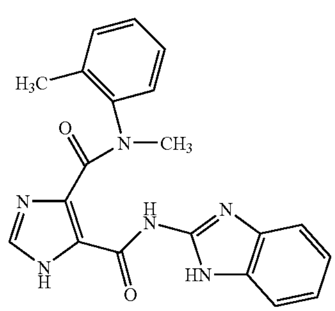 | $N^5$-1H-benzimidazol-2-yl-$N^4$-methyl-$N^4$-(2-methylphenyl)-1H-imidazole-4,5-dicarboxamide |
| 59 | 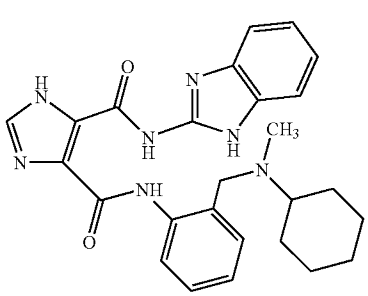 | $N^5$-1H-benzimidazol-2-yl-$N^4$-(2-{[cyclohexyl(methyl)amino]methyl}phenyl)-1H-imidazole-4,5-dicarboxamide |

TABLE 1-continued

| Cpd No. | Structure | Name |
|---|---|---|
| 60 | 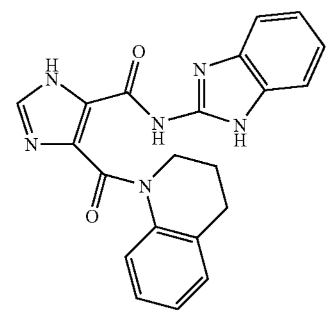 | N-1H-benzimidazol-2-yl-4-(3,4-dihydroquinolin-1(2H)-ylcarbonyl)-1H-imidazole-5-carboxamide |
| 61 | 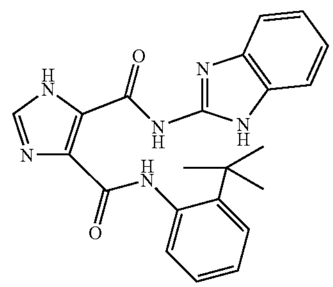 | $N^5$-1H-benzimidazol-2-yl-$N^4$-[2-(1,1-dimethylethyl)phenyl]-1H-imidazole-4,5-dicarboxamide |
| 62 | 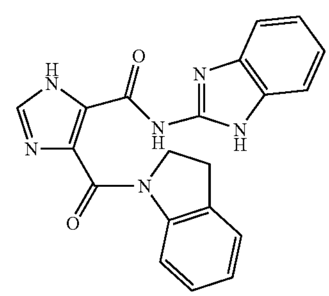 | N-1H-benzimidazol-2-yl-4-(2,3-dihydro-1H-indol-1-ylcarbonyl)-1H-imidazole-5-carboxamide |
| 63 | 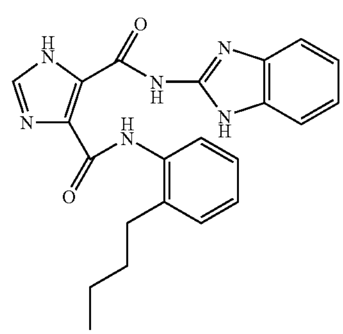 | $N^5$-1H-benzimidazol-2-yl-$N^4$-(2-butylphenyl)-1H-imidazole-4,5-dicarboxamide |
| 64 | 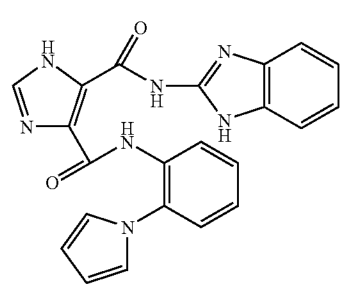 | $N^5$-1H-benzimidazol-2-yl-$N^4$-[2-(1H-pyrrol-1-yl)phenyl]-1H-imidazole-4,5-dicarboxamide |

TABLE 1-continued

| Cpd No. | Structure | Name |
|---|---|---|
| 65 | 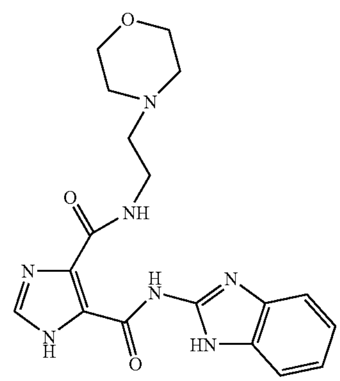 | $N^5$-1H-benzimidazol-2-yl-$N^4$-(2-morpholin-4-ylethyl)-1H-imidazole-4,5-dicarboxamide |
| 66 | 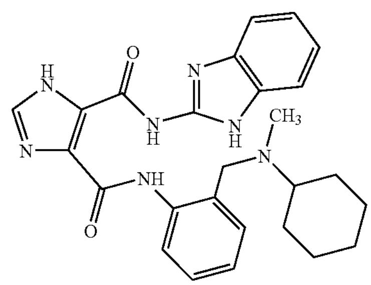 | $N^5$-1H-benzimidazol-2-yl-$N^4$-(2-{[cyclohexyl(methyl)amino]methyl}phenyl)-1H-imidazole-4,5-dicarboxamide |
| 67 | 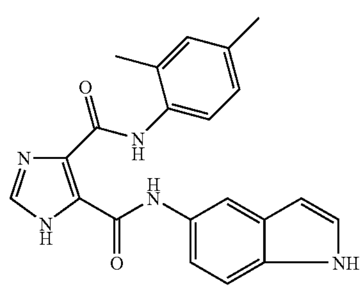 | $N^4$-(2,4-dimethylphenyl)-$N^5$-1H-indol-5-yl-1H-imidazole-4,5-dicarboxamide |
| 68 | 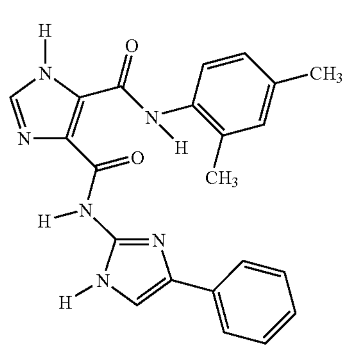 | $N^5$-(2,4-dimethylphenyl)-$N^4$-(4-phenyl-1H-imidazol-2-yl)-1H-imidazole-4,5-dicarboxamide |

TABLE 1-continued

| Cpd No. | Structure | Name |
|---|---|---|
| 69 | 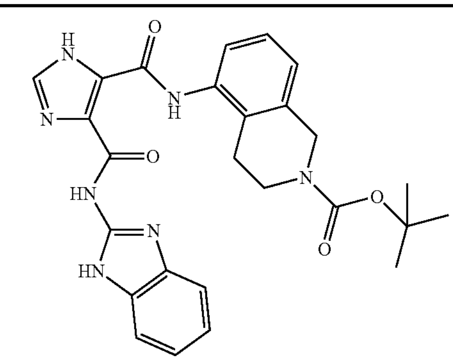 | 1,1-dimethylethyl 5-[({4-[(1H-benzimidazol-2-ylamino)carbonyl]-1H-imidazol-5-yl}carbonyl)amino]-3,4-dihydroisoquinoline-2(1H)-carboxylate |
| 70 | 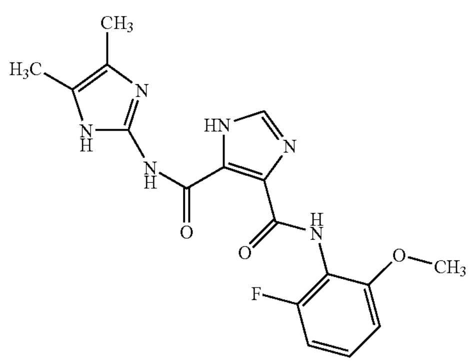 | $N^5$-(4,5-dimethyl-1H-imidazol-2-yl)-$N^4$-[2-fluoro-6-(methyloxy)phenyl]-1H-imidazole-4,5-dicarboxamide |
| 71 | 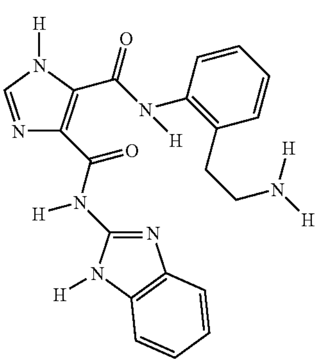 | $N^5$-[2-(2-aminoethyl)phenyl]-$N^4$-1H-benzimidazol-2-yl-1H-imidazole-4,5-dicarboxamide |
| 72 | 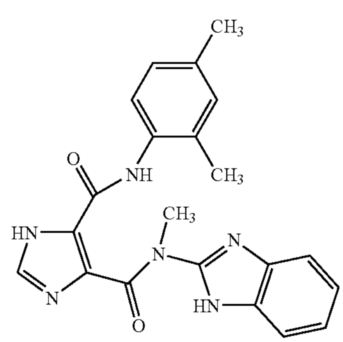 | $N^4$-1H-benzimidazol-2-yl-$N^5$-(2,4-dimethylphenyl)-$N^4$-methyl-1H-imidazole-4,5-dicarboxamide |

TABLE 1-continued

| Cpd No. | Structure | Name |
|---|---|---|
| 73 | 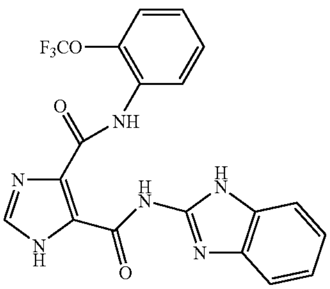 | N$^5$-1H-benzimidazol-2-yl-N$^4$-{2-[(trifluoromethyl)oxy]phenyl}-1H-imidazole-4,5-dicarboxamide |
| 74 | 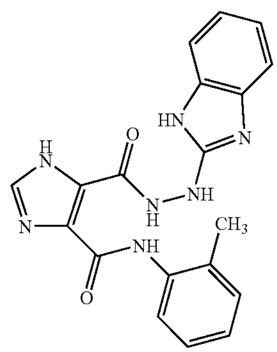 | 5-{[2-(1H-benzimidazol-2-yl)hydrazino]carbonyl}-N-(2-methylphenyl)-1H-imidazole-4-carboxamide |
| 75 | 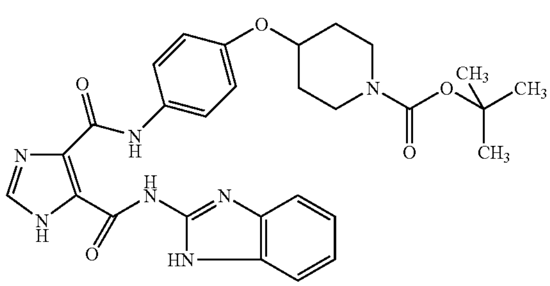 | 1,1-dimethylethyl 4-({4-[({5-[(1H-benzimidazol-2-ylamino)carbonyl]-1H-imidazol-4-yl}carbonyl)amino]phenyl}oxy)piperidine-1-carboxylate |
| 76 | 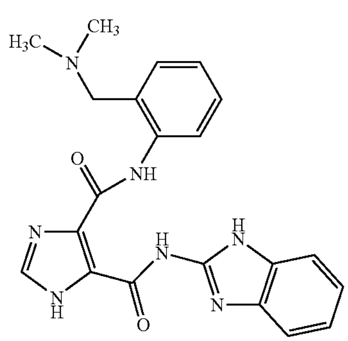 | N$^5$-1H-benzimidazol-2-yl-N$^4$-{2-[(dimethylamino)methyl]phenyl}-1H-imidazol-4,5-dicarboxamide |

TABLE 1-continued

| Cpd No. | Structure | Name |
|---|---|---|
| 77 | 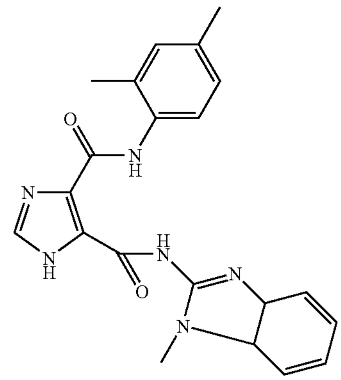 | $N^4$-(2,4-dimethylphenyl)-$N^5$-(1-methyl-1H-benzimidazol-2-yl)-1H-imidazole-4,5-dicarboxamide |
| 78 | 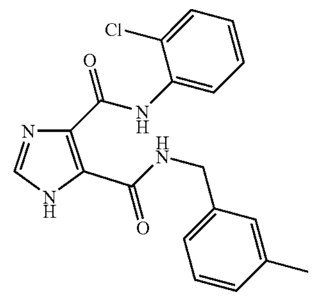 | $N^4$-(2-chlorophenyl)-$N^5$-[(3-methylphenyl)methyl]-1H-imidazole-4,5-dicarboxamide |
| 79 | 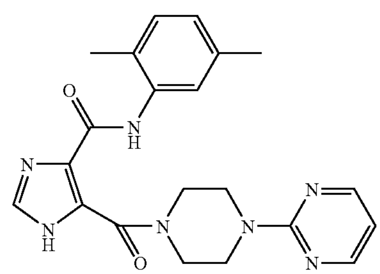 | N-(2,5-dimethylphenyl)-5-[(4-pyrimidin-2-ylpiperazin-1-yl)carbonyl]-1H-imidazole-4-carboxamide |
| 80 | 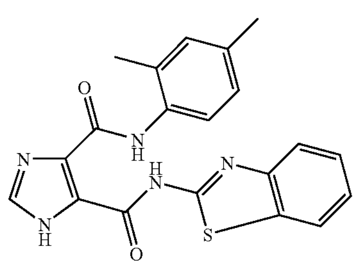 | $N^5$-1,3-benzothiazol-2-yl-$N^4$-(2,4-dimethylphenyl)-1H-imidazole-4,5-dicarboxamide |
| 81 | 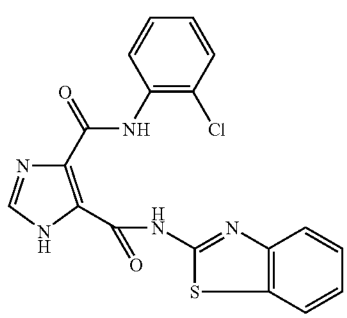 | $N^5$-1,3-benzothiazol-2-yl-$N^4$-(2-chlorophenyl)-1H-imidazole-4,5-dicarboxamide |

TABLE 1-continued

| Cpd No. | Structure | Name |
|---|---|---|
| 82 | 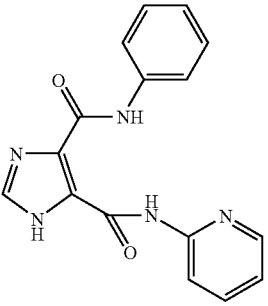 | $N^4$-phenyl-$N^5$-pyridin-2-yl-1H-imidazole-4,5-dicarboxamide |
| 83 | 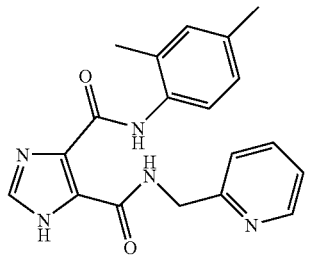 | $N^4$-(2,4-dimethylphenyl)-$N^5$-(pyridin-2-ylmethyl)-1H-imidazole-4,5-dicarboxamide |
| 84 | 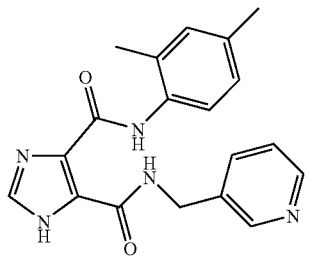 | $N^4$-(2,4-dimethylphenyl)-$N^5$-(pyridin-3-ylmethyl)-1H-imidazole-4,5-dicarboxamide |
| 85 | 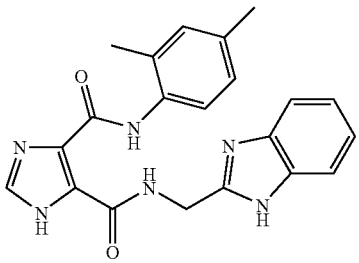 | $N^5$-(1H-benzimidazol-2-ylmethyl)-$N^4$-(2,4-dimethylphenyl)-1H-imidazole-4,5-dicarboxamide |
| 86 | 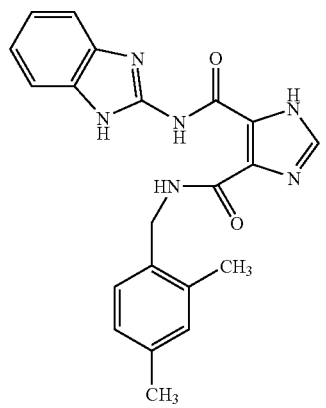 | $N^5$-1H-benzimidazol-2-yl-$N^4$-[(2,4-dimethylphenyl)methyl]-1H-imidazole-4,5-dicarboxamide |

TABLE 1-continued

| Cpd No. | Structure | Name |
|---|---|---|
| 87 | 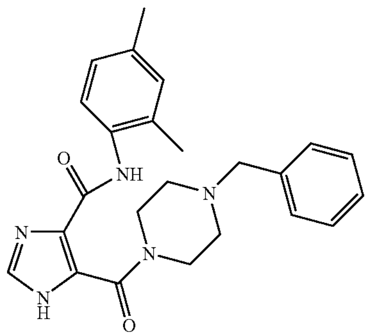 | N-(2,4-dimethylphenyl)-5-{[4-(phenylmethyl)piperazin-1-yl]carbonyl}-1H-imidazole-4-carboxamide |
| 88 | 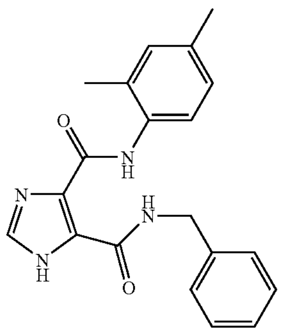 | $N^4$-(2,4-dimethylphenyl)-$N^5$-(phenylmethyl)-1H-imidazole-4,5-dicarboxamide |
| 89 | 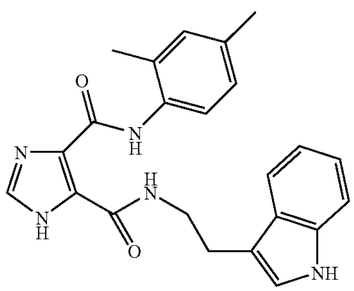 | $N^4$-(2,4-dimethylphenyl)-$N^5$-[2-(1H-indol-3-yl)ethyl]-1H-imidazole-4,5-dicarboxamide |
| 90 | 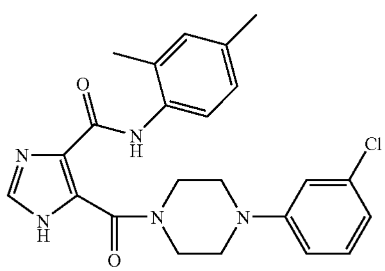 | 5-{[4-(3-chlorophenyl)piperazin-1-yl]carbonyl}-N-(2,4-dimethylphenyl)-1H-imidazole-4-carboxamide |
| 91 | 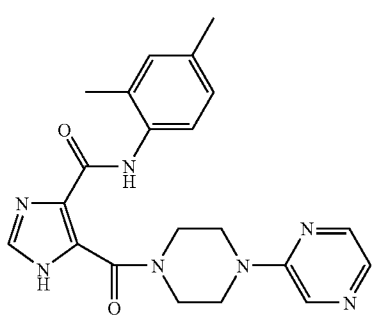 | N-(2,4-dimethylphenyl)-5-[(4-pyrazin-2-ylpiperazin-1-yl)carbonyl]-1H-imidazole-4-carboxamide |

TABLE 1-continued

| Cpd No. | Structure | Name |
|---|---|---|
| 92 | 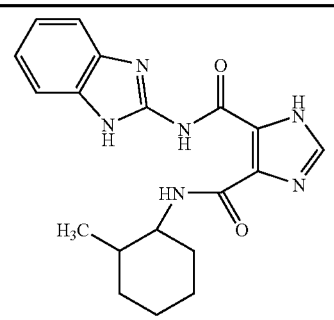 | $N^5$-1H-benzimidazol-2-yl-$N^4$-(2-methylcyclohexyl)-1H-imidazole-4,5-dicarboxamide |
| 93 | 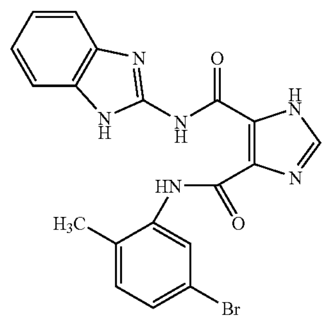 | $N^5$-1H-benzimidazol-2-yl-$N^4$-(5-bromo-2-methylphenyl)-1H-imidazole-4,5-dicarboxamide |
| 94 | 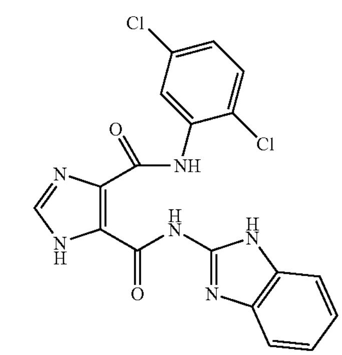 | $N^5$-1H-benzimidazol-2-yl-$N^4$-(2,5-dichlorophenyl)-1H-imidazole-4,5-dicarboxamide |
| 95 | 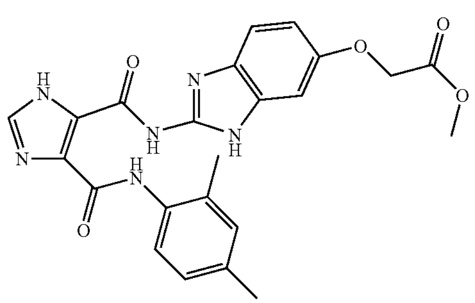 | methyl[(2-{[(4-{[(2,4-dimethylphenyl)amino]carbonyl}-1H-imidazol-5-yl)carbonyl]amino}-1H-benzimidazol-6-yl)oxy]acetate |
| 96 | 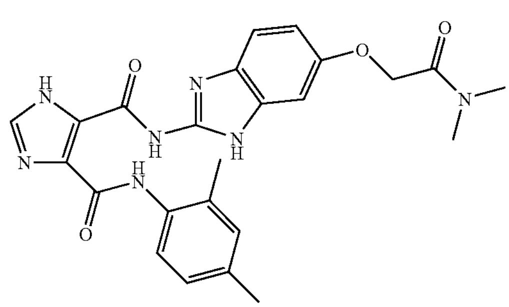 | $N^5$-(6-{[2-(dimethylamino)-2-oxoethyl]oxy}-1H-benzimidazol-2-yl)-$N^4$-(2,4-dimethylphenyl)-1H-imidazole-4,5-dicarboxamide |

TABLE 1-continued

| Cpd No. | Structure | Name |
|---|---|---|
| 97 | 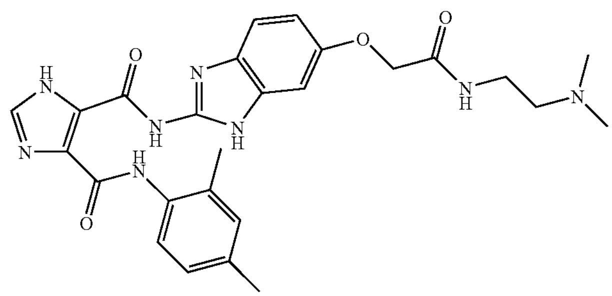 | N$^5$-{6-[(2-{[2-(dimethylamino)ethyl]amino}-2-oxoethyl)oxy]-1H-benzimidazol-2-yl}-N$^4$-(2,4-dimethylphenyl)-1H-imidazole-4,5-dicarboxamide |
| 98 | 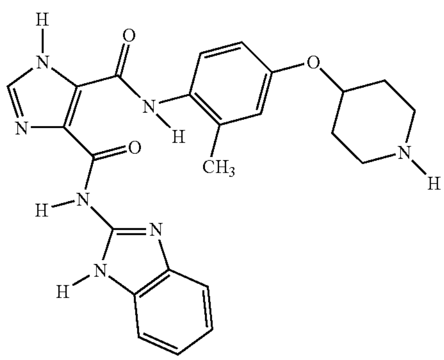 | N$^4$-1H-benzimidazol-2-yl-N$^5$-[2-methyl-4-(piperidin-4-yloxy)phenyl]-1H-imidazole-4,5-dicarboxamide |
| 99 | 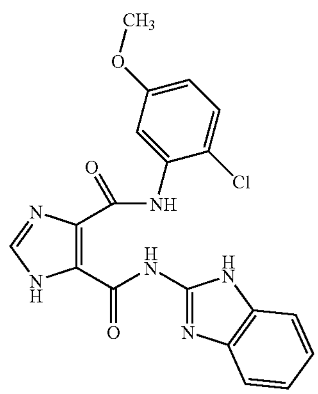 | N$^5$-1H-benzimidazol-2-yl-N$^4$-[2-chloro-5-(methyloxy)phenyl]-1H-imidazole-4,5-dicarboxamide |
| 100 | 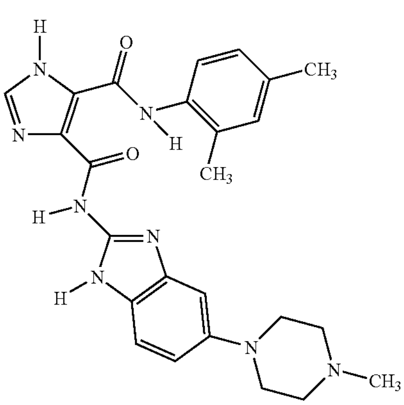 | N$^5$-(2,4-dimethylphenyl)-N$^4$-[5-(4-methylpiperazin-1-yl)-1H-benzimidazol-2-yl]-1H-imidazole-4,5-dicarboxamide |

TABLE 1-continued

| Cpd No. | Structure | Name |
|---|---|---|
| 101 | 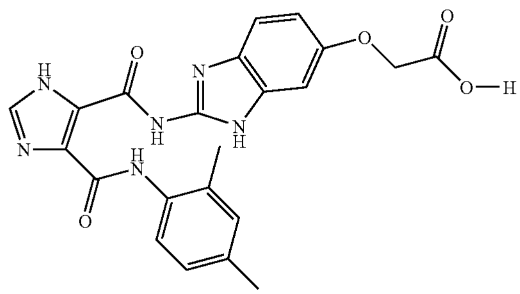 | [(2-{[(4-{[(2,4-dimethylphenyl)amino]carbonyl}-1H-imidazol-5-yl)carbonyl]amino}-1H-benzimidazol-6-yl)oxy]acetic acid |
| 102 | 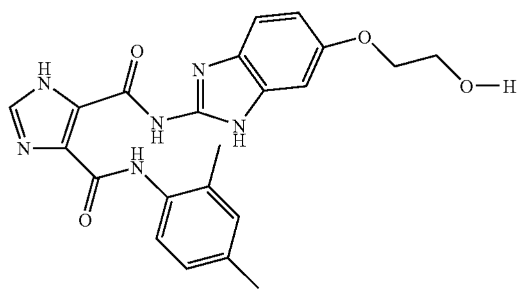 | $N^4$-(2,4-dimethylphenyl)-$N^5$-{6-[(2-hydroxyethyl)oxy]-1H-benzimidazol-2-yl}-1H-imidazole-4,5-dicarboxamide |
| 103 | 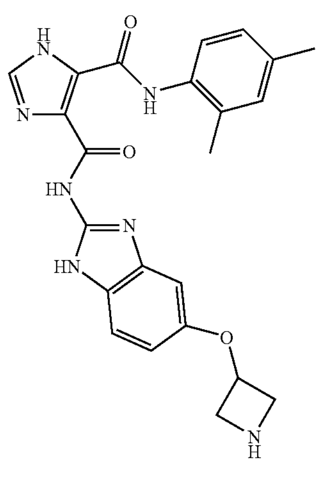 | $N^4$-[5-(azetidin-3-yloxy)-1H-benzimidazol-2-yl]-$N^5$-(2,4-dimethylphenyl)-1H-imidazole-4,5-dicarboxamide |
| 104 | 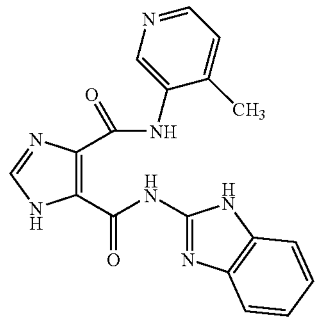 | $N^5$-1H-benzimidazol-2-yl-$N^4$-(4-methylpyridin-3-yl)-1H-imidazole-4,5-dicarboxamide |

TABLE 1-continued

| Cpd No. | Structure | Name |
|---|---|---|
| 105 | 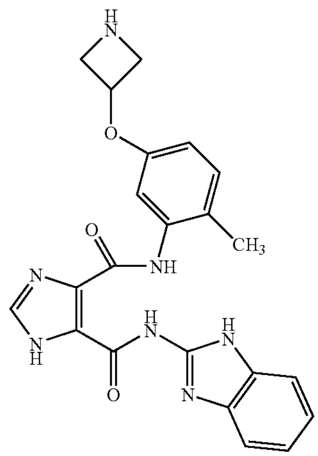 | $N^4$-[5-(azetidin-3-yloxy)-2-methylphenyl]-$N^5$-1H-benzimidazol-2-yl-1H-imidazole-4,5-dicarboxamide |
| 106 | 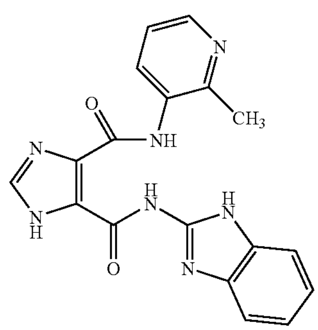 | $N^5$-1H-benzimidazol-2-yl-$N^4$-(2-methylpyridin-3-yl)-1H-imidazole-4,5-dicarboxamide |
| 107 | 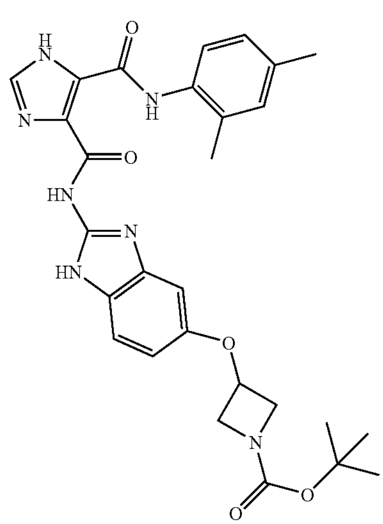 | 1,1-dimethylethyl 3-[(2-{[(5-{[(2,4-dimethylphenyl)amino]carbonyl}-1H-imidazol-4-yl)carbonyl]amino}-1H-benzimidazol-5-yl)oxy]azetidine-1-carboxylate |

TABLE 1-continued

| Cpd No. | Structure | Name |
|---|---|---|
| 108 | 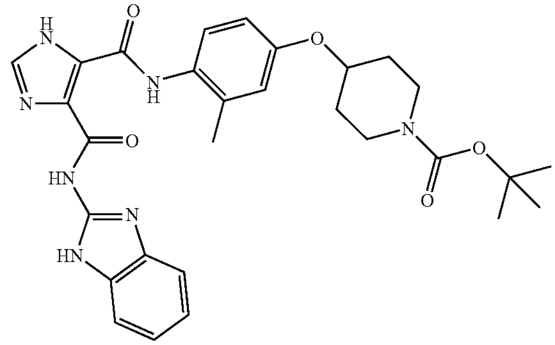 | 1,1-dimethylethyl 4-({4-[({4-[(1H-benzimidazol-2-ylamino)carbonyl]-1H-imidazol-5-yl}carbonyl)amino]-3-methylphenyl}oxy)piperidine-1-carboxylate |
| 109 | 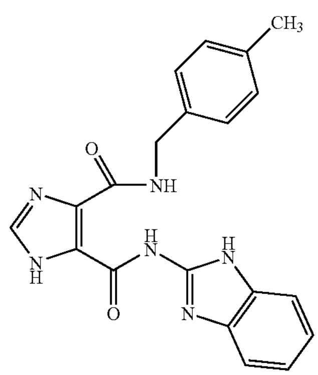 | $N^5$-1H-benzimidazol-2-yl-$N^4$-[(4-methylphenyl)methyl]-1H-imidazole-4,5-dicarboxamide |
| 110 | 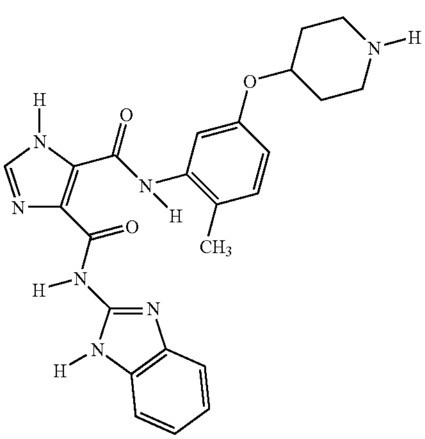 | $N^4$-1H-benzimidazol-2-yl-$N^5$-[2-methyl-5-(piperidin-4-yloxy)phenyl]-1H-imidazole-4,5-dicarboxamide |

TABLE 1-continued

| Cpd No. | Structure | Name |
|---|---|---|
| 111 | 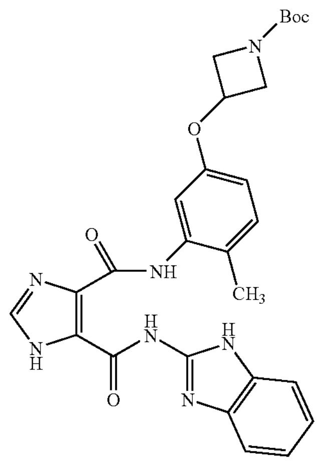 | 1,1-dimethylethyl 3-({3-[({5-[(1H-benzimidazol-2-ylamino)carbonyl]-1H-imidazol-4-yl}carbonyl)amino]-4-methylphenyl}oxy)azetidine-1-carboxylate |
| 112 | 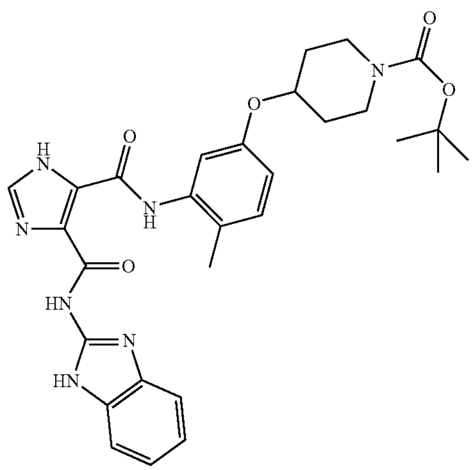 | 1,1-dimethylethyl 4-({3-[({4-[(1H-benzimidazol-2-ylamino)carbonyl]-1H-imidazol-5-yl}carbonyl)amino]-4-methylphenyl}oxy)piperidine-1-carboxylate |
| 113 | 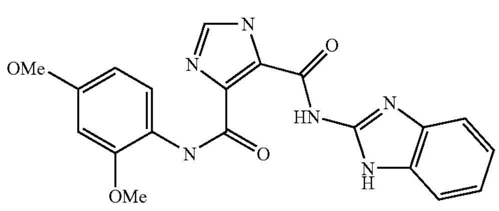 | $N^5$-1H-benzimidazol-2-yl-$N^4$-[2,4-bis(methyloxy)phenyl]-1H-imidazole-4,5-dicarboxamide |
| 114 | 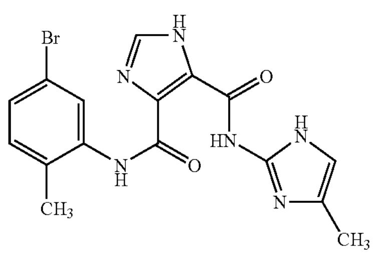 | $N^4$-(5-bromo-2-methylphenyl)-$N^5$-(4-methyl-1H-imidazol-2-yl)-1H-imidazole-4,5-dicarboxamide |

TABLE 1-continued

| Cpd No. | Structure | Name |
|---|---|---|
| 115 | 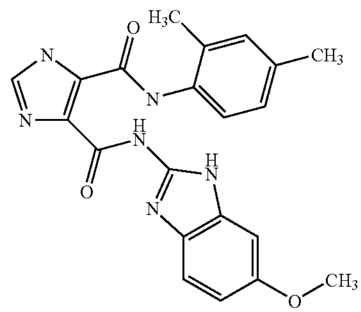 | $N^5$-(2,4-dimethylphenyl)-$N^4$-[6-(methyloxy)-1H-benzimidazol-2-yl]-1H-imidazole-4,5-dicarboxamide |
| 116 | 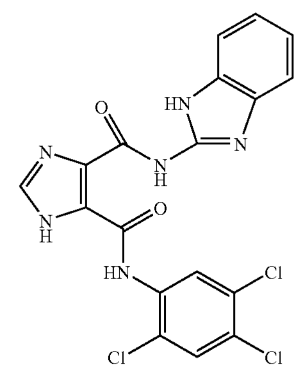 | $N^4$-1H-benzimidazol-2-yl-$N^5$-(2,4,5-trichlorophenyl)-1H-imidazole-4,5-dicarboxamide |
| 117 | 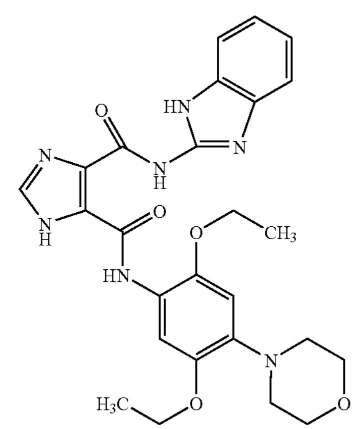 | $N^4$-1H-benzimidazol-2-yl-$N^5$-[2,5-bis(ethyloxy)-4-morpholin-4-ylphenyl]-1H-imidazole-4,5-dicarboxamide |
| 118 | 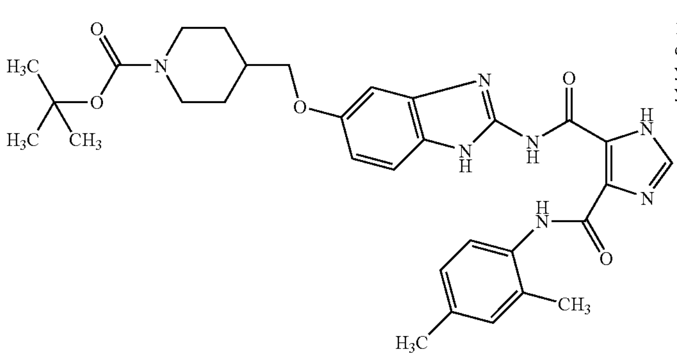 | 1,1-dimethylethyl 4-{[(2-{[(4-{[(2,4-dimethylphenyl)amino]carbonyl}-1H-imidazol-5-yl)carbonyl]amino}-1H-benzimidazol-5-yl)oxy]methyl}piperidine-1-carboxylate |

TABLE 1-continued

| Cpd No. | Structure | Name |
|---|---|---|
| 119 | 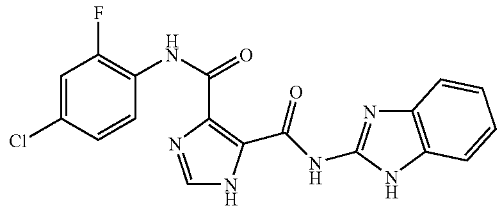 | $N^5$-1H-benzimidazol-2-yl-$N^4$-(4-chloro-2-fluorophenyl)-1H-imidazole-4,5-dicarboxamide |
| 120 | 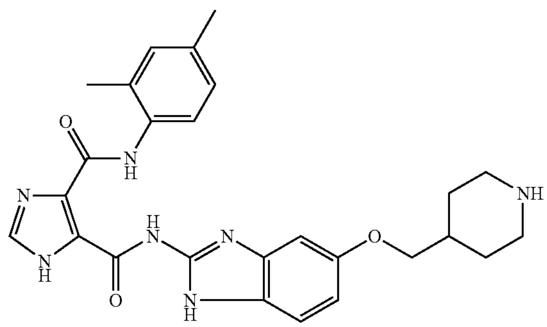 | $N^4$-(2,4-dimethylphenyl)-$N^5$-{5-[(piperidin-4-ylmethyl)oxy]-1H-benzimidazol-2-yl}-1H-imidazole-4,5-dicarboxamide |
| 121 | 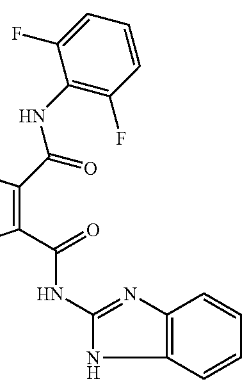 | $N^5$-1H-benzimidazol-2-yl-$N^4$-(2,6-difluorophenyl)-1H-imidazole-4,5-dicarboxamide |
| 122 | 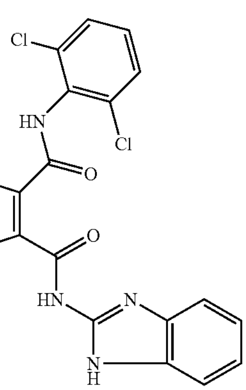 | $N^5$-1H-benzimidazol-2-yl-$N^4$-(2,6-dichlorophenyl)-1H-imidazole-4,5-dicarboxamide |

TABLE 1-continued

| Cpd No. | Structure | Name |
|---|---|---|
| 123 | 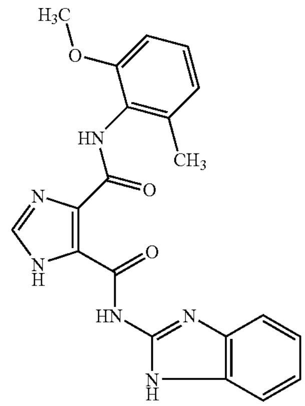 | $N^5$-1H-benzimidazol-2-yl-$N^4$-[2-methyl-6-(methyloxy)phenyl]-1H-imidazole-4,5-dicarboxamide |
| 124 | 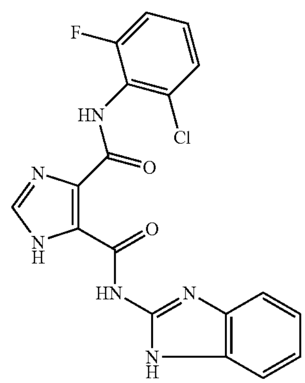 | $N^5$-1H-benzimidazol-2-yl-$N^4$-(2-chloro-6-fluorophenyl)-1H-imidazole-4,5-dicarboxamide |
| 125 | 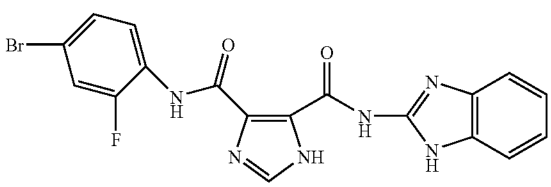 | $N^5$-1H-benzimidazol-2-yl-$N^4$-(4-bromo-2-fluorophenyl)-1H-imidazole-4,5-dicarboxamide |
| 126 | 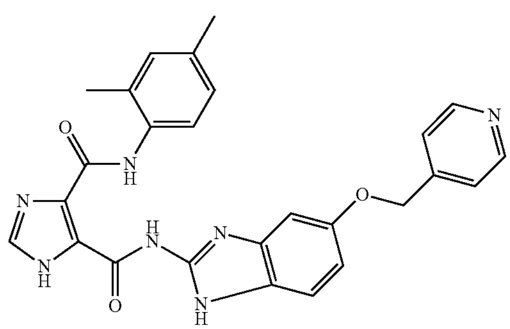 | $N^4$-(2,4-dimethylphenyl)-$N^5$-{5-[(pyridin-4-ylmethyl)oxy]-1H-benzimidazol-2-yl}-1H-imidazole-4,5-dicarboxamide |

TABLE 1-continued

| Cpd No. | Structure | Name |
| --- | --- | --- |
| 127 | 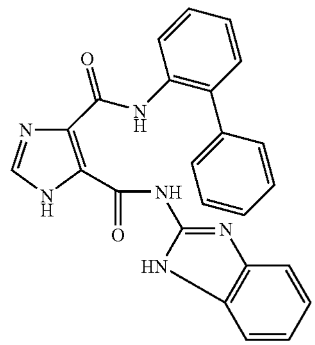 | $N^5$-1H-benzimidazol-2-yl-$N^4$-biphenyl-2-yl-1H-imidazole-4,5-dicarboxamide |
| 128 | 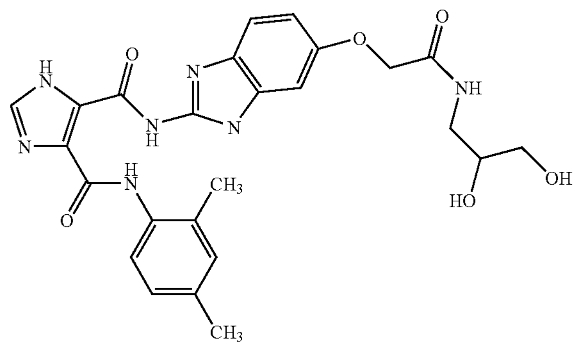 | $N^5$-[6-({2-[(2,3-dihydroxypropyl)amino]-2-oxoethyl}oxy)-1H-benzimidazol-2-yl]-$N^4$-(2,4-dimethylphenyl)-1H-imidazole-4,5-dicarboxamide |
| 129 | 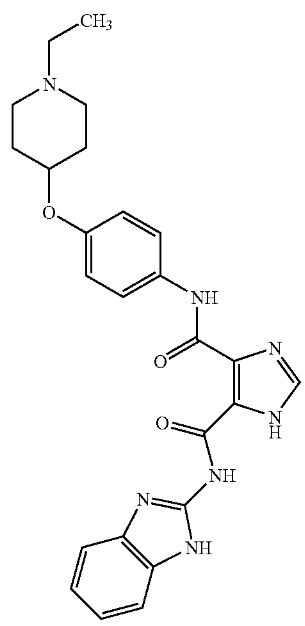 | $N^5$-1H-benzimidazol-2-yl-$N^4$-{4-[(1-ethylpiperidin-4-yl)oxy]phenyl}-1H-imidazole-4,5-dicarboxamide |
| 130 | 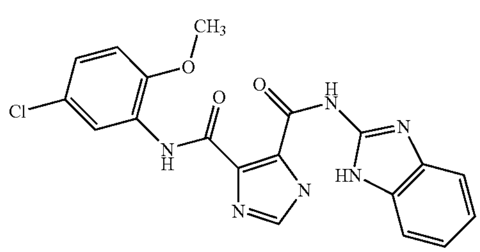 | $N^5$-1H-benzimidazol-2-yl-$N^4$-[5-chloro-2-(methyloxy)phenyl]-1H-imidazole-4,5-dicarboxamide |

TABLE 1-continued

| Cpd No. | Structure | Name |
|---|---|---|
| 131 | 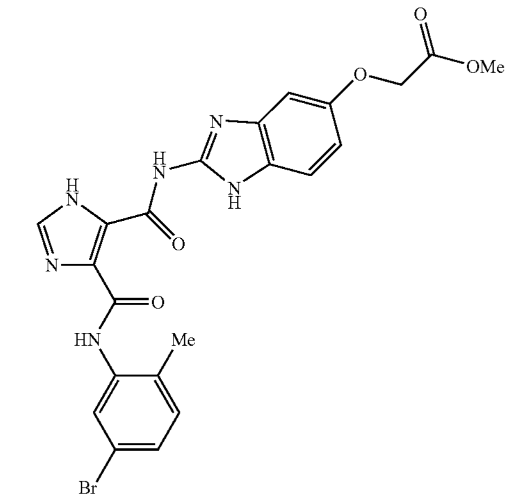 | methyl[(2-{[(4-{[(5-bromo-2-methylphenyl)amino]carbonyl}-1H-imidazol-5-yl)carbonyl]amino}-1H-benzimidazol-5-yl)oxy]acetate |
| 132 | 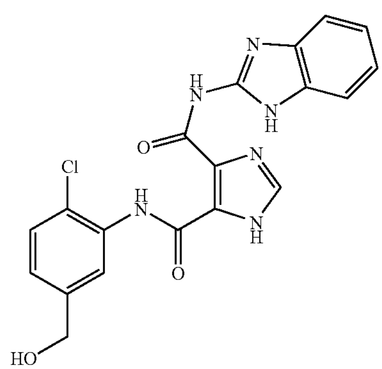 | $N^4$-1H-benzimidazol-2-yl-$N^5$-[2-chloro-5-(hydroxymethyl)phenyl]-1H-imidazole-4,5-dicarboxamide |
| 133 | 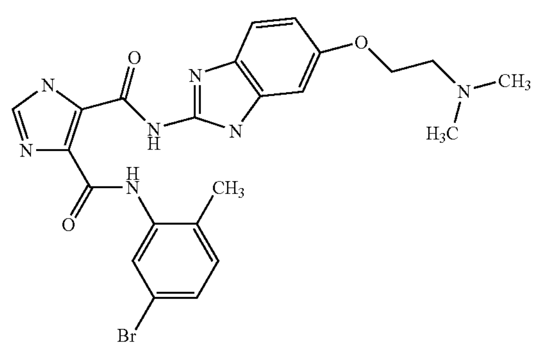 | $N^4$-(5-bromo-2-methylphenyl)-$N^5$-(6-{[2-(dimethylamino)ethyl]oxy}-1H-benzimidazol-2-yl)-1H-imidazole-4,5-dicarboxamide |
| 134 | 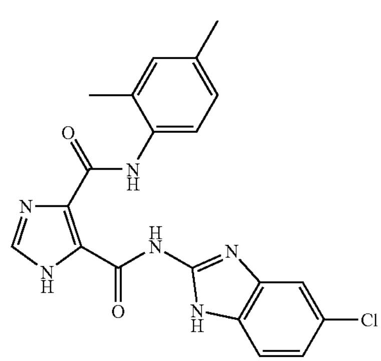 | $N^5$-(5-chloro-1H-benzimidazol-2-yl)-$N^4$-(2,4-dimethylphenyl)-1H-imidazole-4,5-dicarboxamide |

TABLE 1-continued

| Cpd No. | Structure | Name |
|---|---|---|
| 135 | 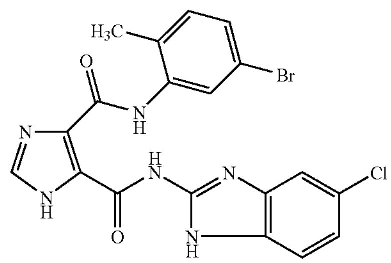 | $N^4$-(5-bromo-2-methylphenyl)-$N^5$-(5-chloro-1H-benzimidazol-2-yl)-1H-imidazole-4,5-dicarboxamide |
| 136 | 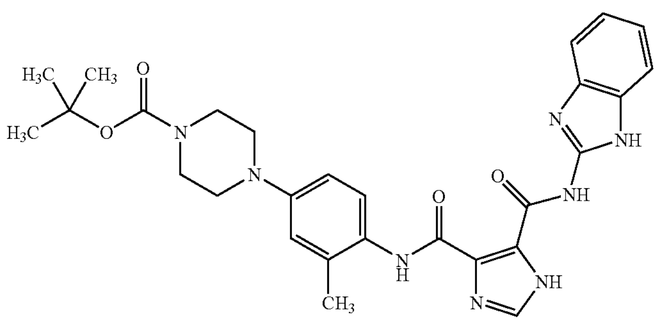 | 1,1-dimethylethyl 4-{4-[({5-[(1H-benzimidazol-2-ylamino)carbonyl]-1H-imidazol-4-yl}carbonyl)amino]-3-methylphenyl}piperazine-1-carboxylate |
| 137 | 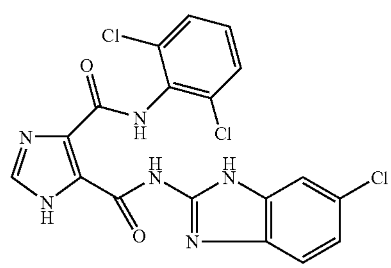 | $N^5$-(6-chloro-1H-benzimidazol-2-yl)-$N^4$-(2,6-dichlorophenyl)-1H-imidazole-4,5-dicarboxamide |
| 138 | 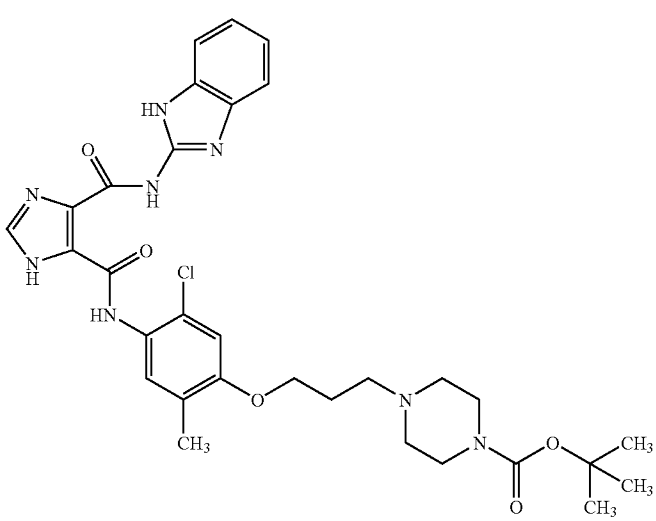 | 1,1-dimethylethyl 4-[3-({4-[({4-[(1H-benzimidazol-2-ylamino)carbonyl]-1H-imidazol-5-yl}carbonyl)amino]-5-chloro-2-methylphenyl}oxy)propyl]piperazine-1-carboxylate |

TABLE 1-continued

| Cpd No. | Structure | Name |
|---|---|---|
| 139 | 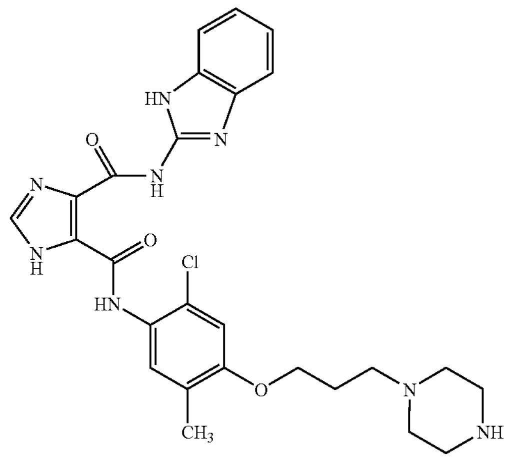 | $N^4$-1H-benzimidazol-2-yl-$N^5$-{2-chloro-5-methyl-4-[(3-piperazin-1-ylpropyl)oxy]phenyl}-1H-imidazole-4,5-dicarboxamide |
| 140 | 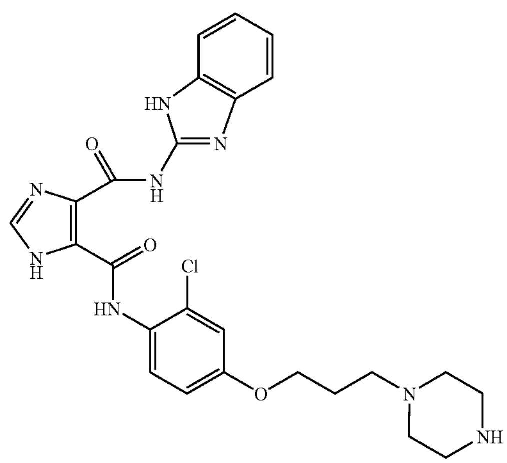 | $N^4$-1H-benzimidazol-2-yl-$N^5$-{2-chloro-4-[(3-piperazin-1-ylpropyl)oxy]phenyl}-1H-imidazole-4,5-dicarboxamide |
| 141 | 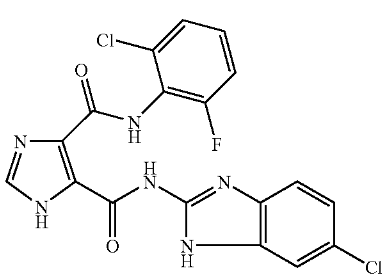 | $N^5$-(6-chloro-1H-benzimidazol-2-yl)-$N^4$-(2-chloro-6-fluorophenyl)-1H-imidazole-4,5-dicarboxamide |

TABLE 1-continued

| Cpd No. | Structure | Name |
|---|---|---|
| 142 | 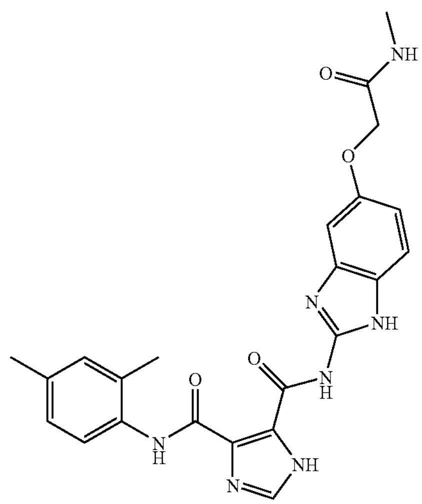 | $N^4$-(2,4-dimethylphenyl)-$N^5$-(5-{[2-(methylamino)-2-oxoethyl]oxy}-1H-benzimidazol-2-yl)-1H-imidazole-4,5-dicarboxamide |
| 143 | 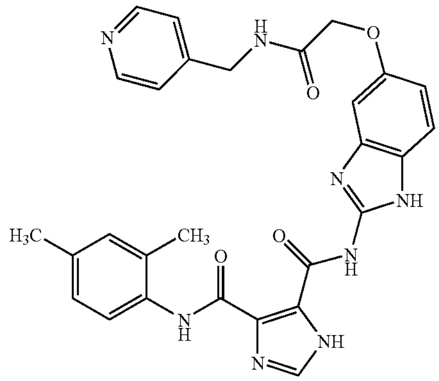 | $N^4$-(2,4-dimethylphenyl)-$N^5$-[5-({2-oxo-2-[(pyridin-4-ylmethyl)amino]ethyl}oxy)-1H-benzimidazol-2-yl]-1H-imidazole-4,5-dicarboxamide |
| 144 | 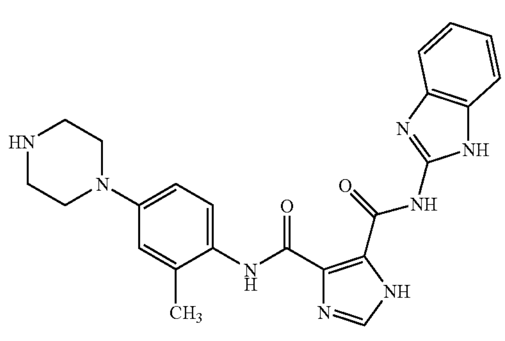 | $N^5$-1H-benzimidazol-2-yl-$N^4$-(2-methyl-4-piperazin-1-ylphenyl)-1H-imidazole-4,5-dicarboxamide |

TABLE 1-continued

| Cpd No. | Structure | Name |
|---|---|---|
| 145 | 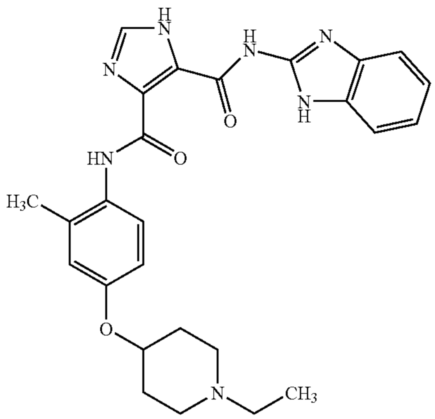 | $N^5$-1H-benzimidazol-2-yl-$N^4$-{4-[(1-ethylpiperidiin-4-yl)oxy]-2-methylphenyl}-1H-imidazole-4,5-dicarboxamide |
| 146 | 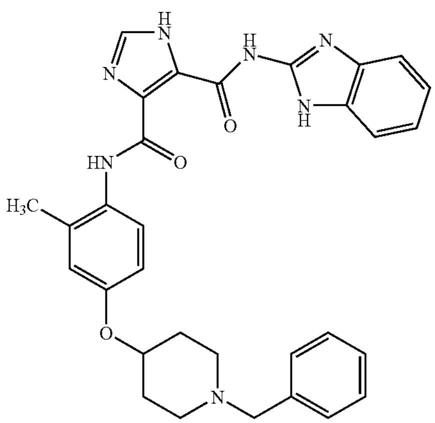 | $N^5$-1H-benzimidazol-2-yl-$N^4$-(2-methyl-4-{[1-(phenylmethyl)piperidin-4-yl]oxy}phenyl)-1H-imidazole-4,5-dicarboxamide |
| 147 | 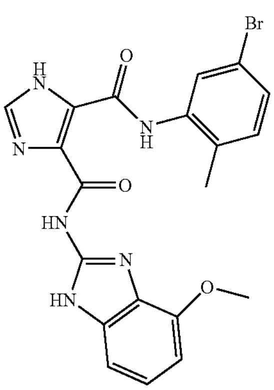 | $N^5$-(5-bromo-2-methylphenyl)-$N^4$-[4-(methyloxy)-1H-benzimidazol-2-yl]-1H-imidazole-4,5-dicarboxamide |

TABLE 1-continued

| Cpd No. | Structure | Name |
|---|---|---|
| 148 | 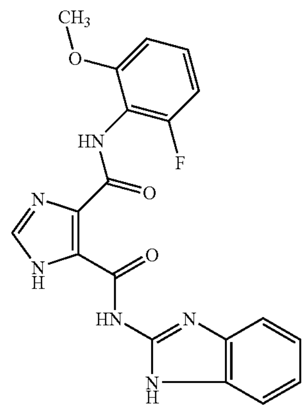 | N⁵-1H-benzimidazol-2-yl-N⁴-[2-fluoro-6-(methyloxy)phenyl]-1H-imidazole-4,5-dicarboxamide |
| 149 | 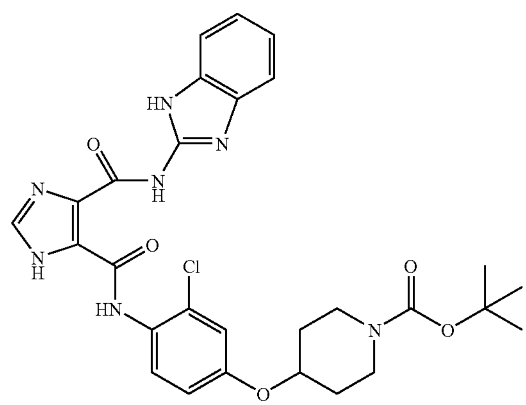 | 1,1-dimethylethyl 4-({4-[({4-[(1H-benzimidazol-2-ylamino)carbonyl]-1H-imidazol-5-yl}carbonyl)amino]-3-chlorophenyl}oxy)piperidine-1-carboxylate |
| 150 | 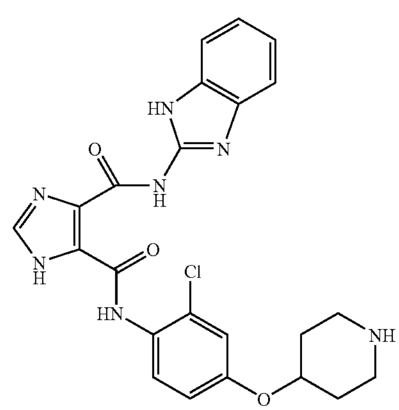 | N⁴-1H-benzimidazol-2-yl-N⁵-[2-chloro-4-(piperidin-4-yloxy)phenyl]-1H-imidazole-4,5-dicarboxamide |
| 151 | 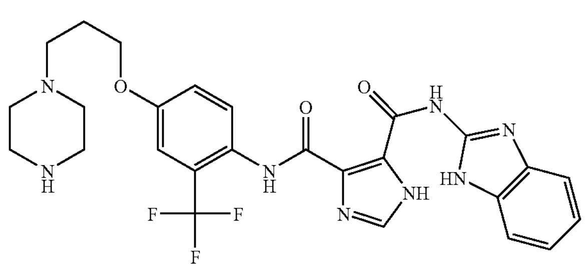 | N⁵-1H-benzimidazol-2-yl-N~4~-{4-[(3-piperazin-1-ylpropyl)oxy]-2-(trifluoromethyl)phenyl}-1H-imidazole-4,5-dicarboxamide |

TABLE 1-continued
| Cpd No. | Structure | Name |
|---|---|---|
| 152 | 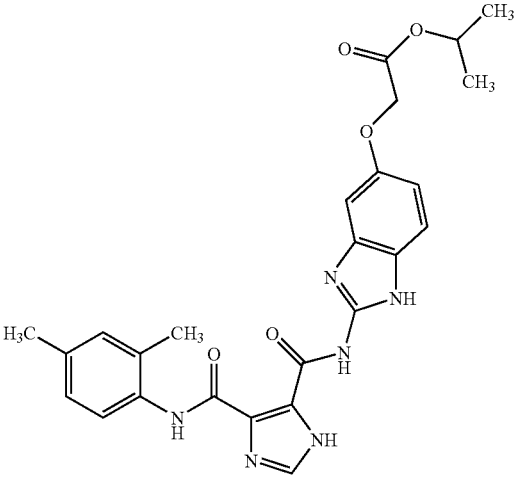 | 1-methylethyl[(2-{[(4-{[(2,4-dimethylphenyl)amino]carbonyl}-1H-imidazol-5-yl)carbonyl]amino}-1H-benzimidazol-5-yl)oxy]acetate |
| 153 | 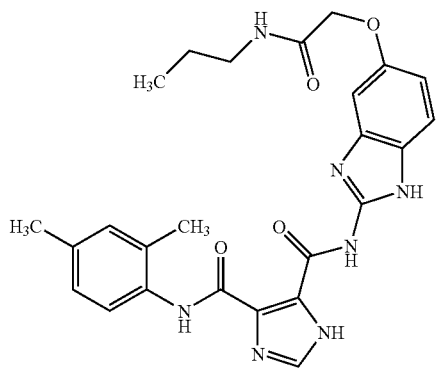 | $N^4$-(2,4-dimethylphenyl)-$N^5$-(5-{[2-oxo-2-(propylamino)ethyl]oxy}-1H-benzimidazol-2-yl)-1H-imidazole-4,5-dicarboxamide |
| 154 | 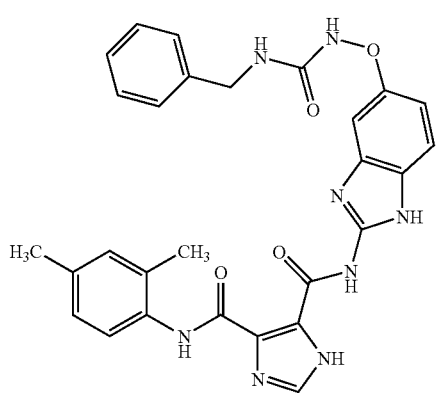 | $N^4$-(2,4-dimethylphenyl)-$N^5$-[5-({2-oxo-2-[(phenylmethyl)amino]ethyl}oxy)-1H-benzimidazol-2-yl]-1H-imidazole-4,5-dicarboxamide |

TABLE 1-continued

| Cpd No. | Structure | Name |
|---|---|---|
| 155 | 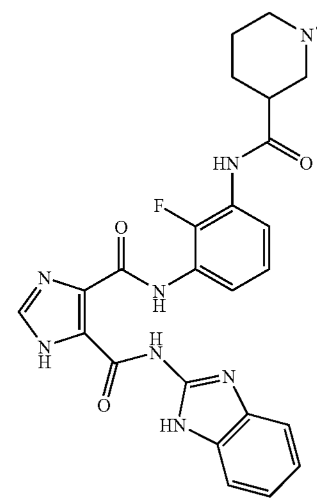 | $N^5$-1H-benzimidazol-2-yl-$N^4$-(2-fluoro-3-{[(1-methylpiperidin-3-yl)carbonyl]amino}phenyl)-1H-imidazole-4,5-dicarboxamide |
| 156 | 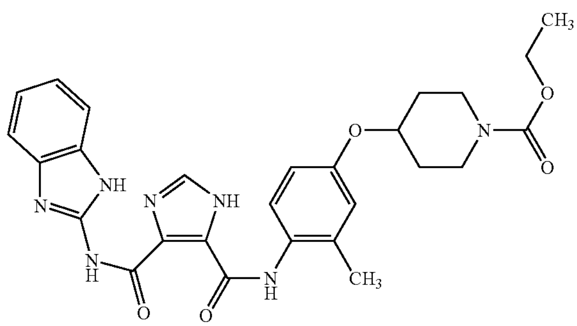 | ethyl 4-({4-[({4-[(1H-benzimidazol-2-ylamino)carbonyl]-1H-imidazol-5-yl}carbonyl)amino]-3-methylphenyl}oxy)piperidine-1-carboxylate |
| 157 | 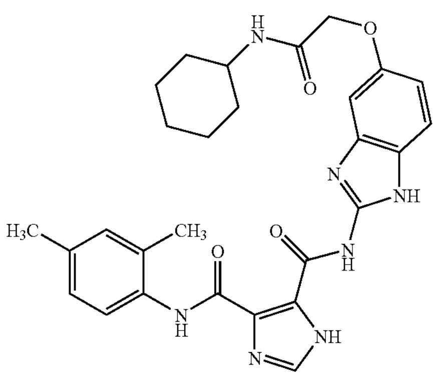 | $N^5$-(5-{[2-(cyclohexylamino)-2-oxoethyl]oxy}-1H-benzimidazol-2-yl)-$N^4$-(2,4-dimethylphenyl)-1H-imidazole-4,5-dicarboxamide |
| 158 | 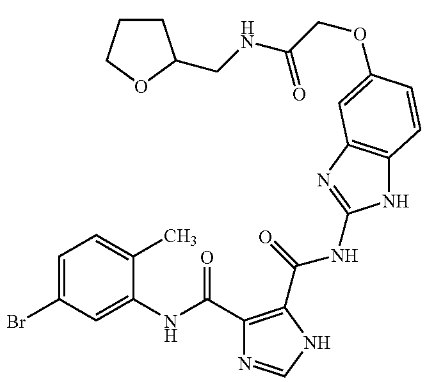 | $N^4$-(5-bromo-2-methylphenyl)-$N^5$-[5-({2-oxo-2-[(tetrahydrofuran-2-ylmethyl)amino]ethyl}oxy)-1H-benzimidazol-2-yl]-1H-imidazole-4,5-dicarboxamide |

TABLE 1-continued

| Cpd No. | Structure | Name |
|---|---|---|
| 159 | 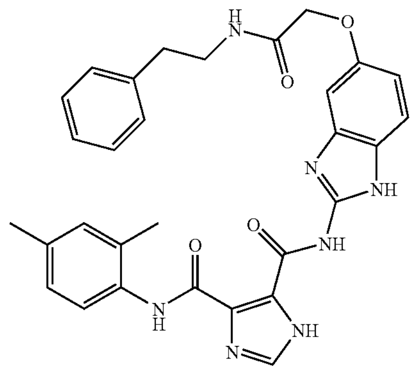 | $N^4$-(2,4-dimethylphenyl)-$N^5$-[5-({2-oxo-2-[(2-phenylethyl)amino]ethyl}oxy)-1H-benzimidazol-2-yl]-1H-imidazole-4,5-dicarboxamide |
| 160 | 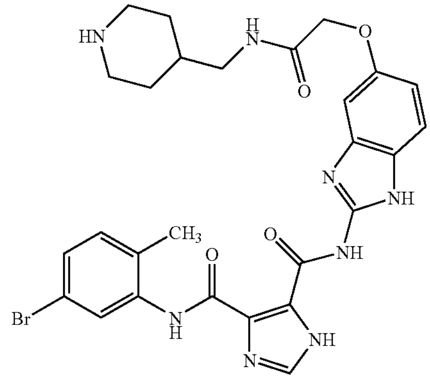 | $N^4$-(5-bromo-2-methylphenyl)-$N^5$-[5-({2-oxo-2-[(piperidin-4-ylmethyl)amino]ethyl}oxy)-1H-benzimidazol-2-yl]-1H-imidazole-4,5-dicarboxamide |
| 161 | 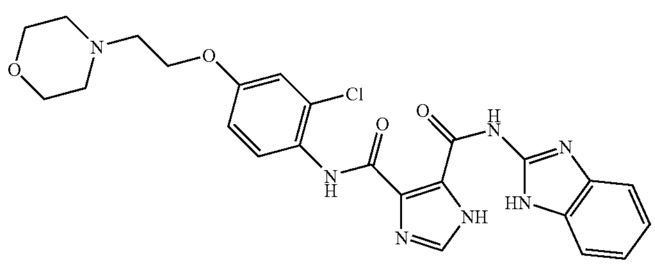 | $N^5$-1H-benzimidazol-2-yl-$N^4$-{2-chloro-4-[(2-morpholin-4-ylethyl)oxy]phenyl}-1H-imidazole-4,5-dicarboxamide |
| 162 | 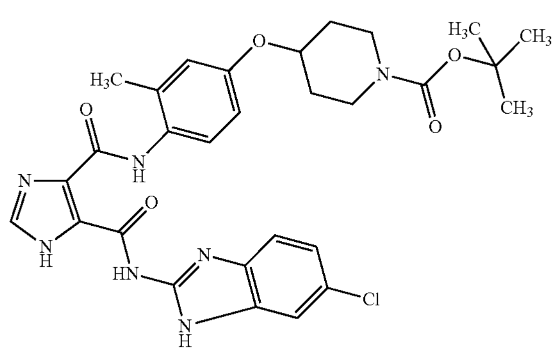 | 1,1-dimethylethyl 4-[(4-{[(5-{[(6-chloro-1H-benzimidazol-2-yl)amino]carbonyl}-1H-imidazol-4-yl)carbonyl]amino}-3-methylphenyl)oxy]piperidine-1-carboxylate |

TABLE 1-continued

| Cpd No. | Structure | Name |
|---|---|---|
| 163 | 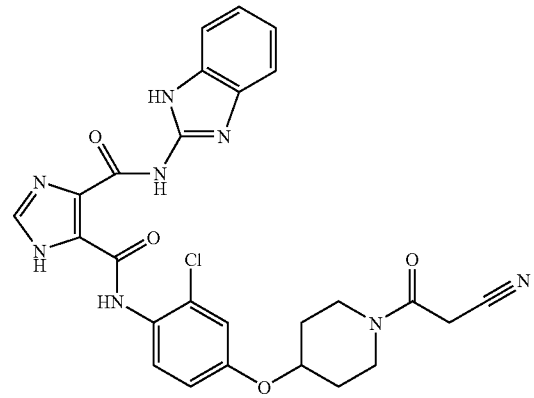 | $N^4$-1H-benzimidazol-2-yl-$N^5$-(2-chloro-4-{[1-(cyanoacetyl)piperidin-4-yl]oxy}phenyl)-1H-imidazole-4,5-dicarboxamide |
| 164 | 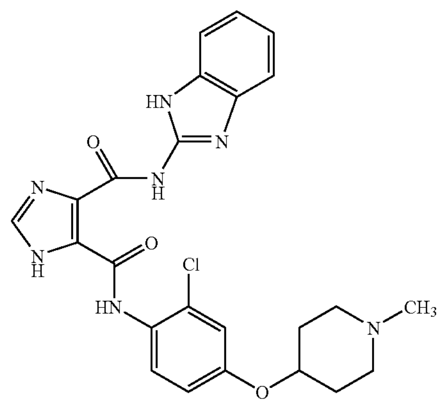 | $N^4$-1H-benzimidazol-2-yl-$N^5$-{2-chloro-4-[(1-methylpiperidin-4-yl)oxy]phenyl}-1H-imidazole-4,5-dicarboxamide |
| 165 | 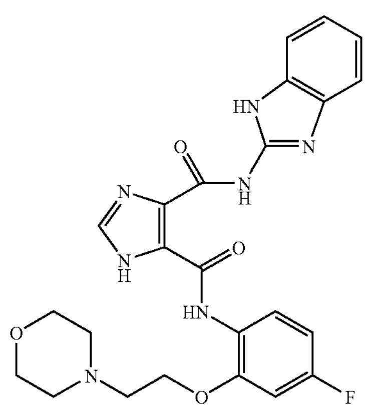 | $N^4$-1H-benzimidazol-2-yl-$N^5$-{4-fluoro-2-[(2-morpholin-4-ylethyl)oxy]phenyl}-1H-imidazole-4,5-dicarboxamide |

TABLE 1-continued

| Cpd No. | Structure | Name |
|---|---|---|
| 166 | 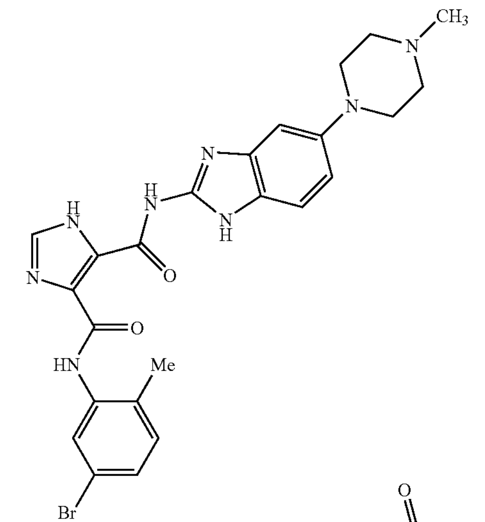 | $N^4$-(5-bromo-2-methylphenyl)-$N^5$-[5-(4-methylpiperazin-1-yl)-1H-benzimidazol-2-yl]-1H-imidazole-4,5-dicarboxamide |
| 167 | 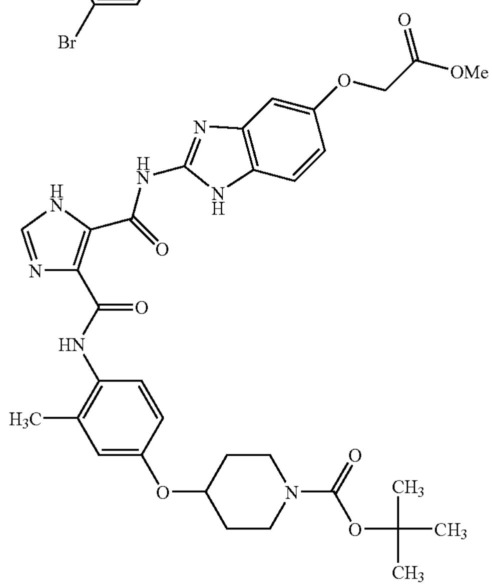 | 1,1-dimethylethyl 4-[(3-methyl-4-{[(5-{[(5-{[2-(methyloxy)-2-oxoethyl]oxy}-1H-benzimidazol-2-yl)amino]carbonyl}-1H-imidazol-4-yl)carbonyl]amino}phenyl)oxy]piperidine-1-carboxylate |
| 168 | 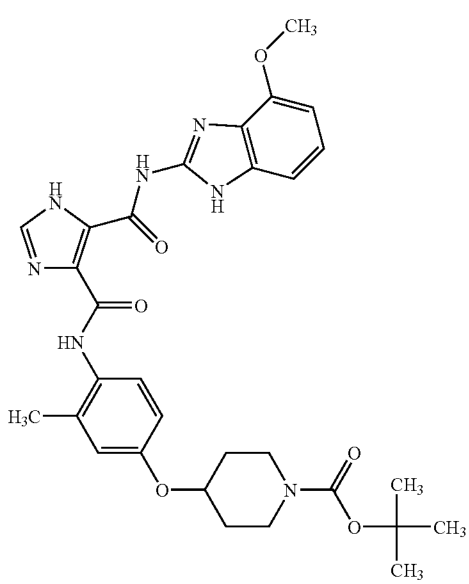 | 1,1-dimethylethyl 4-{[3-methyl-4-({[5-({[4-(methyloxy)-1H-benzimidazol-2-yl]amino}carbonyl)-1H-imidazol-4-yl]carbonyl}amino)phenyl]oxy}piperidine-1-carboxylate |

TABLE 1-continued

| Cpd No. | Structure | Name |
|---|---|---|
| 169 | 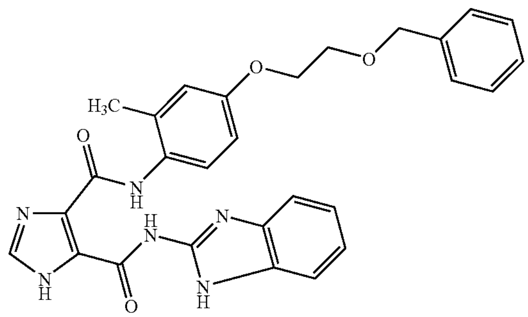 | $N^5$-1H-benzimidazol-2-yl-$N^4$-[2-methyl-4-({2-[(phenylmethyl)oxy]ethyl}oxy)phenyl]-1H-imidazole-4,5-dicarboxamide |
| 170 | 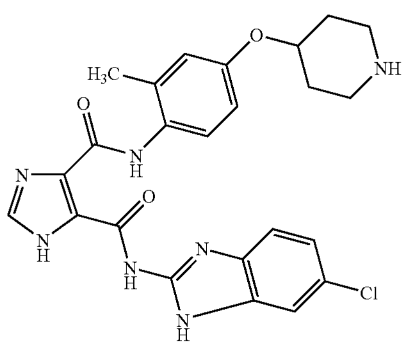 | $N^5$-(6-chloro-1H-benzimidazol-2-yl)-$N^4$-[2-methyl-4-(piperidin-4-yloxy)phenyl]-1H-imidazole-4,5-dicarboxamide |
| 171 | 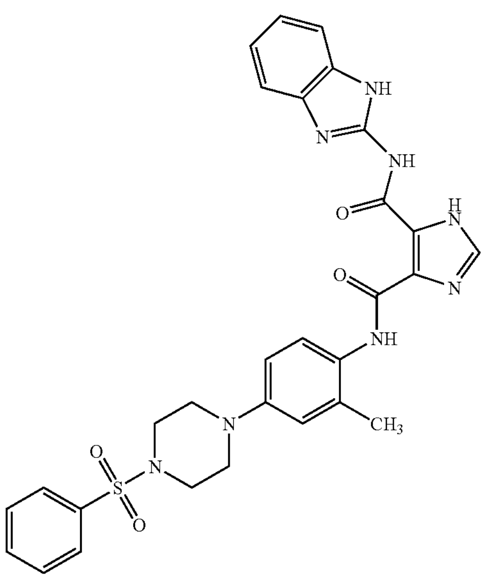 | $N^5$-1H-benzimidazol-2-yl-$N^4$-{2-methyl-4-[4-(phenylsulfonyl)piperazin-1-yl]phenyl}-1H-imidazole-4,5-dicarboxamide |

TABLE 1-continued

| Cpd No. | Structure | Name |
|---|---|---|
| 172 | 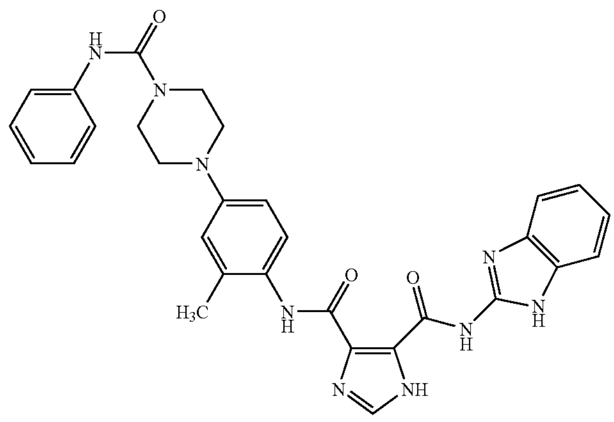 | N⁵-1H-benzimidazol-2-yl-N⁴-(2-methyl-4-{4-[(phenylamino)carbonyl]piperazin-1-yl}phenyl)-1H-imidazole-4,5-dicarboxamide |
| 173 | 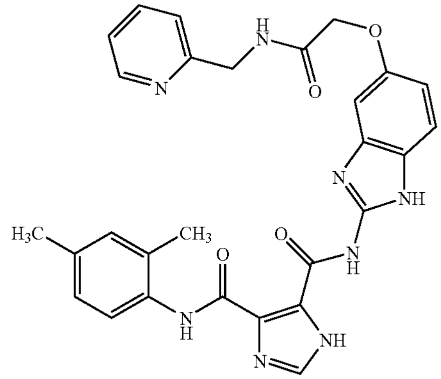 | N⁴-(2,4-dimethylphenyl)-N⁵-[5-({2-oxo-2-[(pyridin-2-ylmethyl)amino]ethyl}oxy)-1H-benzimidazol-2-yl]-1H-imidazole-4,5-dicarboxamide |
| 174 | 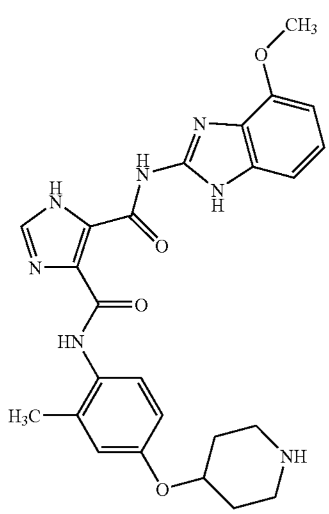 | N⁵-[4-(methyloxy)-1H-benzimidazol-2-yl]-N⁴-[2-methyl-4-(piperidin-4-yloxy)phenyl]-1H-imidazole-4,5-dicarboxamide |

TABLE 1-continued

| Cpd No. | Structure | Name |
|---|---|---|
| 175 | 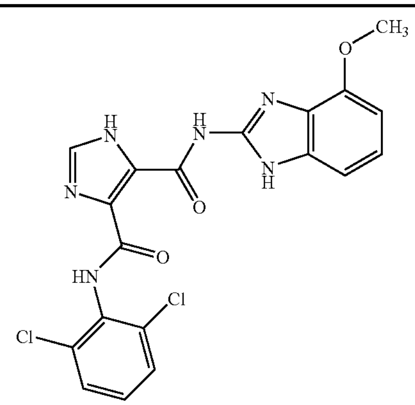 | N⁴-(2,6-dichlorophenyl)-N⁵-[4-(methyloxy)-1H-benzimidazol-2-yl]-1H-imidazole-4,5-dicarboxamide |
| 176 | 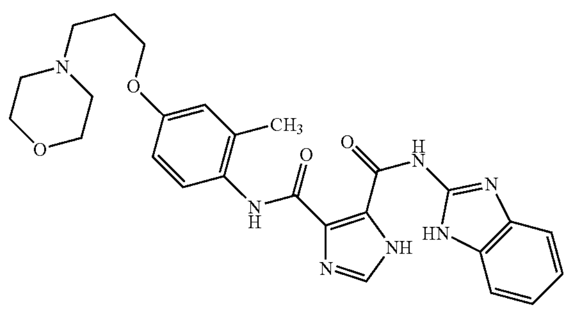 | N⁵-1H-benzimidazol-2-yl-N⁴-{2-methyl-4-[(3-morpholin-4-ylpropyl)oxy]phenyl}-1H-imidazole-4,5-dicarboxamide |
| 177 | 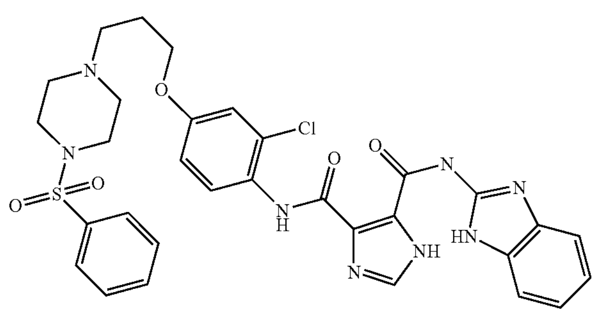 | N⁵-1H-benzimidazol-2-yl-N⁴-[2-chloro-4-({3-[4-(phenylsulfonyl)piperazin-1-yl]propyl}oxy)phenyl]-1H-imidazole-4,5-dicarboxamide |
| 178 | 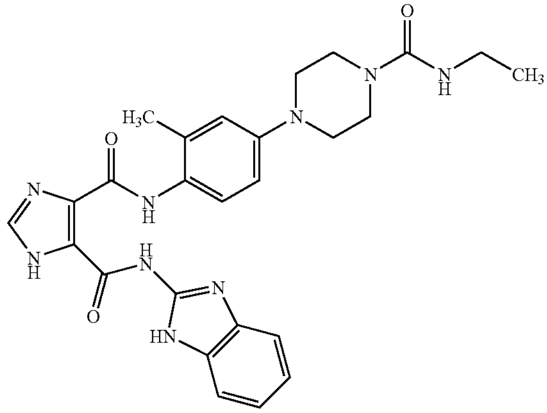 | N⁵-1H-benzimidazol-2-yl-N⁴-(4-{4-[(ethylamino)carbonyl]piperazin-1-yl}-2-methylphenyl)-1H-imidazole-4,5-dicarboxamide |

| Cpd No. | Structure | Name |
|---|---|---|
| 179 | 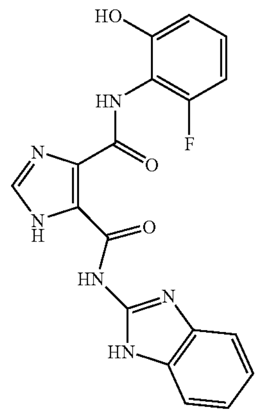 | $N^5$-1H-benzimidazol-2-yl-$N^4$-(2-fluoro-6-hydroxyphenyl)-1H-imidazole-4,5-dicarboxamide |
| 180 | 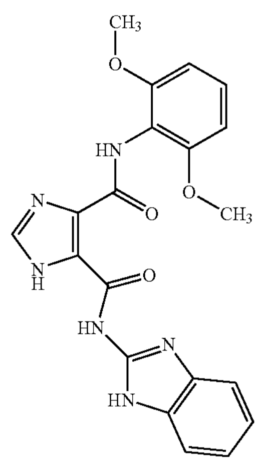 | $N^5$-1H-benzimidazol-2-yl-$N^4$-[2,6-bis(methyloxy)phenyl]-1H-imidazole-4,5-dicarboxamide |
| 181 | 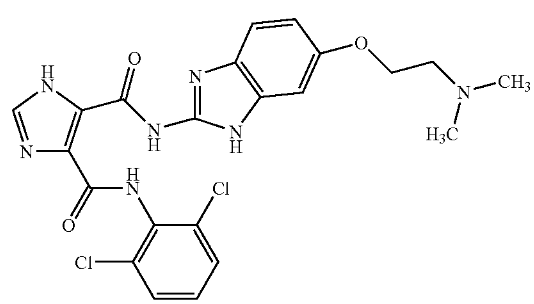 | $N^4$-(2,6-dichlorophenyl)-$N^5$-(6-{[2-(dimethylamino)ethyl]oxy}-1H-benzimidazol-2-yl)-1H-imidazole-4,5-dicarboxamide |
| 182 | 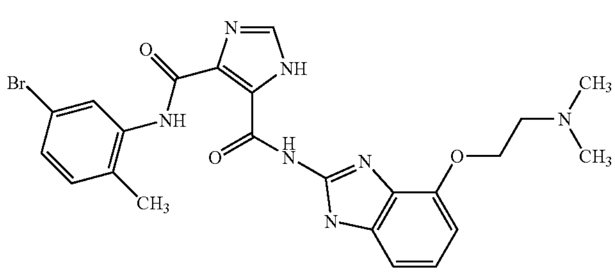 | $N^4$-(5-bromo-2-methylphenyl)-$N^5$-(4-{[2-(dimethylamino)ethyl]oxy}-1H-benzimidazol-2-yl)-1H-imidazole-4,5-dicarboxamide |

TABLE 1-continued

| Cpd No. | Structure | Name |
|---|---|---|
| 183 | 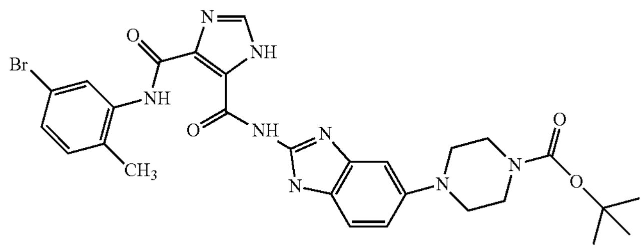 | 1,1-dimethylethyl 4-(2-{[(4-{[(5-bromo-2-methylphenyl)amino]carbonyl}-1H-imidazol-5-yl)carbonyl]amino}-1H-benzimidazol-5-yl)piperazine-1-carboxylate |
| 184 | 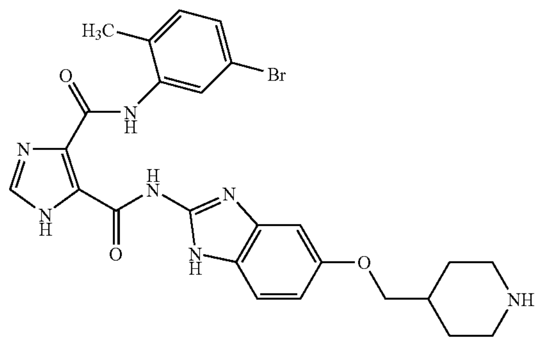 | $N^4$-(5-bromo-2-methylphenyl)-$N^5$-{5-[(piperidin-4-ylmethyl)oxy]-1H-benzimidazol-2-yl}-1H-imidazole-4,5-dicarboxamide |
| 185 | 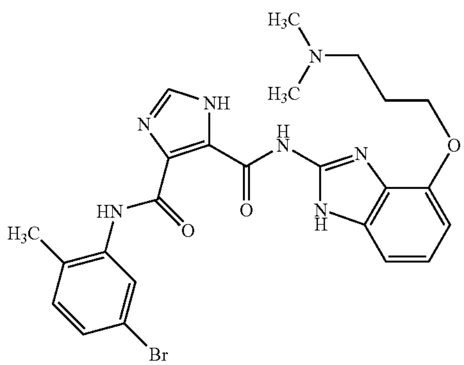 | $N^4$-(5-bromo-2-methylphenyl)-$N^5$-(4-{[3-(dimethylamino)propyl]oxy}-1H-benzimidazol-2-yl)-1H-imidazole-4,5-dicarboxamide |
| 186 | 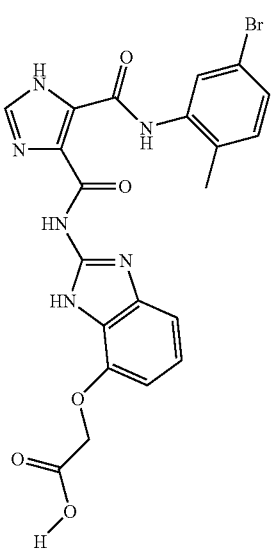 | [(2-{[(5-{[(5-bromo-2-methylphenyl)amino]carbonyl}-1H-imidazol-4-yl)carbonyl]amino}-1H-benzimidazol-7-yl)oxy]acetic acid |

TABLE 1-continued

| Cpd No. | Structure | Name |
|---|---|---|
| 187 | 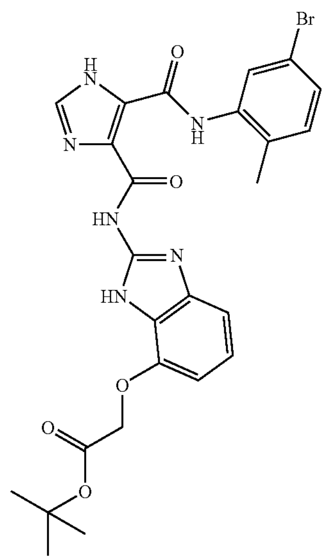 | 1,1-dimethylethyl[(2-{[(5-{[(5-bromo-2-methylphenyl)amino]carbonyl}-1H-imidazol-4-yl)carbonyl]amino}-1H-benzimidazol-7-yl)oxy]acetate |
| 188 | 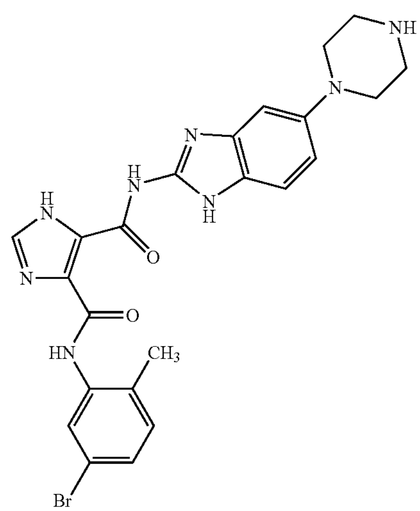 | $N^4$-(5-bromo-2-methylphenyl)-$N^5$-(5-piperazin-1-yl-1H-benzimidazol-2-yl)-1H-imidazole-4,5-dicarboxamide |
| 189 | 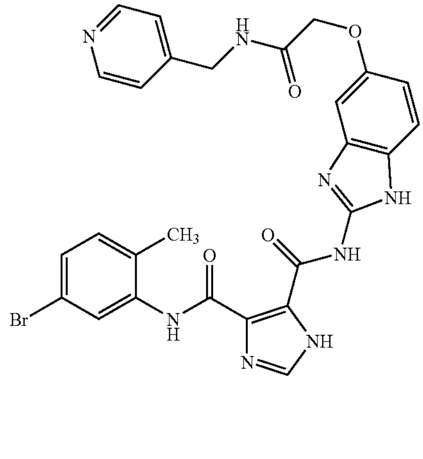 | $N^4$-(5-bromo-2-methylphenyl)-$N^5$-[5-({2-oxo-2-[(pyridin-4-ylmethyl)amino]ethyl}oxy)-1H-benzimidazol-2-yl]-1H-imidazole-4,5-dicarboxamide |

| Cpd No. | Structure | Name |
|---|---|---|
| 190 | 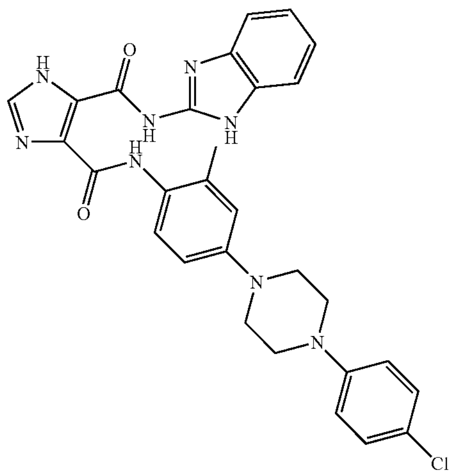 | $N^5$-1H-benzimidazol-2-yl-$N^4$-{4-[4-(4-chlorophenyl)piperazin-1-yl]-2-methylphenyl}-1H-imidazole-4,5-dicarboxamide |
| 191 | 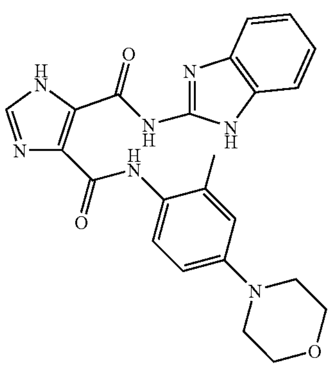 | $N^5$-1H-benzimidazol-2-yl-$N^4$-(2-methyl-4-morpholin-4-ylphenyl)-1H-imidazole-4,5-dicarboxamide |
| 192 | 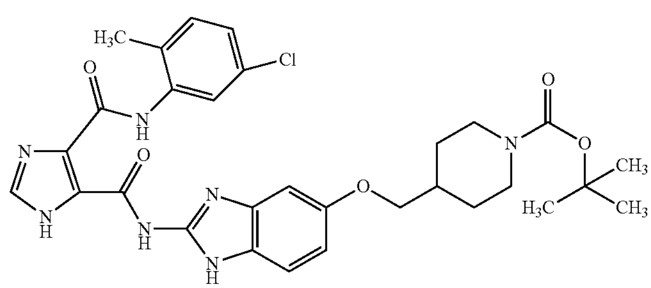 | 1,1-dimethylethyl 4-{[(2-{[(4-{[(5-chloro-2-methylphenyl)amino]carbonyl}-1H-imidazol-5-yl)carbonyl]amino}-1H-benzimidazol-5-yl)oxy]methyl}piperidine-1-carboxylate |

| Cpd No. | Structure | Name |
|---|---|---|
| 193 | 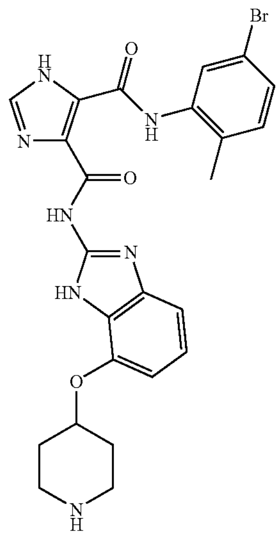 | $N^5$-(5-bromo-2-methylphenyl)-$N^4$-[7-(piperidin-4-yloxy)-1H-benzimidazol-2-yl]-1H-imidazole-4,5-dicarboxamide |
| 194 | 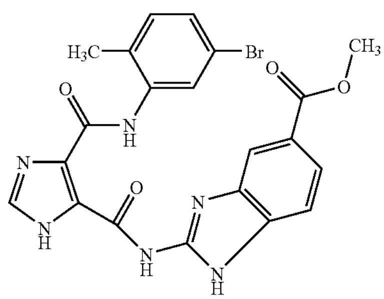 | methyl 2-{[(4-{[(5-bromo-2-methylphenyl)amino]carbonyl}-1H-imidazol-5-yl)carbonyl]amino}-1H-benzimidazole-5-carboxylate |
| 195 | 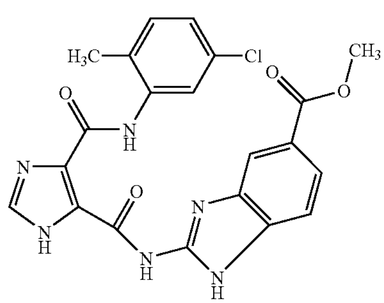 | methyl 2-{[(4-{[(5-chloro-2-methylphenyl)amino]carbonyl}-1H-imidazol-5-yl)carbonyl]amino}-1H-benzimidazole-5-carboxylate |
| 196 | 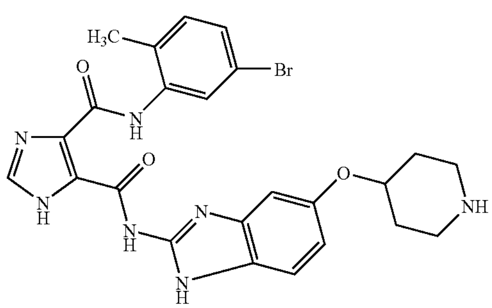 | $N^4$-(5-bromo-2-methylphenyl)-$N^5$-[5-(piperidin-4-yloxy)-1H-benzimidazol-2-yl]-1H-imidazole-4,5-dicarboxamide |

TABLE 1-continued

| Cpd No. | Structure | Name |
|---|---|---|
| 197 | 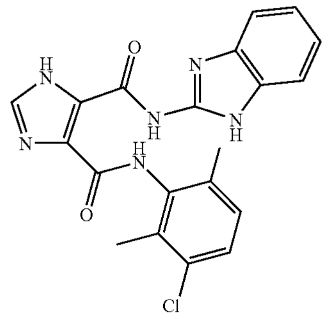 | N5-1H-benzimidazol-2-yl-N4-(3-chloro-2,6-dimethylphenyl)-1H-imidazole-4,5-dicarboxamide |
| 198 | 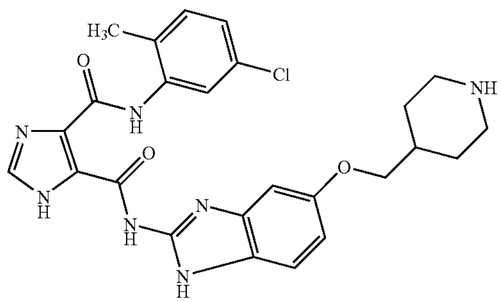 | N4-(5-chloro-2-methylphenyl)-N5-{5-[(piperidin-4-ylmethyl)oxy]-1H-benzimidazol-2-yl}-1H-imidazole-4,5-dicarboxamide |
| 199 | 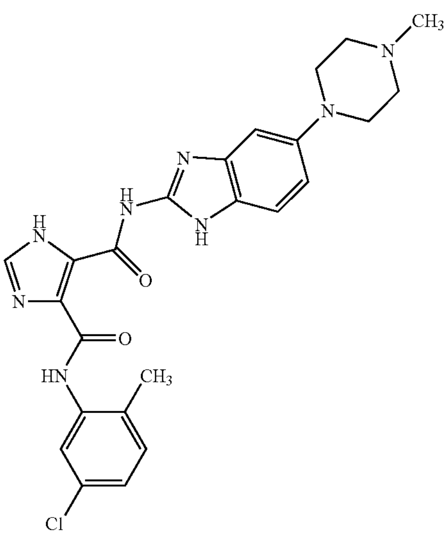 | N4-(5-chloro-2-methylphenyl)-N5-[5-(4-methylpiperazin-1-yl)-1H-benzimidazol-2-yl]-1H-imidazole-4,5-dicarboxamide |
| 200 | 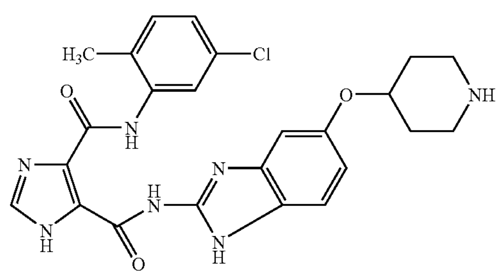 | N4-(5-chloro-2-methylphenyl)-N5-[5-(piperidin-4-yloxy)-1H-benzimidazol-2-yl]-1H-imidazole-4,5-dicarboxamide |

TABLE 1-continued

| Cpd No. | Structure | Name |
|---|---|---|
| 201 | 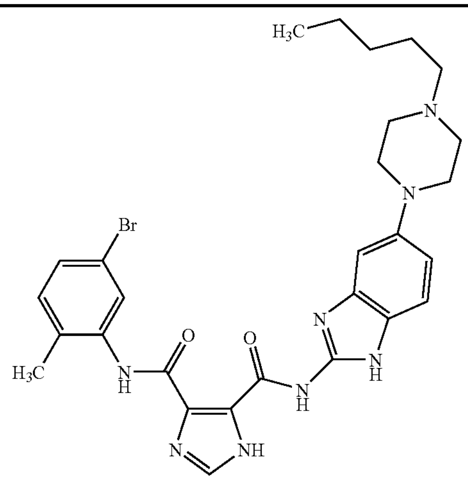 | $N^4$-(5-bromo-2-methylphenyl)-$N^5$-[5-(4-pentylpiperazin-1-yl)-1H-benzimidazol-2-yl]-1H-imidazole-4,5-dicarboxamide |
| 202 | 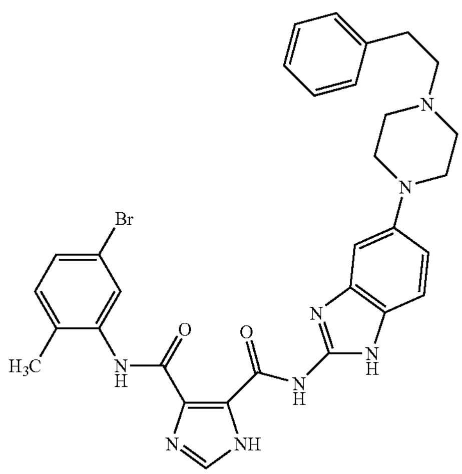 | $N^4$-(5-bromo-2-methylphenyl)-$N^5$-{5-[4-(2-phenylethyl)piperazin-1-yl]-1H-benzimidazol-2-yl}-1H-imidazole-4,5-dicarboxamide |
| 203 | 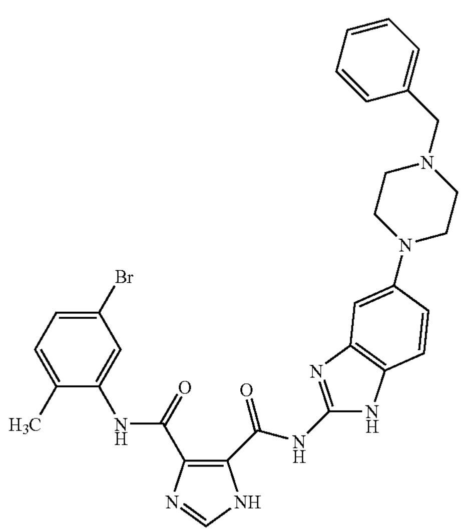 | $N^4$-(5-bromo-2-methylphenyl)-$N^5$-{5-[4-(phenylmethyl)piperazin-1-yl]-1H-benzimidazol-2-yl}-1H-imidazole-4,5-dicarboxamide |

TABLE 1-continued
| Cpd No. | Structure | Name |
|---|---|---|
| 204 | 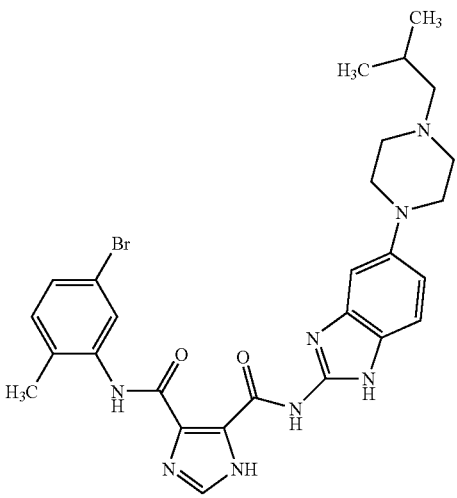 | N[4]-(5-bromo-2-methylphenyl)-N[5]-{5-[4-(2-methylpropyl)piperazin-1-yl]-1H-benzimidazol-2-yl}-1H-imidazole-4,5-dicarboxamide |
| 205 | 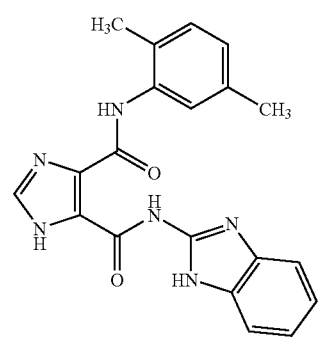 | N[5]-1H-benzimidazol-2-yl-N[4]-(2,5-dimethylphenyl)-1H-imidazole-4,5-dicarboxamide |
| 206 | 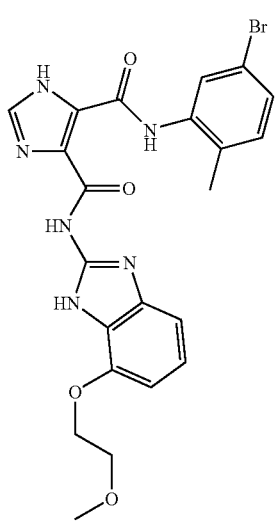 | N[5]-(5-bromo-2-methylphenyl)-N[4]-(7-{[2-(methyloxy)ethyl]oxy}-1H-benzimidazol-2-yl)-1H-imidazole-4,5-dicarboxamide |

TABLE 1-continued

| Cpd No. | Structure | Name |
|---|---|---|
| 207 | 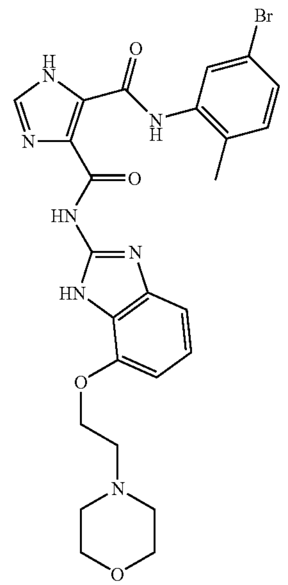 | $N^5$-(5-bromo-2-methylphenyl)-$N^4$-{7-[(2-morpholin-4-ylethyl)oxy]-1H-benzimidazol-2-yl}-1H-imidazole-4,5-dicarboxamide |
| 208 | 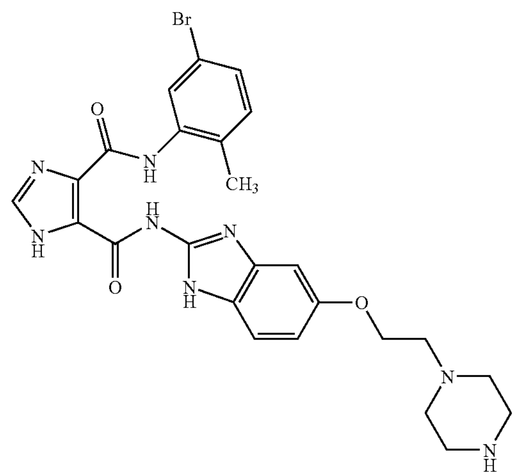 | $N^4$-(5-bromo-2-methylphenyl)-$N^5$-{5-[(2-piperazin-1-ylethyl)oxy]-1H-benzimidazol-2-yl}-1H-imidazole-4,5-dicarboxamide |
| 209 | 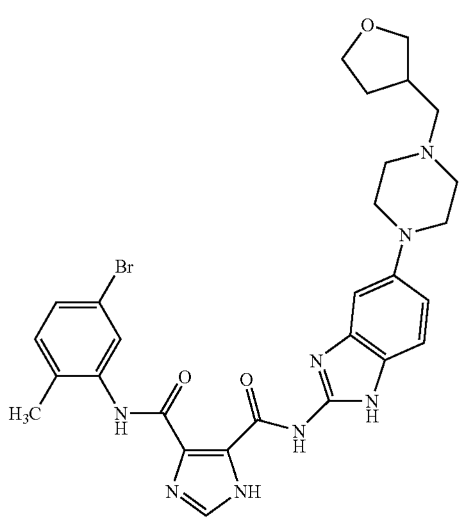 | $N^4$-(5-bromo-2-methylphenyl)-$N^5$-{5-[4-(tetrahydrofuran-3-ylmethyl)piperazin-1-yl]-1H-benzimidazol-2-yl}-1H-imidazole-4,5-dicarboxamide |

| Cpd No. | Structure | Name |
|---|---|---|
| 210 | 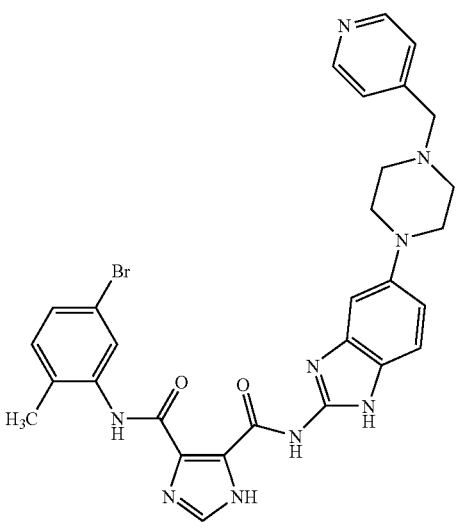 | $N^4$-(5-bromo-2-methylphenyl)-$N^5$-{5-[4-(pyridin-4-ylmethyl)piperazin-1-yl]-1H-benzimidazol-2-yl}-1H-imidazole-4,5-dicarboxamide |
| 211 | 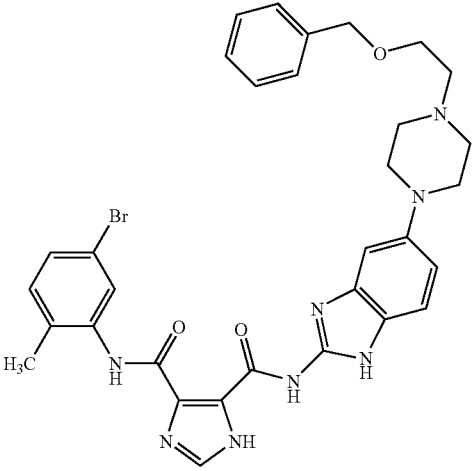 | $N^4$-(5-bromo-2-methylphenyl)-$N^5$-[5-(4-{2-[(phenylmethyl)oxy]ethyl}piperazin-1-yl)-1H-benzimidazol-2-yl]-1H-imidazole-4,5-dicarboxamide |
| 212 | 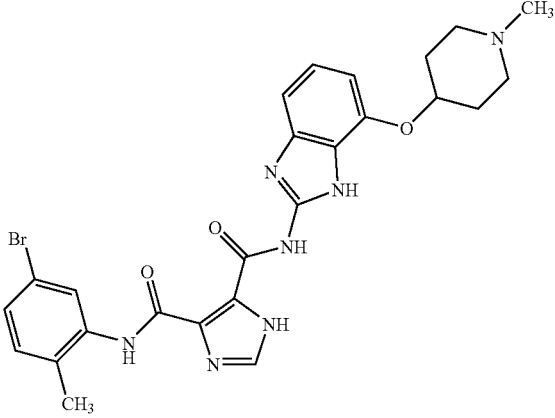 | $N^4$-(5-bromo-2-methylphenyl)-$N^5$-{7-[(1-methylpiperidin-4-yl)oxy]-1H-benzimidazol-2-yl}-1H-imidazole-4,5-dicarboxamide |

TABLE 1-continued

| Cpd No. | Structure | Name |
|---|---|---|
| 213 | 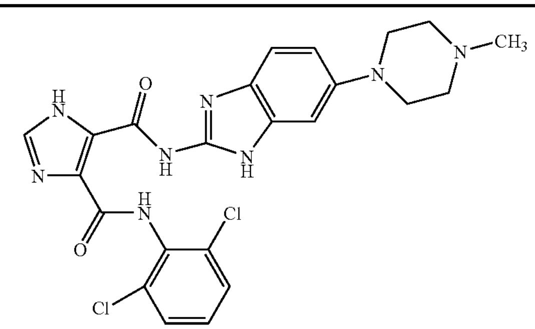 | $N^4$-(2,6-dichlorophenyl)-$N^5$-[6-(4-methylpiperazin-1-yl)-1H-benzimidazol-2-yl]-1H-imidazole-4,5-dicarboxamide |
| 214 | 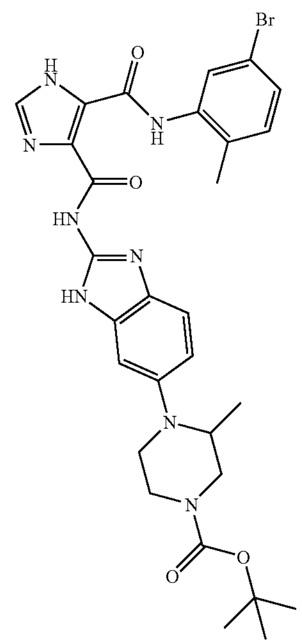 | 1,1-dimethylethyl 4-(2-{[(5-{[(5-bromo-2-methylphenyl)amino]carbonyl}-1H-imidazol-4-yl)carbonyl]amino}-1H-benzimidazol-6-yl)-3-methylpiperazine-1-carboxylate |
| 215 | 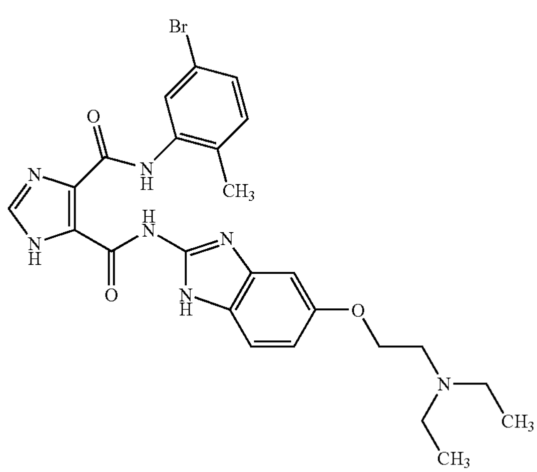 | $N^4$-(5-bromo-2-methylphenyl)-$N^5$-(5-{[2-(diethylamino)ethyl]oxy}-1H-benzimidazol-2-yl)-1H-imidazole-4,5-dicarboxamide |

TABLE 1-continued

| Cpd No. | Structure | Name |
|---|---|---|
| 216 | 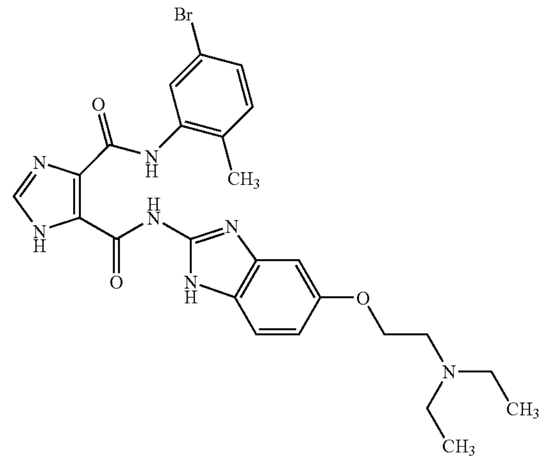 | $N^4$-(5-bromo-2-methylphenyl)-$N^5$-(5-{[2-(4-methylpiperazin-1-yl)ethyl]oxy}-1H-benzimidazol-2-yl)-1H-imidazole-4,5-dicarboxamide |
| 217 | 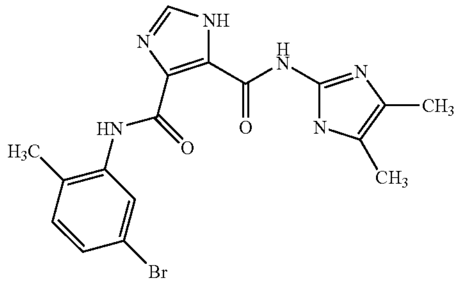 | $N^4$-(5-bromo-2-methylphenyl)-$N^5$-(4,5-dimethyl-1H-imidazol-2-yl)-1H-imidazole-4,5-dicarboxamide |
| 218 | 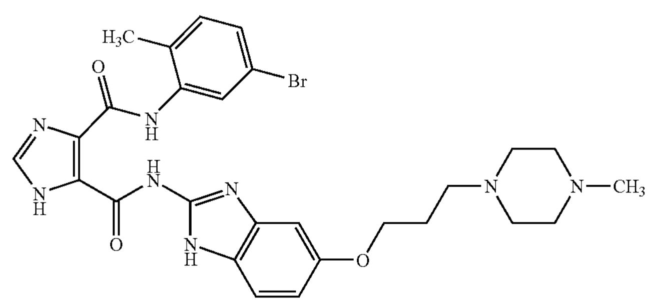 | $N^4$-(5-bromo-2-methylphenyl)-$N^5$-(5-{[3-(4-methylpiperazin-1-yl)propyl]oxy}-1H-benzimidazol-2-yl)-1H-imidazole-4,5-dicarboxamide |
| 219 | 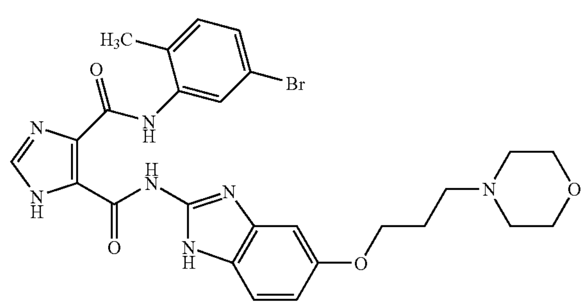 | $N^4$-(5-bromo-2-methylphenyl)-$N^5$-{5-[(3-morpholin-4-ylpropyl)oxy]-1H-benzimidazol-2-yl}-1H-imidazole-4,5-dicarboxamide |

TABLE 1-continued

| Cpd No. | Structure | Name |
| --- | --- | --- |
| 220 | 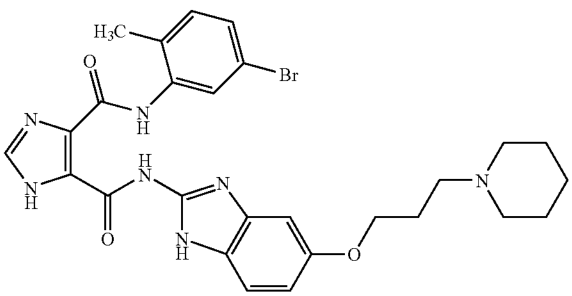 | $N^4$-(5-bromo-2-methylphenyl)-$N^5$-{5-[(3-piperidin-1-ylpropyl)oxy]-1H-benzimidazol-2-yl}-1H-imidazole-4,5-dicarboxamide |
| 221 | 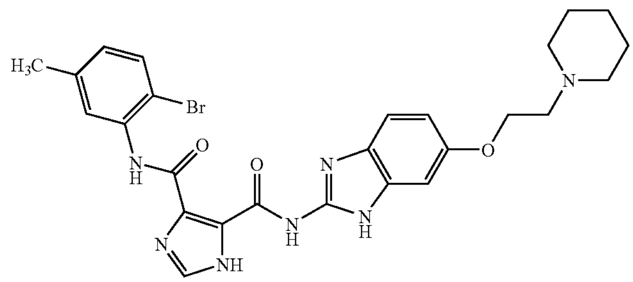 | $N^4$-(2-bromo-5-methylphenyl)-$N^5$-{6-[(2-piperidin-1-ylethyl)oxy]-1H-benzimidazol-2-yl}-1H-imidazole-4,5-dicarboxamide |
| 222 | 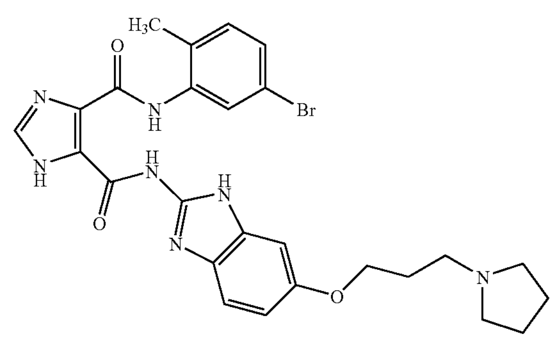 | $N^4$-(5-bromo-2-methylphenyl)-$N^5$-{6-[(3-pyrrolidin-1-ylpropyl)oxy]-1H-benzimidazol-2-yl}-1H-imidazole-4,5-dicarboxamide |
| 223 | 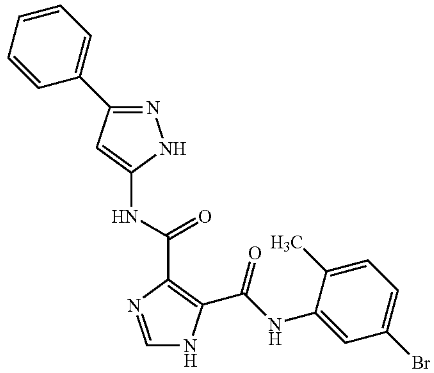 | $N^5$-(5-bromo-2-methylphenyl)-$N^4$-(3-phenyl-1H-pyrazol-5-yl)-1H-imidazole-4,5-dicarboxamide |

TABLE 1-continued

| Cpd No. | Structure | Name |
|---|---|---|
| 224 | 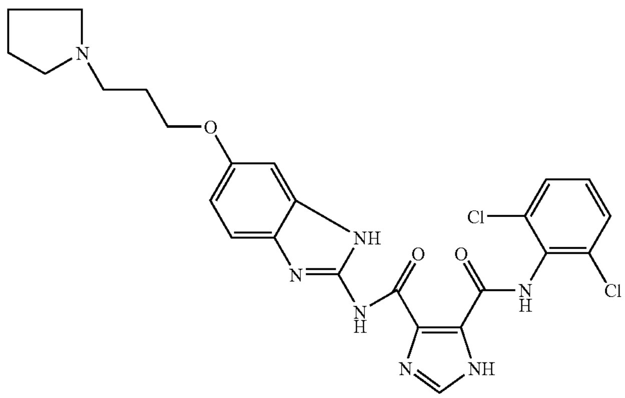 | $N^5$-(2,6-dichlorophenyl)-$N^4$-{6-[(3-pyrrolidin-1-ylpropyl)oxy]-1H-benzimidazol-2-yl}-1H-imidazole-4,5-dicarboxamide |
| 225 | 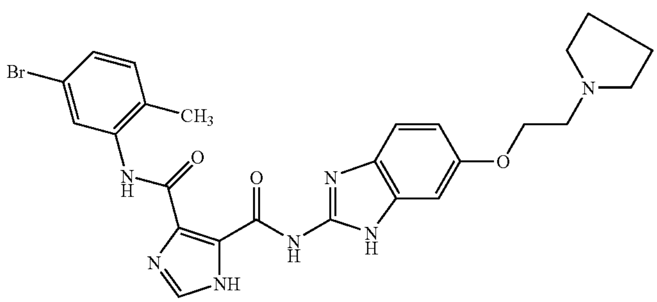 | $N^4$-(5-bromo-2-methylphenyl)-$N^5$-{6-[(2-pyrrolidin-1-ylethyl)oxy]-1H-benzimidazol-2-yl}-1H-imidazole-4,5-dicarboxamide |
| 226 | 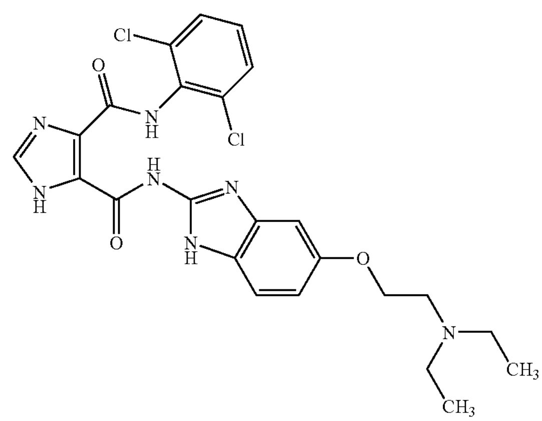 | $N^4$-(2,6-dichlorophenyl)-$N^5$-(5-{[2-(diethylamino)ethyl]oxy}-1H-benzimidazol-2-yl)-1H-imidazole-4,5-dicarboxamide |
| 227 | 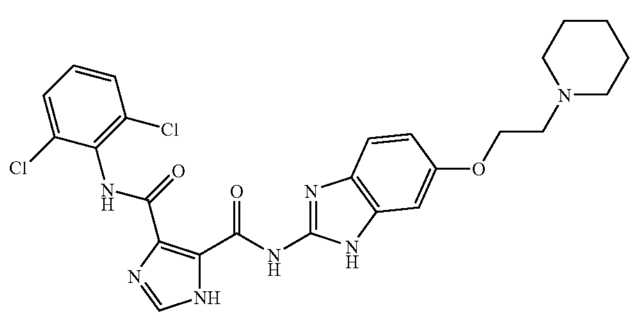 | $N^4$-(2,6-dichlorophenyl)-$N^5$-{6-[(2-piperidin-1-ylethyl)oxy]-1H-benzimidazol-2-yl}-1H-imidazole-4,5-dicarboxamide |

TABLE 1-continued

| Cpd No. | Structure | Name |
|---|---|---|
| 228 | 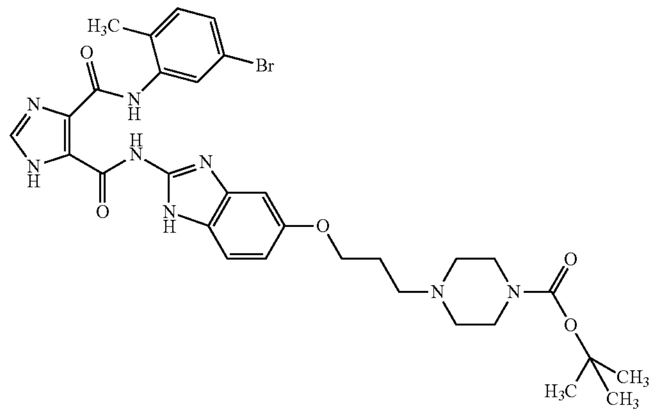 | 1,1-dimethylethyl 4-{3-[(2-{[(4-{[(5-bromo-2-methylphenyl)amino]carbonyl}-1H-imidazol-5-yl)carbonyl]amino}-1H-benzimidazol-5-yl)oxy]propyl}piperazine-1-carboxylate |
| 229 | 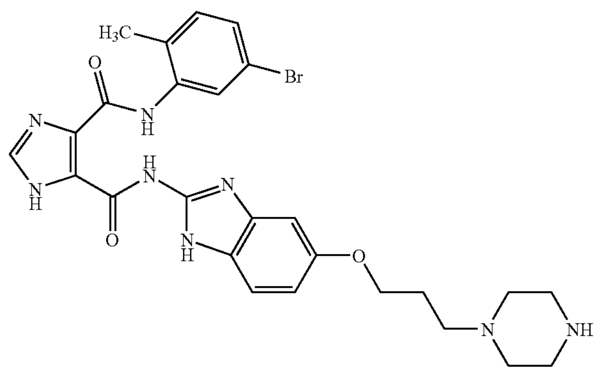 | $N^4$-(5-bromo-2-methylphenyl)-$N^5$-{5-[(3-piperazin-1-ylpropyl)oxy]-1H-benzimidazol-2-yl}-1H-imidazole-4,5-dicarboxamide |
| 230 | 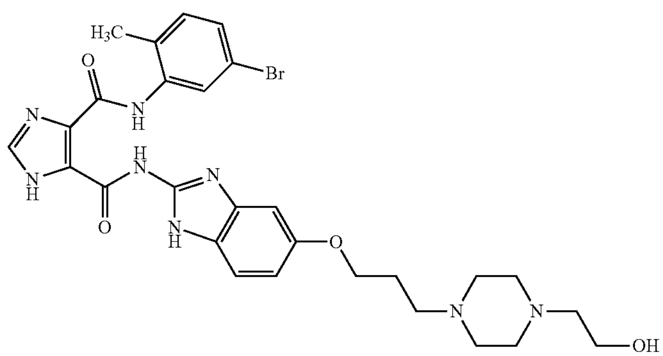 | $N^4$-(5-bromo-2-methylphenyl)-$N^5$-[5-({3-[4-(2-hydroxyethyl)piperazin-1-yl]propyl}oxy)-1H-benzimidazol-2-yl]-1H-imidazole-4,5-dicarboxamide |
| 231 | 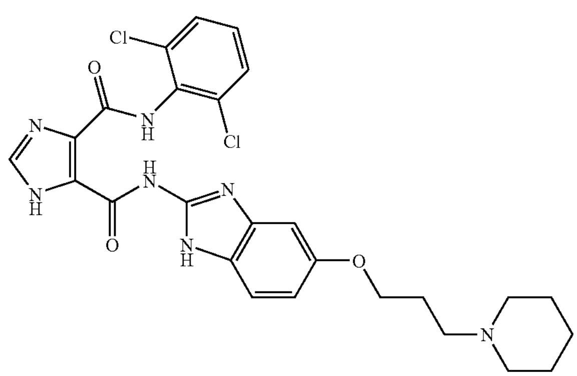 | $N^4$-(2,6-dichlorophenyl)-$N^5$-{5-[(3-piperidin-1-ylpropyl)oxy]-1H-benzimidazol-2-yl}-1H-imidazole-4,5-dicarboxamide |

TABLE 1-continued

| Cpd No. | Structure | Name |
|---|---|---|
| 232 | 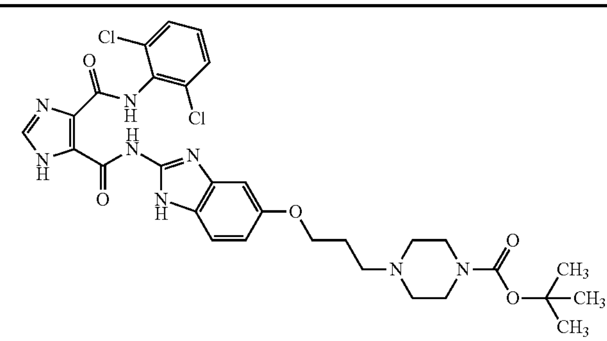 | 1,1-dimethylethyl 4-{3-[(2-{[(4-{[(2,6-dichlorophenyl)amino]carbonyl}-1H-imidazol-5-yl)carbonyl]amino}-1H-benzimidazol-5-yl)oxy]propyl}piperazine-1-carboxylate |
| 233 | 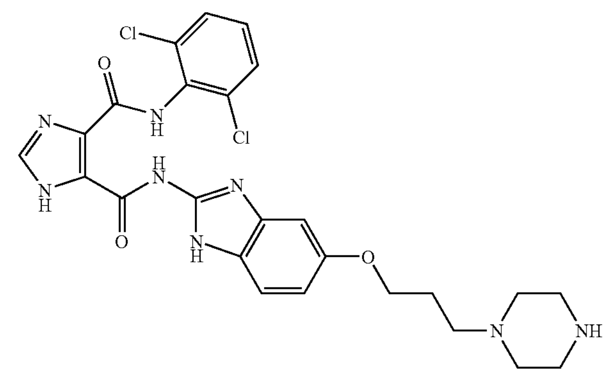 | $N^4$-(2,6-dichlorophenyl)-$N^5$-{5-[(3-piperazin-1-ylpropyl)oxy]-1H-benzimidazol-2-yl}-1H-imidazole-4,5-dicarboxamide |
| 234 | 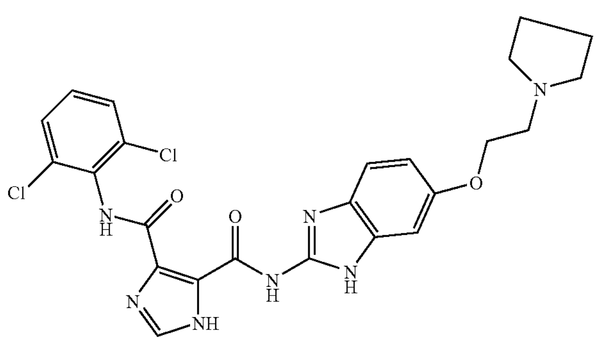 | $N^4$-(2,6-dichlorophenyl)-$N^5$-{6-[(2-pyrrolidin-1-ylethyl)oxy]-1H-benzimidazol-2-yl}-1H-imidazole-4,5-dicarboxamide |
| 235 | 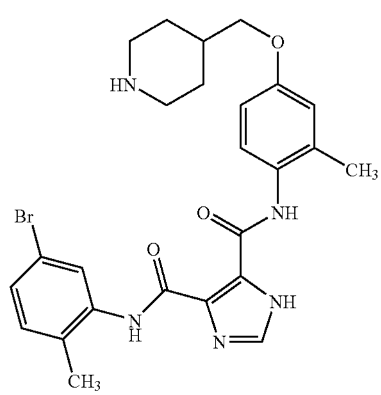 | $N^4$-(5-bromo-2-methylphenyl)-$N^5$-{2-methyl-4-[(piperidin-4-ylmethyl)oxy]phenyl}-1H-imidazole-4,5-dicarboxamide |

TABLE 1-continued

| Cpd No. | Structure | Name |
|---|---|---|
| 236 | 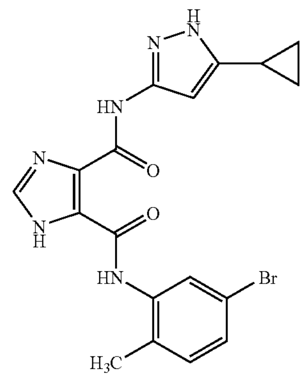 | $N^5$-(5-bromo-2-methylphenyl)-$N^4$-(5-cyclopropyl-1H-pyrazol-3-yl)-1H-imidazole-4,5-dicarboxamide |
| 237 | 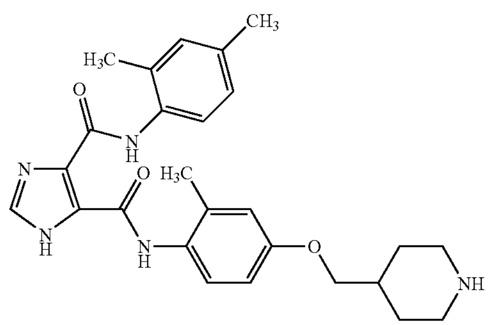 | $N^4$-(2,4-dimethylphenyl)-$N^5$-{2-methyl-4-[(piperidin-4-ylmethyl)oxy]phenyl}-1H-imidazole-4,5-dicarboxamide |
| 238 | 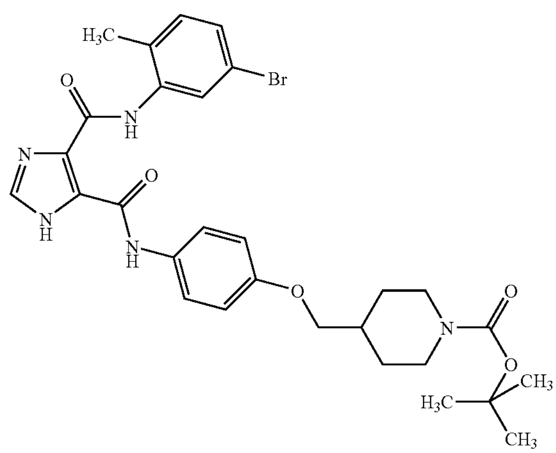 | 1,1-dimethylethyl 4-{[(4-{[(4-{[(5-bromo-2-methylphenyl)amino]carbonyl}-1H-imidazol-5-yl)carbonyl]amino}phenyl)oxy]methyl}piperidine-1-carboxylate |
| 239 | 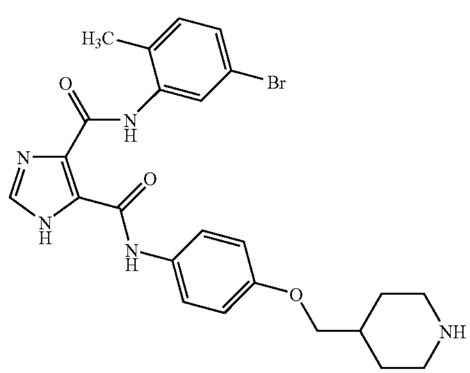 | $N^4$-(5-bromo-2-methylphenyl)-$N^5$-{4-[(piperidin-4-ylmethyl)oxy]phenyl}-1H-imidazole-4,5-dicarboxamide |

TABLE 1-continued

| Cpd No. | Structure | Name |
|---|---|---|
| 240 | 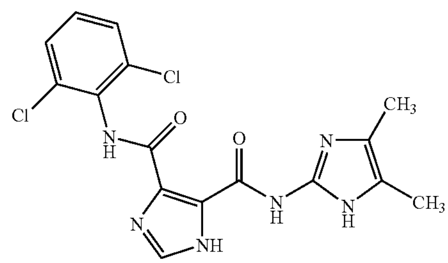 | N[4]-(2,6-dichlorophenyl)-N[5]-(4,5-dimethyl-1H-imidazol-2-yl)-1H-imidazole-4,5-dicarboxamide |
| 241 | 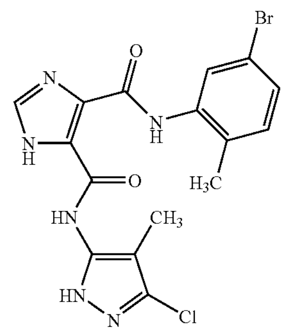 | N[4]-(5-bromo-2-methylphenyl)-N[5]-(3-chloro-4-methyl-1H-pyrazol-5-yl)-1H-imidazole-4,5-dicarboxamide |
| 242 | 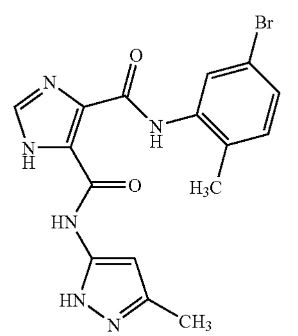 | N[4]-(5-bromo-2-methylphenyl)-N[5]-(3-methyl-1H-pyrazol-5-yl)-1H-imidazole-4,5-dicarboxamide |
| 243 | 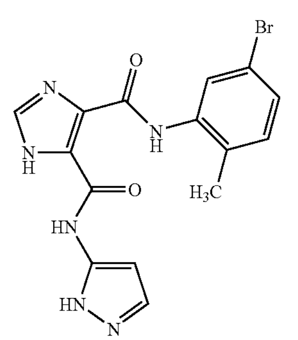 | N[4]-(5-bromo-2-methylphenyl)-N[5]-1H-pyrazol-5-yl-1H-imidazole-4,5-dicarboxamide |

TABLE 1-continued

| Cpd No. | Structure | Name |
|---|---|---|
| 244 | 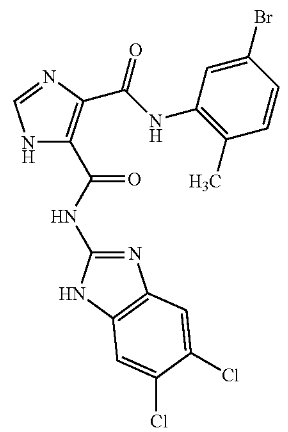 | $N^4$-(5-bromo-2-methylphenyl)-$N^5$-(5,6-dichloro-1H-benzimidazol-2-yl)-1H-imidazole-4,5-dicarboxamide |
| 245 | 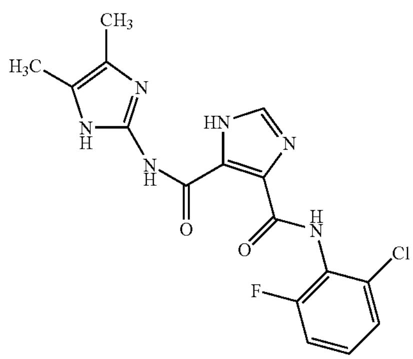 | $N^4$-(2-chloro-6-fluorophenyl)-$N^5$-(4,5-dimethyl-1H-imidazol-2-yl)-1H-imidazole-4,5-dicarboxamide |
| 246 | 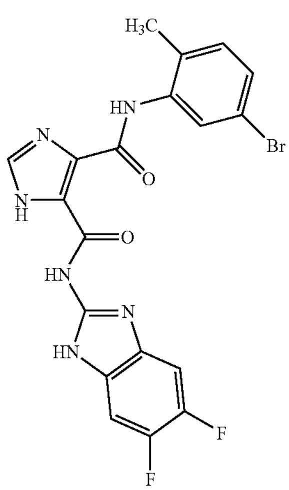 | $N^4$-(5-bromo-2-methylphenyl)-$N^5$-(5,6-difluoro-1H-benzimidazol-2-yl)-1H-imidazole-4,5-dicarboxamide |
| 247 | 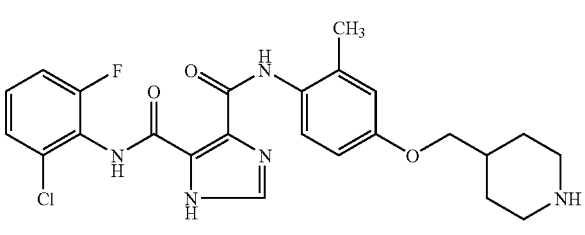 | $N^5$-(2-chloro-6-fluorophenyl)-$N^4$-{2-methyl-4-[(piperidin-4-ylmethyl)oxy]phenyl}-1H-imidazole-4,5-dicarboxamide |

TABLE 1-continued

| Cpd No. | Structure | Name |
|---|---|---|
| 248 | 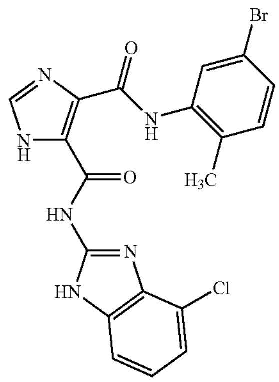 | $N^4$-(5-bromo-2-methylphenyl)-$N^5$-(4-chloro-1H-benzimidazol-2-yl)-1H-imidazole-4,5-dicarboxamide |
| 249 | 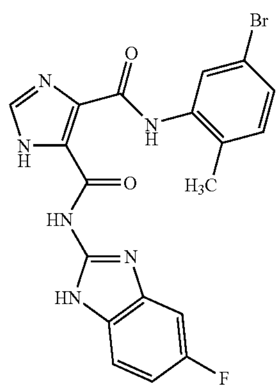 | $N^4$-(5-bromo-2-methylphenyl)-$N^5$-(5-fluoro-1H-benzimidazol-2-yl)-1H-imidazole-4,5-dicarboxamide |
| 250 | 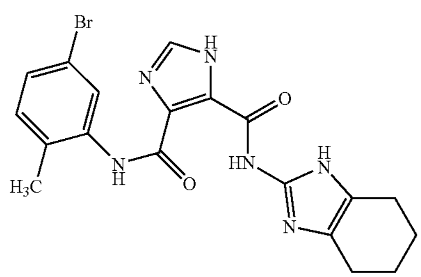 | $N^4$-(5-bromo-2-methylphenyl)-$N^5$-(4,5,6,7-tetrahydro-1H-benzimidazol-2-yl)-1H-imidazole-4,5-dicarboxamide |
| 251 | 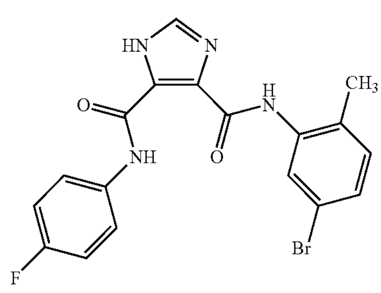 | $N^4$-(5-bromo-2-methylphenyl)-$N^5$-(4-fluorophenyl)-1H-imidazole-4,5-dicarboxamide |

TABLE 1-continued

| Cpd No. | Structure | Name |
|---|---|---|
| 252 | 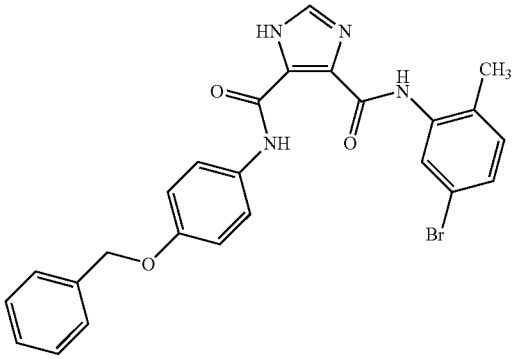 | $N^4$-(5-bromo-2-methylphenyl)-$N^5$-{4-[(phenylmethyl)oxy]phenyl}-1H-imidazole-4,5-dicarboxamide |
| 253 | 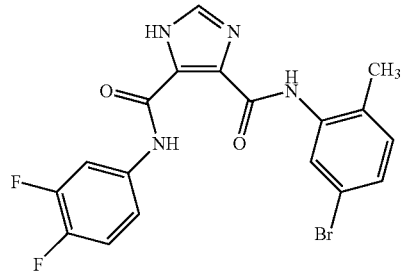 | $N^4$-(5-bromo-2-methylphenyl)-$N^5$-(3,4-difluorophenyl)-1H-imidazole-4,5-dicarboxamide |
| 254 | 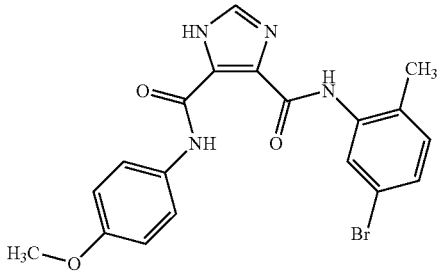 | $N^4$-(5-bromo-2-methylphenyl)-$N^5$-[4-(methyloxy)phenyl]-1H-imidazole-4,5-dicarboxamide |
| 255 | 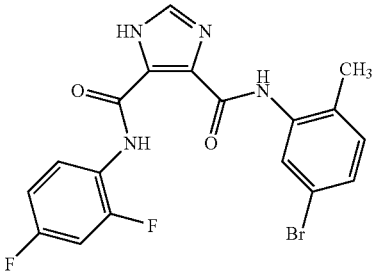 | $N^4$-(5-bromo-2-methylphenyl)-$N^5$-(2,4-difluorophenyl)-1H-imidazole-4,5-dicarboxamide |
| 256 | 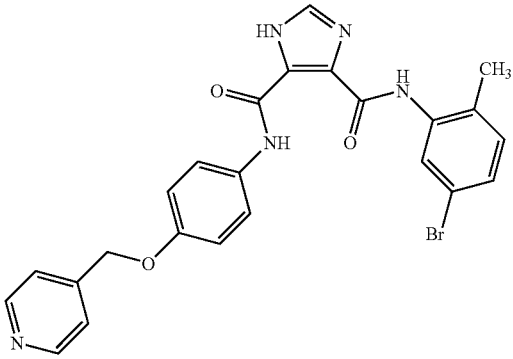 | $N^4$-(5-bromo-2-methylphenyl)-$N^5$-{4-[(pyridin-4-ylmethyl)oxy]phenyl}-1H-imidazole-4,5-dicarboxamide |

TABLE 1-continued

| Cpd No. | Structure | Name |
|---|---|---|
| 257 | 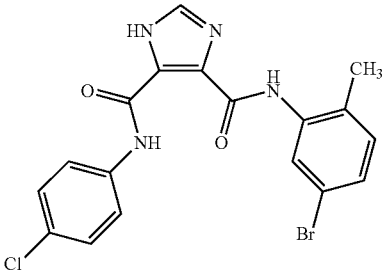 | $N^4$-(5-bromo-2-methylphenyl)-$N^5$-(4-chlorophenyl)-1H-imidazole-4,5-dicarboxamide |
| 258 | 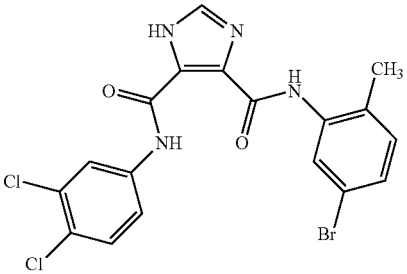 | $N^4$-(5-bromo-2-methylphenyl)-$N^5$-(3,4-dichlorophenyl)-1H-imidazole-4,5-dicarboxamide |
| 259 | 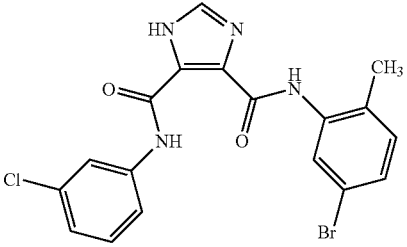 | $N^4$-(5-bromo-2-methylphenyl)-$N^5$-(3-chlorophenyl)-1H-imidazole-4,5-dicarboxamide |
| 260 | 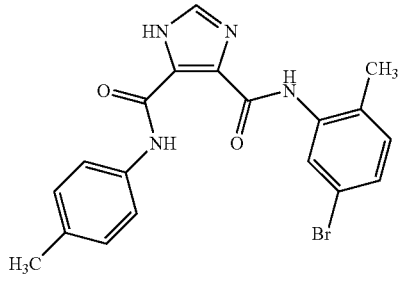 | $N^4$-(5-bromo-2-methylphenyl)-$N^5$-(4-methylphenyl)-1H-imidazole-4,5-dicarboxamide |
| 261 | 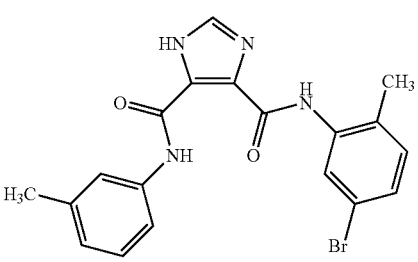 | $N^4$-(5-bromo-2-methylphenyl)-$N^5$-(3-methylphenyl)-1H-imidazole-4,5-dicarboxamide |

TABLE 1-continued

| Cpd No. | Structure | Name |
|---|---|---|
| 262 | 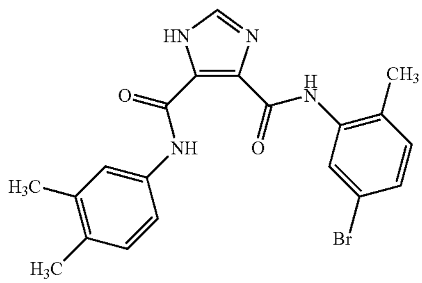 | $N^4$-(5-bromo-2-methylphenyl)-$N^5$-(3,4-dimethylphenyl)-1H-imidazole-4,5-dicarboxamide |
| 263 | 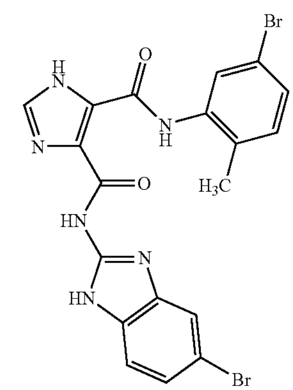 | $N^4$-(5-bromo-1H-benzimidazol-2-yl)-$N^5$-(5-bromo-2-methylphenyl)-1H-imidazole-4,5-dicarboxamide |
| 264 | 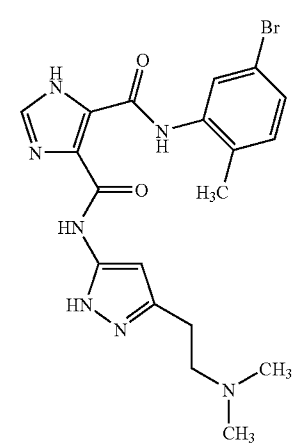 | $N^5$-(5-bromo-2-methylphenyl)-$N^4$-{3-[2-(dimethylamino)ethyl]-1H-pyrazol-5-yl}-1H-imidazole-4,5-dicarboxamide |

TABLE 1-continued

| Cpd No. | Structure | Name |
|---|---|---|
| 265 | (structure) | $N^4$-[2-chloro-4-(piperidin-4-yloxy)phenyl]-$N^5$-(4,5-dimethyl-1H-imidazol-2-yl)-1H-imidazole-4,5-dicarboxamide |

The compounds in the table above can be prepared using art recognized methods.

ABBREVIATIONS AND DEFINITIONS

The following abbreviations and terms have the indicated meanings throughout:

| Abbreviation | Meaning |
|---|---|
| Ac | Acetyl |
| ° C. | degrees Celsius |
| CBZ | CarboBenZoxy = benzyloxycarbonyl |
| D | Doublet |
| DIPEA | N,N-diisopropylethylamine |
| DMF | N,N-dimethylformamide |
| DMSO | dimethyl sulfoxide |
| EI | Electron Impact ionization |
| Et | Ethyl |
| G | gram(s) |
| GC | gas chromatography |
| h or hr | hour(s) |
| HOAc | acetic acid |
| HOBt | Hydroxybenzotriazole |
| HPLC | high pressure liquid chromatography |
| l or L | liter(s) |
| M | molar or molarity |
| M | Multiplet |
| Me | Methyl |
| Mesyl | Methanesulfonyl |
| Mg or mg | milligram(s) |
| MHz | megahertz (frequency) |
| Min | minute(s) |
| mL | milliliter(s) |
| mM | Millimolar |
| Mmol | millimole(s) |
| Mol or mol | mole(s) |
| MS | mass spectral analysis |
| MTBE | methyl t-butyl ether |
| N | normal or normality |
| NBS | N-bromosuccinimide |
| NCS | N-chlorosuccinimide |
| nM | Nanomolar |
| NMO | N-methylmorpholine oxide |
| NMR | nuclear magnetic resonance spectroscopy |
| Ph | Phenyl |

| Abbreviation | Meaning |
|---|---|
| PhOH | Phenol |
| PPTS | Pyridinium p-toluenesulfonate |
| Q | Quartet |
| RT or rt | Room temperature |
| Sat'd | Saturated |
| S | Singlet |
| t | Triplet |
| TFA | trifluoroacetic acid |
| THF | Tetrahydrofuran |
| TMOF | trimethyl orthoformate |
| TMS | Trimethylsilyl |
| Tosyl | p-toluenesulfonyl |
| uL | microliter(s) |
| uM | Micromole(s) or micromolar |

DEFINITIONS

As used in the present specification, the following words and phrases are generally intended to have the meanings as set forth below, except to the extent that the context in which they are used indicates otherwise or they are expressly defined to mean something different.

The symbol "—" means a single bond, "=" means a double bond, "≡" means a triple bond, "----" means a single or double bond. When a group is depicted removed from its parent Formula, the "⌇" symbol will be used at the end of the bond which was theoretically cleaved in order to separate the group from its parent structural Formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual Formula as having a hydrogen or hydrogens as substitution (expressly defined hydrogen), for example, —$CH_2CH_2$—. It is understood by one of ordinary skill in the art that the aforementioned descriptive techniques are common in the chemical arts to provide brevity and simplicity to description of otherwise complex structures.

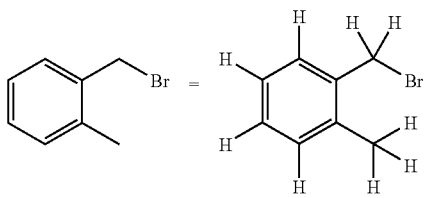

If a group "R" is depicted as "floating" on a ring system, as for example in the Formula:

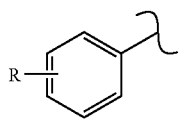

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the Formulae:

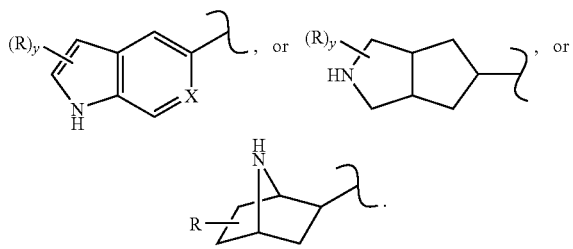

then, unless otherwise defined, a substituent "R" may reside on any atom of the fused ring system, assuming replacement of a depicted hydrogen (for example the —NH— in the Formula above), implied hydrogen (for example as in the Formula above, where the hydrogens are not shown but understood to be present), or expressly defined hydrogen (for example where in the Formula above, "X" equals =CH—) from one of the ring atoms, so long as a stable structure is formed. In the example depicted, the "R" group may reside on either the 5-membered or the 6-membered ring of the fused ring system. In the Formula depicted above, when y is 2 for example, then the two "R's" may reside on any two atoms of the ring system, again assuming each replaces a depicted, implied, or expressly defined hydrogen on the ring.

When a group "R" is depicted as existing on a ring system containing saturated carbons, as for example in the Formula:

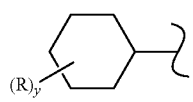

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the Formula:

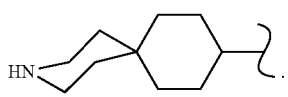

"($C_1$-$C_6$)alkyl" is intended to mean $C_1$-$C_6$ linear or branched structures and combinations thereof, inclusively. For example, "$C_6$ alkyl" can refer to an n-hexyl, iso-hexyl, and the like. "($C_1$-$C_6$)alkyl is intended to include "($C_1$-$C_3$) alkyl. Examples of lower alkyl groups include methyl, ethyl, propyl, isopropyl, butyl, s-butyl, t-butyl, isobutyl, pentyl, hexyl and the like. In this application, alkyl refers to alkanyl, alkenyl, and alkynyl residues (and combinations thereof); it is intended to include vinyl, allyl, isoprenyl, and the like. Thus when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-ynyl groups; and for example, "propyl" or "$C_3$ alkyl" each include n-propyl, propenyl, and isopropyl.

"($C_3$-$C_{10}$)cycloalkyl" means a non-aromatic mono- or multicyclic ring system comprising about 3 to 10 carbon atoms. ($C_3$-$C_{10}$)cycloalkyl is intended to include ($C_5$-$C_6$)cycloalkyl. Non-limiting examples of monocyclic cycloalkyls include cyclopropyl, cyclopentyl, cyclohexyl, cycloheptyl and the like. Non-limiting examples of multicyclic cycloalkyls include 1-decalin, norbornyl, adamantyl and the like. Cycloalkyls can be fused or bridge ring systems or spirocyclic systems.

"Alkylene" is a subset of alkyl and refers to straight or branched chain divalent group consisting solely of carbon and hydrogen atoms, containing no unsaturation and having from one to six carbon atoms, for example, methylene, ethylene, propylene, n-butylene and the like. Alkylene refers to the same residues as alkyl, but having two points of attachment and, specifically, fully saturated. Examples of alkylene include ethylene (—$CH_2CH_2$—), propylene (—$CH_2CH_2CH_2$—), and dimethylpropylene (—$CH_2C(CH_3)_2CH_2$—).

"Alkylidene" is a subset of alkyl and refers to a straight or branched chain unsaturated divalent group consisting solely of carbon and hydrogen atoms, having from two to six carbon atoms, for example, ethylidene, propylidene, n-butylidene, and the like. Alkylidene refers to the same residues as alkyl, but having two points of attachment and, specifically, double bond unsaturation. The unsaturation present includes at least one double bond.

"Alkylidyne" refers to a straight or branched chain unsaturated divalent group consisting solely of carbon and hydrogen atoms having from two to ten carbon atoms, for example, propylid-2-ynyl, n-butylid-1-ynyl, and the like. Alkylidyne is a subset of alkyl, referring to the same residues as alkyl, but having two points of attachment and, specifically, triple bond unsaturation. The unsaturation present includes at least one triple bond.

Any of the above groups, "alkylene," "alkylidene" and "alkylidyne," when optionally substituted, can contain alkyl substitution which itself contains unsaturation. For example, 2-(2-phenylethynyl-but-3-enyl)-naphthalene (IUPAC name) contains an n-butylid-3-ynyl group with a vinyl substituent at the 2-position of said group.

"$(C_1$-$C_6)$alkoxy" refers to the group O—$(C_1$-$C_6)$alkyl, wherein the term "$(C_1$-$C_6)$alkyl" is as defined hereinabove. "$(C_1$-$C_6)$alkoxy" is intended to include $(C_1$-$C_3)$alkoxy. Examples include methoxy, ethoxy, propoxy, isopropoxy, and the like.

"$(C_6$-$C_{10})$aryl" means a monovalent six- to ten-membered mono- or multicyclic ring, wherein the monocyclic ring is aromatic and at least one of the rings in the multicyclic ring is aromatic. "$(C_6$-$C_{10})$aryl" is intended to include "$(C_6)$aryl or phenyl". Representative non-limiting examples of aryl include phenyl, naphthyl, and indanyl, and the like.

Whenever two groups are connected such as "Arylalkyl," then the point of attachment to the parent moiety is the alkyl group.

"Arylalkyl" means a residue in which an aryl moiety, as defined above, is attached to a parent structure via one of an alkylene, alkylidene, or alkylidyne group. Examples include benzyl, phenethyl, phenylvinyl, phenylallyl and the like.

Whenever two groups are connected and depicts the point of attachment by a bond, such as "—$(C_1$-$C_6)$alkyl-$(C_6$-$C_{10})$aryl," then the point of attachment to the parent moiety is the $(C_1$-$C_6)$alkylene group by the bond.

"—$(C_1$-$C_6)$alkyl-$(C_6$-$C_{10})$aryl," is intended to mean a $(C_6$-$C_{10})$aryl moiety attached to a parent structure via $(C_1$-$C_6)$ alkylene group. Examples include benzyl, phenethyl, and the like.

In some examples, as appreciated by one of ordinary skill in the art, two adjacent groups on an aromatic system can be fused together to form a ring structure. The fused ring structure can contain heteroatoms and can be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems includes non-aromatic and aromatic systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the invention can themselves have spiro rings attached thereto via a single ring atom of the fused-polycyclic.

"Halogen" or "halo" refers to fluorine, chlorine, bromine or iodine. "Haloalkyl" and "haloaryl" refer generically to alkyl and aryl groups that are substituted with one or more halogens, respectively. Non-limiting examples of "haloalkyl" include —$CH_2F$, —$CHCl_2$ or —$CF_3$.

"Heteroatom" refers to O, S, N, or P.

"(4-10 membered)heterocycloalkyl" refers to a stable four- to ten-membered ring substituent that consists of carbon atoms and from one to five heteroatoms selected from the nitrogen, phosphorus, oxygen and sulfur. For purposes of this invention, the heterocycloalkyl substituent can be a monocyclic or a multicyclic ring system, which can include fused or bridged ring systems as well as spirocyclic systems.

"(5-10 membered)heteroaryl" refers to a stable five- to ten-membered ring substituent that consists of carbon atoms and from one to five heteroatoms selected from the nitrogen, phosphorus, oxygen and sulfur. For purposes of this invention, the heteroaryl substituent can be a monocyclic or a multicyclic ring system, which can include fused or bridged ring systems as well as spirocyclic systems.

In the above heteroaryl and heterocycloalkyl substituents, the nitrogen, phosphorus, carbon or sulfur atoms can be optionally oxidized to various oxidation states. In a specific example, the group —$S(O)_{0-2}$—, refers to —S-(sulfide), —S(O)-(sulfoxide), and —$SO_2$— (sulfone) respectively. For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms can be optionally quaternized; and the ring substituent can be partially or fully saturated or aromatic.

Non-limiting examples of (4-10 membered)heterocycloalkyl and (5-10 membered)heteroaryl groups include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, dioxaphospholanyl, oxadiazolyl, tetrahydrofuranyl, tetrahydroisoquinolinyl, and tetrahydroquinolinyl.

Representative examples of "(5-10 membered)heteroaryl" include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzdioxolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Fused, bridged, and spiro moieties are also included within the scope of this definition.

When a group is referred to as "—$(C_1$-$C_6)$alkyl -(4-10 membered)heterocycloalkyl" the heterocycloalkyl is attached to a parent structure via one of an alkylene, alkylidene, or alkylidyne group. Examples include (4-methylpiperazin-1-yl)methyl, (morpholin-4-yl)methyl, (pyridine-4-yl) methyl, 2-(oxazolin-2-yl)ethyl, 4-(4-methylpiperazin-1-yl)-2-butenyl, and the like. Both the heterocyclyl and the corresponding alkylene, alkylidene, or alkylidyne portion of a heterocyclylalkyl group can be optionally substituted.

"Optional" or "optionally" means that the subsequently described event or circumstance can or can not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term. So, for example, in the term "optionally substituted arylalkyl," both the "alkyl" portion and the "aryl" portion of the molecule can or can not be substituted. A list of exemplary optional substitutions is presented below in the definition of "substituted."

"Saturated bridged ring system" refers to a bicyclic or polycyclic ring system that is not aromatic. Such a system can contain isolated or conjugated unsaturation, but not aromatic or heteroaromatic rings in its core structure (but can have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system."

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

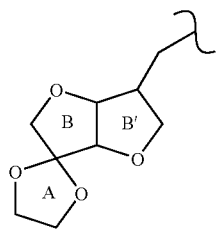

"Substituted" alkyl, aryl, heteroaryl and cycloheteroaryl, refer respectively to alkyl, aryl, heteroaryl and cycloheteroaryl, one or more (for example up to about five, in another example, up to about three) hydrogen atoms are replaced by a substituent independently selected from: alkyl (for example, fluoromethyl), aryl (for example, 4-hydroxyphenyl), arylalkyl (for example, 1-phenyl-ethyl), heterocyclylalkyl (for example, 1-pyridin-3-yl-ethyl), heterocyclyl (for example, 5-chloro-pyridin-3-yl or 1-methyl-piperidin-4-yl), alkoxy, alkylenedioxy (for example methylenedioxy), amino (for example, alkylamino and dialkylamino), amidino, aryloxy (for example, phenoxy), arylalkyloxy (for example, benzyloxy), carboxy (—CO$_2$H), carboalkoxy (that is, acyloxy or —OC(=O)R), carboxyalkyl (that is, esters or —CO$_2$R), carboxamido, benzyloxycarbonylamino (CBZ-amino), cyano, acyl, halogen, hydroxy, nitro, sulfanyl, sulfinyl, sulfonyl, thiol, halogen, hydroxy, oxo, carbamyl, acylamino, and sulfonamido. And each substituent of a substituted group is optionally substituted, but these optional substituents themselves are not further substituted. Thus, an optionally substituted moiety is one that can or can not have one or more substituents, and each of the substituents can or can not have one or more substituents. But, the substituents of the substituents can not be substituted.

Some of the compounds of the invention may have imino, amino, oxo or hydroxy substituents off aromatic heterocyclyl systems. For purposes of this disclosure, it is understood that such imino, amino, oxo or hydroxy substituents may exist in their corresponding tautomeric form, i.e., amino, imino, hydroxy or oxo, respectively.

Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS).

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one of ordinary skill in the art would recognize that theoretically some constructs which would not normally be considered as stable compounds (that is, sterically practical and/or synthetically feasible, supra).

When a particular group with its bonding structure is denoted as being bonded to two partners; that is, a divalent group, for example, —OCH$_2$—, then it is understood that either of the two partners may be bound to the particular group at one end, and the other partner is necessarily bound to the other end of the particular group, unless stated explicitly otherwise. Stated another way, divalent groups are not to be construed as limited to the depicted orientation, for example "—OCH$_2$-" is meant to mean not only "—OCH$_2$-" as drawn, but also "—CH$_2$O—."

In addition to the preferred embodiments recited hereinabove, also preferred are embodiments comprising combinations of preferred embodiments.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents or by converting on enantiomer to the other by asymmetric transformation.

For a mixture of enantiomers, enriched in a particular enantiomer, the major component enantiomer may be further enriched (with concomitant loss in yield) by recrystallization.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostrate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

"Prodrug" refers to compounds that are transformed (typically rapidly) in vivo to yield the parent compound of the above Formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

One of ordinary skill in the art would understand that certain crystallized, protein-ligand complexes, in particular JAK-2-ligand complexes, and their corresponding x-ray structure coordinates can be used to reveal new structural information useful for understanding the biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds of the invention as their ligand component, are an aspect of the invention.

As well, one of ordinary skill in the art would appreciate that such suitable x-ray quality crystals can be used as part of a method of identifying a candidate agent capable of binding to and modulating the activity of kinases. Such methods may be characterized by the following aspects: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one skilled in the art would appreciate that such methods may further entail: employing a candidate agent, so-determined to fit spatially into the ligand binding domain, in a biological activity assay for kinase modulation, and determining whether said candidate agent modulates kinase activity in the assay. Such methods may also include administering the candidate agent, determined to modulate kinase activity, to a mammal suffering from a condition treatable by kinase modulation, such as those described above.

Also, one skilled in the art would appreciate that compounds of the invention can be used in a method of evaluating the ability of a test agent to associate with a molecule or molecular complex comprising a ligand binding domain of a kinase. Such a method may be characterized by the following aspects: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

General Administration

Pharmaceutical compositions of the invention can comprise an inhibitor of JAK-2 according to the invention and a pharmaceutically acceptable carrier, excipient, or diluent. In certain other preferred embodiments, administration may preferably be by the oral route. Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol,) ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic Formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Utility of Compounds of the Invention as Screening Agents

To employ the compounds of the invention in a method of screening for candidate agents that bind to, for example PI3K, the protein is bound to a support, and a compound of the invention is added to the assay. Alternatively, the compound of the invention is bound to the support and the protein is added. Classes of candidate agents among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate agent to, for example, JAK-2 may be done in a number of ways. In one example, the candidate agent (the compound of the invention) is labeled, for example, with a fluorescent or radioactive moiety and binding determined directly. For example, this may be done by attaching all or a portion of the JAK-2 protein to a solid support, adding a labeled agent (for example a compound of the invention in which at least one atom has been replaced by a detectable isotope), washing off excess reagent, and determining whether the amount of the label is that present on the solid support. Various blocking and washing steps may be utilized as is known in the art.

The term "labeled" as used herein is meant to include both direct and indirect labeling with a compound that provides a detectable signal, for example, radioisotope, fluorescent tag, enzyme, antibodies, particles such as magnetic particles, chemiluminescent tag, or specific binding molecules, and the like. Specific binding molecules include pairs, such as biotin and streptavidin, digoxin and antidigoxin, and the like. For the specific binding members, the complementary member would normally be labeled with a molecule which provides for detection, in accordance with known procedures, as outlined above. The label can directly or indirectly provide a detectable signal.

In some embodiments, only one of the components is labeled. For example, JAK-2 protein may be labeled at tyrosine positions using $^{125}$I, or with fluorophores. Alternatively, more than one component may be labeled with different labels; using $^{125}$I for the proteins, for example, and a fluorophor for the candidate agents.

The compounds of the invention may also be used as competitors to screen for additional drug candidates. The terms "candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to JAK-2.

Candidate agents can encompass numerous chemical classes, though typically they are organic molecules having a molecular weight of more than about 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often comprise cyclical carbon or heterocyclyl structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to JAK-2, such as an antibody, peptide, binding partner, ligand, etc. Under certain circumstances, there may be competitive binding as between the candidate agent and the binding moiety, with the binding moiety displacing the candidate agent.

In some embodiments, the candidate agent is labeled. Either the candidate agent, or the competitor, or both, is added first to JAK-2 protein for a time sufficient to allow binding, if present. Incubations may be performed at any temperature that facilitates optimal activity, typically between 4° C. and 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to JAK-2 and thus is capable of binding to, and potentially modulating the activity of the JAK-2. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to JAK-2 with a higher affinity. Thus, if the candidate agent is labeled, the presence of the label on the support, coupled with a lack of competitor binding, may indicate the candidate agent is capable of binding to JAK-2.

It may be of value to identify the binding site of JAK-2. This can be done in a variety of ways. In one embodiment, once JAK-2 is identified as binding to the candidate agent, the JAK-2 is fragmented or modified and the assays repeated to identify the necessary components for binding.

Modulation is tested by screening for candidate agents capable of modulating the activity of JAK-2 comprising the steps of combining a candidate agent with JAK-2, as above, and determining an alteration in the biological activity of the JAK-2. Thus, in this embodiment, the candidate agent should both bind to (although this may not be necessary), and alter its biological or biochemical activity as defined herein. The methods include both in vitro screening methods and in vivo screening of cells for alterations in cell viability, morphology, and the like.

Alternatively, differential screening may be used to identify drug candidates that bind to native JAK-2, but cannot bind to modified JAK-2.

Positive controls and negative controls can be used in the assays. For example, all control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components can be added in any order that provides for the requisite binding.

One of ordinary skill in the art would understand that certain crystallized, protein-ligand complexes, in particular JAK-2-ligand complexes, and their corresponding x-ray structure coordinates can be used to reveal new structural information useful for understanding the biological activity of JAK-2 kinase's as described herein. As well, the key structural features of the aforementioned proteins, particularly, the shape of the ligand binding site, are useful in methods for designing or identifying selective modulators of JAK-2 kinase's and in solving the structures of other proteins with similar features. Ligands of such complexes may include compounds of the invention as described herein.

As well, one of ordinary skill in the art would appreciate that such suitable x-ray quality crystals can be used as part of a method of identifying a candidate agent capable of binding to and modulating the activity of JAK-2 kinases. Such methods may be characterized by the following aspects: a) introducing into a suitable computer program, information defining a ligand binding domain of a JAK-2 kinase in a conformation (e.g. as defined by x-ray structure coordinates obtained from suitable x-ray quality crystals as described above) the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one skilled in the art would appreciate that such methods may further entail: employing a candidate agent, so-determined to fit spatially into the ligand binding domain, in a biological activity assay for JAK-2 kinase modulation, and determining whether said candidate agent modulates JAK-2 kinase activity in the assay. Such methods may also include administering the candidate agent, determined to modulate JAK-2 kinase activity, to a mammal suffering from a condition treatable by JAK-2 kinase modulation, such as those described above.

Also, one skilled in the art would appreciate that compounds of the invention can be used in a method of evaluating the ability of a test agent to associate with a molecule or molecular complex comprising a ligand binding domain of a JAK-2 kinase. Such a method may be characterized by the following aspects: a) creating a computer model of a JAK-2 kinase binding pocket using structure coordinates obtained from suitable x-ray quality crystals of the JAK-2 kinase, b) employing computational algorithms to perform a fitting operation between the test agent and the computer model of the binding pocket, and c) analyzing the results of the fitting operation to quantify the association between the test agent and the computer model of the binding pocket.

The disclosures in this application of all articles and references, including patents, are incorporated herein by reference.

Synthetic Procedures

Scheme 1 depicts the general synthetic procedure for the compounds of the invention. Synthesis of the compounds of the invention is not limited by the procedure of Scheme 1. One skilled in the art will know that other procedures can be used to synthesize the compounds of the invention, and that the procedure described in Scheme 1 is only one such procedure. In the descriptions below, one of ordinary skill in the art would recognize that specific reaction conditions, added reagents, solvents, and reaction temperatures can be modified for the synthesis of specific compounds of the invention. Thus, the general synthetic procedure depicted in Scheme 1 in conjunction with the specific examples that follow provide sufficient information and guidance to allow one of ordinary skill in the art to synthesize compounds of the invention.

Referring to Scheme 1, intermediate (2), 5,10-Dioxo-5H, 10H-diimidazo[1,5-a; 1',5'-d]pyrazine-1,6-dicarbonyl dichloride, is prepared as described by Wiznycia and Bauers, J. Org. Chem. 2002, 67, 7151-7154. Compounds of Formula (6) that are within the scope of the invention are prepared through the subsequent addition of an amine or aniline component (3) to form the intermediate compound (4) followed by an appropriately substituted benzimidazole (5). Minor variations in reaction conditions allow this sequence to be performed either stepwise with the isolation of the intermediate compound (4) or in a single reaction vessel without workup or isolation of intermediate (4).

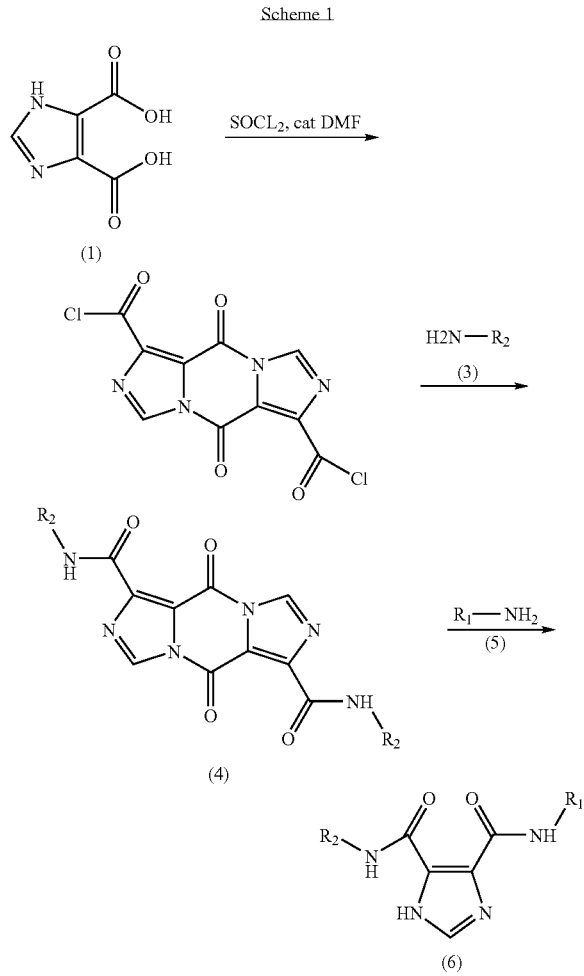

Scheme 1 wherein $R_2$ is as defined in the specification, and $R_1$ is benzimidazole optionally substituted with any of the substituents as defined in the specification for benzimidazole.

In some cases, the products of Scheme 1 may undergo subsequent chemical transformations to modify the $R_1$ and $R_2$ substituents. For example an ester may be hydrolyzed to an acid, protecting groups for amines and alcohols may be removed to unmask these polar functionalities, or alkylated thiols may be oxidized to sulfones or sulfoxides.

EXAMPLES

The following examples serve to more fully describe the manner of making the compounds of the invention, as well as to set forth the best modes contemplated for carrying out the invention. These examples in no way serve to limit the scope of the invention, but rather are presented for illustrative purposes. All references cited herein are incorporated by reference in their entirety. Generally, each example is set out below with a corresponding multi-step synthesis procedure. All reactants and reagents that are disclosed in the examples for which there is no description of how to make them are commercially available reactants and reagents whether this is explicitly stated or not for each of these reactants and reagents.

Following some of the working examples is a list of compounds that were made in a similar way.

Example 1

Synthesis of $N^5$-1H-benzimidazol-2-yl-$N^4$-(2,4-dimethylphenyl)-1H-imidazole-4,5-dicarboxamide To a dry round-bottom flask was added 1.57 g (5 mmol) of 5,10-Dioxo-5H-10H-diimidazo[1,5-a; 1',5'-d]pyrazine-1,6-dicarbonyl dichloride, compound (2) as illustrated in Scheme 1, and 20 mL of dry THF. To this stirred suspension at 0° C. was added drop wise 2,4-dimethylaniline (1.22 g, 10 mol) followed by DIPEA (2 equiv., 10 mmol, 1.7 mL) over 10 minutes. The solution was stirred at room temperature for 12 h. The suspension was filtered and washed with DCM (50 mL) to give a solid intermediate, which was contaminated with DIPEA-HCl salt (observed in LC-MS), and was used directly in the next step without further purification.

To a solution of 2-aminobenzimidazole (998 mg, 7.5 mmol, 3.75 equiv.) in DCM (20 mL) was added the isolated crude intermediate (965 mg, 2 mmol). The mixture was stirred under reflux and the reaction was completed after 4 h. The suspension was filtered, and the collected solid was suspended in 20 mL of 1N HCl, stirred for 2 hours, and filtered to remove excess 2-aminobenzimidazole. The procedure was repeated until substantially all traces of the benzimidazole was removed as indicated by LCMS analysis. The solid was then suspended in 10 mL of half saturated $K_2CO_3$ solution stirred and filtered. The resulting solid was washed with water, sonicated in MeOH for 20 min., and filtered to give 500 mg of the title compound (33% yield). MS: 375 ($M^+$+1). $^1$H-NMR (400 MHz, DMSO-d6): δ=12.20 (s, 1h), 10.21 (s, 1H), 8.18 (s, 1H), 7.56-7.38 (m, 3H), 7.18-7.0 (m, 4H), 2.25 (s, 3H), 2.21 (s, 3H).

Example 2

Synthesis of $N^4$-(5-bromo-2-methylphenyl)-$N^5$-(4-methyl-1H-imidazol-2-yl)-1H-imidazole-4,5-dicarboxamide

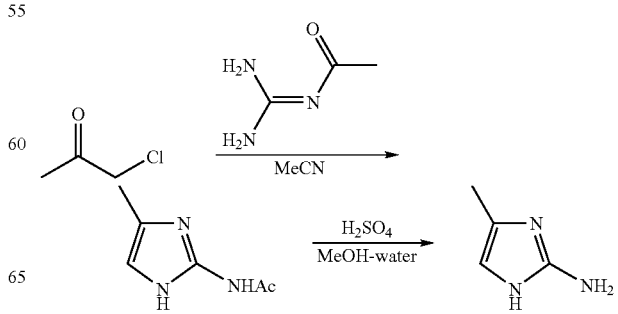

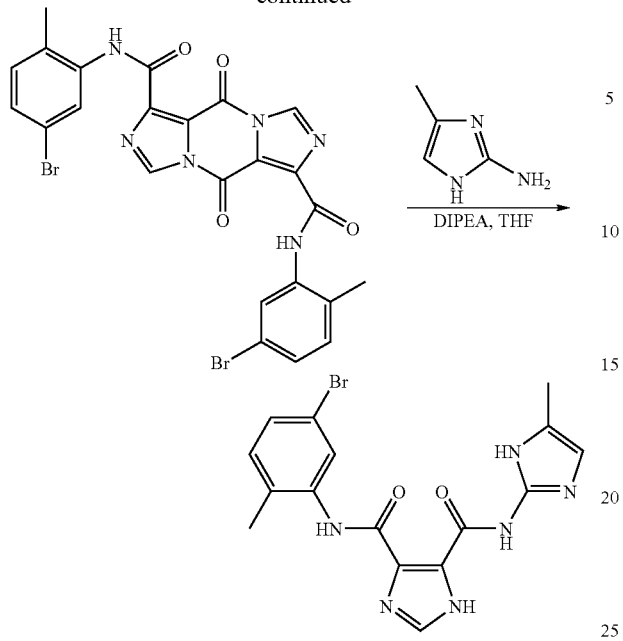

Synthesis of N-(4-methyl-1H-imidazol-2-yl)acetamide

N-Acetylguanidine (1.516 g, 15 mmol, 3 equivalents, commercially available Aldrich) was added to 1-chloropropan-2-one (0.462 g, 5 mmol, 1 equiv) in acetonitrile (30 ml). The reaction mixture was heated to reflux for 12 hours under argon. Upon cooling, the reaction mixture was evaporated to dryness and the isolated residue was washed with water, filtered and air-dried to give 0.324 g N-(4-methyl-1H-imidazol-2-yl)acetamide. $^1$H-NMR (400 MHz, DMSO-d6): δ 13.3 (bs, 1H), 10.29 (bs, 1H), 6.80 (s, 1H), 2.27 (s, 3H), 2.02 (s, 3).

Synthesis of 4-methyl-1H-imidazol-2-amine

N-(4-methyl-1H-imidazol-2-yl)acetamide (0.300 g) was heated to reflux in 5 ml of a 1:1 methanol/water mixture containing 5 drops of concentrated sulfuric acid for 12 hours. The mixture was cooled and evaporated to dryness on the lyophilizer to give 0.263 g of -imidazol-2-amine. $^1$H-NMR (400 MHz, DMSO-d6): δ 13.30 (bs, 1H), 6.78 (s, 1H), 6.59 (bs, 2H), 2.27 (s, 3H).

Synthesis of $N^4$-(5-bromo-2-methylphenyl)-$N^5$-(4-methyl-1H-imidazol-2-yl)-1H-imidazole-4,5-dicarboxamide $N^4$-(5-Bromo-2-methylphenyl)-$N^5$-(4-methyl-1H-imidazol-2-yl)-1H-imidazole-4,5-dicarboxamide was prepared in a similar manner as that used for $N^4$-(5-bromo-2-methylphenyl)-$N^5$-(4,5-dimethyl-1H-imidazol-2-yl)-1H-imidazole-4,5-dicarboxamide in Example 109 at 35% yield. $^1$H-NMR (400 MHz, DMSO-d6): d 13.72 (s, br, 1H), 11.51 (s, br, 1H), 8.26 (s, br, 1H), 7.98 (s, 1H), 7.31-7.24 (m, 3H), 3.91 (s, 3H), 2.33 (s, 3H). MS (EI): 404 (MH+).

Example 3

Synthesis of $N^5$-1H-benzimidazol-2-yl-$N^4$-[(2-chlorophenyl)methyl]-1H-imidazole-4,5-dicarboxamide To a dry round-bottom flask was added (3.13 g, 10 mmol) of acid chloride (2) and 40 mL of dry THF. To this stirred suspension at 0° C. was added dropwise 2-chlorobenzylamine (2.8 mL, 20 mmol, 2 equiv.) followed by DIPEA (3.5 mL, 20 mmol) over 10 minutes. The solution was stirred at room temp overnight. The suspension was filtered, washed with DCM (100 mL) and used to next step.

To a dry flask was added the crude intermediate (1.047 g, 2 mmol) and 20 mL dry DCM, followed by 2-aminobenzimidazole (533 mg, 4 mmol, 2 equiv.). The mixture was stirred overnight at 33° C. The suspension was filtered, the collected solid was washed with 1N HCl, potassium carbonate solution and MeOH to give the title compound. MS: 395 ($M^+$+1). $^1$H-NMR (DMSO-d6): δ=9.8 (s, 1h), 8.32 (s, 1H), 7.64-7.60 (m, 2H), 7.52-7.49 (m, 1H), 7.40-7.30 (m, 5H), 4.69 (s, 2H).

Example 4

Synthesis of $N^5$-1H-benzimidazol-2-yl-$N^4$-(5-chloro-2-methylphenyl)-1H-imidazole-4,5-dicarboxamide To a dry around-bottom flask was charged 939 mg (3 mmol) of acid chloride, compound (2) illustrated in Scheme 1 and 15 mL of dry THF. To this stirred suspension at 0° C. was added drop wise 2-methyl-5-chloroaniline (850 mg, 6.0 mmol) followed by DIPEA (7.7 mmol) over 10 min. After 5 hours stirring at room temperature, 2-aminobenzoimidazole (865 mg, 6.5 mmol) was added and the reaction mixture was stirred at 55° C. overnight. The suspension was filtered, the collected solid was suspended in MeOH and 1 N HCl solution. This suspension was sonicated 2 hours and filtered. Purification of the solid material by this method was repeated until all traces of the benzimidazole were removed as indicated by LCMS. The solid was washed with water, sonicated in MeOH for 20 min. and filtered to give the desired product. MS (EI): 395 ($M^+$+1). $^1$H-NMR (400 MHz, DMSO-d6): δ=13.92 (s, br, 1H), 12.4 (s, br, 1H), 10.4 (s, 1H), 8.18 (s, 1h), 7.80 (s, 1H), 7.54-7.42 (m, 2H), 7.35-7.05 (m, 4H), 2.30 (s, 3H).

Example 5

Synthesis of $N^5$-[4-(azetidin-3-yloxy)-2-methylphenyl]-$N^4$-1H-benzimidazol-2-yl-1H-imidazole-4,5-dicarboxamide The synthesis of the title compound is outlined in Scheme 2. Scheme 2 is a representative procedure for the synthesis of the title compound, and does limit the scope of the invention. Subsequent modification that is, Boc removal to expose a secondary amine, is carried out to the molecule after incorporation of the benzimidazole.

Scheme 2

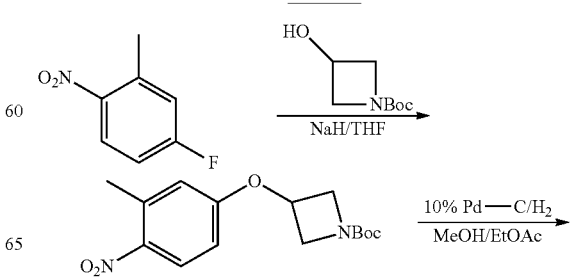

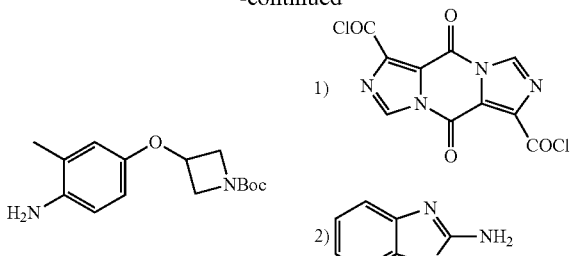

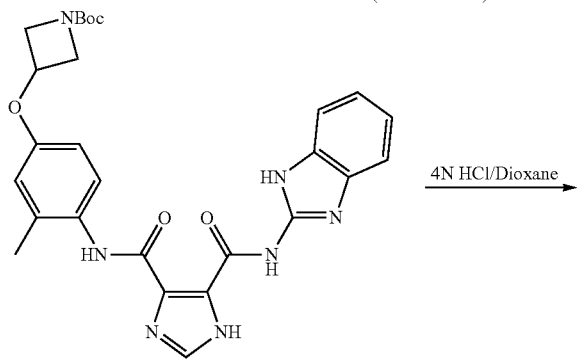

(See Scheme 1)

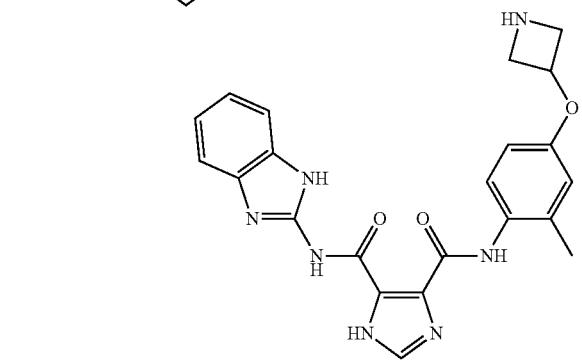

Synthesis of 3-(3-Methyl-4-nitro-phenoxy)-azetidine-1-carboxylic acid tert-butyl ester. In a dry flask, N-Boc-3-hydroxy-azetidine (9.8 g, 57 mmol) was dissolved in 200 mL of dry THF. The solution was cooled with an ice-water bath and sodium hydride (2.0 g, 83.mmol) was added in several portions. The suspension was stirred for an additional 0.5 hours, then 7.9 g of 2-nitro-5-fluorotoluene (7.9 g, 51 mmol) in 100 mL of dry THF was added dropwise. The solution was stirred overnight at room temperature. The THF was removed under vacuum and the residue was partitioned between ethyl acetate and water (100 mL each). The organic layer was collected and the aqueous layer was subsequently extracted twice with ethyl acetate. The combined organic layers were washed with 1 N HCl, water, saturated sodium bicarbonate and brine (50 mL each). The organic layer was dried over anhydrous sodium sulfate, concentrated. The residue was purified by silica gel column (EtOAc/Hexanes 1:19→1:4 gradient) to give 12.0 g (43 mmol, 84% yield) of the title compound, which was used directly in the next step. MS: 309 (M$^+$+1).

Synthesis of 3-(4-Amino-3-methyl-phenoxy)-azetidine-1-carboxylic acid tert-butyl ester. The 3-(3-Methyl-4-nitro-phenoxy)-azetidine-1-carboxylic acid tert-butyl ester (12.0 g, 43 mmol) was dissolved in 50 mL methanol and 50 mL ethyl acetate. An amount of 1.0 g of 10% wet Pd—C (50% w/w) was added. The reaction mixture was subjected to hydrogenation under 40 PSI of hydrogen for 3 hours. The solution was then filtered through Celite to remove catalyst. The filtrate was concentrated under reduced pressure to give the desired product (10.8 g, 39 mmol). $^1$H-NMR (400 MHz, CDCl$_3$): δ=6.60 (m, 1H), 6.02 (m, 1H), 5.95 (m, 1H), 4.78 (m, 1H), 4.24 (m, 2H), 3.95 (m, 2H), 3.45 (br, 1H), 2.15 (s, 3H), 1.45 (s, 9H). MS: 301 (M$^+$+23).

Synthesis of 1,1-dimethylethyl 3-({4-[({4-[(1H-benzimidazol-2-ylamino)carbonyl]-1H-imidazol-5-yl}carbonyl) amino]-3-methylphenyl}oxy)azetidine-1-carboxylate. This compound was prepared using 3-(4-amino-3-methyl-phenoxy)-azetidine-1-carboxylic acid tert-butyl ester using the procedure detailed in Example 1. $^1$H-NMR (400 MHz, DMSO-d6): δ=13.8 (br, 1H), 10.2 (br, 2H), 8.18 (s, 1H), 7.44 (m, 2H), 7.05 (m, 2H), 6.88 (m, 2H), 6.78 (m, 1H), 5.05 (m, 1H), 4.35 (m, 2H), 3.85 (m, 2H), 2.23 (s, 3H), 1.38 (s, 9H). MS: 532 (M$^+$+1).

Synthesis of $N^5$-[4-(azetidin-3-yloxy)-2-methylphenyl]-$N^4$-1H-benzimidazol-2-yl-1H-imidazole-4,5-dicarboxamide. 1,1-dimethylethyl 3-({4-[({4-[(1H-benzimidazol-2-ylamino)carbonyl]-1H-imidazol-5-yl}carbonyl)amino]-3-methylphenyl}oxy)azetidine-1-carboxylate (155.0 mg, 0.29 mmol) was suspended in 5 mL of ethyl acetate, which was cooled with an ice-water bath. 3 mL of 4 N HCl in dioxane was added dropwise. The reaction mixture was stirred overnight. The suspension was filtered and the solid was washed with 5 mL of ethyl acetate, dried under vacuum to afford the desired product (102 mg, 0.22 mmol) as the hydrochloride salt. $^1$H-NMR (400 MHz, DMSO-d6): δ=10.9 (br, 1H), 9.85 (br, 2H), 8.32 (s, 1H), 7.63 (m, 2H), 7.38 (m, 3H), 6.84 (m, 1H), 6.78 (m, 1H), 5.05 (m, 1H), 4.43 (m, 2H), 3.94 (m, 2H), 2.25 (s, 3H). MS: 432 (M$^+$+1).

Example 6

Synthesis of $N^5$-[6-({2-[(2,3-dihydroxypropyl) amino]-2-oxoethyl}oxy)-1H-benzimidazol-2-yl]-$N^4$-(2,4-dimethylphenyl)-1H-imidazole-4,5-dicarboxamide

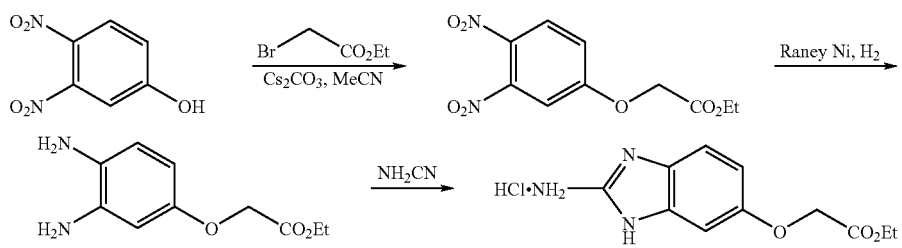

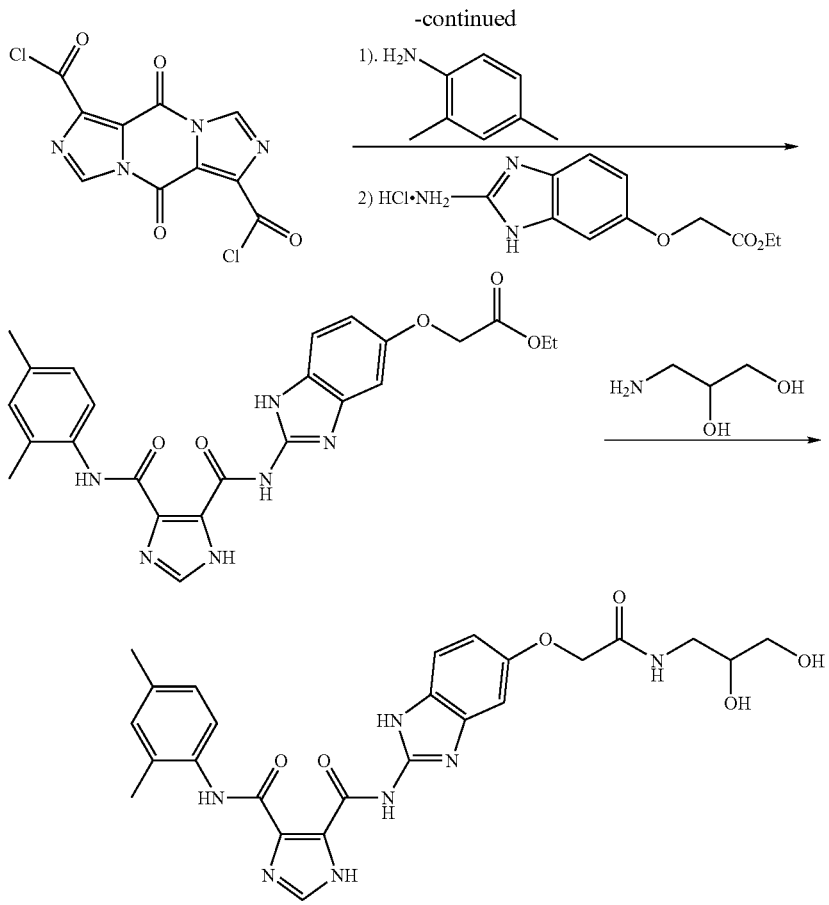

Synthesis of Ethyl 2-(3,4-dinitrophenoxy)acetate

A round-bottom flask was charged with 3,4-dinitrophenol (11.04 g, 60 mmol, commercially available from Fluka-Sigma-Aldrich), ethyl bromoacetate (11.02 g, 66 mmol), acetonitrile (120 mL) and cesium carbonate (21.6 g). The mixture was stirred at room temperature overnight. The mixture was filtered, and the recovered solid was washed with ethyl acetate. The filtrate was further diluted with ethyl acetate and water. The aqueous layer was extracted with ethyl acetate and combined organic solvent was washed with saturated brine, dried and concentrated under reduced pressure. The residue was triturated with ether to give ethyl 2-(3,4-dinitrophenoxy)acetate (13.0 g, 80% yield). $^1$H-NMR (400 MHz, MeOH-d4): δ 8.15 (d, 1H), 7.55 (s, 1H), 7.35 (d, 1H), 4.95 (s, 2H), 4.23 (q, 2H), 1.25 (t, 3H). MS (EI): 271 (MH+).

Synthesis of Ethyl 2-(3,4-diaminophenoxy)acetate Dihydrochloride

To a Parr hydrogenation bottle was added 13.0 g of 2-(3,4-dinitrophenoxy)acetate, Raney Nickel (2.0 g, wet), THF (100 mL) and EtOH (150 mL). The atmosphere of the vessel was replaced by hydrogen gas. The reaction was shaken on a Parr hydrogenator at 40 psi at room temperature, overnight. The catalyst was filtered through a plug of Celite and the filtrate was concentrated under reduced pressure to give a residue, which was dissolved in methanol, acidified with 4 N hydrogen chloride in 1,4-dioxane and filtered. The resulting filtrate was concentrated under reduced pressure to give ethyl 2-(3,4-diaminophenoxy)acetate dihydrochloride (8.5 g, 83%), and was used directly in the next step without any further purification. MS (EI): 276 (MH+).

Synthesis of Ethyl 2-(2-amino-1H-benzoimidazol-6-yloxy)acetate Hydrochloride A solution of ethyl 2-(3,4-diaminophenoxy)acetate dihydrochloride (2.0 g, 7 mmol) in 10 mL of water was cooled to 0° C. and treated with a solution of cyanogens bromide (5M in acetonitrile, 1.1 equivalents) and solid sodium bicarbonate (2 equivalents, 60 mmol, 1.18 g). The solution was stirred at room temperature for 12 hours. The mixture was made basic with 1M sodium bicarbonate solution and concentrated under reduced pressure. The residue was dissolved in methanol. The resulting solution was acidified with 4 N hydrogen chloride in 1,4-dioxane. The resulting suspension was stirred for 10 minutes at room temperature and subsequently filtered. The filtrate was concentrated under reduced pressure to give ethyl 2-(2-amino-1H-benzoimidazol-6-yloxy)acetate hydrochloride. (1.85 g, 96%). $^1$H-NMR (400 MHz, MeOH-d4): δ 8.15 (s, br, 2H), 7.20 (d, 1H), 6.90 (s, 1H), 6.75 (d, 1H), 4.90 (s, 2H), 4.10 (q, 2H), 1.70 (t, 3H). MS (EI): 235 (MH+).

Synthesis of $N^5$-[6-({2-[(2,3-dihydroxypropyl)amino]-2-oxoethyl}oxy)-1H-benzimidazol-2-yl]-$N^4$-(2,4-dimethylphenyl)-1H-imidazole-4,5-dicarboxamide A General Procedure for the Synthesis of Amide and Ester Derivatives of This Nature.

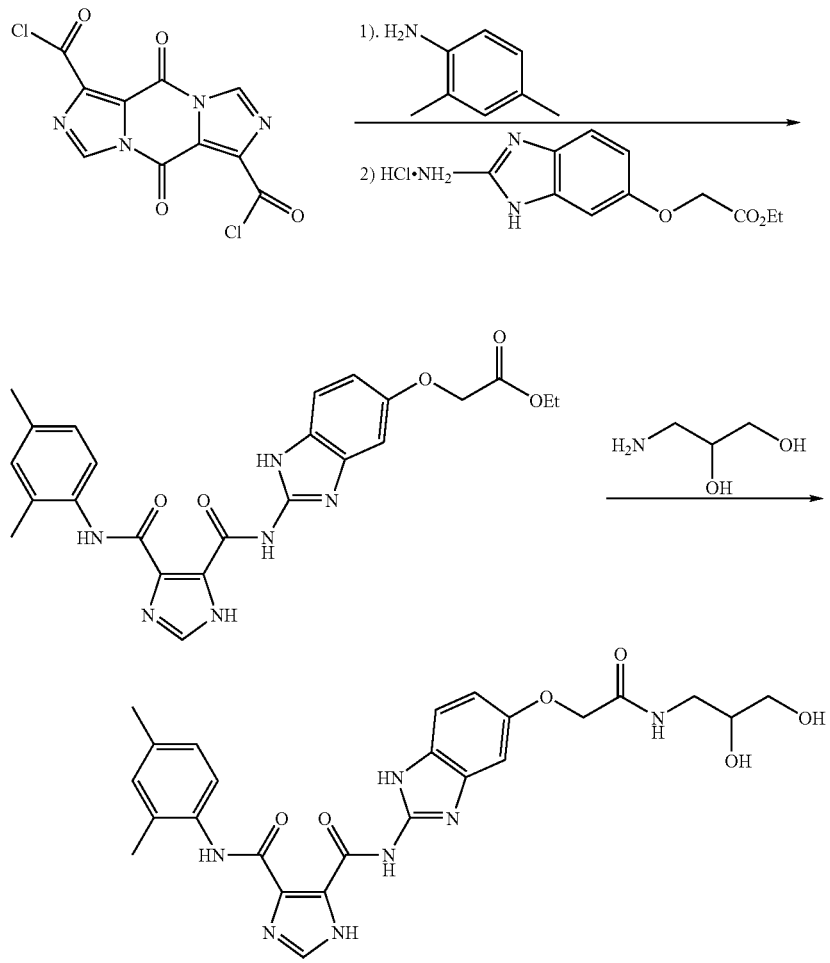

To a seal tube was added ethyl 2-(2-(4-(2,4-dimethylphenylcarbamoyl)-1H-imidazole-5-carboxamido)-1H-benzo[d]imidazol-5-yloxy)acetate (230 mg, 0.5 mmol), 3-aminopropane-1,2-diol (180 mg, 2 mmol), DMA (3 mL) and THF (3 mL), the mixture was heated to 90° C. overnight. The reaction was allowed to cool to room temperature, concentrated under reduced pressure and purified by preparative reverse phase HPLC (aqueous ammonium acetate—acetonitrile) to give 64 mg of $N^5$-[6-({2-[(2,3-dihydroxypropyl)amino]-2-oxoethyl}oxy)-1H benzimidazol-2-yl]-$N^4$-(2,4-dimethylphenyl)-1H-imidazole-4,5-dicarboxamide as the desired product. $^1$H-NMR (DMSO-d6) δ 8.05 (s, 1H), 7.68 (d, 2H), 7.43 (s, br 2H), 7.05 (dd, 2H), 6.93 (d, 2H), 4.31 (m, 1H), 2.65 (m, 2H), 2.29 (q, 2H), 2.14 (m, 2H), 1.88 (m, 2H), 1.59 (m, 2H), 0.95 (t, 3H). MS (EI): 474 (MH+).

Example 7

Synthesis of $N^4$-(2,4-Dimethylphenyl)-$N^5$-{5-[(pyridin-4-ylmethyl)oxy]-1H-benzimidazol-2-yl}-1H-imidazole-4,5-dicarboxamide

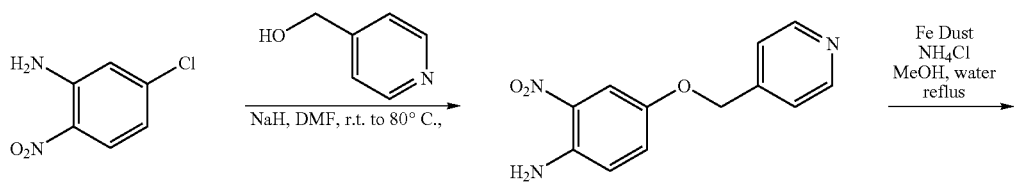

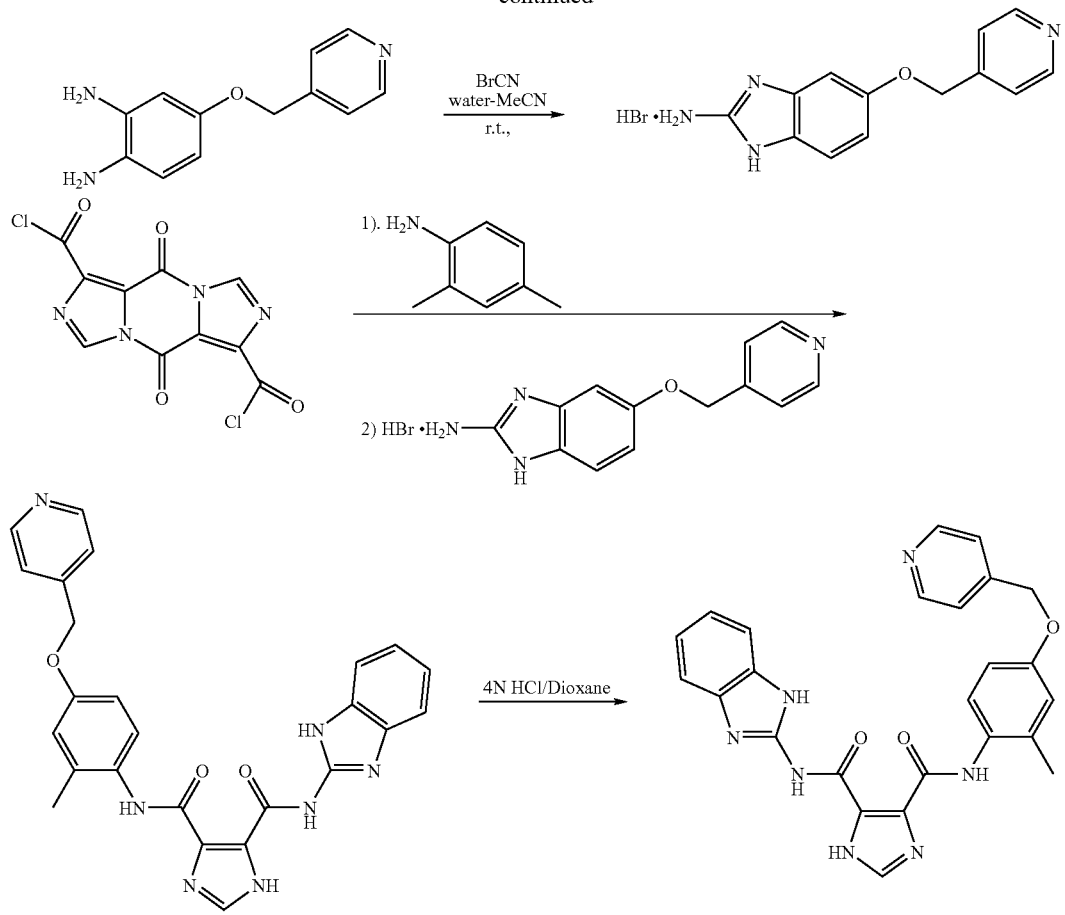

Synthesis of 2-Nitro-4-(pyridin-4-ylmethoxy)aniline

4-Hydroxymethylpyridine (50 mmoles, 5.45 g, 1 equivalent, commercially available from Aldrich) was added in a drop wise fashion to a stirred suspension of 60% sodium hydride (in oil) (55 mmoles, 2.2 g, 1.1 equivalent) in anhydrous DMA (100 ml) at room temperature, over a period of 5 minutes. Upon completion of addition the resulting green reaction mixture was stirred at room temperature for 20 minutes. 4-chloro-2-nitroaniline (50 mmoles, 8.62 g, 1 equivalent) was added to the stirred green reaction mixture over the course of 10 minutes. The reaction mixture was stirred at 80° C. for 12 hours. The reaction mixture was allowed to cool to room temperature, poured into ice-water (300 ml) and extracted with ethyl acetate (3×200 ml). The combined ethyl acetate solutions were washed with water (2×100 ml) and saturated sodium chloride solution (100 ml), dried over anhydrous sodium sulfate, filtered and evaporated under reduced pressure. The resulting crude material was purified by silica flash column chromatography using 20% ethyl acetate-hexane to give 1.576 g of 2-nitro-4-(pyridin-4-ylmethoxy) aniline. (Yield 13%). $^1$H-NMR (400 MHz, DMSO-d6) §8.60 (d, 2H), 7.91 (d, 1H), 7.52 (br s, 2H), 7.43 (d, 2H), 6.50 (d, 1H), 6.34 (d, 1H), 5.31 (s, 2H). (MS (EI): 246 (MH+).

Synthesis of 4-(Pyridin-4-ylmethoxy)benzene-1,2-diamine

A single necked 50 ml flask fitted with a Teflon stirrer, Claisen head fitted with a rubber septa and reflux condenser was charged with iron powder (Aldrich, 6.2 mmoles, 3 equivalents, 0.358 g) and an aqueous solution of ammonium chloride (10.70 mmoles, 5 equivalents, 0.573 g). The slurry was rapidly stirred and a solution of 2-nitro-4-(pyridin-4-ylmethoxy)aniline (2.14 mmoles, 0.525 g) in methanol (10 ml, 5 ml./mmole of nitro compound) was prepared with gentle heating to ensure complete dissolution. The methanolic solution of methyl 2-nitro-4-(pyridin-4-ylmethoxy) aniline was added over a period of 10 minutes using a syringe and needle. Upon completion of addition the reaction mixture was brought to a gentle reflux and the progress of the reaction was monitored by TLC (silica, 100% ethyl acetate or dichloromethane, visualizing by UV). After 1.5 hours, additional iron powder (Aldrich, 6.2 mmoles, 3 equivalents, 0.358 g), ammonium chloride (10.70 mmoles, 5 equivalents, 0.573 g) and methanol (10 ml) was added. The reaction was found to be complete after 2.5 hours. A sintered filtered funnel (60 ml, medium grade sintered) was packed with Celite (20 mm thick) and connected to a Buchner flask. The hot reaction mixture was filtered through the pad of Celite, the flask rinsed with hot methanol (2×25 ml), filtered and the filtered pad washed with more hot methanol (2×40 ml). The combined filtrate was evaporated to dryness. The recovered material was dissolved in 50 ml cold water and 100 ml dichloromethane and allowed to separate. The dichloromethane layer was dried over sodium sulfate, filtered and evaporated under reduced pressure to give 0.497 of 4-(pyridin-4-yl-methoxy)benzene-1,2-diamine which was used in the next step without any further purification. $^1$H-NMR (400 MHz, DMSO-d6) δ10.50 (br s, 4H), 7.68 (d, 2H), 7.42 (m, 2H), 6.60 (d, 1H), 6.41 (s, 1H), 6.22 (d, 1H), 5.12 (s, 2H). (MS (EI): 216 (MH+).

Synthesis of 5-(Pyridin-4-ylmethoxy)-1H-benzo[d]imidazol-2-amine Hydrobromide 4-(Pyridin-4-ylmethoxy)benzene-1,2-diamine (21.4 mmoles, 0.460 g, 1 equivalent) was dissolved in acetonitrile (10 ml) and water (5 ml) and cooled to 0-5° C. (ice-water). Cyanogen bromide (0.226 g, 21.4 mmoles, 1 equivalent) was added in one lot and the reaction mixture was allowed to go to room temperature and stirred for 16 hours. The reaction mixture was then evaporated under reduced pressure to 0.4571 g of 5-(pyridin-4-ylmethoxy)-1H-benzo[d]imidazol-2-amine hydrobromide (yield: 86%) which was used directly in the next reaction without any further reaction. $^1$H-NMR (400 MHz, DMSO-d6) δ12.60 (br s, 1H), 8.56 (s, 2H), 7.58 (m, 1H), 8.23 (br s, 3h), 7.57 (m, 1H), 7.40 (m, 1H), 5.28 (s, 2H). (MS (EI): 241 (MH+).

Synthesis of $N^4$-(2,4-dimethylphenyl)-$N^5$-{5-[(pyridin-4-ylmethyl)oxy]-1H-benzimidazol-2-yl}-1H-imidazole-4,5-dicarboxamide $N^4$-(2,4-Dimethylphenyl)-$N^5$-{5-[(pyridin-4-ylmethyl)oxy]-1H-benzimidazol-2-yl}-1H-imidazole-4,5-dicarboxamide was prepared by the general method used for the synthesis of $N^5$-1H-benzimidazol-2-yl-$N^4$-(2,4-dimethylphenyl)-1H-imidazole-4,5-dicarboxamide in Example 1 in 49% yield. $^1$H-NMR (400 MHz, DMSO-d6) d 13.90 (br s, 1H), 12.05 (br s, 1H), 10.22 (s, 1H), 8.58 (d, 2H), 8.15 (s, 1H), 7.50 (d, 1H), 7.48 (d, 2H), 7.37 (d, 1H), 7.13, (s, 1H), 7.08 (s, 2H), 5.19 (s, 2H), 2.30 (s, 3H), 2.26 (s, 3H). MS (EI): 482 (MH+).

Example 8

Synthesis of N-4-1H-benzimidazol-2-yl-N-5-(2,4-dimethylphenyl)-2-methyl-1H-imidazole-4,5-dicarboxamide

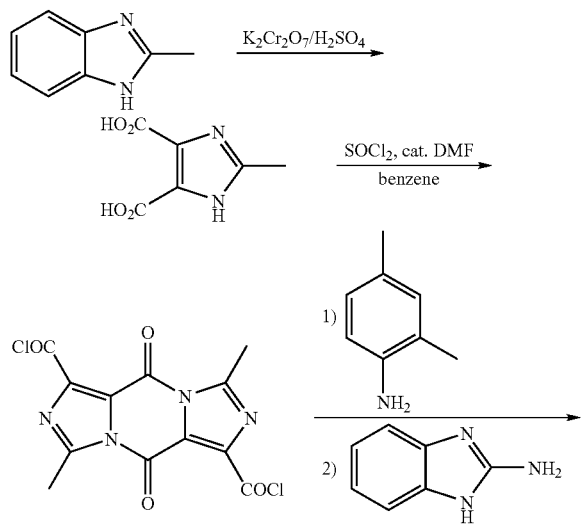

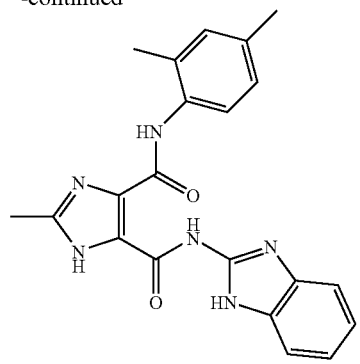

Synthesis of 2-Methyl-4,5-imidazoledicarboxylic Acid

2-Methylbenzimidazole (5 g, commercially available from Aldrich) was added to a mixture of concentrated sulfuric acid (55 mL) and water (55 mL) at 90° C. This was followed by the addition of potassium dichromate (37 g). After 15-20 minutes, the mixture was cooled to room temperature and diluted with 1 L of water, which was then kept overnight at room temperature. The resulting solid was filtered off, washed with cold water and air dried to give 4 g of 2-methyl-4,5-imidazoledicarboxylic acid which was used without any further purification. $^1$H-NMR (DMSO-d6): δ 2.46 (s, 3H). MS (EI): 171 (MH+).

Synthesis of $N^4$-1H-benzimidazol-2-yl-$N^5$-(2,4-dimethylphenyl)-2-methyl-1H-imidazole-4,5-dicarboxamide $N^4$-1H-benzimidazol-2-yl-$N^5$-(2,4-dimethylphenyl)-2-methyl-1H-imidazole-4,5-dicarboxamide was prepared by a method similar to the synthesis of $N^5$-1H-benzimidazol-2-yl-$N^4$-(2,4-dimethylphenyl)-1H-imidazole-4,5-dicarboxamide in Example 1 in 32% yield. $^1$H-NMR (400 MHz, DMSO-d6): δ 13.9 (s, br, 1H), 13.7 (s, 1H), 12.2 (s, 1H), 10.4 (s, 1H), 8.41-8.39 (m, 1H), 8.15 (s, 1H), 8.01 (s, 1H), 7.45 (s, 2H), 7.07 (s, 2H). MS (EI): 450 (MH+).

Example 9

Synthesis of $N^5$-(2,4-dimethylphenyl)-$N^4$-[6-(methyloxy)-1H-benzimidazol-2-yl]-1H-imidazole-4,5-dicarboxamide

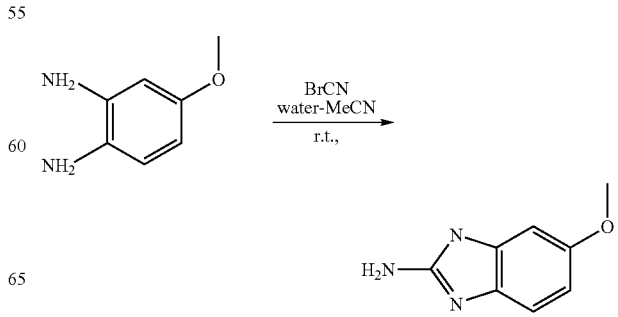

-continued

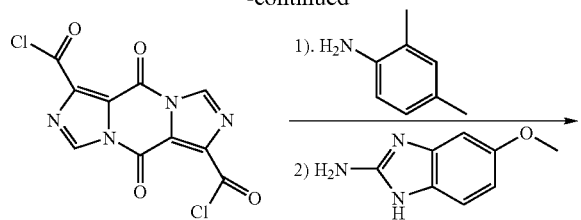

Synthesis of 6-methoxy-1H-benzoimidazol-2-amine

A solution of 4-methoxy-1,2-phenylenediamine dihydrochloride (6.33 g, 30 mmol, commercially available from Alfa-Aesar) in water (50 mL) was cooled to 0° C. and treated with a solution of cyanogens bromide (5M in acetonitrile, 1.1 equivalents, 33 mmol) and solid sodium bicarbonate (2 equivalents, 60 mmol, 5.04 g). The reaction mixture was stirred at room temperature for 12 hours. The mixture was made basic with 1M sodium carbonate solution and concentrated under reduced pressure. The residue was triturated with hot ethanol (three times), and the residual solid was filtered off. The filtrated was concentrated to give 6-methoxy-1H-benzoimidazol-2-amine (4.0 g, 82%), which was used to next step. $^1$H-NMR (400 MHz, DMSO-d6): δ 7.0 (d, 1H), 6.75 (s, 1H), 6.55 (d, 1H), 6.45 (s, 2H), 3.75 (s, 3H). MS (EI): 164 (MH+).

Synthesis of $N^5$-(2,4-dimethylphenyl)-$N^4$-[6-(methyloxy)-1H-benzimidazol-2-yl]-1H-imidazole-4,5-dicarboxamide $N^5$-(2,4-Dimethylphenyl)-$N^4$-[6-(methyloxy)-1H-benzimidazol-2-yl]-1H-imidazole-4,5-dicarboxamide was prepared by the general method used for the synthesis of $N^5$-1H-benzimidazol-2-yl-$N^4$-(2,4-dimethylphenyl)-1H-imidazole-4,5-dicarboxamide in Example 1 in 37% yield. $^1$H-NMR (400 MHz, DMSO-d6): 10.40 (s, br, 1H), 7.95 (s, 1H), 7.62 (d, 1H), 7.36 (d, 1H), 7.20-7.00 (m, 3H), 6.75 (dd, 1H), 3.77 (s, 3H), 2.38 (s, 3H), 2.30 (s, 3H). MS (EI): 405 (MH+).

Example 10

Synthesis of $N^4$-1H-benzimidazol-2-yl-$N^5$-(2,4,5-trichlorophenyl)-1H-imidazole-4,5-dicarboxamide $N^4$-1H-Benzimidazol-2-yl-$N^5$-(2,4,5-trichlorophenyl)-1H-imidazole-4,5-dicarboxamide was prepared by the general method used for the synthesis of $N^5$-1H-benzimidazol-2-yl-$N^4$-(2,4-dimethylphenyl)-1H-imidazole-4,5-dicarboxamide in Example 1 in 56% yield. $^1$H-NMR (400 MHz, DMSO-d6): δ 13.9 (s, br, 1H), 13.7 (s, 1H), 12.2 (s, 1H), 10.4 (s, 1H), 8.41-8.39 (m, 1H), 8.15 (s, 1H), 8.01 (s, 1H), 7.45 (s, 2H), 7.07 (s, 2H). MS (EI): 450 (MH+).

Example 11

Synthesis of $N^4$-1H-benzimidazol-2-yl-$N^5$-[2,5-bis(ethyloxy)-4-morpholin-4-ylphenyl]-1H-imidazole-4,5-dicarboxamide $N^4$-1H-Benzimidazol-2-yl-$N^5$-[2,5-bis(ethyloxy)-4-morpholin-4-ylphenyl]-1H-imidazole-4,5-dicarboxamide was prepared by the general method used for the synthesis of $N^5$-1H-benzimidazol-2-yl-$N^4$-(2,4-dimethylphenyl)-1H-imidazole-4,5-dicarboxamide in Example 1 in 47% yield. $^1$H-NMR (400 MHz, DMSO-d6): δ 14.0 (s, 1H), 13.9 (s, 1H), 12.2 (s, 1H), 10.2 (s, 1H), 8.16 (s, 1H), 8.15-8.00 (m, 1H), 7.52-7.48 (m, 2H), 7.12-7.10 (m, 2H), 6.69 (s, 1H), 4.15 (q, 7.0 Hz, 2H), 4.05 (q, 7.0 Hz, 2H), 3.74-3.71 (m, 4H), 3.03-3.01 (m, 4H), 1.36 (t, 6.6 Hz, 6H). MS (EI): 520 (MH+).

Example 12

Synthesis 1,1-dimethylethyl 4-{[(2-{[(4-{[(2,4-dimethylphenyl)amino]carbonyl}-1H-imidazol-5-yl)carbonyl]amino}-1H-benzimidazol-5-yl)oxy]methyl}piperidine-1-carboxylate

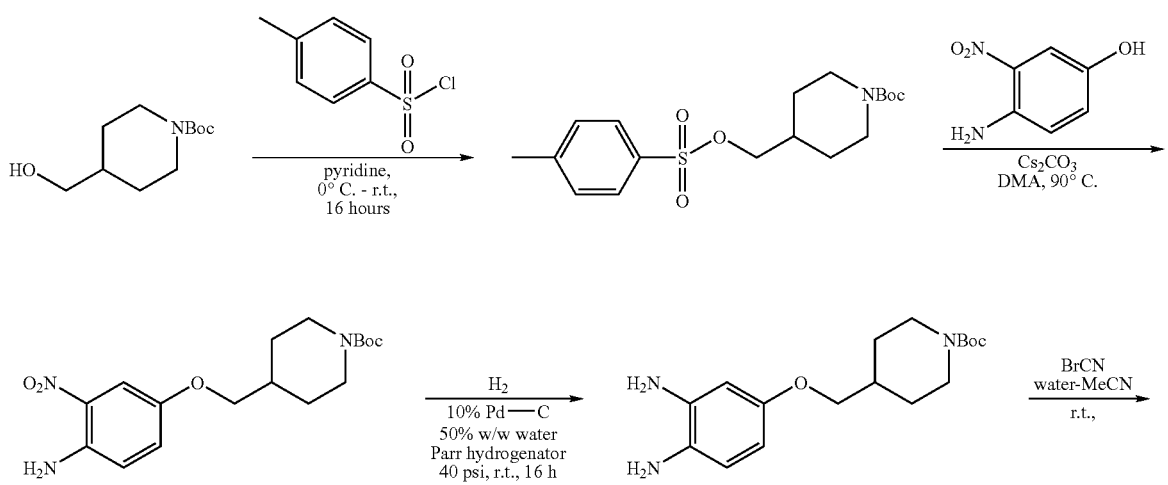

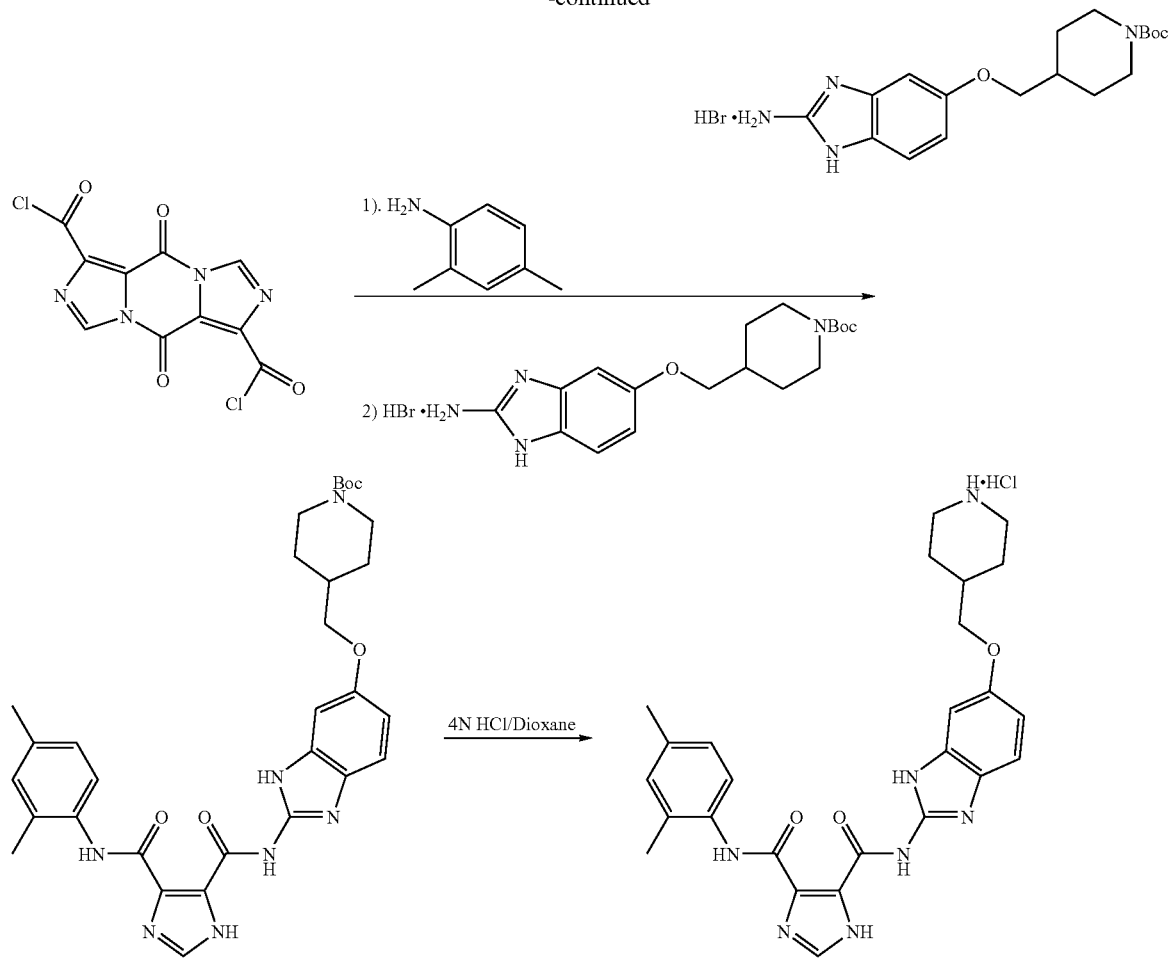

Synthesis of tert-Butyl 4-(tosyloxymethyl)piperidine-1-carboxylate

4-Hydroxylmethyl-N-(tert-butylcarboxylate)piperidine (10.76 g, 50 mmoles, 1 equivalent, commercially available from Aldrich) was dissolved in anhydrous pyridine (40 ml) and cooled to 0° C. in an ice-water-salt bath. p-Toluenesulfonyl chloride (10.48 g, 55 mmoles, 1.1 equivalent) was added in one lot to the stirred reaction mixture. The reaction mixture was then allowed to warm to room temperature and stirred for 16 hours. The reaction mixture was poured into water (200 ml) and extracted with ethyl acetate (3×200 ml). The combined ethyl acetate solution was washed with 5% aqueous hydrochloric acid (200 ml), water (200 ml) and saturated sodium chloride solution (200 ml). The ethyl acetate solution was dried over anhydrous sodium sulfate solution filtered and evaporated under reduced pressure to give 16.86 g of tert-butyl 4-(tosyloxymethyl)piperidine-1-carboxylate (yield, 91%). $^1$H-NMR (400 MHz, DMSO-d6) δ 7.88 (d, 2H), 7.45 (d, 2H), 3.84 (m, 4H), 3.65 (m, 2H), 2.40 (s, 3H), 1.76 (m, 1H), 1.54 (m, 2H) 1.38 (s, 9H), 0.95 (m, 2H). MS (EI) 370 (MH+).

Synthesis of tert-Butyl 4-((4-amino-3-nitrophenoxy)methyl)piperidine-1-carboxylate Cesium carbonate (16.29 g, 50 mmoles, 2 equivalents) was added to a stirred solution of 4-amino-3-nitrophenol (3.85 g, 25 mmoles, 1 equivalent) and tert-butyl 4-(tosyloxymethyl) piperidine-1-carboxylate (10.16 g, 27.5 mmoles, 1.1 equivalent) in anhydrous DMA (25 mls). The stirred reaction mixture was then heated to 90° C. (thermostatically controlled heating mantle) for 22 hours. The reaction mixture was then allowed to cool to room temperature and was filtered through a plug of Celite. The reaction flask and the Celite were then washed with ethyl acetate (250 ml). The organic solution was then transferred to a separatory funnel and extracted with additional ethyl acetate (3×200 ml). The combined ethyl acetate solution was then washed with water (2×100 ml), saturated sodium chloride (2×100 ml), dried over anhydrous magnesium sulfate, filtered and evaporated under reduced pressure to give a crude product. This material was triturated with diethylether to give a solid which was filtered off and washed with ether to give 4.76 g of tert-butyl 4-((4-amino-3-nitrophenoxy)methyl)piperidine-1-carboxylate as a yellow solid (yield=54%). $^1$H-NMR (400 MHz, DMSO-d6) δ 8.80 (s, 1H), 7.89 (d, 1H), 7.74 (d, 1H), 3.82 (d, 2H), 3.65 (m, 2H), 2.40 (s, 3H), 1.76 (m, 1H), 1.54 (m, 2H), 1.38 (s, 9H), 0.98 (m, 2H). MS (EI): 352 (MH+).

Synthesis of tert-Butyl 4-((3,4-diaminophenoxy)methyl)piperidine-1-carboxylate tent-Butyl 4-((4-amino-3-nitrophenoxy)methyl)piperidine-1-carboxylate (3.58 g, 10.18 mmoles,) was dissolved in ethyl acetate (60 ml) and methanol (40 ml). The solution was treated with 600 mg of 10% palladium on carbon (50% water w/w). The slurry was then shaken on a Parr hydrogenator and treated with a 40 psi atmosphere of hydrogen gas, at room temperature. After 16 hours, the slurry was filtered through a plug of Celite, which was subsequently washed with ethyl acetate (50 ml) and methanol (50 ml). The resulting filtrate was then evaporated at reduced pressure to give 3.42 g of tert-butyl 4-((3,4-diaminophenoxy)methyl)piperidine-1-carboxylate (100% yield). The material was used in the next step without any further purification. $^1$H-NMR (400 MHz, DMSO-d6) δ 8.40 (s, 1H), 7.49 (d, 1H), 7.24 (d, 1H), 5.32 (br s, 4H), 3.82 (d, 2H), 3.65 (m, 2H), 2.40 (s, 3H), 1.76 (m, 1H), 1.54 (m, 2H), 1.38 (s, 9H), 0.98 (m, 2H). MS (EI): 322 (MH+).

Synthesis tert-Butyl 4-((2-amino-1H-benzo[d]imidazol-5-yloxy)methyl)piperidine-1-carboxylate hydrobromide tert-Butyl 4-((3,4-diaminophenoxy)methyl)piperidine-1-carboxylate (10.18 mmoles, 3.27 g, 1 equivalent) was dissolved in acetonitrile (40 ml) and water (20 ml) and cooled to 0-5° C. (ice-water). Cyanogen bromide (1.112 g, 10.5 mmoles) was added in one lot and the reaction mixture was allowed to go to room temperature and stirred for 16 hours. The reaction mixture was then evaporated under reduced pressure to give 3.53 g of tert-butyl 4-((2-amino-1H-benzo[d]imidazol-5-yloxy)methyl)piperidine-1-carboxylate hydrobromide (yield n 100%) which was used directly in the next step without any further purification. $^1$H-NMR (400 MHz, DMSO-d6) δ 12.22 (br s, 2H), 8.30 (s, 2H), 7.21 (d, 1H), 6.90 (s, 1H), 6.79 (d, 1H), 3.96 (m, 2H), 3.82 (d, 2H), 2.73 (m, 2H), 1.91 (m, 1H), 1.74 (d, 2H), 1.39 (s, 9H), 1.26 (m, 2H). MS (EI): 347 (MH+).

Synthesis of 1,1-dimethylethyl 4-{[(2-{[(4-{[(2,4-dimethylphenyl)amino]carbonyl}-1H-imidazol-5-yl)carbonyl]amino}-1H-benzimidazol-5-yl)oxy]methyl}piperidine-1-carboxylate 1,1-Dimethylethyl 4-{[(2-{[(4-{[(2,4-dimethylphenyl)amino]carbonyl}-1H-imidazol-5-yl)carbonyl]amino}-1H-benzimidazol-5-yl)oxy]methyl}piperidine-1-carboxylate was prepared by the general method used for the synthesis of $N^5$-1H-benzimidazol-2-yl-$N^4$-(2,4-dimethylphenyl)-1H-imidazole-4,5-dicarboxamide in Example 1 in 52% yield. $^1$H-NMR (DMSO-d6) 13.8 (bs, 1H), 12.04 (bs, 1H), 10.21 (bs, 1H), 8.15 (bs, 1H), 7.52 (d, 1H), 7.36 (d, 1H), 7.30 (d, 1H), 7.13 (s, 1H), 7.07 (m, 2H), 6.93 (s, 1H), 6.75 (m, 1H), 3.97 (bs, 2H), 3.81 (d, 2H), 2.72 (bs, 2H), 2.30 (s, 3H), 2.26 (s, 3H), 1.90 (bs, 1H), 1.75 (bs, 2H), 1.40 (s, 9H), 1.18 (m, 2H). MS (EI): 589 (M+).

Example 13

Synthesis $N^4$-(2,4-Dimethylphenyl)-$N^5$-{5-[(piperidin-4-ylmethyl)oxy]-1H-benzimidazol-2-yl}-1H-imidazole-4,5-dicarboxamide Hydrochloride $N^4$-(2,4-Dimethylphenyl)-$N^5$-{5-[(piperidin-4-ylmethyl)oxy]-1H-benzimidazol-2-yl}-1H-imidazole-4,5-dicarboxamide hydrochloride was prepared in the same manner as $N^5$-[4-(azetidin-3-yloxy)-2-methylphenyl]-$N^4$-1H-benzimidazol-2-yl-1H-imidazole-4,5-dicarboxamide in Example 5. $^1$H-NMR (400 MHz, DMSO-d$_6$) δ 14.00 (br s, 1H) 10.6 (br s, 2H), 9.97 (d, 1H), 8.68 (d, 1H), 8.31 (s, 1H), 7.50 (d, 1H), 7.41 (br s, 1H), 7.15 (s, 1H), 7.09 (d, 1H), 6.97 (d, 1H), 3.99 (d, 2H), 3.56 (bs, 2H), 3.29 (d, 2H), 2.90 (m, 2H), 2.31 (s, 3H), 2.26 (s, 3H), 2.08 (m, 1H), 1.92 (d, 2H), 1.53 (m, 2H). MS (EI): 488 (MH+).

Example 14

Synthesis of $N^5$-1H-benzimidazol-2-yl-$N^4$-(4-chloro-2-fluorophenyl)-1H-imidazole-4,5-dicarboxamide $N^5$-1H-Benzimidazol-2-yl-$N^4$-(4-chloro-2-fluorophenyl)-1H-imidazole-4,5-dicarboxamide was prepared by the general method used for the synthesis of $N^5$-1H-benzimidazol-2-yl-$N^4$-(2,4-dimethylphenyl)-1H-imidazole-4,5-dicarboxamide in Example 1 in 56% yield. $^1$H-NMR (400 MHz, DMSO-d6): 13.98 (m, br, 1H), 12.22 (s, br, 1H), 10.51 (s, br, 1H), 8.19 (s, br, 1H), 7.89 (s, br, 1H), 7.63 (dd, 1H), 7.45 (m, br, 3H), 7.13 (s, br, 2H). MS (EI): 399 (MH+).

Example 15

Synthesis of $N^5$-1H-benzimidazol-2-yl-$N^4$-(2,6-difluorophenyl)-1H-imidazole-4,5-dicarboxamide $N^5$-1H-Benzimidazol-2-yl)-$N^4$-(2,6-difluorophenyl)-1H-imidazole-4,5-dicarboxamide was prepared by the general method used for the synthesis of $N^5$-1H-benzimidazol-2-yl-$N^4$-(2,4-dimethylphenyl)-1H-imidazole-4,5-dicarboxamide in Example 1 in 61% yield. $^1$H-NMR (400 MHz, DMSO-d6): δ 13.92 (s, br, 1H), 12.21 (s, br, 1H), 10.82 (s, 1H), 8.23 (s, 1H), 7.52-7.05 (m, 7H). MS (EI): 383 (MH+).

Example 16

Synthesis of $N^5$-(4,5-dimethyl-1H-imidazol-2-yl)-$N^4$-[2-fluoro-6-(methyloxy)phenyl]-1H-imidazole-4,5-dicarboxamide $N^5$-(4,5-Dimethyl-1H-imidazol-2-yl)-$N^4$-[2-fluoro-6-(methyloxy)phenyl]-1H-imidazole-4,5-dicarboxamide was prepared in a similar as that used for $N^4$-(5-bromo-2-methylphenyl)-$N^5$-(4-methyl-1H-imidazol-2-yl)-1H-imidazole-4,5-dicarboxamide in Example 2 after purification by reverse phase preparative HPLC (aqueous ammonium acetate-acetonitrile). $^1$H-NMR (400 MHz, DMSO-d6): 8.21 (s, 1H), 8.04 (s, br, 1H), 7.41 (m, 3H), 3.81 (s, 3H), 2.02 (6H). MS (EI): 372.1 (MH+).

Example 17

Synthesis of $N^5$-1H-benzimidazol-2-yl-$N^4$-[2-methyl-6-(methyloxy)phenyl]-1H-imidazole-4,5-dicarboxamide $N^5$-1H-benzimidazol-2-yl-$N^4$-[2-methyl-6-(methyloxy)phenyl]-1H-imidazole-4,5-dicarboxamide was prepared by the general method used for the synthesis of $N^5$-1H-benzimidazol-2-yl-$N^4$-(2,4-dimethylphenyl)-1H-imidazole-4,5-dicarboxamide in Example 1 in 69% yield. $^1$H-NMR (400 MHz, DMSO-d6): 12.19 (s, br, 1H), 8.16 (s, 1H), 7.72 (s, br, 1H), 7.38 (s, br, 1H), 7.27 (m, 1H), 7.08 (m, 2H), 6.93 (m, 2H), 3.79 (s, 3H), 2.22 (s, 3H). MS (EI): 391 (MH+).

Example 18

Synthesis of $N^5$-1H-benzimidazol-2-yl-$N^4$-(2-chloro-6-fluorophenyl)-1H-imidazole-4,5-dicarboxamide $N^5$-1H-Benzimidazol-2-yl-$N^4$-(2-chloro-6-fluorophenyl)-1H-imidazole-4,5-dicarboxamide was prepared by the general method used for the synthesis of N⁵-1H-benzimidazol-2-yl-N⁴-(2,4-dimethylphenyl)-1H-imidazole-4,5-dicarboxamide in Example 1 in 49% yield. ¹H-NMR (400 MHz, DMSO-d6): δ 13.93 (s, br, 1H), 12.20 (s, br, 1H), 10.81 (s, 1H), 8.21 (s, 1H), 7.63 (m, 2H), 7.49-7.37 (m, 3H), 7.16 (m, 2H). MS (EI): 399 (MH+).

Example 19

Synthesis of N⁵-1H-benzimidazol-2-yl-N⁴-(4-bromo-2-fluorophenyl)-1H-imidazole-4,5-dicarboxamide N⁵-1H-Benzimidazol-2-yl-N⁴-(4-bromo-2-fluorophenyl)-1H-imidazole-4,5-dicarboxamide was prepared by the general method used for the synthesis of N⁵-1H-benzimidazol-2-yl-N⁴-(2,4-dimethylphenyl)-1H-imidazole-4,5-dicarboxamide in Example 1 in 53% yield. ¹H-NMR (400 MHz, DMSO-d6): δ 13.82 (s, br, 1H), 12.22 (s, br, 1H), 10.61 (s, br, 1H), 8.15 (s, br, 1H), 7.93 (s, br, 1H), 7.72 (dd, 1H), 7.51 (m, br, 3H), 7.13 (m, 2H). MS (EI): 444 (MH+).

Example 20

Synthesis of N⁵-1H-benzimidazol-2-yl-N⁴-{4-[(1-ethylpiperidin-4-yl)oxy]phenyl}-1H-imidazole-4,5-dicarboxamide

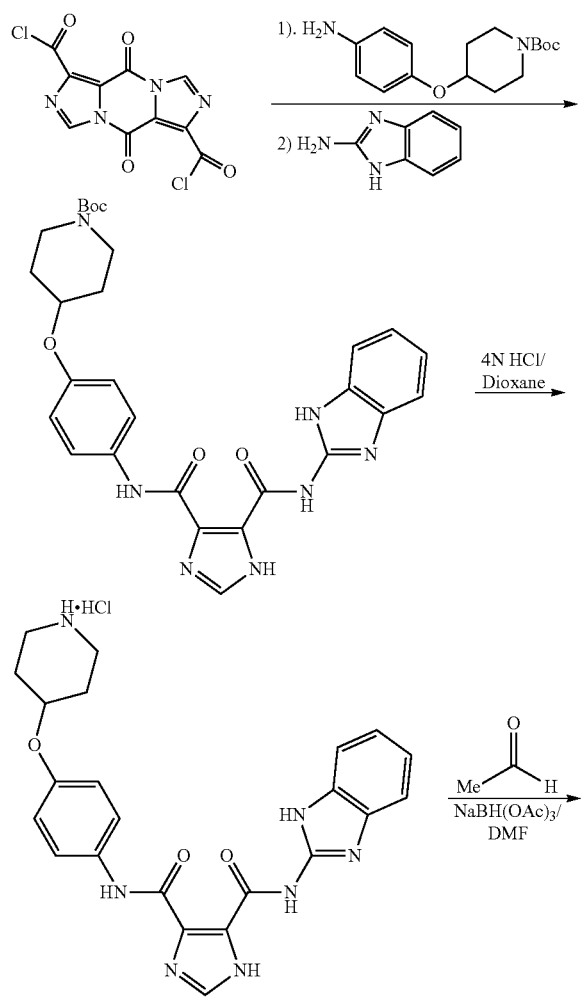

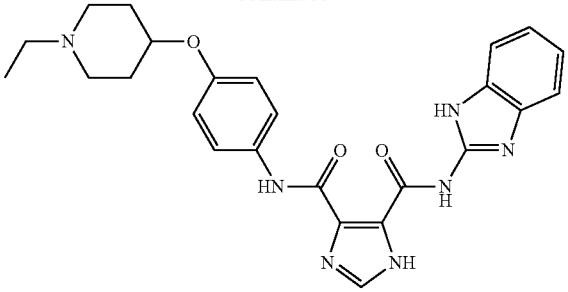

Synthesis of tert-butyl 4-(4-(5-(1H-benzo[d]imidazol-2-ylcarbamoyl)-1H-imidazole-4-carboxamido)phenoxy)piperidine-1-carboxylate tert-Butyl 4-(4-(5-(1H-benzo[d]imidazol-2-ylcarbamoyl)-1H-imidazole-4-carboxamido)phenoxy)piperidine-1-carboxylate was prepared using tent-butyl 4-(4-aminophenoxy)piperidine-1-carboxylate (commercially available form Tyger Scientific) by the general method used for the synthesis of N⁵-1H-benzimidazol-2-yl-N⁴-(2,4-dimethylphenyl)-1H-imidazole-4,5-dicarboxamide in Example 1. MS (EI): 546 (MH+).

Synthesis of N⁵-(1H-benzo[d]imidazol-2-yl)-N⁴-(4-(piperidin-4-yloxy)phenyl)-1H-imidazole-4,5-dicarboxamide Hydrochloride N⁵-(1H-Benzo[d]imidazol-2-yl)-N⁴-(4-(piperidin-4-yloxy)phenyl)-1H-imidazole-4,5-dicarboxamide was prepared by in a manner similar to that used for N⁵-[4-(azetidin-3-yloxy)-2-methylphenyl]-N⁴-1H-benzimidazol-2-yl-1H-imidazole-4,5-dicarboxamide in Example 5. MS (EI): 446 (MH+).

Synthesis of N⁵-1H-benzimidazol-2-yl-N⁴-{4-[(1-ethylpiperidin-4-yl)oxy]phenyl}-1H-imidazole-4,5-dicarboxamide Acetaldehyde (0.088 g, 2.0 mmol) was weighed out into a dry 25 ml round bottom flask. N⁵-(1H-benzo[d]imidazol-2-yl)-N⁴-(4-(piperidin-4-yloxy)phenyl)-1H-imidazole-4,5-dicarboxamide (0.0446 g, 0.1 mmol) was added, followed by DMF (3.0 ml) of sodium triacetoxyborohydride (0.106 g, 0.5 mmol). The reaction mixture was stirred at room temperature over night (16 hours). The reaction mixture was then treated with 1 mL of 1N hydrochloric acid and concentrated under reduced pressure. The resulting crude material was purified by reverse phase HPLC (ammonium acetate/acetonitrile) to give N⁵-1H-benzimidazol-2-yl-N⁴-{4-[(1-ethylpiperidin-4-yl)oxy]phenyl}-1H-imidazole-4,5-dicarboxamide as an grey-white solid. ¹H-NMR (DMSO-d6) 8.05 (s, 1H), 7.68 (d, 2H), 7.43 (s, br 2H), 7.05 (dd, 2H), 6.93 (d, 2H), 4.31 (m, 1H), 2.65 (m, 2H), 2.29 (q, 2H), 2.14 (m, 2H), 1.88 (m, 2H), 1.59 (m, 2H), 0.95 (t, 3H). MS (EI): 474 (MH+).

Example 21

Synthesis of N⁵-1H-benzimidazol-2-yl-N⁴-[5-chloro-2-(methyloxy)phenyl]-1H-imidazole-4,5-dicarboxamide N⁵-1H-Benzimidazol-2-yl-N⁴-[5-chloro-2-(methyloxy)phenyl]-1H-imidazole-4,5-dicarboxamide was prepared by the general method used for the synthesis of N⁵-1H-benzimidazol-2-yl-N⁴-(2,4-dimethylphenyl)-1H-imidazole-4,5-dicarboxamide in Example 1 in 54% yield. ¹H-NMR (400 MHz, DMSO-d6): δ 10.21 (s, 1H), 8.44-8.42 (m, 1H), 8.18-8.12 (m, 1H), 7.54-7.46 (m, 2H), 7.27-7.23 (m, 1H), 7.20-7.18 (m, 1H), 7.13-7.11 (m, 2H), 3.94 (s, 3H). MS (EI): 411 (MH+).

Example 22

Synthesis of Methyl[(2-{[(4-{[(5-bromo-2-methylphenyl)amino]carbonyl}-1H-imidazol-5-yl)carbonyl]amino}-1H-benzimidazol-5-yl)oxy]acetate Methyl[(2-{[(4-{[(5-bromo-2-methylphenyl)amino]carbonyl}-1H-imidazol-5-yl)carbonyl]amino}-1H-benzimidazol-5-yl)oxy]acetate was prepared by the general method used for the synthesis of N⁵-1H-benzimidazol-2-yl-N⁴-(2,4-dimethylphenyl)-1H-imidazole-4,5-dicarboxamide in Example 1 in 48% yield. ¹H-NMR (400 MHz, DMSO-d6): 13.83 (s, 1H), 12.09 (s, 1H), 10.34 (s, 1H), 8.17 (s, 1H), 7.93 (s, 1H), 7.39 (s, 2H), 7.30 (d, 1H), 7.05 (d, 1H), 6.80 (d, 1H), 4.77 (s, 2H), 3.71 (s, 3H), 2.29 (s, 3H); MS (EI): 528.5 (MH+).

Example 23

Synthesis of N⁴-1H-benzimidazol-2-yl-N⁵-[2-chloro-5-(hydroxymethyl)phenyl]-1H-imidazole-4,5-dicarboxamide

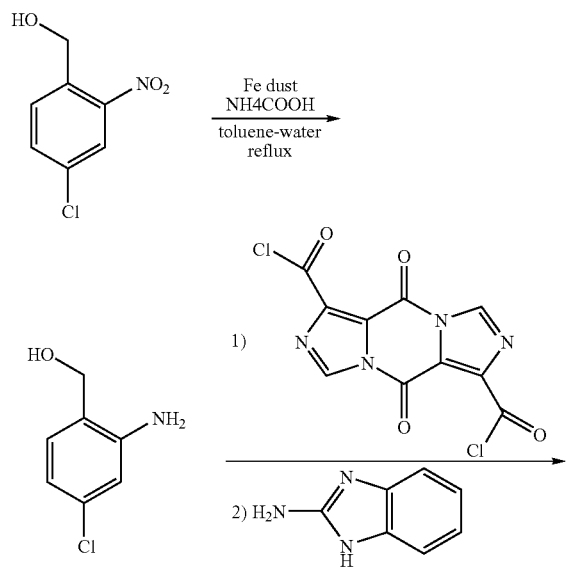

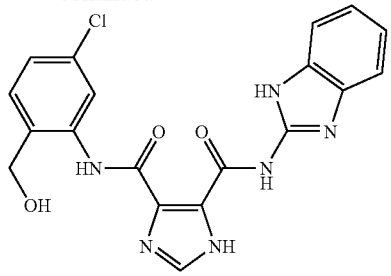

Synthesis of 3-Amino-4-chlorophenyl)methanol

A 100 mL flask was charged with (4-chloro-3-nitrophenyl)methanol (commercially available from Acros; 1.0 g, 5.5 mmol), ammonium formate (1.4 g, 22 mmol), and iron powder (1.2 g, 22 mmol). Toluene (15 mL) and water (15 mL) were added to the flask and the mixture was heated to reflux for 4 hours, after which time, the mixture was filtered through a plug of Celite. The supernatant was washed with ethyl acetate (3×50 ml). The combined organic solution was washed with water (100 ml), saturated sodium chloride solution (100 ml), dried over anhydrous sodium sulfate and filtered. The organic solvent was removed on a rotary evaporator under reduced pressure to yield (3-amino-4-chlorophenyl)methanol (0.74 g, 85% yield). The material was used without further purification. ¹H-NMR (400 MHz, CDCl₃) δ 6.88 (d, 1H), 6.56 (d, 1H), 6.40 (s, 1H), 5.85 (bs, 2H), 5.39 (bs, 1H), 5.85 (bs, 1H), 4.79 (s, 2H): MS (EI): 158 (MH+).

Synthesis of N⁴-1H-benzimidazol-2-yl-N⁵-[2-chloro-5-(hydroxymethyl)phenyl]-1H-imidazole-4,5-dicarboxamide N⁴-1H-Benzimidazol-2-yl-N⁵-[2-chloro-5-(hydroxymethyl)phenyl]-1H-imidazole-4,5-dicarboxamide was prepared by the general method used for the synthesis of N⁵-1H-benzimidazol-2-yl-N⁴-(2,4-dimethylphenyl)-1H-imidazole-4,5-dicarboxamide in Example 1 in 46% yield. ¹H-NMR (400 MHz, DMSO-d6): δ 13.9 (m, 2H), 12.2 (s, 1H), 10.4 (s, 1H), 8.19 (s, 2H), 7.56-7.44 (m, 3H), 7.22-7.20 (m, 2H), 7.13-7.10 (m, 1H), 5.45 (t, 5.7 Hz, 1H), 4.56 (d, 5.7 Hz, 2H). MS (EI): 411 (MH+).

Example 24

Synthesis of N⁴-(5-bromo-2-methylphenyl)-N⁵-(6-{[2-(dimethylamino)ethyl]oxy}-1H-benzimidazol-2-yl)-1H-imidazole-4,5-dicarboxamide

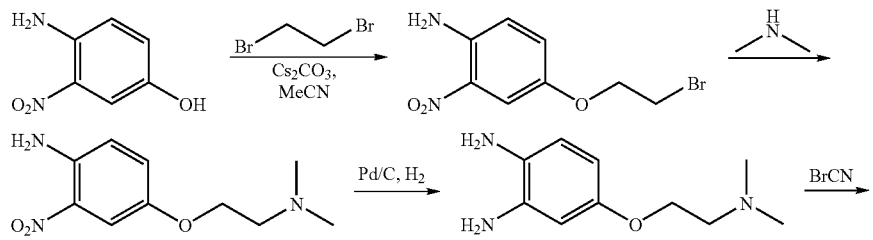

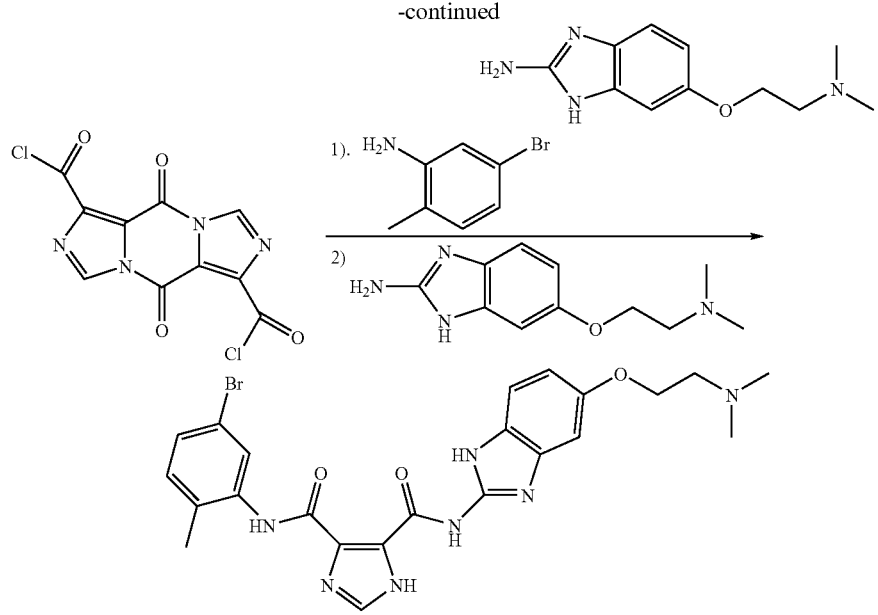

Synthesis of 4-(2-bromoethoxy)-2-nitroaniline

A round-bottom flask was charged with 4-amino-3-nitrophenol (15.4 g, 0.1 mol, commercially available from Aldrich), acetone (600 mL), 1,2-dibromoethane (34.5 mL, 0.4 mol) and cesium carbonate (39 g, 0.12 mol). The mixture was refluxed 15 hours with stirring. The mixture was filtered to remove the salt, the filtrate was concentrated. Purification by the silica gel chromatography gave 4-(2-bromoethoxy)-2-nitroaniline (6.5 g). $^1$H-NMR (400 MHz, CDCl$_3$): δ 7.57 (d, 1H), 7.12 (dd, 1H), 6.80 (d, 1H), 5.95 (s, br, 2H), 4.27 (t, 2H), 3.64 (t, 3H). MS (EI): 262 (MH+).

Synthesis of 4-(2-(dimethylamino)ethoxy)-2-nitroaniline

To a seal tube was added 4-(2-bromoethoxy)-2-nitroaniline (4.5 g, 17 mmol), THF and 40 mL of 2M dimethylamine in THF. The mixture was heated to 80° C. and was stirred overnight. The suspension was concentrated, and the residue was triturated with ether to give 3.5 g of 4-(2-(dimethylamino)ethoxy)-2-nitroaniline which was used in the next step without further purification. $^1$H-NMR (400 MHz, CDCl$_3$): δ 7.24 (s, 1H), 6.91 (d, 1H), 6.61 (d, 1H), 5.85 (bs, 2H), 4.04 (t, 2H), 2.78 (t, 2H), 2.27 (s, 6H). MS (EI): 226 (MH+).

Synthesis of 4-(2-(dimethylamino)ethoxy)benzene-1,2-diamine

To a Parr hydrogenation bottle was added 3.5 g of 4-(2-(dimethylamino)ethoxy)-2-nitroaniline, 10% palladium in carbon (50% w/w water, 1.0 g) and methanol (100 mL). The atmosphere of the vessel was replaced by hydrogen gas. The reaction was carried out on the Parr shaker at 40 psi at room temperature for 1 hour. The reaction mixture was filtered through a plug of Celite. 2.0 g of sodium bicarbonate was subsequently added to the filtrate, which was stirred for 10 minutes. The filtrate was concentrated reduced pressure and the resulting residue was triturated with diethylether to give 4-(2-(dimethylamino)ethoxy)benzene-1,2-diamine (2.2 g, 73%). $^1$H-NMR (400 MHz, MeOH-d4): δ 6.67 (d, 1H), 6.44 (d, 1H), 6.27 (dd, 1H), 4.18 (t, 2H), 3.50 (t, 3H), 2.92 (s, 6H). MS (EI): 196 (MH+).

Synthesis of 6-(2-(dimethylamino)ethoxy)-1H-benzoimidazol-2-amine

A solution of 4-(2-(dimethylamino)ethoxy)benzene-1,2-diamine (2.0 g, 10 mmol) in 15 mL of water was cooled to 0° C. and treated with a solution of cyanogens bromide (5M in acetonitrile, 1.1 eq.). The reaction mixture was stirred at room temperature for 12 hours. The mixture was made basic with sodium bicarbonate and concentrated under reduced pressure. The residue was extracted with methanol and concentrated. The residue was purified by preparative reverse phase (aqueous ammonium acetate-acetonitrile) HPLC to give 0.763 g of 6-(2-(dimethylamino)ethoxy)-1H-benzoimidazol-2-amine. $^1$H-NMR (400 MHz, MeOH-d4): δ 7.78 (s, br, 2H), 7.20 (d, 1H), 6.95 (s, 1H), 6.78 (d, 1H), 4.30 (t, 2H), 3.42 (t, 3H), 2.90 (s, 6H). MS (EI): 221 (MH+).

Synthesis of N$^4$-(5-bromo-2-methylphenyl)-N$^5$-(6-{[2-(dimethylamino)ethyl]oxy}-1H-benzimidazol-2-yl)-1H-imidazole-4,5-dicarboxamide N$^4$-(5-Bromo-2-methylphenyl)-N$^5$-(6-{[2-(dimethylamino)ethyl]oxy}-1H-benzimidazol-2-yl)-1H-imidazole-4,5-dicarboxamide was prepared by the general method used for the synthesis of N$^5$-1H-benzimidazol-2-yl-N$^4$-(2,4-dimethylphenyl)-1H-imidazole-4,5-dicarboxamide in Example 1 in 54% yield. $^1$H-NMR (400 MHz, DMSO-d6): 12.15 (s, 1H), 10.38 (s, 1H), 8.20 (s, 1H), 7.95 (s, 1H), 7.40-7.30 (m, 3H), 7.15 (s, 1H), 6.84 (d, 1H), 4.05 (t, 2H), 2.65 (t, 2H), 2.30 (s, 3H), 2.23 (s, 6H). MS (EI): 526 (MH+).

Example 25

Synthesis of N⁵-(5-chloro-1H-benzimidazol-2-yl)-N⁴-(2,4-dimethylphenyl)-1H-imidazole-4,5-dicarboxamide

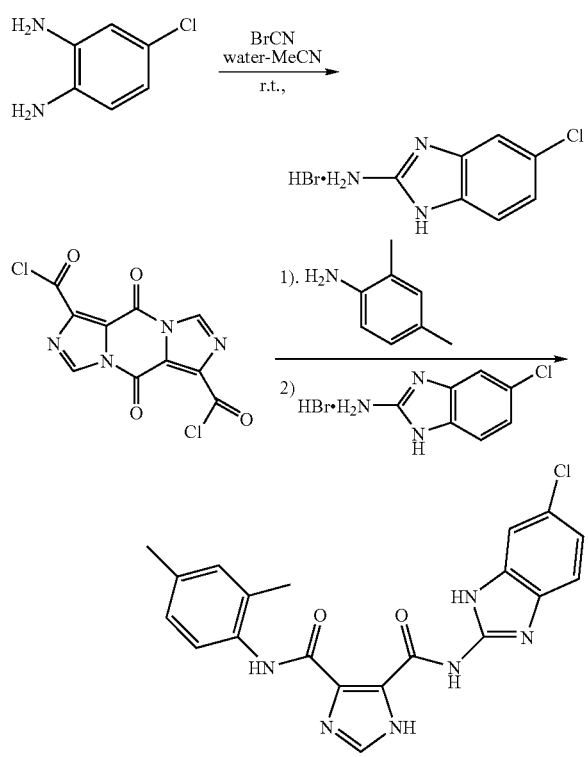

Synthesis of 5-chloro-1H-benzo[d]imidazol-2-amine Hydrobromide

5-Chloro-1,2,-phenylene diamine (100 mmoles, 14.24 g, 1 equivalent, commercially available from Aldrich) was dissolved in acetonitrile (200 ml) and water (50 ml) and cooled to 0-5° C. (ice-water). Cyanogen bromide (10.59 g, 100 mmoles, 1 equivalent) was added over a period of 5 minutes and the reaction mixture was allowed to go to room temperature and was stirred for 16 hours. The reaction mixture was then evaporated under reduced pressure to 22.20 g of 5-chloro-1H-benzo[d]imidazol-2-amine hydrobromide (yield: 89%) which was used directly in the next reaction without purification. ¹H-NMR (400 MHz, DMSO-d6) δ 10.80 (br s, 2H), 7.04 (d, 2H), 6.81 (d, 1H), 6.34 (s, 3H). MS (EI): 248 (MH+).

Synthesis of N⁵-(5-chloro-1H-benzimidazol-2-yl)-N⁴-(2,4-dimethylphenyl)-1H-imidazole-4,5-dicarboxamide N⁵-(5-Chloro-1H-benzimidazol-2-yl)-N⁴-(2,4-dimethylphenyl)-1H-imidazole-4,5-dicarboxamide was prepared by the general method used for the synthesis of N⁵-1H-benzimidazol-2-yl-N⁴-(2,4-dimethylphenyl)-1H-imidazole-4,5-dicarboxamide in Example 1 in 38% yield. ¹H-NMR (400 MHz, DMSO-d6): δ 12.15 (s, 1H), 10.38 (s, 1H), 8.20 (s, 1H), 7.95 (s, 1H), 7.40-7.30 (m, 3H), 7.15 (s, 1H), 6.84 (d, 1H), 4.05 (t, 2H), 2.65 (t, 2H), 2.30 (s, 3H), 2.23 (s, 6H). MS (EI): 526 (MH+).

Example 26

Synthesis of N⁴-(5-bromo-2-methylphenyl)-N⁵-(5-chloro-1H-benzimidazol-2-yl)-1H-imidazole-4,5-dicarboxamide N⁴-(5-Bromo-2-methylphenyl)-N⁵-(5-chloro-1H-benzimidazol-2-yl)-1H-imidazole-4,5-dicarboxamide was prepared by the general method used for the synthesis of N⁵-1H-benzimidazol-2-yl-N⁴-(2,4-dimethylphenyl)-1H-imidazole-4,5-dicarboxamide in Example 1 in 31% yield. ¹H-NMR (400 MHz, DMSO-d6) δ 13.80 (br s, 2H), 11.85 (br s, 2H), 8.32 (s, 1H), 7.88 (s, 1H), 7.61 (s, 1H), 7.57 (s, 1H), 7.42 (d, 1H), 7.31 (m, 2H), 2.29 (s, 3H). MS (EI): 474 (MH+).

Example 27

Synthesis of 1,1-dimethylethyl 4-{4-[({5-[(1H-benzimidazol-2-ylamino)carbonyl]-1H-imidazol-4-yl}carbonyl)amino]-3-methylphenyl}piperazine-1-carboxylate

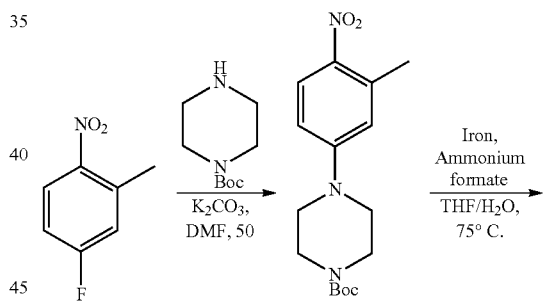

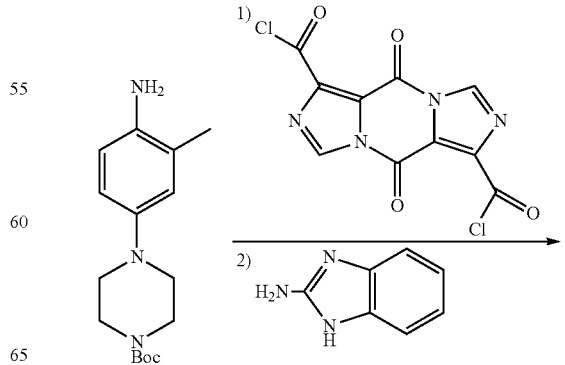

193

-continued

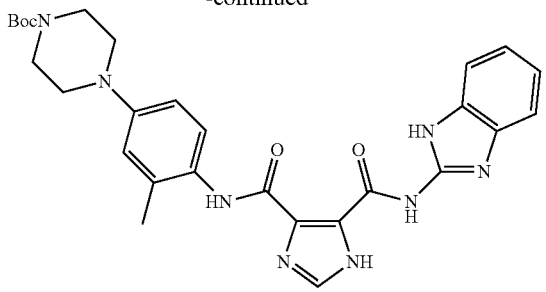

Synthesis of tert-butyl 4-(3-methyl-4-nitrophenyl)piperazine-1-Carboxylate

5-Fluoro-2-nitrotoluene (1 mL, 8.20 mmol, commercially available from Aldrich), Boc-piperazine (1.68 g, 9.02 mmol, commercially available from Aldrich), anhydrous potassium carbonate (2.27 g, 16.40 mmol) and DMF (25 mL) were combined and heated to 50° C. for 24 hours. Upon allowing the reaction mixture to cool to room temperature, water was added to the reaction mixture and the resulting precipitate was filtered as product, washed with ether and dried under reduced pressure to give 2.21 g tert-butyl 4-(3-methyl-4-nitrophenyl)piperazine-1-carboxylate. $^1$H-NMR (400 MHz, CDCl$_3$), δ 7.96 (d, 1H), 6.90 (s, 1H), 6.85 (s, 1H), 3.35 (m, 4H), 3.19 (m, 4H), 2.55 (s, 3H), 1.42 (s, 9H). MS (EI): 322 (MH+).

Synthesis of tert-butyl 4-(4-amino-3-methylphenyl)piperazine-1-Carboxylate tert-Butyl 4-(3-methyl-4-nitrophenyl)piperazine-1-carboxylate (1.25 g, 3.90 mmoles), 1 equivalent), tetrahydrofuran (10 ml), water (10 ml), iron dust (1.09 g, 19.5 mmoles, 5 equivalents), and ammonium formate (1.23 g, 19.5 mmoles, 5 equivalents) were combined and heated, with stirring to 75° C. for 12 hours (overnight). The hot mixture was filtered through a plug of Celite and washed with ethyl acetate. The filtrate was evaporated under reduced pressure and extracted with ethyl acetate. The ethyl acetate solution was washed with water and saturated sodium chloride solution. The ethyl acetate solution was dried over anhydrous sodium sulfate, filtered and evaporated under reduced pressure to give 1.11 g of tert-butyl 4-(4-amino-3-methylphenyl)piperazine-1-carboxylate. $^1$H-NMR (400 MHz, CDCl$_3$), δ 6.47 (d, 1H), 6.16 (d, 1H), 6.14 (d, 1H), 5.85 (bs, 2H), 3.35 (m, 4H), 3.19 (m, 4H), 2.35 (s, 3H), 1.42 (s, 9H). MS (EI) for C16H25N3O2, 292 (MH+).

Synthesis of 1,1-dimethylethyl 4-{4-[({5-[(1H-benzimidazol-2-ylamino)carbonyl]-1H-imidazol-4-yl}carbonyl)amino]-3-methylphenyl}piperazine-1-carboxylate 1,1-Dimethylethyl 4-{4-[({5-[(1H-benzimidazol-2-ylamino)carbonyl]-1H-imidazol-4-yl}carbonyl)amino]-3-methylphenyl}piperazine-1-carboxylate dicarboxamide was prepared by the general method used for the synthesis of N$^5$-1H-benzimidazol-2-yl-N$^4$-(2,4-dimethylphenyl)-1H-imidazole-4,5-dicarboxamide in Example 1 in 49% yield. $^1$H-NMR (400 MHz, DMSO-d6): δ 12.13 (s, br, 1H), 10.21 (s, br, 1H), 7.82 (s, br, 1H), 7.57 (d, 1H), 7.44 (s, br, 2H), 7.08 (m, 2H), 6.91 (d, 1H), 6.86 (m, 1H), 3.48 (m, 4H), 3.09 (m, 4H), 2.27 (s, 3H), 1.43 (s, 9H). MS (EI): 545 (MH+).

Example 28

Synthesis of N$^5$-(6-chloro-1H-benzimidazol-2-yl)-N$^4$-(2,6-dichlorophenyl)-1H-imidazole-4,5-dicarboxamide N$^5$-(6-Chloro-1H-benzimidazol-2-yl)-N$^4$-(2,6-dichlorophenyl)-1H-imidazole-4,5-dicarboxamide was prepared by the general method used for the synthesis of N$^5$-1H-benzimidazol-2-yl-N$^4$-(2,4-dimethylphenyl)-1H-imidazole-4,5-dicarboxamide in Example 1 in 38% yield. $^1$H-NMR (400 MHz, DMSO-d6) δ 13.90 (br s, 1H), 12.35 (br s, 1H), 10.85 (br s, 1H), 8.21 (s, 1H), 7.64 (d, 2H), 7.48 (d, 2H), 7.14 (s, 1H), 7.42 (d, 1H), 7.31 (m, 2H). MS (EI): 450 (MH+).

Example 29

Synthesis of 1,1-dimethylethyl 4-[3-({4-[({4-[(1H-benzimidazol-2-ylamino)carbonyl]-1H-imidazol-5-yl}carbonyl)amino]-5-chloro-2-methylphenyl}oxy)propyl]piperazine-1-carboxylate

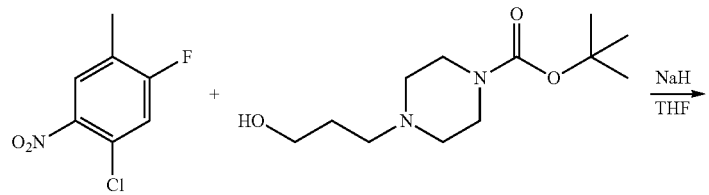

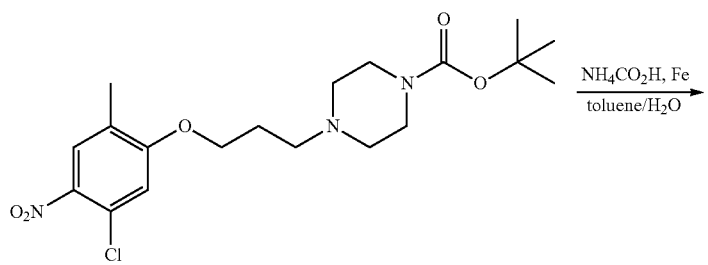

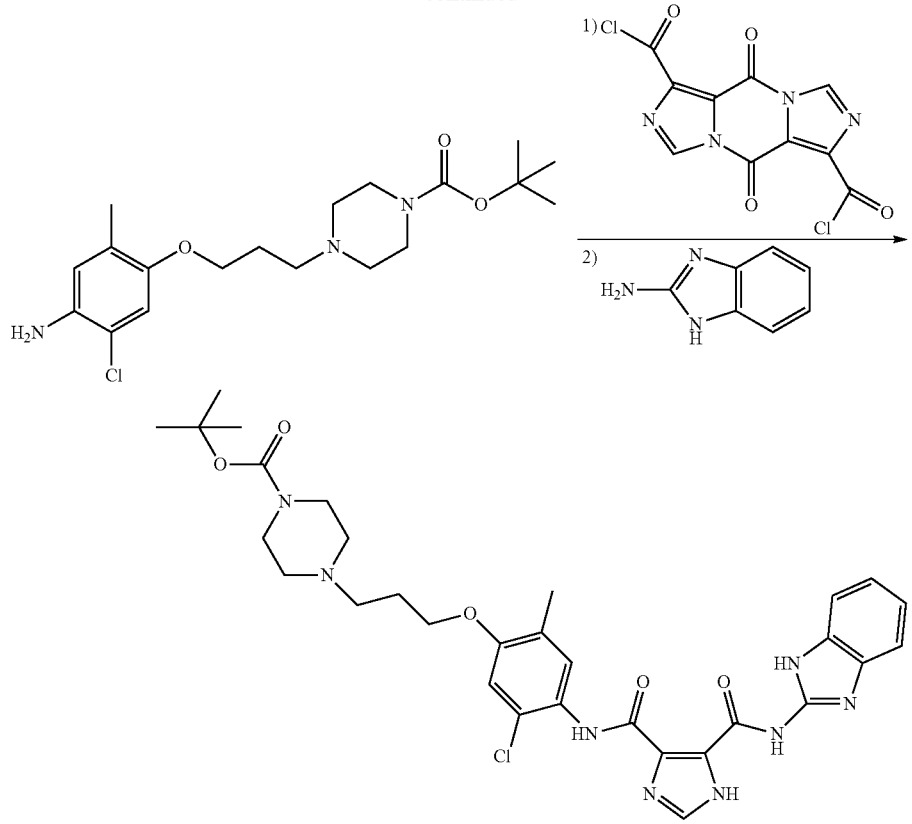

Synthesis of tert-butyl 4-(3-(5-chloro-2-methyl-4-nitrophenoxy)propyl)piperazine-1-carboxylate A flask was charged with tert-butyl 4-(3-hydroxypropyl) piperazine-1-carboxylate (905 mg, 3.7 mmol, commercially available from Alrich), sodium hydride, 95% (24 mg, 4.6 mmol) and THF (10 mL), and the mixture was stirred under $N_2$ for 15 minutes, after which time a solution of 1-chloro-5-fluoro-4-methyl-2-nitrobenzene (700 mg, 3.7 mmol, commercially available from Aldrich) in THF (10 mL) was added to the sodium hydride mixture at 0° C. The reaction mixture was heated to 65° C. for 15 hours. Water was added to the cooled reaction mixture and the mixture was extracted with ethyl acetate. The organic solvent was concentrated under reduced pressure and the resulting solid was purified by silica column chromatography eluting with 5% methanol in dichloromethane, to give 1.2 g (78 5 yield) of tert-butyl 4-(3-(5-chloro-2-methyl-4-nitrophenoxy) propyl)piperazine-1-carboxylate. $^1$H-NMR (400 MHz, CDCl$_3$) δ 7.82 (s, 1H), 6.92 (s, 1H), 3.92 (t, 2H), 3.06 (m, 4H), 2.62 (m, 4H), 2.36 (m, 2H), 2.34 (s, 3H), 1.84 (m, 2H), 1.42 (s, 9H). MS (EI): 414 (MH+).

Synthesis of tert-Butyl 4-(3-(4-amino-5-chloro-2-methylphenoxy)propyl)piperazine-1-carboxylate A flask was charged with tert-butyl 4-(3-(5-chloro-2-methyl-4-nitrophenoxy)propyl)-piperazine-1-carboxylate (1.2 g, 2.9 mmol), ammonium formate (0.84 g, 13 mmol), and iron powder (0.74 g, 13 mmol). Toluene (20 mL) and water (20 mL) were added to the flask and the mixture was heated to reflux for 6 hours, after which time, the mixture was filtered through a plug of Celite. The supernatant was extracted with ethyl acetate and water. The organic solvent was removed on a rotary evaporator under reduced pressure to yield tert-butyl 4-(3-(4-amino-5-chloro-2-methylphenoxy)propyl)piperazine-1-carboxylate as a brown oil (0.99 g, 89% yield). $^1$H-NMR (400 MHz, DMSO-d6): δ 6.77 (s, 1H), 6.61 (s, 1H), 4.76 (s, 2H), 3.86 (t, 6.1 Hz, 2H), 3.30 (s, br, 4H), 2.50 (m, 2H), 2.31 (m, 2H), 2.03 (s, 3H), 1.82 (m, 2H), 1.39 (s, 9H). MS (EI): 384 (MH+).

Synthesis of 1,1-dimethylethyl 4-[3-({4-[({4-[(1H-benzimidazol-2-ylamino)carbonyl]-1H-imidazol-5-yl}carbonyl)amino]-5-chloro-2-methylphenyl}oxy) propyl]piperazine-1-carboxylate 1,1-Dimethylethyl 4-[3-({4-[({4-[(1H-benzimidazol-2-ylamino)carbonyl]-1H-imidazol-5-yl}carbonyl)amino]-5-chloro-2-methylphenyl}oxy)propyl]piperazine-1-carboxylate) was prepared by the general method used for the synthesis of $N^5$-1H-benzimidazol-2-yl-$N^4$-(2,4-dimethylphenyl)-1H-imidazole-4,5-dicarboxamide in Example 1 in 42% yield. $^1$H-NMR (400 MHz, DMSO-d6): δ 14.1 (s, 1H), 13.8 (br s, 1H), 12.2 (s, 1H), 10.3 (s, 1H), 8.15 (s, 1H), 7.77 (s, 1H), 7.52-7.41 (m, 2H), 7.15-7.04 (m, 3H), 4.06 (t, 2H), 3.30 (m, 2H), 3.20 (m, 4H), 2.34 (m, 4H), 2.19 (s, 3H), 1.90 (m, 2H), 1.38 (s, 9H). MS (EI): 637 (MH+).

Example 30

Synthesis of N⁴-1H-benzimidazol-2-yl-N⁵-{2-chloro-5-methyl-4-[(3-piperazin-1-ylpropyl)oxy]phenyl}-1H-imidazole-4,5-dicarboxamide

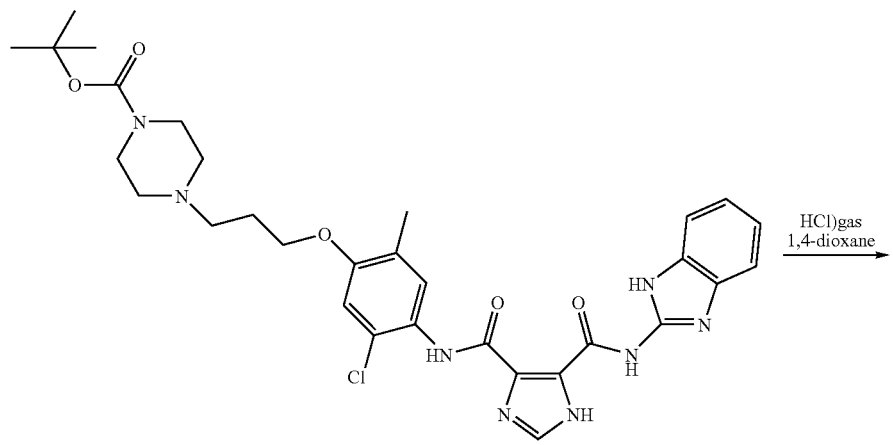

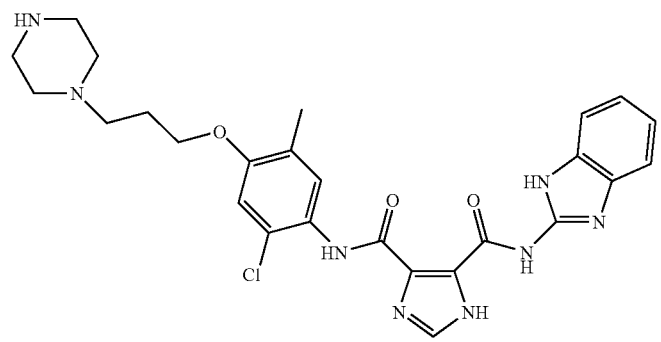

N⁴-1H-benzimidazol-2-yl-N⁵-{2-chloro-5-methyl-4-[(3-piperazin-1-ylpropyl)oxy]phenyl}-1H-imidazole-4,5-dicarboxamide was prepared by in a manner similar to that used for N⁵-[4-(azetidin-3-yloxy)-2-methylphenyl]-N⁴-1H-benzimidazol-2-yl-1H-imidazole-4,5-dicarboxamide in Example 5 in 79% yield. ¹H-NMR (400 MHz, DMSO-d6): δ 7.89 (s, 1H), 7.72 (s, 1H), 7.40 (m, 2H), 7.08 (s, 1H), 7.03-7.01 (m, 3H), 3.99 (t, 6.2 Hz, 2H), 3.26 (m, 2H), 2.67 (t, 4.8 Hz, 4H), 2.36 (t, 7.0 Hz, 2H), 2.27-2.26 (m, 4H), 2.15 (s, 3H). MS (EI): 537 (MH+).

Example 31

Scheme for the synthesis of N⁴-1H-benzimidazol-2-yl-N⁵-{2-chloro-4-[(3-piperazin-1-ylpropyl)oxy]phenyl}-1H-imidazole-4,5-dicarboxamide

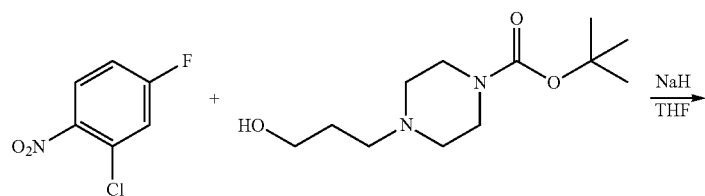

-continued
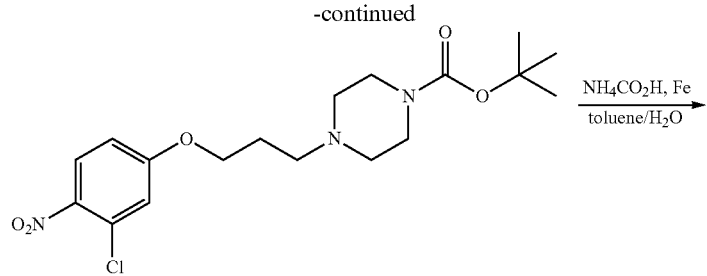
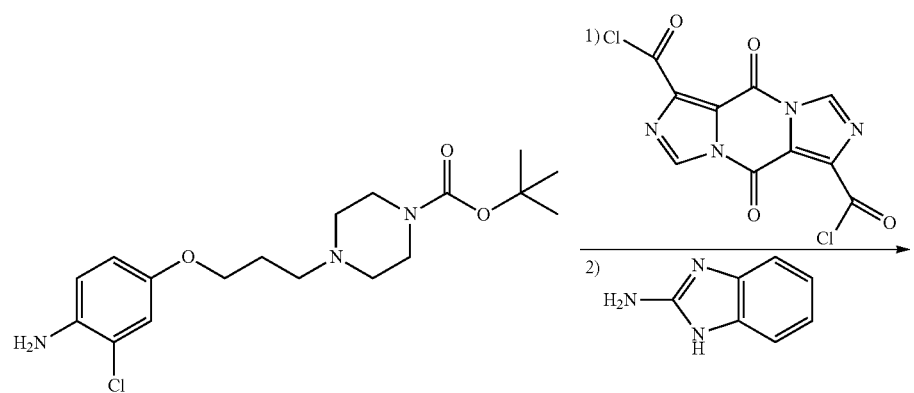
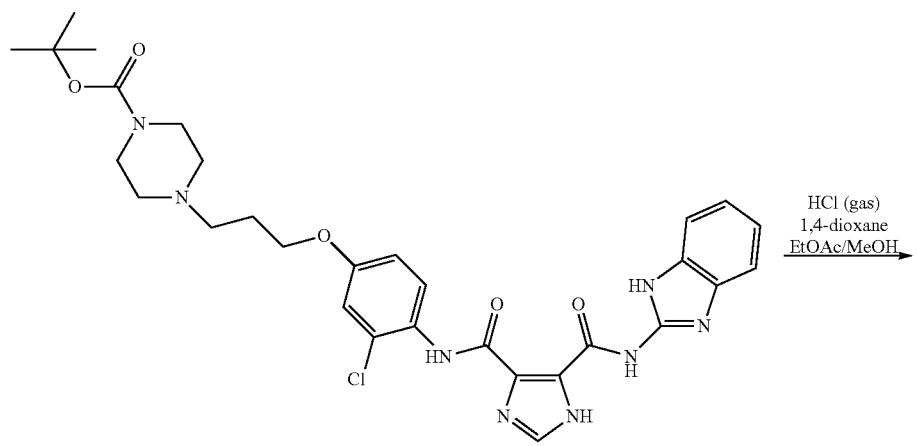
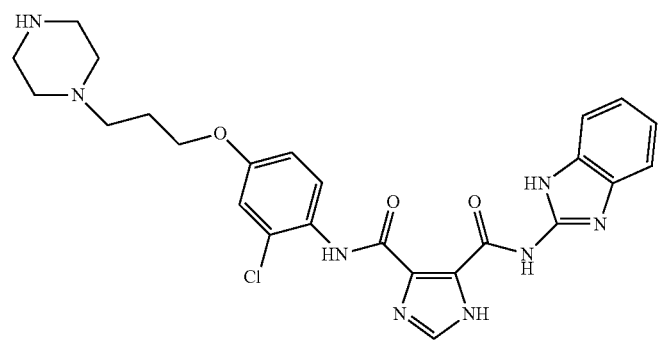

Synthesis of tert-butyl 4-(3-(4-n-3-chlorophenoxy)propyl)piperazine-1-carboxylate The key aniline, tert-butyl 4-(3-(4-amino-3-chlorophenoxy)propyl)piperazine-1-carboxylate was prepared in an analogous fashion to tent-butyl 4-(3-(4-amino-5-chloro-2-methylphenoxy)propyl)piperazine-1-carboxylate. $^1$H-NMR (400 MHz, CDCl$_3$): δ 6.85 (d, 2.3 Hz, 1H), 6.72-6.66 (m, 2H), 3.93 (t, 6.3 Hz, 2H), 3.74 (s, br, 2H), 3.44 (m, 4H), 2.50 (t, 7.4 Hz, 2H), 2.40 (m, 4H), 1.92 (quin, 2H), 1.46 (s, 9H). MS (EI): 370 (MH+).

Synthesis of tert-butyl 4-(3-(4-(5-(1H-benzo[d]imidazol-2-ylcarbamoyl)-1H-imidazole-4-carboxamido)-3-chlorophenoxy)propyl)piperazine-1-carboxylate tert-Butyl 4-(3-(4-(5-(1H-benzo[d]imidazol-2-ylcarbamoyl)-1H-imidazole-4-carboxamido)-3-chlorophenoxy)propyl)piperazine-1-carboxylate dicarboxamide was prepared by the general method used for the synthesis of N$^5$-1H-benzimidazol-2-yl-N$^4$-(2,4-dimethylphenyl)-1H-imidazole-4,5-dicarboxamide in Example 1 in 74% yield. MS (EI): 624 (MH+).

Synthesis of N$^4$-1H-benzimidazol-2-yl-N$^5$-{2-chloro-4-[(3-piperazin-1-ylpropyl)oxy]phenyl}-1H-imidazole-4,5-dicarboxamide hydrochloride N$^4$-1H-Benzimidazol-2-yl-N$^5$-{2-chloro-4-[(3-piperazin-1-ylpropyl)oxy]phenyl}-1H-imidazole-4,5-dicarboxamide hydrochloride was prepared by the general method used for the synthesis of N$^5$-[4-(azetidin-3-yloxy)-2-methylphenyl]-N$^4$-1H-benzimidazol-2-yl-1H-imidazole-4,5-dicarboxamide in Example 5 in 68% yield. $^1$H-NMR (400 MHz, DMSO-d6): δ 8.07 (d, 9.2 Hz, 1H), 7.62 (s, 1H), 7.40 (m, 2H), 7.32-7.30 (m, 1H), 7.11 (d, 3.1 Hz, 1H), 7.03-6.94 (m, 4H), 3.98 (t, 6.6 Hz, 2H), 3.25 (m, 2H), 2.65 (t, 4.8 Hz, 4H), 2.33 (t, 7.0 Hz, 2H), 2.26 (m, 4H), 1.82-1.79 (m, 2H). MS (EI): 523 (MH+).

Example 32

Synthesis of N$^5$-(6-chloro-1H-benzimidazol-2-yl)-N$^4$-(2-chloro-6-fluorophenyl)-1H-imidazole-4,5-dicarboxamide N$^5$-(6-Chloro-1H-benzimidazol-2-yl)-N$^4$-(2-chloro-6-fluorophenyl)-1H-imidazole-4,5-dicarboxamide was prepared by the general method used for the synthesis of N$^5$-1H-benzimidazol-2-yl-N$^4$-(2,4-dimethylphenyl)-1H-imidazole-4,5-dicarboxamide in Example 1 in 33% yield. $^1$H-NMR (400 MHz, DMSO-d6) δ 14.00 (br s, 1H), 12.35 (br s, 1H), 10.82 (br s, 1H), 8.23 (s, 1H), 7.53 (m, 2H), 7.49 (d, 2H), 7.42 (m, 1H), 7.28 (d, 1H), 7.23 (m, 2H). MS (EI): 432 (MH+).

Example 33

Synthesis of N$^4$-(2,4-dimethylphenyl)-N$^5$-(5-{[2-(methylamino)-2-oxoethyl]oxy}-1H-benzimidazol-2-yl)-1H-imidazole-4,5-dicarboxamide N$^4$-(2,4-Dimethylphenyl)-N$^5$-(5-{[2-(methylamino)-2-oxoethyl]oxy}-1H-benzimidazol-2-yl)-1H-imidazole-4,5-dicarboxamide was made using the protocol utilized for the synthesis of N$^5$-[6-({2-[(2,3-dihydroxypropyl)amino]-2-oxoethyl}oxy)-1H-benzimidazol-2-yl]-N$^4$-(2,4-dimethylphenyl)-1H-imidazole-4,5-dicarboxamide in Example 6. $^1$H-NMR (400 MHz, DMSO-d6): δ 8.11 (s, 1H), 8.04 (s, br, 1H), 7.55 (d, 1H), 7.37 (s, 1H), 7.08 (m, 3H), 6.81 (dd, 1H), 4.44 (s, 2H), 2.60 (s, 3H), 2.31 (s, 3H), 2.28 (s, 3H). MS (EI): 462.3 (MH+).

Example 34

Synthesis of N$^4$-(2,4-dimethylphenyl)-N$^5$-[5-({2-oxo-2-[(pyridin-4-ylmethyl)amino]ethyl}oxy)-1H-benzimidazol-2-yl]-1H-imidazole-4,5-dicarboxamide N$^4$-(2,4-Dimethylphenyl)-N$^5$-[5-({2-oxo-2-[(pyridin-4-ylmethyl)amino]ethyl}oxy)-1H-benzimidazol-2-yl]-1H-imidazole-4,5-dicarboxamide was made using the protocol utilized for the synthesis of N$^5$-[6-({2-[(2,3-dihydroxypropyl)amino]-2-oxoethyl}oxy)-1H-benzimidazol-2-yl]-N$^4$-(2,4-dimethylphenyl)-1H-imidazole-4,5-dicarboxamide in Example 6. $^1$H-NMR (400 MHz, DMSO-d6): δ 8.77 (s, 1H), 8.45 (dd, 1H), 7.99 (s, 1H), 7.60 (d, 1H), 7.22 (d, 2H), 7.12 (s, 1H), 7.08 (d, 2H), 6.84 (dd, 1H), 4.58 (s, 2H), 4.37 (s, 2H), 3.30 (s, 3H), 2.28 (s, 3H). MS (EI): 539.8 (MH+).

Example 35

Scheme for the synthesis of N$^5$-1H-benzimidazol-2-yl-N$^4$-(2-methyl-4-piperazin-1-ylphenyl)-1H-imidazole-4,5-dicarboxamide

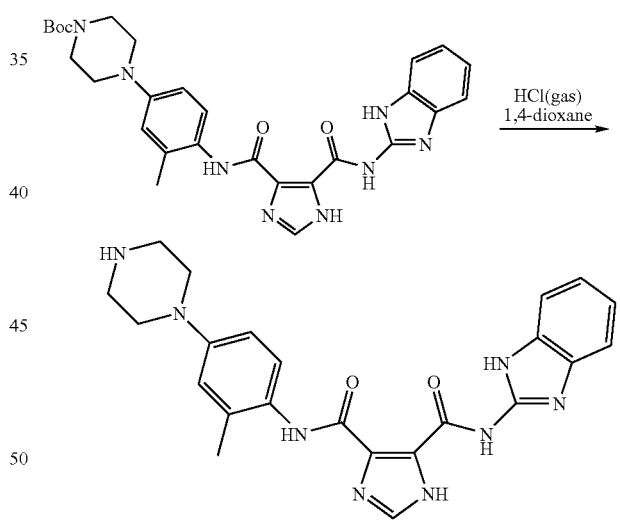

Synthesis of N$^5$-1H-benzimidazol-2-yl-N$^4$-(2-methyl-4-piperazin-1-ylphenyl)-1H-imidazole-4,5-dicarboxamide Hydrochloride N$^5$-1H-Benzimidazol-2-yl-N$^4$-(2-methyl-4-piperazin-1-ylphenyl)-1H-imidazole-4,5-dicarboxamide was prepared in a manner similar to N$^5$-[4-(azetidin-3-yloxy)-2-methylphenyl]-N$^4$-1H-benzimidazol-2-yl-1H-imidazole-4,5-dicarboxamide in Example 5 in 83% yield. $^1$H-NMR (400 MHz, MeOH-d4): δ 8.10 (s, 1H), 7.65 (m, 3H), 7.50 (m, 2H), 7.03 (d, 1H), 6.97 (dd, 1H), 3.43 (m, 8H), 2.38 (s, 3H). MS (EI): 445 (MH+).

Example 36

Scheme for N⁵-1H-benzimidazol-2-yl-N⁴-{4-[(1-ethylpiperidin-4-yl)oxy]-2-methylphenyl}-1H-imidazole-4,5-dicarboxamide

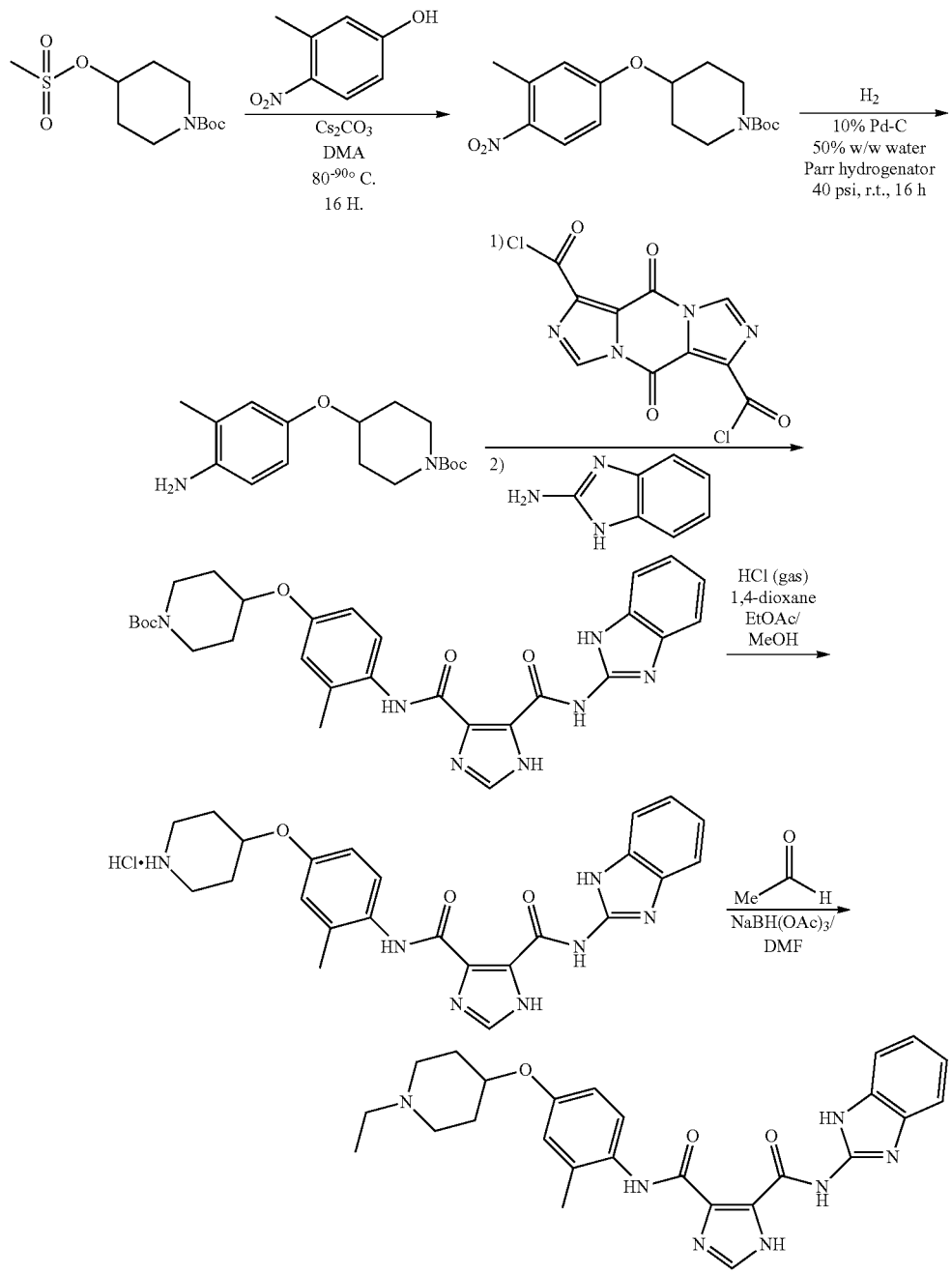

Synthesis of tert-Butyl 4-(3-methyl-4-nitrophenoxy) piperidine-1-carboxylate Cesium carbonate (11.76 g, 26.11 mmoles, 2 equivalents) was added to a stirred solution of 3-methyl-4-nitrophenol (2.76 g, 18.05 mmoles, 1 equivalent) and tert-butyl 4-(methylsulfonyloxy)piperidine-1-carboxylate (7.34 g, 19.96 mmoles, 1.1 equivalents) in anhydrous DMA (50 mls). The stirred reaction mixture was then heated to 90° C. (thermostatically controlled heating mantle) for 22 hours. The reaction mixture was then allowed to cool to room temperature and was filtered through a plug of Celite. The reaction flask and the Celite were then washed with ethyl acetate (250 ml). The organic solution was then transferred to a separatory funnel and extracted with additional ethyl acetate (3×200 ml).

The combined ethyl acetate solution was then washed with water (2×100 ml), saturated sodium chloride (2×100 ml), dried over anhydrous magnesium sulfate, filtered and evaporated under reduced pressure to give a product. This material was triturated with diethylether to give a crystalline solid which was filtered off, washed with diethylether and dried under reduced pressure to give 5.2 g of tert-butyl 4-(3-methyl-4-nitrophenoxy)piperidine-1-carboxylate (yield=82%). $^1$H-NMR (400 MHz, DMSO-d6) δ 8.80 (s, 1H), 7.89 (d, 1H), 7.74 (d, 1H), 3.82 (d, 2H), 3.65 (m, 2H), 2.40 (s, 3H), 1.76 (m, 1H), 1.54 (m, 2H), 1.38 (s, 9H), 0.98 (m, 2H). MS (EI): 351 (MH+).

Synthesis of tert-Butyl 4-(3-methyl-4-aminophenoxy)piperidine-1-carboxylate tert-Butyl 4-(3-methyl-4-nitrophenoxy)piperidine-1-carboxylate (5.2 g, 14.30 mmoles) was dissolved in ethyl acetate (60 ml) and methanol (10 ml). The solution was treated with 500 mg of 10% palladium on carbon (50% water w/w). The slurry was then shaken on a Parr hydrogenator and treated with a 40 psi atmosphere of hydrogen gas, at room temperature. After 18 hours, the slurry was filtered through a plug of Celite, which was subsequently washed with ethyl acetate (50 ml) and methanol (50 ml). The resulting filtrate was then evaporated at reduced pressure and then triturated with hexane to give a solid. This material was filtered off and dried at reduced pressure to give 4.87 g of tert-butyl 4-(3-methyl-4-aminophenoxy)piperidine-1-carboxylate (100% yield). $^1$H-NMR (400 MHz, DMSO-d6) δ 6.33 (d, 1H), 6.32 (s, 1H), 6.23 (s, 1H), 5.85 (bs, 2H), 3.70 (m, 1H), 3.39 (m, 2H), 3.29 (m, 2H), 2.35 (s, 3H), 2.00 (m, 2H), 1.75 (m, 2H), 1.42 (s, 9H). MS (EI): for C18H28N2O3: 320 (MH+).

Synthesis of tert-butyl 4-(4-(5-(1H-benzo[d]imidazol-2-ylcarbamoyl)-1H-imidazole-4-carboxamido)-3-methylphenoxy)piperidine-1-carboxylate tert-Butyl 4-(4-(5-(1H-benzo[d]imidazol-2-ylcarbamoyl)-1H-imidazole-4-carboxamido)-3-methylphenoxy)piperidine-1-carboxylate was prepared in a manner similar to $N^5$-1H-benzimidazol-2-yl-$N^4$-(2,4-dimethylphenyl)-1H-imidazole-4,5-dicarboxamide as in Example 1. MS (EI): 560 (MH+).

Synthesis of $N^5$-(1H-benzo[d]imidazol-2-yl)-$N^4$-(2-methyl-4-(piperidin-4-yloxy)phenyl)-1H-imidazole-4,5-dicarboxamide Hydrochloride $N^5$-(1H-Benzo[d]imidazol-2-yl)-$N^4$-(2-methyl-4-(piperidin-4-yloxy)phenyl)-1H-imidazole-4,5-dicarboxamide was prepared in a manner similar to $N^5$-[4-(azetidin-3-yloxy)-2-methylphenyl]-$N^4$-1H-benzimidazol-2-yl-1H-imidazole-4,5-dicarboxamide in Example 5 in 81% yield. MS (EI): 460 (MH+).

Synthesis of $N^5$-1H-benzimidazol-2-yl-$N^4$-{4-[(1-ethylpiperidin-4-yl)oxy]-2-methylphenyl}-1H-imidazole-4,5-dicarboxamide Acetaldehyde (0.088 g, 2.0 mmol) was weighed out into a dry 25 ml round bottom flask. $N^5$-(1H-benzo[d]imidazol-2-yl)-$N^4$-(2-methyl-4-(piperidin-4-yloxy)phenyl)-1H-imidazole-4,5-dicarboxamide (0.0465 g, 0.1 mmol) was added, followed by a DMF solution (3.0 ml) of sodium triacetoxyborohydride (0.106 g, 0.5 mmol). The reaction mixture was stir at room temperature over night (16 hours). The reaction mixture was then treated with 1 mL of 1N hydrochloric acid and concentrated under reduced pressure. The resulting crude material was purified by reverse phase HPLC (ammonium acetate/acetonitrile) to give $N^5$-1H-benzimidazol-2-yl-$N^4$-{4-[(1-ethylpiperidin-4-yl)oxy]-2-methylphenyl}-1H-imidazole-4,5-dicarboxamide. $^1$H-NMR (400 MHz, DMSO-d6): δ 9.49 (s, 1H), 8.22 (s, 1H), 7.52 (m, 1H), 7.41 (m, 2H), 7.23 (m, 2H), 6.97 (m, 2H), 4.75 (m, 1H), 3.54 (m, 2H), 3.37 (m, 3H), 3.12 (m, 4H), 2.24 (m, 4H), 1.22 (s, 3H); MS (EI): 488.7 (MH+).

Example 37

Synthesis of $N^5$-1H-benzimidazol-2-yl-$N^4$-(2-methyl-4-{[1-(phenylmethyl)piperidin-4-yl]oxy}phenyl)-1H-imidazole-4,5-dicarboxamide $N^5$-1H-Benzimidazol-2-yl-$N^4$-(2-methyl-4-{[1-(phenylmethyl)piperidin-4-yl]oxy}phenyl)-1H-imidazole-4,5-dicarboxamide was prepared in a similar manner as $N^5$-1H-benzimidazol-2-yl-$N^4$-{4-[(1-ethylpiperidin-4-yl)oxy]-2-methylphenyl}-1H-imidazole-4,5-dicarboxamide. Benzaldehyde and $N^5$-(1H-benzo[d]imidazol-2-yl)-$N^4$-(2-methyl-4-(piperidin-4-yloxy)phenyl)-1H-imidazole-4,5-dicarboxamide (0.1 mmol) were treated with a DMF solution of sodium triacetoxyborohydride. The reaction mixture was stir at room temperature over night (16 hours). The reaction mixture was then treated with 1 mL of 1N hydrochloric acid and concentrated under reduced pressure. The resulting crude material was purified by reverse phase HPLC (ammonium acetate/acetonitrile) to give 31 mg of $N^5$-1H-benzimidazol-2-yl-$N^4$-(2-methyl-4-{[1-(phenylmethyl)piperidin-4-yl]oxy}phenyl)-1H-imidazole-4,5-dicarboxamide as its acetate salt. $^1$H-NMR (400 MHz, DMSO-d6): 12.12 (s, 1H), 8.06 (s, 1H), 7.38 (m, 3H), 7.25 (m, 4H), 7.19 (m, 1H), 7.04 (m, 2H), 6.85 (d, 1H), 6.79 (dd, 1H), 4.34 (m, 1H), 3.43 (s, 2H), 2.60 (m, 2H), 2.44 (t, 2H), 2.18 (s, 3H), 1.88 (m, 2H), 1.58 (m, 2H); MS (EI): 550.9 (MH+).

Example 38

Synthesis of $N^5$-(5-bromo-2-methylphenyl)-$N^4$-[4-(methyloxy)-1H-benzimidazol-2-yl]-1H-imidazole-4,5-dicarboxamide

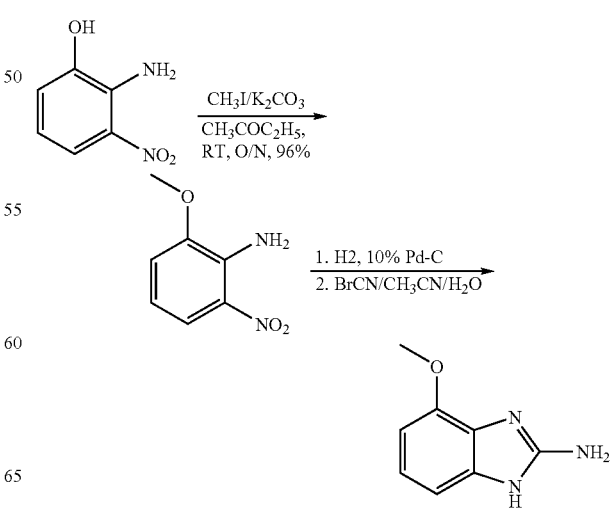

-continued

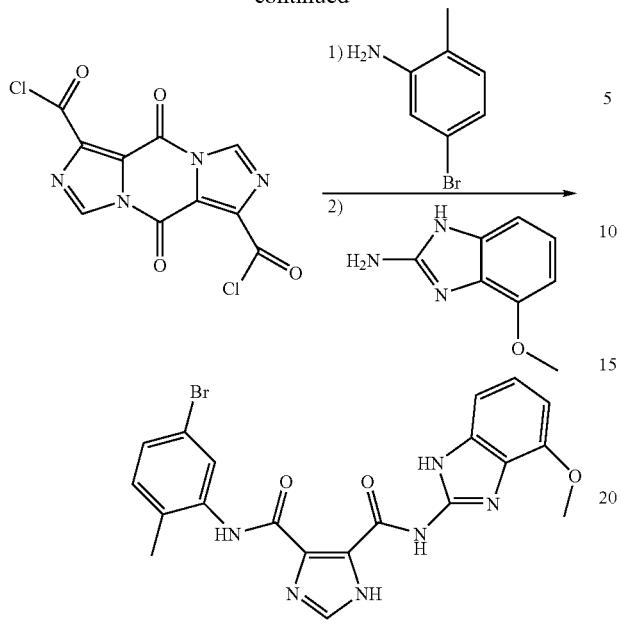

Synthesis of 2-methoxy-6-nitroaniline

2-Amino-3-nitrophenol (0.5 g, 3.2 mmol) was dissolved in 10 mL 2-butanone, and potassium carbonate (0.54 g, 3.9 mmol) and methyl iodide (0.4 mL) were added. The suspension was stirred overnight at room temperature. The reaction mixture was filtered through a plug of Celite, and the solid residue was washed with ethyl acetate. The resulting filtrate was washed with water, saturated sodium chloride solution, dried over anhydrous sodium sulfate, filtered and concentrated under reduced pressure to give 0.52 g of 2-methoxy-6-nitroaniline, which was used without further purification. $^1$H-NMR (400 MHz, CDCl$_3$): δ 7.74 (d, 1H), 6.87 (d, 1H), 6.61 (dd, 1H), 6.42 (b, 2H), 3.92 (s, 3H). MS (EI): 169 (MH+).

Synthesis of 4-methoxy-1H-benzo[d]imidazol-2-amine

The material was prepared by the catalytic reduction of 2-methoxy-6-nitroaniline to 3-methoxybenzene-1,2-diamine using a hydrogen atmosphere at 40 psi and 10% palladium on carbon (50% w/w water) in methanol. The resulting crude diamine was subsequently reacted with cyanogen bromide in an acetonitrile-water mixture according to previous procedure and used without further purification. $^1$H-NMR (400 MHz, CDCl$_3$), δ 12.40 (bs, 1H), 7.26 (d, 1H), 7.15 (t, 1H), 6.77 (d, 1H), 6.59 (bs, 2H), 3.73 (s, 3H). MS (EI): 164 (MH+).

Synthesis of N$^5$-(5-bromo-2-methylphenyl)-N$^4$-[4-(methyloxy)-1H-benzimidazol-2-yl]-1H-imidazole-4,5-dicarboxamide N$^5$-(5-Bromo-2-methylphenyl)-N$^4$-[4-(methyloxy)-1H-benzimidazol-2-yl]-1H-imidazole-4,5-dicarboxamide was prepared in manner similar to N$^5$-1H-benzimidazol-2-yl-N$^4$-(2,4-dimethylphenyl)-1H-imidazole-4,5-dicarboxamide in Example 1 in 56% yield. $^1$H-NMR (400 MHz, DMSO-d6): δ 10.90 (br, 1H), 8.37 (s, 1H), 7.89 (s, 1H), 7.31-7.44 (m, 4H), 7.01 (m, 1H), 3.97 (s, 3H), 2.31 (s, 3H). MS (EI): 469 (MH+).

Example 39

Synthesis of N$^5$-1H-benzimidazol-2-yl-N$^4$-(2-fluoro-6-methoxyphenyl)-1H-imidazole-4,5-dicarboxamide N$^5$-1H-Benzimidazol-2-yl)-N$^4$-(2-fluoro-6-methoxyphenyl)-1H-imidazole-4,5-dicarboxamide was prepared in manner similar to N$^5$-1H-benzimidazol-2-yl-N$^4$-(2,4-dimethylphenyl)-1H-imidazole-4,5-dicarboxamide in Example 1 in 46% yield. $^1$H-NMR (400 MHz, DMSO-d6): δ 13.90 (s, br, 1H), 12.21 (s, br, 1H), 10.12 (s, 1H), 8.18 (s, 1H), 7.62-7.39 (m, 3H), 7.16-6.93 (m, 4H), 3.82 (s, 3H). MS (EI): 395 (MH+).

Example 40

Scheme for the synthesis of 1,1-dimethylethyl 4-({4-[({4-[(1H-benzimidazol-2-ylamino)carbonyl]-1H-imidazol-5-yl}carbonyl)amino]-3-chlorophenyl}oxy)piperidine-1-carboxylate

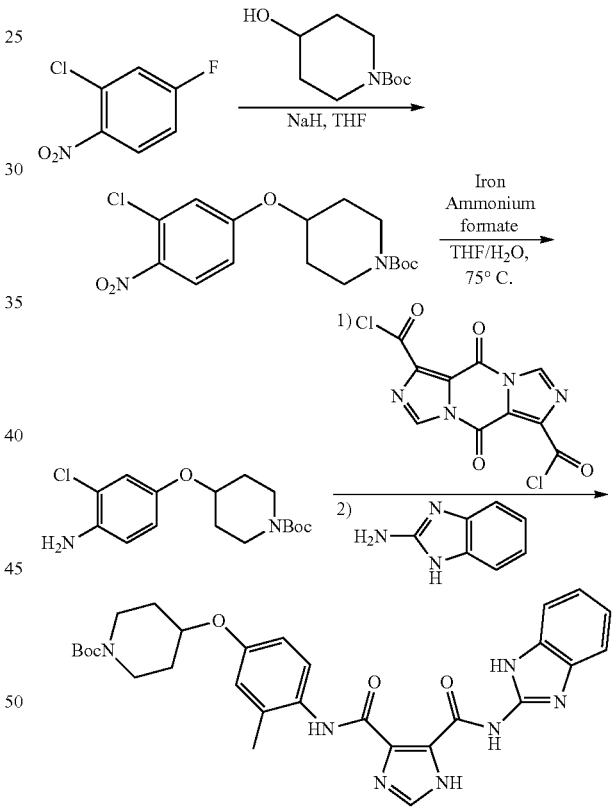

Synthesis of tert-butyl 4-(4-amino-3-chlorophenoxy)piperidine-1-carboxylate tert-Butyl 4-(4-amino-3-chlorophenoxy)piperidine-1-carboxylate was prepared in the same manner as tert-Butyl 4-(3-(4-amino-5-chloro-2 methylphenoxy)propyl)piperazine-1-carboxylate. Reaction of N-Boc-4-hydroxypiperidine with sodium hydride in anhydrous THF, followed by 2-chloro-4-fluoro-1-nitrobenzene (commercially available from Acros) gave tert-butyl 4-(3-chloro-4-nitrophenoxy)piperidine-1-carboxylate. Reduction of the tent-butyl 4-(3-chloro-4-nitrophenoxy)piperidine-1-carboxylate using ammonium formate and iron dust in refluxing toluene-water mixture gave tert-butyl 4-(4-amino-3-chlorophenoxy)piperidine-1-carboxylate in 79% yield. $^1$H-NMR (400 MHz, CDCl$_3$): δ 6.88 (m, 1H), 6.70 (m, 2H), 4.26 (m, 1H), 3.79 (s, br, 2H), 3.68 (m, 2H), 3.30 (m, 2H), 1.86 (m, 2H), 1.71 (m, 2H), 1.56 (s, 9H). MS (EI): 227 (MH+).

Synthesis of 1,1-dimethylethyl 4-({4-[({4-[(1H-benzimidazol-2-ylamino)carbonyl]-1H-imidazol-5-yl}carbonyl)amino]-3-chlorophenyl}oxy)piperidine-1-carboxylate 1,1-Dimethylethyl 4-({4-[({4-[(1H-benzimidazol-2-ylamino)carbonyl]-1H-imidazol-5-yl}carbonyl)amino]-3-chlorophenyl}oxy)piperidine-1-carboxylate was prepared in manner similar to N$^5$-1H-benzimidazol-2-yl-N$^4$-(2,4-dimethylphenyl)-1H-imidazole-4,5-dicarboxamide in Example 1 in 59% yield. $^1$H-NMR (400 MHz, DMSO-d6): δ 13.8 (s br, 1H), 12.2 (s, 1H), 10.3 (s, 1H), 8.16 (s, 1H), 7.92-7.86 (m, 1H), 7.52-7.40 (m, 2H), 7.26 (d, 2.6 Hz, 1H), 7.11-7.06 (m, 4H), 4.64-4.61 (m, 1H), 3.68-3.62 (m, 2H), 3.30-3.18 (m, 2H), 1.92-1.90 (m, 2H), 1.54-1.49 (m, 2H), 1.91 (s, 9H). MS (EI): 580 (MH+).

Example 41

Synthesis of N$^4$-1H-benzimidazol-2-yl-N$^5$-[2-chloro-4-(piperidin-4-yloxy)phenyl]-1H-imidazole-4,5-dicarboxamide N$^4$-1H-Benzimidazol-2-yl-N$^5$-[2-chloro-4-(piperidin-4-yloxy)phenyl]-1H-imidazole-4,5-dicarboxamide was prepared in a manner similar to N$^5$-[4-(azetidin-3-yloxy)-2-methylphenyl]-N$^4$-1H-benzimidazol-2-yl-1H-imidazole-4,5-dicarboxamide.

1-dimethylethyl 4-({4-[({4-[(1H-benzimidazol-2-ylamino)carbonyl]-1H-imidazol-5-yl}carbonyl)amino]-3-chlorophenyl}oxy)piperidine-1-carboxylate was treated with 4M hydrogen chloride in dioxane to give N$^4$-1H-benzimidazol-2-yl-N$^5$-[2-chloro-4-(piperidin-4-yloxy)phenyl]-1H-imidazole-4,5-dicarboxamide as its hydrochloride salt in 83% yield. $^1$H-NMR (400 MHz, DMSO-d6): 13.9 (s, br, 1H), 13.7 (s, 1H), 12.2 (s, 1H), 10.4 (s, 1H), 8.41-8.39 (m, 1H), 8.15 (s, 1H), 8.01 (s, 1H), 7.45 (s, 2H), 7.07 (s, 2H). MS (EI): 450 (MH+).

Example 42

Synthesis of N$^5$-1H-benzimidazol-2-yl-N$^4$-{4-[(3-piperazin-1-ylpropyl)oxy]-2-(trifluoromethyl)phenyl}-1H-imidazole-4,5-dicarboxamide

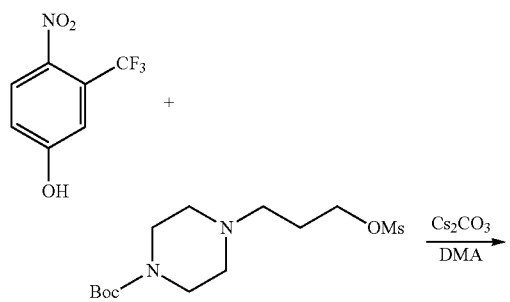

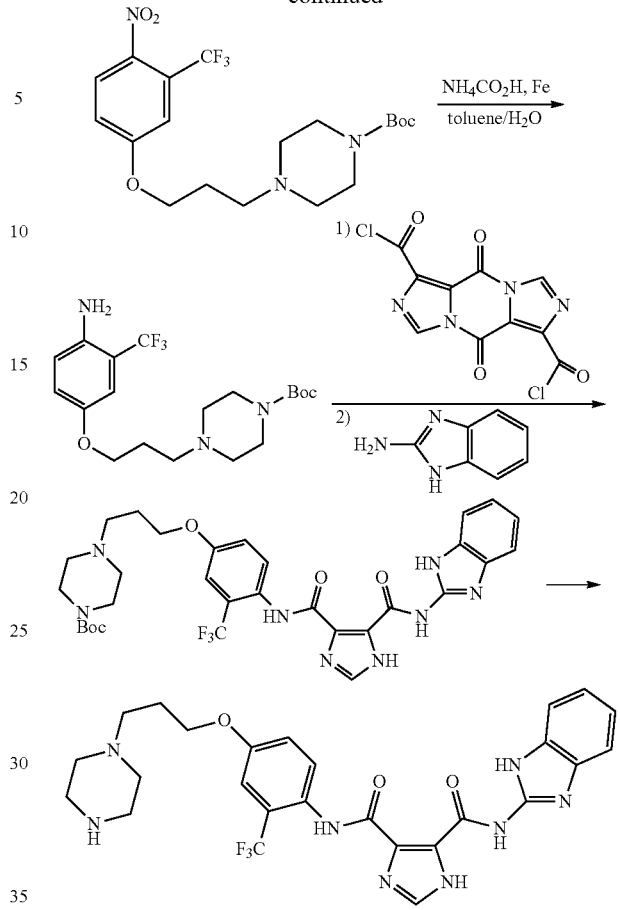

Synthesis of tert-butyl 4-(3-(4-nitro-3-(trifluoromethyl)phenoxy)propyl)piperazine-1-carboxylate A 100 mL flask was charged with 4-nitro-3-(trifluoromethyl)phenol (commercially available from Acros; 0.31 g, 1.8 mmol), tert-butyl 4-(3-(methylsulfonyloxy)propyl)piperazine-1-carboxylate (0.64 g, 2.0 mmol), cesium carbonate (1.2 g, 3.6 mmol) and DMA. The reaction mixture was heated to 90° C. for 15 hours. The reaction mixture was allowed to cool to room temperature, extracted with ethyl acetate and 10% aqueous lithium chloride solution. The organic solvent was removed on a rotary evaporator under reduced pressure to yield tert-butyl 4-(3-(4-nitro-3-(trifluoromethyl)phenoxy)propyl)piperazine-1-carboxylate that was used without further purification. MS (EI): 434 (MH+).

Synthesis of tert-butyl 4-(3-(4-amino-3-(trifluoromethyl)phenoxy)propyl)piperazine-1-carboxylate A flask was charged with tert-butyl 4-(3-(4-nitro-3-(trifluoromethyl)phenoxy)propyl)piperazine-1-carboxylate (0.78 g, 1.8 mmol), ammonium formate (0.45 g, 7.2 mmol), and iron powder (0.40 g, 7.2 mmol). Toluene (15 mL) and water (15 mL) were added to the flask and the mixture was heated to reflux for 2 hours, after which time, the hot mixture was filtered through a plug of Celite. The solvent was removed on a rotary evaporator under reduced pressure to yield tert-butyl 4-(3-(4-amino-3-(trifluoromethyl)phenoxy)

propyl)piperazine-1-carboxylate. The material was used without further purification. MS (EI): 404 (MH+).

Synthesis of tert-butyl 4-(3-(4-(5-(1H-benzo[d]imidazol-2-ylcarbamoyl)-1H-imidazole-4-carboxamido)-3-(trifluoromethyl)phenoxy)propyl)piperazine-1-carboxylate tent-Butyl 4-(3-(4-(5-(1H-benzo[d]imidazol-2-ylcarbamoyl)-1H-imidazole-4-carboxamido)-3-(trifluoromethyl)phenoxy)propyl)piperazine-1-carboxylate was prepared in a manner analogous to $N^5$-1H-benzimidazol-2-yl-$N^4$-(2,4-dimethylphenyl)-1H-imidazole-4,5-dicarboxamide in Example 1 in 58% yield. MS (EI): 657 (MH+).

Synthesis of $N^5$-1H-benzimidazol-2-yl-$N^4$-{4-[(3-piperazin-1-ylpropyl)oxy]-2-(trifluoromethyl)phenyl}-1H-imidazole-4,5-dicarboxamide Hydrochloride $N^5$-1H-Benzimidazol-2-yl-$N^4$-{4-[(3-piperazin-1-ylpropyl)oxy]-2-(trifluoromethyl)phenyl}-1H-imidazole-4,5-dicarboxamide was prepared in a manner analogous to $N^5$-[4-(azetidin-3-yloxy)-2-methylphenyl]-$N^4$-1H-benzimidazol-2-yl-1H-imidazole-4,5-dicarboxamide in Example 5 as its hydrochloride salt in 81% yield. $^1$H-NMR (400 MHz, DMSO-$d_6$): δ 8.00 (s br, 1H), 7.76 (m, 1H), 7.39-7.27 (m, 3H), 7.22 (d, 2.7 Hz, 1H), 7.06-7.02 (m, 2H), 4.06 (t, 6.3 Hz, 2H), 2.77 (t, 4.7 Hz, 4H), 2.40-2.34 (m, 6H), 1.86-1.83 (m, 2H). MS (EI): 577 (MH+).

Example 43

Synthesis of 1-Methylethyl[(2-{[(4-{[(2,4-dimethylphenyl)amino]carbonyl}-1H-imidazol-5-yl)carbonyl]amino}-1H-benzimidazol-5-yl)oxy]acetate 1-Methylethyl[(2-{[(4-{[(2,4-dimethylphenyl)amino]carbonyl}-1H-imidazol-5-yl)carbonyl]amino}-1H-benzimidazol-5-yl)oxy]acetate was prepared in manner analogous to $N^5$-[6-({2-[(2,3-dihydroxypropyl)amino]-2-oxoethyl}oxy)-1H-benzimidazol-2-yl]-$N^4$-(2,4-dimethylphenyl)-1H-imidazole-4,5-dicarboxamide in Example 6 in 47% yield. $^1$H-NMR (400 MHz, DMSO-d6): δ 12.09 (s, 1H), 8.13 (s, 11-1), 7.54 (s, 1H), 7.35 (d, 1H), 7.13 (s, 1H), 7.08 (d, 1H), 6.95 (d, 1H), 6.76 (s, 1H), 5.00 (m, 1H), 4.70 (s, 2H), 2.31 (s, 3H), 2.27 (s, 3H), 1.22 (s, 6H). MS (EI): 491.6 (MH+).

Example 44

Synthesis of $N^4$-(2,4-dimethylphenyl)-$N^5$-(5-{[2-oxo-2-(propylamino)ethyl]oxy}-1H-benzimidazol-2-yl)-1H-imidazole-4,5-dicarboxamide $N^4$-(2,4-Dimethylphenyl)-$N^5$-(5-{[2-oxo-2-(propylamino)ethyl]oxy}-1H-benzimidazol-2-yl)-1H-imidazole-4,5-dicarboxamide was prepared in manner analogous fashion to $N^5$-[6-({2-[(2,3-dihydroxypropyl)amino]-2-oxoethyl}oxy)-1H-benzimidazol-2-yl]-$N^4$-(2,4-dimethylphenyl)-1H-imidazole-4,5-dicarboxamide in Example 6. $^1$H-NMR (400 MHz, DMSO-d6): δ 8.10 (m, 2H), 7.55 (d, 1H), 7.13 (s, 1H), 7.08 (d, 1H), 6.82 (dd, 1H), 4.44 (s, 2H), 3.09 (m, 2H), 2.31 (s, 3H), 2.28 (s, 3H), 1.44 (m, 2H), 0.82 (t, 3H). MS (EI): 490.2 (MH+).

Example 45

Synthesis of $N^4$-(2,4-dimethylphenyl)-$N^5$-[5-({2-oxo-2-[(phenylmethyl)amino]ethyl}oxy)-1H-benzimidazol-2-yl]-1H-imidazole-4,5-dicarboxamide $N^4$-(2,4-Dimethylphenyl)-$N^5$-[5-({2-oxo-2-[(phenylmethyl)amino]ethyl}oxy)-1H-benzimidazol-2-yl]-1H-imidazole-4,5-dicarboxamide was prepared in manner analogous fashion to $N^5$-[6-({2-[(2,3-dihydroxypropyl)amino]-2-oxoethyl}oxy)-1H-benzimidazol-2-yl]-$N^4$-(2,4-dimethylphenyl)-1H-imidazole-4,5-dicarboxamide in Example 6. $^1$H-NMR (400 MHz, DMSO-d6): δ 8.68 (t, 1H), 8.09 (s, 1H), 7.56 (d, 1H), 7.24 (m, 5H), 7.13 (s, 1H), 7.10 (s, 1H), 7.08 (s, 1H), 6.84 (dd, 1H), 4.54 (s, 2H), 4.35 (d, 2H), 2.31 (s, 3H), 2.28 (s, 3H). MS (EI): 538.7 (MH+).

Example 46

Synthesis of $N^5$-1H-benzimidazol-2-yl-$N^4$-(2-fluoro-3-{[(1-methylpiperidin-3-yl)carbonyl]amino}phenyl)-1H-imidazole-4,5-dicarboxamide

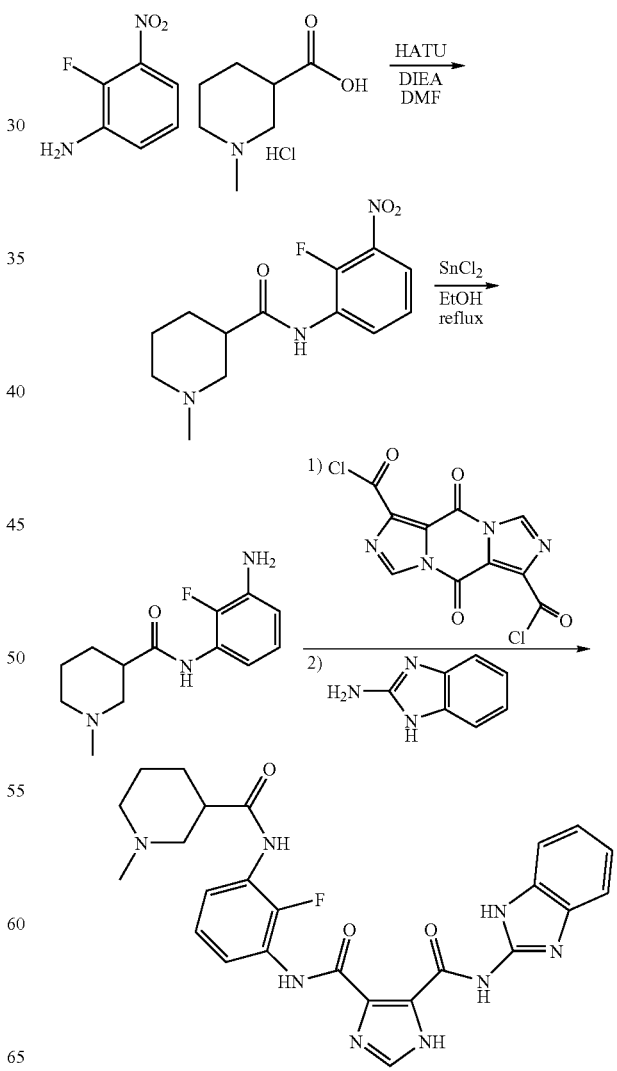

Synthesis of N-(2-fluoro-3-nitrophenyl)-1-methylpiperidine-3-carboxamide

A 100 mL flask was charged with 2-fluoro-3-nitroaniline (19.108 mmol, commercially available from Aldrich), DMF (50 mL), HATU (26.05 mmol) and DIEA (52.11 mmol) and stirred at room temperature over night. The reaction mixture was diluted with ethyl acetate and washed with 10% lithium chloride solution (3×), 2 M sodium chloride (3×), dried over anhydrous sodium sulfate, filtered and the solvent was removed using the rotary evaporator under reduced pressure to yield N-(2-fluoro-3-nitrophenyl)-1-methylpiperidine-3-carboxamide which was used in the next step without further purification. MS (EI): 282 (MH+).

benzimidazol-2-yl-$N^4$-(2,4-dimethylphenyl)-1H-imidazole-4,5-dicarboxamide in Example 1 in 46% yield. $^1$H-NMR (400 MHz, DMSO-d6): δ 8.00 (s br, 1H), 7.76 (m, 1H), 7.39-7.27 (m, 3H), 7.22 (d, 2.7 Hz, 1H), 7.06-7.02 (m, 2H), 4.06 (t, 6.3 Hz, 2H), 2.77 (t, 4.7 Hz, 4H), 2.40-2.34 (m, 6H), 1.86-1.83 (m, 2H). MS (EI): 577 (MH+).

Example 47

Synthesis of ethyl 4-({4-[({4-[(1H-benzimidazol-2-ylamino)carbonyl]-1H-imidazol-5-yl}carbonyl)amino]-3-methylphenyl}oxy)piperidine-1-carboxylate

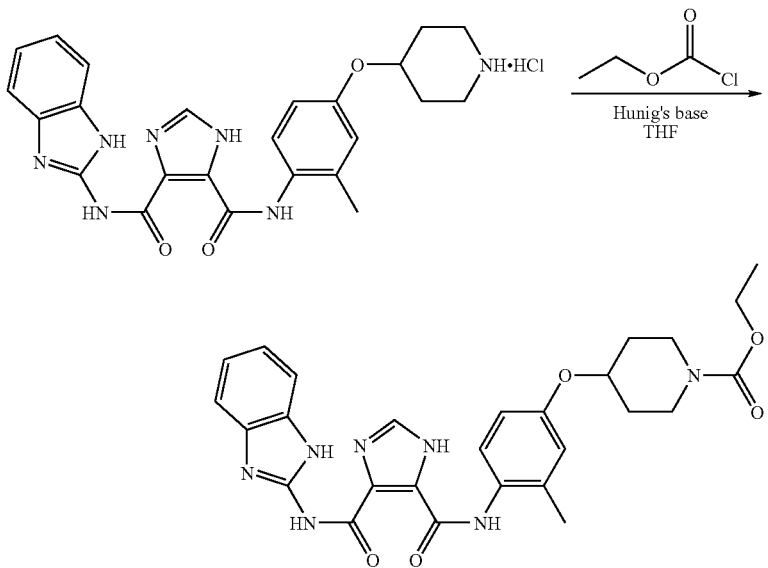

Synthesis of N-(3-amino-2-fluorophenyl)-1-methylpiperidine-3-carboxamide

To the solution of N-(2-fluoro-3-nitrophenyl)-1-methylpiperidine-3-carboxamide in ethanol (100 mL) was charged with tin (II) chloride (52.11 mmol) and stirred at reflux temperature. The reaction was completed after 2 hours as shown by (LC-MS). The reaction mixture was cooled to room temperature. The solvent was reduced to half the volume and then treated with 2 M sodium hydroxide solution and a sodium hydroxide pellet, adjusting the pH reading to 14. The reaction mixture was extracted with ethyl acetate, which was dried over anhydrous sodium sulfate, filtered and concentrated using a rotary evaporator under reduced pressure to afford 4.4 g of N-(3-amino-4-fluorophenyl)-1-methylpiperidine-3-carboxamide (quantitative yield). MS (EI): 252 (MH+).

Synthesis of $N^5$-1H-benzimidazol-2-yl-$N^4$-(2-fluoro-3-{[(1-methylpiperidin-3-yl)carbonyl]amino}phenyl)-1H-imidazole-4,5-dicarboxamide $N^5$-1H-benzimidazol-2-yl-$N^4$-(2-fluoro-3-{[(1-methylpiperidin-3-yl)carbonyl]amino}phenyl)-1H-imidazole-4,5-dicarboxamide was prepared in a manner similar to $N^5$-1H-

Ethyl chloroformate (0.1 mmol) in anhydrous THF was slowly added to a solution of $N^4$-(1H-benzo[d]imidazol-2-yl)-$N^5$-(2-methyl-4-(piperidin-4-yloxy)phenyl)-1H-imidazole-4,5-dicarboxamide (0.10 mmol) and diisopropylethylamine (0.20 mmol) in anhydrous DMA (5 mL) at 0° C. LCMS indicated that the reaction was complete in 5 minutes. The reaction mixture was concentrated under reduced pressure. The resulting residue was purified by preparative reverse phase HPLC (ammonium acetate/acetonitrile) to give 3.4 mg of ethyl 4-({4-[({4-[(1H-benzimidazol-2-ylamino)carbonyl]-1H-imidazol-5-yl}carbonyl)amino]-3-methylphenyl}oxy)piperidine-1-carboxylate. $^1$H-NMR (400 MHz, DMSO-d6): δ 12.19 (s, 1H), 8.13 (s, 1H), 7.48 (m, 2H), 7.11 (m, 2H), 6.96 (s, 1H), 6.88 (dd, 1H), 4.60 (m, 1H), 4.05 (m, 2H), 3.70 (m, 2H), 3.30 (m, 1H), 2.26 (s, 3H), 1.91 (m, 2H), 1.57 (m, 2H), 1.19 (t, 3H). MS (EI): 532.4 (MH+).

Example 48

Synthesis of $N^5$-(5-{[2-(cyclohexylamino)-2-oxoethyl]oxy}-1H-benzimidazol-2-yl)-$N^4$-(2,4-dimethylphenyl)-1H-imidazole-4,5-dicarboxamide $N^5$-(5-{[2-(cyclohexylamino)-2-oxoethyl]oxy}-1H-benzimidazol-2-yl)-$N^4$-(2,4-dimethylphenyl)-1H-imidazole-4,5-dicarboxamide was prepared in a manner analogous to $N^5$-

[6-({2-[(2,3-dihydroxypropyl)amino]-2-oxoethyl}oxy)-1H-benzimidazol-2-yl]-N⁴-(2,4-dimethylphenyl)-1H-imidazole-4,5-dicarboxamide in Example 6. ¹H-NMR (400 MHz, DMSO-d6): δ 8.06 (s, 1H), 7.86 (d, 1H), 7.57 (d, 1H), 7.13 (s, 1H), 7.08 (d, 1H), 6.81 (d, 1H), 4.42 (s, 1H), 2.31 (s, 3H), 2.28 (s, 3H), 1.68 (m, 5H), 1.26 (m, 5H). MS (EI): 530.6 (MH+).

Example 49

Synthesis of N⁴-(5-bromo-2-methylphenyl)-N⁵-[5-({2-oxo-2-[(tetrahydrofuran-2-ylmethyl)amino]ethyl}oxy)-1H-benzimidazol-2-yl]-1H-imidazole-4,5-dicarboxamide N⁴-(5-Bromo-2-methylphenyl)-N⁵-[5-({2-oxo-2-[(tetrahydrofuran-2-ylmethyl)amino]ethyl}oxy)-1H-benzimidazol-2-yl]-1H-imidazole-4,5-dicarboxamide was prepared in manner analogous fashion to N⁵-[6-({2-[(2,3-dihydroxypropyl)amino]-2-oxoethyl}oxy)-1H-benzimidazol-2-yl]-N⁴-(2,4-dimethylphenyl)-1H-imidazole-4,5-dicarboxamide in Example 6. ¹H-NMR (400 MHz, DMSO-d6): δ 8.06 (m, 2H), 8.00 (s, 1H), 7.38 (dd, 2H), 7.29 (d, 1H), 7.06 (s, 1H), 6.82 (dd, 1H), 4.47 (s, 2H), 3.89 (m, 1H), 3.72 (m, 1H), 3.60 (m, 1H), 3.21 (t, 1H), 3.17 (s, 1H), 2.31 (s, 1H), 1.75 (m, 3H), 1.50 (m, 1H). MS (EI): 597.5 (MH+).

Example 50

Synthesis of N⁴-(2,4-dimethylphenyl)-N⁵-[5-({2-oxo-2-([2-phenylethyl)amino]ethyl}oxy)-1H-benzimidazol-2-yl]-1H-imidazole-4,5-dicarboxamide N⁴-(2,4-Dimethylphenyl)-N⁵-[5-({2-oxo-2-[(2-phenylethyl)amino]ethyl}oxy)-1H-benzimidazol-2-yl]-1H-imidazole-4,5-dicarboxamide was prepared in manner analogous fashion to N⁵-[6-({2-[(2,3-dihydroxypropyl)amino]-2-oxoethyl}oxy)-1H-benzimidazol-2-yl]-N⁴-(2,4-dimethylphenyl)-1H-imidazole-4,5-dicarboxamide in Example 6. ¹H-NMR (400 MHz, DMSO-d6): δ 12.09 (s, br, 1H), 8.17 (t, 1H), 8.10 (s, 1H), 7.55 (d, 1H), 7.27 (m, 2H), 7.19 (m, 3H), 7.13 (s, 1H), 7.08 (d, 1H), 6.80 (dd, 1H), 4.44 (s, 2H), 3.38 (t, 2H), 2.76 (t, 2H), 2.31 (s, 3H), 2.28 (s, 3H). MS (EI): 552.6 (MH+).

Example 51

Synthesis of N⁴-(5-bromo-2-methylphenyl)-N⁵-[5-({2-oxo-2-[piperidin-4-ylmethyl)amino]ethyl}oxy)-1H-benzimidazol-2-yl]-1H-imidazole-4,5-dicarboxamide N⁴-(5-Bromo-2-methylphenyl)-N⁵-[5-({2-oxo-2-[piperidin-4-ylmethyl)amino]ethyl}oxy)-1H-benzimidazol-2-yl]-1H-imidazole-4,5-dicarboxamide was prepared in a manner analogous fashion to N⁵-[6-({2-[(2,3-dihydroxypropyl)amino]-2-oxoethyl}oxy)-1H-benzimidazol-2-yl]-N⁴-(2,4-dimethylphenyl)-1H-imidazole-4,5-dicarboxamide in Example 6. ¹H-NMR (400 MHz, DMSO-d6): δ 8.15 (m, 2H), 7.76 (s, 1H), 7.37 (d, 1H), 7.32 (dd, 1H), 7.30 (d, 1H), 7.06 (s, 1H), 6.80 (dd, 1H), 4.47 (s, 2H), 3.08 (m, 5H), 2.61 (t, 2H), 2.31 (s, 2H), 1.88 (s, 3H), 1.63 (d, 2H), 1.13 (m, 2H). MS (EI): 610.7 (MH+).

Example 52

Synthesis of N⁵-1H-benzimidazol-2-yl-N⁴-{2-chloro-4-[(2-morpholin-4-ylethyl)oxy]phenyl}-1H-imidazole-4,5-dicarboxamide

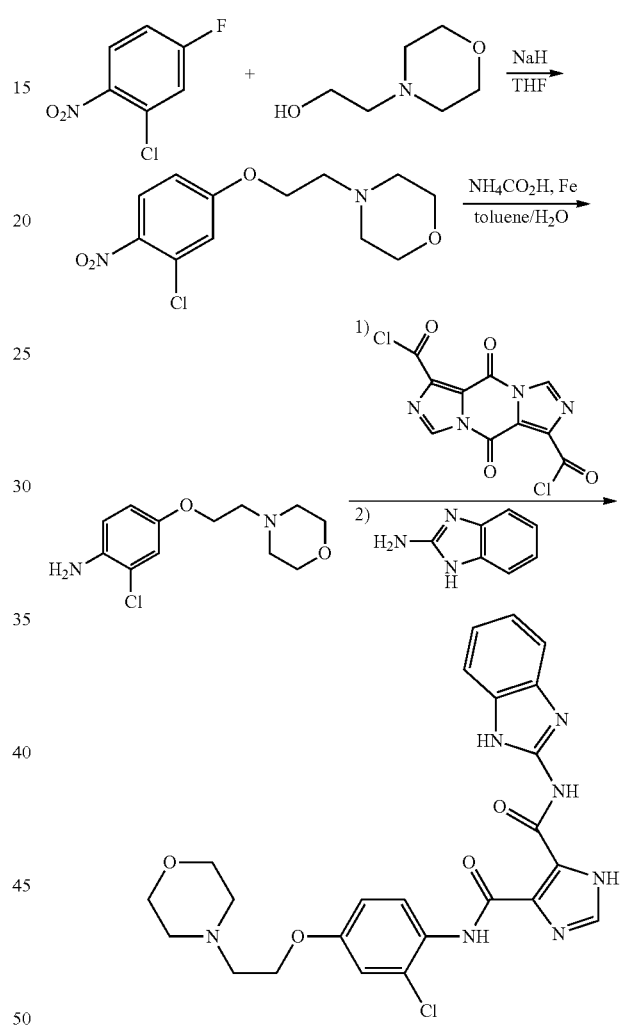

Synthesis of 4-(2-(3-chloro-4-nitrophenoxy)ethyl)morpholine 4-(2-(3-Chloro-4-nitrophenoxy)ethyl)morpholine was prepared in a manner analogous to that used for was prepared in a manner analogous to that used for tent-butyl 4-(3-(4-amino-5-chloro-2 methylphenoxy)propyl)piperazine-1-carboxylate. Reaction of 2-morpholinoethanol (commercially available from Acros). with sodium hydride in anhydrous THF, followed by reaction with 2-chloro-4-fluoro-1-nitrobenzene (commercially available from Acros) gave tert-butyl 4-(3-chloro-4-nitrophenoxy)piperidine-1-carboxylate in 83% yield. ¹H-NMR (DMSO-d6) δ 8.02 (d, 2H), 7.04 (S, 1H), 6.91 (d, 1H), 4.06 (t, 2H), 3.56 (t, 4H), 2.69 (t, 2H), 2.50 (t, 4H). MS (EI): 287 (MH+).

217

Synthesis of 2-chloro-4-(2-morpholinoethoxy)aniline

2-Chloro-4-(2-morpholinoethoxy)aniline was prepared in a manner analogous to that used for 2-methyl-4-(3-morpholinopropoxy)aniline in Example 69. 4-(2-(3-chloro-4-nitrophenoxy)ethyl)morpholine was reduced using ammonium formate and iron powder in refluxing toluene-water mixture to give 2-chloro-4-(2 morpholinoethoxy)aniline in 87% yield. $^1$H-NMR (DMSO-d6) δ 6.53 (s, 1H), 6.40 (d, 1H), 6.29 (d, 1H), 5.85 (br s, 2H), 4.06 (t, 2H), 3.56 (t, 4H), 2.69 (t, 2H), 2.50 (t, 4H). (MS (EI): 257 (MH+).

Synthesis of $N^5$-1H-benzimidazol-2-yl-$N^4$-{2-chloro-4-[(2-morpholin-4-ylethyl)oxy]phenyl}-1H-imidazole-4,5-dicarboxamide $N^5$-1H-Benzimidazol-2-yl-$N^4$-{2-chloro-4-[(2-morpholin-4-ylethyl)oxy]phenyl}-1H-imidazole-4,5-dicarboxamide was prepared in a manner analogous to $N^5$-1H-benzimidazol-2-yl-$N^4$-{2-methyl-4-[(2-morpholin-4-ylethyl)oxy]phenyl}-1H-imidazole-4,5-dicarboxamide in Example 1 in 47% yield. $^1$H-NMR (400 MHz, DMSO-d6): δ 10.19 (s, br, 1H), 10.31 (s, br, 1H), 8.16 (s, 1H), 7.91 (m, 1H), 7.50-7.41 (m, 2H), 7.22 (s, br, 1H), 7.10-7.03 (m, 3H), 4.14 (m, 2H), 3.57 (m, 4H), 3.33 (m, 4H), 2.69 (m, 2H). MS (EI): 510 (MH+).

Example 53

Synthesis of 1,1-dimethylethyl 4-[(4-{[(5-{[(6-chloro-1H-benzimidazol-2-yl)amino]carbonyl}-1H-imidazol-4-yl)carbonyl]amino}-3-methylphenyl)oxy]piperidine-1-carboxylate 1,1-Dimethylethyl 4-[(4-{[(5-{[(6-chloro-1H-benzimidazol-2-yl)amino]carbonyl}-1H-imidazol-4-yl)carbonyl]amino}-3-methylphenyl)oxy]piperidine-1-carboxylate was prepared in a manner analogous to $N^5$-1H-benzimidazol-2-yl-$N^4$-(2,4-dimethylphenyl)-1H-imidazole-4,5-dicarboxamide in Example 1 in 64% yield. $^1$H-NMR (DMSO-d6) δ 13.80 (bs, 1H), 12.30 (bs, 1H), 10.22 (bs, 1H), 8.12 (bs, 1H), 7.50 (dd, 1H), 7.00 (m, 1H), 7.10 (d, 2H), 7.92 (s, 1H), 7.83 (m, 2H), 4.58 (bs, 1H), 3.82 (m, 2H), 3.20 (bs2H), 2.22 (s, 3H), 1.90 (m, 2H), 7.51 (m, 2H), 1.40 (s, 9H). MS (EI): 595 (MH+).

Example 54

Synthesis of $N^4$-1H-benzimidazol-2-yl-$N^5$-(2-chloro-4-{[1-(cyanoacetyl)piperidin-4-yl]oxy}phenyl)-1H-imidazole-4,5-dicarboxamide

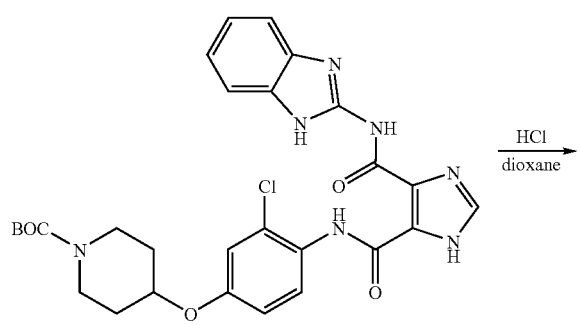

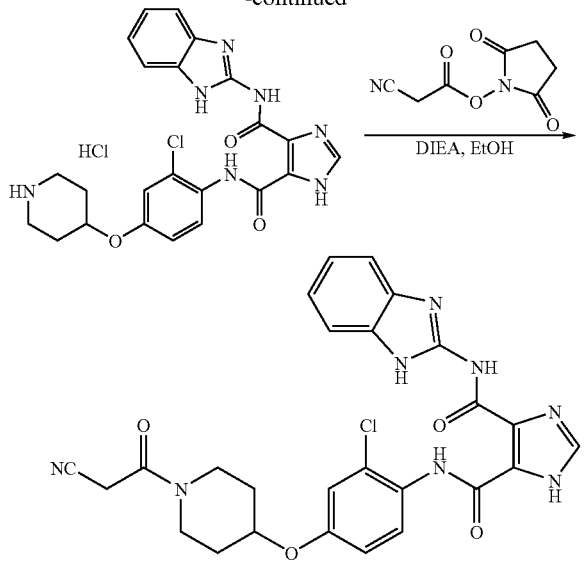

Synthesis of $N^4$-(1H-benzo[d]imidazol-2-yl)-$N^5$-(2-chloro-4-(piperidin-4-yloxy)phenyl)-1H-imidazole-4,5-dicarboxamide Hydrochloride A flask was charged with tert-butyl 4-(4-(4-(1H-benzo[d]imidazol-2-ylcarbamoyl)-1H-imidazole-5-carboxamido)-2-chlorophenoxy)piperidine-1-carboxylate (260 mg, 0.45 mmol), 4 N hydrogen chloride in 1,4-dioxane (1 mL, 4 mmol) and 1,4-dioxane (50 mL), and the reaction mixture was stirred for 15 hours at room temperature. The resulting solid was filtered off and air dried to give 0.228 g of $N^4$-(1H-benzo[d]imidazol-2-yl)-$N^5$-(2-chloro-4-(piperidin-4-yloxy)phenyl)-1H-imidazole-4,5-dicarboxamide hydrochloride (99% yield). $^1$H-NMR (400 MHz, DMSO-d6): δ 13.9 (s, br, 1H), 13.7 (s, 1H), 12.2 (s, 1H), 10.4 (s, 1H), 8.41-8.39 (m, 1H), 8.15 (s, 1H), 8.01 (s, 1H), 7.45 (s, 2H), 7.07 (s, 2H). MS (EI): 450 (MH+).

Synthesis of $N^4$-(1H-benzo[d]imidazol-2-yl)-$N^5$-(2-chloro-4-(1-(2-cyanoacetyl)piperidin-4-yloxy)phenyl)-1H-imidazole-4,5-dicarboxamide A mixture of $N^4$-(1H-benzo[d]imidazol-2-yl)-$N^5$-(2-chloro-4-(piperidin-4-yloxy)phenyl)-1H-imidazole-4,5-dicarboxamide hydrochloride (110 mg, 0.21 mmol), 2,5-dioxopyrrolidin-1-yl 2-cyanoacetate (48 mg, 0.26 mmol) and DIEA (0.07 mL, 0.4 mmol) in ethanol (20 mL), THF (10 mL) and acetonitrile (10 mL) was heated to 60° C. for 3 days. The reaction mixture was cooled to room temperature and filtered, and the precipitate was discarded. The product was first purified by reverse phase HPLC using ammonium acetate and acetonitrile as eluent to afford the product in >75% purity. $N^4$-(1H-benzo[d]imidazol-2-yl)-$N^5$-(2-chloro-4-(1-(2-cyanoacetyl)piperidin-4-yloxy)phenyl)-1H-imidazole-4,5-dicarboxamide as the trifluoroacetate salt was isolated in >95% purity by reverse phase HPLC using 1% TFA/H$_2$O and acetonitrile as eluent. $^1$H-NMR (400 MHz, DMSO-d6): δ 14.4 (s, br, 1H), 13.9 (s, br, 1H), 10.4 (s, br, 1H), 8.16 (s, br, 1H), 7.79-7.77 (m, 1H), 7.45 (m, 2H), 7.24 (m, 1H), 7.13-7.03 (m, 3H), 6.50 (s, br, 1H), 4.67-4.64 (m, 1H), 4.03 (s, 2H), 3.75 (m, 2H), 3.29 (m, 2H), 1.93-1.86 (m, 2H), 1.69-1.51 (m, 2H). MS (EI): 545 (MH+).

Example 55

Synthesis of $N^4$-1H-benzimidazol-2-yl-$N^5$-{2-chloro-4-[(1-methylpiperidin-4-yl)oxy]phenyl}-1H-imidazole-4,5-dicarboxamide

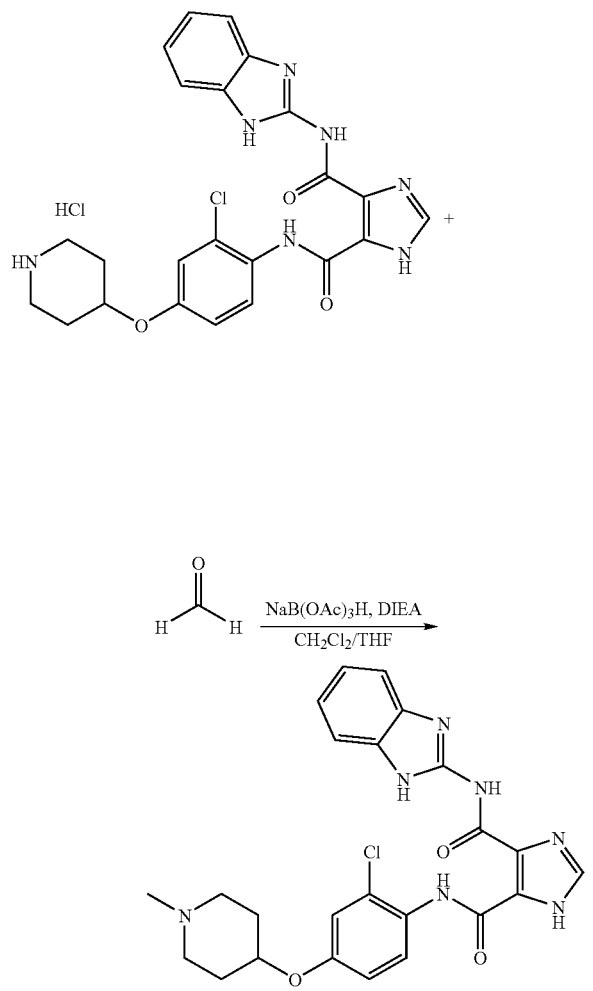

A flask was charged with $N^4$-(1H-benzo[d]imidazol-2-yl)-$N^5$-(2-chloro-4-(piperidin-4-yloxy)phenyl)-1H-imidazole-4,5-dicarboxamide hydrochloride (115 mg, 0.22 mmol), formaldehyde, 30% wt (0.030 mL, 4 mmol), DIEA (0.080 mL, 0.5 mmol), dichloromethane (20 mL) and THF (20 mL), and the reaction mixture was stirred for 15 hours at room temperature. The reaction mixture was filtered, and the precipitate was discarded. The product was purified by reverse phase HPLC using ammonium acetate and acetonitrile as eluent to afford 60 mg (55% yield) of $N^4$-1H-benzimidazol-2-yl-$N^5$-(2-chloro-4-{[1-(methyl)piperidin-4-yl]oxy}phenyl)-1H-imidazole-4,5-dicarboxamide. $^1$H-NMR (400 MHz, DMSO-d6): δ 8.06 (s, 1H), 7.91 (d, 9 Hz, 1H), 7.46 (s, br, 2H), 7.21 (d, 3 Hz, 1H), 7.12-7.03 (m, 3H), 4.44-4.42 (m, 1H), 2.61-2.50 (m, 2H), 2.20-2.17 (m, 5H), 1.96-1.89 (m, 2H), 1.67-1.61 (m, 2H). MS (EI): 494 (MH+).

Example 56

Synthesis of N4-1H-benzimidazol-2-yl-$N^5$-{4-fluoro-2-[(2-morpholin-4-ylethyl)oxy]phenyl}-1H-imidazole-4,5-dicarboxamide

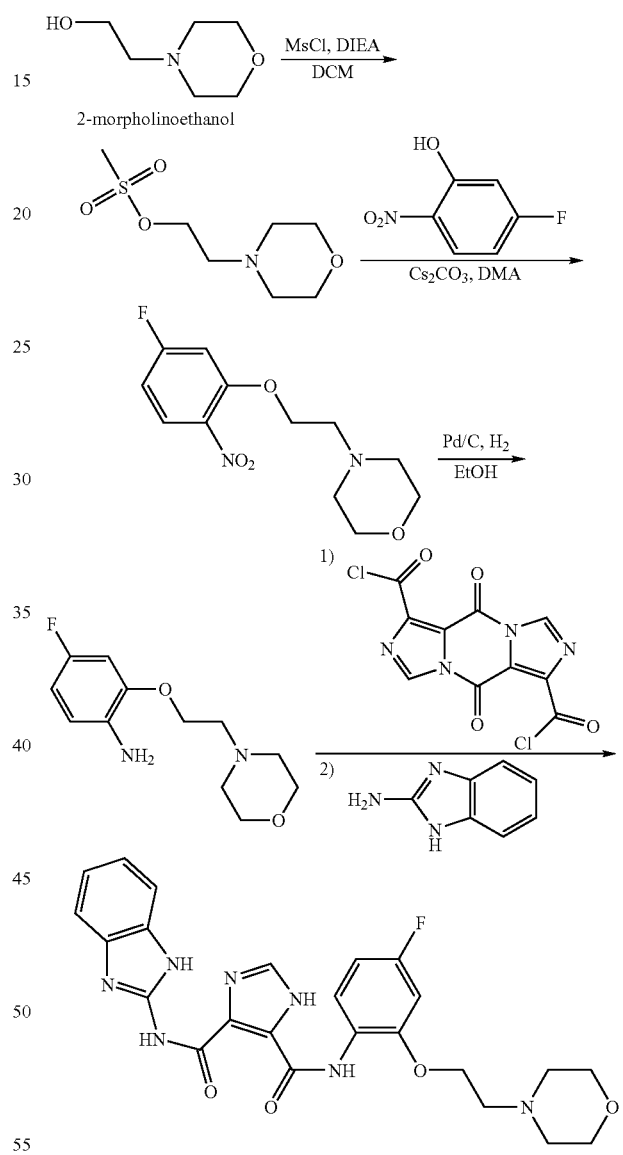

Synthesis of 2-morpholinoethyl Methanesulfonate

A flask was charged with 2-morpholinoethanol (1.0 g, 7.1 mmol), DIEA (2.4 mL, 14 mmol) and dichloromethane (100 mL). Mesylchloride (0.64 mL, 8.3 mmol) was added in a dropwise fashion to the dichloromethane mixture and the reaction mixture was stirred at room temperature for 15 hours. Concentration of the reaction mixture gave rise to a quantitative yield of 2-morpholinoethyl methanesulfonate, which was used in the next step without any without further purification. EI (MS); 210 (MH+).

Synthesis of 4-(2-(5-fluoro-2-nitrophenoxy)ethyl)morpholine

A flask was charged with 2-morpholinoethyl methanesulfonate (1.5 g, 6.9 mmol), 5-fluoro-2-nitrophenol (0.99 g, 6.3 mmol), cesium carbonate (4.0 g, 12 mmol) and DMA (100 mL), and the reaction mixture was heated to 90° C. for 15 hours. Ethyl acetate (200 ml) was added to the cooled reaction mixture and the mixture was extracted with water (2×100 ml), 1N sodium hydroxide (2×50 ml) and aqueous 5% lithium chloride (2×50 ml). The organic solvent was removed on a rotary evaporator under reduced pressure. Purified of the crude product by silica column chromatography using 50:50 ethyl acetate:hexanes as eluant gave 0.71 g of 4-(2-(5-fluoro-2-nitrophenoxy)ethyl)morpholine (39% yield). EI (MS): 271 (MH+).

Synthesis of 4-fluoro-2-(2-morpholinoethoxy)aniline

An ethanolic (20 mL) solution of 4-(2-(4-fluoro-2-nitrophenoxy)ethyl)morpholine (0.75 g, 2.7 mmol) was subjected to hydrogenation using the H-cube (Pd/C catalyst cartridge and $H_2$, 1-5 bar) for 1 hour. 2-Methyl-4-(3-morpholinopropoxy)aniline was isolated by concentration under reduced pressure (0.22 g, 32% yield). $^1$H-NMR (DMSO-d6), δ 6.33 (d, 1H), 6.28 (d, 1H), 6.22 (t, 1H), 6.23 (d, 1H), 5.85 (br s, 2H), 4.04 (t, 2H), 3.52 (t, 4H), 2.69 (t, 2H), 2.37 (t, 4H). EI (MS): 241 (MH+).

Synthesis of $N^4$-1H-benzimidazol-2-yl-$N^5$-{4-fluoro-2-[(2-morpholin-4-ylethyl)oxy]phenyl}-1H-imidazole-4,5-dicarboxamide $N^4$-1H-Benzimidazol-2-yl-$N^5$-{4-fluoro-2-[(2-morpholin-4-ylethyl)oxy]phenyl}-1H-imidazole-4,5-dicarboxamide was prepared in a similar a manner to $N^5$-1H-benzimidazol-2-yl-$N^4$-(2,4-dimethylphenyl)-1H-imidazole-4,5-dicarboxamide in Example 1 in 64% yield. $^1$H-NMR (400 MHz, DMSO-d6): δ 14.1 (s, 1H), 13.8 (s, 1H), 12.2 (s br, 1H), 10.1 (s, 1H), 8.24-8.20 (m, 1H), 8.11 (s, 1H), 7.46-7.42 (m, 2H), 7.13-7.05 (m, 3H), 6.87-6.80 (m, 1H), 4.22 (s br, 2H), 3.46 (s br, 4H), 3.33 (s br, 4H), 2.70 (s br, 2H). MS (EI): 494 (MH+).

Example 57

Scheme for the synthesis of $N^4$-(5-bromo-2-methylphenyl)-$N^5$-[5-(4-methylpiperazin-1-yl)-1H-benzimidazol-2-yl]-1H-imidazole-4,5-dicarboxamide

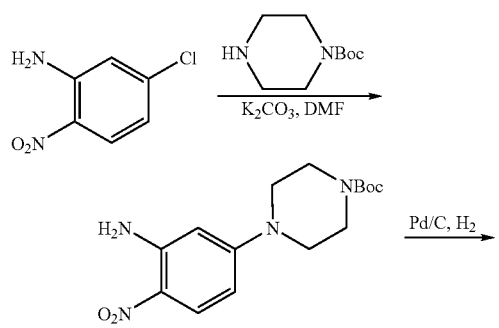

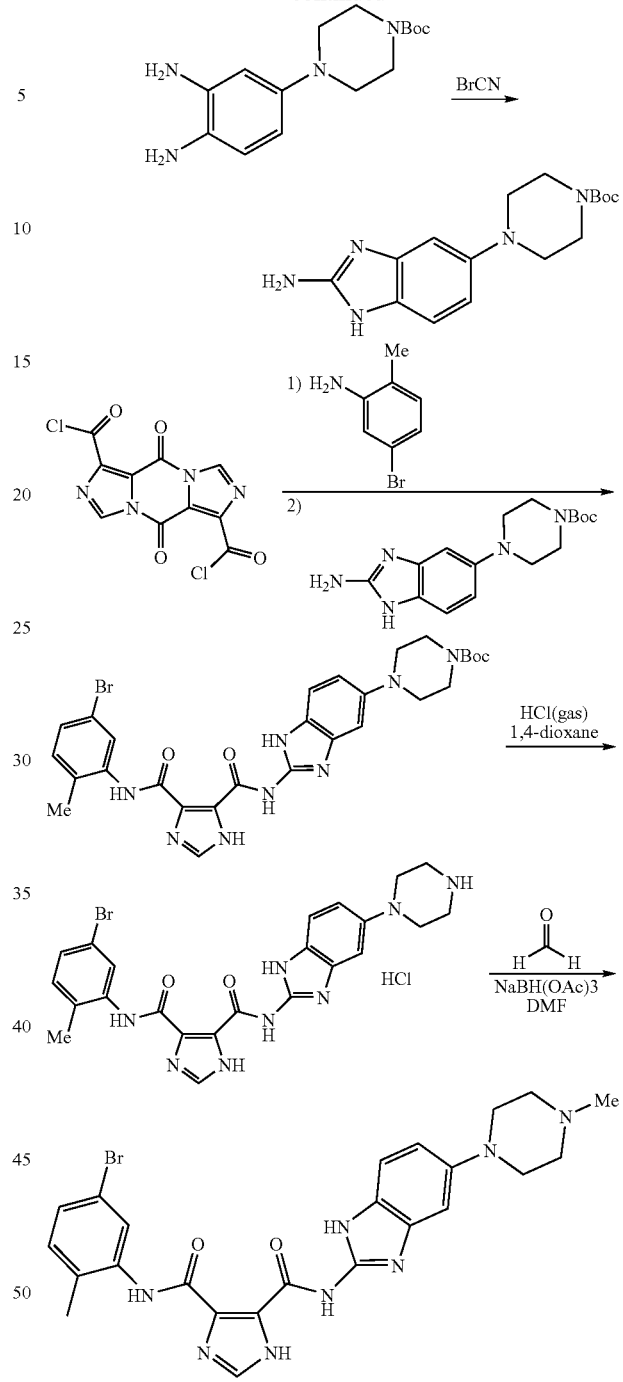

Synthesis of tert-butyl 4-(3-amino-4-nitrophenyl)piperazine-1-carboxylate

5-Chloro-2-nitroaniline (8.60 g, 50 mmol, commercially available from Aldrich), 1-tert-butoxycarbonyl piperazine (14.0 g, 75 mmol, commercially available from Aldrich)), anhydrous potassium carbonate (6.9 g, 50 mmol) and DMA (60 mL) were combined in a thick walled pressure fitted with a Teflon stirrer bar and sealed with a Teflon screw-top stopper. The reaction mixture was heated to 144° C. with stirring for 24 hours. The reaction mixture was allowed to cool to room temperature, filtered and the recovered solid washed with ethyl acetate. The filtrate was partitioned between water and ethyl acetate, and the organic layer was washed with saturated sodium chloride, dried over anhydrous sodium sulfate, filtered and concentrated under reduced pressure. The resulting crude material was purified by silica chromatography eluting with 25% ethyl acetate-hexane which gave 11.8 g of tent-butyl 4-(3-amino-4-nitrophenyl)piperazine-1-carboxylate (80% yield). $^1$H-NMR (400 MHz, MeOH-d4): 7.95 (d, 1H), 6.37 (dd, 1H), 6.18 (d, 1H), 3.53 (s, 4H) 3.35 (s, 4H), 1.43 (s, 9H). MS (EI): 323 (MH+).

Synthesis of tert-butyl
4-(3,4-diaminophenyl)piperazine-1-carboxylate

A 500 ml Parr hydrogenation flask was charged with tert-butyl 4-(3-amino-4-nitrophenyl)piperazine-1-carboxylate (9.0 g), methanol (250 mL) and 10% palladium on carbon (50% w/w water, 2.0 g). The atmosphere of the vessel was replaced by hydrogen gas. The reaction was shaken under a hydrogen atmosphere at 40 psi at room temperature for 1 hour. The reaction mixture was filtered through a plug of Celite, which was washed with additional methanol. The filtrate was concentrated at reduced pressure and the residue was triturated with ether to give 7.0 g of tert-butyl 4-(3,4-diaminophenyl)piperazine-1-carboxylate (yield 85%). $^1$H-NMR (400 MHz, MeOH-d4): δ 6.65 (d, 1H), 6.47 (s, 1H), 6.30 (d, 1H), 3.52 (s, 4H) 2.90 (s, 4H), 1.48 (s, 9H). MS (EI) for: 293 (MH+).

Synthesis of tert-butyl 4-(2-amino-1H-benzo[d]imidazol-5-yl)piperazine-1-carboxylate A solution of 1-tert-butoxycarbonyl-4-(3,4-diaminophenyl)piperazine (3.0 g, 10.2 mmol) in methanol (200 mL) was cooled to 0° C. and treated with a solution of cyanogen bromide (5M in acetonitrile, 1.1 equivalents). The reaction mixture was stirred at room temperature for 4 hours. The mixture was made basic with sodium bicarbonate and concentrated under reduced pressure. The residue was extracted with methanol and concentrated. The resulting residue was triturated with ether to give 2.74 g of tent-butyl 4-(2-amino-1H-benzo[d]imidazol-5-yl)piperazine-1-carboxylate (yield 85%). $^1$H-NMR (400 MHz, MeOH-d4): δ 7.25 (s, 1H), 7.00-6.92 (m, 2H), 3.60-3.53 (m, 4H), 3.10-3.05 (m, 4H), 1.50 (s, 9H). MS (EI): 318 (MH+).

Synthesis of 1,1-dimethylethyl 4-(2-{[(4-{[(5-bromo-2-methylphenyl)amino]carbonyl}-1H-imidazol-5-yl)carbonyl]amino}-1H-benzimidazol-5-yl)piperazine-1-carboxylate 1,1-dimethylethyl 4-(2-{[(4-{[(5-bromo-2-methylphenyl)amino]carbonyl}-1H-imidazol-5-yl)carbonyl]amino}-1H-benzimidazol-5-yl)piperazine-1-carboxylate was prepared in the same manner as $N^5$-1H-benzimidazol-2-yl-$N^4$-(2,4-dimethylphenyl)-1H-imidazole-4,5-dicarboxamide in Example 1 in 71% yield. MS (EI): 424 (MH+).

Example 58

Synthesis of $N^4$-(5-bromo-2-methylphenyl)-$N^5$-(5-piperazin-1-yl-1H-benzimidazol-2-yl)-1H-imidazole-4,5-dicarboxamide hydrochloride To a solution of 1,1-dimethylethyl 4-(2-{[(4-{[(5-bromo-2-methylphenyl)amino]carbonyl}-1H-imidazol-5-yl)carbonyl]amino}-1H-benzimidazol-5-yl)piperazine-1-carboxy-late (2.5 g, 4 mmol) in methanol (100 mL) was added 4 N hydrogen chloride in 1,4-dioxane (20 mL). The solution was stirred at room temperature for 48 hours. The resulting suspension was filtered to give 2.0 g of $N^4$-(5-bromo-2-methylphenyl)-$N^5$-(5-piperazin-1-yl-1H-benzimidazol-2-yl)-1H-imidazole-4,5-dicarboxamide hydrochloride. $^1$H-NMR (400 MHz, DMSO-d6) δ 12.62 (br s, 1H), 12.50 (br s, 1H), 11.20 (br s, 1H), 9.28 (d, 1H), 9.00 (d, 1H), 8.39 (s, 1H), 7.86 (s, 1H), 7.60 (d, 1H), 7.42 (d, 1H), 7.31 (d, 1H), 7.21 (s, 1H), 7.03 (d, 1H), 4.23 (br s 2H), 3.94 (m, 2H), 3.33 (m, 2H), 2.91 (m, 2H), 2.29 (s, 3H), 2.11 (m, 1H), 1.94 (m, 2H), 1.54 (m, 2H). MS (EI): 553 (MH+).

Synthesis of $N^4$-(5-bromo-2-methylphenyl)-$N^5$-[5-(4-methylpiperazin-1-yl)-1H-benzimidazol-2-yl]-1H-imidazole-4,5-dicarboxamide Paraformaldehyde (0.088 g, 2.0 mmol) was weighed out into a dry 25 ml round bottom flask. $N^4$-(5-bromo-2-methylphenyl)-$N^5$-(5-piperazin-1-yl-1H-benzimidazol-2-yl)-1H-imidazole-4,5-dicarboxamide hydrochloride (0.0465 g, 0.1 mmol) was added, followed by sodium triacetoxyborohydride (0.106 g, 0.5 mmol) dissolved in DMF (3.0 ml). The reaction mixture was stirred at room temperature over night (16 hours). The reaction mixture was then treated with 1 mL of 1N hydrochloric acid and concentrated under reduced pressure. The resulting crude material was purified by reverse phase HPLC (ammonium acetate/acetonitrile) which gave $N^4$-(5-bromo-2-methylphenyl)-$N^5$-[5-(4-methylpiperazin-1-yl)-1H-benzimidazol-2-yl]-1H-imidazole-4,5-dicarboxamide. $^1$H-NMR (400 MHz, DMSO-d6): δ 9.83 (s, 1H), 8.28 (s, 1H), 7.88 (s, 1H), 7.45 (dd, 1H), 7.30 (m, 2H), 7.12 (m, 1H), 7.05 (m, 1H), 3.77 (d, 2H), 3.56 (d, 2H), 3.21 (d, 2H), 2.97 (m, 2H), 2.89 (s, 3H), 2.30 (s, 3H); MS (EI): 538.7 (MH+).

Example 59

Synthesis of 1,1-dimethylethyl 4-[(3-methyl-4-{[(5-{[(5-{[2-(methyloxy)-2-oxoethyl]oxy}-1H-benzimidazol-2-yl)amino]carbonyl}-1H-imidazol-4-yl)carbonyl]amino}phenyl)oxy]piperidine-1-carboxylate 1,1-Dimethylethyl 4-[(3-methyl-4-{[(5-{[(5-{[2-(methyloxy)-2-oxoethyl]oxy}-1H-benzimidazol-2-yl)amino]carbonyl}-1H-imidazol-4-yl)carbonyl]amino}phenyl)oxy]piperidine-1-carboxylate was prepared in a similar a manner to $N^5$-1H-benzimidazol-2-yl-$N^4$-(2,4-dimethylphenyl)-1H-imidazole-4,5-dicarboxamide in Example 1 in 56% yield. $^1$H-NMR (400 MHz, DMSO-d6): δ 8.09 (s, 1H), 7.43 (d, 1H), 7.36 (m, 1H), 6.93 (s, 1H), 6.86 (d, 1H), 6.75 (m, 2H), 4.74 (s, 2H), 3.68 (s, 3H), 3.62 (m, 4H), 3.19 (m, 1H), 2.23 (s, 3H), 1.89 (s, 2H), 1.52 (m, 2H), 1.39 (s, 9H); MS (EI): 648.7 (MH+).

Example 60

Synthesis of 1,1-dimethylethyl 4-{[3-methyl-4-({[5-({[4-(methyloxy)-1H-benzimidazol-2-yl]amino)carbonyl}-1H-imidazol-4-yl]carbonyl}amino)phenyl]oxy}piperidine-1-carboxylate 1,1-Dimethylethyl 4-{[3-methyl-4-({[5-({[4-(methyloxy)-1H-benzimidazol-2-yl]amino)carbonyl}-1H-imidazol-4-yl]carbonyl}amino)phenyl]oxy}piperidine-1-carboxylate was prepared in similar manner to $N^5$-1H- benzimidazol-2-yl-N⁴-(2,4-dimethylphenyl)-1H-imidazole-4,5-dicarboxamide in Example 1. MS (EI): 590 (MH+).

Example 61

Scheme for the synthesis of N⁵-1H-benzimidazol-2-yl-N⁴-[2-methyl-4-({2-[(phenylmethyl)oxy]ethyl}oxy)phenyl]-1H-imidazole-4,5-dicarboxamide

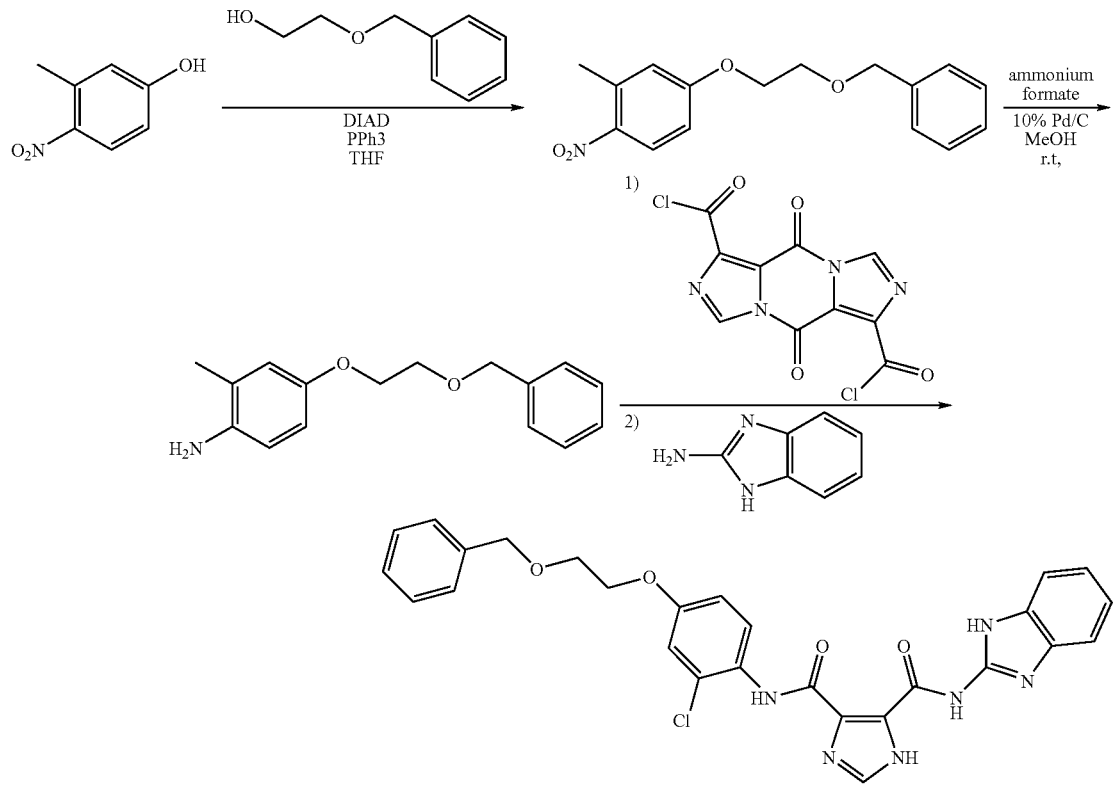

Synthesis of 4-(2-(benzyloxy)ethoxy)-2-methyl-1-nitrobenzene

3-Methyl-4-nitrophenol (17.48 g, 114 mmoles), 2-benzyloxyethanol (17.38 g, 114 mmoles, 16.22 ml) and triphenylphosphine (44.6 g, 170.2 mmoles) were dissolved in anhydrous tetrahydrofuran (200 ml) under nitrogen at room temperature. The stirred reaction mixture was then cooled to 0° C. and stirred for 10 minutes. Diisoproplyazo-dicarboxylate (23.49 g, 116.2 mmoles, 22.97 ml) was then added in one lot, and the reaction mixture was allowed to warm to room temperature and stirred overnight (16 hours). The solvent was removed under reduced pressure and the crude mixture was purified via column chromatography (silica gel, 5% ethyl acetate-hexane) to give the product. The remaining impurities were removed by means of crystallization from hexane ethyl acetate. The result crystals were filtered off and the mother liquor was evaporated under reduced pressure to give 21.56 g of 4-(2-(benzyloxy)ethoxy)-2-methyl-1-nitrobenzene. ¹H-NMR (CDCl₃) 8.08 (d, 1H), 7.38.7.31 (m, 3H), 6.82 (m, 2H), 4.65 (s, 2H), 4.23 (t, 2H), 3.87 (t, 2H), 2.63 (s, 3H).

Synthesis of 4-(2-(benzyloxy)ethoxy)-2-methylaniline

A 500 ml round bottomed flask fitted with a teflon stirrer bar was charged with 4-(2-(benzyloxy)ethoxy)-2-methyl-1-nitrobenzene (5.15 g) and methanol (200 ml) and stirred to dissolve all material. The reaction mixture was charged with 10% palladium on charcoal (50% water w/w) and stirred at room temperature. Ammonium formate (20.5 g) was added in one lot and the reaction mixture was stirred at room temperature. After 1 hour, additional ammonium formate (20.5 g) was added, and the progress of the reaction was followed by TLC (silica, dichloromethane). After 4 hours, the reaction was found to be complete. The reaction mixture was then filtered through a plug of Celite, which was washed with methanol (2×50 ml). The resulting filtrate was evaporated under reduced pressure to give a solid. This material was dissolved in water (300 ml), extracted with diethylether (3×100 ml). The combined ethereal solutions were washed with water (2×100 ml) and saturated sodium chloride solution (2×100 ml), dried over anhydrous sodium sulfate, filtered and evaporated under reduced pressure to give 4.79 g of 4-(2-(benzyloxy)ethoxy)-2-methylaniline, ¹H-NMR (CDCl₃) 7.39 (m, 2H), 7.37 (s, 1H), 7.31 (m, 2H), 6.33 (m, 1H), 6.30 (s, 1H), 6.23 (m, 1H), 5.85 (bs, 2H), 4.63 (s, 2H), 4.11 (m, 2H), 3.79 (m, 2H), 2.35 (s, 3H).

Synthesis of N⁵-1H-benzimidazol-2-yl-N⁴-[2-methyl-4-({2-[(phenylmethyl)oxy]ethyl}oxy)phenyl]-1H-imidazole-4,5-dicarboxamide N⁵-1H-Benzimidazol-2-yl-N⁴-[2-methyl-4-({2-[(phenylmethyl)oxy]ethyl}oxy)phenyl]-1H-imidazole-4,5-dicarboxamide was prepared in a manner similar to N⁵-1H-benzimidazol-2-yl-N⁴-(2,4-dimethylphenyl)-1H-imidazole-4,5-dicarboxamide in Example 1 in 41% yield. ¹H-NMR (DMSO-d6) 13.78 (bs, 1H), 12.20 (bs, 1H), 10.20 (bs, 1H), 1.12 (bs, 1H), 7.52 (m, 1H), 7.41 (m, 1H), 7.39 (m, 5H), 7.11

(m, 2H), 6.92 (m, 1H), 6.83 (m, 1H), 4.58 (s, 2H0, 4.16 (m, 2H), 3.78 (m, 2H), 2.22 (s, 3H). MS (EI): 511 (MH+).

Example 62

Synthesis of $N^5$-(6-chloro-1H-benzimidazol-2-yl)-$N^4$-[2-methyl-4-(piperidin-4-yloxy)phenyl]-1H-imidazole-4,5-dicarboxamide hydrochloride $N^5$-(6-Chloro-1H-benzimidazol-2-yl)-$N^4$-[2-methyl-4-(piperidin-4-yloxy)phenyl]-1H-imidazole-4,5-dicarboxamide hydrochloride was prepared in a manner similar to $N^4$-(5-bromo-2-methylphenyl)-$N^5$-(5-piperazin-1-yl-1H-benzimidazol-2-yl)-1H-imidazole-4,5-dicarboxamide hydrochloride in Example 58. $^1$H-NMR (400 MHz, DMSO-d6) δ 13.90 (br s 1H), 12.25 (br s, 1H), 10.58 (br s, 1H), 8.22 (s, 1H), 7.48 (d, 1H), 7.42 (d, 1H), 7.42 (d, 1H), 7.23 (d, 1H), 7.05 (s, 1H), 6.96 (m, 1H), 4.63 (m, 1H), 3.80 (br s, 2H), 3.24 (m, 2H), 3.06 (m, 2H), 2.24 (s, 3H), 2.05 (m, 2H), 1.96 (m, 2H). MS (EI): 494 (MH+).

Example 63

Synthesis of $N^5$-1H-benzimidazol-2-yl-$N^4$-{2-methyl-4-[4-(phenylsulfonyl)piperazin-1-yl]phenyl}-1H-imidazole-4,5-dicarboxamide

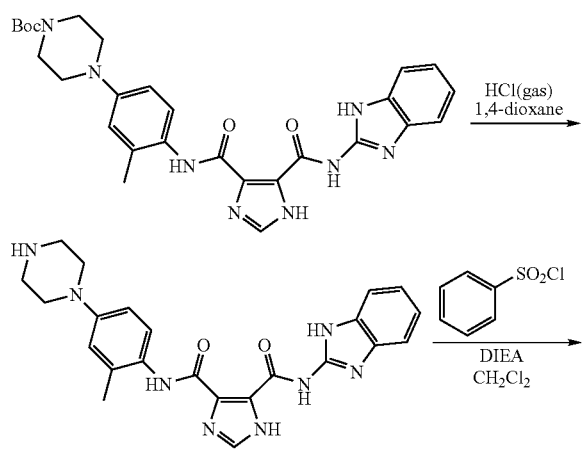

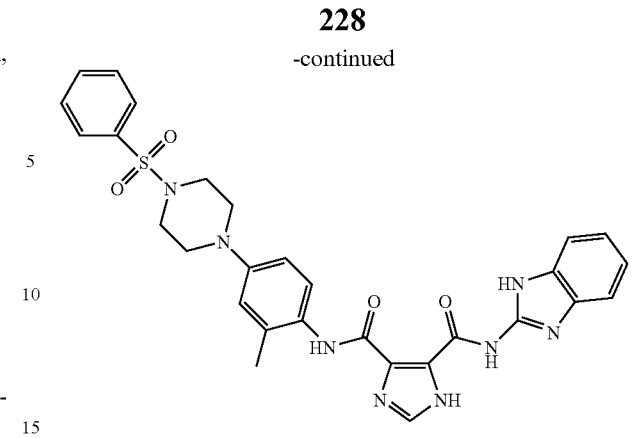

tert-Butyl 4-(4-(5-(1H-benzo[d]imidazol-2-ylcarbamoyl)-1H-imidazole-4-carboxamido)-3-methylphenyl)piperazine-1-carboxylate was stirred in 4 N hydrogen chloride in 1,4-dioxane for 4 hours. The reaction mixture was evaporated under reduced pressure. The crude product was dissolved in ethyl acetate, washed with 2 N sodium hydroxide solution, dried over anhydrous sodium sulfate, and filtered and evaporated under reduced pressure. The impure $N^5$-(1H-benzo[d]imidazol-2-yl)-$N^4$-(2-methyl-4-(piperazin-1-yl)phenyl)-1H-imidazole-4,5-dicarboxamide was used in the next step without any further purification. MS (EI): 445 (MH+).

Synthesis of $N^5$-1H-benzimidazol-2-yl-$N^4$-{2-methyl-4-[4-(phenylsulfonyl)piperazin-1-yl]phenyl}-1H-imidazole-4,5-dicarboxamide $N^5$-(1H-Benzo[d]imidazol-2-yl)-$N^4$-(2-methyl-4-(piperazin-1-yl)phenyl)-1H-imidazole-4,5-dicarboxamide (1 equivalent), dichloromethane, benzenesulfonyl chloride (1.5 equiv), and DIEA (1.5 equiv.) were added and stirred at room temperature. After 1 hour, LC-MS indicated the reaction was complete. The reaction mixture was evaporated under reduced pressure. The resulting crude product was purified by reverse phase HPLC (aqueous ammonium acetate/acetonitrile to give $N^5$-1H-benzimidazol-2-yl-$N^4$-{2-methyl-4-[4-(phenylsulfonyl)piperazin-1-yl]phenyl}-1H-imidazole-4,5-dicarboxamide in 43% yield. $^1$H-NMR (400 MHz, DMSO-d6): δ 10.9 (s, br, 1H), 8.36 (s, 1H), 7.80 (m, 2H), 7.73-7.64 (m, 4), 7.43 (m, 2H), 7.33 (m, br, 1H), 6.97 (m, br, 2H), 3.31 (s, br, 4H), 3.09 (s, br, 4H). 2.24 (s, 3H). MS (EI): 585 (MH+).

Example 64

Synthesis of $N^5$-1H-benzimidazol-2-yl-$N^4$-(2-methyl-4-{4-[(phenylamino)carbonyl]piperazin-1-yl}phenyl)-1H-imidazole-4,5-dicarboxamide

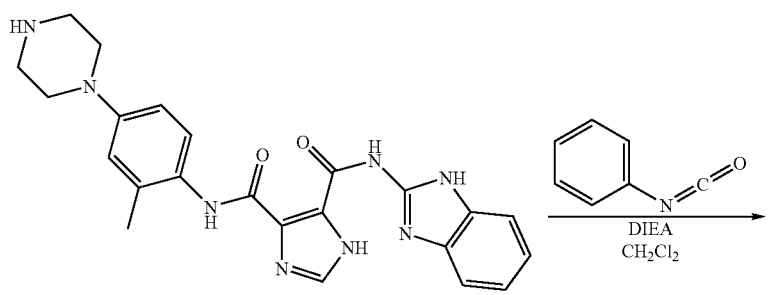

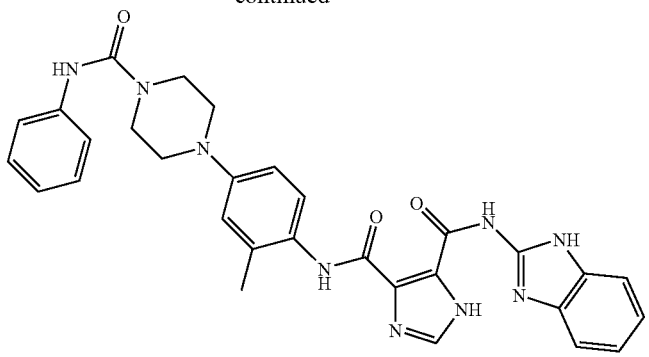

$N^5$-(1H-Benzo[d]imidazol-2-yl)-$N^4$-(2-methyl-4-(piperazin-1-yl)phenyl)-1H-imidazole-4,5-dicarboxamide (1 equivalent) and dichloromethane were stirred for 5 minutes. Phenyl isocyanate (1.5 equiv) was added and the reaction mixture was stirred at room temperature for 16 hours. The reaction mixture was evaporated under reduced pressure. The resulting crude product was purified by reverse phase HPLC (aqueous ammonium acetate/acetonitrile to give $N^5$-1H-benzimidazol-2-yl-$N^4$-(2-methyl-4-{4-[(phenylamino)carbonyl]piperazin-1-yl}phenyl)-1H-imidazole-4,5-dicarboxamide. $^1$H-NMR (400 MHz, DMSO-d6): δ 8.86 (s, br, 1H), 8.38 (s, br, 1H), 7.67 (m, 2H), 7.52 (m, 3H), 7.43 (m, 3H), 7.26 (m, 2H), 6.97 (m, 1H), 3.84 (s, br, 4H), 3.41 (s, br, 4H), 2.33 (s, 3H). MS (EI): 564 (MH+).

Example 65

Synthesis of $N^4$-(2,4-dimethylphenyl)-$N^5$-[5-({2-oxo-2-[(pyridin-2-ylmethyl)amino]ethyl}oxy)-1H-benzimidazol-2-yl]-1H-imidazole-4,5-dicarboxamide $N^4$-(2,4-Dimethylphenyl)-$N^5$-[5-({2-oxo-2-[(pyridin-2-ylmethyl)amino]ethyl}oxy)-1H-benzimidazol-2-yl]-1H-imidazole-4,5-dicarboxamide was made using the protocol utilized for the synthesis of $N^5$-[6-({2-[(2,3 dihydroxypropyl)amino]-2-oxoethyl}oxy)-1H-benzimidazol-2-yl]-$N^4$-(2,4-dimethylphenyl)-1H-imidazole-4,5-dicarboxamide in Example 6. $^1$H-NMR (400 MHz, DMSO-d6): δ 12.11 (s, 1H), 10.30 (s, 1H), 8.72-5.75 (t, 1H), 8.49-8.50 (s, 2H), 8.07 (s, 1H), 7.69-7.72 (t, 1H), 7.57-7.59 (d, 1H), 7.36 (s, 1H), 7.23-7.25 (m, 2H), 7.07-7.13 (m, 2H), 6.85-6.88 (m, 1H), 4.58 (s, 3H), 4.44-4.46 (d, 2H); 2.33 (s, 3H); 2.31 (s, 3H), MS (EI): 539.6 (MH+).

Example 66

Synthesis of $N^5$-[4-(methyloxy)-1H-benzimidazol-2-yl]-$N^4$-[2-methyl-4-(piperidin-4-yloxy)phenyl]-1H-imidazole-4,5-dicarboxamide $N^5$-[4-(Methyloxy)-1H-benzimidazol-2-yl]-$N^4$-[2-methyl-4-(piperidin-4-yloxy)phenyl]-1H-imidazole-4,5-dicarboxamide was prepared in a manner similar to $N^5$-1H-benzimidazol-2-yl-$N^4$-(2,4-dimethylphenyl)-1H-imidazole-4,5-dicarboxamide in Example 1 followed by removal of the Boc group using 4M hydrogen chloride in 1,4-dioxane as its hydrochloride salt in 68% yield. $^1$H-NMR (400 MHz, DMSO-d6): δ 8.93 (s, 1H), 8.28 (s, 1H), 7.44 (d, 1H), 7.24 (d, 2H), 6.90 (d, 1H), 6.93 (d, 1H), 6.91 (d, 1H), 4.67 (m, 1H), 3.93 (s, 3H), 3.23 (m, 2H), 3.09 (m, 2H), 2.27 (s, 3H), 2.12 (m, 2H), 1.91 (s, 1H), 1.87 (m, 2H); MS (EI): 490.5 (MH+).

Example 67

Synthesis of $N^4$-(2,6-dichlorophenyl)-$N^5$-[4-(methyloxy)-1H-benzimidazol-2-yl]-1H-imidazole-4,5-dicarboxamide $N^4$-(2,6-Dichlorophenyl)-$N^5$-[4-(methyloxy)-1H-benzimidazol-2-yl]-1H-imidazole-4,5-dicarboxamide was prepared in a manner similar to $N^5$-1H-benzimidazol-2-yl-$N^4$-(2,4-dimethylphenyl)-1H-imidazole-4,5-dicarboxamide in Example 1 in 72% yield. $^1$H-NMR (400 MHz, DMSO-d6): δ 13.90 (s, 1H), 10.83 (s, 1H), 8.20 (s, 1H), 7.63 (d, 2H), 7.46 (m, 1H), 7.12 (d, 1H), 7.02 (m, 1H), 6.68 (m, 1H), 3.87 (s, 3H); MS (EI): 446.4 (MH+).

Example 68

Scheme for $N^5$-1H-benzimidazol-2-yl-$N^4$-{2-methyl-4-[(3-morpholin-4-ylpropyl)oxy]phenyl}-1H-imidazole-4,5-dicarboxamide

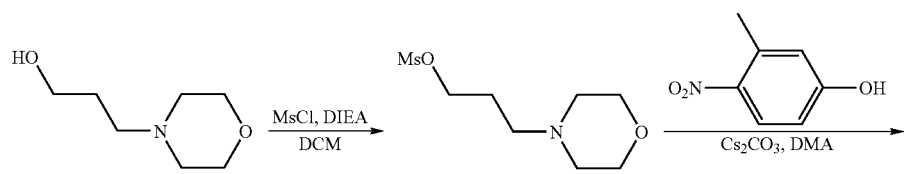

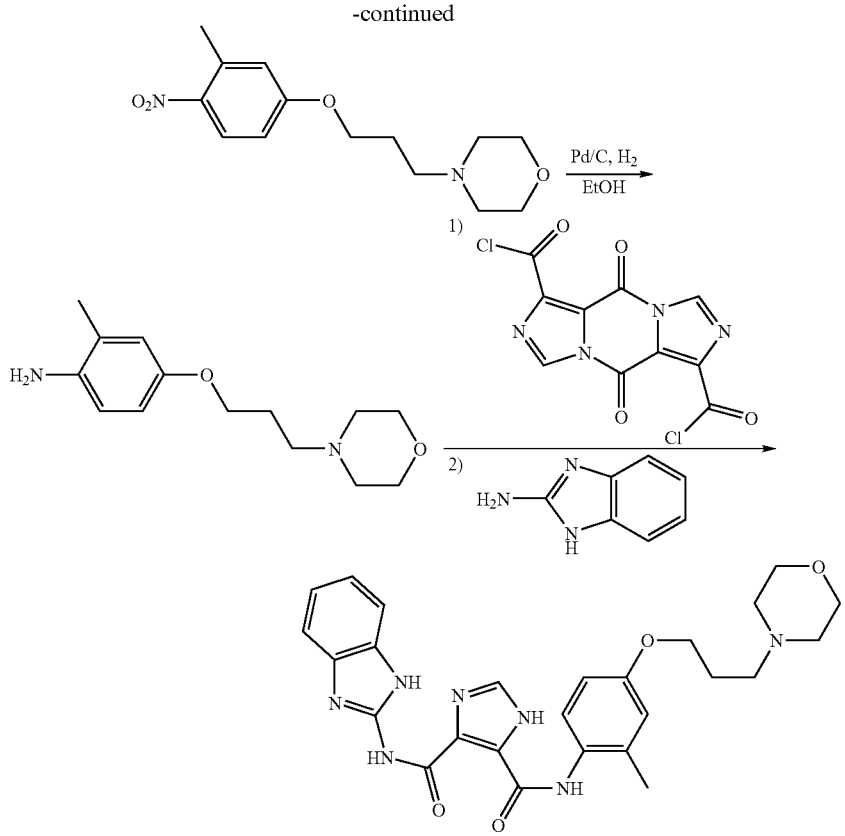

Synthesis of 3-morpholinopropyl Methanesulfonate

A flask was charged with 3-morpholinopropan-1-ol (1.0 g, 6.9 mmol), DIEA (2.4 mL, 14 mmol) and dichloromethane (100 mL). Mesylchloride (0.64 mL, 8.3 mmol) was added in a drop wise fashion to the dichloromethane mixture and the reaction mixture was stirred at room temperature for 15 hours. Concentration of the reaction mixture gave rise to a quantitative yield of 3-morpholinopropyl methanesulfonate, which was used in the next step without any further purification.

Synthesis of 4-(3-(3-methyl-4-nitrophenoxy)propyl)morpholine

A flask was charged with 3-morpholinopropyl methanesulfonate (1.5 g, 6.9 mmol), 3-methyl-4-nitrophenol (0.96 g, 6.3 mmol), cesium carbonate (4.0 g, 12 mmol) and DMA (100 mL), and the reaction mixture was heated to 90° C. for 15 hours. Ethyl acetate (200 ml) was added to the cooled reaction mixture, and the mixture was extracted with water (2×100 ml), 1N sodium hydroxide (2×50 ml) and aqueous 5% lithium chloride (2×50 ml). The organic solvent was removed on a rotary evaporator under reduced pressure. Purification of the crude product by silica column chromatography using 50:50 ethyl acetate:hexanes as eluant gave 0.75 g of 4-(3-(3-methyl-4-nitrophenoxy)propyl)morpholine. (39% yield). MS (EI): 281 (MH+).

Synthesis of 2-methyl-4-(3-morpholinopropoxy)aniline

An ethanolic (20 mL) solution of 4-(3-(3-methyl-4-nitrophenoxy)propyl) morpholine (0.75 g, 2.7 mmol) was subjected to hydrogenation using the H-cube (Pd/C catalyst cartridge and $H_2$, 1-5 bar) for 1 hour. 2-Methyl-4-(3-morpholinopropoxy)aniline was isolated by concentration under reduced pressure (0.22 g, 32% yield). $^1$H-NMR (400 MHz DMSO-d6): δ 6.57-6.51 (m, 3H), 3.85 (t, 6.4 Hz, 2H), 3.69-3.62 (m, 4H), 3.46-3.43 (m, 2H), 2.56 (m, 4H), 2.02 (s, 3H), 1.88-1.85 (m, 2H). MS (EI): 251 (MH+).

Synthesis of $N^5$-1H-benzimidazol-2-yl-$N^4$-{2-methyl-4-[(3-morpholin-4-ylpropyl)oxy]phenyl}-1H-imidazole-4,5-dicarboxamide $N^5$-1H-Benzimidazol-2-yl-$N^4$-{2-methyl-4-[(3-morpholin-4-ylpropyl)oxy]phenyl}-1H-imidazole-4,5-dicarboxamide was prepared in a manner similar to $N^5$-1H-benzimidazol-2-yl-$N^4$-(2,4-dimethylphenyl)-1H-imidazole-4,5-dicarboxamide in Example 1 in 63% yield. $^1$H-NMR (400 MHz DMSO-d6): δ 13.75 (s, br, 1H), 12.15 (s, br, 1H), 10.16 (s, br, 1H), 8.13 (s, 1H), 7.50-7.39 (m, 3H), 7.10 (m, 2H), 6.89-6.88 (m, 1H), 6.83-6.81 (m, 1H), 4.01 (t, 6.2 Hz, 2H), 3.56 (t, 4.8 Hz, 4H), 2.48 (t, 1.8 Hz, 2H), 2.36 (m, 4H), 2.24 (s, 3H), 1.89-1.85 (m 2H). MS (EI): 504 (MH+).

Example 69

Synthesis of $N^5$-1H-benzimidazol-2-yl-$N^4$-[2-chloro-4-({3-[4-(phenylsulfonyl)piperazin-1-yl]propyl}oxy)phenyl]-1H-imidazole-4,5-dicarboxamide

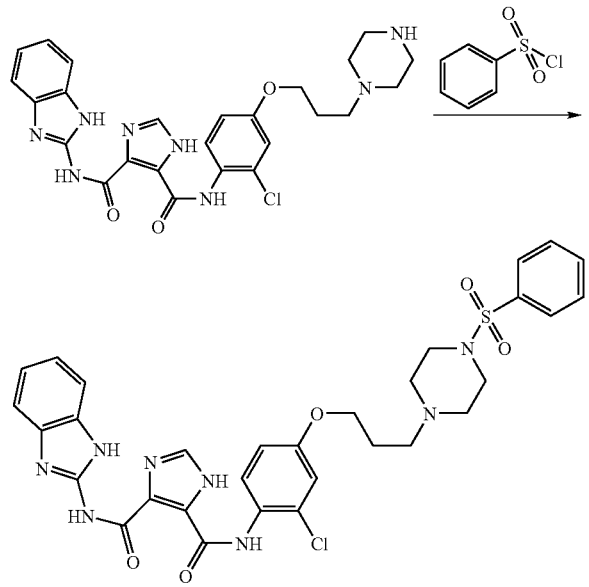

Synthesis of $N^5$-1H-benzimidazol-2-yl-N4-[2-chloro-4-({3-[4-(phenylsulfonyl)piperazin-1-yl]propyl}oxy)phenyl]-1H-imidazole-4,5-dicarboxamide $N^5$-1H-Benzimidazol-2-yl-N4-[2-chloro-4-({3-[4-(phenylsulfonyl)piperazin-1-yl]propyl}oxy)phenyl]-1H-imidazole-4,5-dicarboxamide was prepared in the same manner as $N^5$-1H-benzimidazol-2-yl-$N^4$-{2-methyl-4-[4-(phenylsulfonyl)piperazin-1-yl]phenyl}-1H-imidazole-4,5-dicarboxamide in Example 63 in 41% yield. $^1$H-NMR (400 MHz, DMSO-d6): δ 12.2 (s, 1H), 10.3 (s, 1H), 8.18 (s, 1H), 7.89 (s, 1H), 7.87 (s, 1H), 7.76-7.73 (m, 3H), 6.99 (m, 1H), 7.69-7.65 (m, 2H), 7.52 (m, 1H), 7.42 (m, 1H), 7.16-7.13 (m, 3H), 4.00 (t, 6.3 Hz, 2H), 2.89 (s br, 4H), 2.49-2.41 (m, 6H), 1.82 (m 2H). MS (EI): 664 (MH+).

Example 70

Synthesis of $N^5$-1H-benzimidazol-2-yl-$N^4$-(4-{4-[(ethylamino)carbonyl]piperazin-1-yl}-2-methylphenyl)-1H-imidazole-4,5-dicarboxamide $N^5$-1H-Benzimidazol-2-yl-$N^4$-(4-{4-[(ethylamino)carbonyl]piperazin-1-yl}-2-methylphenyl)-1H-imidazole-4,5-dicarboxamide was prepared using the same procedure as used for the preparation of $N^5$-1H-benzimidazol-2-yl-$N^4$-(2-methyl-4-{4-[(phenylamino)carbonyl]piperazin-1-yl}phenyl)-1H-imidazole-4,5-dicarboxamide in Example 64 in 25% yield. $^1$H-NMR (400 MHz, DMSO-d6): δ 12.8 (s, 1H), 12.2 (s, br, 1H), 10.2 (s, 1H), 8.2 (s, 1H), 7.25 (m, 3H), 7.15 (m, 2H), 6.9 (m, 2H), 6.6 (t, 1H), 3.45 (t, 4H), 3.2 (m, 7H), 2.3 (s, 3H), 1.0 (t, 3H). MS (EI): 516.1 (MH+).

Example 71

Synthesis of $N^5$-1H-benzimidazol-2-yl-$N^4$-(2-fluoro-6-hydroxyphenyl)-1H-imidazole-4,5-dicarboxamide $N^5$-1H-Benzimidazol-2-yl)-$N^4$-(2-fluoro-6-hydroxyphenyl)-1H-imidazole-4,5-dicarboxamide was prepared in a manner similar to $N^5$-1H-benzimidazol-2-yl-$N^4$-(2,4-dimethylphenyl)-1H-imidazole-4,5-dicarboxamide Example 1 in 35% yield. $^1$H-NMR (400 MHz, DMSO-d6): δ 8.22 (s, 1H), 7.74 (m, 2H), 7.29-7.17 (m, 3H), 6.79-6.72 (m, 2H). MS (EI): 381 (MH+).

Example 72

Synthesis of $N^5$-1H-benzimidazol-2-yl-$N^4$-[2,6-bis(methyloxy)phenyl]-1H-imidazole-4,5-dicarboxamide $N^5$-1H-Benzimidazol-2-yl)-$N^4$-(2,6-dimethoxyphenyl)-1H-imidazole-4,5-dicarboxamide was prepared in a manner similar to $N^5$-1H-benzimidazol-2-yl-$N^4$-(2,4-dimethylphenyl)-1H-imidazole-4,5-dicarboxamide in Example 1 in 43% yield. $^1$H-NMR (400 MHz, DMSO-d6): δ 12.17 (s, br, 1H), 8.09 (s, 1H), 7.47-7.26 (m, 3H), 7.09 (m, 2H), 6.89 (m, 2H), 2.88 (s, 6H). MS (EI): 407 (MH+).

Example 73

Synthesis of $N^4$-(2,6-dichlorophenyl)-$N^5$-(6-{[2-(dimethylamino)ethyl]oxy}-1H-benzimidazol-2-yl)-1H-imidazole-4,5-dicarboxamide $N^4$-(2,6-Dichlorophenyl)-$N^5$-(6-{[2-(dimethylamino)ethyl]oxy}-1H-benzimidazol-2-yl)-1H-imidazole-4,5-dicarboxamide was prepared using the procedure used for $N^4$-(5-bromo-2-methylphenyl)-$N^5$-(6-{[2-(dimethylamino) ethyl]oxy}-1H-benzimidazol-2-yl)-1H-imidazole-4,5-dicarboxamide in Example 24 in 39% yield. $^1$H-NMR (400 MHz, MeOH-d4): δ 7.95 (s, 1H), 7.55 (d, 2H), 7.40-7.35 (m, 2H), 7.05 (s, 1H), 6.85 (d, 1H), 4.23 (t, 2H), 3.20 (t, 2H), 2.68 (s, 6H). MS (EI): 503 (MH+).

Example 74

Synthesis of $N^4$-(5-bromo-2-methylphenyl)-$N^5$-(4-{[2-(dimethylamino)ethyl]oxy}-1H-benzimidazol-2-yl)-1H-imidazole-4,5-dicarboxamide $N^4$-(5-Bromo-2-methylphenyl)-$N^5$-(4-{[2-(dimethylamino)ethyl]oxy}-1H-benzimidazol-2-yl)-1H-imidazole-4,5-dicarboxamide was prepared in manner analogous to that used for $N^5$-(5-bromo-2-methylphenyl)-N4-[4-(methyloxy)-1H-benzimidazol-2-yl]-1H-imidazole-4,5-dicarboxamide in Example 38 in 38% yield. $^1$H-NMR (400 MHz, DMSO-d6): δ 10.47 (s, 1H), 8.29 (s, 1H), 7.89 (s, 1H), 7.42 (dd, 1H), 7.30 (dd, 21-1), 7.19 (m, 1H), 6.91 (d, 1H), 4.56 (t, 2H), 3.58 (s, 2H), 2.89 (s, 6H), 2.30 (s, 3H); MS (EI): 527.5 (MH+).

Example 75

Synthesis of 1,1-dimethylethyl 4-(2-{[(4-{[(5-bromo-2-methylphenyl)amino]carbonyl}-1H-imidazol-5-yl)carbonyl]amino}-1H-benzimidazol-5-yl)piperazine-1-carboxylate 1,1-dimethylethyl 4-(2-{[(4-{[(5-bromo-2-methylphenyl)amino]carbonyl}-1H-imidazol-5-yl)carbonyl]amino}-1H-benzimidazol-5-yl)piperazine-1-carboxylate was prepared in a manner similar to $N^5$-1H-benzimidazol-2-yl-$N^4$-(2,4-dimethylphenyl)-1H-imidazole-4,5-dicarboxamide in Example 1. $^1$H-NMR (400 MHz, DMSO-d6): δ 12.0 (s, 1H), 10.35 (s, 1H), 8.15 (s, 1H), 7.90 (s, 1H), 7.42-7.23 (m, 3H), 7.10-7.00 (s, 1H), 6.92-6.85 (m, 1H), 3.55-3.45 (m, 4H), 3.15-3.00 (m, 4H), 2.57 (s, 3H), 2.28 (s, 3H), 1.42 (s, 9H). MS (EI): 624 (MH+).

Example 76

Synthesis of $N^4$-(5-bromo-2-methylphenyl)-$N^5$-{5-[(piperidin-4-ylmethyl)oxy]-1H-benzimidazol-2-yl}-1H-imidazole-4,5-dicarboxamide hydrochloride $N^4$-(5-Bromo-2-methylphenyl)-$N^5$-{5-[(piperidin-4-ylmethyl)oxy]-1H-benzimidazol-2-yl}-1H-imidazole-4,5-dicarboxamide hydrochloride was prepared in a manner similar to 1,1-dimethylethyl 4-{[(2-{[(4-{[(2,4-dimethylphenyl)amino]carbonyl}-1H-imidazol-5-yl)carbonyl]amino}-1H-benzimidazol-5-yl)oxy]methyl}piperidine-1-carboxylate in Example 12 by removal of the Boc group with 4M hydrogen chloride in 1,4-dioxane to give $N^4$-(5-bromo-2-methylphenyl)-$N^5$-{5-[(piperidin-4-ylmethyl)oxy]-1H-benzimidazol-2-yl}-1H-imidazole-4,5-dicarboxamide as its hydrochloride salt in 78% yield. $^1$H-NMR (400 MHz, DMSO-d6) δ 12.62 (br s, 1H), 12.50 (br s, 1H), 11.20 (br s, 1H), 9.28 (d, 1H), 9.00 (d, 1H), 8.39 (s, 1H), 7.86 (s, 1H), 7.60 (d, 1H), 7.42 (d, 1H), 7.31 (d, 1H), 7.21 (s, 1H), 7.03 (d, 1H), 4.23 (br s 2H), 3.94 (m, 2H), 3.33 (m, 2H), 2.91 (m, 2H), 2.29 (s, 3H), 2.11 (m, 1H), 1.94 (m, 2H), 1.54 (m, 2H). MS (EI): 553 (MH+).

Example 77

Synthesis of $N^4$-(5-bromo-2-methylphenyl)-$N^5$-(4-{[3-(dimethylamino)propyl]oxy}-1H-benzimidazol-2-yl)-1H-imidazole-4,5-dicarboxamide $N^4$-(5-Bromo-2-methylphenyl)-$N^5$-(4-{[3-(dimethylamino)propyl]oxy}-1H-benzimidazol-2-yl)-1H-imidazole-4,5-dicarboxamide was prepared in a manner analogous to that used for $N^5$-(5-bromo-2-methylphenyl)-$N^4$-[4-(methyloxy)-1H-benzimidazol-2-yl]-1H-imidazole-4,5-dicarboxamide in Example 38 in 46% yield. $^1$H-NMR (400 MHz, DMSO-d6): δ 8.07 (s, 1H), 7.97 (d, 1H), 7.38 (dd, 1H), 7.29 (m, 1H), 7.12 (m, 1H), 7.01 (m, 1H), 6.64 (m, 1H), 4.17 (t, 2H), 2.30 (m, 5H), 2.17 (d, 6H), 1.19 (m, 2H); MS (EI): 541.7 (MH+).

Example 78

Synthesis of [(2-{[(5-{[(5-bromo-2-methylphenyl)amino]carbonyl}-1H-imidazol-4-yl)carbonyl]amino}-1H-benzimidazol-7-yl)oxy]acetic Acid

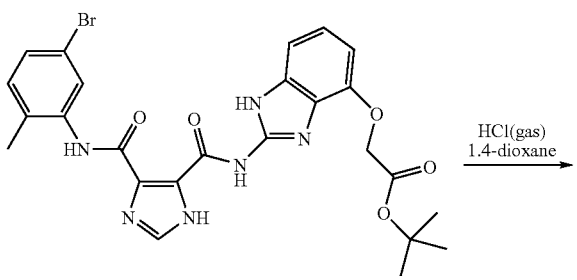

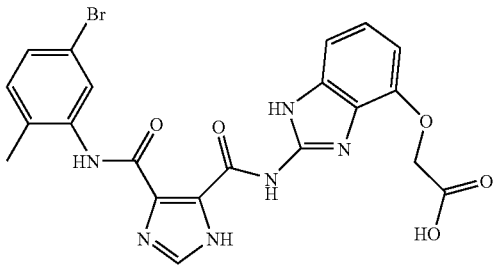

Synthesis of [(2-{[(5-{[(5-bromo-2-methylphenyl)amino]carbonyl}-1H-imidazol-4-yl)carbonyl]amino}-1H-benzimidazol-7-yl)oxy]acetic acid 1,1-Dimethylethyl[(2-{[(5-{[(5-bromo-2-methylphenyl)amino]carbonyl}-1H-imidazol-4-yl)carbonyl]amino}-1H-benzimidazol-7-ypoxy]acetate (230 mg) was suspended in 5 mL of dichloromethane. 2 mL of 4N hydrogen chloride in 1,4-dioxane was added at room temperature, followed by a few drops of water. The reaction mixture was stirred for 5 hours and then concentrated under reduced pressure. The residue was suspended in 5 mL of dichloromethane, filtrated and dried under reduced pressure to give 200 mg of [(2-{[(5-{[(5-bromo-2-methylphenyl)amino]carbonyl}-1H-imidazol-4-yl)carbonyl]amino}-1H-benzimidazol-7-yl)oxy]acetic acid: $^1$H-NMR (400 MHz, DMSO-d6): δ 8.36 (s, 1H), 7.85 (s, 1H), 7.28-7.44 (m, 4H), 6.85 (m, 1H), 4.94 (s, 2H), 2.31 (s, 3H). MS (EI): 513 (MH+).

Example 79

Synthesis of 1,1-dimethylethyl[(2-{[(5-{[(5-bromo-2-methylphenyl)amino]carbonyl}-1H-imidazol-4-yl)carbonyl]amino}-1H-benzimidazol-7-yl)oxy]acetate

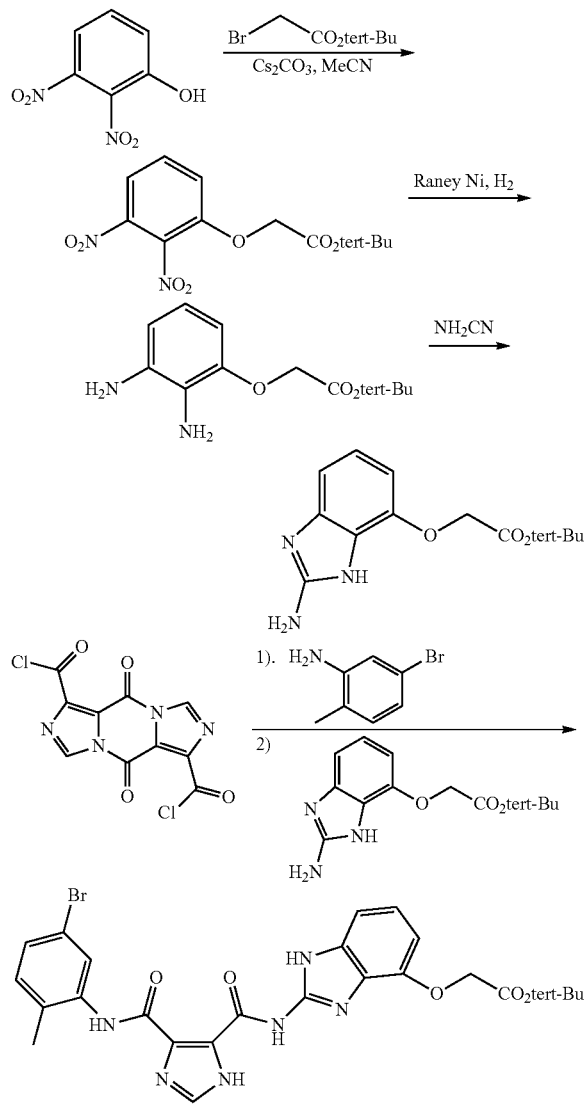

Synthesis of tert-butyl 2-(2,3-dinitrophenoxy)acetate

A round-bottom flask was charged with 2,3-dinitrophenol (11.04 g, 60 mmol, commercially available from Fluka-Sigma-Aldrich), tert-butyl bromoacetate (14.05 g, 66 mmol), acetonitrile (120 mL) and cesium carbonate (21.6 g). The mixture was stirred at room temperature overnight. The mixture was filtered, and the recovered solid was washed with ethyl acetate. The filtrate was further diluted with ethyl acetate and water. The aqueous layer was extracted with ethyl acetate and combined organic solvent was washed with saturated brine, dried and concentrated under reduced pressure. The residue was triturated with ether to give ethyl 2-(2,3-dinitrophenoxy)acetate (13.0 g, 70% yield). $^1$H-NMR (DMSO-d6) δ 7.84 (d, 2H), 7.42 (s, 1H), 4.90 (s, 2H), 1.40 (S, 9H).

Synthesis of tert-butyl 2-(2,3-diaminophenoxy)acetate

To a Parr hydrogenation bottle was added 12.0 g of 2-(2,3-dinitrophenoxy)acetate, Raney Nickel (2.0 g, wet), THF (100 mL) and EtOH (150 mL). The atmosphere of the vessel was replaced by hydrogen gas. The reaction was shaken on a Parr hydrogenator at 40 psi at room temperature, overnight. The catalyst was filtered over a plug Celite and the filtrate was concentrated under reduced pressure to give a residue, which was dissolved in methanol, acidified with 4 N hydrogen chloride in 1,4-dioxane and filtered. The resulting filtrate was concentrated under reduced pressure to give tent-butyl 2-(2,3-diaminophenoxy)acetate dihydrochloride (8.7 g, 82%), and was used directly in the next step without any further purification. MS (EI): 239 (MH+).

Synthesis of tert-butyl 2-(2-amino-1H-benzo[d]imidazol-7-yloxy)acetate Hydrochloride A solution of tert-butyl 2-(2,3-diaminophenoxy)acetate dihydrochloride (2.0 g, 7 mmol) in 10 mL of water was cooled to 0° C. and treated with a solution of cyanogens bromide (5M in acetonitrile, 1.1 equivalents) and solid sodium bicarbonate (2 equivalents, 60 mmol, 1.18 g). The solution was stirred at room temperature for 12 hours. The mixture was made basic with 1M sodium bicarbonate solution and concentrated under reduced pressure. The residue was dissolved in methanol. The resulting solution was acidified with 4 N hydrogen chloride in 1,4-dioxane. The resulting suspension was stirred for 10 minutes at room temperature and subsequently filtered. The filtrate was concentrated under reduced pressure to give tert-butyl 2-(2-amino-1H-benzo[d]imidazol-7-yloxy)acetate hydrochloride. (1.65 g, 91%). $^1$H-NMR (400 MHz, MeOH-d4): δ 8.15 (s, br, 2H), 7.20 (d, 1H), 6.90 (s, 1H), 6.75 (d, 1H), 4.10 (q, 2H), 1.40 (s, 9H).

Synthesis of 1,1-dimethylethyl[(2-{[(5-{[(5-bromo-2-methylphenyl)amino]carbonyl}-1H-imidazol-4-yl)carbonyl]amino}-1H-benzimidazol-7-yl)oxy]acetate 1,1-Dimethylethyl[(2-{[(5-{[(5-bromo-2-methylphenyl)amino]carbonyl}-1H-imidazol-4-yl)carbonyl]amino}-1H-benzimidazol-7-yl)oxy]acetate was prepared in a manner analogous to that used for $N^5$-(5-bromo-2-methylphenyl)-$N^4$-[4-(methyloxy)-1H-benzimidazol-2-yl]-1H-imidazole-4,5-dicarboxamide in Example 38 in 73% yield. $^1$H-NMR (400 MHz, DMSO-d6): δ 12.21 (s, 1H), 10.40 (s, br, 1H), 8.15 (s, 1H), 7.55 (s, 1H), 6.99-7.44 (m, 4H), 6.57 (m, 1H), 4.91 (s, 2H), 3.36 (s, 9H), 1.38 (s, 3H). MS (EI): 569 (MH+).

Example 80

Synthesis of $N^4$-(5-bromo-2-methylphenyl)-$N^5$-[5-({2-oxo-2-[(pyridin-4-ylmethyl)amino]ethyl}oxy)-1H-benzimidazol-2-yl]-1H-imidazole-4,5-dicarboxamide $N^4$-(5-Bromo-2-methylphenyl)-$N^5$-[5-({2-oxo-2-[(pyridin-4-ylmethyl)amino]ethyl}oxy)-1H-benzimidazol-2-yl]-

1H-imidazole-4,5-dicarboxamide was prepared using the protocol utilized for the synthesis of $N^5$-[6-({2-[(2,3-dihydroxypropyl)amino]-2-oxoethyl}oxy)-1H-benzimidazol-2-yl]-$N^4$-(2,4-dimethylphenyl)-1H-imidazole-4,5-dicarboxamide in Example 6. $^1$H-NMR (400 MHz, DMSO-d6): δ 12.18 (s, 1H), 10.32 (s, 1H), 8.78 (t, 1H), 8.44-8.46 (dd, 2H), 8.16 (s, 1H), 7.95 (s, 1H), 7.40 (d, 2H), 7.30 (d, 1H), 7.22 (d, 2H), 6.87 (dd, 1H), 4.59 (s, 2H), 4.38 (d, 2H), 2.30.58 (s, 3H), MS (EI): 604.3 (MH+).

Example 81

Synthesis of $N^5$-1H-benzimidazol-2-yl-$N^4$-(4-[4-(4-chlorophenyl)piperazin-1-yl]-2-methylphenyl)-1H-imidazole-4,5-dicarboxamide $N^5$-1H-benzimidazol-2-yl-$N^4$-{4-[4-(4-chlorophenyl)piperazin-1-yl]-2-methylphenyl}-1H-imidazole-4,5-dicarboxamide was prepared in a manner similar to $N^5$-1H-benzimidazol-2-yl-$N^4$-(2,4-dimethylphenyl)-1H-imidazole-4,5-dicarboxamide in Example 1 in 67% yield. $^1$H-NMR (400 MHz, DMSO-d6): δ 12.19 (s, br, 1H), 10.2 (s, 1H), 8.18 (s, 1H), 7.56-6.87 (m, 12H), 3.31 (s, 8H), 2.23 (s, 3H). MS (EI): 555 (MH+).

Example 82

Synthesis of $N^5$-1H-benzimidazol-2-yl-$N^4$-(2-methyl-4-morpholin-4-ylphenyl)-1H-imidazole-4,5-dicarboxamide $N^5$-1H-benzimidazol-2-yl-$N^4$-(2-methyl-4-morpholin-4-ylphenyl)-1H-imidazole-4,5-dicarboxamide was prepared in a manner similar to $N^5$-1H-benzimidazol-2-yl-$N^4$-(2,4-dimethylphenyl)-1H-imidazole-4,5-dicarboxamide in Example 1 in 45% yield. $^1$H-NMR (400 MHz, DMSO-d6): δ 12.19 (s, br, 1H), 10.2 (s, br, 1H), 8.07 (s, 1H), 7.47 (m, 3H), 7.12 (m, 2H), 6.92 (m, 2H), 3.77 (m, 4H), 3.17 (m, 4H), 2.23 (s, 3H). MS (EI): 446 (MH+).

Example 83

Synthesis of 1,1-dimethylethyl 4-[(2-{[(5-{[(5-bromo-2-methylphenyl)amino]carbonyl}-1H-imidazol-4-yl)carbonyl]amino}-1H-benzimidazol-7-yl)oxy]piperidine-1-carboxylate

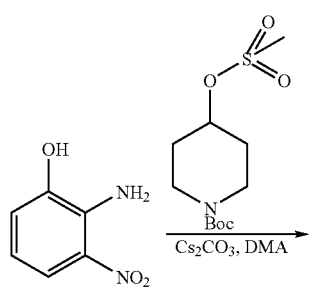

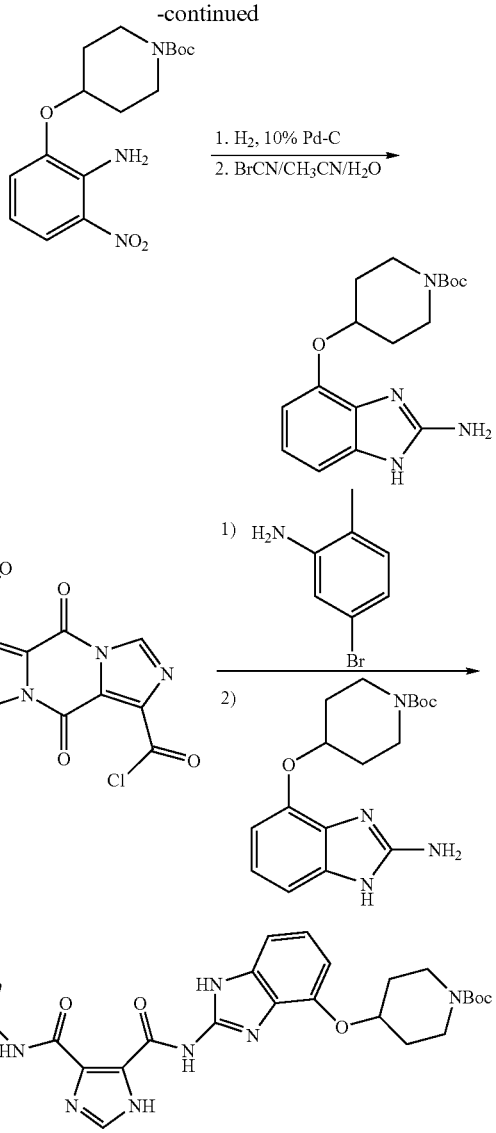

Synthesis of tert-butyl 4-(2-amino-3-nitrophenoxy)piperidine-1-carboxylate

A round-bottom flask was charged with 2-amino-3-nitrophenol (10.64 g, 60 mmol, commercially available from Aldrich), tert-butyl 4-(methylsulfonyloxy)-piperidine-1-carboxylate (18.05 g, 66 mmol, commercially available from AnandChem Ltd.,), DMA (100 mL) and cesium carbonate (21.6 g). The mixture was stirred at room temperature overnight. The mixture was filtered, and the recovered solid was washed with ethyl acetate. The filtrate was further diluted with ethyl acetate and water. The aqueous layer was extracted with ethyl acetate and combined organic solvent was washed with saturated brine, dried and concentrated under reduced pressure. The residue was triturated with ether to give tert-butyl 4-(2-amino-3-nitrophenoxy)piperidine-1-carboxylate (8.0 g, 56% yield). MS (EI): 338 (MH+).

Synthesis of tert-butyl 4-(2,3-diaminophenoxy)piperidine-1-carboxylate

To a Parr hydrogenation bottle was added 7.0 g of tert-butyl 4-(2-amino-3-nitrophenoxy)piperidine-1-carboxylate, 10% palladium on carbon (50% w/w water) (2.0 g, wet), ethyl acetate (100 mL) and MeOH (150 mL). The atmosphere of the vessel was replaced by hydrogen gas. The reaction was shaken on a Parr hydrogenator at 40 psi at room temperature, overnight. The catalyst was filtered through a plug of Celite and the filtrate was concentrated under reduced pressure to give a residue, which was dissolved in methanol, cooled in an ice bath and carefully acidified with 4 N hydrogen chloride in 1,4-dioxane and filtered. The resulting filtrate was concentrated under reduced pressure to give of tert-butyl 4-(2,3-diaminophenoxy)piperidine-1-carboxylate dihydrochloride (6.7 g), and was used directly in the next step without any further purification. MS (EI): 308 (MH+).

Synthesis of tert-butyl 4-(2-amino-1H-benzo[d]imidazol-4-yloxy)piperidine-1-carboxylate A solution of tert-butyl 4-(2,3-diaminophenoxy)piperidine-1-carboxylate dihydrochloride (2.0 g, 7 mmol) in 10 mL of water was cooled to 0° C. and treated with a solution of cyanogens bromide (5M in acetonitrile, 1.1 equivalents) and solid sodium bicarbonate (2 equivalents, 60 mmol, 1.18 g). The solution was stirred at room temperature for 12 hours. The mixture was made basic with 1M sodium bicarbonate solution and concentrated under reduced pressure. The residue was dissolved in methanol. The resulting solution was acidified with 4 N hydrogen chloride in 1,4-dioxane. The resulting suspension was stirred for 10 minutes at room temperature and subsequently filtered. The filtrate was concentrated under reduced pressure to tert-butyl 4-(2-amino-1H-benzo[d]imidazol-4-yloxy)piperidine-1-carboxylate hydrochloride. MS (EI): 333 (MH+).

Synthesis of 1,1-dimethylethyl 4-[(2-{[(5-{[(5-bromo-2-methylphenyl)amino]carbonyl}-1H-imidazol-4-yl)carbonyl]amino}-1H-benzimidazol-7-yl)oxy]piperidine-1-carboxylate 1,1-Dimethylethyl 4-[(2-{[(5-{[(5-bromo-2-methylphenyl)amino]-carbonyl}-1H-imidazol-4-yl)carbonyl]amino}-1H-benzimidazol-7-yl)oxy]piperidine-1-carboxylate was prepared in a similar fashion as $N^4$-(5-bromo-2-methylphenyl)-$N^5$-(4-methyl-1H-imidazol-2-yl)-1H-imidazole-4,5-dicarboxamide Example 2 at 54% yield. $^1$H-NMR (DMSO-d6): δ 13.85 (br, 1H), 12.20 (s, 1H), 10.38 (s, 1H), 8.20 (s, 1H), 7.95 (s, 1H), 7.40 (m, 1H), 7.31 (m, 1H), 7.16 (m, 1H), 7.05 (m, 1H), 6.75 (m, 1H), 4.95 (m, 1H), 3.70 (m, 2H), 3.75 (m, 2H), 2.28 (s, 3H), 1.95 (m, 2H), 1.80 (m, 2H), 1.41 (s, 9H). MS (EI): 639 (MH+).

Example 84

Synthesis of 1,1-dimethylethyl 4-{[(2-{[(4-{[(5-chloro-2-methylphenyl)amino]carbonyl}-1H-imidazol-5-yl)carbonyl]amino}-1H-benzimidazol-5-yl)oxy]methyl}piperidine-1-carboxylate

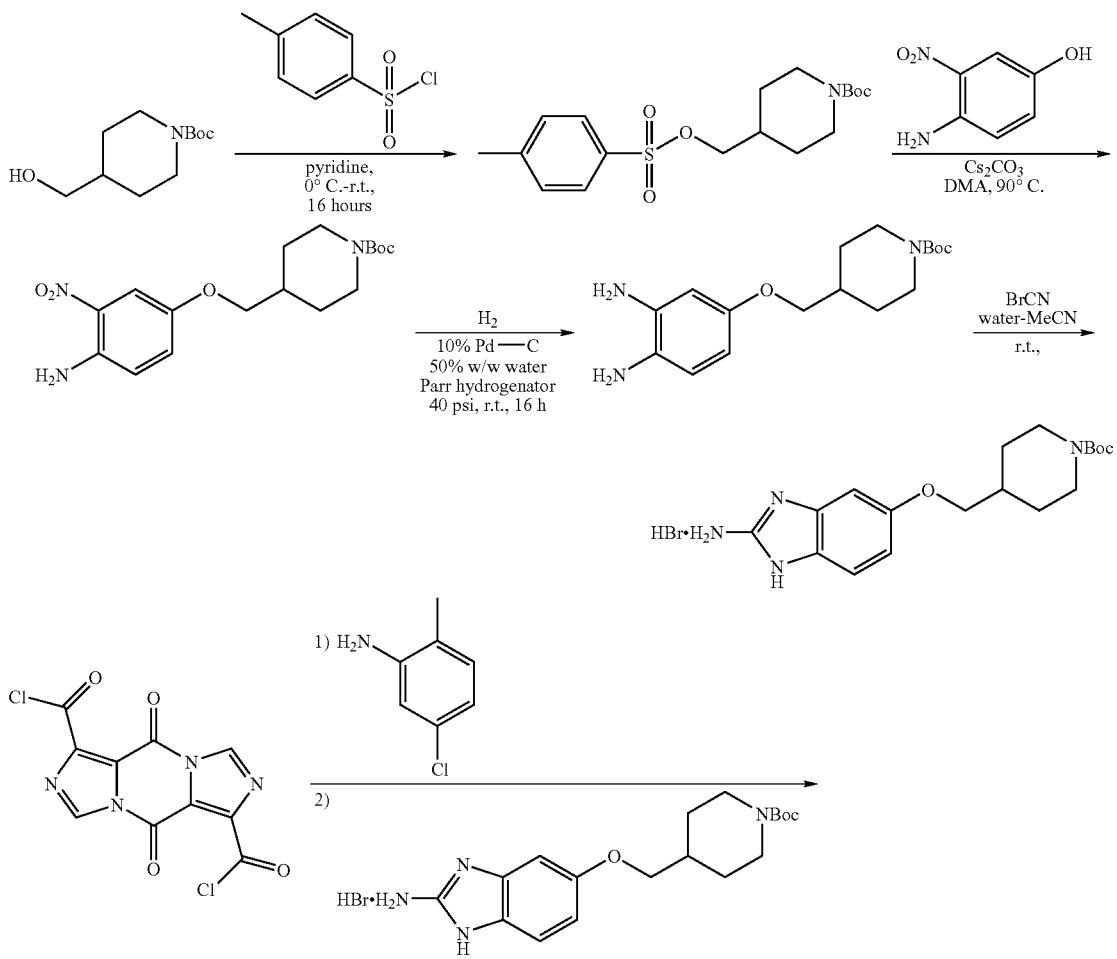

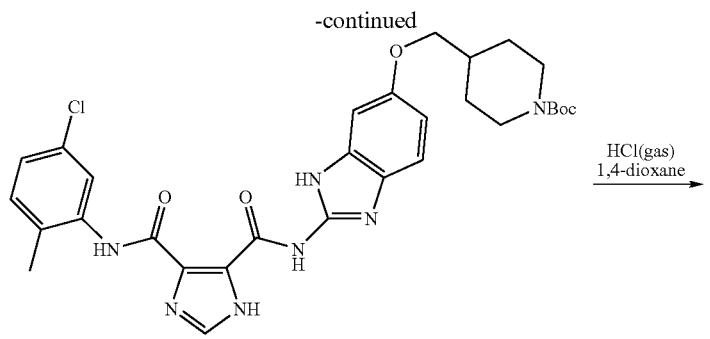

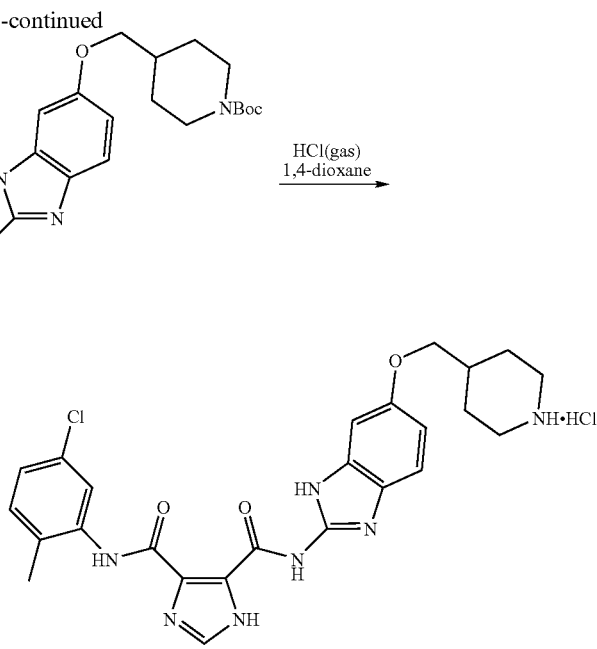

Synthesis of tert-Butyl 4-(tosyloxymethyl)piperidine-1-carboxylate

4-Hydroxylmethyl-N-(tert-butylcarboxylate)piperidine (10.76 g, 50 mmoles, 1 equivalent, commercially available from Aldrich) was dissolved in anhydrous pyridine (40 ml) and cooled to 0° C. in an ice-water-salt bath. p-Toluenesulfonyl chloride (10.48 g, 55 mmoles, 1.1 equivalent) was added in one lot to the stirred reaction mixture. The reaction mixture was then allowed to warm to room temperature and stirred for 16 hours. The reaction mixture was poured into water (200 ml) and extracted with ethyl acetate (3×200 ml). The combined ethyl acetate solution was washed with 5% aqueous hydrochloric acid (200 ml), water (200 ml) and saturated sodium chloride solution (200 ml). The ethyl acetate solution was dried over anhydrous sodium sulfate, filtered and evaporated under reduced pressure to give 16.86 g of tent-butyl 4-(tosyloxymethyl)piperidine-1-carboxylate (yield, 91%). $^1$H-NMR (400 MHz, DMSO-d6) δ 7.88 (d, 2H), 7.45 (d, 2H), 3.84 (m, 4H), 3.65 (m, 2H), 2.40 (s, 3H), 1.76 (m, 1H), 1.54 (m, 2H) 1.38 (s, 9H), 0.95 (m, 2H). MS (EI): 370 (MH+).

Synthesis of tert-Butyl 4-((4-amino-3-nitrophenoxy)methyl)piperidine-1-carboxylate Cesium carbonate (16.29 g, 50 mmoles, 2 equivalents) was added to a stirred solution of 4-amino-3-nitrophenol (3.85 g, 25 mmoles, 1 equivalent) and tert-butyl 4-(tosyloxymethyl) piperidine-1-carboxylate (10.16 g, 27.5 mmoles, 1.1 equivalent) in anhydrous DMA (25 mls). The stirred reaction mixture was then heated to 90° C. (thermostatically controlled heating mantle) for 22 hours. The reaction mixture was then allowed to cool to room temperature and was filtered through a plug of Celite. The reaction flask and the Celite were then washed with ethyl acetate (250 ml). The organic solution was then transferred to a separatory funnel and extracted with additional ethyl acetate (3×200 ml). The combined ethyl acetate solution was then washed with water (2×100 ml), saturated sodium chloride (2×100 ml), dried over anhydrous magnesium sulfate, filtered and evaporated under reduced pressure. This material was triturated with diethylether to give a crystalline solid which was filtered off, washed with ether to give 4.76 g of tert-butyl 4-((4-amino-3-nitrophenoxy) methyl)piperidine-1-carboxylate (yield=54%). $^1$H-NMR (400 MHz, DMSO-d6) δ 8.80 (s, 1H), 7.89 (d, 1H), 7.74 (d, 1H), 3.82 (d, 2H), 3.65 (m, 2H), 2.40 (s, 3H), 1.76 (m, 1H), 1.54 (m, 2H), 1.38 (s, 9H), 0.98 (m, 2H). MS (EI): 352 (MH+).

Synthesis of tert-Butyl 4-((3,4-diaminophenoxy)methyl)piperidine-1-carboxylate tert-Butyl 4-((4-amino-3-nitrophenoxy)methyl)piperidine-1-carboxylate (3.58 g, 10.18 mmoles,) was dissolved in ethyl acetate (60 ml) and methanol (40 ml). The solution was treated with 600 mg of 10% palladium on carbon (50% water w/w). The slurry was then shaken on a Parr hydrogenator and treated with a 40 psi of hydrogen gas, at room temperature. After 16 hours, the slurry was filtered through a plug of Celite, which was subsequently washed with ethyl acetate (50 ml) and methanol (50 ml). The resulting filtrate was then evaporated at reduced pressure to give 3.42 g of tent-butyl 4-((3,4-diaminophenoxy)methyl)piperidine-1-carboxylate (100% yield). The material was used in the next step without any further purification. $^1$H-NMR (400 MHz, DMSO-d6) δ 8.40 (s, 1H), 7.49 (d, 1H), 7.24 (d, 1H), 5.32 (br s, 4H), 3.82 (d, 2H), 3.65 (m, 2H), 2.40 (s, 3H), 1.76 (m, 1H), 1.54 (m, 2H), 1.38 (s, 9H), 0.98 (m, 2H). MS (EI): 322 (MH+).

Synthesis of tert-Butyl 4-((2-amino-1H-benzo[d] imidazol-5-yloxy)methyl)piperidine-1-carboxylate hydrobromide tert-Butyl 4-((3,4-diaminophenoxy)methyl)piperidine-1-carboxylate (10.18 mmoles, 3.27 g, 1 equivalent) was dissolved in acetonitrile (40 ml) and water (20 ml) and cooled to 0-5° C. (ice-water). Cyanogen bromide (1.112 g, 10.5 mmoles) was added in one lot and the reaction mixture was allowed to go to room temperature and stirred for 16 hours.

The reaction mixture was then evaporated under reduced pressure to give 3.53 g of tert-butyl 4-((2-amino-1H-benzo[d]imidazol-5-yloxy)methyl)piperidine-1-carboxylate hydrobromide (yield 100%) which was used directly in the step. ¹H-NMR (400 MHz, DMSO-d6) δ 12.22 (br s, 2H), 8.30 (s, 2H), 7.21 (d, 1H), 6.90 (s, 1H), 6.79 (d, 1H), 3.96 (m, 2H), 3.82 (d, 2H), 2.73 (m, 2H), 1.91 (m, 1H), 1.74 (d, 2H), 1.39 (s, 9H), 1.26 (m, 2H), MS (EI): 347 (MH+).

Synthesis of 1,1-Dimethylethyl 4-{[(2-{[(4-{[(5-chloro-2-methylphenyl)amino]carbonyl}-1H-imidazol-5-yl)carbonyl]amino}-1H-benzimidazol-5-yl)oxy]methyl}piperidine-1-carboxylate 1,1-Dimethylethyl 4-{[(2-{[(4-{[(5-chloro-2-methylphenyl)amino]carbonyl}-1H-imidazol-5-yl)carbonyl]amino}-1H-benzimidazol-5-yl)oxy]methyl}piperidine-1-carboxylate was prepared in a manner analogous to that used for the synthesis of N⁵-1H-benzimidazol-2-yl-N⁴-(2,4-dimethylphenyl)-1H-imidazole-4,5-dicarboxamide in Example 1 in 63% yield. ¹H-NMR (400 MHz, DMSO-d6) δ 13.88 (br s, 1H), 12.04 (d, 1H), 10.30 (s, 1H), 8.19 (s, 1H), 7.80 (s, 1H), 7.36 (m, 2H), 7.26 (m, 1H), 7.09 (s, 1H), 6.98 (s, 1H), 6.76 (m, 1H), 3.98 (m, 1H), 3.83 (d, 1H), 2.76 (br s, 1H), 2.30 (s, 3H), 1.82 (br s, 1H), 1.76 (d, 2H), 1.40, (s, 9H), 1.34 (m, 2H). MS (EI): 609 (MH+).

Example 85

Synthesis of N⁴-(5-chloro-2-methylphenyl)-N⁵-{5-[(piperidin-4-ylmethyl)oxy]-1H-benzimidazol-2-yl}-1H-imidazole-4,5-dicarboxamide Hydrochloride N⁴-(5-Chloro-2-methylphenyl)-N⁵-{5-[(piperidin-4-ylmethyl)oxy]-1H-benzimidazol-2-yl}-1H-imidazole-4,5-dicarboxamide hydrochloride was prepared in a manner similar to N⁵-[4-(azetidin-3-yloxy)-2-methylphenyl]-N⁴-1H-benzimidazol-2-yl-1H-imidazole-4,5-dicarboxamide hydrochloride in Example 5. ¹H-NMR (400 MHz, DMSO-d6) δ 14.00 (br s, 1H), 11.10 (br s, 1H), 9.38 (br s, 1H), 9.06 (br s, 1H), 8.38 (s, 1H), 7.75 (s, 1H), 7.60 (d, 1H), 7.37 (d, 1H), 7.30 (d, 1H), 7.21 (s, 1H), 7.03 (d, 1H), 3.90 (d, 2H), 3.28 (m, 2H), 2.35 (s, 3H), 2.10 (m, 1H), 1.91 (2H), 1.58 (m, 2H). MS (EI): 508 (MH+).

Example 86

Synthesis of N⁵-(5-bromo-2-methylphenyl)-N⁴-[7-(piperidin-4-yloxy)-1H-benzimidazol-2-yl]-1H-imidazole-4,5-dicarboxamide N⁵-(5-Bromo-2-methylphenyl)-N⁴-[7-(piperidin-4-yloxy)-1H-benzimidazol-2-yl]-1H-imidazole-4,5-dicarboxamide was prepared in a manner similar to N⁵-(5-bromo-2-methylphenyl)-N⁴-[4-(methyloxy)-1H-benzimidazol-2-yl]-1H-imidazole-4,5-dicarboxamide in Example 38 followed by removal of the Boc group with 4M hydrogen chloride in 1,4-dioxane. ¹H-NMR (400 MHz, DMSO-d6): 9.15 (br, 2H), 8.18 (s, 1H), 7.85 (s, 1H), 7.20-7.44 (m, 4H), 7.05 (m, 1H), 4.95 (s, 1H), 3.35 (m, 2H), 3.15 (m, 2H), 2.24 (s, 3H), 2.15 (m, 2H), 1.98 (m, 2H). MS (EI): 538 (MH+).

Example 87

Synthesis of methyl 2-{[(4-{[(5-bromo-2-methylphenyl)amino]carbonyl}-1H-imidazol-5-yl)carbonyl]amino}-1H-benzimidazole-5-carboxylate

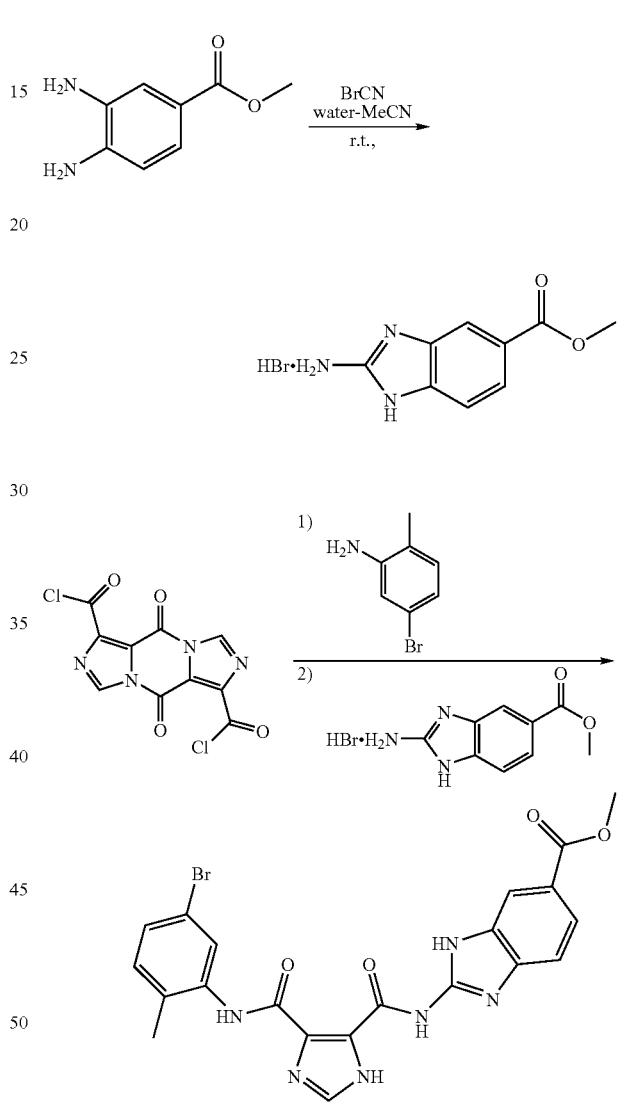

Synthesis of Methyl 2-amino-1H-benzo[d]imidazole-5-carboxylate hydrobromide 3,4-Diaminobenzoic acid methyl ester (58.72 mmoles, 9.35 g, 1 equivalent, commercially available from Oakwood Products) was dissolved in acetonitrile (20 ml) and water (200 ml) and cooled to 0-5° C. (ice-water). Cyanogen bromide (8.64 g, 81.55 mmoles, 1.4 equivalent) was added over a period of 5 minutes, and the reaction mixture was allowed to go to room temperature and stirred for 16 hours. The reaction mixture was then evaporated under reduced pressure to 15.60 g of methyl 2-amino-1H-benzo[d]imidazole-5-carboxylate hydrobromide (yield: 98%) which was used directly in the next reaction without any further reaction. $^1$H-NMR (400 MHz DMSO-d6) δ 12.64 (br s, 2H), 8.80 (bs, 3H), 7.91 (s, 1H), 7.82 (d, 1H), 7.51 (d, 1H), 3.82 (s, 3H). MS (EI): 192 (MH+).

Synthesis of Methyl 2-{[(4-{[(5-bromo-2-methylphenyl)amino]carbonyl}-1H-imidazol-5-yl)carbonyl]amino}-1H-benzimidazole-5-carboxylate Methyl 2-{[(4-{[(5-bromo-2-methylphenyl)amino]carbonyl}-1H-imidazol-5-yl)carbonyl]amino}-1H-benzimidazole-5-carboxylate was prepared in a manner similar to $N^5$-1H-benzimidazol-2-yl-$N^4$-(2,4-dimethylphenyl)-1H-imidazole-4,5-dicarboxamide in Example 1 in 75% yield. $^1$H-NMR (400 MHz, DMSO-d6) d δ 13.91 (br s, 1H), 12.50 (br s, 1H), 10.40 (br s, 1H), 8.21 (s, 1H), 8.16 (s, 1H), 7.94 (s, 1H), 7.80 (d, 1H), 7.56 (d, 1H), 7.38 (s, 1H), 7.34 (d, 1H), 3.82 (s, 3H), 2.30 (s, 3H). MS (EI): 497 (MH+).

Example 88

Synthesis of methyl 2-{[(4-{[(5-chloro-2-methylphenyl)amino]carbonyl}-1H-imidazol-5-yl)carbonyl]amino}-1H-benzimidazole-5-carboxylate Methyl 2-{[(4-{[(5-chloro-2-methylphenyl)amino]carbonyl}-1H-imidazol-5-yl)carbonyl]amino}-1H-benzimidazole-5-carboxylate was prepared in the same manner as methyl 2-{[(4-{[(5-bromo-2-methylphenyl)amino]carbonyl}-1H-imidazol-5-yl)carbonyl]amino}-1H-benzimidazole-5-carboxylate in Example 87 in 71% yield. $^1$H-NMR (400 MHz, DMSO-d6) δ 13.91 (br s, 1H), 12.60 (br s, 1H), 10.80 (br s, 1H), 10.40 (br s, 1H), 8.21 (s, 1H), 8.16 (s, 1H), 7.78 (d, 2H), 7.56 (d, 1H), 7.38 (s, 1H), 7.34 (d, 1H), 3.83 (s, 3H), 2.32 (s, 3H). MS (EI): 453 (MH+).

Example 89

Synthesis of $N^4$-(5-bromo-2-methylphenyl)-$N^5$-[5-(piperidin-4-yloxy)-1H-benzimidazol-2-yl]-1H-imidazole-4,5-dicarboxamide hydrochloride

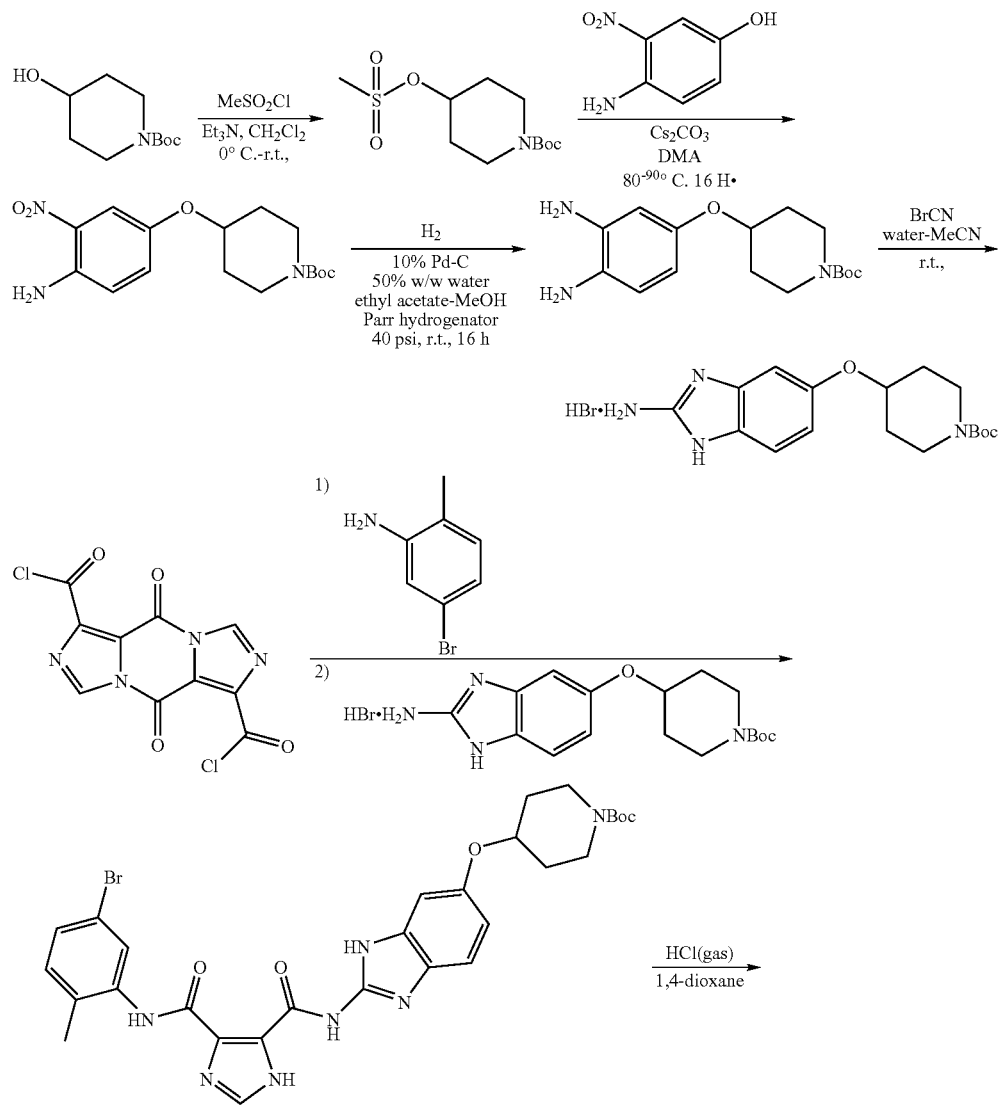

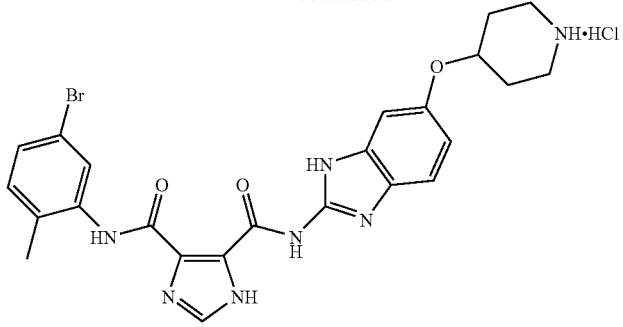

Synthesis of tert-butyl 4-(methylsulfonyloxy)piperidine-1-carboxylate

A solution of 4-hydroxy-N-(tert-butylcarboxylate) piperidine (10 g, 49.68 mmoles, 1 equivalent, commercially available from Aldrich) and triethylamine (7.54 g, 74.50 mmoles, 1.5 equivalents, 10.38 ml) in anhydrous dichloromethane (200 ml) at 0-5° C. was treated with methanesulfonyl chloride (6.88 g, 60.12 mmoles, 4.65 ml, 1.21 equivalents). After 3 hours, the reaction mixture was diluted with dichloromethane (200 ml), transferred to a separatory funnel and washed with aqueous 2M sodium carbonate solution (200 ml) and saturated sodium chloride solution (200 ml). The organic solution was then dried over anhydrous magnesium sulfate, filtered, and evaporated under reduced pressure to give 14.51 g of tert-butyl 4-(methylsulfonyloxy)piperidine-1-carboxylate which solidified upon standing (yield=100%). $^1$H-NMR (400 MHz, DMSO-d6) δ 4.80 (m, 1H), 3.39 (m, 2H), 3.29 (m, 2H), 2.94 (s, 3H), 1.77 (m, 2H), 1.52 (m, 2H). MS (EI): 280 (MH+).

Synthesis of tert-butyl 4-(4-amino-3-nitrophenoxy)piperidine-1-carboxylate

Cesium carbonate (14.19 g, 43.56 mmoles, 2 equivalents) was added to a stirred solution of 4-amino-3-nitrophenol (3.35 g, 21.78 mmoles, 1 equivalent) and tert-butyl 4-(methylsulfonyloxy)piperidine-1-carboxylate (6.69 g, 23.96 mmoles, 1.1 equivalent) in anhydrous DMA (30 ml). The stirred reaction mixture was then heated to 90° C. (thermostatically controlled heating mantle) for 22 hours. The reaction mixture was then allowed to cool to room temperature and was filtered through a plug of Celite. The reaction flask and the Celite were then washed with ethyl acetate (250 ml). The organic solution was then transferred to a separatory funnel and extracted with additional ethyl acetate (3×200 ml). The combined ethyl acetate solution was then washed with water (2×100 ml), saturated sodium chloride (2×100 ml), dried over anhydrous magnesium sulfate, filtered and evaporated under reduced pressure.

This material was triturated with diethylether which was filtered off and washed with diethylether to give 4.76 g of tent-butyl 4-(4-amino-3-nitrophenoxy)piperidine-1-carboxylate (yield=64%). $^1$H-NMR (400 MHz, DMSO-d6) δ 7.42 (s, 1H), 7.22 (d, 1H), 7.01 (d, 1H), 4.18 (m, 1H), 3.79 (m, 2H), 3.10 (m, 2H), 1.80 (m, 2H), 1.43 (m, 2H), 1.29 (s, 9H). MS (EI): 338 (MH+).

Synthesis of tert-butyl 4-(3,4-diaminophenoxy)piperidine-1-carboxylate tert-Butyl 4-(4-amino-3-nitrophenoxy)piperidine-1-carboxylate (2.125 g, 6.30 mmoles) was dissolved in ethyl acetate (60 ml) and methanol (10 ml). The solution was treated with 500 mg of 10% palladium on carbon (50% water w/w). The slurry was then shaken on a Parr hydrogenator and treated with a 40 psi of hydrogen gas, at room temperature. After 18 hours, the slurry was filtered through a plug of celite, which was subsequently washed with ethyl acetate (50 ml) and methanol (50 ml). The resulting filtrate was then evaporated at reduced pressure to give an oil, which was triturated with hexane to give. This material was filtered off and dried at reduced pressure to give 1.929 g of tent-butyl 4-(3-methyl-4-aminophenoxy)piperidine-1-carboxylate (100% yield). $^1$H-NMR (400 MHz, DMSO-d6) δ 6.40 (d, 1H), 6.19 (s, 1H), 6.02 (d, 1H), 4.38 (br s, 4H), 4.18 (m, 1H), 3.79 (m, 2H), 3.10 (m, 2H), 1.80 (m, 2H), 1.43 (m, 2H), 1.29 (s, 9H). MS (EI): 308 (MH+).

Synthesis of tert-butyl 4-(2-amino-1H-benzo[d]imidazol-5-yloxy)piperidine-1-carboxylate Hydrobromide tert-Butyl 4-(3,4-diaminophenoxy)piperidine-1-carboxylate (5.673 mmoles, 1.914 g, 1 equivalent) was dissolved in acetonitrile (20 ml) and water (20 ml) and cooled to 0-5° C. (ice-water). Cyanogen bromide (5.67 mmoles, 0.721 g, 1.4 equivalents) was added in one lot and the reaction mixture was allowed to go to room temperature and stirred for 16 hours. The reaction mixture was then evaporated under reduced pressure to 2.41 g of tert-butyl 4-(2-amino-1H-benzo[d]imidazol-5-yloxy)piperidine-1-carboxylate hydrobromide (yield: 100%) which was used directly in the next reaction without any further purification. $^1$H-NMR (400 MHz, DMSO-d6) δ 12.22 (br s, 2H), 8.39 (s, 2H), 7.22 (d, 1H), 6.91 (s, 1H), 7.83 (d, 1H), 4.50 (m, 1H), 3.61 (m, 2H), 2.19 (, 2H), 1.90 (m, 2H), 1.40 (s, 9H). MS (EI): 333 (MH+).

Synthesis of tert-butyl 4-(2-(4-(5-bromo-2-methylphenylcarbamoyl)-1H-imidazole-5-carboxamido)-1H-benzo[d]imidazol-6-yloxy)piperidine-1-carboxylate tert-Butyl 4-(2-(4-(5-bromo-2-methylphenylcarbamoyl)-1H-imidazole-5-carboxamido)-1H-benzo[d]imidazol-6-yloxy)piperidine-1-carboxylate was prepared in a manner analogous to that used for the synthesis of $N^5$-1H-benzimidazol-2-yl-$N^4$-(2,4-dimethylphenyl)-1H-imidazole-4,5-dicarboxamide in Example 1. MS (EI): 639 (MH+).

Synthesis of $N^4$-(5-Bromo-2-methylphenyl)-$N^5$-[5-(piperidin-4-yloxy)-1H-benzimidazol-2-yl]-1H-imidazole-4,5-dicarboxamide hydrochloride $N^4$-(5-Bromo-2-methylphenyl)-$N^5$-[5-(piperidin-4-yloxy)-1H-benzimidazol-2-yl]-1H-imidazole-4,5-dicarboxamide hydrochloride was prepared in a manner similar to N⁵-[4-(azetidin-3-yloxy)-2-methylphenyl]-N⁴-1H-benzimidazol-2-yl-1H-imidazole-4,5-dicarboxamide hydrochloride in Example 5 in 64% yield. ¹H-NMR (400 MHz, DMSO-d6) δ 11.05 (br s 1H), 9.12 (br s, 2H), 8.38 (s, 1H), 7.82 (br 1H), 7.58 (d, 1H), 7.42 (d, 1H), 7.30 (d, 1H), 7.23 (s, 1H), 7.11 (d, 1H), 4.64 (M, 1H), 3.82 (br s, 2H), 3.23 (m, 2H), 3.08 (m, 2H), 3.20 (s, 3H), 2.11 (m, 2H), 1.91 (m, 214). MS (EI): 539 (MH+).

Example 90

Synthesis of N⁵-1H-benzimidazol-2-yl-N⁴-(3-chloro-2,6-dimethylphenyl)-1H-imidazole-4,5-dicarboxamide N⁵-1H-Benzimidazol-2-yl-N⁴-(3-chloro-2,6-dimethylphenyl)-1H-imidazole-4,5-dicarboxamide was prepared in a similar manner to N⁵-1H-benzimidazol-2-yl-N⁴-(2,4-dimethylphenyl)-1H-imidazole-4,5-dicarboxamide in Example 1 in 61% yield. ¹H-NMR (400 MHz, DMSO-d6): δ 13.85 (s, 1H), 12.20 (s, 1H), 10.60 (s, 1H), 8.18 (s, 1H), 7.52 (s, 1H), 7.42-7.35 (m, 2H), 7.22 (d, 1H), 7.15-7.08 (m, 2H), 2.50 (s, 3H), 2.40 (s, 3H). MS (EI): 409 (MH+).

Example 91

Synthesis of N⁴-(5-chloro-2-methylphenyl)-N⁵-[5-(4-methylpiperazin-1-yl)-1H-benzimidazol-2-yl]-1H-imidazole-4,5-dicarboxamide

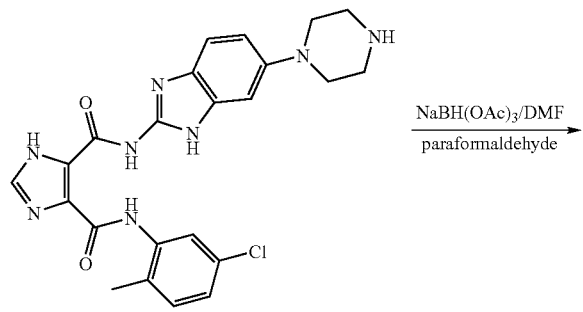

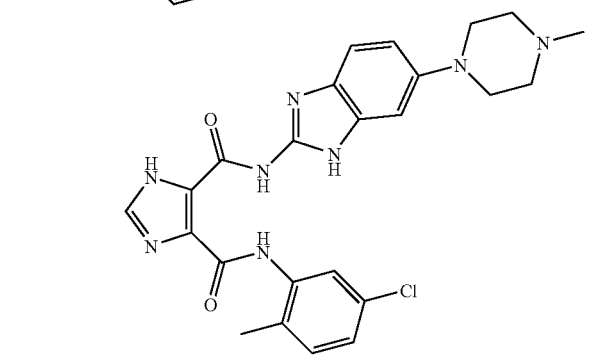

A round-bottom flask was charged with paraformaldehyde (2.0 mmol) and N⁴-(5-chloro-2-methylphenyl)-N⁵-(6-(piperazin-1-yl)-1H-benzo[d]imidazol-2-yl)-1H-imidazole-4,5-dicarboxamide (0.2 mmol), anhydrous DMF (5 mL) and sodium triacetoxybrohydride (1.0 mmol). The reaction mixture was stirred at room temperature overnight. The solution was concentrated under reduced pressure and purified by preparative scale —HPLC (aqueous ammonium acetate/ac-etonitrile) to give N⁴-(5-chloro-2-methylphenyl)-N⁵-[5-(4-methylpiperazin-1-yl)-1H-benzimidazol-2-yl]-1H-imidazole-4,5-dicarboxamide. ¹H-NMR (400 MHz, MeOH-d4): δ 8.15 (s, 1H), 7.92 (s, 1H), 7.38 (d, 3H), 7.24 (s, 1H), 7.18-7.14 (m, 2H), 6.96 (dd, 1H), 3.35-3.25 (m, 4H), 3.00-2.90 (m, 4H), 2.57 (s, 3H), 2.40 (s, 3H). MS (EI): 493 (MH+).

Example 92

N⁴-(5-chloro-2-methylphenyl)-N⁵-[5-(piperidin-4-yloxy)-1H-benzimidazol-2-yl]-1H-imidazole-4,5-dicarboxamide Hydrochloride Synthesis of tert-butyl 4-(2-(4-(5-chloro-2-methylphenylcarbamoyl)-1H-imidazole-5-carboxamido)-1H-benzo[d]imidazol-6-yloxy)piperidine-1-carboxylate tent-Butyl 4-(2-(4-(5-chloro-2-methylphenylcarbamoyl)-1H-imidazole-5-carboxamido)-1H-benzo[d]imidazol-6-yloxy)piperidine-1-carboxylate was prepared in a manner analogous to that used for the synthesis of N⁵-1H-benzimidazol-2-yl-N⁴-(2,4-dimethylphenyl)-1H-imidazole-4,5-dicarboxamide in Example 1. MS (EI): 595 (MH+).

Synthesis of N⁴-(5-chloro-2-methylphenyl)-N⁵-[5-(piperidin-4-yloxy)-1H-benzimidazol-2-yl]-1H-imidazole-4,5-dicarboxamide Hydrochloride N⁴-(5-Chloro-2-methylphenyl)-N⁵-[5-(piperidin-4-yloxy)-1H-benzimidazol-2-yl]-1H-imidazole-4,5-dicarboxamide hydrochloride was treated with 4M hydrogen chloride in 1,4-dioxane for 48 hours at room temperature to give N⁴-(5-chloro-2-methylphenyl)-N⁵-[5-(piperidin-4-yloxy)-1H-benzimidazol-2-yl]-1H-imidazole-4,5-dicarboxamide as its hydrochloride salt in 61% yield. ¹H-NMR (400 MHz, DMSO-d6) δ 14.00 (br s, 1H), 11.95 (br s, 1H), 10.62 (br s, 1H), 9.23 (d, 2H), 8.30 (s, 1H), 7.78 (br s, 1H), 7.56 (d, 1H), 7.39 (dd, 1H), 7.30 (dd, 1H), 7.23 (s, 1H), 7.03 (dd, 1H), 4.76 (m, 1H), 3.23 (m, 2H), 3.04 (m, 2H), 2.33 (s, 3H), 2.12 (m, 2H), 1.90 (m, 2H). MS (EI): 494 (MH+).

Example 93

Synthesis of N⁴-(5-bromo-2-methylphenyl)-N⁵-[5-(4-pentylpiperazin-1-yl)-1H-benzimidazol-2-yl]-1H-imidazole-4,5-dicarboxamide

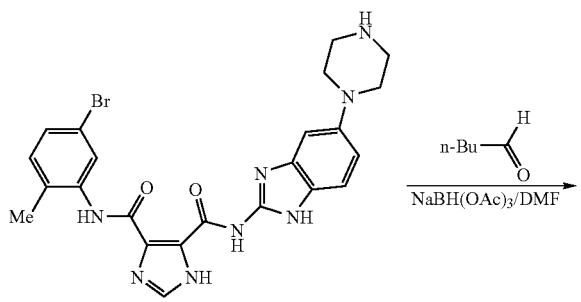

-continued

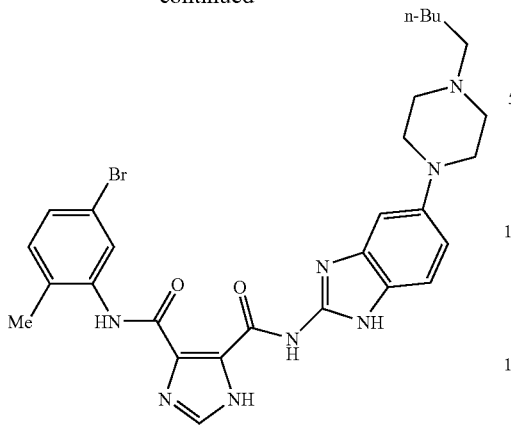

A round-bottom flask was charged with pentanal (0.177 g, 2.0 mmol) and $N^4$-(5-bromo-2-methylphenyl)-$N^5$-(6-(piperazin-1-yl)-1H-benzo[d]imidazol-2-yl)-1H-imidazole-4,5-dicarboxamide (0.104 g 0.2 mmol), anhydrous DMF (5 mL) and sodium triacetoxybrohydride (0.212 g, 1.0 mmol). The reaction mixture was stirred overnight at room temperature. The reaction mixture was concentrated under reduced pressure and subsequently purified by preparative reverse phase HPLC (ammonium acetate/acetonitrile) to give $N^4$-(5-bromo-2-methylphenyl)-$N^5$-[5-(4-pentylpiperazin-1-yl)-1H-benzimidazol-2-yl]-1H-imidazole-4,5-dicarboxamide acetate. $^1$H-NMR (400 MHz, DMSO-d6): δ 8.09 (s, 1H), 7.99 (d, 1H), 7.39 (dd, 1H), 7.29-7.3 (m, 2H), 6.87 (dd, 1H), 3.07 (t, 4H), 2.31 (t, 7H), 1.91 (s, 2H), 1.43-1.50 (m, 2H), 1.23-1.34 (m, 4H), 0.90 (t, 3H), MS (EI): 594.8 (MH+).

Example 94

Synthesis of $N^4$-(5-bromo-2-methylphenyl)-$N^5$-{5-[4-(2-phenylethyl)piperazin-1-yl]-1H-benzimidazol-2-yl}-1H-imidazole-4,5-dicarboxamide $N^4$-(5-bromo-2-methylphenyl)-$N^5$-{5-[4-(2-phenylethyl)piperazin-1-yl]-1H-benzimidazol-2-yl}-1H-imidazole-4,5-dicarboxamide was prepared in the same manner as $N^4$-(5-bromo-2-methylphenyl)-$N^5$-[5-(4-pentylpiperazin-1-yl)-1H-benzimidazol-2-yl]-1H-imidazole-4,5-dicarboxamide in Example 93. $^1$H-NMR (400 MHz, DMSO-d6): δ 13.85 (s, 1H), 12.03 (s, 1H), 10.35 (s, 1H), 8.89 (s, 1H), 7.92 (s, 1H), 7.20-7.38 (m, 5H), 7.10 (d, 2H), 6.93 (d, 2H), 3.58 (m, 4H), 2.73 (dd, 4H), 2.65 (m, 4H), 2.29 (s, 3H), MS (EI): 628.8 (MH+).

Example 95

Synthesis of $N^4$-(5-bromo-2-methylphenyl)-$N^5$-{5-[4-(phenylmethyl)piperazin-1-yl]-1H-benzimidazol-2-yl}-1H-imidazole-4,5-dicarboxamide $N^4$-(5-bromo-2-methylphenyl)-$N^5$-{5-[4-(phenylmethyl)piperazin-1-yl]-1H-benzimidazol-2-yl}-1H-imidazole-4,5-dicarboxamide was prepared in the same manner as $N^4$-(5-bromo-2-methylphenyl)-$N^5$-[5-(4-pentylpiperazin-1-yl)-1H-benzimidazol-2-yl]-1H-imidazole-4,5-dicarboxamide in Example 93. $^1$H-NMR (400 MHz, DMSO-d6): δ 8.10 (s, 1H), 7.98 (s, 1H), 7.39 (dd, 1H), 7.35 (m, 2H), 7.29 (s, 1H), 6.93 (s, 1H), 6.86 (dd, 1H), 3.07 (m, 4H), 2.31 (s, 3H), 2.09 (d, 2H), 1.91 (s, 1H), 1.78-1.83 (m, 2H), 0.90 (d, 6H), MS (EI): 580.4 (MH+).

Example 96

Synthesis of $N^4$-(5-bromo-2-methylphenyl)-$N^5$-{5-[4-(2-methylpropyl)piperazin-1-yl]-1H-benzimidazol-2-yl}-1H-imidazole-4,5-dicarboxamide $N^4$-(5-Bromo-2-methylphenyl)-$N^5$-{5-[4-(2-methylpropyl)piperazin-1-yl]-1H-benzimidazol-2-yl}-1H-imidazole-4,5-dicarboxamide was prepared in the same manner as $N^4$-(5-bromo-2-methylphenyl)-$N^5$-[5-(4-pentylpiperazin-1-yl)-1H-benzimidazol-2-yl]-1H-imidazole-4,5-dicarboxamide in Example 93. $^1$H-NMR (400 MHz, DMSO-d6): δ 10.40 (br s, 1H), 8.24 (s, 1H), 7.56 (m, 1H), 7.44 (br s, 1H), 7.24 (m, 1H), 7.22 (d, J=8 Hz, 2H), 7.04 (d, J=8 Hz, 2H), 2.33 (s, 3H), 2.07 (s, 3H). MS (EI): 375 (MH+).

Example 97

Synthesis of $N^5$-1H-benzimidazol-2-yl-$N^4$-(2,5-dimethylphenyl)-1H-imidazole-4,5-dicarboxamide $N^5$-1H-Benzimidazol-2-yl-$N^4$-(2,5-dimethylphenyl)-1H-imidazole-4,5-dicarboxamide was prepared in a manner similar to that used for $N^5$-1H-benzimidazol-2-yl-$N^4$-(2,4-dimethylphenyl)-1H-imidazole-4,5-dicarboxamide in Example 1 in 64% yield. $^1$H-NMR (400 MHz, DMSO-d6): δ 10.40 (br s, 1H), 8.24 (s, 1H), 7.56 (m, 1H), 7.44 (br s, 1H), 7.24 (m, 1H), 7.22 (d, J=8 Hz, 2H), 7.04 (d, J=8 Hz, 2H), 2.33 (s, 3H), 2.07 (s, 3H). MS (EI): 375 (MH+).

Example 98

Synthesis of $N^5$-(5-bromo-2-methylphenyl)-$N^4$-(7-{[2-(methyloxy)ethyl]oxy}-1H-benzimidazol-2-yl)-1H-imidazole-4,5-dicarboxamide

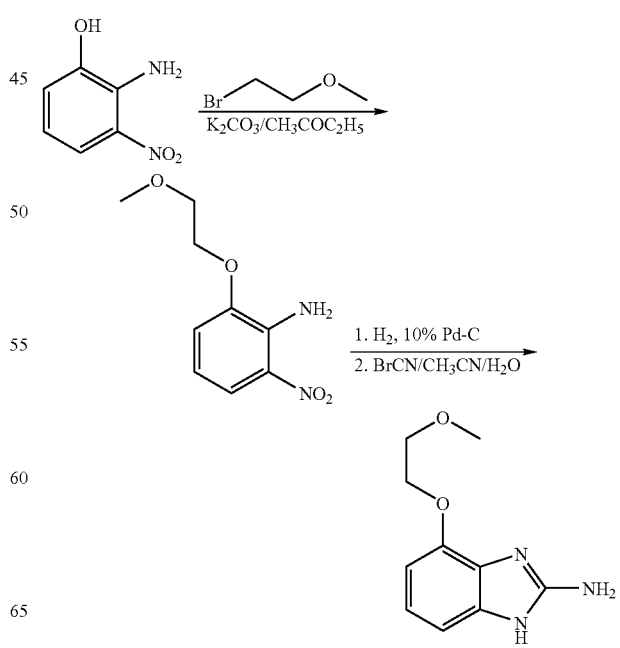

-continued

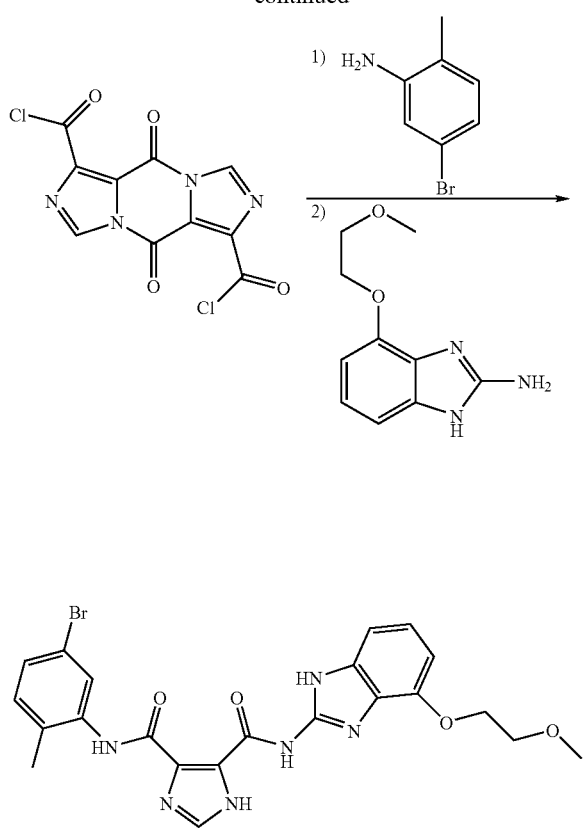

Synthesis of 2-(2-methoxyethoxy)-6-nitroaniline 2-(2-Methoxyethoxy)-6-nitroaniline was prepared in a manner analogous to 2-methoxy-6-nitroaniline in Example 38 and used without further purification. $^1$H-NMR (400 MHz, CDCl$_3$): δ 7.75 (d, 2H), 6.94 (d, 2H), 6.60 (dd, 2H), 6.55 (br, 2H), 4.19 (d, 2H), 3.78 (d, 2H), 3.42 (s, 3H). MS (EI) (MH+).

Synthesis of 4-(2-methoxyethoxy)-1H-benzo[d]imidazol-2-amine 4-(2-Methoxyethoxy)-1H-benzo[d]imidazol-2-amine was prepared according to the procedure of 4-methoxy-1H-benzo[d]imidazol-2-amine in Example 38, and used without further purification. MS (EI): 208 (MH+).

Synthesis of N$^5$-(5-Bromo-2-methylphenyl)-N$^4$-(7-{[2-(methyloxy)ethyl]oxy}-1H-benzimidazol-2-yl)-1H-imidazole-4,5-dicarboxamide N$^5$-(5-Bromo-2-methylphenyl)-N$^4$-(7-{[2-(methyloxy)ethyl]oxy}-1H-benzimidazol-2-yl)-1H-imidazole-4,5-dicarboxamide was prepared in a manner similar to that used for N$^5$-1H-benzimidazol-2-yl-N$^4$-(2,4-dimethylphenyl)-1H-imidazole-4,5-dicarboxamide in Example 1 in 43% yield. $^1$H-NMR (400 MHz, DMSO-d6): δ 13.95 (s, br, 1H), 12.20 (s, br, 1H), 10.39 (s, 1H), 8.20 (s, 1H), 7.85 (s, 1H), 7.05-7.44 (m, 4H), 6.65 (m, 1H), 4.25 (m, 2H), 3.95 (m, 2H), 3.35 (s, 3H), 2.24 (s, 3H). MS (EI): 513 (MH+).

Example 99

Synthesis of N$^5$-(5-bromo-2-methylphenyl)-N$^4$-{7-[(2-morpholin-4-ylethyl)oxy]-1H-benzimidazol-2-yl}-1H-imidazole-4,5-dicarboxamide

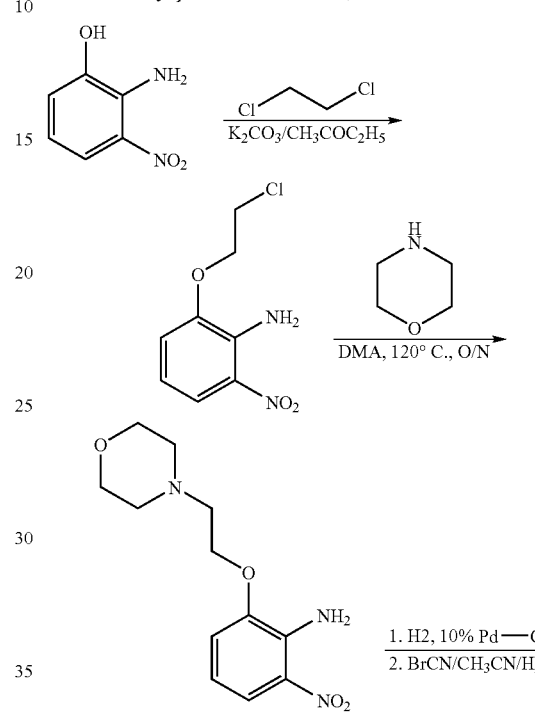

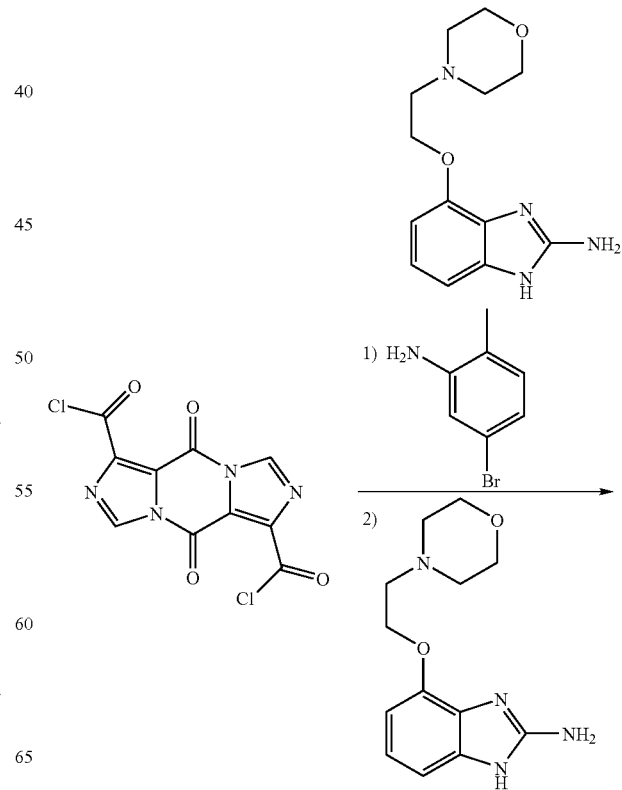

-continued

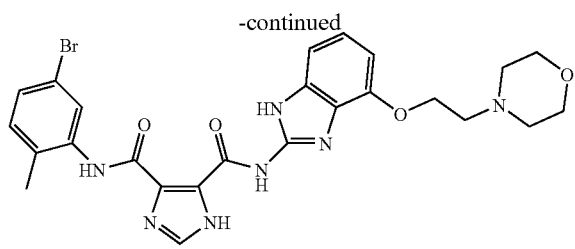

Synthesis of 2-(2-chloroethoxy)-6-nitroaniline

2-Amino-3-nitrophenol (10.0 g, 64.9 mmol, commercially available from Aldrich) was dissolved in 200 mL 2-butanone, potassium carbonate (18.0 g, 0.13 mol) and dichloroethane (15 mL) were added. The suspension was refluxed for 20 hours. The reaction was allowed to cool to room temperature and filtered through a plug of Celite and the retained solid residue was washed with ethyl acetate. The combined filtrate was concentrated under reduced pressure. The crude material was redissolved in 200 mL of ethyl acetate, washed with water, 1N sodium hydroxide solution water, saturated sodium chloride solution dried over anhydrous sodium sulfate, filtered and concentrated at reduced pressure to give 9.8 g of 2-(2-Chloroethoxy)-6-nitroaniline (70% yield), which was used without further purification. $^1$H-NMR (400 MHz, CDCl$_3$): δ 7.80 (d, 1H), 6.95 (d, 1H), 6.61 (dd, 1H), 6.42 (b, 2H), 4.30 (t, 2H), 3.90 (t, 2H). MS (EI): 217 (MH+).

Synthesis of 2-(2-morpholinoethoxy)-6-nitroaniline 2-(2-Chloroethoxy)-6-nitroaniline (1.9 g, 4.63 mmol), morpholine (0.5 mL) was dissolved in 5 mL of DMA. The mixture was heated at 110° C. in a pressure bottle overnight, and then cooled to room temperature. The reaction mixture was separated between ethyl acetate and water, the combined organic layers were washed with water, brine, dried, and concentrated to get 1.3 g of 2-(2-Morpholinoethoxy)-6-nitroaniline, which was used without any further purification. $^1$H-NMR (400 MHz, CDCl$_3$): δ 7.78 (d, 1H), 6.95 (d, 1H), 6.72 (b, 2H), 6.61 (dd, 1H), 4.16 (t, 2H), 3.75 (t, 2H), 2.82 (m, 2H), 2.58 (m, 4H), 2.10 (m, 2H). MS (EI): 263 (MH+).

Synthesis of 4-(2-Morpholinoethoxy)-1H-benzo[d]imidazol-2-amine 4-(2-Morpholinoethoxy)-1H-benzo[d]imidazol-2-amine was prepared according to the procedure of 4-Methoxy-1H-benzo[d]imidazol-2-amine in Example 38 and used without further purification. MS (EI): 263 (MH+).

Synthesis of N$^5$-(5-bromo-2-methylphenyl)-N$^4$-{7-[(2-morpholin-4-ylethyl)oxy]-1H-benzimidazol-2-yl}-1H-imidazole-4,5-dicarboxamide N$^5$-(5-Bromo-2-methylphenyl)-N$^4$-{7-[(2-morpholin-4-ylethyl)oxy]-1H-benzimidazol-2-yl}-1H-imidazole-4,5-dicarboxamide was prepared in a similar manner to that used for N$^5$-1H-benzimidazol-2-yl-N$^4$-(2,4-dimethylphenyl)-1H-imidazole-4,5-dicarboxamide in Example 1 in 43% yield. $^1$H-NMR (400 MHz, DMSO-d6): δ 12.20 (br, 1H), 10.39 (br, 1H), 8.20 (s, 1H), 7.85 (s, 1H), 7.05-7.44 (m, 4H), 6.70 (m, 1H), 4.27 (m, 2H), 3.59 (m, 4H), 3.35 (m, 4H), 2.76 (m, 2H), 2.29 (s, 3H). MS (EI): 568 (MH+).

Example 100

Synthesis of N$^4$-(5-bromo-2-methylphenyl)-N$^5$-{5-[(2-piperazin-1-ylethyl)oxy]-1H-benzimidazol-2-yl}-1H-imidazole-4,5-dicarboxamide Hydrochloride

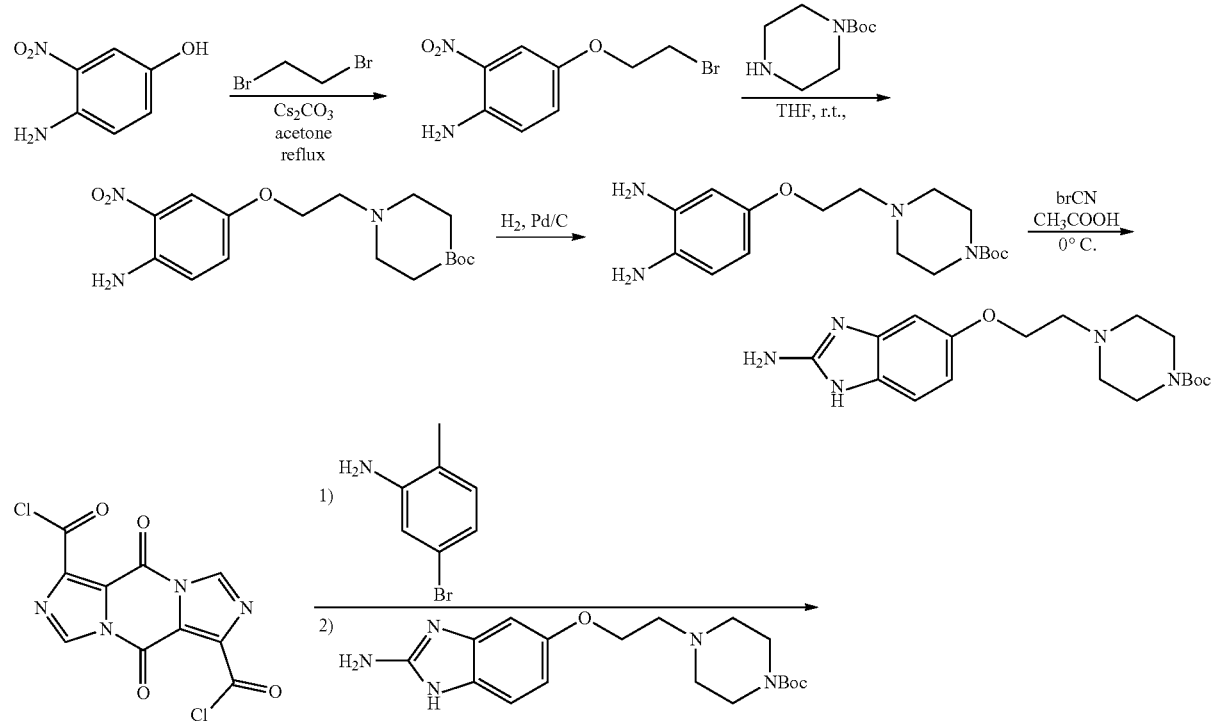

-continued

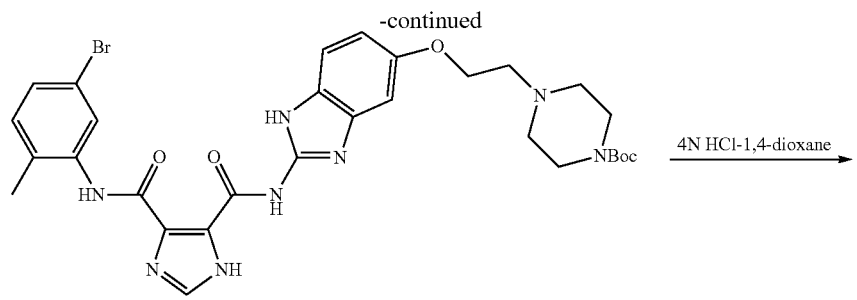

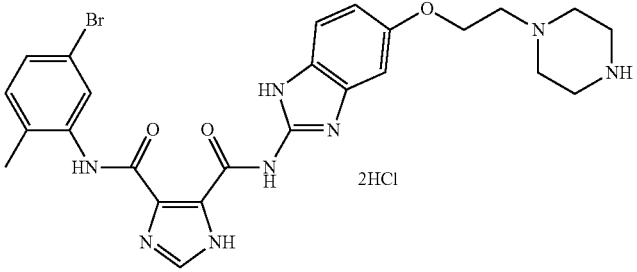

2HCl

Synthesis of 4-(2-bromoethoxy)-2-nitroaniline

A 500 mL flask was charged with 4-amino-3-nitrophenol (15.4 g, 100 mmol, commercially available from Aldrich). Acetone (300 mL), cesium carbonate (39.09 g, 120 mmol) and 1,3-dibromopropane (40.84 mL, 400 mmol) were added to the flask and stirred at refluxed temperature. The reaction was monitored by LCMS. After 6 hours, the reaction mixture was cooled to room temperature, filtered and washed with acetone. The organic layer was removed on a rotary evaporator under reduced pressure and the resulting material was purified by silica column chromatography using 40% hexane in dichloromethane as eluant. 20 g of 4-(2-bromoethoxy)-2-nitroaniline was isolated which was used in the next step without any further purification. MS (EI): 275 (MH+).

Synthesis of tert-butyl 4-(2-(4-amino-3-nitrophenoxy)ethyl)piperazine-1-carboxylate A 100 mL flask was charged with 4-(2-bromoethoxy)-2-nitroaniline (2.2 g, 8.4 mmol) in THF (20 mL) and 4-N-boc-piperazine (1.56 g, 8.4 mmol) was added and stirred at room temperature. The reaction was monitored by LCMS. After 30 minutes, the reaction mixture was treated with deionized water (100 mL) and sonicated. The resulting solid was collected by filtration and dried at reduced pressure to give 1.75 g of tert-butyl 4-(2-(4-amino-3-nitrophenoxy)ethyl)piperazine-1-carboxylate (59% yield). MS (EI): 367 (MH+).

Synthesis of tert-butyl 4-(2-(3,4-diaminophenoxy)ethyl)piperazine-1-carboxylate A hydrogenation vessel was charged with tert-butyl 4-(2-(4-amino-3-nitrophenoxy)ethyl)piperazine-1-carboxylate (1.74 g, 4.76 mmol), ethanol (100 mL) and 10% palladium on charcoal (w/w 50% water) (1 g). The reaction vessel was shaken on a Parr Hydrogenation under an atmosphere of hydrogen gas (40 psi). The reaction was completed in 2 hours as determined by LCMS. The reaction mixture was filtered through a plug of Celite and washed with methanol. The filtered was evaporated under pressure to give 1.53 g of tert-butyl 4-(2-(3,4-diaminophenoxy)ethyl)piperazine-1-carboxylate (95% yield) and was used in the next step without any further purification. MS (EI): 337 (MH+).

Synthesis of tert-butyl 4-(2-(2-amino-1H-benzo[d]imidazol-5-yloxy)ethyl)piperazine-1-carboxylate diacetate A 100 mL flasked was charged of tert-butyl 4-(2-(3,4-diaminophenoxy)ethyl)piperazine-1-carboxylate (1.53 g, 4.54 mmol), water (50 mL) and acetic acid (2 mL) and stirred at room temperature for 15 minutes. The reaction mixture was placed in an ice bath and then charged with cyanogen bromine (0.526 g, 5 mmol) and continued to stir at 0° C. The reaction temperature was allowed to warm to room temperature and it was stirred over night. The reaction was completed as determined by LCMS. The reaction mixture was concentrated under reduced pressure and the resulting residue was dissolved in acetone, dried over anhydrous sodium sulfate, filtered and evaporated under reduced pressure to give 1.7 g of tert-butyl 4-(2-(2-amino-1H-benzo[d]imidazol-5-yloxy)ethyl)piperazine-1-carboxylate as a di-acetate salt as black foam. MS (EI): 362 (MH+).

Synthesis of tert-butyl 4-(2-(2-(4-(5-bromo-2-methylphenylcarbamoyl)-1H-imidazole-5-carboxamido)-1H-benzo[d]imidazol-5-yloxy)ethyl)piperazine-1-carboxylate tert-Butyl 4-(2-(2-(4-(5-bromo-2-methylphenylcarbamoyl)-1H-imidazole-5-carboxamido)-1H-benzo[d]imidazol-5-yloxy)ethyl)piperazine-1-carboxylate was prepared in a manner similar to $N^5$-1H-benzimidazol-2-yl-$N^4$-(2,4-dimethylphenyl)-1H-imidazole-4,5-dicarboxamide in Example 1 in 67% yield. MS (EI): 668 (MH+).

Synthesis of $N^4$-(5-bromo-2-methylphenyl)-$N^5$-{5-[(2-piperazin-1-ylethyl)oxy]-1H-benzimidazol-2-yl}-1H-imidazole-4,5-dicarboxamide Hydrochloride $N^4$-(5-Bromo-2-methylphenyl)-$N^5$-{5-[(2-piperazin-1-ylethyl)oxy]-1H-benzimidazol-2-yl}-1H-imidazole-4,5-dicarboxamide hydrochloride was prepared in a manner similar to that used for $N^5$-[4-(azetidin-3-yloxy)-2-methylphenyl]-$N^4$-

1H-benzimidazol-2-yl-1H-imidazole-4,5-dicarboxamide in Example 5 in 47% yield. ¹H-NMR (400 MHz, DMSO-d6): δ 8.08 (d, 1H), 7.92 (s, 1H), 7.37-7.33 (m, 2H), 7.3-7.26 (m, 1H), 7.05 (d, 1H), 6.76 (dd, 1H), 4.06 (t, 2H), 2.8 (t, 4H), 2.7 (t, 2H), 2.5 (m, 4H), 2.3 (s, 3H). MS (EI): 567 (MH+).

Example 101

Synthesis of N⁴-(5-bromo-2-methylphenyl)-N⁵-{5-[4-(tetrahydrofuran-3-ylmethyl)piperazin-1-yl]-1H-benzimidazol-2-yl}-1H-imidazole-4,5-dicarboxamide N⁴-(5-Bromo-2-methylphenyl)-N⁵-{5-[4-(tetrahydrofuran-3-ylmethyl)piperazin-1-yl]-1H-benzimidazol-2-yl}-1H-imidazole-4,5-dicarboxamide was prepared in the same manner as N⁴-(5-bromo-2-methylphenyl)-N⁵-[5-(4-pentylpiperazin-1-yl)-1H-benzimidazol-2-yl]-1H-imidazole-4,5-dicarboxamide in Example 93. ¹H-NMR (400 MHz, DMSO-d6): δ 8.06 (s, 1H), 8.01 (d, 1H), 7.38 (dd, 1H), 7.32 (d, 1H), 7.01 (s, 1H), 6.86 (dd, 1H), 3.70-3.76 (m, 2H), 3.59-3.65 (m, 1H), 3.07 (t, 4H), 2.52-2.61 (m, 4H), 2.33 (s, 1H), 2.31 (s, 3H), 1.93-1.98 (m, 1H), 1.91 (s, 3H), 1.50-1.58 (s, 2H), MS (EI): 608.3 (MH+).

Example 102

Synthesis of N⁴-(5-bromo-2-methylphenyl)-N⁵-{5-[4-(pyridin-4-ylmethyl)piperazin-1-yl]-1H-benzimidazol-2-yl}-1H-imidazole-4,5-dicarboxamide N⁴-(5-Bromo-2-methylphenyl)-N⁵-{5-[4-(pyridin-4-ylmethyl)piperazin-1-yl]-1H-benzimidazol-2-yl}-1H-imidazole-4,5-dicarboxamide was prepared in the same manner as N⁴-(5-bromo-2-methylphenyl)-N⁵-[5-(4-pentylpiperazin-1-yl)-1H-benzimidazol-2-yl]-1H-imidazole-4,5-dicarboxamide in Example 93. ¹H-NMR (400 MHz, DMSO-d6): δ 13.81 (s, 1H), 11.58 (s, 1H), 10.44 (s, 1H), 8.71 (d, 2H), 8.22 (s, 1H), 7.41 (d, 2H), 7.42 (d, 2H), 7.30 (d, 1H), 6.93 (s, 1H), 6.98 (d, 1H), 4.01 (s, 2H), 3.67 (M, 4H), 2.73 (m, 4H), 2.29 (s, 3H), MS (EI): 615.4 (MH+).

Example 103

Synthesis of N⁴-(5-bromo-2-methylphenyl)-N⁵-[5-(4-{2-[(phenylmethyl)oxy]ethyl}piperazin-1-yl)-1H-benzimidazol-2-yl]-1H-imidazole-4,5-dicarboxamide N⁴-(5-Bromo-2-methylphenyl)-N⁵-[5-(4-{2-[(phenylmethyl)oxy]ethyl}piperazin-1-yl)-1H-benzimidazol-2-yl]-1H-imidazole-4,5-dicarboxamide was prepared in the same manner as N⁴-(5-bromo-2-methylphenyl)-N⁵-[5-(4-pentylpiperazin-1-yl)-1H-benzimidazol-2-yl]-1H-imidazole-4,5-dicarboxamide in Example 93. ¹H-NMR (400 MHz, DMSO-d6): δ 11.93 (s, 1H), 10.26 (s, 1H), 7.99-8.09 (d, 1H), 1.28-7.39 (m, 7H), 7.27 (s, 1H), 6.86-7.27 (d, 1H), 4.50 (s, 2H), 3.58-3.60 (t, 2H), 73.07 (s, 4H), 2.59-2.60 (d, 6H), 2.31 (s, 3H), MS (EI): 578.6 (MH+).

Example 104

Synthesis of N⁴-(5-bromo-2-methylphenyl)-N⁵-{7-[(1-methylpiperidin-4-yl)oxy]-1H-benzimidazol-2-yl}-1H-imidazole-4,5-dicarboxamide

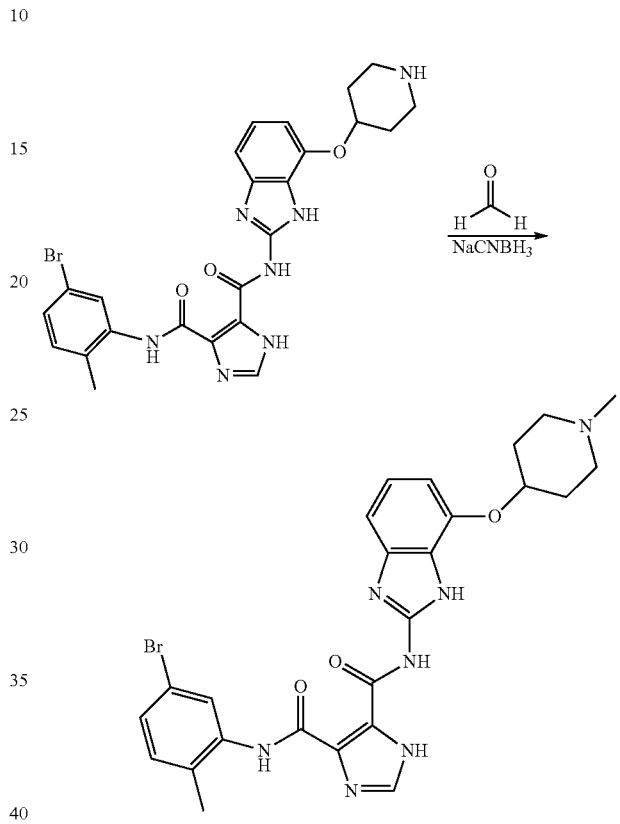

N⁴-(5-Bromo-2-methylphenyl)-N⁵-(7-(piperidin-4-yloxy)-1H-benzo[d]imidazol-2-yl)-1H-imidazole-4,5-dicarboxamide (0.1 mmol) was weighted out into a round bottomed flask and acetonitrile (5 mL) was added and the resulting solution was stirred at 25° C. Formaldehyde (1.0 mmol) and sodium cyanoborohydride (0.32 mmol) was added. The reaction mixture was kept neutral by the addition of acetic acid. After 2 hours, the reaction mixture was concentrated under reduced pressure. The crude product was purified via reverse phase HPLC (aqueous ammonium acetate/acetonitrile) to give N⁴-(5-bromo-2-methylphenyl)-N⁵-{7-[(1-methylpiperidin-4-yl)oxy]-1H-benzimidazol-2-yl}-1H-imidazole-4,5-dicarboxamide as a white solid. ¹H-NMR (400 MHz, DMSO-d6): δ 8.06 (s, 1H), 7.97 (s, 1H), 7.35 (m, 1H), 7.28 (d, 1H), 7.12 (dd, 1H), 6.99 (m, 1H), 6.67 (m, 1H), 4.67 (m, 1H), 2.32 (m, 4H), 2.19 (s, 3H), 1.89 (m, 5H), MS (EI): 553.3 (MH+).

Example 105

Synthesis of N⁴-(2,6-dichlorophenyl)-N⁵-[6-(4-methylpiperazin-1-yl)-1H-benzimidazol-2-yl]-1H-imidazole-4,5-dicarboxamide N⁴-(2,6-Dichlorophenyl)-N⁵-[6-(4-methylpiperazin-1-yl)-1H-benzimidazol-2-yl]-1H-imidazole-4,5-dicarboxamide was prepared in a similar fashion as $N^4$-(5-chloro-2-methylphenyl)-$N^5$-[5-(4-methylpiperazin-1-yl)-1H-benzimidazol-2-yl]-1H-imidazole-4,5-dicarboxamide utilizing N-methylpiperazine (commercially available from Aldrich). $^1$H-NMR (400 MHz, DMSO-d6): δ 7.97 (s, 1H), 7.58-7.53 (m, 2H), 7.40-7.35 (m, 2H), 7.06 (s, 1H), 6.95-6.90 (m, 1H), 3.22-3.21 (s, 4H), 2.78 (s, 4H), 2.45 (s, 3H). MS (EI): 513 (MH+).

Example 106

Synthesis of 1,1-dimethylethyl 4-(2-{[(5-{[(5-bromo-2-methylphenyl)amino]carbonyl}-1H-imidazol-4-yl)carbonyl]amino}-1H-benzimidazol-6-yl)-3-methylpiperazine-1-carboxylate

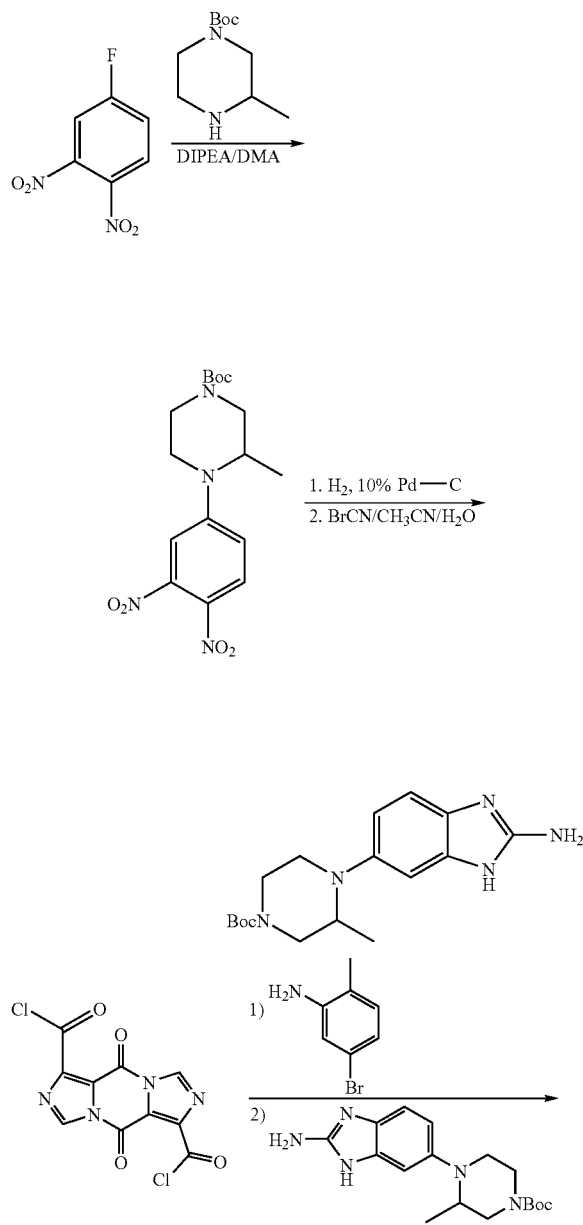

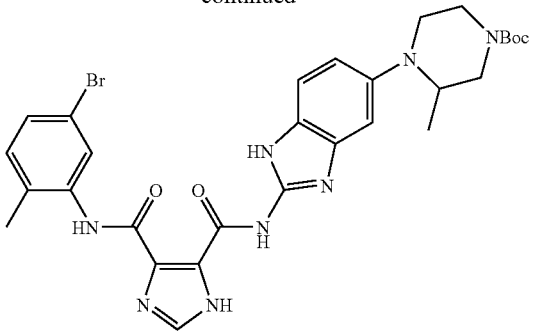

Synthesis of tert-Butyl 4-(3,4-dinitrophenyl)-3-methylpiperazine-1-carboxylate

4-Fluoro-1,2-dinitrobenzene (0.93 g, 5.0 mmol, commercially available from Oakwood Products) and tert-butyl 3-methylpiperazine-1-carboxylate (1.0 g, 5.0 mmol) were dissolved in 3 mL of DMA, and 3 mL of diisopropylethylamine was added. The mixture was stirred at 50° C. overnight, and then cooled to room temperature, separated between ethyl acetate and water. The combined organic were washed with water, brine, dried with anhydrous magnesium sulfate, filtered and concentrated under reduced pressure. The residue was separated by silica gel column (20% to 40% ethyl acetate in hexanes) to give 1.0 g of tert-butyl 4-(3,4-dinitrophenyl)-3-methylpiperazine-1-carboxylate. $^1$H-NMR (400 MHz, CDCl$_3$): δ 8.05 (d, 2H), 6.84 (m, 2H), 3.90-4.10 (m, 3H), 3.05-3.60 (m, 4H), 1.50 (s, 9H), 1.10 (s, 3H). MS (EI): 367 (MH+).

Synthesis of tert-butyl 4-(2-amino-1H-benzo[d]imidazol-6-yl)-3-methylpiperazine-1-carboxylate tert-Butyl 4-(2-amino-1H-benzo[d]imidazol-6-yl)-3-methylpiperazine-1-carboxylate was prepared in a fashion analogous was prepared in a fashion analogous to 4-methoxy-1H-benzo[d]imidazol-2-amine in Example 38, in quantitative yield, which was used without any further purification. MS (EI): 332 (MH+).

Synthesis of 1,1-dimethylethyl 4-(2-{[(5-{[(5-bromo-2-methylphenyl)amino]carbonyl}-1H-imidazol-4-yl)carbonyl]amino}-1H-benzimidazol-6-yl)-3-methylpiperazine-1-carboxylate 1,1-Dimethylethyl 4-(2-{[(5-{[(5-bromo-2-methylphenyl)amino]carbonyl}-1H-imidazol-4-yl)carbonyl]amino}-1H-benzimidazol-6-yl)-3-methylpiperazine-1-carboxylate was prepared in a manner similar to that use for $N^5$-1H-benzimidazol-2-yl-$N^4$-(2,4-dimethylphenyl)-1H-imidazole-4,5-dicarboxamide as in Example 1 in 57% yield. $^1$H NMR (400 MHz, DMSO-d6): δ 12.10 (br, 1H), 9.70 (br, 1H), 8.49 (s, 1H), 8.30 (s, 1H), 6.85-7.40 (m, 5H), 3.45 (m, 3H), 3.06 (m, 2H), 2.40 (m, 2H), 2.35 (s, 3H), 1.45 (s, 9H), 0.98 (s, 3H). MS (EI): 637 (MH+).

Example 107

Synthesis of N⁴-(5-bromo-2-methylphenyl)-N⁵-(5-{[2-(diethylamino)ethyl]oxy}-1H-benzimidazol-2-yl)-1H-imidazole-4,5-dicarboxamide N⁴-(5-Bromo-2-methylphenyl)-N⁵-(5-{[2-(diethylamino)ethyl]oxy}-1H-benzimidazol-2-yl)-1H-imidazole-4,5-dicarboxamide was prepared in a fashion analogous to N⁴-(5-bromo-2-methylphenyl)-N⁵-{5-[(2-piperazin-1-ylethyl)oxy]-1H-benzimidazol-2-yl}-1H-imidazole-4,5-dicarboxamide in Example 100. ¹H-NMR, DMSO-d6): δ 8.04 (d, 1H), 8.0 (s, 1H), 7.38-7.33 (m, 2H), 7.3-7.27 (m, 1H), 7.04 (d, 1H), 6.76 (dd, 1H), 4.0 (t, 2H), 2.8 (t, 2H), 2.55 (q, 4H), 2.3 (s, 3H), 1.0 (t, 6H). MS (EI): 554 (MH+).

Example 108

Scheme for the synthesis of N⁴-(5-bromo-2-methylphenyl)-N⁵-(5-{[2-(4-methylpiperazin-1-yl)ethyl]oxy}-1H-benzimidazol-2-yl)-1H-imidazole-4,5-dicarboxamide

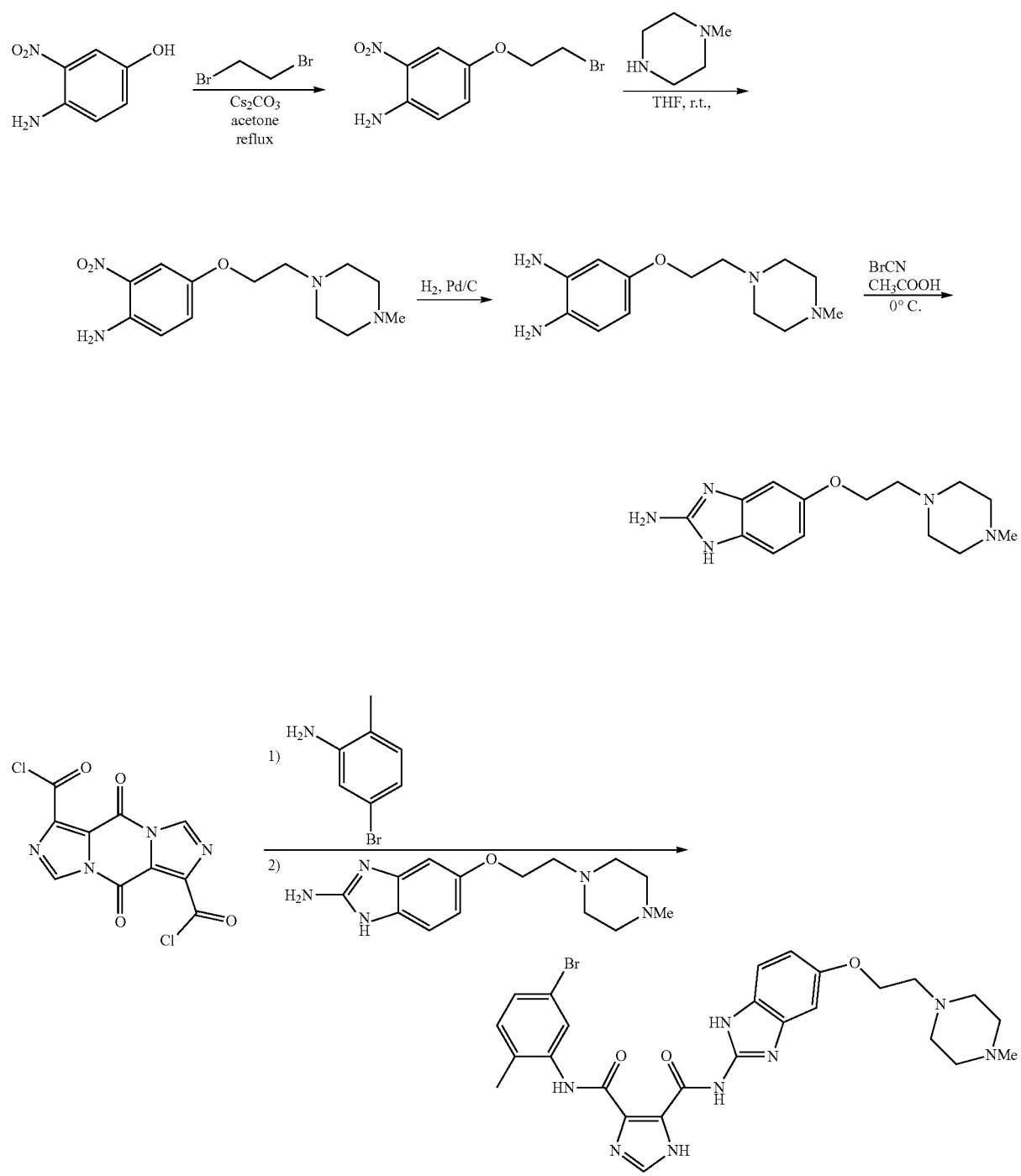

Synthesis of 4-(2-(4-methylpiperazin-1-yl)ethoxy)-2-nitroaniline

A 100 mL flask was charged with 4-(3-bromoethoxy)-2-nitroaniline (8.02 mmol) and 4-methylpiperazine (10 mL) and stirred at 100° C. The reaction was monitored by LCMS and completed in 60 minutes. The reaction mixture was treated with water (100 mL) and sonicated in an ultrasonic bath. The resulting solid was filtered off and dried under reduced pressure to give 1.4 g of 4-(2-(4-methylpiperazin-1-yl)ethoxy)-2-nitroaniline (69 yield). MS (EI): 276 (MH+).

Synthesis of 4-(2-(4-methylpiperazin-1-yl)ethoxy)benzene-1,2-diamine

A hydrogenation vessel was charged with 4-(3-(4-methylpiperazin-1-yl)ethoxy)-2-nitroaniline (1.3 g, 4.76 mmol), ethanol (100 mL) and 10% palladium on charcoal (1 g). The reaction vessel was shaken on Parr hydrogenation apparatus. After 2 hours the reaction mixture was filtered through a plug of Celite and washed with methanol. The resulting filtrate was concentrated under reduced pressure to 1.2 g of 4-(2-(4-methylpiperazin-1-yl)ethoxy)benzene-1,2-diamine as a black solid (95% yield), and was used without any further purification. MS (EI): 251 (MH+).

Synthesis of 5-(2-(4-methylpiperazin-1-yl)ethoxy)-1H-benzo[d]imidazol-2-amine A 100 mL flasked was charged with 4-(2-(4-methylpiperazin-1-yl)ethoxy)benzene-1,2-diamine (4.35 mmol), water (50 mL) and acetic acid (2 mL) and stirred at room temperature for 15 minutes. The reaction mixture was placed in an ice bath and then charged with cyanogen bromide (0.526 g, 5 mmol). The reaction mixture was allowed to warm to room temperature and stirred over night. The reaction mixture was concentrated under reduced pressure and redissolved in acetone, dried over anhydrous sodium sulfate, filtered and the filtrate was concentrated under reduced pressure to give 1.79 g of 5-(2-(4-methylpiperazin-1-yl)ethoxy)-1H-benzo[d]imidazol-2-amine. This material was used without any further purification. MS (EI): 276 (MH+).

Synthesis of $N,^4$-(5-bromo-2-methylphenyl)-$N^5$-(5-{[2-(4-methylpiperazin-1-yl)ethyl]oxy}-1H-benzimidazol-2-yl)-1H-imidazole-4,5-dicarboxamide $N^4$-(5-Bromo-2-methylphenyl)-$N^5$-(5-{[2-(4-methylpiperazin-1-yl)ethyl]oxy}-1H-benzimidazol-2-yl)-1H-imidazole-4,5-dicarboxamide was prepared in a manner similar to that use for $N^5$-1H-benzimidazol-2-yl-$N^4$-(2,4-dimethylphenyl)-1H-imidazole-4,5-dicarboxamide as in Example 1 at 34% yield. $^1$H-NMR (400 MHz, DMSO-d6): δ 8.12 (s, 1H), 7.98 (d, 1H), 7.4-7.34 (m, 2H), 7.32-7.28 (m, 1H), 7.04 (d, 1H), 6.76 (dd, 1H), 4.06 (t, 2H), 2.7 (t, 2H), 2.56-2.46 (t, br, 4H), 2.36-2.28 (t, br, 4H), 2.3 (s, 3H), 2.15 (s, 3H). MS (EI): 581 (MH+).

Example 109

Synthesis of $N^4$-(5-bromo-2-methylphenyl)-$N^5$-(4,5-dimethyl-1H-imidazol-2-yl)-1H-imidazole-4,5-dicarboxamide

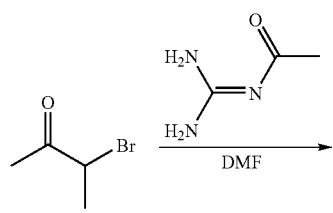

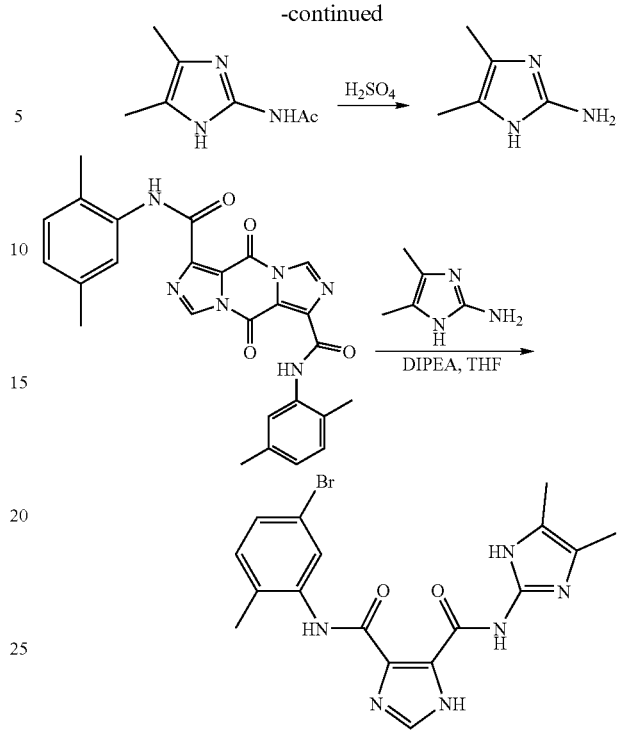

Synthesis of 4,5-dimethyl-1H-imidazol-2-amine

A dry round bottom flask was charged with a 0.3 M (20.0 mmol) solution of 3-bromobutan-2-one. Acetylguanidine (60.0 mmol) in dry DMF was added to the mixture. The mixture was stirred at room temperature for 96 hours. The solvent was evaporated off and the residue was washed with water, filtered, dried and recrystallized with methanol to give crude N-(4,5-dimethyl-1H-imidazol-2-yl)acetamide. This material was suspended in 100 mL of 1:1 MeOH:H$_2$O solution with 1.5 mL of H$_2$SO$_4$, and heated to reflux for 16 hours (overnight). The reaction mixture was then allowed to cool to room temperature and concentrated at reduced pressure. The resulting crude material was treated with ethanol and ether, treated in an ultrasonic bath and concentrated at reduced pressure. The crude product was further purified by silica column chromatography (starting with 5% MeOH in dichloromethane, in increments of 5% to 35% MeOH in dichloromethane) to give 609 mg of 4,5-dimethyl-1H-imidazol-2-amine.

Synthesis of $N^4$-(5-bromo-2-methylphenyl)-$N^5$-(4,5-dimethyl-1H-imidazol-2-yl)-1H-imidazole-4,5-dicarboxamide A dry round bottomed flask was charged with $N^1,N^6$-bis(5-bromo-2-methylphenyl)-5,10-dioxo-5,10-dihydrodiimidazo[1,5-a:1',5'-d]pyrazine-1,6-dicarboxamide (490 mg, 0.8 mmol) and anhydrous THF (15 ml). To this suspension was added 4,5-dimethyl-1H-imidazol-2-amine (196 mg, 1.76 mmol) in anhydrous DMF (2 ml). The reaction mixture was then stirred at 53° C. for 16 hours. The reaction mixture was then allowed to cool to room temperature and concentrated at reduced pressure. The crude material was treated with methanol and 1M hydrochloric acid. Saturated potassium carbonate solution was then added to neutralize the mixture. The resulting solid was filtered off, washed with 1M hydrochloric acid, saturated potassium carbonate solution and dichloromethane. Purification by reverse phase HPLC (aqueous ammonium acetate/acetonitrile) gave 32 mg of $N^4$-(5-bromo-2-methylphenyl)-$N^5$-(4,5-dimethyl-1H-imidazol-2-yl)-1H-imidazole-4,5-dicarboxamide. $^1$H-NMR (400 MHz, DMSO-d6): 7.97 (d, 1H), 7.35 (d, 1H), 7.27 (d, 1H), 2.29 (s, 3H), 2.04 (s, 6H); MS (EI): 418.5 (MO.

Example 110
Scheme for the synthesis of $N^4$-(5-bromo-2-methylphenyl)-$N^5$-(5-{[3-(4-methylpiperazin-1-yl)propyl]oxy}-1H-benzimidazol-2-yl)-1H-imidazole-4,5-dicarboxamide
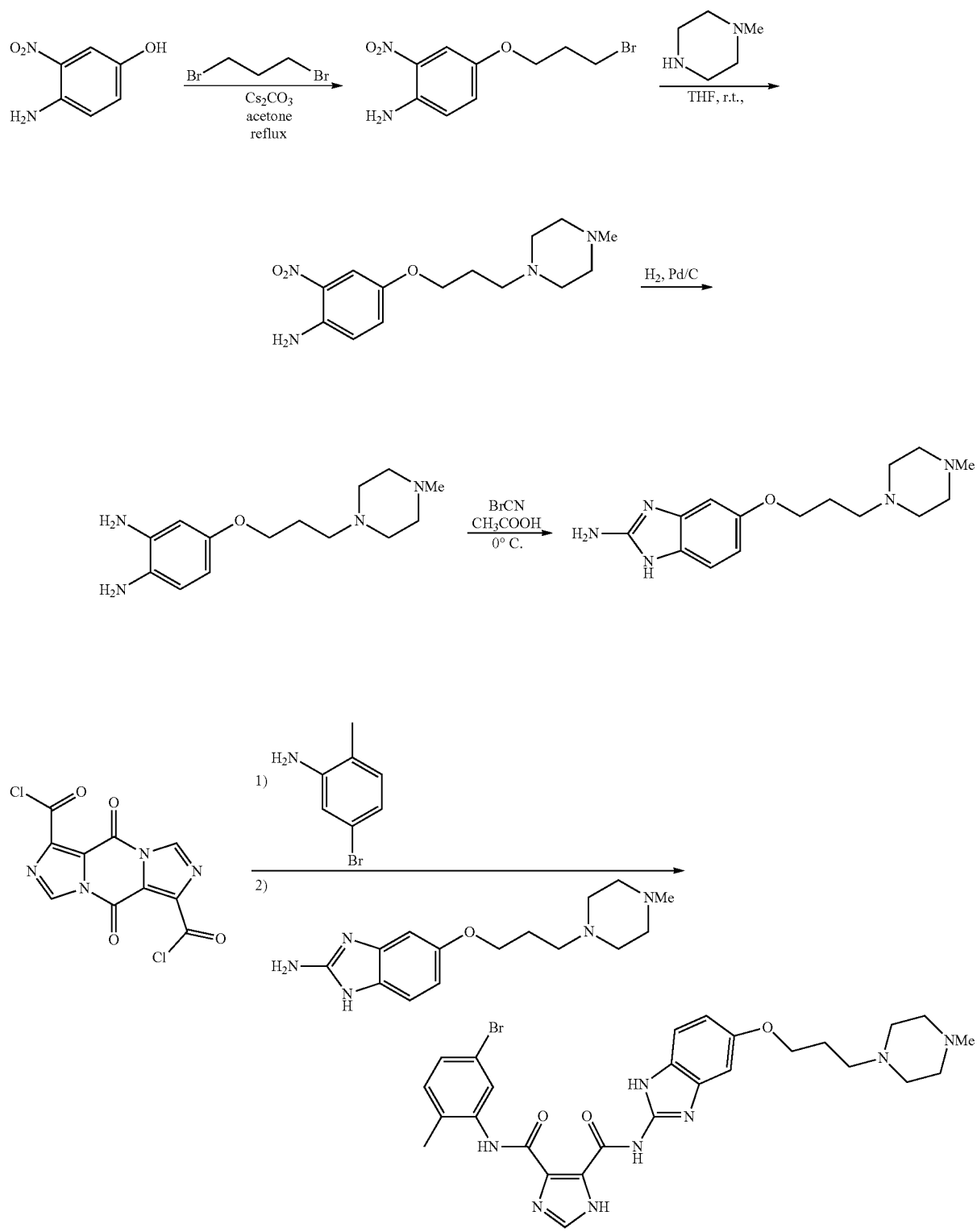

Synthesis of 4-(3-bromopropoxy)-2-nitroaniline

A 500 mL flask was charged with 4-amino-3-nitrophenol (15.4 g, 100 mmol, commercially available from Aldrich). Acetone (300 mL), cesium carbonate (39.09 g, 120 mmol) and 1,3-dibromopropane (40.84 mL, 400 mmol) were added to the flask and stirred at refluxed temperature. The reaction was monitored by LCMS and was complete in 6 hours. The reaction mixture was cooled to room temperature, filtered and washed with excess acetone. The organic layer was removed on a rotary evaporator under reduced pressure and the resulting brown gelatin was purified by silica column chromatography using 40% hexane in dichloromethane as eluent. 20.0 g of 4-(3-bromopropoxy)-2-nitroaniline was obtained as a dark orange liquid which was used without any further purification. MS (EI: 276 (MH+).

Synthesis of 4-(3-(4-methylpiperazin-1-yl)propoxy)-2-nitroaniline

A 100 mL flask was charged with 4-(3-bromopropoxy)-2-nitroaniline (2.2 g, 8.02 mmol) and 4-methylpiperazine (10 mL) and stirred at 100° C. The reaction was monitored by LCMS and complete in 30 minutes. The reaction mixture was treated with water (100 mL) and sonicated in an ultrasonic bath. The resulting solid were filtered off and dried under reduced pressure to give 1.5 g of 4-(3-(4-methylpiperazin-1-yl)propoxy)-2-nitroaniline (60% yield). MS (EI): 295 (MH+).

Synthesis of 4-(3-(4-methylpiperazin-1-yl)propoxy) benzene-1,2-diamine

A hydrogenation vessel was charged with 4-(3-(4-methylpiperazin-1-yl)propoxy)-2-nitroaniline (1.4 g, 4.76 mmol), ethanol (100 mL) and 10% palladium on charcoal (1 g). The reaction vessel was shaken on Parr hydrogenation apparatus. After 2 hours, the reaction mixture was filtered through a plug of Celite and washed with methanol. The resulting filtrate was concentrated under reduced pressure to 1.2 g of 4-(3-(4-methylpiperazin-1-yl)propoxy)benzene-1,2-diamine (95% yield), and was used without any further purification. MS (EI: 265 (MH+).

Synthesis of 5-(3-(4-methylpiperazin-1-yl)propoxy)-1H-benzo[d]imidazol-2-amine A 100 mL flasked was charged with 4-(3-(4-methylpiperazin-1-yl)propoxy)benzene-1,2-diamine (1.15 g, 4.35 mmol), water (50 mL) and acetic acid (2 mL) and stirred at room temperature for 15 minutes. The reaction mixture was placed in an ice bath and then charged with cyanogen bromide (0.526 g, 5 mmol). The reaction mixture was allowed to warm to room temperature and stirred over night. The reaction mixture was concentrated under reduced pressure and redissolved in acetone, dried over anhydrous sodium sulfate, and then filtered. The filtrate was concentrated under reduced pressure to give 1.7 g of 5-(3-(4-methylpiperazin-1-yl)propoxy)-1H-benzo[d]imidazol-2-amine diacetate. This material was used without any further purification. MS (EI): 290 (MH+).

Synthesis of $N^4$-(5-bromo-2-methylphenyl)-$N^5$-(5-{[3-(4-methylpiperazin-1-yl)propyl]oxy}-1H-benzimidazol-2-yl)-1H-imidazole-4,5-dicarboxamide $N^4$-(5-Bromo-2-methylphenyl)-$N^5$-(5-{[3-(4-methylpiperazin-1-yl)propyl]oxy}-1H-benzimidazol-2-yl)-1H-imidazole-4,5-dicarboxamide was prepared in a manner similar to $N^5$-1H-benzimidazol-2-yl-$N^4$-(2,4-dimethylphenyl)-1H-imidazole-4,5-dicarboxamide in Example 1 in 46% yield. $^1$H-NMR (400 MHz, d6-DMSO): δ 8.352 (s, 1H), 7.356 (s, 1H), 7.304 (d, br, 1H), 7.021 (s, br, 1h), 6.668 (q, 1H), 3.972 (t, 2H), 2.447 (t, 4H), 2.336 (s, 5H), 2.142 (s, 3H), 1.868 (t, 2H), 3.5 (s, br, 4H). MS (EI): 597.3 MH+).

Example 111

Synthesis of $N^4$-(5-bromo-2-methylphenyl)-$N^5$-{5-[(3-morpholin-4-ylpropyl)oxy]-1H-benzimidazol-2-yl}-1H-imidazole-4,5-dicarboxamide $N^4$-(5-Bromo-2-methylphenyl)-$N^5$-{5-[(3-morpholin-4-ylpropyl)oxy]-1H-benzimidazol-2-yl}-1H-imidazole-4,5-dicarboxamide was prepared in an analogous fashion to that used for $N^4$-(5-bromo-2-methylphenyl)-$N^5$-(5-{[3-(4-methylpiperazin-1-yl)propyl]oxy}-1H-benzimidazol-2-yl)-1H-imidazole-4,5-dicarboxamide in Example 110. $^1$H-NMR (400 MHz, DMSO-d6): δ 8.321 (s, 1H), 7.422 (s, 1H), 7.311 (d, br, 1H), 7.254 (d, 2H), 7.03 (s, br, 1H), 6.68 (q, 1H), 3.989 (t, 2H), 3.579 (t, 2H), 3.4 (s, 4H), 2.46 (t, 2H), 2.37 (t, 4H), 2.333 (s, 3H). MS (EI): 584.3 (MH+).

Example 112

Synthesis of $N^4$-(5-bromo-2-methylphenyl)-$N^5$-{5-[(3-piperidin-1-ylpropyl)oxy]-1H-benzimidazol-2-yl}-1H-imidazole-4,5-dicarboxamide $N^4$-(5-Bromo-2-methylphenyl)-$N^5$-{5-[(3-piperidin-1-ylpropyl)oxy]-1H-benzimidazol-2-yl}-1H-imidazole-4,5-dicarboxamide was prepared in an analogous fashion to that used for $N^4$-(5-bromo-2-methylphenyl)-$N^5$-(5-{[3-(4-methylpiperazin-1-yl)propyl]oxy}-1H-benzimidazol-2-yl)-1H-imidazole-4,5-dicarboxamide in Example 110. $^1$H-NMR (400 MHz, DMSO-d6): δ 8.325 (s, 1H), 7.403 (s, 1H), 7.254 (d, 2H), 7.025 (s, br, 1h), 6.675 (q, 1H), 3.97 (t, 2H), 3.4 (s, br, 2H), 2.398 (t, 2H), 2.379 (s, br, 5H), 1.848 (m, 2), 1.496 (m, 4H), 1.389 (m, 2H). MS (EI): 581 (M+).

Example 113

Synthesis of $N^4$-(2-bromo-5-methylphenyl)-$N^5$-{6-[(2-piperidin-1-ylethyl)oxy]-1H-benzimidazol-2-yl}-1H-imidazole-4,5-dicarboxamide $N^4$-(2-Bromo-5-methylphenyl)-$N^5$-{6-[(2-piperidin-1-ylethyl)oxy]-1H-benzimidazol-2-yl}-1H-imidazole-4,5-dicarboxamide was prepared in an analogous fashion to that used for $N^4$-(5-bromo-2-methylphenyl)-$N^5$-{5-[(2-piperazin-1-ylethyl)oxy]-1H-benzimidazol-2-yl}-1H-imidazole-4,5-dicarboxamide in Example 100. $^1$H-NMR (400 MHz, DMSO-d6): δ 12.04 (s, br, 1H), 10.36 (s, br, 1H), 8.15 (s, 1H), 7.96 (s, br, 1H), 7.34 (m, br, 3H), 7.05 (m, br, 1H), 6.76 (d, 1H), 4.06 (m, 2H), 2.69 (s, br, 2H), 2.30 (s, 3H), 1.51 (m, br, 4H), 1.39 (m, br, 2H), 1.20 (m, br, 2H), 0.86 (m, br, 2H). MS (EI): 566 (MH+).

Example 114

Synthesis of $N^4$-(5-bromo-2-methylphenyl)-$N,^5$-{6-[(3-pyrrolidin-1-ylpropyl)oxy]-1H-benzimidazol-2-yl}-1H-imidazole-4,5-dicarboxamide $N^4$-(5-Bromo-2-methylphenyl)-$N^5$-{6-[(3-pyrrolidin-1-ylpropyl)oxy]-1H-benzimidazol-2-yl}-1H-imidazole-4,5- dicarboxamide was prepared in an analogous fashion as to that used for N$^4$-(5-bromo-2-methylphenyl)-N$^5$-(5-{[3-(4-methylpiperazin-1-yl)propyl]oxy}-1H-benzimidazol-2-yl)-1H-imidazole-4,5-dicarboxamide in Example 110. $^1$H-NMR (400 MHz, DMSO-d6): 8.249 (s, 1H) 7.57 (s, 1H), 7.342-7.269 (m, 3H), 7.030 (s, 1H), 6.708 (q, 1H), 4.007 (t, 2H), 2.565 (t, 2H), 2.495 (m, 4H), 2333 (s, 3H), 1.893 (m, 2H), 1.683 (m, 4H). MS (EI): 584.3 (MH+).

Example 115

Synthesis of N$^5$-(5-bromo-2-methylphenyl)-N$^4$-(3-phenyl-1H-pyrazol-5-yl)-1H-imidazole-4,5-dicarboxamide N$^5$-(5-Bromo-2-methylphenyl)-N$^4$-(3-phenyl-1H-pyrazol-5-yl)-1H-imidazole-4,5-dicarboxamide was prepared in an analogous fashion as to N$^5$-1H-benzimidazol-2-yl-N$^4$-(2,4-dimethylphenyl)-1H-imidazole-4,5-dicarboxamide in Example 1. $^1$H-NMR (400 MHz, DMSO-d6): δ 13.0 (s, br, 1H), 8.10 (s, 1H), 7.98 (s, 1H), 7.78 (m, 2H), 7.64 (m, 2H), 7.38 (m, 2H), 7.24 (s, 1H), 7.0 (s, br, 1H), 2.30 (s, 3H). MS (EI): 466 (MH+).

Example 116

Synthesis of N$^5$-(2,6-dichlorophenyl)-N$^4$-{6-[(3-pyrrolidin-1-ylpropyl)oxy]-1H-benzimidazol-2-yl}-1H-imidazole-4,5-dicarboxamide N$^5$-(2,6-Dichlorophenyl)-N$^4$-{6-[(3-pyrrolidin-1-ylpropyl)oxy]-1H-benzimidazol-2-yl}-1H-imidazole-4,5-dicarboxamide was prepared in a manner analogous to that used for N$^4$-(5-bromo-2-methylphenyl)-N$^5$-(5-{[3-(4-methylpiperazin-1-yl)propyl]oxy}-1H-benzimidazol-2-yl)-1H-imidazole-4,5-dicarboxamide in Example 110. $^1$H-NMR (400 MHz, DMSO-d6): δ 8.4 (s, 1H) 7.57 (s, 1H), 7.342-7.30 (m, 3H), 7.030 (s, 1H), 6.708 (q, 1H), 4.007 (t, 2H), 2.565 (t, 2H), 2.495 (m, 4H), 1.893 (m, 2H), 1.683 (m, 4H). MS (EI): 543 (MH+).

Example 117

Synthesis of N$^4$-(5-bromo-2-methylphenyl)-N$^5$-{6-[(2-pyrrolidin-1-ylethyl)oxy]-1H-benzimidazol-2-yl}-1H-imidazole-4,5-dicarboxamide N$^4$-(5-Bromo-2-methylphenyl)-N$^5$-{6-[(2-pyrrolidin-1-ylethyl)oxy]-1H-benzimidazol-2-yl}-1H-imidazole-4,5-dicarboxamide was prepared in a manner analogous to that used for N$^4$-(5-bromo-2-methylphenyl)-N$^5$-(5-{[3-(4-methylpiperazin-1-yl)propyl]oxy}-1H-benzimidazol-2-yl)-1H-imidazole-4,5-dicarboxamide in Example 110. $^1$H-NMR (400 MHz, DMSO-d6): δ 8.03 (d, 2H), 7.37 (m, 2H), 7.29 (d, 1H), 7.05 (s, 1H), 6.75 (m, 1H), 4.05 (m, 2H), 2.80 (t, 2H), 2.31 (s, 3H), 1.69 (m, 4H). MS (EI): 552 (MH+).

Example 118

Synthesis of N$^4$-(2,6-dichlorophenyl)-N$^5$-(5-{[2-(diethylamino)ethyl]oxy}-1H-benzimidazol-2-yl)-1H-imidazole-4,5-dicarboxamide N$^4$-(2,6-Dichlorophenyl)-N$^5$-(5-{[2-(diethylamino)ethyl]oxy}-1H-benzimidazol-2-yl)-1H-imidazole-4,5-dicarboxamide was prepared in a manner analogous to that used for N$^4$-(5-bromo-2-methylphenyl)-N$^5$-{5-[(2-piperazin-1-ylethyl)oxy]-1H-benzimidazol-2-yl}-1H-imidazole-4,5-dicarboxamide in Example 100. $^1$H-NMR (400 MHz, DMSO-d6): δ 10.7 (s, br, 1H), 9.38 (s, br, 1H), 8.2 (s, 1H), 7.64 (d, 2H), 7.48 (t, 1H), 7.4 (d, 1H), 7.07 (s, 1H), 6.83 (d, 1H), 4.3 (t, 2H), 3.54 (t, 2H), 3.25 (q, 4H), 1.25 (t, 6H). MS (EI): 530 (MH+).

Example 119

Synthesis of N$^4$-(2,6-dichlorophenyl)-N$^5$-{6-[(2-piperidin-1-ylethyl)oxy]-1H-benzimidazol-2-yl}-1H-imidazole-4,5-dicarboxamide N$^4$-(2,6-Dichlorophenyl)-N$^5$-{6-[(2-piperidin-1-ylethyl)oxy]-1H-benzimidazol-2-yl}-1H-imidazole-4,5-dicarboxamide was prepared in a manner analogous to that used for N$^4$-(5-bromo-2-methylphenyl)-N$^5$-{5-[(2-piperazin-1-ylethyl)oxy]-1H-benzimidazol-2-yl}-1H-imidazole-4,5-dicarboxamide in Example 100. $^1$H-NMR (400 MHz, DMSO-d6): δ 7.94 (s, 1H), 7.61 (d, 2H), 7.43 (t, 1H), 7.28 (d, br, 1H), 6.98 (s, br, 1H), 6.71 (d, 1H), 4.03 (m, 2H), 2.65 (m, 2H), 2.43 (s, br, 4H), 1.49 (m, br, 4H), 1.37 (m, br, 2H). MS (EI): 542 (MH+).

Example 120

Synthesis of 1,1-dimethylethyl 4-{3-[(2-{[(4-{[(5-bromo-2-methylphenyl)amino]carbonyl}-1H-imidazol-5-yl)carbonyl]amino}-1H-benzimidazol-5-yl)oxy]propyl}piperazine-1-carboxylate 1,1-Dimethylethyl 4-{3-[(2-{[(4-{[(5-bromo-2-methylphenyl)amino]carbonyl}-1H-imidazol-5-yl)carbonyl]amino}-1H-benzimidazol-5-yl)oxy]propyl}piperazine-1-carboxylate dicarboxamide was prepared in a manner analogous to that used for N$^4$-(5-bromo-2-methylphenyl)-N$^5$-(5-{[3-(4-methylpiperazin-1-yl)propyl]oxy}-1H-benzimidazol-2-yl)-1H-imidazole-4,5-dicarboxamide in Example 110. $^1$H-NMR (400 MHz, DMSO-d6): δ 8.116 (s, 1H), 7.826 (s, br, 1H), 7.348-7.328 (m, 2H), 7.267 (d, 1H), 7.033 (s, br, 1H), 3.734-6.707 (q, 1H), 3.989 (t, 2H), 3.3 (m, 4H), 2.473 (t, 2H), 2.33 (m, 7H), 1.887 (m, 2H), 1.405 (s, 9H). MS (EI): 683.1 (MH+).

Example 121

Synthesis of N$^4$-(5-bromo-2-methylphenyl)-N$^5$-{5-[(3-piperazin-1-ylpropyl)oxy]-1H-benzimidazol-2-yl}-1H-imidazole-4,5-dicarboxamide Hydrochloride N$^4$-(5-Bromo-2-methylphenyl)-N$^5$-{5-[(3-piperazin-1-ylpropyl)oxy]-1H-benzimidazol-2-yl}-1H-imidazole-4,5-dicarboxamide was prepared in a manner analogous to that used for N$^4$-(5-bromo-2-methylphenyl)-N$^5$-(5-{[3-(4-methylpiperazin-1-yl)propyl]oxy}-1H-benzimidazol-2-yl)-1H-imidazole-4,5-dicarboxamide in Example 110. $^1$H-NMR (400 MHz, DMSO-d6): δ 12.3 (s, br, 1H), 10.2 (s, br, 2H), 8.35 (s, 1H), 7.9 (s, br, 1H), 7.55 (d, 1H), 7.45 (d, 1H), 7.3 (d, 1H), 7.15 (s, br, 1H), 7.0 (d, 1H), 4.13 (t, 2H), 3.75 (s, br, 4H), 3.5 (s, 4H), 3.35 (t, 2H), 2.35 (s, 3H), 2.25 (m, 2H). MS (EI): 583.1 (MH+).

Example 122

Synthesis of N$^4$-(5-bromo-2-methylphenyl)-N$^5$-[5-({3-[4-(2-hydroxyethyl)piperazin-1-yl]propyl}oxy)-1H-benzimidazol-2-yl]-1H-imidazole-4,5-dicarboxamide N$^4$-(5-Bromo-2-methylphenyl)-N$^5$-[5-({3-[4-(2-hydroxyethyl)piperazin-1-yl]propyl}oxy)-1H-benzimidazol-2-yl]-

1H-imidazole-4,5-dicarboxamide was prepared in a manner analogous to that used for $N^4$-(5-bromo-2-methylphenyl)-N+-(5-{[3-(4-methylpiperazin-1-yl)propyl]oxy}-1H-benzimidazol-2-yl)-1H-imidazole-4,5-dicarboxamide. This compound was made from N-(hydroxyethyl)piperazine (commercially available from Acros) and 3-bromopropoxy)-2-nitroaniline resulting in the formation of 3-(4-(2-(4-amino-3-nitrophenoxy)ethyl)piperazin-1-yl)propan-1-ol. Catalytic hydrogenation gave 3-(4-(2-(3,4-diaminophenoxy)ethyl)piperazin-1-yl)propan-1-ol, which was subsequently converted into 3-(4-(2-(2-amino-1H-benzo[d]imidazol-5-yloxy)ethyl)piperazin-1-yl)propan-1-ol. Dioxo-5H,10H-diimidazo[1,5-a; 1',5'-d]pyrazine-1,6-dicarbonyl dichloride was then sequentially reacted with 3-(4-(2-(2-amino-1H-benzo[d]imidazol-5-yloxy)ethyl)piperazin-1-yl)propan-1-ol, in the presence of DIPEA, in anhydrous THF to give $N^4$-(5-bromo-2-methylphenyl)-$N^5$-[5-({3-[4-(2-hydroxyethyl)piperazin-1-yl]propyl}oxy)-1H-benzimidazol-2-yl]-1H-imidazole-4,5-dicarboxamide. $^1$H-NMR (400 MHz, DMSO-d6): δ 8.116 (d, 1H), 8.091 (s, 1H), 7.578 (d, 1H), 7.342 (q, 1H), 7.257 (d, 1H), 7.2 (d, 1H), 7.112 (q, 1H), 4.2 (t, 2H), m 3.914 (t, 2H), 3.74-3.693 (d, br, 8H), 3.465 (t, 2H), 3.39 (t, 2H), 2.375 (t, 3H), 2.31 (m, 2H). MS (EI): 627.3 (MH+).

Example 123

Synthesis of $N^4$-(2,6-dichlorophenyl)-$N^5$-{5-[(3-piperidin-1-ylpropyl)oxy]-1H-benzimidazol-2-yl}-1H-imidazole-4,5-dicarboxamide $N^4$-(2,6-Dichlorophenyl)-$N^5$-{5-[(3-piperidin-1-ylpropyl)oxy]-1H-benzimidazol-2-yl}-1H-imidazole-4,5-dicarboxamide was prepared in a manner analogous to that used for $N^4$-(5-bromo-2-methylphenyl)-$N^5$-(5-{[3-(4-methylpiperazin-1-yl)propyl]oxy}-1H-benzimidazol-2-yl)-1H-imidazole-4,5-dicarboxamide. benzimidazol-2-yl)-1H-imidazole-4,5-dicarboxamide in Example 110. $^1$H-NMR (400 MHz, DMSO-d6): δ 7.813 (s, 1H), 7.616 (d, 2H), 7.13 (t, 1H). 7.278 (d, 1H), 6.974 (s, br, 1H), 6.708 (d, 1H), 3.956 (t, 2H), 2.411-2.331 (m, 6H), 1.856 (m, 2H), 1.488 (m, 4H), 1.369 (m, 2H). MS (EI): 556.1 (MH+).

Example 124

Synthesis of 1,1-dimethylethyl 4-{3-[(2-{[(4-{[(2,6-dichlorophenyl)amino]carbonyl}-1H-imidazol-5-yl)carbonyl]amino}-1H-benzimidazol-5-yl)oxy]propyl}piperazine-1-carboxylate 1,1-Dimethylethyl 4-{3-[(2-{[(4-{[(2,6-dichlorophenyl)amino]carbonyl}-1H-imidazol-5-yl)carbonyl]amino}-1H-benzimidazol-5-yl)oxy]propyl}piperazine-1-carboxylate was prepared in a manner analogous to that used for $N^4$-(5-bromo-2-methylphenyl)-$N^5$-(5-{[3-(4-methylpiperazin-1-yl)propyl]oxy}-1H-benzimidazol-2-yl)-1H-imidazole-4,5-dicarboxamide in Example 110. $^1$H-NMR (400 MHz, DMSO-d6): δ 7.666 (s, br, 1H), 7.605 (d, 2H), 7.394 (t, 1H), 7.277 (s, br, 1H), 6.944 (s, br, 1H), 6.677 (q, 1H), 3.967 (t, 2H), 3.3 (t, 4H), 2.444 (t, 2H), 2.333 (t, 4H), 1.855 (m, 2H), 1.389 (s, 9H). MS (EI): 657.3 (MH+).

Example 125

Synthesis of $N^4$-(2,6-dichlorophenyl)-$N^5$-{5-[(3-piperazin-1-ylpropyl)oxy]-1H-benzimidazol-2-yl}-1H-imidazole-4,5-dicarboxamide $N^4$-(2,6-Dichlorophenyl)-$N^5$-{5-[(3-piperazin-1-ylpropyl)oxy]-1H-benzimidazol-2-yl}-1H-imidazole-4,5-dicarboxamide was prepared in a manner analogous to that used for $N^4$-(5-bromo-2-methylphenyl)-$N^5$-(5-{[3-(4-methylpiperazin-1-yl)propyl]oxy}-1H-benzimidazol-2-yl)-1H-imidazole-4,5-dicarboxamide in Example 110. $^1$H-NMR (400 MHz, DMSO-d6): δ 8.129 (s, 1H), 7.563-7.528 (m, 3H), 7.406 (t, 1H), 7.228 (d, 1H), 7.105 (q, 1H), 4.205 (t, 2H), 3.748-3.652 (m, 6H), 3.589-3.522 (m, 4H), 2.378 (m, 2H). MS (EI): 557.1 (MH+).

Example 126

Synthesis of $N^4$-(2,6-dichlorophenyl)-$N^5$-{6-[(2-pyrrolidin-1-ylethyl)oxy]-1H-benzimidazol-2-yl}-1H-imidazole-4,5-dicarboxamide $N^4$-(2,6-Dichlorophenyl)-$N^5$-{6-[(2-pyrrolidin-1-ylethyl)oxy]-1H-benzimidazol-2-yl}-1H-imidazole-4,5-dicarboxamide was prepared in a manner analogous to that used for $N^4$-(5-bromo-2-methylphenyl)-$N^5$-{5-[(2-piperazin-1-ylethyl)oxy]-1H-benzimidazol-2-yl}-1H-imidazole-4,5-dicarboxamide in Example 100. $^1$H-NMR (400 MHz, DMSO-d6): δ 8.15 (s, 1H), 7.64 (d, 2H), 7.46 (t, 1H), 6.74 (m, 1H), 4.05 (t, 2H), 2.80 (m, 2H), 2.55 (m, 4H), 1.69 (m, 4H). MS (EI): 528 (MH+).

Example 127

Synthesis of $N^4$-(5-bromo-2-methylphenyl)-$N^5$-{2-methyl-4-[(piperidin-4-ylmethyl)oxy]phenyl}-1H-imidazole-4,5-dicarboxamide hydrochloride $N^4$-(5-bromo-2-methylphenyl)-$N^5$-{2-methyl-4-[(piperidin-4-ylmethyl)oxy]phenyl}-1H-imidazole-4,5-dicarboxamide hydrochloride was prepared in a manner analogous to that used for 1,1-dimethylethyl 4-{[(2-{[(4-{[(2,4-dimethylphenyl)amino]carbonyl}-1H-imidazol-5-yl)carbonyl]amino}-1H-benzimidazol-5-yl)oxy]methyl}piperidine-1-carboxylate in Example 12, followed by removal of the Boc protecting group using hydrogen chloride. $^1$H-NMR (400 MHz, DMSO-d6): δ 8.97 (d, 1H), 8.63 (d, 1H), 8.13 (s, 1H), 8.05 (s, 1H), 7.53 (d, 1H), 7.29 (dd, 1H), 7.23 (d, 1H), 6.88 (d, 1H), 6.82 (dd, 1H), 3.86 (d, 2H), 2.90 (m, 4H), 2.7 (d, 6H), 1.92 (d, 2H), 1.44-1.54 (m, 4H), MS (EI): 527.3 (MH+).

Example 128

Synthesis of $N^5$-(5-bromo-2-methylphenyl)-N,$^4$-(5-cyclopropyl-1H-pyrazol-3-yl)-1H-imidazole-4,5-dicarboxamide $N^5$-(5-Bromo-2-methylphenyl)-$N^4$-(5-cyclopropyl-1H-pyrazol-3-yl)-1H-imidazole-4,5-dicarboxamide was prepared in an analogous fashion as $N^5$-1H-benzimidazol-2-yl-$N^4$-(2,4-dimethylphenyl)-1H-imidazole-4,5-dicarboxamide as in Example 1. $^1$H-NMR (400 MHz, DMSO-d6): 13.6 (s, br, 1H), 13.0 (s, br, 1H), 10.19 (s, br, 1H), 8.02 (s, 1H), 7.95 (s, br, 1H), 7.38 (s, br, 1H), 7.25 (m, 1H), 6.37 (s, 1H), 1.91 (m, 1H), 0.93 (m, 2H), 0.71 (m, 2H). MS (EI): 430 (MH+).

Example 129

Synthesis of N⁴-(2,4-dimethylphenyl)-N⁵-{2-methyl-4-[(piperidin-4-ylmethyl)oxy]phenyl}-1H-imidazole-4,5-dicarboxamide N⁴-(2,4-Dimethylphenyl)-N⁵-{2-methyl-4-[(piperidin-4-ylmethyl)oxy]phenyl}-1H-imidazole-4,5-dicarboxamide was prepared in a manner analogous to that used for 1,1-dimethylethyl 4-{[(2-{[(4-{[(2,4-dimethylphenyl)amino]carbonyl}-1H-imidazol-5-yl)carbonyl]amino}-1H-benzimidazol-5-yl)oxy]methyl}piperidine-1-carboxylate in Example 12 followed by removal of the Boc group with 4M hydrogen chloride in 1,4-dioxane. ¹H-NMR (400 MHz, DMSO-d6) δ 13.2 (bs, 1H), 10.25 (bs, 2H), 8.92 (s, 1H), 7.59 (d, 2H), 7.21 (d, 1H), 7.01 (s, 1H), 6.84 (d, 2H), 3.92 (s, 2H), 2.74 (m, 4H), 2.24 (S, 3H), 2.16 (s, 3H), 2.00 (m, 1H), 1.46 (m, 4H). (MS (EI): 462 (MH+).

Example 130

1,1-dimethylethyl 4-{[(4-{[(4-{[(5-bromo-2-methylphenyl)amino]carbonyl}-1H-imidazol-5-yl)carbonyl]amino}phenyl)oxy]methyl}piperidine-1-carboxylate

Example 131

N⁴-(5-Bromo-2-methylphenyl)-N⁵-{4-[(piperidin-4-ylmethyl)oxy]phenyl}-1H-imidazole-4,5-dicarboxamide

Synthesis of 1,1-dimethylethyl 4-{[(4-{[(4-{[(5-bromo-2-methylphenyl)amino]carbonyl}-1H-imidazol-5-yl)carbonyl]amino}phenyl)oxy]methyl}piperidine-1-carboxylate and N⁴-(5-Bromo-2-methylphenyl)-N⁵-{4-[(piperidin-4-ylmethyl)oxy]phenyl}-1H-imidazole-4,5-dicarboxamide

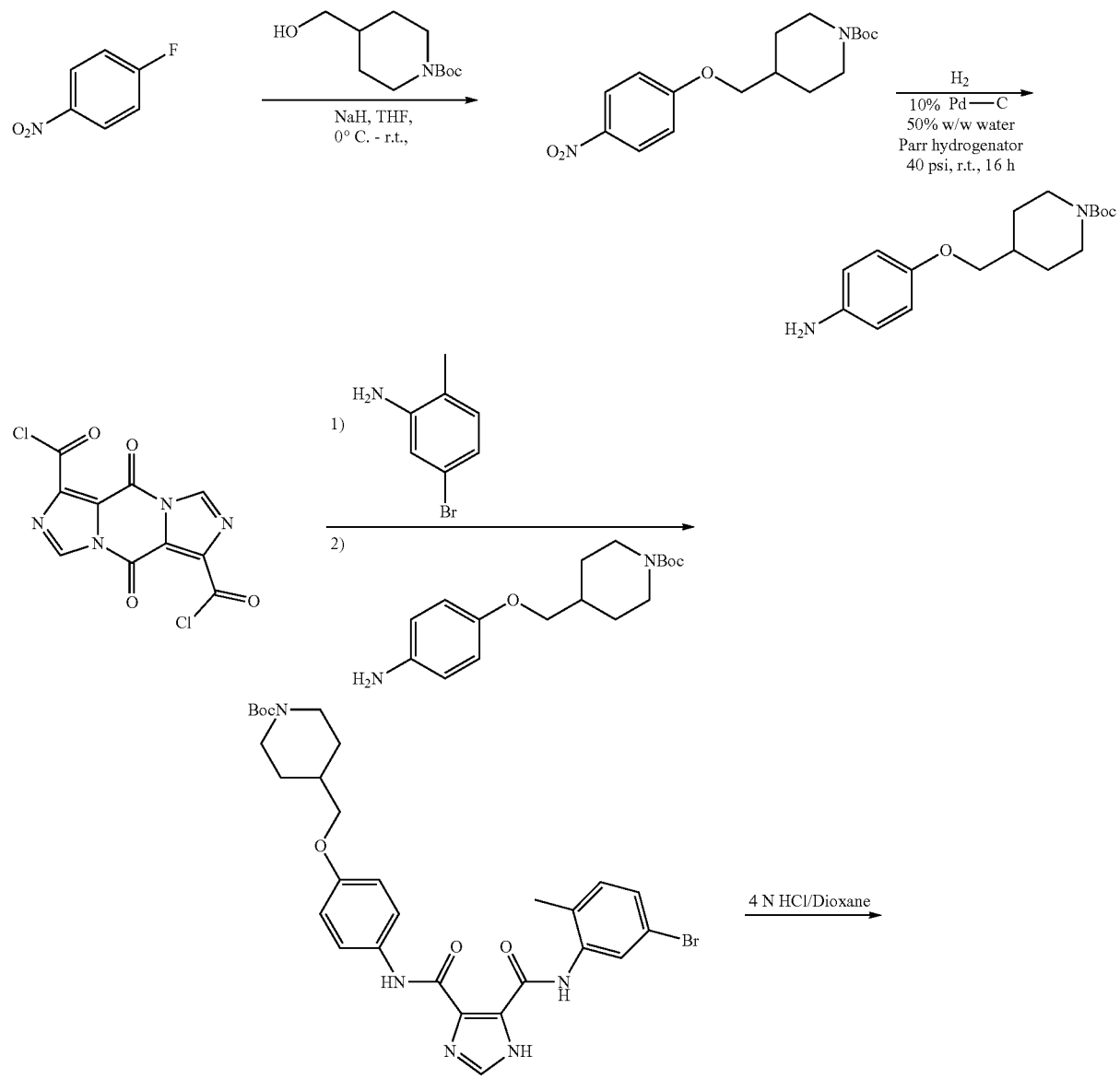

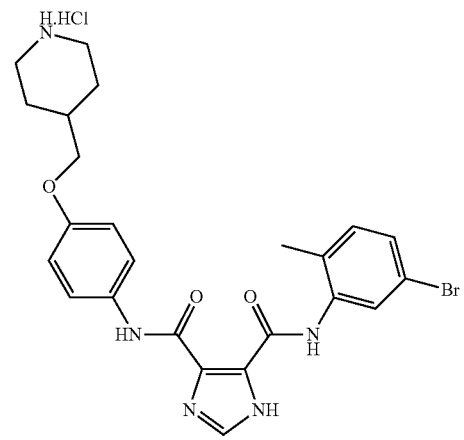

Synthesis of tert-butyl 4-((4-nitroxy)methyl)piperidine-1-carboxylate

Sodium hydride (60% in oil, 75 mmoles, 1.80 g) was gradually added to a stirred solution of N-Boc-pioperidine-4-methanol (70 mmoles, 15.07 g, commercially available from Astatech) in anhydrous THF (125 ml) at room temperature. Upon completion of addition the reaction mixture was allowed to stir at room temperature for 1 hour. 4-Fluoronitrobenzene (69 mmoles, 9.87 g, 7.45 ml), commercially available from Aldrich) was added in a drop wise fashion. Upon completion of addition, the reaction mixture was stirred for a further 18 hours at room temperature. The reaction was quenched with water, and the mixture extracted with dichloromethane (3×200 ml). The combined organic mixture was washed with water, dried over anhydrous magnesium sulfate, filtered, and evaporated under reduced pressure. The resulting solid was triturated with hexane, filtered, and air dried to give 7.52 g of tert-butyl 4-((4-aminophenoxy)methyl)piperidine-1-carboxylate. $^1$H-NMR (DMSO-d6). δ 8.20 (d, 2H), 7.09 (d, 2H), 3.90 (s, 2H), 3.34 (m, 4H), 2.00 (m, 1H), 1.46 (m., 4H), 1.42 (s, 9H). MS (EI): 337 (MH+).

Synthesis of tert-butyl 4-((4-aminophenoxy)methyl)piperidine-1-carboxylate

A hydrogenation vessel was charged with tert-butyl 4-((4-nitroxy)methyl)piperidine-1-carboxylate (4.53 g, 126 mmoles) in ethyl acetate (200 ml) and methanol (50 ml)) and 10% palladium on charcoal (1 g, 50% w/w water). The reaction vessel was shaken on Parr hydrogenation apparatus. After 2 hours, the reaction mixture was filtered through a plug of Celite and washed with methanol. The resulting filtrate was concentrated under reduced pressure to a solid which was triturated with hexane to give 3.44 g of tent-butyl 4-((4-aminophenoxy)methyl)piperidine-1-carboxylate. (89% yield), and was used without any further purification. $^1$H-NMR (400 MHz, DMSO-d6). 6.52 (d, 2H), 6.35 (d, 2H), 5.85 (br s, 2H), 3.90 (s, 2H), 3.34 (m, 4H), 2.00 (m, 1H), 1.46 (m, 4H), 1.42 (s, 9H). MS (EI): 307 (MH+).

Example 132

Synthesis of 1,1-dimethylethyl 4-{[(4-{[(4-{[(5-bromo-2-methylphenyl)amino]carbonyl}-1H-imidazol-5-yl)carbonyl]amino}phenyl)oxy]methyl}piperidine-1-carboxylate 1,1-Dimethylethyl 4-{[(4-{[(4-{[(5-bromo-2-methylphenyl)amino]-carbonyl}1H-imidazol-5-yl)carbonyl] amino}phenyl)oxy]-methyl}piperidine-1-carboxylate was prepared in a manner analogous to that used for 1,1-dimethylethyl 4-{[(2-{[(4-{[(2,4-dimethylphenyl)amino]carbonyl}-1H-imidazol-5-yl)carbonyl]amino}-1H-benzimidazol-5-yl)oxy]methyl}piperidine-1-carboxylate in Example 12. $^1$H-NMR (400 MHz, DMSO-d6) 13.20 (bs, 1H), 10.25 (bs, 2H), 8.93 (s, 1H), 7.69 (s, 1H), 7.59 (d, 2H), 7.05 (, 1H), 6.93 (m, 1H), 6.83 (d, 2H), 3.92 (M, 2H), 3.34 (m, 4H), 2.35 (s, 3H), 2.00 (m, 1H), 1.46 (m, 4H), 1.43 (s, 9H). MS (EI): 613 (MH+).

Example 133

Synthesis of $N^4$-(5-Bromo-2-methylphenyl)-$N^5$-{4-[(piperidin-4-ylmethyl)oxy]phenyl}-1H-imidazole-4,5-dicarboxamide hydrochloride $N^4$-(5-Bromo-2-methylphenyl)-$N^5$-{4-[(piperidin-4-ylmethyl)oxy]phenyl}-1H-imidazole-4,5-dicarboxamide was prepared in a manner analogous to that used for $N^4$-(5-bromo-2-methylphenyl)-$N^5$-{4-[(piperidin-4-ylmethyl)oxy]phenyl}-1H-imidazole-4,5-dicarboxamide. $^1$H-NMR (400 MHz, DMSO-d6) δ 14.00 (br s, 1H), 11.82 (br s, 1H), 11.62 (br s, 1H), 9.12 (br s, 1H), 8.78 (br s, 1H), 8.15 (s, 1H), 8.08 (s, 1H), 7.90 (d, 2H), 7.29 (m, 2H), 6.97 (d, 2H), 3.85 (d, 2H), 3.37 (d, 2H), 2.87 (q, 2H), 2.32 (s, 3H), 2.05 (m, 1H), 1.92 (m, 2H), 1.52 (m, 2H). MS (EI): 513 (MH+).

Example 134

Synthesis of $N^4$-(2,6-dichlorophenyl)-$N^5$-(4,5-dimethyl-1H-imidazol-2-yl)-1H-imidazole-4,5-dicarboxamide $N^4$-(2,6-Dichlorophenyl)-$N^5$-(4,5-dimethyl-1H-imidazol-2-yl)-1H-imidazole-4,5-dicarboxamide was prepared in a manner analogous to that used for $N^4$-(5-bromo-2-methylphenyl)-$N^5$-(4,5-dimethyl-1H-imidazol-2-yl)-1H-imidazole-4,5-dicarboxamide in Example 109 in 46% yield. $^1$H-NMR ((400 MHz, DMSO-d6): δ 13.55 (s, 1H), 11.22 (s, 1H), 8.20 (s, 1H), 7.63 (d, 2H), 7.45 (t, 1H), 2.05 (s, 6H). MS (EI): 394 (MH+).

Example 135

Synthesis of $N^4$-(5-bromo-2-methylphenyl)-$N^5$-(3-chloro-4-methyl-1H-pyrazol-5-yl)-1H-imidazole-4,5-dicarboxamide $N^4$-(5-Bromo-2-methylphenyl)-$N^5$-(3-chloro-4-methyl-1H-pyrazol-5-yl)-1H-imidazole-4,5-dicarboxamide was prepared in a manner analogous to that used for $N^5$-1H-benzimidazol-2-yl-$N^4$-(2,4-dimethylphenyl)-1H-imidazole-4,5-dicarboxamide in Example 1 in 23% yield. $^1$H-NMR (400 MHz, DMSO-d6): δ 8.09 (s, 1H), 7.99 (s, 1H), 7.28 (dd, 1H), 7.21 (d, 1H), 2.24 (s, 3H), 2.19 (s, 3H). MS (EI): 435.0 (MH+).

Example 136

Synthesis of $N^4$-(5-bromo-2-methylphenyl)-$N^5$-(3-methyl-1H-pyrazol-5-yl)-1H-imidazole-4,5-dicarboxamide $N^4$-(5-Bromo-2-methylphenyl)-$N^5$-(3-methyl-1H-pyrazol-5-yl)-1H-imidazole-4,5-dicarboxamide was prepared in a manner analogous to that used for $N^5$-1H-benzimidazol-2-yl-$N^4$-(2,4-dimethylphenyl)-1H-imidazole-4,5-dicarboxamide in Example 1 in 37% yield. $^1$H-NMR (400 MHz, DMSO-d6): δ 8.05 (s, 2H), 7.35 (dd, 1H), 7.27 (d, 1H), 6.43 (s, 1H), 2.31 (s, 3H), 2.24 (s, 3H). MS (EI): 402.9 (MH+).

Example 137

Synthesis of $N^4$-(5-bromo-2-methylphenyl)-$N^5$-1H-pyrazol-5-yl-1H-imidazole-4,5-dicarboxamide $N^4$-(5-Bromo-2-methylphenyl)-$N^5$-1H-pyrazol-5-yl-1H-imidazole-4,5-dicarboxamide was prepared in a manner analogous to that used for $N^5$-1H-benzimidazol-2-yl-$N^4$-(2,4-dimethylphenyl)-1H-imidazole-4,5-dicarboxamide in Example 1 in 37% yield. $^1$H-NMR (400 MHz, DMSO-d6): δ 8.07 (s, 2H), 7.69 (d, 1H), 7.35 (dd, 1H), 7.27 (d, 1H), 6.65 (d, 1H), 2.31 (s, 3H). MS (EI): 388.9 (MH+).

Example 138

Synthesis of $N^4$-(5-bromo-2-methylphenyl)-$N^5$-(5,6-dichloro-1H-benzimidazol-2-yl)-1H-imidazole-4,5-dicarboxamide

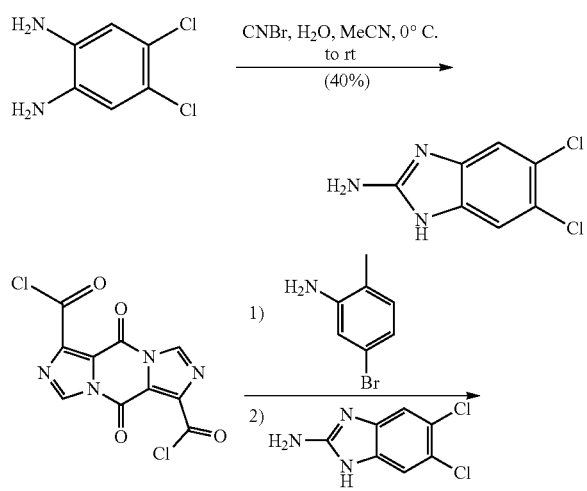

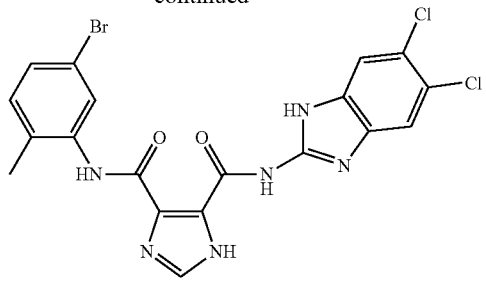

Synthesis of 5,6-dichloro-1H-benzo[d]imidazol-2-amine 4,5-Dichlorobenzene-1,2-diamine (0.81 g, 0.562 mmol, commercially available from Aldrich) in acetonitrile (10 mL) and water (2 ml) at 0° C. was treated with cyanogen bromide (0.063 g, 0.6 mmol). The reaction mixture was allowed to warm to room temperature, and then stirred for 14 hours. The reaction mixture was then treated with saturated aqueous sodium hydrogen carbonate solution (50 ml) and shaken. The resulting solid was filtered off, washed with water, and dried under reduced pressure to give 0.43 g of 5,6-difluoro-1H-benzo[d]imidazol-2-amine (yield, 50%). MS (EI): 203 (MH+).

Synthesis of $N^4$-(5-bromo-2-methylphenyl)-$N^5$-(5,6-dichloro-1H-benzimidazol-2-yl)-1H-imidazole-4,5-dicarboxamide $N^4$-(5-Bromo-2-methylphenyl)-$N^5$-(5,6-dichloro-1H-benzimidazol-2-yl)-1H-imidazole-4,5-dicarboxamide was prepared in a manner analogous to that used for $N^5$-1H-benzimidazol-2-yl-$N^4$-(2,4-dimethylphenyl)-1H-imidazole-4,5-dicarboxamide in Example 1 in 39% yield. $^1$H-NMR (400 MHz, DMSO-d6): δ 10.39 (s, br, 1H), 8.21 (s, 1H), 7.89 (s, 1H), 7.71 (s, 2H), 7.41 (d, 1H), 7.31 (d, 2H), 2.29 (s, 3H). MS (EI): 475.2 (MH+).

Example 139

Synthesis of $N^4$-(2-chloro-6-fluorophenyl)-$N.^5$-(4,5-dimethyl-1H-imidazol-2-yl)-1H-imidazole-4,5-dicarboxamide $N^4$-(2-Chloro-6-fluorophenyl)-$N.^5$-(4,5-dimethyl-1H-imidazol-2-yl)-1H-imidazole-4,5-dicarboxamide was prepared in analogous manner used for $N^4$-(5-bromo-2-methylphenyl)-$N^5$-(4,5-dimethyl-1H-imidazol-2-yl)-1H-imidazole-4,5-dicarboxamide in Example 109 in 39% yield. $^1$H-NMR (400 MHz, DMSO-d6): δ 8.43 (s, 1H), 7.59 (d, 1H), 7.05 (m, 2H), 2.41 (s, 3H), 2.32 (s, 3H). MS (EI): 376.9 (MH+).

Example 140

Synthesis of $N^4$-(5-bromo-2-methylphenyl)-$N^5$-(5,6-difluoro-1H-benzimidazol-2-yl)-1H-imidazole-4,5-dicarboxamide

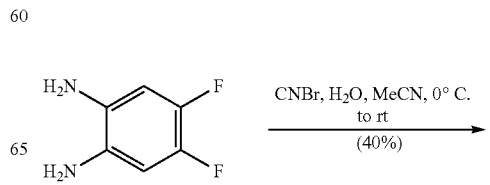

-continued

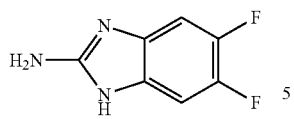

Synthesis of 5,6-difluoro-1H-benzo[d]imidazol-2-amine 4,5-Difluorobenzene-1,2-diamine (0.651 g, 0.562 mmol, commercially available from Matrix Scientific) in acetonitrile (10 mL) and water (2 ml) at 0° C. was treated with cyanogen bromide (0.063 g, 0.6 mmol). The reaction mixture was allowed to warm to room temperature, and then stirred for 14 hours. The reaction mixture was then treated with saturated aqueous sodium hydrogen carbonate solution (50 ml) and shaken. The resulting solid was filtered off, washed with water and dried under reduced pressure to give 0.39 g of 5,6-difluoro-1H-benzo[d]imidazol-2-amine (yield, 40%). MS (EI): 186 (MH+).

Synthesis of $N^4$-(5-bromo-2-methylphenyl)-$N^5$-(5,6-difluoro-1H-benzimidazol-2-yl)-1H-imidazole-4,5-dicarboxamide $N^4$-(5-Bromo-2-methylphenyl)-$N^5$-(5,6-difluoro-1H-benzimidazol-2-yl)-1H-imidazole-4,5-dicarboxamide was made in a analogous manner to that used for $N^4$-(5-bromo-2-methylphenyl)-$N^5$-(5,6-dichloro-1H-benzimidazol-2-yl)-1H-imidazole-4,5-dicarboxamide in Example 1 in 44% yield. $^1$H-NMR (400 MHz, DMSO-d6): δ 10.41 (s, br, 1H), 8.20 (s, 1H), 7.95 (s, 1H), 7.52-7.48 (m, 2H), 7.41 (d, 1H), 7.31 (d, 2H), 2.29 (s, 3H). MS (EI): 475.2 (MH+).

Example 141

Synthesis of $N^5$-(2-chloro-6-fluorophenyl)-$N^4$-{2-methyl-4-[(piperidin-4-ylmethyl)oxy]phenyl}-1H-imidazole-4,5-dicarboxamide Hydrochloride

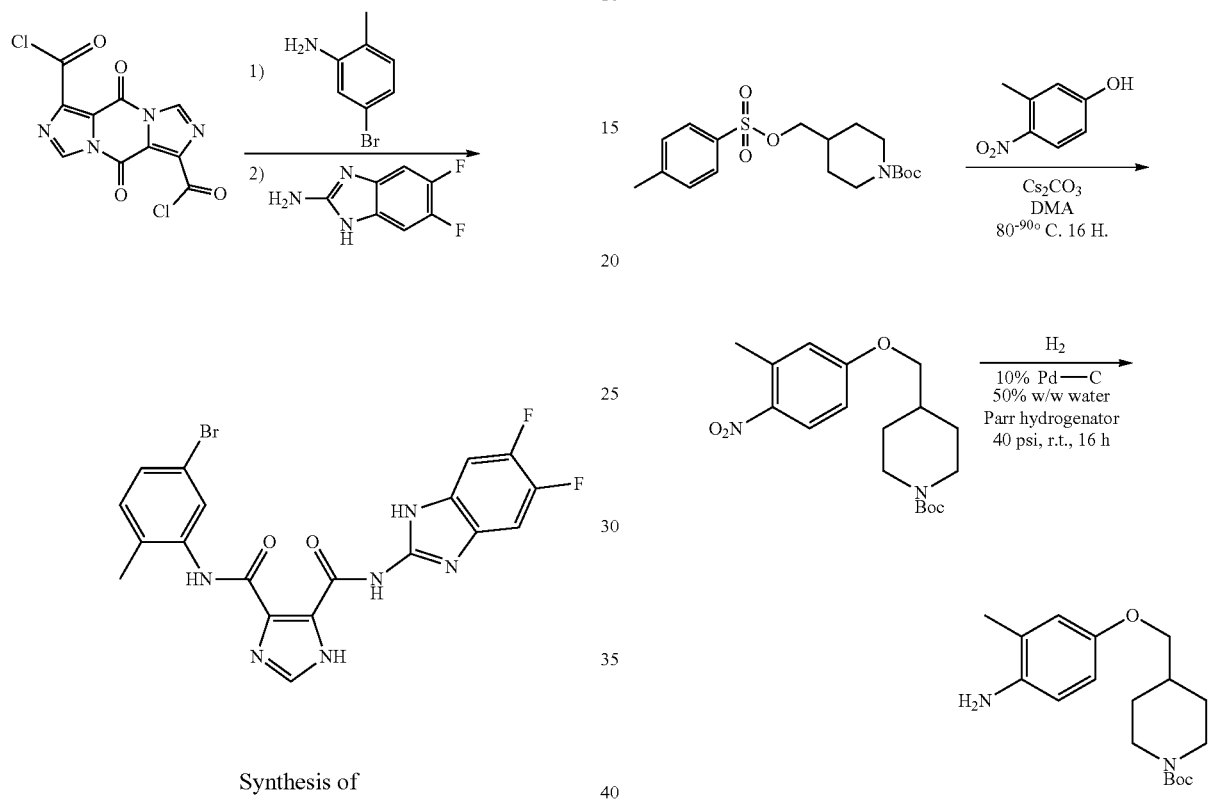

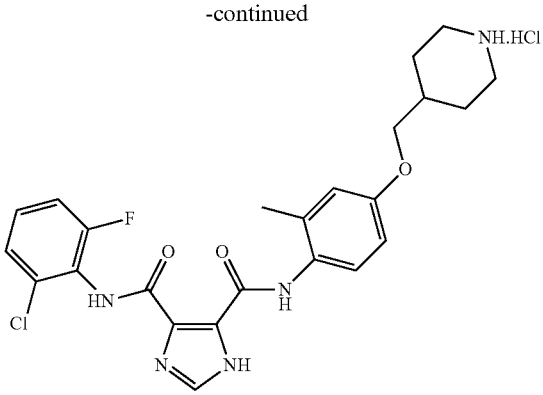

Synthesis of tert-butyl 4-(tosyloxymethyl)piperidine-1-carboxylate

4-Hydroxylmethyl-N-(tert-butylcarboxylate)piperidine (10.76 g, 50 mmoles, 1 equivalent, commercially available from Astatech) was dissolved in anhydrous pyridine (40 ml) and cooled to 0° C. in an ice-water-salt bath. p-Toluenesulfonyl chloride (10.48 g, 55 mmoles, 1.1 equivalent) was added in one lot to the stirred reaction mixture. The reaction mixture was then allowed to warm to room temperature and stirred for 16 hours. The reaction mixture was poured into water (200 ml) and extracted with ethyl acetate (3× with 200 ml). The combined ethyl acetate solution was washed with 5% aqueous hydrochloric acid (200 ml), water (200 ml) and saturated sodium chloride solution (200 ml). The ethyl acetate solution was dried over anhydrous sodium sulfate, filtered and evaporated under reduced pressure to give 16.86 g of tert-butyl 4-(tosyloxymethyl)piperidine-1-carboxylate (yield, 91%). $^1$H-NMR (400 MHz, DMSO-d6) δ 7.88 (d, 2H), 7.45 (d, 2H), 3.84 (m, 4H), 3.65 (m, 2H), 2.40 (s, 3H), 1.76 (m, 1H), 1.54 (m, 2H) 1.38 (s, 9H), 0.95 (m, 2H). MS (EI): 370 (MH+).

Synthesis of tert-butyl 4-((3-methyl-4-nitrophenoxy)methyl)piperidine-1-carboxylate Cesium carbonate (16.29 g, 50 mmoles, 2 equivalents) was added to a stirred solution of 3-methyl-4-nitrophenol (3.82 g, 25 mmoles, 1 equivalent) and tert-butyl 4-(tosyloxymethyl)piperidine-1-carboxylate (10.16 g, 27.5 mmoles, 1.1 equivalent) in anhydrous DMA (25 ml). The stirred reaction mixture was then heated to 90° C. (thermostatically controlled heating mantle) for 22 hours. The reaction mixture was then allowed to cool to room temperature and was filtered through a plug of Celite. The reaction flask and the Celite were then washed with ethyl acetate (250 ml). The organic solution was then transferred to a separatory funnel and extracted with additional ethyl acetate (3×200 ml). The combined ethyl acetate solution was then washed with water (2×100 ml), saturated sodium chloride (2×100 ml), dried over anhydrous magnesium sulfate, filtered and evaporated under reduced pressure to give a crude product. This material was triturated with diethylether to give a solid which was filtered off, washed with ether to give 6.82 g of tert-butyl 4-((3-methyl-4-nitrophenoxy)methyl)piperidine-1-carboxylate (yield=78%). $^1$H-NMR (400 MHz, DMSO-d6) δ 8.06 (d, 1H), 8.64 (d, 1H), 8.62 (s, 1H), 3.9 (s, 2H), 3.34 (m, 4H), 2.00 (m, 1H), 1.46 (m, 1.46), 1.42 (s, 9H). MS (EI): 351 (MH+).

Synthesis of tert-butyl 4-((4-amino-3-methylphenoxy)methyl)piperidine-1-carboxylate tert-Butyl 4-((3-methyl-4-nitrophenoxy)methyl)piperidine-1-carboxylate (5.68 g, 16.22 mmoles) was dissolved in ethyl acetate (60 ml) and methanol (40 ml). The solution was treated with 600 mg of 10% palladium on carbon (50% water w/w). The slurry was then shaken on a Parr hydrogenator and treated with a 40 psi of hydrogen gas, at room temperature. After 16 hours, the slurry was filtered through a plug of Celite, which was subsequently washed with ethyl acetate (50 ml) and methanol (50 ml). The resulting filtrate was then evaporated at reduced pressure to give 3.42 g of tert-butyl 4-((4-amino-3-methylphenoxy)methyl)piperidine-1-carboxylate as a pink solid (100% yield). The material was used in the next step without any further purification. $^1$H-NMR (400 MHz, DMSO-d6) d 6.34 (d, 1H), 6.32 (s, 1H), 6.23 (d, 1H), 5.84 (br s, 2H), 3.90 (s, 2H), 3.34 (m, 4H), 2.00 (m, 1H), 1.46 (m, 4H), 1.42 (s, 9H). MS (EI): 321 (MH+).

Synthesis of N,$^5$-(2-Chloro-6-fluorophenyl)-N$^4$-{2-methyl-4-[(piperidin-4-ylmethyl)oxy]phenyl}-1H-imidazole-4,5-dicarboxamide Hydrochloride N$^5$-(2-Chloro-6-fluorophenyl)-N$^4$-{2-methyl-4-[(piperidin-4-ylmethyl)oxy]phenyl}-1H-imidazole-4,5-dicarboxamide hydrochloride was prepared in a manner analogous to that used for 1,1-dimethylethyl 4-{[(2-{[(4-{[(2,4-dimethylphenyl)amino]carbonyl}-1H-imidazol-5-yl)carbonyl]amino}-1H-benzimidazol-5-yl)oxy]methyl}piperidine-1-carboxylate in Example 12, followed by Boc-deprotection using 4M hydrogen chloride in 1,4-dioxane. $^1$H-NMR (400 MHz, DMSO-d6) δ 14.00 (br s, 1H), 11.60 (br s, 1H), 11.30 (br s, 1H), 9.11 (m, 1H), 8.72 (m, 1H), 8.03 (m, 1H), 7.52 (m, 2H), 7.44 ((m, 2H), 7.41 (m, 2H), 6.80 (m, 2H), 3.85 (d, 2H), 3.37 (d, 2H), 2.87 (q, 2H), 2.32 (s, 3H), 2.05 (m, 1H), 1.92 (m, 2H), 1.52 (m, 2H). MS (EI): 486 (MH+).

Example 142

Synthesis of N$^4$-(5-bromo-2-methylphenyl)-N$^5$-(4-chloro-1H-benzimidazol-2-yl)-1H-imidazole-4,5-dicarboxamide

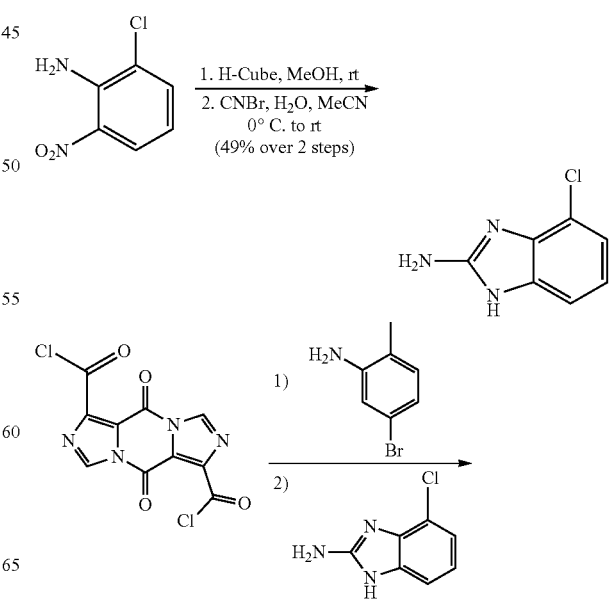

-continued

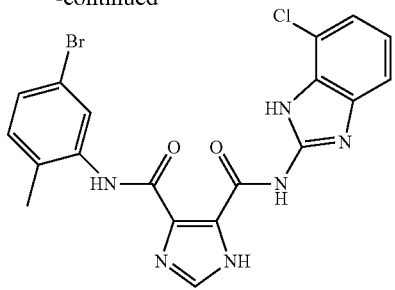

Synthesis of 3-chlorobenzene-1,2-diamine

A solution of 2-chloro-6-nitroaniline (1.0 g, 5.81 mmol, commercially available from Apollo International) in methanol (20 mL) was passed through the H-Cube® (Thales Nanotechnology Inc.) operating at 40 bars and ambient temperature with a flow rate of 1 mL/min. The H-Cube® was equipped with a 10% Pd/C cartridge (Catcart™). The reaction mixture was collected and concentrated after being exposed to the hydrogenation conditions. The crude 3-chlorobenzene-1,2-diamine was carried on without further purification. MS (EI): 145 (MH+).

Synthesis of 4-chloro-1H-benzo[d]imidazol-2-amine

Cyanogen bromide was added to a solution of 3-chlorobenzene-1,2-diamine (0.81 g, 0.570 mmol) in acetonitrile (10 mL) and water (2 ml) at 0° C. The reaction mixture was allowed to warm to room temperature and stirred for 14 hours. The reaction was quenched with saturated aqueous sodium hydrogen carbonate (50 ml) and shaken. The resulting solid was filtered off, was washed with water and dried at reduced pressure to 0.49 g of 4-chloro-1H-benzo[d]imidazol-2-amine (yield, 49%). MS (EI): 168 (MH+).

Synthesis of N4-(5-bromo-2-methylphenyl)-$N^5$-(4-chloro-1H-benzimidazol-2-yl)-1H-imidazole-4,5-dicarboxamide $N^4$-(5-Bromo-2-methylphenyl)-$N^5$-(4-chloro-1H-benzimidazol-2-yl)-1H-imidazole-4,5-dicarboxamide was prepared in a similar manner as to that used for $N^5$-1H-benzimidazol-2-yl-$N^4$-(2,4-dimethylphenyl)-1H-imidazole-4,5-dicarboxamide in Example 1 in 49% yield. $^1$H-NMR (400 MHz, DMSO-d6): δ 10.45 (s, br, 1H), 8.16 (s, 1H), 7.90 (s, 1H), 7.50 (d, 1H), 7.45 (d, 1H), 7.31 (d, 1H), 7.20 (d, 1H), 7.11 (t, 1H), 2.30 (s, 3H). MS (EI): 471.1 (MH+).

Example 143

Synthesis of $N^4$-(5-bromo-2-methylphenyl)-$N^5$-(5-fluoro-1H-benzimidazol-2-yl)-1H-imidazole-4,5-dicarboxamide

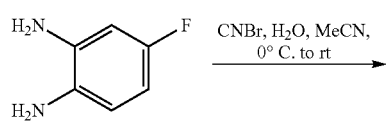

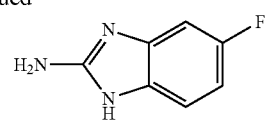

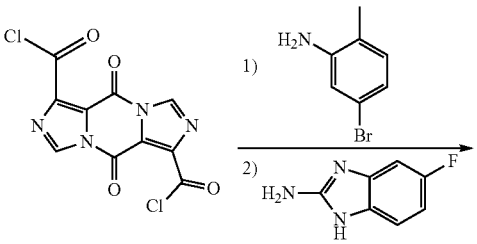

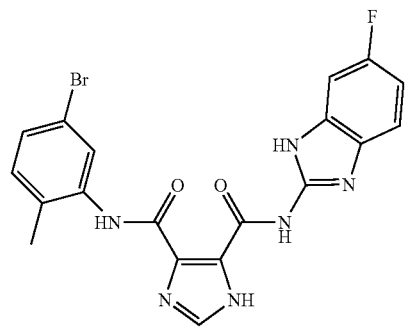

Synthesis of 5-fluoro-1H-benzo[d]imidazol-2-amine

Cyanogen bromide was added to a solution of 4-fluoro-1,2-phenyldiamine (1.26 g, 10 mmole, commercially available from Aldrich) in acetonitrile (10 mL) and water (2 ml) at 0° C. The reaction mixture was allowed to warm to room temperature and stirred for 14 hours. The reaction was quenched with saturated aqueous sodium hydrogen carbonate (50 ml) and shaken. The resulting solid was filtered off, was washed with water and dried at reduced pressure to 0.89 g of 5-fluoro-1H-benzo[d]imidazol-2-amine (yield, 58%). MS (EI): 152 (MH+).

Synthesis of $N^4$-(5-bromo-2-methylphenyl)-$N^5$-(5-fluoro-1H-benzimidazol-2-yl)-1H-imidazole-4,5-dicarboxamide $N^4$-(5-Bromo-2-methylphenyl)-$N^5$-(5-fluoro-1H-benzimidazol-2-yl)-1H-imidazole-4,5-dicarboxamide was made in manner analogous to that used for $N^4$-(5-bromo-2-methylphenyl)-$N^5$-(4-chloro-1H-benzimidazol-2-yl)-1H-imidazole-4,5-dicarboxamide in Example 142 at 49% yield. $^1$H-NMR (400 MHz, DMSO-d6): 10.37 (s, br, 1H), 8.15 (s, 1H), 7.95 (s, 1H), 7.49-7.39 (m, 2H), 7.31-7.24 (m, 2H), 6.97 (t, 1H), 2.30 (s, 3H). MS (EI): 457 (MH+).

Example 144

Scheme for the synthesis of N⁴-(5-bromo-2-methylphenyl)-N⁵-(4,5,6,7-tetrahydro-1H-benzimidazol-2-yl)-1H-imidazole-4,5-dicarboxamide

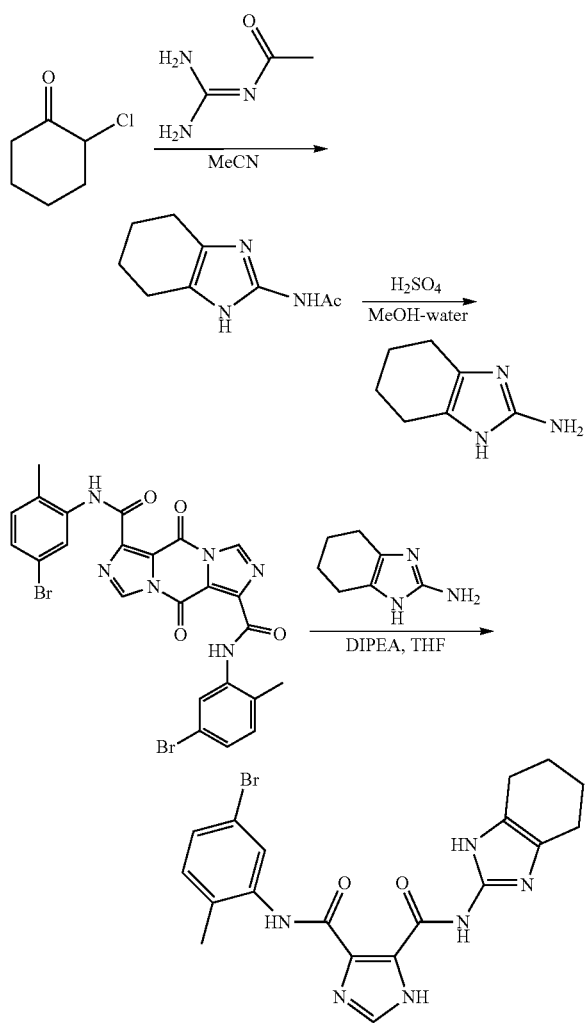

Synthesis of N-(4,5,6,7-tetrahydro-1H-benzo[d]imidazol-2-yl)acetamide

N-Acetylguanidine (1.516 g, 15 mmol, 3 equivalents, commercially available from Aldrich) was added to 2-chlorocyclohexanone (5 mmol, 1 equiv) in acetonitrile (30 ml). The reaction mixture was heated to reflux for 12 hours under argon. Upon cooling, it was evaporated to dryness and the residue washed with water, filtered and air-dried to give 0.13 g of N-(4,5,6,7-tetrahydro-1H-benzo[d]imidazol-2-yl)acetamide. ¹H-NMR (400 MHz, DMSO-d6) 13.4 (bs, 1H), 10.31 (bs, 1H), 2.55 (m, 2H), 2.49 (m, 2H). 2.02 (s, 3H), 1.67 (m, 2H), 1.62 (m, 2H).

Synthesis of 4,5,6,7-tetrahydro-1H-benzo[d]imidazol-2-amine

N-(4,5,6,7-Tetrahydro-1H-benzo[d]imidazol-2-yl)acetamide (0.40 g) was heated at reflux in a stirred solution of 1:1 methanol/water (5 mL) containing 5 drops of concentrated sulfuric acid for 12 hours. The mixture was cooled and evaporated to dryness on the lyophilizer to give 0.31 g of 4,5,6,7-tetrahydro-1H-benzo[d]imidazol-2-amine. ¹H-NMR (400 MHz, DMSO-d6) 13.4 (bs, 1H), 6.59 (bs, 2H), 2.55 (m, 2H), 2.49 (m, 2H), 1.67 (m, 2H), 1.62 (m, 2H).

Synthesis of N⁴-(5-bromo-2-methylphenyl)-N⁵-(4,5,6,7-tetrahydro-1H-benzimidazol-2-yl)-1H-imidazole-4,5-dicarboxamide N⁴-(5-Bromo-2-methylphenyl)-N⁵-(4,5,6,7-tetrahydro-1H-benzimidazol-2-yl)-1H-imidazole-4,5-dicarboxamide was prepared in a manner similar to that used for N⁵-1H-benzimidazol-2-yl-N⁴-(2,4-dimethylphenyl)-1H-imidazole-4,5-dicarboxamide in Example 1 at 29% yield. ¹H-NMR (400 MHz, DMSO-d6): δ 11.13 (s, br, 1H), 10.92 (s, br, 1H), 6.37 (br s, 3H), 8.18 (s, 1h), 7.80 (s, 1H), 7.54-7.42 (m, 2H), 3.39-2.67 (m, 4H), 2.45 (s, 3H). MS (EI): 444 (MH+).

Example 145

Synthesis of N⁴-(5-bromo-2-methylphenyl)-N⁵-(4-fluorophenyl)-1H-imidazole-4,5-dicarboxamide N⁴-(5-Bromo-2-methylphenyl)-N⁵-(4-fluorophenyl)-1H-imidazole-4,5-dicarboxamid was prepared in the same fashion as N⁵-1H-benzimidazol-2-yl-N⁴-(2,4-dimethylphenyl)-1H-imidazole-4,5-dicarboxamide in Example 1 after purification by preparative HPLC (aqueous ammonium acetate-acetonitrile. MS (EI): 418 (MH+).

Example 146

Synthesis of N⁴-(5-bromo-2-methylphenyl)-N⁵-{4-[(phenylmethyl)oxy]phenyl}-1H-imidazole-4,5-dicarboxamide N⁴-(5-Bromo-2-methylphenyl)-N⁵-{4-[(phenylmethyl)oxy]phenyl}-1H-imidazole-4,5-dicarboxamide was prepared in the same fashion as N⁵-1H-benzimidazol-2-yl-N⁴-(2,4-dimethylphenyl)-1H-imidazole-4,5-dicarboxamide as in Example 1 after purification by preparative HPLC (aqueous ammonium acetate-acetonitrile. MS (EI): 506 (MH+).

Example 147

Synthesis of N⁴-(5-bromo-2-methylphenyl)-N⁵-(3,4-difluorophenyl)-1H-imidazole-4,5-dicarboxamide N⁴-(5-Bromo-2-methylphenyl)-N⁵-(3,4-difluorophenyl)-1H-imidazole-4,5-dicarboxamide was prepared in the same fashion as N⁵-1H-benzimidazol-2-yl-N⁴-(2,4-dimethylphenyl)-1H-imidazole-4,5-dicarboxamide as in Example 1 after purification by preparative HPLC (aqueous ammonium acetate-acetonitrile. MS (EI): 436 (MH+)

Example 148

Synthesis of N⁴-(5-bromo-2-methylphenyl)-N⁵-[4-(methyloxy)phenyl]-1H-imidazole-4,5-dicarboxamide N⁴-(5-Bromo-2-methylphenyl)-N⁵-[4-(methyloxy)phenyl]-1H-imidazole-4,5-dicarboxamide was prepared in the same fashion as N⁵-1H-benzimidazol-2-yl-N⁴-(2,4-dimethylphenyl)-1H-imidazole-4,5-dicarboxamide as in Example 1 after purification by preparative HPLC (aqueous ammonium acetate-acetonitrile. $^1$H-NMR (400 MHz, DMSO-d6): δ 8.03 (s, 1H), 7.70 (d, 2H), 7.32 (m, 1H), 7.26 (m, 1H), 6.97 (m, 1H), 6.95 (m, 1H), 3.75 (s, 3H), 2.33 (s, 3H); MS (EI): 431 (MH+).

Example 149

Synthesis of $N^4$-(5-bromo-2-methylphenyl)-$N^5$-(2,4-difluorophenyl)-1H-imidazole-4,5-dicarboxamide $N^4$-(5-Bromo-2-methylphenyl)-$N^5$-(2,4-difluorophenyl)-1H-imidazole-4,5-dicarboxamide was prepared in the same fashion as $N^5$-1H-benzimidazol-2-yl-$N^4$-(2,4-dimethylphenyl)-1H-imidazole-4,5-dicarboxamide as in Example 1 after purification by preparative HPLC (aqueous ammonium acetate-acetonitrile. (EI): 436 (MH+).

Example 150

Synthesis of $N^4$-(5-bromo-2-methylphenyl)-$N^5$-{4-[(pyridin-4-ylmethyl)oxy]phenyl}-1H-imidazole-4,5-dicarboxamide $N^4$-(5-Bromo-2-methylphenyl)-$N^5$-{4-[(pyridin-4-ylmethyl)oxy]phenyl}-1H-imidazole-4,5-dicarboxamide was prepared in the same fashion as $N^5$-1H-benzimidazol-2-yl-$N^4$-(2,4-dimethylphenyl)-1H-imidazole-4,5-dicarboxamide in Example 1 after purification by preparative HPLC (aqueous ammonium acetate-acetonitrile. MS (EI): 507 (MH+).

Example 151

Synthesis of $N^4$-(5-bromo-2-methylphenyl)-$N^5$-(4-chlorophenyl)-1H-imidazole-4,5-dicarboxamide $N^4$-(5-Bromo-2-methylphenyl)-$N^5$-(4-chlorophenyl)-1H-imidazole-4,5-dicarboxamide was prepared in the same fashion as $N^5$-1H-benzimidazol-2-yl-$N^4$-(2,4-dimethylphenyl)-1H-imidazole-4,5-dicarboxamide in Example 1 after purification by preparative HPLC (aqueous ammonium acetate-acetonitrile. (EI): 434 (MH+).

Example 152

Synthesis of $N^4$-(5-bromo-2-methylphenyl)-$N^5$-(3,4-dichlorophenyl)-1H-imidazole-4,5-dicarboxamide $N^4$-(5-Bromo-2-methylphenyl)-$N^5$-(3,4-dichlorophenyl)-1H-imidazole-4,5-dicarboxamide was prepared in the same fashion as $N^5$-1H-benzimidazol-2-yl-$N^4$-(2,4-dimethylphenyl)-1H-imidazole-4,5-dicarboxamide in Example 1 after purification by preparative HPLC (aqueous ammonium acetate-acetonitrile. MS (EI): 469 (MH+).

Example 153

Synthesis of $N^4$-(5-bromo-2-methylphenyl)-$N^5$-(3-chlorophenyl)-1H-imidazole-4,5-dicarboxamide $N^4$-(5-Bromo-2-methylphenyl)-$N^5$-(3-chlorophenyl)-1H-imidazole-4,5-dicarboxamide was prepared in the same fashion as $N^5$-1H-benzimidazol-2-yl-$N^4$-(2,4-dimethylphenyl)-1H-imidazole-4,5-dicarboxamide Example 1 after purification by preparative HPLC (aqueous ammonium acetate-acetonitrile. MS (EI): 434 (MH+).

Example 154

Synthesis of $N^4$-(5-bromo-2-methylphenyl)-$N^5$-(4-methylphenyl)-1H-imidazole-4,5-dicarboxamide $N^4$-(5-Bromo-2-methylphenyl)-$N^5$-(4-methylphenyl)-1H-imidazole-4,5-dicarboxamide was prepared in the same fashion as $N^5$-1H-benzimidazol-2-yl-$N^4$-(2,4-dimethylphenyl)-1H-imidazole-4,5-dicarboxamide in Example 1 after purification by preparative HPLC (aqueous ammonium acetate-acetonitrile. MS (EI): 314 (MH+).

Example 155

Synthesis of $N^4$-(5-bromo-2-methylphenyl)-$N^5$-(3-methylphenyl)-1H-imidazole-4,5-dicarboxamide $N^4$-(5-Bromo-2-methylphenyl)-$N^5$-(3-methylphenyl)-1H-imidazole-4,5-dicarboxamide was prepared in the same fashion as $N^5$-1H-benzimidazol-2-yl-$N^4$-(2,4-dimethylphenyl)-1H-imidazole-4,5-dicarboxamide in Example 1 after purification by preparative HPLC (aqueous ammonium acetate-acetonitrile. MS (EI): 414 (MH+).

Example 156

Synthesis of $N^4$-(5-bromo-2-methylphenyl)-$N^5$-(3,4-dimethylphenyl)-1H-imidazole-4,5-dicarboxamide $N^4$-(5-bromo-2-methylphenyl)-$N^5$-(3,4-dimethylphenyl)-1H-imidazole-4,5-dicarboxamide was prepared in a manner similar to that used for $N^5$-1H-benzimidazol-2-yl-$N^4$-(2,4-dimethylphenyl)-1H-imidazole-4,5-dicarboxamide in Example 1 after purification by preparative HPLC (aqueous ammonium acetate-acetonitrile. MS (EI): 428 (MH+).

Example 157

Scheme for the synthesis of $N^4$-(5-bromo-1H-benzimidazol-2-yl)-$N^5$-(5-bromo-2-methylphenyl)-1H-imidazole-4,5-dicarboxamide

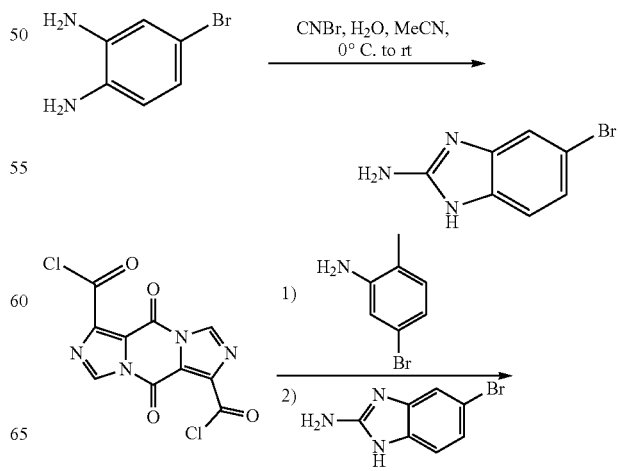

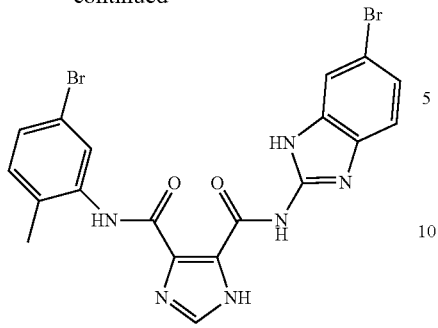

Synthesis of 5-bromo-1H-benzo[d]imidazol-2-amine

Cyanogen bromide was added to a solution of 4-bromo-1, 2-phenyldiamine (1.87 g, 10 mmole, commercially available from Aldrich) in acetonitrile (10 mL) and water (2 ml) at 0° C. The reaction mixture was allowed to warm to room temperature and stirred for 14 hours. The reaction was quenched with saturated aqueous sodium hydrogen carbonate (50 ml) and shaken. The resulting solid was filtered off, washed with water and dried at reduced pressure to give 1.13 g of 5-bromo-1H-benzo[d]imidazol-2-amine (yield, 53%) as a yellow solid. MS (EI): 213 (MH+).

Synthesis of $N^4$-(5-bromo-1H-benzimidazol-2-yl)-$N^5$-(5-bromo-2 methylphenyl)-1H-imidazole-4,5-dicarboxamide $N^4$-(5-Bromo-1H-benzimidazol-2-yl)-$N^5$-(5-bromo-2 methylphenyl)-1H-imidazole-4,5-dicarboxamide was prepared in fashion analogous to $N^4$-(5-bromo-2-methylphenyl)-$N^5$-(4-chloro-1H-benzimidazol-2-yl)-1H-imidazole-4,5-dicarboxamide in Example 142 at 41% yield. $^1$H-NMR (400 MHz, DMSO-d6): δ 10.44 (s, br, 1H), 8.30 (s, 1H), 8.22 (s, 1H), 7.91 (s, 1H), 7.67 (s, 1H), 7.47 (d, 1H), 7.42 (d, 1H), 7.32-7.26 (m, 2H), 2.29 (s, 3H). MS (EI): 516.8 (MH+).

Example 158

Synthesis of $N^5$-(5-Bromo-2-methylphenyl)-$N^4$-{3-[2-(dimethylamino)ethyl]-1H-pyrazol-5-yl}-1H-imidazole-4,5-dicarboxamide

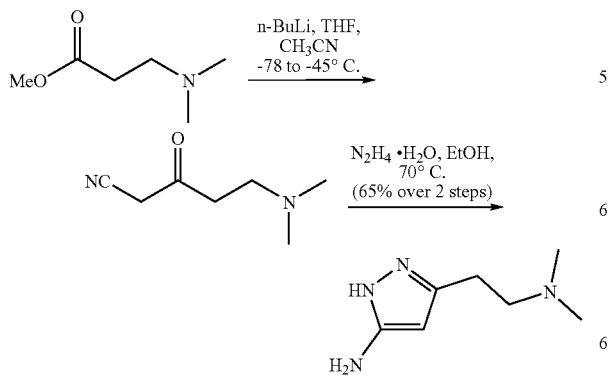

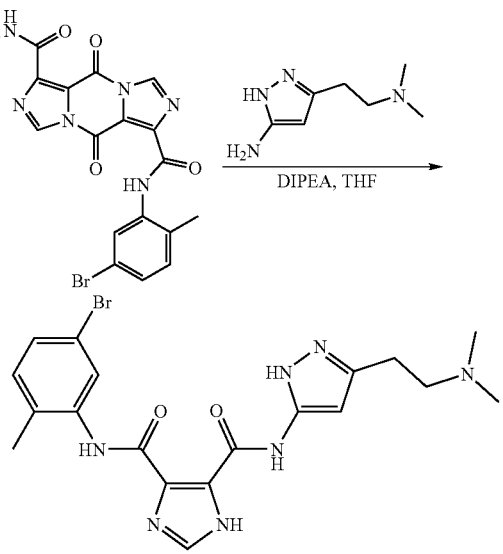

Synthesis of (dimethylamino)-3-oxopentanenitrile

Anhydrous acetonitrile (2.052 g, 50 mmol, 2.28 ml) was added to a solution of n-butyl lithium (59.0 mL of a 1.0 M solution in hexanes, 59.0 mmol) in anhydrous THF (130 mL), under a nitrogen atmosphere at −78° C. The reaction was stirred for 1 hour at −78° C. and methyl 3-(dimethylamino)propanoate (5.45 mL, 38.1 mmol) was added in a dropwise fashion maintaining the temperature at −60° C. The reaction mixture was allowed to warm to −45° C. and stirred for 2 hours. The reaction mixture was quenched with 2 N hydrochloric acid (50 mL) and the aqueous layer was concentrated to afford 5.1 g (dimethylamino)-3-oxopentanenitrile which was used without further purification.

Synthesis of 3-(2-(dimethylamino)ethyl)-1H-pyrazol-5-amine

To a solution of 5-(dimethylamino)-3-oxopentanenitrile (4.9 g) in ethanol (20 mL) at ambient temperature was added hydrazine monohydrate (1.72 mL, 35.5 mmol) and the reaction mixture was heated to 70° C. for 2 hours. The reaction mixture was then filtered and the filtrate was concentrated under reduced pressure to give 3.81 g of 3-(2-(dimethylamino)ethyl)-1H-pyrazol-5-amine (65% over 2 steps) which was carried on without further purification. $^1$H-NMR (400 MHz, DMSO-d6): δ 12.60 (bs, 1H), 6.52 (bs, 2H), 6.1 (s, 1H), 2.69 (m, 2H), 2.65 (m, 2H), 2.27 (s, 6H).

$N^5$-(5-Bromo-2-methylphenyl)-$N^4$-{3-[2-(dimethylamino)ethyl]-1H-pyrazol-5-yl}-1H-imidazole-4,5-dicarboxamide $N^5$-(5-Bromo-2-methylphenyl)-$N^4$-{3-[2-(dimethylamino)ethyl]-1H-pyrazol-5-yl}-1H-imidazole-4,5-dicarboxamide was prepared in fashion analogous to $N^4$-(5-bromo-2-methylphenyl)-$N^5$-(4-chloro-1H-benzimidazol-2-yl)-1H-imidazole-4,5-dicarboxamide in Example 142 at 27% yield. $^1$H-NMR (400 MHz, d6-DMSO): δ 8.35 (s, 1H), 7.53

(d, 1H), 6.93 (s, 1H), 6.59 (d, 1H), 3.73 (m, 1H), 2.92 (m, 4H), 2.37 (s, 3H), 2.30 (s, 3H), 1.73 (m, 4H). MS (EI): 458.0 (MH+).

Example 159

Synthesis of $N^4$-[2-chloro-4-(piperidin-4-yloxy)phenyl]-$N^5$-(4,5-dimethyl-1H-imidazol-2-yl)-1H-imidazole-4,5-dicarboxamide $N^4$-[2-Chloro-4-(piperidin-4-yloxy)phenyl]-$N^5$-(4,5-dimethyl-1H-imidazol-2-yl)-1H-imidazole-4,5-dicarboxamide was prepared in a similar fashion as $N^5$-[4-(azetidin-3-yloxy)-2-methylphenyl]-$N^4$-1H-benzimidazol-2-yl-1H-imidazole-4,5-dicarboxamide in Example 5 at 25% yield. $^1$H-NMR (400 MHz, DMSO-d6): δ 8.35 (s, 1H), 7.53 (d, 1H), 6.93 (s, 1H), 6.59 (d, 1H), 3.73 (m, 1H), 2.92 (m, 4H), 2.37 (s, 3H), 2.30 (s, 3H), 1.73 (m, 4H). MS (EI): 458.0 (MH+).

Example 160

Synthesis of $N^5$-1H-benzimidazol-2-yl-$N^4$-(2,6-dichlorophenyl)-1H-imidazole-4,5-dicarboxamide $N^5$-1H-benzimidazol-2-yl-$N^4$-(2,6-dichlorophenyl)-1H-imidazole-4,5-dicarboxamide was prepared by the general method used for the synthesis of $N^5$-1H-benzimidazol-2-yl-$N^4$-(2,4-dimethylphenyl)-1H-imidazole-4,5-dicarboxamide in Example 1 in 73% yield. $^1$H-NMR (400 MHz, DMSO-d6): δ 13.93 (s, br, 1H), 12.20 (s, br, 1H), 10.81 (s, 1H), 8.21 (s, 1H), 7.63 (m, 2H), 7.49-7.27 (m, 3H), 7.16 (m, 2H). MS (EI): 415 (MH+).

By using the appropriate synthetic steps described from the previous examples and synthetic scheme(s), and by substituting the appropriate commercially available reactants and reagents that the skilled artisan can easily obtain, the following compounds were made:

$N^5$-1H-benzimidazol-2-yl-$N^4$-(5-chloro-2-methylphenyl)-1H-imidazole-4,5-dicarboxamide.
  $^1$H NMR (400 MHz, DMSO-d6): δ 12.20 (s, 1H), 10.21 (s, 1H), 8.18 (s, 1H), 7.56-7.38 (m, 3H), 7.18-7.0 (m, 4H), 2.25 (s, 3H), 2.21 (s, 3H). MS (EI) for $C_{20}H_{18}N_6O_2$: 375 (MH+).

$N^4$-1H-benzimidazol-2-yl-$N^5$-(2,6-dimethylphenyl)-1H-imidazole-4,5-dicarboxamide
  $^1$H NMR (400 MHz, DMSO-d6): δ 10.27 (br s, 1H), 8.22 (s, 1H), 7.45 (d, 2H), 7.20 (d, 2H), 7.20-7.15 (m, 5H), 2.20 (s, 6H). MS (EI) for $C_{20}H_{18}N_6O_2$: 375 (MH+).

$N^5$-1H-benzimidazol-2-yl-$N^4$-(2-methylphenyl)-1H-imidazole-4,5-dicarboxamide. $^1$H NMR (400 MHz, DMSO-d6): δ 8.07 (s, 1H), 7.72 (d, 1H), 7.47 (s, 2H), 7.30 (dd, 2H), 7.20 (t, 1H), 7.11 (m, 2H), 2.33 (s, 3H). MS (D) for $C_{19}H_{15}N_6O_2$: 361 (MH+).

$N^5$-1H-benzimidazol-2-yl-$N^4$-(5-fluoro-2-methylphenyl)-1H-imidazole-4,5-dicarboxamide. $^1$H NMR (400 MHz, DMSO-d6): δ 8.42 (s, 1H), 7.83-7.62 (m, 3H), 7.58-7.38 (m, 3H), 7.10-7.06 (m, 1H), 2.37 (s, 3H). MS (EI) for $C_{19}H_{15}FN_6O_2$: 379 (MH+).

$N^5$-1H-benzimidazol-2-yl-$N^4$-[2-methyl-5-(methyloxy)phenyl]-1H-imidazole-4,5-dicarboxamide. $^1$H NMR (400 MHz, CD3OD): δ 9.14 (m, 1H), 8.44 (m, 2H), 8.19 (m, 2H), 8.03 (m, 2H), 7.63 (m, 1H), 4.55 (s, 4H), 3.29 (s, 4H), 3.04 (s, 3H), 0.78 (s, 3H). MS (EI) for $C_{20}H_{18}N_6O_3$: 391 (MH+).

$N^5$-1H-benzimidazol-2-yl-$N^4$-[2-(1-methylethyl)phenyl]-1H-imidazole-4,5-dicarboxamide.
  $^1$H NMR (400 MHz, CD3OD): δ 8.10 (s, 1H), 7.65 (dd, 3H), 7.48 (dd, 3H), 7.26-7.35 (m, 2H) 3.30 (m 1H), 1.29 (s, 3H), 1.28 (s, 3H). MS (EI) for $C_{21}H_{20}N_6O_2$: 389 (MH+).

$N^5$-1H-benzimidazol-2-yl-$N^4$-(2-ethylphenyl)-1H-imidazole-4,5-dicarboxamide.
  $^1$H NMR (400 MHz, CD3OD): δ 8.10 (s, 1H), 7.78 (m, 1H), 7.66 (dd, 2H), 7.49 (dd, 2H), 7.35 (m, 1H), 7.28 (m, 2H), 2.78 (dd, 2H), 1.25 (dd, 3H). MS (EI) for $C_{20}H_{18}N_6O_2$: 375 (MH+).

$N^4$-1H-benzimidazol-2-yl-$N^5$-(2-bromophenyl)-1H-imidazole-4,5-dicarboxamide. $^1$H NMR (400 MHz, DMSO-d6): δ 11.50 (br, 1H), 11.10 (br, 1H), 8.37 (s, 1H), 7.80 (d, 1H), 7.64-7.74 m, 3H), 7.39-7.50 (m, 3H), 7.24-7.45 (m, 1H). MS (EI) for $C_{18}H_{13}BrN_6O_2$: 426 (MH+).

$N^5$-1H-benzimidazol-2-yl-$N^4$-(2-chlorophenyl)-1H-imidazole-4,5-dicarboxamide.
  $^1$H NMR (400 MHz, DMSO-d6): δ 12.1 (br s, 1H), 10.6 (br s, 1H), 8.56 (dd, 1H), 7.58 (dd, 1H), 7.45 (dd, 1H), 7.42-7.37 (m, 2H), 7.35 (s, 1H), 7.18-7.10 (m, H), 7.1-6.95 (m, 2H). MS (EI) for $C_{18}H_{13}ClN_6O_2$: 382 (MH+, Cl-37, 100%), 380 (MH+, Cl-35, 32%).

$N^5$-1H-benzimidazol-2-yl-$N^4$-[2-methyl-6-(1-methylethyl)phenyl]-1H-imidazole-4,5-dicarboxamide.
  $^1$H NMR (400 MHz, DMSO-d6): δ 12.1 (br s, 1H), 10.6 (br s, 1H), 8.86 (dd, 1H), 7.78 (dd, 1H), 7.65 (dd, 1H), 7.52-7.41 (m, 2H), 7.35 (s, 1H), 7.18-7.10 (m, H), 7.1-6.95 (m, 2H). MS (EI) for $C_{19}H_{13}N_7O_2$: 372 (MH+).

$N^5$-(2,4-dimethylphenyl)-$N^4$-[6-(methyloxy)-1H-benzimidazol-2-yl]-1H-imidazole-4,5-dicarboxamide.
  $^1$H NMR (400 MHz, DMSO-d6): δ 14.0 (br s, 1H), 12.66 (br s, 1H), 8.35 (s, 1H), 7.62 (s, 2H), 7.40 (s, 2H), 7.27 (s, 2H), 7.19 (S, 1H), 3.12 (m, 1H), 2.23 (s, 3H), 1.28 (s, 3H), 1.17 (s, 3H). MS (EI) for $C_{22}H_{22}N_6O_2$: 403 (MH+).

$N^4$-1H-benzimidazol-2-yl-$N^5$-(2,4,6-trimethylphenyl)-1H-imidazole-4,5-dicarboxamide.
  $^1$H NMR (400 MHz, DMSO-d6): δ 10.41 (s, 1H), 7.98 (s, 1H), 7.64-7.61 (m, 1H), 7.38-7.36 (m, 1H), 7.16-7.0 (m, 3H), 6.74-6.71 (m, 1H), 3.78 (s, 3H), 2.36 (s, 3H), 2.33 (s, 3H). MS (EI) for $C_{21}H_{20}N_6O_3$: 405 (MH+).

$N^4$-1H-benzimidazol-2-yl-$N^5$-(2-fluorophenyl)-1H-imidazole-4,5-dicarboxamide.
  $^1$H NMR (400 MHz, DMSO-d6): δ 10.65 (br, 1H), 8.31 (s, 1H), 7.58 (d, 2H), 7.36 (d, 2H), 6.96 (s, 2H), 2.25 (s, 3H), 2.16 (s, 6H). MS (EI) for $C_{21}H_{20}N_6O_2$: 389 (MH+).

$N^5$-1H-benzimidazol-2-yl-$N^4$-[2-methyl-4-(methyloxy)phenyl]-1H-imidazole-4,5-dicarboxamide.
  $^1$H NMR (400 MHz, DMSO-d6): δ 11.50 (br, 1H), 8.45 (s, 1H), 7.90 (s, 1H), 7.40 (m, 2H), 7.30-7.71 (m, 5H). MS (EI) for $C_{18}H_{13}FN_6O_2$: 365 (MH+).

$N^4$-1H-benzimidazol-2-yl-$N^5$-(2,6-diethylphenyl)-1H-imidazole-4,5-dicarboxamide.
  $^1$H NMR (400 MHz, DMSO-d6): δ 8.34 (s, 1H), 7.63 (dd, 2H), 7.39 (dd, 3H), 6.93 (s, 1H), 6.85 (dd, 1H), 2.27 (s, 3H). MS (EI) for $C_{20}H_{18}N_6O_3$: 391 (MH+).

$N^4$-(5-amino-2-methylphenyl)-$N^5$-1H-benzimidazol-2-yl-1H-imidazole-4,5-dicarboxamide.
  $^1$H NMR (400 MHz, DMSO-d6): δ 13.80 (br, 1H), 12.20 (br, 1H), 10.40 (br, 1H), 8.18 (s, 1H), 7.40 (s, 2H), 7.24 (m, 1H), 7.18 (m, 2H), 7.10 (m, 2H), 2.55 (m, 4H), 1.12 (m, 6H). MS (EI) for $C_{22}H_{22}N_6O_2$: 403 (MH+).

$N^5$-1H-benzimidazol-2-yl-$N^4$-(2-propylphenyl)-1H-imidazole-4,5-dicarboxamide.
  $^1$H NMR (400 MHz, DMSO-d6): δ 10.9 (br, 1H), 9.85 (br, 2H), 8.32 (s, 1H), 7.63 (m, 2H), 7.38 (m, 3H), 6.84 (m, 1H), 6.78 (m, 1H), 5.05 (m, 1H), 4.43 (m, 2H), 3.94 (m, 2H), 2.25 (s, 3H). MS (EI) for $C_{22}H_2,N_7O_3$: 432 (MH+).

$N^5$-1H-benzimidazol-2-yl-$N^4$-(2-propylphenyl)-1H-imidazole-4,5-dicarboxamide.
$^1$H NMR (400 MHz, DMSO-d6): δ 13.80 (s, 1H), 12.20 (s, 1H), 10.30 (s, 1H), 8.20 (s, 1H), 7.78-7.05 (m, 8H), 2.78-2.62 (m, 2H), 1.70-1.60 (m, 2H), 1.0-0.94 (m, 3H). MS (EI) for $C_{21}H_{20}N_6O_2$: 389 (MH+).

$N^5$-1H-benzimidazol-2-yl-$N^4$-[2-(trifluoromethyl)phenyl]-1H-imidazole-4,5-dicarboxamide.
$^1$H NMR (400 MHz, DMSO-d6): δ 8.40 (s, 1H), 7.87 (d, 2H), 7.72 (dd, 2H), 7.45 (m, 4H), 7.24 (t, 1H). MS (EI) for $C_{18}H_{14}N_6O_2$: 347 (MH+).

$N^5$-1H-benzimidazol-2-yl-$N^4$-[(2-chlorophenyl)methyl]-1H-imidazole-4,5-dicarboxamide.
$^1$H NMR (400 MHz, DMSO-d6): δ 8.30 (s, 1H), 7.62 (dd, 2H), 7.50 (dd, 1H), 7.37 (m, 5H), 4.69 (m, 2H). MS (EI) for $C_{19}H_{15}ClN_6O_2$: 395 (MH+).

$N^5$-1H-benzimidazol-2-yl-$N^4$-(3-chloro-2-methylphenyl)-1H-imidazole-4,5-dicarboxamide.
$^1$H NMR (400 MHz, DMSO-d6): δ 8.30 (s, 1H), 7.62 (dd, 2H), 7.50 (dd, 1H), 7.37 (m, 5H), 4.69 (m, 2H). MS (EI) for $C_{19}H_{15}ClN_6O_2$: 395 (MH+).

$N^4$-(2,4-dimethylphenyl)-$N^5$-1H-imidazol-2-yl-1H-imidazole-4,5-dicarboxamide.
$^1$H NMR (400 MHz, DMSO-d6): δ 10.93 (s, br, 1H), 8.36 (s, 1H), 7.62-7.25 (m, 7H), 2.34 (s, 3H). MS (EI) for $C_{19}H_{15}ClN_6O_2$: 395 (MH+).

$N^5$-1H-benzimidazol-5-yl-$N^4$-(2,4-dimethylphenyl)-1H-imidazole-4,5-dicarboxamide.
$^1$H NMR (400 MHz, DMSO-d6): δ 12.1 (br s, 1H), 8.92 (s, 1H), 8.4 (br s, 1H), 8.0 (br s, 1H), 7.85-7.72 (m, 1H), 7.65 (s, 2H), 7.51 (s, 1H), 7.12 (s, 1H), 7.08 (S, 1H), 2.13 (s, 6H). MS (EI) for $C_{16}H_{16}N_6O_2$: 325 (MH+).

$N^5$-1H-benzimidazol-2-yl-$N^4$-(5,6,7,8-tetrahydronaphthalen-1-yl)-1H-imidazole-4,5-dicarboxamide.
$^1$H NMR (400 MHz, DMSO-d6): δ 13.77 (br s, 1H), 9.42-9.40 (t, 1H), 9.06-9.05 (t, 1H), 8.07-8.04 (t, 1H), 7.82-7.79 (m, 1H), 7.62 (b s, 2H), 7.10 (s, 1H), 7.05-7.04 (d, 1H), 2.27 (s, 3H), 2.26 (s, 3H). MS (EI) for $C_{20}H_{18}N_6O_2$: 375 (MH+).

$N^5$-1H-benzimidazol-2-yl-$N^4$-(3-methylphenyl)-1H-imidazole-4,5-dicarboxamide.
$^1$H NMR (400 MHz, DMSO-d6): δ 13.90 (s, 1H), 12.20 (s, br, 1H), 10.20 (s, 1H), 8.20 (s, 1H), 7.55-7.40 (m, 3H), 7.20-6.95 (m, 4H), 2.80-2.60 (m, 4H), 1.80-1.65 (m, 4H). MS (EI) for $C_{22}H_{20}N_6O_2$: 401 (MH+).

1,1-dimethylethyl (2-{2-[({4-[(1H-benzimidazol-2-ylamino)carbonyl]-1H-imidazol-5-yl}carbonyl)amino]phenyl}ethyl)carbamate
$^1$H NMR (400 MHz, DMSO-d6): δ 10.20 (s, 1H), 8.37 (s, 1H), 7.75-7.65 (m, 4H), 7.45-30 (m, 3H), 7.08-7.0 (m, 1H), 2.35 (s, 3H). MS (EI) for $C_{19}H_{16}N_6O_2$: 361 (MH+).

$N^5$-1H-benzimidazol-2-yl-$N^4$-[4-(methyloxy)phenyl]-1H-imidazole-4,5-dicarboxamide. $^1$H NMR (400 MHz, DMSO-d6): δ 13.70 (br, 1H), 12.20 (br, 1H), 10.40 (br, 1H), 8.18 (s, 1H), 7.40-7-60 (m, 2H), 7.29 (m, 2H), 7.10 (m, 2H), 6.82 (m, 2H), 3.18 (m, 2H), 2.78 (m, 2H), 1.28 (s, 9H). MS (EI) for $C_{25}H_{27}N_7O_4$: 490 (MH+).

$N^5$-1H-benzimidazol-2-yl-$N^4$—(1-phenylethyl)-1H-imidazole-4,5-dicarboxamide.
$^1$H NMR (400 MHz, DMSO-d6): δ 9.85 (s, 1H), 8.30 (s, 1H), 7.68 (dd, 2H), 7.49 (d, 2H), 7.43 (dd, 2H), 7.37 (t, 2H), 7.27 (t, 1H), 5.30 (dd, 1H), 1.62 (s, 3H). MS (EI) for $C_{20}H_{18}N_6O_2$: 375 (MH+).

$N^5$-1H-benzimidazol-2-yl-$N^4$-[2,5-bis(methyloxy)phenyl]-1H-imidazole-4,5-dicarboxamide.
$^1$H NMR (400 MHz, DMSO-d6): δ 9.85 (s, 1H), 8.30 (s, 1H), 7.68 (dd, 2H), 7.49 (d, 2H), 7.43 (dd, 2H), 7.37 (t, 2H), 7.27 (t, 1H), 5.30 (dd, 1H), 1.62 (s, 3H). MS (EI) for $C_{20}H_{18}N_6O_2$: 375 (MH+).

$N^5$-1H-benzimidazol-2-yl-$N^4$-cyclohexyl-1H-imidazole-4,5-dicarboxamide.
$^1$H NMR (400 MHz, CD3OD): δ 8.06 (d, 1H), 7.95 (s, 1H), 7.65 (dd, 2H), 7.49 (dd, 2H), 6.78 (d, 1H), 6.46 (dd, 1H), 3.81 (s, 3H), 3.63 (s, 3H). MS (EI) for $C_{20}H_{18}N_6O_4$: 407 (MH+).

$N^5$-(2-acetylphenyl)-$N^4$-1H-benzimidazol-2-yl-1H-imidazole-4,5-dicarboxamide.
$^1$H NMR (400 MHz, CD3OD): δ 8.06 (d, 1H), 7.95 (s, 1H), 7.65 (dd, 2H), 7.49 (dd, 2H), 6.78 (d, 1H), 6.46 (dd, 1H), 3.81 (s, 3H), 3.63 (s, 3H). MS (EI) for $C_{20}H_{18}N_6O_4$: 407 (MH+).

$N^5$-1H-benzimidazol-2-yl-$N^4$-[4-(piperidine-yloxy)phenyl]-1H-imidazole-4,5-dicarboxamide.
$^1$H NMR (400 MHz, DMSO-d6): δ 13.14 (br, 1H), 8.88 (s, 1H), 8.22 (s, 1H), 8.11 (d, 1H), 7.62-7.68 (m, 3H), 7.28-7.36 (m, 3H), 2.67 (s, 3H). MS (EI) for $C_{20}H_{16}N_6O_3$: 389 (MH+).

$N^4$-(2,4-dimethylphenyl)-$N^5$-quinolin-6-yl-1H-imidazole-4,5-dicarboxamide.
$^1$H NMR (400 MHz, DMSO-d6): δ 11.35 (br s), 9.11 (br s), 8.37 (br s, 1H), 7.79-7.77 (d, 1H), 7.71-7.69 (dd, 2H), 7.44-7.42 (dd, 2H), 7.10-7.08 (d, 2H), 4.70-4.66 (m, 1H), 3.76 (br s, 2H), 3.22 (m, 2H), 3.07 (m, 2H), 2.13-2.10 (m, 2H), 1.91-1.82 (m, 2H). MS (EI) for $C_{23}H_{23}N_7O_3$: 446 (MH+).

1,1-dimethylethyl {3-[({5-[(1H-benzimidazol-2-ylamino)carbonyl]-1H-imidazol-4-yl}carbonyl)amino]-4-methylphenyl}carbamate.
$^1$H NMR (400 MHz, DMSO-d6): δ 12.90 (br s, 1H), 11.10 (br s, 2H), 9.12 (s, 1H), 9.10-9.09 (d, 1H), 9.01-8.99 (d, 1H), 8.73 (s, 1H), 8.29 (s, 1H), 8.09 (s, 1H) 7.94-7.90 (dd, 1H), 7.58-7.56 (d, 1H), 7.09 (s, 1H), 7.05-7.03 (d, 1H), 2.27 (s, 6H). MS (EI) for $C_{22}H_{19}N_5O_2$, 386 (MH+).

$N^5$-1H-benzimidazol-2-yl-$N^4$-(phenylmethyl)-1H-imidazole-4,5-dicarboxamide.
$^1$H NMR (400 MHz, DMSO-d6): δ 13.80 (s, 1H), 12.20 (s, 1H), 10.25 (s, 1H), 9.40 (s, 1H), 8.18 (s, 1H), 7.80-7.10 (m, 7H), 2.20 (s, 3H), 1.50-1.40 (m, 9H). MS (EI) for $C_{24}H_{25}N_7O_4$: 476 (MH+).

$N^4$-1H-benzimidazol-2-yl-$N^5$-(4-chloro-2-methylphenyl)-1H-imidazole-4,5-dicarboxamide.
$^1$H NMR (400 MHz, DMSO-d6): δ 9.13 (s, 1H), 7.42 (s, 2H), 7.35 (m, 4H), 7.24 (t, 1H), 7.04 (dd, 2H), 4.52 (d, 2H). MS (EI) for $C_{19}H_{16}N_6O_2$: 361 (MH+).

$N^5$-1H-benzimidazol-2-yl-$N^4$-naphthalen-1-yl-1H-imidazole-4,5-dicarboxamide.
$^1$H NMR (400 MHz, DMSO-d6): δ 8.38 (s, 1H), 7.78-7.74 (d, 2H), 7.73-7.68 (m, 2H), 7.46-7.40 (m, 2H), 7.28-7.22 (d, 2H), 2.30 (s, 3H). MS (EI) for $C_{19}H_{16}N_6O_2$: 361 (MH+).

$N^5$-1H-benzimidazol-2-yl-$N^4$-(4-methylphenyl)-1H-imidazole-4,5-dicarboxamide.
$^1$H NMR (400 MHz, DMSO-d6): δ 13.95 (br s, 1H), 12.28 (s, 1H), 10.9 (s, 1H), 8.22 (s, 1H), 7.93 (m, 2H), 7.82 (m, 1H), 7.49 (m, 3H), 7.13 (m, 2H). MS (EI) for $C_{22}H_{16}N_6O_2$, 397 (MH+).

$N^5$-1H-benzimidazol-2-yl-$N^4$-[2,4-bis(methyloxy)phenyl]-1H-imidazole-4,5-dicarboxamide.
$^1$H NMR (400 MHz, DMSO-d6): δ 8.38 (s, 1H), 7.78-7.74 (d, 2H), 7.73-7.68 (m, 2H), 7.46-7.40 (m, 2H), 7.28-7.22 (d, 2H), 2.30 (s, 3H). MS (EI) for $C_{19}H_{16}N_6O_2$: 361 (MH+).

$N^5$-1H-benzimidazol-2-yl-$N^4$-[3-(methyloxy)phenyl]-1H-imidazole-4,5-dicarboxamide. $^1$H NMR (400 MHz, DMSO-d6): δ 8.31 (s, 1H), 8.03 (s, 1H), 7.65 (dd, 2H), 7.39 (dd, 1H), 6.71 (d, 1H), 6.59 (dd, 1H), 3.86 (s, 3H), 3.78 (s, 3H). MS (EI) for $C_{20}H_{18}N_6O_4$: 407 (MH+).

$N^5$-1H-benzimidazol-2-yl-$N^4$-[3-(1-methylethyl)phenyl]-1H-imidazole-4,5-dicarboxamide.

$^1$H NMR (400 MHz, DMSO-d6): δ 12.30 (s, 1H), 8.20 (m, 1H), 7.60 (m, 5H), 7.19 (dd, 2H), 6.84 (m, 1H), 3.85 (d, 3H). MS (EI) for $C_{19}H_{16}N_6O_3$: 377 (MH+).

$N^5$-1H-benzimidazol-2-yl-$N^4$-{[3-(methyloxy)phenyl]methyl}-1H-imidazole-4,5-dicarboxamide.

$^1$H NMR (400 MHz, DMSO-d6): δ 12.69 (br s, 1H), 11.88 (br s, 1H), 8.37 (br s, 1H), 8.05 (s, 1H), 7.69-7.66 (m, 4H), 7.39-7.32 (d, 2H), 7.11-7.04 (d, 2H), 2.93 (m, 1H), 1.24-1.22 (d, 6H). MS (EI) for $C_{21}H_{20}N_6O_2$, 389 (MH+).

$N^5$-1H-benzimidazol-2-yl-$N^4$-{[2-(methyloxy)phenyl]methyl}-1H-imidazole-4,5-dicarboxamide.

$^1$H NMR (400 MHz, DMSO-d6): δ 13.70 (s, br, 1H), 12.10 (s, br, 1H), 9.50 (s, br, 1H), 8.08 (s, 1H), 7.60-6.70 (m, 8H), 4.50 (s, 2H), 3.70 (s, 3H). MS (EI) for $C_{20}H_{18}N_6O_3$: 391 (MH+).

$N^5$-1H-benzimidazol-2-yl-$N^4$-(pyridin-2-ylmethyl)-1H-imidazole-4,5-dicarboxamide.

$^1$H NMR (400 MHz, DMSO-d6): δ 13.72 (s, 1H), 12.17 (s, 1H), 9.54 (s, 1H), 8.56 (d, 1H), 8.12 (s, 1H), 7.79 (t, 1H), 7.52 (m, 1H), 7.38 (d, 2H), 7.30 (t, 1H), 7.11 (m, 3H), 4.69 (d, 2H). MS (EI) for $C_{18}H_{15}N_7O_2$: 362 (MH+).

1,1-dimethylethyl 3-({4-[({4-[(1H-benzimidazol-2-ylamino)carbonyl]-1H-imidazol-5-yl}carbonyl)amino]-3-methylphenyl}oxy)azetidine-1-carboxylate.

$^1$H NMR (400 MHz, DMSO-d6): δ 13.72 (s, 1H), 12.17 (s, 1H), 9.54 (s, 1H), 8.56 (d, 1H), 8.12 (s, 1H), 7.79 (t, 1H), 7.52 (m, 1H), 7.38 (d, 2H), 7.30 (t, 1H), 7.11 (m, 3H), 4.69 (d, 2H). MS (EI) for $C_{18}H_{15}N_7O_2$: 362 (MH+).

$N^4$-(2,4-dimethylphenyl)-$N^5$-(1,3-dimethyl-1H-pyrazol-5-yl)-1H-imidazole-4,5-dicarboxamide.

$^1$H NMR (400 MHz, DMSO-d6): δ 13.8 (br, 1H), 10.2 (br, 2H), 8.18 (s, 1H), 7.44 (m, 2H), 7.05 (m, 2H), 6.88 (m, 2H), 6.78 (m, 1H), 5.05 (m, 1H), 4.35 (m, 2H), 3.85 (m, 2H), 2.23 (s, 3H), 1.38 (s, 9H). MS (EI) for $C_{27}H_{29}N_7O_5$: 532 (MH+).

$N^4$-1H-benzimidazol-2-yl-$N^5$-(1,2,3,4-tetrahydroisoquinolin-5-yl)-1H-imidazole-4,5-dicarboxamide.

$^1$H NMR (400 MHz, DMSO-d6): δ 12.78 (br s, 1H), 10.86 (br s, 1H), 9.15 (s, 1H), 8.08 (s, 1H), 7.56-7.54 (d, 1H), 7.09 (s, 1H), 7.06-704 (d, 1H), 8.29 (s, 1H), 2.28 (s, 3H), 2.25 (s, 6H), 21.4 (s, 3H). MS (EI) for $C_{18}H_{20}N_6O_2$, 353 (MH+).

$N^5$-1H-benzimidazol-2-yl-$N^4$-piperidin-4-yl-1H-imidazole-4,5-dicarboxamide.

$^1$H NMR (400 MHz, d6-DMSO): δ 11.0 (br, 1H), 9.76 (br, 2H), 8.33 (s, 1H), 7.62 (m, 2H), 7.51 (m, 1H), 7.34-7.36 (m, 2H), 7.19 (d, 2H), 4.30 (s, 2H), 3.34 (m, 2H), 3.00 (m, 2H). MS (EI) for $C_{21}H_{19}N_7O_2$: 402 (MH+).

$N^5$-1H-benzimidazol-2-yl-$N^4$-(cyclohexylmethyl)-1H-imidazole-4,5-dicarboxamide.

$^1$H NMR (400 MHz, DMSO-d6): δ 12.18 (s, 1H), 9.14 (s, 1H), 8.08 (s, 1H), 7.49 (s, 2H), 7.12 (dd, 2H), 4.15 (m, 1H), 2.98 (t, 2H), 1.87-1.98 (m, 4H). MS (EI) for C17H19N7O2: 354 (MH+).

$N^5$-1H-benzimidazol-2-yl-$N^4$-{[4-(methyloxy)phenyl]methyl}-1H-imidazole-4,5-dicarboxamide.

$^1$H NMR (400 MHz, DMSO-d6): δ 13.70 (m, 1H), 12.21 (m, 1H), 9.04 (m, 1H), 8.11 (d, 1H), 7.49-7.57 (m, 2H), 7.17 (m, 2H), 3.26 (m, 2H), 1.75 (m, 6H), 1.24 (m, 3H), 1.01 (m, 2H). MS (EI) for $C_{19}H_{22}N_6O_2$: 367 (MH+).

$N^5$-1H-benzimidazol-2-yl-$N^4$-[2-(methylsulfonyl)phenyl]-1H-imidazole-4,5-dicarboxamide.

$^1$H NMR (400 MHz, DMSO-d6): δ 9.42 (m, 1H), 7.92 (s, 1H), 7.47 (m, 2H), 7.32 (d, 2H), 7.10 (dd, 2H), 6.90 (d, 2H), 4.47 (s, 2H), 3.72 (s, 3H). MS (EI) for $C_{20}H_{18}N_6O_3$: 391 (MH+).

$N^5$-{2-[2,5-bis(methyloxy)phenyl]ethyl}-$N^4$-(2,4-dimethylphenyl)-1H-imidazole-4,5-dicarboxamide.

$^1$H NMR (400 MHz, DMSO-d6): δ 11.45 (s, br, 1H), 8.45 (s, br, 1H), 8.34 (s, 1H), 8.05-8.0 (m, 1H), 7.92-7.85 (m, 1H), 7.66-7.54 (m, 3H), 7.40-7.34 (m, 2H), 3.35 (s, 3H). MS (EI) for $C_{19}H_{16}N_6O_4S$: 425 (MH+).

$N^5$-1H-benzimidazol-2-yl-$N^4$-[2-(ethyloxy)phenyl]-1H-imidazole-4,5-dicarboxamide.

$^1$H NMR (400 MHz, DMSO-d6): δ 13.37 (br s, 1H), 12.76 (s, 1H), 10.87-10.85 (t, 1H), 9.88 (s, 1H), 8.72-8.69 (t, 1H), 7.89 (s, 1H), 7.74-7.72 (d, 1H), 7.06-7.03 (m, 1H), 6.85-6.82 (m, 1H), 6.75-6.74 (d, 1H), 6.72-6.71 (d, 1H), 6.71-6.69 (m, 1H), 3.70 (s, 3H), 3.65 (s, 3H), 3.52-3.47 (m, 2H), 2.81-2.73 (m, 2H), 2.27 (s, 3H), 2.24 (s, 3H). MS (EI) for $C_{23}H_{26}N_4O_4$: 423 (MH+).

$N^4$-(2,4-dimethylphenyl)-$N^5$-methyl-$N^5$-(2-pyridin-2-ylethyl)-1H-imidazole-4,5-dicarboxamide.

$^1$H NMR (400 MHz, DMSO-d6): δ 9.15 (s, 1H), 8.34 (d, 2H), 7.68 (dd, 2H), 7.41 (dd, 2H), 7.19 (m, 2H), 7.06 (t, 1H), 4.19 (dd, 2H), 1.39 (d, 3H). MS (EI) for $C_{20}H_{18}N_6O_3$: 391 (MH+).

$N^5$-1H-benzimidazol-2-yl-$N^4$-methyl-$N^4$-(2-methylphenyl)-1H-imidazole-4,5-dicarboxamide.

$^1$H NMR (400 MHz, DMSO-d6): δ 12.75 (br s, 1H), 8.56 (br s, 1H), 8.53-8.51 (m, 2H), 7.79-7.75 (m, 2H), 7.59 (s, 1H), 7.58-7.54 (d, 1H), 7.35-7.33 (d, 2H), 7.31-7.29 (m, 2H). MS (EI) for $C_{21}H_{23}N_5O_2$: 378 (MH+).

$N^5$-1H-benzimidazol-2-yl-$N^4$-(2-{[cyclohexyl(methyl)amino]methyl}phenyl)-1H-imidazole-4,5-dicarboxamide.

$^1$H NMR (400 MHz, DMSO-d6): δ 8.24 (s, 1H), 7.87 (s, 1H), 7.74-7.67 (m, 2H), 7.44-7.28 (m, 4H), 7.20-7.04 (m, 2H), 3.36 (s, 3H), 2.23 (s, 3H). MS (EI) for $C_{20}H_{18}N_6O_2$: 375 (MH+).

N-1H-benzimidazol-2-yl-4-(3,4-dihydroquinolin-1(2H)-ylcarbonyl)-1H-imidazole-5-carboxamide.

$^1$H NMR (400 MHz, DMSO-d6): δ 13.81 (s, 1H), 12.40 (s, 1H), 12.20 (s, 1H), 8.24 (d, 1H), 8.08 (s, 1H), 7.56-7.37 (m, 3H), 7.32-7.28 (m, 1H), 7.18-7.10 (m, 3H), 3.68 (s, 2H), 2.17 (s, 3H), 2.04-1.96 (m, 2H), 1.82-1.76 (m, 2H), 1.62-1.58 (m, 1H), 1.40-1.05 (m, 6H). MS (EI) for $C_{26}H_{29}N_7O_2$: 472 (MH+).

$N^5$-1H-benzimidazol-2-yl-$N^4$-[2-(1,1-dimethylethyl)phenyl]-1H-imidazole-4,5-dicarboxamide.

$^1$H NMR (400 MHz, DMSO-d6): δ 8.16 (s, 1H), 7.72-7.64 (m, 2H), 7.44-7.36 (m, 2H), 7.24-6.92 (m, 4H), 4.00-3.60 (m, 2H), 2.88-2.75 (m, 2H), 2.10-1.92 (m, 2H). MS (EI) for $C_{21}H_{18}N_6O_2$: 387 (MH+).

$N^5$-1H-benzimidazol-2-yl-$N^4$-[2-(1,1-dimethylethyl)phenyl]-1H-imidazole-4,5-dicarboxamide.

$^1$H NMR (400 MHz, DMSO-d6): δ 13.95 (s, 1H), 12.20 (s, 1H), 10.20 (s, 1H), 8.20 (s, 1H), 7.62-7.48 (m, 3H), 7.44-7.38 (m, 1H), 7.36-7.28 (m, 2H), 7.15-6.90 (m, 2H), 1.40 (s, 9H). MS (EI) for C22H22N6O2: 403 (MH+).

$N^5$-1H-benzimidazol-2-yl-$N^4$-(2-butylphenyl)-1H-imidazole-4,5-dicarboxamide.

$^1$H NMR (400 MHz, DMSO-d6): δ 11.80 (s, 1H), 7.90 (s, 1H), 7.78-7.60 (m, 4H), 7.25-7.10 (m, 4H), 2.30 (s, 6H). MS (EI) for $C_{19}H_{18}N_4O_2$: 335 (MH+).

$N^5$-1H-benzimidazol-2-yl-$N^4$-[2-(1H-pyrrol-1-yl)phenyl]-1H-imidazole-4,5-dicarboxamide.

$^1$H NMR (400 MHz, DMSO-d6): δ 13.95 (s, 1H), 12.30 (s, br, 1H), 10.38 (s, 1H), 8.19 (s, 1H), 7.70-7.63 (d, 1H), 7.55-7.42 (m, 2H), 7.37-7.20 (m, 3H), 7.18-7.08 (m, 2H), 2.68 (t, 2H), 1.60-1.50 (m, 2H), 1.38-1.24 (m, 2H), 0.9-0.75 (m, 3H). MS (EI) for $C_{22}H_{22}N_6O_2$: 403 (MH+).

N⁵-1H-benzimidazol-2-yl-N⁴-(2-morpholin-4-ylethyl)-1H-imidazole-4,5-dicarboxamide.

¹H NMR (400 MHz, DMSO-d6): δ 13.67 (m, 1H), 12.17 (s, 1H), 8.86 (m, 1H), 8.07 (s, 1H), 7.52 (m, 1H), 7.45 (m, 1H), 7.11 (d, 2H), 3.59 (t, 4H), 3.50 (dd, 2H), 2.45 (m, 4H). MS (EI) for $C_{18}H_{21}N_7O_3$: 384 (MH+).

N⁴-(2,4-dimethylphenyl)-N⁵-1H-indol-5-yl-1H-imidazole-4,5-dicarboxamide.

¹H NMR (400 MHz, DMSO-d6): δ 13.67 (m, 1H), 12.17 (s, 1H), 8.86 (m, 1H), 8.07 (s, 1H), 7.52 (m, 1H), 7.45 (m, 1H), 7.11 (d, 2H), 3.59 (t, 4H), 3.50 (dd, 2H), 2.45 (m, 4H). MS (EI) for $C_{18}H_{21}N_7O_3$: 384 (MH+).

N⁵-(2,4-dimethylphenyl)-N⁴-(4-phenyl-1H-imidazol-2-yl)-1H-imidazole-4,5-dicarboxamide.

¹H NMR (400 MHz, DMSO-d6): δ 13.95 (s, 1H), 12.42 (s, 1H), 12.10 (s, 1H), 8.30 (d, 1H), 8.04 (s, 1H), 7.60-7.37 (m, 3H), 7.33-7.25 (m, 1H), 7.20-7.07 (m, 3H), 7.18-7.08 (m, 2H), 3.77 (d, 2H), 2.17 (s, 3H), 2.10-1.90 (m, 2H), 1.82-1.74 (m, 2H), 1.65-1.55 (m, 1H), 1.38-1.00 (m, 6H). MS (EI) for $C_{26}H_{29}N_7O_2$: 472 (MH+).

1,1-dimethylethyl 5-[({4-[(1H-benzimidazol-2-ylamino)carbonyl]-1H-imidazol-5-yl}carbonyl)amino]-3,4-dihydroisoquinoline-2(1H)-carboxylate.

¹H NMR (400 MHz, DMSO-d6): δ 13.60 (br s, 1H), 11.10 (s, 1H), 10.16 (br s, 1H), 9.09 (br s, 1H), 8.01-7.96 (d, 2H), 7.48-7.35 (m, 2H, 7.11 (s, 1H), 7.07-7.05 (d, 1H), 6.45-6.42 (d, 1H), 2.29 (s, 6H). MS (EI) for $C_{21}H_{19}N_5O_2$: 374 (MH+).

N⁵-[2-(2-aminoethyl)phenyl]-N⁴-1H-benzimidazol-2-yl-1H-imidazole-4,5-dicarboxamide.

¹H NMR (400 MHz, DMSO-d6): δ13.80 (br s, 1H), 12.4 (br s, 1H), 10.25 (br s, 1H), 9.35 (br s, 1H), 7.37 (m, 1H), 7.26 (m, 2H), 7.22 (m, 2H), 7.13 (m, 3H), 2.98 (m, 2H), 2.83 (m, 2H), 2.0 (br s, 2H). MS (EI) for $C_{20}H_{19}N_7O_2$: 390 (MH+).

N⁴-1H-benzimidazol-2-yl-N⁵-(2,4-dimethylphenyl)-N⁴-methyl-1H-imidazole-4,5-dicarboxamide.

¹H NMR (400 MHz, DMSO-d6): δ 13.80 (br, 1H), 12.20 (br, 1H), 10.40 (br, 1H), 8.16 (s, 1H), 4.42 8 m, 2H), 7.23 (m, 2H), 7.05 (m, 2H), 4.56 (s, 2H), 3.58 (m, 2H), 2.67 (m, 2H), 1.41 (s, 9H). MS (EI) for $C_{26}H_{27}N_7O_4$: 502 (MH+).

N⁵-1H-benzimidazol-2-yl-N⁴-{2-[(trifluoromethyl)oxy]phenyl}-1H-imidazole-4,5-dicarboxamide.

¹H NMR (400 MHz, DMSO-d6): δ 13.8 (br s, 1H), 10.53 (br s, 1H), 8.23 (br s, 1H), 7.89-7.87 (m, 2H), 7.53-7.49 (m, 3H), 7.45-7.43 (m, 2H), 7.39-7.36 (m, 7H). MS (EI) for C24H18N6O2: 423 (MH+).

5-{[2-(1H-benzimidazol-2-yl)hydrazino]carbonyl}-N-(2-methylphenyl)-1H-imidazole-4-carboxamide.

¹H NMR (400 MHz, DMSO-d6): δ 8.36 (s, 1H), 8.27 (m, 2H), 7.66 (m, 2H), 7.34-7.42 (m, 4H), 2.04-3.06 (m, 4H). MS (EI) for $C_{20}H_{19}N_7O_2$: 390 (MH+).

1,1-dimethylethyl 4-([{4-({5-[(1H-benzimidazol-2-ylamino)carbonyl]-1H-imidazol-4-yl}carbonyl)amino]phenyl}oxy)piperidine-1-carboxylate.

¹H NMR (400 MHz, DMSO-d6): δ 10.78 (s, 1H), 7.77 (s, 1H), 7.60-7.67 (m, 3H), 7.44 (m, 2H), 7.42 d, 1H), 7.07 (d, 1H), 3.65 (s, 3H), 2.30 (s, 3H), 2.24 (s, 3H). MS (EI) for $C_{21}H_{20}N_6O_2$: 389 (MH+).

N⁵-1H-benzimidazol-2-yl-N⁴-{2-[(dimethylamino)methyl]phenyl}-1H-imidazole-4,5-dicarboxamide.

¹H NMR (400 MHz, DMSO-d6): δ 8.33-8.40 (m, 1H), 8.06-8.12 (m, 1H), 7.54-7.64 (m, 5H), 7.23 (m, 1H), 7.18 (m, 1H). MS (EI) for $C_{19}H_{19}F_{13}N_6O_3$: 431 (MH+).

N⁴-(2,4-dimethylphenyl)-N⁵-(1-methyl-1H-benzimidazol-2-yl)-1H-imidazole-4,5-dicarboxamide.

¹H NMR (400 MHz, DMSO-d6): δ 13.4 (br s, 1H), 10.25 (br s, 1H), 9.35 (br s, 1H), 7.59 (m, 1H), 7.22 (m, 3H), 7.09 (m, 2H), 7.02 (d, 1H), 3.47 (s, 3H), 2.34 (s, 3H), 2.12 (s, 2.12). MS (EI) for $C_{21}H_{20}N_6O_2$: 389 (MH+).

N⁴-(2-chlorophenyl)-N⁵-[(3-methylphenyl)methyl]-1H-imidazole-4,5-dicarboxamide.

¹H NMR (400 MHz, DMSO-d6): δ 13.90 (s, br, 1H), 12.38 (s, 1H), 12.21 (s, 1H), 8.30 (d, 1H), 8.12 (s, 1H), 7.56-7.40 (m, 3H), 7.32-7.27 (m, 1H), 7.20-7.10 (m, 3H), 3.58 (s, 2H), 2.26 (s, 6H). MS (EI) for $C_{21}H_{21}N_7O_2$: 404 (MH+).

N-(2,5-dimethylphenyl)-5-[(4-pyrimidin-2-ylpiperazin-1-yl)carbonyl]-1H-imidazole-4-carboxamide.

¹H NMR (400 MHz, DMSO-d6): δ 13.80 (br s, 1H), 12.07 (br s, 1H), 10.05 (br s, 1H), 7.77-7.75 (d, 1H), 7.46-7.44 (d, 1H), 7.39-7.36 (m, 2H), 7.12 (m, 2H), 7.02 (s, 1H), 6.99-6.97 (d, 1H), 3.60 (s, 3H), 2.24 (s, 6H). MS (EI) for $C_{21}H_{20}N_6O_2$: 389 (MH+).

N⁵-1,3-benzothiazol-2-yl-N⁴-(2,4-dimethylphenyl)-1H-imidazole-4,5-dicarboxamide.

¹H NMR (400 MHz, DMSO-d6): δ 13.56 (br s, 1H), 10.30 (br s, 1H), 9.32 (br s, 1H), 8.10 (s. 1H), 7.99 (s, 1H), 7.54 (s, 1H), 7.38 (s, 1H), 7.21-7.16 (m, 4H), 4.49 (s, 2H), 2.28 (s, 3H). MS (EI) for $C_{19}H_{17}ClN_4O_2$: 369 (MH+).

N⁵-1,3-benzothiazol-2-yl-N⁴-(2-chlorophenyl)-1H-imidazole-4,5-dicarboxamide.

¹H NMR (400 MHz, DMSO-d6): δ 11.70 (br s, 1H), 8.14-8.12 (m, 1H), 7.94 (S, 1H), (br s, 1H), 7.58-7.53 (m, 1H), 7.06 (s, 1H), 7.02-7.00 (d, 1H), 6.86-6.84 (d, 1H), 6.68-6.65 (m, 1H), 4.19 (m, 2H), 3.80 (m, 2H), 3.63 (m, 2H), 3.59 (m, 2H), 2.29 (s, 3H), 2.25 (s, 3H). MS (EI) for $C_{21}H_{23}N_7O_2$: 406 (MH+)

N⁴-phenyl-N⁵-pyridin-2-yl-1H-imidazole-4,5-dicarboxamide.

¹H NMR (400 MHz, DMSO-d6): δ 13.58 (br s, 1H), 10.4 (br s, 1H), 8.08 (br s, 1H), 8.00-7.98 (d, 1H), 7.75-7.73 (d, 1H), 7.54-7.52 (d, 1H), 7.45-7.41 (t, 1H), 7.32-7.28 (t, 1H), 7.13 (s, 1H), 7.10-7.07 (d, 1H), 2.31 (s, 3H), 2.28 (s, 3H). MS (EI) for $C_{20}H_{17}N_5O_2$: 392 (MH+).

N⁴-(2,4-dimethylphenyl)-N⁵-(pyridin-2-ylmethyl)-1H-imidazole-4,5-dicarboxamide.

¹H NMR (400 MHz, DMSO-d6): δ 13.87 (br s, 1H), 12.25 (br s, 1H), 10.53 (s, 1H), 8.23 (s, 1H), 8.15-8.13 (d, 1H), 8.06-8.04 (d, 1H), 7.83-7.81 (d, 1H), 7.63-7.59 (d, 1H), 7.49-7.45 (m, 2H), 7.37-7.31 (m, 2H). MS (EI) for $C_{18}H_{12}ClN_5O_2$: 398 (MH+).

N⁴-(2,4-dimethylphenyl)-N⁵-(pyridin-3-ylmethyl)-1H-imidazole-4,5-dicarboxamide.

¹H NMR (400 MHz, DMSO-d6): δ 13.68 (br s, 1H), 13.22 (br s, 1H), 10.58 (br s, 1H), 7.68 (m, 2H), 7.73 (m, 2H), 7.43-7.39 (m, 3H), 7.17 (m, 2H). MS (EI) for $C_{16}H_{13}N_5O_2$: 308 (MH+).

N⁵-(1H-benzimidazol-2-ylmethyl)-N⁴-(2,4-dimethylphenyl)-1H-imidazole-4,5-dicarboxamide.

¹H NMR (400 MHz, DMSO-d6): δ 12.77 (br s, 1H), 11.30 (br s, 1H), 9.96 (br s, 1H), 9.34 (br s, 1H), 7.49 (s, 1H), 7,7607.74 (d, 1H), 7.55 (s, 1H), 4.51-4.49 (d, 2H), 2.28 (s, 3H), 2.26 (s, 3H). MS (EI) for $C_{19}H_{19}N_5O_2$: 350 (MH+).

N⁵-1H-benzimidazol-2-yl-N⁴-[(2,4-dimethylphenyl)methyl]-1H-imidazole-4,5-dicarboxamide.

¹H NMR (400 MHz, DMSO-d6): δ 12.70 (br s, 1H), 11.38 (br s, 1H), 9.98 (br, 1H), 9.45 (t, 1H), 8.65 (d, 1H), 8.59 (d, 1H), 8.58-8.56 (m, 1H), 7.94 (s, 1H), 7.88-7.86 (m, 1H), 7.76-7.74 (m, 1H), 7.55 (m, 1H), 7.48-7.45 (m, 1H), 7.37-7.34 (m, 1H), 7.06 (s, 1H), 7.02-7.00 (d, 1H), 4.52-4.50 (d, 2H), 2.33 (s, 3H), 2.26 (s, 3H). MS (EI) for $C_{19}H_{19}N_5O_2$: 350 (MH+).

N-(2,4-dimethylphenyl)-5-{[4-(phenylmethyl)piperazin-1-yl]carbonyl}-1H-imidazole-4-carboxamide.

$^1$H NMR (400 MHz, DMSO-d6): δ 13.57 (br s, 1H), 12.37 (br s, 1H), 9.63 (br s, 1H), 9.11 (s, 1H), 8.04 (s, 1H), 7.77-7.75 (m, 2H), 7.67 (b s, 1H), 7.53-7.51 (2H), 7.02-7.00 (m, 2H), 5.04-5.03 (d, 2H), 2.24 (s, 3H), 2.15 (s, 3H). MS (EI) for $C_{21}H_{20}N_6O_2$: 389 (MH+).

$N^4$-(2,4-dimethylphenyl)-$N^5$-(phenylmethyl)-1H-imidazole-4,5-dicarboxamide.

$^1$H NMR (400 MHz, DMSO-d6): δ 8.30 (m, 1H), 7.65 (dd, 2H), 7.40 (dd, 2H), 7.14 (d, 1H), 7.02 (s, 1H), 6.98 (d, 1H), 4.55 (d, 2H), 2.32 (s, 3H), 2.24 (s, 3H). MS (EI) for $C_{21}H_{20}N_6O_2$: 389 (MH+).

$N^4$-(2,4-dimethylphenyl)-$N^5$-[2-(1H-indol-3-yl)ethyl]-1H-imidazole-4,5-dicarboxamide. $^1$H NMR (400 MHz, DMSO-d6): δ 12.82 (br s, 1H) 8.85 (s, 1H), 7.56 (s, 2H), 7.43-7.23 (m, 6H), 3.32 (m, 8H), 3.08-3.06 (m, 2H),), 2.48 (s, 6H). MS (EI) for $C_{24}H_{27}N_5O_2$: 402 (MH+).

5-{[4-(3-chlorophenyl)piperazin-1-yl]carbonyl}-N-(2,4-dimethylphenyl)-1H-imidazole-4-carboxamide.

$^1$H NMR (400 MHz, DMSO-d6): δ 13.3 (br s, 1H), 10.26 (br s, 1), 8.25, 7.21 (m, 2H), 7.08 (d, 1H), 7.02 (d, 1H), 6.95 (d, 1H), 6.83 (m, 2H), 3.36 (m, 8H), 2.34 (s, 3H), 2.12 (s, 3H). MS (EI) for $C_{23}H_{24}ClN_5O_2$: 439 (MH+).

N-(2,4-dimethylphenyl)-5-[(4-pyrazin-2-ylpiperazin-1-yl)carbonyl]-1H-imidazole-4-carboxamide.

$^1$H NMR (400 MHz, DMSO-d6): δ 13.4 (br s, 1H), 10.25 (br s, 1H), 8.40 (m, 1H), 8.35 (m, 2H), 8.25 (s, 1H), 7.21 (m, 1H), 7.04 (m, 2H), 3.81 (s, 4H), 3.34 (s, 4H), 2.34 (s, 3H), 2.12 (s, 3H). MS (EI) for $C_{21}H_{23}N_7O_2$: 406 (MH+).

$N^5$-1H-benzimidazol-2-yl-$N^4$-(2-methylcyclohexyl)-1H-imidazole-4,5-dicarboxamide.

$^1$H NMR (400 MHz, DMSO-d6): δ 13.70 (m, 1H), 12.21 (m, 1H), 9.04 (m, 1H), 8.11 (d, 1H), 7.49-7.57 (m, 2H), 7.17 (m, 2H), 3.26 (m, 2H), 1.75 (m, 6H), 1.24 (m, 3H), 1.01 (m, 2H). MS (EI) for $C_{19}H_{22}N_6O_2$: 367 (MH+).

$N^5$-1H-benzimidazol-2-yl-$N^4$-(5-bromo-2-methylphenyl)-1H-imidazole-4,5-dicarboxamide.

$^1$H NMR (400 MHz, DMSO-d6): δ 8.36 (s, 1H), 7.86 (s, 1H), 7.64 (m, 2H), 7.43 (d, 1H), 7.38 (dd, 2H), 7.33 (d, 1H), 2.31 (s, 3H). MS (EI) for $C_{19}H_{15}BrN_6O_2$: 440 (MH+).

$N^5$-1H-benzimidazol-2-yl-$N^4$-(2,5-dichlorophenyl)-1H-imidazole-4,5-dicarboxamide.

$^1$H NMR (400 MHz, DMSO-d6): δ 8.41 (m, 1H), 8.19 (d, 1H), 7.70 (s, 1H), 7.67 (dd, 2H), 7.44 (d, 1H), 7.39-7.42 (m, 2H). MS (EI) for $C_{18}H_{12}Cl_2N_6O_2$: 416 (MH+).

methyl[(2-{[(4-{[(2,4-dimethylphenyl)amino]carbonyl}-1H-imidazol-5-yl)carbonyl]amino}-1H-benzimidazol-6-yl)oxy]acetate.

$^1$H NMR (400 MHz, DMSO-d6): δ 13.80 (s, 1H), 10.21 (s, 1H), 8.08 (s, 1H), 7.60-7.30 (m, 2H), 7.20-6.90 (m, 3H), 6.77 (s, 1H), 4.75 (s, 2H), 3.70 (s, 3H), 2.30-2.15 (m, 6H). MS (EI) for $C_{23}H_{22}N_6O_5$: 463 (MH+).

$N^5$-(6-{[2-(dimethylamino)-2-oxoethyl]oxy}-1H-benzimidazol-2-yl)-$N^4$-(2,4-dimethylphenyl)-1H-imidazole-4,5-dicarboxamide.

$^1$H NMR (400 MHz, DMSO-d6): δ 11.95 (s, 1H), 10.20 (s, 1H), 7.98 (s, 1H), 7.40-7.25 (m, 2H), 7.10-6.90 (m, 3H), 6.78-6.70 (m, 1H), 4.78 (s, 2H), 3.10 (s, 3H), 2.90 (s, 3H), 2.30-2.20 (m, 6H). MS (EI) for $C_{24}H_{25}N_7O_4$: 476 (MH+).

$N^5$-(6-{[2-(dimethylamino)-2-oxoethyl]oxy}-1H-benzimidazol-2-yl)-$N^4$-(2,4-dimethylphenyl)-1H-imidazole-4,5-dicarboxamide.

$^1$H NMR (400 MHz, DMSO-d6): δ 12.10 (s, 1H), 10.22 (s, 1H), 8.18 (s, 1H), 8.0 (s, 1H), 7.58-7.30 (m, 2H), 7.15-7.00 (m, 2H), 6.82-6.78 (m, 1H), 4.45 (s, 2H), 3.35 (t, 3H), 3.20 (t, 3H), 2.35 (s, 3H), 2.25 (s, 3H), 2.20 (s, br, 6H). MS (EI) for $C_{26}H_{30}N_8O_4$: 519 (MH+).

$N^4$-1H-benzimidazol-2-yl-$N^5$-[2-methyl-4-(piperidin-4-yloxy)phenyl]-1H-imidazole-4,5-dicarboxamide.

$^1$H NMR (400 MHz, DMSO-d6): δ 13.4 (br s 1H), 10.26 (br s, 2H), 8.26 (s, 1H), 7.61 (m, 1H0, 7.22 (m, 1H), 7.05 (m, 2H), 7.00 (d, 1H), 6.81 (m, 1H), 3.72 (m, 1H), 2.78 (m, 2H), 2.71 (m, 2H), 2.35 (s, 3H), 2.12 (s, 3H), 2.01 (m, 2H), 1.81 (m, 2H). MS (EI) for $C_{24}H_{25}N_7O_3$: 460 (MH+).

$N^5$-1H-benzimidazol-2-yl-$N^4$-[2-chloro-5-(methyloxy)phenyl]-1H-imidazole-4,5-dicarboxamide.

$^1$H NMR (400 MHz, DMSO-d6): δ 8.38 (s, 1H), 7.72 (d, 1H), 7.67 (dd, 2H), 7.53 (m, 1H), 7.40 (dd, 2H), 6.94 (dd, 1H), 3.83 (s, 3H). MS (EI) for $C_{19}H_{15}ClN_6O_3$: 411.9 (MH+).

$N^5$-(2,4-dimethylphenyl)-$N^4$-[5-(4-methylpiperazin-1-yl)-1H-benzimidazol-2-yl]-1H-imidazole-4,5-dicarboxamide:

$^1$H NMR (400 MHz, DMSO-d6): δ 13.4 (br s, 1H), 10.28 (br s, 1H), 9.35 (br s, 1H), 8.26 (s, 1H), 7.42 (m, 1H), 7.22 (m, 1H), 7.09 (d, 1H), 7.02 (m, 2H), 3.46 (s, 4H), 2.39 (s, 4H), 2.32 (s, 3H), 2.14 (s, 3H). MS (EI) for $C_{25}H_{28}N_8O_2$: 473 (MH+).

[(2-{[(4-{[(2,4-dimethylphenyl)amino]carbonyl}-1H-imidazol-5-yl)carbonyl]amino}-1H-benzimidazol-6-yl)oxy]acetic acid $^1$H NMR (400 MHz, DMSO-d6): δ 8.35 (s, 1H), 7.53-7.40 (m, 2H), 7.17 (s, 1H), 7.12-7.05 (m, 2H), 7.00-6.95 (m, 1H), 4.75 (s, 2H), 2.30 (s, 3H), 2.25 (s, 3H). MS (EI) for $C_{22}H_{20}N_6O_5$: 449 (MH+).

$N^4$-(2,4-dimethylphenyl)-$N^5$-{6-[(2-hydroxyethyl)oxy]-1H-benzimidazol-2-yl}-1H-imidazole-4,5-dicarboxamide.

$^1$H NMR (400 MHz, DMSO-d6): δ 10.50 (s, 1H), 8.25 (s, 1H), 7.55-7.40 (m, 2H), 7.18-7.08 (m, 2H), 6.98-6.90 (m, 2H), 4.00 (t, 2H), 3.75 (t, 2H), 2.30 (s, 3H), 2.25 (s, 3H). MS (EI) for $C_{22}H_{22}N_6O_4$: 435 (MH+).

$N^4$-[5-(azetidin-3-yloxy)-1H-benzimidazol-2-yl]-$N^5$-(2,4-dimethylphenyl)-1H-imidazole-4,5-dicarboxamide.

$^1$H NMR (DMSO-d6): δ 9.05 (br, 1H), 8.79 (br, 1H), 8.13 (s, 1H), 7.40 (m, 2H), 7.05 (s, 1H), 7.04 (m, 1H), 6.85 (m, 1H), 6.70 (m, 1H), 5.02 (m, 1H), 4.19 (m, 2H), 3.95 (m, 2H), 2.24 (s, 3H), 2.20 (s, 3H). MS (EI) for $C_{23}H_{23}N_7O_3$: 446 (MH+).

$N^5$-1H-benzimidazol-2-yl-$N^4$-(4-methylpyridin-3-yl)-1H-imidazole-4,5-dicarboxamide.

$^1$H NMR (400 MHz, DMSO-d6): δ 9.56 (s, 1H), 8.92 (s, 1H), 8.71 (m, 1H), 8.15 (m, 1H), 7.81 (s, 2H), 7.69 (s, 2H), 2.94 (s, 3H). MS (EI) for $C_{18}H_{15}N_7O_2$: 362.5 (MH+).

$N^4$-[5-(azetidin-3-yloxy)-2-methylphenyl]-$N^5$-1H-benzimidazol-2-yl-1H-imidazole-4,5-dicarboxamide.

$^1$H NMR (400 MHz, DMSO-d6): δ 8.21 (m, 1H), 7.51 (m, 2H), 7.26 (m, 4H), 6.71 (m, 1H), 5.10 (m, 1H), 4.25 (m, 2H), 4.03 (m, 2H), 2.67 (m, 1H), 2.26 (s, 3H). MS (EI) for $C_{22}H_{21}N_7O_3$: 432 (MH$^+$).

$N^5$-1H-benzimidazol-2-yl-$N^4$-(2-methylpyridin-3-yl)-1H-imidazole-4,5-dicarboxamide.

$^1$H NMR (400 MHz, DMSO-d6): δ 8.67 (m, 2H), 8.50 (m, 1H), 7.90 (m, 1H), 7.67 (s, 2H), 7.40 (s, 2H), 2.82 (s, 3H). MS (EI) for $C_{19}H_{15}N_7O_2$: 362 (MH+).

1,1-dimethylethyl 3-[(2-{[(5-{[(2,4-dimethylphenyl)amino]carbonyl}-1H-imidazol-4-yl)carbonyl]amino}-1H-benzimidazol-5-yl)oxy]azetidine-1-carboxylate.

$^1$H NMR (DMSO-d6): δ 8.21 (s, 1H), 7.40 (m, 2H), 7.07 (s, 1H), 7.04 (m, 1H), 6.89 (m, 1H), 6.80 (m, 1H), 4.95 (m, 1H), 4.21 (m, 2H), 3.77 (m, 2H), 2.24 (s, 3H), 2.20 (s, 3H). MS (EI) for $C_{28}H_{31}N_7O_5$: 546 (MH+).

1,1-dimethylethyl 4-({4-[({4-[(1H-benzimidazol-2-ylamino)carbonyl]-1H-imidazol-5-yl}carbonyl)amino]-3-methylphenyl}oxy)piperidine-1-carboxylate.
¹H NMR (DMSO-d6): δ 10.22 (br, 1H), 8.15 (s, 1H), 7.47 (m, 3H), 7.13 (m, 2H), 6.93 (s, 1H), 6.88 (m, 1H), 6.80 (m, 1H), 4.55 (m, 1H), 3.62 (m, 2H), 3.20 (m, 2H), 2.23 (s, 3H), 1.89 (m, 2H), 1.50 (m, 2H), 1.39 (s, 9H). MS (EI) for $C_{29}H_{33}N_7O_5$: 560 (MH+).

$N^5$-1H-benzimidazol-2-yl-$N^4$-[(4-methylphenyl)methyl]-1H-imidazole-4,5-dicarboxamide:
¹H NMR (400 MHz, DMSO-d6): δ 13.70 (s, 1H), 9.45 (s, 1H), 8.10 (s, 1H), 7.49 (m, 2H), 7.28 (s, 1H), 7.60 (s, 1H), 7.15 (d, 4H), 4.51 (d, 2H), 2.27 (s, 3H). MS (EI) for $C_{20}H_{18}N_6O_2$: 375 (MH+).

$N^4$-1H-benzimidazol-2-yl-$N^5$-[2-methyl-5-(piperidin-4-yloxy)phenyl]-1H-imidazole-4,5-dicarboxamide.
¹H NMR (400 MHz, DMSO-d6): δ 13.4 (br s, 1H), 10.28 (br s, 1H), 9.39 (br s, 1H), 8.29 (s, 1H), 7.23 (m, 3H), 7.21 (m, 3H), 7.11 (m, 3H), 6.87 (m, 1H), 5.67 (br s, 2H), 2.83 (m, 2H), 2.71 (m, 2H), 2.14 (s, 3H), 2.03 (m, 2H), 1.81 (m, 2H). MS (EI) for $C_{24}H_{25}N_7O_3$: 460 (MH+).

1,1-dimethylethyl 3-({3-[({5-[(1H-benzimidazol-2-ylamino)carbonyl]-1H-imidazol-4-yl}carbonyl)amino]-4-methylphenyl}oxy)azetidine-1-carboxylate.
¹H NMR (400 MHz, DMSO-d6): δ 8.27 (s, 1H), 7.57 (m, 2H), 7.24 (m, 4H), 6.69 (m, 1H), 4.99 (m, 1H), 4.31 (m, 2H), 3.81 (d, 2H), 2.26 (s, 3H), 1.39 (s, 9H). MS (EI) for $C_{27}H_{29}N_7O_5$: 532.7 (MH⁺).

1,1-dimethylethyl 4-({3-[({4-[(1H-benzimidazol-2-ylamino)carbonyl]-1H-imidazol-5-yl}carbonyl)amino]-4-methylphenyl}oxy)piperidine-1-carboxylate.
¹H NMR (DMSO-d6): δ 8.12 (s, 1H), 7.56 (m, 3H), 7.19-7.28 (m, 3H), 6.83 (m, 1H), 4.50 (m, 1H), 3.65 (m, 2H), 3.18 (m, 2H), 2.21 (s, 3H), 1.90 (m, 2H), 1.50 (m, 2H), 1.39 (s, 9H). MS (EI) for $C_{29}H_{33}N_7O_5$: 560 (MH+).

$N^4$-1H-benzimidazol-2-yl-$N^5$-(2,4-dimethylphenyl)-2-methyl-1H-imidazole-4,5-dicarboxamide.
¹H NMR (DMSO-d6): δ 12.46 (br s, 1H), 10.25 (br s, 1H), 9.35 (br s, 1H), 7.22 (m, 3H), 7.11 (d, 1H), 7.12 (m, 2H), 7.04 (br m, 3H), 2.61 (s, 3H), 2.33 (s, 3H), 2.12 (s, 3H). MS (EI) for $C_{21}H_{20}N_6O_2$: 389 (MH+).

$N^5$-(2,4-dimethylphenyl)-$N^4$-[6-(methyloxy)-1H-benzimidazol-2-yl]-1H-imidazole-4,5-dicarboxamide.
¹H NMR (400 MHz, DMSO-d6): δ 10.43 (s, br, 1H), 7.98 (s, 1H), 7.63 (d, 1H), 7.38 (d, 1H), 7.18-7.00 (m, 3H), 6.79 (d, 1H), 3.78 (s, 3H), 2.24 (m, 6H). MS (EI) for $C_{21}H_{20}N_6O_3$: 405 (MH+).

$N^5$-1H-benzimidazol-2-yl-$N^4$-(2-fluoro-6-hydroxyphenyl)-1H-imidazole-4,5-dicarboxamide.
¹H-NMR (400 MHz, CDCl₃): δ 13.82 (s br, 1H), 12.22 (s br, 1H), 10.62 (s br, 1H), 8.15 (s, 1H), 7.93 (s, 1H), 7.72 (dd, 1H), 7.51 (m, 3H), 7.13 (m, 2H). MS (EI) $C_{18}H_{12}BrFN_6O_2$: 444.9 (MH+).

$N^5$-1H-benzimidazol-2-yl-$N^4$-(4-{4-[(ethylamino)carbonyl]piperazin-1-yl}-2-methylphenyl)-1H-imidazole-4,5-dicarboxamide.
¹H NMR (400 MHz, DMSO-d6): δ 13.79 (s, br, 1H), 12.22 (s, br, 1H), 10.17 (s, 1H), 8.18 (s, 1H), 7.57-7.38 (m, 3H), 7.19-7.07 (m, 2H), 7.97-7.85 (m, 2H), 7.56-7.62 (m, 1H), 3.48-3.41 (m, 4H), 3.14-3.03 (m, 7H), 2.24 (s, 3H), 1.02 (m, 3H). MS (EI) for $C_{26}H_{29}N_9O_3$: 516.1 (MH+).

$N^5$-1H-benzimidazol-2-yl-$N^4$-(2-fluoro-6-hydroxyphenyl)-1H-imidazole-4,5-dicarboxamide.
¹H NMR (400 MHz, DMSO-d6): δ 8.22 (s, 1H), 7.74 (m, 2H), 7.29-7.17 (m, 3H), 6.79-6.72 (m, 2H). MS (EI) for $C_{18}H_{13}FN_6O_3$: 381 (MH+).

$N^5$-1H-benzimidazol-2-yl-$N^4$-biphenyl-2-yl-1H-imidazole-4,5-dicarboxamide.
¹H NMR (400 MHz, DMSO-d6): δ 8.20 (s, 1H), 7.78 (d, 1H), 7.74 (s, 1H), 7.40 (m, 2H), 7.30 (m, 2H), 7.06-7.18 (m, 3H), 2.28 (s, 3H), 2.26 (s, 3H). MS (EI) for $C_{22}H_{20}N_6O_2$: 401 (MH+).

Biological Assays

Assay Example 1

Measurement of JAK-2 Kinase Activity by ATP Hydrolysis

JAK-2 kinase activity was measured by monitoring peptide substrate dependent hydrolysis of ATP via quantitation of remaining ATP with luciferase based chemiluminescence. For compound evaluation, 0.5 µl of the compound dissolved in DMSO was added to 10 µl of JAK-2 dissolved in assay buffer (20 mM HEPES pH 7.5, 10 mM MgCl₂, 0.03% Triton and 1 mM DTT). After preincubation for 30 minutes at room temperature, the reaction was initiated by addition of 10 µl of ATP and the substrate peptide poly-Glu-Tyr in assay buffer. Final enzyme, ATP, and peptide concentrations were 3 nM, 1 ΞM, and 2 µM, respectively. After incubation for 60 minutes at room temperature, reaction progress was quantitated by addition of 10 µl Kinase-Glo (Promega) and measurement of chemiluminescence in a Victor reader (Perkin Elmer). A reaction in which compound was omitted was used to determine maximum reaction progress. Omission of compound and enzyme from the reaction was used to determine zero reaction progress.

Assay Example 2

Measurement of JAK-3 Kinase Activity by ATP Hydrolysis

JAK-3 was assayed similarly as JAK-2 (see Assay Example 1) except that the enzyme reaction was carried out for 180 minutes and enzyme, ATP, and peptide concentrations were 30 nM, 2 µM, and 4 µM, respectively.

Another embodiment relates to compounds according to Table 1 having less than 5000 µM of activity against JAK-2.
Another embodiment relates to compounds according to Table 1 having less than 1000 µM of activity against JAK-2.
Another embodiment relates to compounds according to Table 1 having less than 500 µM of activity against JAK-2.
Another embodiment relates to compounds according to Table 1 having less than 200 µM of activity against JAK-2.
Another embodiment relates to compounds according to Table 1 having less than 100 µM of activity against JAK-2.
Another embodiment relates to compounds according to Table 1 having less than 50 µM of activity against JAK-2.
Another embodiment relates to compounds according to Table 1 having less than 40 µM of activity against JAK-2.
Another embodiment relates to compounds according to Table 1 having less than 30 µM of activity against JAK-2.
Another embodiment relates to compounds according to Table 1 having less than 25 µM of activity against JAK-2.
Another embodiment relates to compounds according to Table 1 having less than 20 µM of activity against JAK-2.
Another embodiment relates to compounds according to Table 1 having less than 15 µM of activity against JAK-2.
Another embodiment relates to compounds according to Table 1 having less than 10 µM of activity against JAK-2.
Another embodiment relates to compounds according to Table 1 having less than 5 µM of activity against JAK-2.

From the foregoing it will be appreciated that, although specific embodiments of the invention have been described herein for purposes of illustration, various modifications may

What is claimed is:

1. A compound according to Formula I:

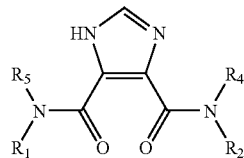

I or a pharmaceutically acceptable salt thereof, wherein
$R_1$ is selected from benzimidazole, indole, quinoline, dihydroquinoline, imidazole, piperazine, benzothiazole, —$CH_2$-pyridine, and —$CH_2$-benzimidazole, wherein each benzimidazole, indole, quinoline, dihydroquinoline, imidazole, piperazine, benzothiazole, $CH_2$-pyridine, and —$CH_2$-benzimidazole is optionally substituted with 1 or 2 substituents selected from halo, —($C_3$-$C_{10}$)cycloalkyl, —($C_1$-$C_6$)alkyl, —($C_1$-$C_6$)alkoxy, -(4-10 membered)heterocycloalkyl, —O-(4-10 membered)heterocycloalkyl, —C(O)O($C_1$-$C_6$)alkyl, —O—($C_1$-$C_6$)alkyl-C(O)$NR_8R_8R_9$, —O—($C_1$-$C_6$)alkyl-C(O)O($C_1$-$C_6$)alkyl, —O—($C_1$-$C_6$)alkyl(4-10 membered)heterocycloalkyl-C(O)O—($C_1$-$C_6$)alkyl, -(4-10 membered)heterocycloalkyl($C_1$-$C_6$)alkyl, -(4-10 membered)heterocycloalkyl($C_1$-$C_6$)alkyl($C_6$-$C_{10}$)aryl, -(4-10 membered)heterocycloalkyl($C_1$-$C_6$)alkyl(4-10 membered)heterocycloalkyl, -(4-10 membered)heterocycloalkyl($C_1$-$C_6$)alkyl(5-10 membered)heteroaryl, —O—($C_1$-$C_6$)alkyl-(4-10 membered)heterocycloalkyl, —O($C_1$-$C_6$)alkyl-C(O)NH($C_5$-$C_{10}$)cycloalkyl, —O($C_1$-$C_6$)alkyl-C(O)NH($C_1$-$C_6$)alkyl($R_6$)($R_7$), -(4-10 membered)heterocycloalkyl($C_6$-$C_{10}$)aryl, —($C_1$-$C_6$)alkyl-NH[($C_1$-$C_6$)alkyl]$_2$, —O—($C_1$-$C_6$)alkyl-NH[($C_1$-$C_6$)alkyl]$_2$, -(4-10 membered)heterocycloalkyl($C_1$-$C_6$)alkyl, —($C_1$-$C_6$)alkoxy-NH[($C_1$-$C_6$)alkyl]$_2$, —($C_6$-$C_{10}$)aryl, —($C_1$-$C_6$)alkoxy($C_1$-$C_6$)alkoxy, -(4-10 membered)heterocycloalkyl-C(O)O—($C_1$-$C_6$)alkyl, —($C_1$-$C_6$)alkoxy(4-10 membered)heterocycloalkyl and —O—($C_1$-$C_6$)alkyl-C(O)OH;
$R_2$ is selected from —($C_6$-$C_{10}$)aryl, —($C_1$-$C_6$)alkyl($C_6$-$C_{10}$)aryl, —NHC(O)($C_4$-$C_{10}$)heterocycloalkyl($C_1$-$C_6$)alkyl, -(5-10 membered)heteroaryl, -(5-10 membered)heteroaryl($C_1$-$C_6$)alkyl, -(4-6 membered)heterocycloalkyl, —O—($C_1$-$C_6$)alkyl(4-10 membered)heterocycloalkyl-C(O)O—($C_1$-$C_6$)alkyl, —O—($C_1$-$C_6$)alkyl-(4-10 membered)heterocycloalkyl, and —($C_1$-$C_6$)alkyl-($C_3$-$C_{10}$)cycloalkyl, wherein each —($C_6$-$C_{10}$)aryl, —NHC(O)($C_4$-$C_{10}$)heterocycloalkyl($C_1$-$C_6$)alkyl, —($C_1$-$C_6$)alkyl($C_6$-$C_{10}$)aryl, -(5-10 membered)heteroaryl, -(5-10 membered)heteroaryl($C_1$-$C_6$)alkyl, -(4-10 membered)heterocycloalkyl, —O—($C_1$-$C_6$)alkyl(4-10 membered)heterocycloalkyl-C(O)O—($C_1$-$C_6$)alkyl, —O—($C_1$-$C_6$)alkyl-(4-10 membered)heterocycloalkyl, and —($C_1$-$C_6$)alkyl-($C_3$-$C_{10}$)cycloalkyl, is optionally substituted with 1, 2, 3, 4 or 5 substituents selected from —($C_1$-$C_6$)alkyl, —($C_1$-$C_6$)alkyl-$R_{12}$, —($C_1$-$C_6$)alkyl)NHC(O)O($C_1$-$C_6$)alkyl, —($C_1$-$C_6$)alkylhydroxy, —($C_1$-$C_6$)alkoxy($C_1$-$C_6$)alkoxy($C_6$-$C_{10}$)aryl, —($C_5$-$C_{10}$)heteroaryl, -(4-10 membered)heterocycloalkyl-S(O)$_2$—($C_6$-$C_{10}$)aryl, -(4-10 membered)heterocycloalkyl, -(4-10 membered)heterocycloalkyl($C_6$-$C_{10}$)aryl, -(4-10 membered)heterocycloalkyl($C_6$-$C_{10}$)aryl-$R_{12}$, —NHC(O)($C_4$-$C_{10}$)heterocycloalkyl($C_1$-$C_6$)alkyl, -(4-10 membered heterocycloalkyl)C(O)NH($C_6$-$C_{10}$)aryl, -(4-10 membered)heterocycloalkylC(O)NH($C_1$-$C_6$)alkyl, —O—($C_1$-$C_6$)alkyl(4-10 membered)heterocycloalkyl, —O—($C_1$-$C_6$)alkyl(4-10 membered)heterocycloalkyl-S(O)$_2$—($C_6$-$C_{10}$)aryl, —S—($C_1$-$C_6$)alkyl, halo, —($C_1$-$C_6$)alkoxy, cyano, —O-(4-10 membered)heterocycloalkyl, —$NH_2$, —$CF_3$, —NHC(O)O($C_1$-$C_6$)alkyl, —C(O)$CH_3$, —C(O)$OR_{10}$, —O-(4-10 membered)heterocycloalkyl-C(O)O($C_1$-$C_6$)alkyl, -(4-10 membered)heterocycloalkyl-C(O)O($C_1$-$C_6$)alkyl, —S(O)O($C_1$-$C_6$)alkyl, —($C_5$-$C_6$)cycloalkly($C_1$-$C_3$)alkyl, —($C_5$-$C_{10}$)cycloalkly($C_1$-$C_6$)alkyl-amino($C_1$-$C_6$)alkyl, —NHC(O)-(4-10 membered)heterocycloalkyl, —($C_1$-$C_6$)alkyl-$NR_{10}$($C_1$-$C_6$)alkyl($C_5$-$C_6$)cycloalkly, -(4-10 membered) heterocycloalkyl)C(O)$NR_7R_8$, —($C_6$-$C_{10}$)aryl, —NH($C_6$-$C_{10}$)aryl, —O-(4-10 membered)heterocycloalkyl($C_1$-$C_6$)alkyl, —O-(4-10 membered)heterocycloalkyl($C_6$-$C_{10}$)aryl, —O-(4-10 membered)heterocycloalkyl($C_1$-$C_6$)alkyl-($C_6$-$C_{10}$)aryl, —O-(4-10 membered)heterocycloalkyl-C(O)CN, —NH($C_1$-$C_6$)alkyl, —$OCF_3$, —NHC(O)(4-10 membered)heterocycloalkyl($C_1$-$C_6$)alkyl, dimethylaminoalkyl, —N[($C_1$-$C_6$)alkyl]$_2$, —NH($C_1$-$C_6$)alkyl), —($C_1$-$C_6$)alkyl)N[($C_1$-$C_6$)alkyl]$_2$, —O-heterocyloalkyl, —O-(4-10 membered)heterocycloalkyl($C_6$-$C_{10}$)aryl, and —($C_1$-$C_6$)alkoxyhydroxy;
$R_4$ and $R_5$ are each independently H or ($C_1$-$C_6$)alkyl, or $R_1$ and $R_5$, together with the nitrogen atom to which they are attached, form a (5-10 membered)heteroaryl or (5-10 membered)heterocycloalkyl, wherein each of the -(5-10 membered)heteroaryl and -(5-10 membered)heterocycloalkyl groups is optionally substituted with one or more groups independently selected from —($C_1$-$C_6$)alkyl, —($C_1$-$C_6$)alkyl($C_6$-$C_{10}$)aryl, and -(5-10 membered)heteroaryl;
or $R_2$ and $R_4$ together with the nitrogen atom to which they are attached form a -(5-10 membered)heteroaryl or -(5-10 membered)heterocycloalkyl, wherein each of the -(5-10 membered)heteroaryl or -(5-10 membered)heterocycloalkyl groups is optionally substituted with one or more groups independently selected from —($C_1$-$C_6$)alkyl, —($C_1$-$C_6$)alkyl($C_6$-$C_{10}$)aryl, and -(5-10 membered)heteroaryl;
$R_6$ and $R_7$ are each independently selected from hydrogen, hydroxy, (5-10 membered)heteroaryl, (4-10 membered)heterocycloalkyl, and ($C_6$-$C_{10}$)aryl, and each $R_6$ and $R_7$ are independently selected when more than one $R_6$ or $R_7$ occurs;
$R_8$, $R_9$ and $R_{10}$ are each independently selected from H and ($C_1$-$C_6$)alkyl, and $R_8$, $R_9$ and $R_{10}$ are each independently selected when more than one $R_8$, $R_9$ or $R_{10}$ occurs;
$R_{11}$ is selected from hydrogen, ($C_1$-$C_6$)alkyl, —($C_1$-$C_6$)alkyl($R_6$)$R_7$, and —($C_1$-$C_6$)alkyl($R_8$)$R_9$, ($C_5$-$C_{10}$)cycloalkyl; and
$R_{12}$ is halo, —OH or —$NH_2$;
with the proviso that when $R_1$ is

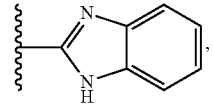

, and R₄ and R₅ are each H, then R₂ is not

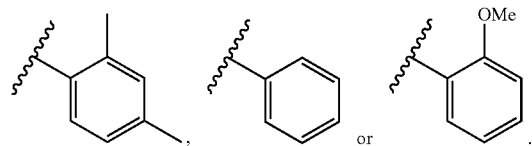

2. The compound according to claim 1, wherein R₂ is selected from phenyl, —CH₂-phenyl, pyrazole, imidazole, naphthalene, piperidine, piperazine, —CH₂-cyclohexane, dihydroindole, and dihydroisoquinoline, wherein each phenyl, —CH₂-phenyl, pyrazole, imidazole, naphthalene, piperidine, piperazine, —CH₂-cyclohexane, dihydroindole or dihydroisoquinoline is optionally substituted with 1, 2 or 3 substituents selected from —(C₁-C₆)alkyl, —(C₁-C₆)alkylhydroxy, -(4-10 membered)heterocycloalkyl(C₆-C₁₀)aryl, —(C₁-C₆)alkylthio, halo, —(C₁-C₆)alkoxy, cyano, —O-(4-6 membered)heterocycloalkyl, amino, —CF₃, —NHC(O)OC(CH₃)₃, —C(O)CH₃, —C(O)OCH₃, —O-(4-10 membered)heterocycloalkyl-C(O)OC(C₁-C₆)alkyl, -(4-10 membered)heterocycloalkyl-C(O)OC(C₁-C₆)alkyl, methylsulfonyl, —(C₅-C₆)cycloalkly(C₁-C₃)alkyl, —(C₅-C₆)cycloalkly(C₁-C₃)alkyl-amino(C₁-C₃)alkyl, —O—(C₁-C₆)alkyl, —NHC(O)-(4-10 membered)heterocycloalkyl, —(C₁-C₆)alkylamino(C₁-C₆)alkyl(C₅-C₆)cycloalkly, -(4-10 membered)heterocycloalkyl)C(O)NR₇R₈, —NH(C₆-C₁₀)aryl, —O-(4-10 membered)heterocycloalkyl(C₁-C₆)alkyl, —O-(4-10 membered)heterocycloalkylaryl, amino(C₁-C₆)alkyl, —OCF₃, —NHC(O)(4-10 membered)heterocycloalkylalkyl, dimethylaminoalkyl, —NH(C₁-C₆)alkyl), —O-heterocycloalkyl, —O-(4-10 membered)heterocycloalkyl(C₆-C₁₀)aryl, and —(C₁-C₆)alkoxyhydroxy.

3. The compound according to claim 1, wherein R₄ and R₅ are each hydrogen.

4. The compound according to claim 1, wherein R₁ is selected from benzimidazole, indole, quinoline, dihydroquinoline, imidazole, piperazine, benzthiazole, —CH₂-pyridine, and —CH₂-benzimidazole, wherein each benzimidazole, indole, quinoline, dihydroquinoline, imidazole, piperazine, benzothiazole, CH₂-pyridine, and —CH₂-benzimidazole is optionally substituted with 1 or 2 substituents selected from halo, —(C₃-C₁₀)cycloalkyl, —(C₁-C₆)alkyl, —(C₁-C₆)alkoxy, -(4-10 membered)heterocycloalkyl, —O-(4-10 membered)heterocycloalkyl, —C(O)O(C₁-C₆)alkyl, —O—(C₁-C₆)alkyl-C(O)NR₈R₉,—O—(C₁-C₆)alkyl-C(O)O(C₁-C₆)alkyl, —O—(C₁-C₆)alkyl(4-10 membered) heterocycloalkyl-C(O)O—(C₁-C₆)alkyl, -(4-10 membered) heterocycloalkyl(C₁-C₆)alkyl, -(4-10 membered)heterocycloalkyl(C₁-C₆)alkyl(C₆-C₁₀)aryl, -(4-10 membered) heterocycloalkyl(C₁-C₆)alkyl(4-10 membered) heterocycloalkyl, -(4-10 membered)heterocycloalkyl(C₁-C₆)alkyl(5-10 membered)heteroaryl, —O—(C₁-C₆)alkyl-(4-10 membered)heterocycloalkyl, —O—(C₁-C₆)alkyl-C(O)NH(C₅-C₁₀)cycloalkyl, —O(C₁-C₆)alkyl-C(O)NH(C₁-C₆)alkyl(R₆)(R₇), -(4-10 membered)heterocycloalkyl(C₆-C₁₀)aryl, —(C₁-C₆)alkyl-N[(C₁-C₆)alkyl]₂, —O—(C₁-C₆)alkylN[(C₁-C₆)alkyl]₂, -(4-10 membered)heterocycloalkyl(C₁-C₆)alkyl, —(C₁-C₆)alkoxy-di[(C₁-C₆)alkyl]amino, —(C₆-C₁₀)aryl, —(C₁-C₆)alkoxy(C₁-C₆)alkoxy, -(4-10 membered) heterocycloalkyl-C(O)O—(C₁-C₆)alkyl, —(C₁-C₆)alkoxy (4-10 membered)heterocycloalkyl and —O—(C₁-C₆)alkyl-C(O)OH; and R₂ is selected from phenyl, —CH₂-phenyl, pyrazole, imidazole, naphthalene, piperidine, piperazine, —CH₂-cyclohexane, dihydroindole, and dihydroisoquinoline, wherein each phenyl, —CH₂-phenyl, pyrazole, imidazole, naphthalene, piperidine, piperazine, —CH₂-cyclohexane, dihydroindole, and dihydroisoquinoline is optionally substituted with 1, 2, 3, 4 or 5 substituents selected from —(C₁-C₆)alkyl, —(C₁-C₆)alkylhydroxy, -(4-10 membered)heterocycloalkyl(C₆-C₁₀)aryl, —(C₁-C₆)alkylthio, halo, —(C₁-C₆)alkoxy, cyano, membered)heterocycloalkyl, amino, —CF₃, —NHC(O)OC(CH₃)₃, —C(O)CH₃, —C(O)OCH₃, —O-(4-10 membered)heterocycloalkyl-C(O)O(C₁-C₆)alkyl, -(4-10 membered)heterocycloalkyl-C(O)O(C₁-C₆) alkyl, methylsulfonyl, —(C₅-C₆)cycloalkly(C₁-C₃) alkyl, —(C₅-C₆)cycloalkly(C₁-C₃)alkyl-NH(C₁-C₃) alkyl, —O—(C₁-C₆)alkyl, —NHC(O)-(4-10 membered)heterocycloalkyl, —(C₁-C₆)alkyl-NH(C₁-C₆)alkyl(C₅-C₆)cycloalkly, -(4-10 membered)heterocycloalkylC(O)NR₇R₈, (C₆-C₁₀)aryl, —NH—(C₆-C₁₀) aryl, —O-(4-10 membered)heterocycloalkyl(C₁-C₆) alkyl, —O-(4-10 membered)heterocycloalkyl(C₅-C₆) aryl, —NH(C₁-C₆)alkyl), —OCF₃, —NHC(O)(4-10 membered)heterocycloalkylalkyl, —(C₁-C₆)alkyl-N(CH₃)₂, —N[(C₁-C₆)alkyl]₂, —NH(C₁-C₆)alkyl), —O-(4-10 membered)heterocycloalkyl, —O-(4-10 membered)heterocycloalkyl(C₆-C₁₀)aryl, and —(C₁-C₆) alkoxyhydroxy.

5. The compound according to claim 1, wherein R₁ is benzamidazole optionally substituted with 1 or 2 substituents selected from —(C₁-C₆)alkoxy(C₁-C₆)alkoxy, —O—(C₁-C₆)alkyl(5-6 membered)heterocycloalkyl, —O—(C₁-C₆) alkyl-C(O)NH(C₁-C₆)alkyl-(five to six membered)heteroaryl, —O—(C₁-C₆)alkyl-N[(C₁-C₆)alkyl]₂, and piperazine optionally substituted with 1 or 2 groups selected from —(C₁-C₆)alkyl, —C(O)O(C₁-C₆)alkyl, —(C₁-C₆)alkyl (C₅-C₆)aryl, and (C₁-C₆)alkyl(5-6 membered)heterocycloalkyl.

6. The compound according to claim 1, wherein R₂ is phenyl substituted with 1, 2 or 3 substituents selected from halo, methyl, methoxy, —O-piperidine, —O-piperazine, —O—(C₁-C₆)alkyl-piperazine, and —O—(C₁-C₆)alkylpiperidine.

7. The compound according to claim 1, wherein R₁ is benzimidazole optionally substituted with 1 or 2 substituents selected from —(C₁-C₆)alkoxy(C₁-C₆)alkoxy, C₆)alkyl(5-6 membered)heterocycloalkyl, —O—(C₁-C₆)alkyl-C(O)NH(C₁-C₆)alkyl-(5-6 membered)heteroaryl, —O—(C₁-C₆) alkyl-N[(C₁-C₆)alkyl]₂, and piperazine optionally substituted with 1 or 2 groups selected from —(C₁-C₆)alkyl, —C(O)O(C₁-C₆)alkyl, —(C₁-C₆)alkyl(C₅-C₆)aryl, or (C₁-C₆)alkyl(5-6 membered)heterocycloalkyl;

R₂ is phenyl substituted with 1, 2 or 3 substituents selected from halo, —(C₁-C₃)alkyl, methoxy, —O-piperidine, —O-piperizine, —O—(C₁-C₆)alkyl-piperazine, and —O—(C₁-C₆)alkylpiperidine;

R₄ is H; and

R₅ is H.

8. The compound according to claim 1, wherein R₁ is benzimidazole, indole, quinoline, dihydroquinoline, imidazole, piperazine, benzothiazole, —CH₂-pyridine, —CH₂-benzimidazole, wherein each benzimidazole, indole, quinoline, dihydroquinoline, imidazole, piperazine, benzothiazole, —CH₂-pyridine, or —CH₂-benzimidazole is substituted with 1 or 2 substituents selected from -(5-10 membered)heteroaryl, —(C₁-C₆)alkyl(5-10 membered)heteroaryl, —(C₆-C₁₀)aryl and -(4-10 membered)heterocycloalkyl is optionally substituted with 1, 2, 3, 4, or 5 substituents selected from halo, —(C₃-C₁₀)cycloalkyl, —(C₁-C₆)alkyl, —(C₁-C₆)alkoxy, -(4-10 membered)heterocycloalkyl, —O-(4-10 membered)heterocycloalkyl, —O-(4-10 membered)heterocycloalkyl-$R_{10}$, —C(O)O($C_1$-$C_6$)alkyl, —O—($C_1$-$C_6$)alkyl-C(O)NR$_8$R$_{11}$, —O—($C_1$-$C_6$)alkyl-C(O)OR$_8$, —O—($C_1$-$C_6$)alkyl(5-10 membered)heteroaryl, —O—($C_1$-$C_6$)alkyl(4-10 membered)heterocycloalkyl-C(O)O—($C_1$-$C_6$)alkyl, -(4-10 membered)heterocycloalkyl($C_1$-$C_6$)alkyl, -(4-10 membered)heterocycloalkyl($C_1$-$C_6$)alkyl($C_6$-$C_{10}$)aryl, -(4-10 membered)heterocycloalkyl($C_1$-$C_6$)alkyl(4-10 membered)heterocycloalkyl, -(4-10 membered)heterocycloalkyl($C_1$-$C_6$)alkyl(5-10 membered)heteroaryl, —O—($C_1$-$C_6$)alkyl-(4-10 membered)heterocycloalkyl, —O—($C_1$-$C_6$)alkyl-(4-10 membered)heterocycloalkyl-$R_{10}$, —O($C_1$-$C_6$)alkyl-C(O)NH($C_5$-$C_{10}$)cycloalkyl, -(4-10 membered)heterocycloalkyl($C_6$-$C_{10}$)aryl, —($C_1$-$C_6$)alkyl-N[($C_1$-$C_6$)alkyl]$_2$, —O—($C_1$-$C_6$)alkylN[($C_1$-$C_6$)alkyl]$_2$, -(4-10 membered)heterocycloalkyl($C_1$-$C_6$)alkyl, —($C_1$-$C_6$)alkoxy-di[($C_1$-$C_6$)alkyl]amino, —($C_6$-$C_{10}$)aryl, —($C_1$-$C_6$)alkoxy($C_1$-$C_6$)alkoxy, -(4-10 membered)heterocycloalkyl-C(O)O—($C_1$-$C_6$)alkyl, —ON(H)C(O)NH($C_1$-$C_6$)alkyl($C_6$-$C_{10}$)aryl, -(4-10 membered)heterocycloalkyl($C_1$-$C_6$)alkyl-O—($C_1$-$C_6$)alkyl-($C_6$-$C_{10}$)aryl, and —($C_1$-$C_6$)alkoxy(4-10 membered)heterocycloalkyl, wherein the aryl, heteroaryl, cycloalkyl or heterocycloalkyl portion of any of the above optional substituents can be further substituted by —($C_1$-$C_6$)alkyl;

$R_2$ is phenyl substituted with 1, 2 or 3 substituents selected from halo, —($C_1$-$C_3$)alkyl and methoxy, —O-piperidine, —O-piperazine, —O—($C_1$-$C_6$)alkyl-piperazine, and —O—($C_1$-$C_6$)alkylpiperidine;

$R_4$ is H; and $R_5$ is H.

9. The compound according to claim 1, wherein $R_1$ is benzimidazole, pyrazole or imidazole optionally substituted with 1, 2 or 3 substituents selected from —($C_1$-$C_6$)alkoxy($C_1$-$C_6$)alkoxy, —O—($C_1$-$C_6$)alkyl(5-6 membered)heterocycloalkyl, —O—($C_1$-$C_6$)alkyl-C(O)NH($C_1$-$C_6$)alkyl-(5-6 membered)heteroaryl, —O—($C_1$-$C_6$)alkyl-N[($C_1$-$C_6$)alkyl]$_2$, and piperazine optionally substituted with 1 or 2 groups selected from —($C_1$-$C_6$)alkyl, —C(O)O($C_1$-$C_6$)alkyl, —($C_1$-$C_6$)alkyl($C_5$-$C_6$)aryl, or ($C_1$-$C_6$)alkyl(5-6 membered)heterocycloalkyl; and $R_2$ is a substituent selected from

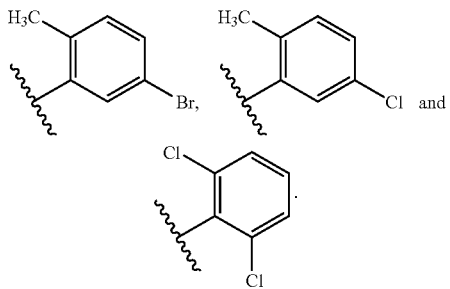

10. A pharmaceutical composition comprising a compound according to claim 1 and a pharmaceutically acceptable carrier, excipient, or diluent.

11. A method of inhibiting JAK-2 in a cell, comprising contacting a cell in which inhibition of JAK-2 is desired with a compound according to claim 1.

12. A compound selected from:

$N^5$-1H-benzimidazol-2-yl-$N^4$-(5-chloro-2-methylphenyl)-1H-imidazole-4,5-dicarboxamide;

$N^4$-1H-benzimidazol-2-yl-$N^5$-(2,6-dimethylphenyl)-1H-imidazole-4,5-dicarboxamide;

$N^5$-1H-benzimidazo 1-2-yl-$N^4$-(2-methylphenyl)-1H-imidazole-4,5-dicarboxamide;

$N^4$-1H-benzimidazol-2-yl-$N^5$-[2-(methylthio)phenyl]-1H-imidazole-4,5-dicarboxamide;

$N^5$-1H-benzimidazol-2-yl-$N^4$-(5-fluoro-2-methylphenyl)-1H-imidazole-4,5-dicarboxamide;

$N^5$-1H-benzimidazol-2-yl-$N^4$-[2-methyl-5-(methyloxy)phenyl]-1H-imidazole-4,5-dicarboxamide;

$N^5$-1H-benzimidazol-2-yl-$N^4$-[2-(1-methylethyl)phenyl]-1H-imidazole-4,5-dicarboxamide;

$N^5$-1H-benzimidazol-2-yl-$N^4$-(2-ethylphenyl)-1H-imidazole-4,5-dicarboxamide;

$N^4$-1H-benzimidazol-2-yl-$N^5$-(2-bromophenyl)-1H-imidazole-4,5-dicarboxamide;

$N^5$-1H-benzimidazol-2-yl-$N^4$-(2-chlorophenyl)-1H-imidazole-4,5-dicarboxamide;

$N^5$-1H-benzimidazol-2-yl-$N^4$-(2-cyanophenyl)-1H-imidazole-4,5-dicarboxamide;

$N^5$-1H-benzimidazol-2-yl-$N^4$-[2-methyl-6-(1-methylethyl)phenyl]-1H-imidazole-4,5-dicarboxamide;

$N^5$-(2,4-dimethylphenyl)-$N^4$-[6-(methyloxy)-1H-benzimidazol-2-yl]-1H-imidazole-4,5-dicarboxamide;

$N^4$-1H-benzimidazol-2-yl-$N^5$-(2,4,6-trimethylphenyl)-1H-imidazole-4,5-dicarboxamide;

$N^4$-1H-benzimidazol-2-yl-$N^5$-(2-fluorophenyl)-1H-imidazole-4,5-dicarboxamide;

$N^5$-1H-benzimidazol-2-yl-$N^4$-[2-methyl-4-(methyloxy)phenyl]-1H-imidazole-4,5-dicarboxamide;

$N^4$-1H-benzimidazol-2-yl-$N^5$-(2,6-diethylphenyl)-1H-imidazole-4,5-dicarboxamide;

$N^4$-(5-amino-2-methylphenyl)-$N^5$-1H-benzimidazol-2-yl-1H-imidazole-4,5-dicarboxamide;

$N^5$-[4-(azetidin-3-yloxy)-2-methylphenyl]-$N^4$-1H-benzimidazol-2-yl-1H-imidazole-4,5-dicarboxamide;

$N^5$-1H-benzimidazol-2-yl-$N^4$-(2-propylphenyl)-1H-imidazole-4,5-dicarboxamide;

$N^5$-1H-benzimidazol-2-yl-$N^4$-(2,3-dimethylphenyl)-1H-imidazole-4,5-dicarboxamide;

$N^5$-1H-benzimidazol-2-yl-$N^4$-[2-(trifluoromethyl)phenyl]-1H-imidazole-4,5-dicarboxamide;

$N^5$-1H-benzimidazo 1-2-yl-$N^4$-[(2-chlorophenyl)methyl]-1H-imidazole-4,5-dicarboxamide;

$N^5$-1H-benzimidazol-2-yl-$N^4$-(3-chloro-2-methylphenyl)-1H-imidazole-4,5-dicarboxamide;

$N^4$-(2,4-dimethylphenyl)-$N^5$-1H-imidazol-2-yl-1H-imidazole-4,5-dicarboxamide;

$N^5$-1H-benzimidazol-5-yl-$N^4$-(2,4-dimethylphenyl)-1H-imidazole-4,5-dicarboxamide;

$N^5$-1H-benzimidazol-2-yl-$N^4$-(5,6,7,8-tetrahydronaphthalen-1-yl)-1H-imidazole-4,5-dicarboxamide;

$N^5$-1H-benzimidazol-2-yl-$N^4$-(3-methylphenyl)-1H-imidazole-4,5-dicarboxamide;

1,1-dimethylethyl (2-{2[({4[(1H-benzimidazol-2-ylamino)carbonyl]-1H-imidazol-5-yl}carbonyl)amino]phenyl}ethyl)carbamate;

$N^5$-1H-benzimidazol-2-yl-$N^4$-[4-(methyloxy)phenyl]-1H-imidazole-4,5-dicarboxamide;

$N^5$-1H-benzimidazol-2-yl-$N^4$-(1-phenylethyl)-1H-imidazole-4,5-dicarboxamide;

$N^5$-1H-benzimidazol-2-yl-$N^4$-[2,5-bis(methyloxy)phenyl]-1H-imidazole-4,5-dicarboxamide;

$N^5$-1H-benzimidazol-2-yl-$N^4$-cyclohexyl-1H-imidazole-4,5-dicarboxamide;

$N^5$-(2-acetylphenyl)-$N^4$-1H-benzimidazol-2-yl-1H-imidazole-4,5-dicarboxamide;

N⁵-1H-benzimidazol-2-yl-N⁴-[4-(piperidin-4-yloxy)phenyl]-1H-imidazole-4,5-dicarboxamide;
N⁴-(2,4-dimethylphenyl)-N⁵-quinolin-6-yl-1H-imidazole-4,5-dicarboxamide;
1,1-dimethylethyl {3-[({5-[(1H-benzimidazol-2-ylamino)carbonyl]-1H-imidazol-4-yl}carbonyl)amino]-4-methylphenyl}carbamate;
N⁵-1H-benzimidazol-2-yl-N⁴-(phenylmethyl)-1H-imidazole-4,5-dicarboxamide;
N⁴-1H-benzimidazol-2-yl-N⁵-(4-chloro-2-methylphenyl)-1H-imidazole-4,5-dicarboxamide;
N⁵-1H-benzimidazol-2-yl-N⁴-naphthalen-1-yl-1H-imidazole-4,5-dicarboxamide;
N⁵-1H-benzimidazol-2-yl-N⁴-(4-methylphenyl)-1H-imidazole-4,5-dicarboxamide;
N⁵-1H-benzimidazol-2-yl-N⁴-[2,4-bis(methyloxy)phenyl]-1H-imidazole-4,5-dicarboxamide;
N⁵-1H-benzimidazol-2-yl-N⁴-[3-(methyloxy)phenyl]-1H-imidazole-4,5-dicarboxamide;
N⁵-1H-benzimidazol-2-yl-N⁴-[3-(1-methylethyl)phenyl]-1H-imidazole-4,5-dicarboxamide;
N⁵-1H-benzimidazol-2-yl-N⁴-{[3-(methyloxy)phenyl]methyl}-1H-imidazole-4,5-dicarboxamide;
N⁵-1H-benzimidazol-2-yl-N⁴-{[2-(methyloxy)phenyl]methyl}-1H-imidazole-4,5-dicarboxamide;
N⁵-1H-benzimidazol-2-yl-N⁴-(pyridin-2-ylmethyl)-1H-imidazole-4,5-dicarboxamide;
1,1-dimethylethyl 3-({4-[({4-[(1H-benzimidazol-2-ylamino)carbonyl]-1H-imidazol-5-yl}carbonyl)amino]-3-methylphenyl}oxy)azetidine-1-carboxylate;
N⁴-(2,4-dimethylphenyl)-N⁵-(1,3-dimethyl-1H-pyrazol-5-yl)-1H-imidazole-4,5-dicarboxamide;
N⁴-1H-benzimidazol-2-yl-N⁵-(1,2,3,4-tetrahydroisoquinolin-5-yl)-1H-imidazole-4,5-dicarboxamide;
N⁵-1H-benzimidazol-2-yl-N⁴-piperidin-4-yl-1H-imidazole-4,5-dicarboxamide;
N⁵-1H-benzimidazol-2-yl-N⁴-(cyclohexylmethyl)-1H-imidazole-4,5-dicarboxamide;
N⁵-1H-benzimidazol-2-yl-N⁴-{[4-(methyloxy)phenyl]methyl}-1H-imidazole-4,5-dicarboxamide;
N⁵-1H-benzimidazol-2-yl-N⁴-[2-(methylsulfonyl)phenyl]-1H-imidazole-4,5-dicarboxamide;
N⁵-{2-[2,5-bis(methyloxy)phenyl]ethyl}-N⁴-(2,4-dimethylphenyl)-1H-imidazole-4,5-dicarboxamide;
N⁵-1H-benzimidazol-2-yl-N⁴-[2-(ethyloxy)phenyl]-1H-imidazole-4,5-dicarboxamide;
N⁴-(2,4-dimethylphenyl)-N⁵-methyl-N⁵-(2-pyridin-2-ylethyl)-1H-imidazole-4,5-dicarboxamide;
N⁵-1H-benzimidazol-2-yl-N⁴-methyl-N⁴-(2-methylphenyl)-1H-imidazole-4,5-dicarboxamide;
N⁵-1H-benzimidazol-2-yl-N⁴-(2-{[cyclohexyl(methyl)amino]methyl}phenyl)-1H-imidazole-4,5-dicarboxamide;
N-1H-benzimidazol-2-yl-4-(3,4-dihydroquinolin-1(2H)-ylcarbonyl)-1H-imidazole-5-carboxamide;
N⁵-1H-benzimidazol-2-yl-N⁴-[2-(1,1-dimethylethyl)phenyl]-1H-imidazole-4,5-dicarboxamide;
N-1H-benzimidazol-2-yl-4-(2,3-dihydro-1H-indol-1-ylcarbonyl)-1H-imidazole-5-carboxamide;
N⁵-1H-benzimidazol-2-yl-N⁴-(2-butylphenyl)-1H-imidazole-4,5-dicarboxamide;
N⁵-1H-benzimidazol-2-yl-N⁴-[2-(1H-pyrrol-1-yl)phenyl]-1H-imidazole-4,5-dicarboxamide;
N⁵-1H-benzimidazol-2-yl-N⁴-(2-morpholin-4-ylethyl)-1H-imidazole-4,5-dicarboxamide;
N⁵-1H-benzimidazol-2-yl-N⁴-(2-{[cyclohexyl(methyl)amino]methyl}phenyl)-1H-imidazole-4,5-dicarboxamide;
N⁴-(2,4-dimethylphenyl)-N⁵-1H-indol-5-yl-1H-imidazole-4,5-dicarboxamide;
N⁵-(2,4-dimethylphenyl)-N⁴-(4-phenyl-1H-imidazol-2-yl)-1H-imidazole-4,5-dicarboxamide;
1,1-dimethylethyl 5-[({4-[(1H-benzimidazol-2-ylamino)carbonyl]-1H-imidazol-5-yl}carbonyl)amino]-3,4-dihydroisoquinoline-2(1H)-carboxylate;
N⁵-[2-(2-aminoethyl)phenyl]-N⁴-1H-benzimidazol-2-yl-1H-imidazole-4,5-dicarboxamide;
N⁴-1H-benzimidazol-2-yl-N⁵-(2,4-dimethylphenyl)-N⁴-methyl-1H-imidazole-4,5-dicarboxamide;
N⁵-1H-benzimidazol-2-yl-N⁴-{2-[(trifluoromethyl)oxy]phenyl}-1H-imidazole-4,5-dicarboxamide;
5-{[2-(1H-benzimidazol-2-yl)hydrazino]carbonyl}-N-(2-methylphenyl)-1H-imidazole-4-carboxamide;
1,1-dimethylethyl 4-({4-[({5-[(1H-benzimidazol-2-ylamino)carbonyl]-1H-imidazol-4-yl}carbonyl)amino]phenyl}oxy)piperidine-1-carboxylate;
N⁵-1H-benzimidazol-2-yl-N⁴-{2-[(dimethylamino)methyl]phenyl}-1H-imidazole-4,5-dicarboxamide;
N⁴-(2,4-dimethylphenyl)-N⁵-(1-methyl-1H-benzimidazol-2-yl)-1H-imidazole-4,5-dicarboxamide;
N⁴-(2-chlorophenyl)-N⁵-[(3-methylphenyl)methyl]-1H-imidazole-4,5-dicarboxamide;
N-(2,5-dimethylphenyl)-5-[(4-pyrimidin-2-ylpiperazin-1-yl)carbonyl]-1H-imidazole-4-carboxamide;
N⁵-1,3-benzothiazol-2-yl-N⁴-(2,4-dimethylphenyl)-1H-imidazole-4,5-dicarboxamide;
N⁵-1,3-benzothiazol-2-yl-N⁴-(2-chlorophenyl)-1H-imidazole-4,5-dicarboxamide;
N⁴-phenyl-N⁵-pyridin-2-yl-1H-imidazole-4,5-dicarboxamide;
N⁴-(2,4-dimethylphenyl)-N⁵-(pyridin-2-ylmethyl)-1H-imidazole-4,5-dicarboxamide;
N⁴-(2,4-dimethylphenyl)-N⁵-(pyridin-3-ylmethyl)-1H-imidazole-4,5-dicarboxamide;
N⁵-(1H-benzimidazol-2-ylmethyl)-N⁴-(2,4-dimethylphenyl)-1H-imidazole-4,5-dicarboxamide;
N⁵-1H-benzimidazol-2-yl-N⁴-[(2,4-dimethylphenyl)methyl]-1H-imidazole-4,5-dicarboxamide;
N-(2,4-dimethylphenyl)-5-{[4-(phenylmethyl)piperazin-1-yl]carbonyl}-1H-imidazole-4-carboxamide;
N⁴-(2,4-dimethylphenyl)-N⁵-(phenylmethyl)-1H-imidazole-4,5-dicarboxamide;
N⁴-(2,4-dimethylphenyl)-N⁵-[2-(1H-indol-3-yl)ethyl]-1H-imidazole-4,5-dicarboxamide
5-{[4-(3-chlorophenyl)piperazin-1-yl]carbonyl}-N-(2,4-dimethylphenyl)-1H-imidazole 4-carboxamide;
N-(2,4-dimethylphenyl)-5-[(4-pyrazin-2-ylpiperazin-1-yl)carbonyl]-1H-imidazole-4-carboxamide;
N⁵-1H-benzimidazol-2-yl-N⁴-(2-methylcyclohexyl)-1H-imidazole-4,5-dicarboxamide;
N⁵-1H-benzimidazol-2-yl-N⁴-(5-bromo-2-methylphenyl)-1H-imidazole-4,5-dicarboxamide;
N⁵-1H-benzimidazol-2-yl-N⁴-(2,5-dichlorophenyl)-1H-imidazole-4,5-dicarboxamide;
methyl [(2-{[(4-{[(2,4-dimethylphenyl)amino]carbonyl}-1H-imidazol-5-yl)carbonyl]amino}-1H-benzimidazol-6-yl)oxy]acetate;
N⁵-(6-{[2-(dimethylamino)-2-oxoethyl]oxy}-1H-benzimidazol-2-yl)-N⁴-(2,4-dimethylphenyl)-1H-imidazole-4,5-dicarboxamide;

$N^5$-{6-[(2-{[2-(dimethylamino)ethyl]amino}-2-oxoethyl)oxy]-1H-benzimidazol-2-yl}$N^4$-(2,4-dimethylphenyl)-1H-imidazole-4,5-dicarboxamide;
$N^4$-1H-benzimidazol-2-yl-$N^5$-[2-methyl-4-(piperidin-4-yloxy)phenyl]-1H-imidazole-4,5-dicarboxamide;
$N^5$-1H-benzimidazol-2-yl-$N^4$-[2-chloro-5-(methyloxy)phenyl]-1H-imidazole-4,5-dicarboxamide;
$N^5$-(2,4-dimethylphenyl)-$N^4$-[5-(4-methylpiperazin-1-yl)-1H-benzimidazol-2-yl]-1H-imidazole-4,5-dicarboxamide;
[(2-{[(4-{[(2,4-dimethylphenyl)amino]carbonyl}-1H-imidazol-5-yl)carbonyl]amino}-1H-benzimidazol-6-yl)oxy]acetic acid;
$N^4$-(2,4-dimethylphenyl)-$N^5$-{6-[(2-hydroxyethyl)oxy]-1H-benzimidazol-2-yl}-1H-imidazole-4,5-dicarboxamide;
$N^4$-[5-(azetidin-3-yloxy)-1H-benzimidazol-2-yl]-$N^5$-(2,4-dimethylphenyl)-1H-imidazole-4,5-dicarboxamide;
$N^5$-1H-benzimidazol-2-yl-$N^4$-(4-methylpyridin-3-yl)-1H-imidazole-4,5-dicarboxamide;
$N^4$-[5-(azetidin-3-yloxy)-2-methylphenyl]-$N^5$-1H-benzimidazol-2-yl-1H-imidazole-4,5-dicarboxamide;
$N^5$-1H-benzimidazol-2-yl-$N^4$-(2-methylpyridin-3-yl)-1H-imidazole-4,5-dicarboxamide;
1,1-dimethylethyl 3-[(2-{[(5-{[(2,4-dimethylphenyl)amino]carbonyl}-1H-imidazol-4-yl)carbonyl]amino}-1H-benzimidazol-5-yl)oxy]azetidine-1-carboxylate;
1,1-dimethylethyl 4-({4-[({4-[(1H-benzimidazol-2-ylamino)carbonyl]-1H-imidazol-5-yl}carbonyl)amino]-3-methylphenyl}oxy)piperidine-1-carboxylate;
$N^5$-1H-benzimidazol-2-yl-$N^4$-[(4-methylphenyl)methyl]-1H-imidazole-4,5-dicarboxamide;
$N^4$-1H-benzimidazol-2-yl-$N^5$-[2-methyl-5-(piperidin-4-yloxy)phenyl]-1H-imidazole-4,5-dicarboxamide;
1,1-dimethylethyl 3-({3-[({5-[(1H-benzimidazol-2-ylamino)carbonyl]-1H-imidazol-4-yl}carbonyl)amino]-4-methylphenyl}oxy)azetidine-1-carboxylate;
1,1-dimethylethyl 4-({3-[({4-[(1H-benzimidazol-2-ylamino)carbonyl]-1H-imidazol-5-yl}carbonyl)amino]-4-methylphenyl}oxy)piperidine-1-carboxylate;
$N^5$-1H-benzimidazol-2-yl-$N^4$-[2,4-bis(methyloxy)phenyl]-1H-imidazole-4,5-dicarboxamide;
$N^4$-1H-benzimidazol-2-yl-$N^5$-(2,4,5-trichlorophenyl)-1H-imidazole-4,5-dicarboxamide;
$N^4$-1H-benzimidazol-2-yl-$N^5$-[2,5-bis(ethyloxy)-4-morpholin-4-ylphenyl]-1H-imidazole-4,5-dicarboxamide;
1,1-dimethylethyl 4-{[(2-{[(4-{[(2,4-dimethylphenyl)amino]carbonyl}-1H-imidazol-5-yl)carbonyl]amino}-1H-benzimidazol-5-yl)oxy]methyl}piperidine-1-carboxylate;
$N^5$-1H-benzimidazol-2-yl-$N^4$-(4-chloro-2-fluorophenyl)-1H-imidazole-4,5-dicarboxamide;
$N^4$-(2,4-dimethylphenyl)-$N^5$-{5-[(piperidin-4-ylmethyl)oxy]-1H-benzimidazol-2-yl}-1H-imidazole-4,5-dicarboxamide;
$N^5$-1H-benzimidazol-2-yl-$N^4$-(2,6-difluorophenyl)-1H-imidazole-4,5-dicarboxamide;
$N^5$-1H-benzimidazol-2-yl-$N^4$-(2,6-dichlorophenyl)-1H-imidazole-4,5-dicarboxamide;
$N^5$-1H-benzimidazol-2-yl-$N^4$-[2-methyl-6-(methyloxy)phenyl]-1H-imidazole-4,5-dicarboxamide;
$N^5$-1H-benzimidazol-2-yl-$N^4$-(2-chloro-6-fluorophenyl)-1H-imidazole-4,5-dicarboxamide;
$N^5$-1H-benzimidazol-2-yl-$N^4$-(4-bromo-2-fluorophenyl)-1H-imidazole-4,5-dicarboxamide;
$N^4$-(2,4-dimethylphenyl)-$N^5$-{5-[(pyridin-4-ylmethyl)oxy]-1H-benzimidazol-2-yl]-1H-imidazole-4,5-dicarboxamide;
$N^5$-[6-({2-[(2,3-dihydroxypropyl)amino]-2-oxoethyl}oxy)-1H-benzimidazol-2-yl]-$N^4$-(2,4-dimethylphenyl)-1H-imidazole-4,5-dicarboxamide;
$N^5$-1H-benzimidazol-2-yl-$N^4$-{4-[(1-ethylpiperidin-4-yl)oxy]phenyl}-1H-imidazole-4,5-dicarboxamide;
$N^5$-1H-benzimidazol-2-yl-$N^4$-[5-chloro-2-(methyloxy)phenyl]-1H-imidazole-4,5-dicarboxamide;
methyl [(2-{[(4-{[(5-bromo-2-methylphenyl)amino]carbonyl}-1H-imidazol-5-yl)carbonyl]amino}-1H-benzimidazol-5-yl)oxy]acetate;
$N^4$-1H-benzimidazol-2-yl-$N^5$-[2-chloro-5-(hydroxymethyl)phenyl]-1H-imidazole-4,5-dicarboxamide;
$N^4$-(5-bromo-2-methylphenyl)-$N^5$-(6-{[2-(dimethylamino)ethyl]oxy}-1H-benzimidazol-2-yl)-1H-imidazole-4,5-dicarboxamide;
$N^5$-(5-chloro-1H-benzimidazol-2-yl)-$N^4$-(2,4-dimethylphenyl)-1H-imidazole-4,5-dicarboxamide;
$N^4$-(5-bromo-2-methylphenyl)-$N^5$-(5-chloro-1H-benzimidazol-2-yl)-1H-imidazole-4,5-dicarboxamide;
1,1-dimethylethyl 4-{-4[({5-[(1H-benzimidazol-2-ylamino)carbonyl]-1H-imidazol-4-yl}carbonyl)amino]-3-methylphenyl}piperazine-1-carboxylate;
$N^5$-(6-chloro-1H-benzimidazol-2-yl)-$N^4$-(2,6-dichlorophenyl)-1H-imidazole-4,5-dicarboxamide;
1,1-dimethylethyl 4-[3-({4-[({-4-[(1H-benzimidazol-2-ylamino)carbonyl]-1H-imidazol-5-yl}carbonyl)amino]-5-chloro-2-methylphenyl}oxy)propyl]piperazine-1-carboxylate;
$N^4$-1H-benzimidazol-2-yl-$N^5$-{2-chloro-5-methyl-4-[(3-piperazin-1-ylpropyl)oxy]phenyl}-1H-imidazole-4,5-dicarboxamide;
$N^4$-1H-benzimidazol-2-yl-$N^5$-{2-chloro-4-[(3-piperazin-1-ylpropyl)oxy]phenyl}-1H-imidazole-4,5-dicarboxamide;
$N^5$-(6-chloro-1H-benzimidazol-2-yl)-$N^4$-(2-chloro-6-fluorophenyl)-1H-imidazole-4,5-dicarboxamide;
$N^4$-(2,4-dimethylphenyl)-$N^5$-(5-{[2-(methylamino)-2-oxoethyl]oxy}-1H-benzimidazol-2-yl)-1H-imidazole-4,5-dicarboxamide;
$N^4$-(2,4-dimethylphenyl)-$N^5$-[5-({2-oxo-2-[(pyridin-4-ylmethyl)amino]ethyl}oxy)-1H-benzimidazol-2-yl]-1H-imidazole-4,5-dicarboxamide;
$N^5$-1H-benzimidazol-2-yl-$N^4$-(2-methyl-4-piperazin-1-ylphenyl)-1H-imidazole-4,5-dicarboxamide;
$N^5$-1H-benzimidazol-2-yl-$N^4$-{4-[(1-ethylpiperidin-4-yl)oxy]-2-methylphenyl}-1H-imidazole-4,5-dicarboxamide;
$N^5$-1H-benzimidazol-2-yl-$N^4$-(2-methyl-4-{[1-(phenylmethyl)piperidin-4-yl]oxy}phenyl)-1H-imidazole-4,5-dicarboxamide;
$N^5$-(5-bromo-2-methylphenyl)-$N^4$-[4-(methyloxy)-1H-benzimidazol-2-yl]-1H-imidazole-4,5-dicarboxamide;
$N^5$-1H-benzimidazol-2-yl-$N^4$-[2-fluoro-6-(methyloxy)phenyl]-1H-imidazole-4,5-dicarboxamide;
1,1-dimethylethyl 4-({-4[({4-[(1H-benzimidazol-2-ylamino)carbonyl]-1H-imidazol-5-yl}carbonyl)amino]-3-chlorophenyl}oxy)piperidine-1-carboxylate;
$N^4$-1H-benzimidazol-2-yl-$N^5$-[2-chloro-4-(piperidin-4-yloxy)phenyl]-1H-imidazole-4,5-dicarboxamide;
$N^5$-1H-benzimidazol-2-yl-N~4~{4-[(3-piperazin-1-ylpropyl)oxy]-2-(trifluoromethyl)phenyl}-1H-imidazole-4,5-dicarboxamide;

1-methylethyl [(2-{[(4-{[(2,4-dimethylphenyl)amino]carbonyl}-1H-imidazol-5-yl)carbonyl]amino}-1H-benzimidazol-5-yl)oxy]acetate;

$N^4$-(2,4-dimethylphenyl)-$N^5$-(5-{[2-oxo-2-(propylamino)ethyl]oxy}-1H-benzimidazol-2-yl)-1H-imidazole-4,5-dicarboxamide;

$N^4$-(2,4-dimethylphenyl)-$N^5$-[5-({2-oxo-2-[(phenylmethyl)amino]ethyl}oxy)-1H-benzimidazol-2-yl]-1H-imidazole-4,5-dicarboxamide;

$N^5$-1H-benzimidazol-2-yl-$N^4$-(2-fluoro-3-{[(1-methylpiperidin-3-yl)carbonyl]amino}phenyl)-1H-imidazole-4,5-dicarboxamide;

ethyl 4-({4-[({4-[(1H-benzimidazol-2-ylamino)carbonyl]-1H-imidazol-5-yl}carbonyl)amino]-3-methylphenyl}oxy)piperidine-1-carboxylate;

$N^5$-(5-{[2-(cyclohexylamino)-2-oxoethyl]oxy}-1H-benzimidazol-2-yl)-$N^4$-(2,4-dimethylphenyl)-1H-imidazole-4,5-dicarboxamide;

$N^4$-(5-bromo-2-methylphenyl)-$N^5$-[5-({2-oxo-2-[(tetrahydrofuran-2-ylmethyl)amino]ethyl}oxy)-1H-benzimidazol-2-yl]-1H-imidazole-4,5-dicarboxamide;

$N^4$-(2,4-dimethylphenyl)-$N^5$-[5-({2-oxo-2-[(2-phenylethyl)amino]ethyl}oxy)-1H-benzimidazol-2-yl]-1H-imidazole-4,5-dicarboxamide;

$N^4$-(5-bromo-2-methylphenyl)-$N^5$-[5-({2-oxo-2-[(piperidin-4-ylmethy)amino]ethyl}oxy)-1H-benzimidazol-2-yl]-1H-imidazole-4,5-dicarboxamide;

$N^5$-1H-benzimidazol-2-yl-$N^4$-{2-chloro-4-[(2-morpholin-4-ylethyl)oxy]phenyl}-1H-imidazole-4,5-dicarboxamide;

1,1-dimethylethyl 4-[(4-{[(5-{[(6-chloro-1H-benzimidazol-2-yl)amino]carbonyl}-1H-imidazol-4-yl)carbonyl]amino}-3-methylphenyl)oxy]piperidine-1-carboxylate;

$N^4$-1H-benzimidazol-2-yl-$N^5$-(2-chloro-4-{[1-(cyanoacetyl)piperidin-4-yl]oxy}phenyl)-1H-imidazole-4,5-dicarboxamide;

$N^4$-1H-benzimidazol-2-yl-$N^5$-{2-chloro-4-[(1-methylpiperidin-4-yl)oxy]phenyl}-1H-imidazole-4,5-dicarboxamide;

$N^4$-1H-benzimidazol-2-yl-$N^5$-{4-fluoro-2-[(2-morpholin-4-ylethyl)oxy]phenyl}-1H-imidazole-4,5-dicarboxamide;

$N^4$-(5-bromo-2-methylphenyl)-$N^5$-[5-(4-methylpiperazin-1-yl)-1H-benzimidazol-2-yl]-1H-imidazole-4,5-dicarboxamide;

1,1-dimethylethyl 4-[(3-methyl-4-{[(5-{[(5-{[2-(methyloxy)-2-oxoethyl]oxy}-1H-benzimidazol-2-yl)amino]carbonyl}-1H-imidazol-4-yl)carbonyl]amino}phenyl)oxy]piperidine-1-carboxylate;

$N^5$-(6-chloro-1H-benzimidazol-2-yl)-$N^4$-[2-methyl-4-(piperidin-4-yloxy)phenyl]-1H-imidazole-4,5-dicarboxamide;

$N^5$-1H-benzimidazol-2-yl-$N^4$-{2-methyl-4-[4-(phenylsulfonyl)piperazin-1-yl]phenyl}1H-imidazole-4,5-dicarboxamide;

$N^5$-1H-benzimidazol-2-yl-$N^4$-(2-methyl-4-{4-[(phenylamino)carbonyl]piperazin-1-yl}phenyl)-1H-imidazole-4,5-dicarboxamide;

$N^4$-(2,4-dimethylphenyl)-$N^5$-[5-({2-oxo-2-[(pyridin-2-ylmethyl)amino]ethyl}oxy)-1H-benzimidazol-2-yl]-1H-imidazole-4,5-dicarboxamide;

$N^5$-[4-(methyloxy)-1H-benzimidazol-2-yl]-$N^4$-[2-methyl-4-(piperidin-4-yloxy)phenyl]-1H-imidazole-4,5-dicarboxamide;

$N^4$-(2,6-dichlorophenyl)-$N^5$-[4-(methyloxy)-1H-benzimidazol-2-yl]-1H-imidazole-4,5-dicarboxamide;

$N^5$-1H-benzimidazol-2-yl-$N^4$-{2-methyl-4-[(3-morpholin-4-ylpropyl)oxy]phenyl}-1H-imidazole-4,5-dicarboxamide;

$N^5$-1H-benzimidazol-2-yl-$N^4$-[2-chloro-4-({3-[4-(phenylsulfonyl)piperazin-1-yl]propyl}oxy)phenyl]-1H-imidazole-4,5-dicarboxamide;

$N^5$-1H-benzimidazol-2-yl-$N^4$-(4-{4-[(ethylamino)carbonyl]piperazin-1-yl}-2-methylphenyl)-1H-imidazole-4,5-dicarboxamide;

$N^5$-1H-benzimidazol-2-yl-$N^4$-(2-fluoro-6-hydroxyphenyl)-1H-imidazole-4,5-dicarboxamide;

$N^5$-1H-benzimidazol-2-yl-$N^4$-[2,6-bis(methyloxy)phenyl]-1H-imidazole-4,5-dicarboxamide;

$N^4$-(2,6-dichlorophenyl)-$N^5$-(6-{[2-(dimethylamino)ethyl]oxy}-1H-benzimidazol-2-yl)-1H-imidazole-4,5-dicarboxamide;

$N^4$-(5-bromo-2-methylphenyl)-$N^5$-(4-{[2-(dimethylamino)ethyl]oxy}-1H-benzimidazol-2-yl)-1H-imidazole-4,5-dicarboxamide;

1,1-dimethylethyl 4-(2-{[(4-{[(5-bromo-2-methylphenyl)amino]carbonyl}-1H-imidazol-5-yl)carbonyl]amino}-1H-benzimidazol-5-yl)piperazine-1-carboxylate;

$N^4$-(5-bromo-2-methylphenyl)-$N^5$-{5-[(piperidin-4-ylmethyl)oxy]-1H-benzimidazol-2-yl}-1H-imidazole-4,5-dicarboxamide;

$N^4$-(5-bromo-2-methylphenyl)-$N^5$-(4-{[3-(dimethylamino)propyl]oxy}-1H-benzimidazol-2-yl)-1H-imidazole-4,5-dicarboxamide;

[(2-{[(5-{[(5-bromo-2-methylphenyl)amino]carbonyl}-1H-imidazol-4-yl)carbonyl]amino}-1H-benzimidazol-7-yl)oxy]acetic acid;

1,1-dimethylethyl [(2-{[(5-{[(5-bromo-2-methylphenyl)amino]carbonyl}-1H-imidazol-4-yl)carbonyl]amino}-1H-benzimidazol-7-yl)oxy]acetate;

$N^4$-(5-bromo-2-methylphenyl)-$N^5$-(5-piperazin-1-yl-1H-benzimidazol-2-yl)-1H-imidazole-4,5-dicarboxamide;

$N^4$-(5-bromo-2-methylphenyl)-$N^5$-[5-({2-oxo-2-[(pyridin-4-ylmethyl)amino]ethyl}oxy)-1H-benzimidazol-2-yl]-1H-imidazole-4,5-dicarboxamide;

$N^5$-1H-benzimidazol-2-yl-$N^4$-{4-[4-(4-chlorophenyl)piperazin-1-yl]-2-methylphenyl}-1H-imidazole-4,5-dicarboxamide;

$N^5$-1H-benzimidazol-2-yl-$N^4$-(2-methyl-4-morpholin-4-ylphenyl)-1H-imidazole-4,5-dicarboxamide;

1,1-dimethylethyl 4-{[(2-{[(4-{[(5-chloro-2-methylphenyl)amino]carbonyl}-1H-imidazol-5-yl)carbonyl]amino}-1H-benzimidazol-5-yl)oxy]methyl}piperidine-1-carboxylate;

$N^5$-(5-bromo-2-methylphenyl)-$N^4$-[7-(piperidin-4-yloxy)-1H-benzimidazol-2-yl]-1H-imidazole-4,5-dicarboxamide;

methyl 2-{[(4-{[(5-bromo-2-methylphenyl)amino]carbonyl}-1H-imidazol-5-yl)carbonyl]amino}-1H-benzimidazole-5-carboxylate;

methyl 2-{[(4-{[(5-chloro-2-methylphenyl)amino]carbonyl}-1H-imidazol-5-yl)carbonyl]amino}-1H-benzimidazole-5-carboxylate;

$N^4$-(5-bromo-2-methylphenyl)-$N^5$-[5-(piperidin-4-yloxy)-1H-benzimidazol-2-yl]-1H-imidazole-4,5-dicarboxamide;

$N^5$-1H-benzimidazol-2-yl-$N^4$-(3-chloro-2,6-dimethylphenyl)-1H-imidazole-4,5-dicarboxamide;

$N^4$-(5-chloro-2-methylphenyl)-N 5-{5-[(piperidin-4-ylmethyl)oxy]-1H-benzimidazol-2-yl}-1H-imidazole-4,5-dicarboxamide;

$N^4$-(5-chloro-2-methylphenyl)-$N^5$-[5-(4-methylpiperazin-1-yl)-1H-benzimidazol-2-yl]-1H-imidazole-4,5-dicarboxamide;

$N^4$-(5-chloro-2-methylphenyl)-$N^5$-[5-(piperidin-4-yloxy)-1H-benzimidazol-2-yl]-1H-imidazole-4,5-dicarboxamide;

$N^4$-(5-bromo-2-methylphenyl)-$N^5$-[5-(4-pentylpiperazin-1-yl)-1H-benzimidazol-2-yl]-1H-imidazole-4,5-dicarboxamide;

$N^4$-(5-bromo-2-methylphenyl)-$N^5$-{5-[4-(2-phenylethyl)piperazin-1-yl]-1H-benzimidazol-2-yl}-1H-imidazole-4,5-dicarboxamide;

$N^4$-(5-bromo-2-methylphenyl)-$N^5$-{5-[4-(phenylmethyl)piperazin-1-yl]-1H-benzimidazol-2-yl}-1H-imidazole-4,5-dicarboxamide;

$N^4$-(5-bromo-2-methylphenyl)-$N^5$-{5-[4-(2-methylpropyl)piperazin-1-yl]-1H-benzimidazol-2-yl}-1H-imidazole-4,5-dicarboxamide;

$N^5$-1H-benzimidazol-2-yl-$N^4$-(2,5-dimethylphenyl)-1H-imidazole-4,5-dicarboxamide;

$N^5$-(5-bromo-2-methylphenyl)-$N^4$-(7-{[2-(methyloxy)ethyl]oxy}-1H-benzimidazol-2-yl)-1H-imidazole-4,5-dicarboxamide;

$N^5$-(5-bromo-2-methylphenyl)-$N^4$-{7-[(2-morpholin-4-ylethyl)oxy]-1H-benzimidazol-2-yl}-1H-imidazole-4,5-dicarboxamide;

$N^4$-(5-bromo-2-methylphenyl)-$N^5$-{5-[(2-piperazin-1-ylethyl)oxy]-1H-benzimidazol-2-yl}-1H-imidazole-4,5-dicarboxamide;

$N^4$-(5-bromo-2-methylphenyl)-$N^5$-{5-[4-(tetrahydrofuran-3-ylmethyl)piperazin-1-yl]-1H-benzimidazol-2-yl}-1H-imidazole-4,5-dicarboxamide;

$N^4$-(5-bromo-2-methylphenyl)-$N^5$-[5-(4-(pyridin-4-ylmethyl)piperazin-1-yl]-1H-benzimidazol-2-yl}-1H-imidazole-4,5-dicarboxamide;

$N^4$-(5-bromo-2-methylphenyl)-$N^5$-[5-(4-{2-[(phenylmethyl)oxy]ethyl}piperazin-1-yl)-1H-benzimidazol-2-yl]-1H-imidazole-4,5-dicarboxamide;

$N^4$-(5-bromo-2-methylphenyl)-N 5-{7-[(1-methylpiperidin-4-yl)oxy]-1H-benzimidazol-2-yl}-1H-imidazole-4,5-dicarboxamide;

$N^4$-(2,6-dichlorophenyl)-$N^5$-[6-(4-methylpiperazin-1-yl)-1H-benzimidazol-2-yl]-1H-imidazole-4,5-dicarboxamide;

1,1-dimethylethyl 4-(2-{[(5-{[(5-bromo-2-methylphenyl)amino]carbonyl}-1H-imidazol-4-yl)carbonyl]amino}-1H-benzimidazol-6-yl)-3-methylpiperazine-1-carboxylate;

$N^4$-(5-bromo-2-methylphenyl)-$N^5$-(5-{[2-(diethylamino)ethyl]oxy}-1H-benzimidazol-2-yl)-1H-imidazole-4,5-dicarboxamide;

$N^4$-(5-bromo-2-methylphenyl)-$N^5$-(5-{[2-(4-methylpiperazin-1-yl)ethyl]oxy}-1H-benzimidazol-2-yl)-1H-imidazole-4,5-dicarboxamide;

$N^4$-(5-bromo-2-methylphenyl)-$N^5$-(4,5-dimethyl-1H-imidazol-2-yl)-1H-imidazole-4,5-dicarboxamide;

$N^4$-(5-bromo-2-methylphenyl)-$N^5$-(5-{[3-(4-methylpiperazin-1-yl)propyl]oxy}-1H-benzimidazol-2-yl)-1H-imidazole-4,5-dicarboxamide;

$N^5$-(2,6-dichlorophenyl)-$N^4$-{6-[(3-pyrrolidin-1-ylpropyl)oxy]-1H-benzimidazol-2-yl}-1H-imidazole-4,5-dicarboxamide;

$N^4$-(5-bromo-2-methylphenyl)-$N^5$-{2-methyl-4-[(piperidin-4-ylmethyl)oxy]phenyl}-1H-imidazole-4,5-dicarboxamide;

$N^4$-(5-bromo-2-methylphenyl)-$N^5$-(4-chloro-1H-benzimidazol-2-yl)-1H-imidazole-4,5-dicarboxamide;

$N^4$-(5-bromo-2-methylphenyl)-$N^5$-(5-fluoro-1H-benzimidazol-2-yl)-1H-imidazole-4,5-dicarboxamide;

$N^5$-1H-benzimidazol-2-yl-$N^4$-biphenyl-2-yl-1H-imidazole-4,5-dicarboxamide;

$N^4$-(5-bromo-2-methylphenyl)-$N^5$-(4-methyl-1H-imidazol-2-yl)-1H-imidazole-4,5-dicarboxamide; and $N^5$-(4,5-dimethyl-1H-imidazol-2-yl)-$N^4$-[2-fluoro-6-(methyloxy)phenyl]-1H-imidazole-4,5-dicarboxamide, or a pharmaceutically acceptable salt of any of the above compounds.

\* \* \* \* \*